US011345662B2

(12) United States Patent
Mueller et al.

(10) Patent No.: US 11,345,662 B2
(45) Date of Patent: May 31, 2022

(54) AZA (INDOLE)-, BENZOTHIOPHENE-, AND BENZOFURAN-3-SULFONAMIDES

(71) Applicant: UCB PHARMA GMBH, Monheim (DE)

(72) Inventors: Christa E. Mueller, Bonn (DE); Cécile Pegurier, Uccle (BE); Michael Louis Robert Deligny, Rhode Saint Genese (BE); Ali El-Tayeb, Bonn (DE); Joerg Hockemeyer, Bonn (DE); Marie Ledecq, Eghezee (BE); Joël Mercier, Floreffe (BE); Laurent Provins, Soignies (BE); Nader M. Boshta, Shebin el-Kom (EG); Sanjay Bhattarai, Lawrence, KS (US); Vigneshwaran Namasivayam, Bonn (DE); Mario Funke, Friedrichshafen (DE); Lukas Schwach, Bonn (DE); Sabrina Gollos, Sternenburgstr (DE); Daniel Von Laufenberg, Siegburg (DE); Anaïs Barré, Montargis (FR)

(73) Assignee: UCB Pharma GmbH, Monheim (DE)

(*) Notice: Subject to any disclaimer, the term of this patent is extended or adjusted under 35 U.S.C. 154(b) by 0 days.

(21) Appl. No.: 16/474,245

(22) PCT Filed: Dec. 27, 2017

(86) PCT No.: PCT/EP2017/084602
§ 371 (c)(1),
(2) Date: Jun. 27, 2019

(87) PCT Pub. No.: WO2018/122232
PCT Pub. Date: Jul. 5, 2018

(65) Prior Publication Data
US 2019/0345104 A1 Nov. 14, 2019

(30) Foreign Application Priority Data
Dec. 28, 2016 (EP) .................................... 16207137

(51) Int. Cl.
*C07D 209/30* (2006.01)
*C07D 307/82* (2006.01)
*C07D 333/62* (2006.01)
*C07D 401/12* (2006.01)
*C07D 405/12* (2006.01)
*C07D 413/12* (2006.01)
*C07D 417/12* (2006.01)
*C07D 421/12* (2006.01)
*C07D 487/04* (2006.01)
*C07D 491/056* (2006.01)

(52) U.S. Cl.
CPC ......... *C07D 209/30* (2013.01); *C07D 307/82* (2013.01); *C07D 333/62* (2013.01); *C07D 401/12* (2013.01); *C07D 405/12* (2013.01); *C07D 413/12* (2013.01); *C07D 417/12* (2013.01); *C07D 421/12* (2013.01); *C07D 487/04* (2013.01); *C07D 491/056* (2013.01)

(58) Field of Classification Search
CPC ..................................................... C07D 209/30
See application file for complete search history.

(56) References Cited

U.S. PATENT DOCUMENTS

| 6,521,658 B1 * | 2/2003 | Li ......................... C07C 311/21 514/415 |
| 10,562,898 B2 * | 2/2020 | Tokumasu ........... C07D 473/04 |

FOREIGN PATENT DOCUMENTS

| WO | WO-2010126002 A1 | 11/2010 |
| WO | WO-2013167177 A1 | 11/2013 |
| WO | WO-2017135472 A1 * | 8/2017 ........... C07D 401/14 |

OTHER PUBLICATIONS

PubChem CID: 135187012 "6-Chloro-N-[2,5-difluoro-4-(trifluoromethyl)phenyl]-1Hpyrrolo[2,3-b]pyridine-3-sulfonamide" Create Date : Dec. 15, 2018.*
MCULE commercial database entry MCULE-8587460154, mcule product ID: P-142661488, for 4-Fluoro-N-[2-fluoro-4-chloro-phenyl]-indole-3-sulfonamide. Jan. 20, 2015, accessed Jun. 12, 2020.*
Database accession No. 1202763292, Chem. Abstracts Service: XP002768590 (Oct. 20, 2016), 1 page.
International Search Report dated Apr. 17, 2018 issued in PCT/EP2017/084602, 9 pages.
Written Opinion dated Apr. 17, 2018 issued in PCT/EP2017/084602, 14 pages.
Rukmankesh Mehra, et al., "Identification and optimization of *Escherichia coli* GlmU inhibitors: An in silico approach with validation thereto", Eur. J. of Med. Chem., 92:78-90 (Mar. 1, 2015).
Rukmankesh Mehra, et al., "Identification and optimization of *Escherichia coli* GlmU inhibitors: An in silico approach with validation thereo—Supplementary data", Eur. J. of Med. Chem., 92:1-23 (Mar. 1, 2015).
Database accession No. 0530646232, Chem. Abstracts Service: XP002768556 (Apr. 7, 2016), 1 page.
Database accession No. 0483961433, Chem. Abstracts Service: XP002768567 (Apr. 7, 2016), 1 page.
Database accession No. 0481880432, Chem. Abstracts Service: XP002768568 (Apr. 7, 2016), 1 page.
Database accession No. 0443605276 Chem. Abstracts Service: XP002768569 (Apr. 7, 2016), 1 page.
Database accession No. 0416866507, Chem. Abstracts Service: XP002768572 (Apr. 7, 2016), 1 page.
Database accession No. 0301000877, Chem. Abstracts Service: XP002768573 (Apr. 7, 2016), 1 page.
Database accession No. 0291559633, Chem. Abstracts Service: XP002768574 (Oct. 20, 2016), 1 page.

(Continued)

*Primary Examiner* — David K O'Dell
(74) *Attorney, Agent, or Firm* — Harness Dickey & Pierce P.L.C.

(57) ABSTRACT

Disclosed are sulfonamide compounds with GPR17 modulating properties, which are useful for treating or preventing a variety of CNS and other diseases, in particular for preventing and treating myelinating diseases or disorders.

47 Claims, 5 Drawing Sheets

(56) References Cited

OTHER PUBLICATIONS

Database accession No. 0291042769, Chem. Abstracts Service: XP002768575 (Sep. 9, 2015), 1 page.
Database accession No. 0287897075, Chem. Abstracts Service: XP002768576 (Apr. 7, 2016), 1 page.
Database accession No. 0278461840, Chem. Abstracts Service: XP002768577 (Apr. 7, 2016), 1 page.
Database accession No. 0236509894, Chem. Abstracts Service: XP002768579 (Apr. 7, 2016), 1 page.
Database accession No. 0232824640, Chem. Abstracts Service: XP002768580 (Apr. 7, 2016), 1 page.
Database accession No. 0169395356, Chem. Abstracts Service: XP002768581 (Sep. 9, 2015), 1 page.
Database accession No. 0123789761, Chem. Abstracts Service: XP002768582 (May 31, 2016), 1 page.
Database accession No. 0115926768, Chem. Abstracts Service: XP002768583 (Apr. 7, 2016), 1 page.
Database accession No. 0017342963, Chem. Abstracts Service: XP002768584 (Apr. 7, 2016), 1 page.
Database accession No. 0014218796, Chem. Abstracts Service: XP002768585 (Apr. 7, 2016), 1 page.
Database accession No. 0802739691, Chem. Abstracts Service: XP002768586 (Oct. 5, 2016), 1 page.
Database accession No. 0777581533, Chem. Abstracts Service: XP002768587 (Oct. 5, 2016), 1 page.
Database accession No. 1895887759, Chem. Abstracts Service: XP002768588 (Oct. 5, 2016), 1 page.
Database accession No. 1871226897, Chem. Abstracts Service: XP002768589 (Apr. 7, 2016), 1 page.
Database accession No. 1202763292, Chem. Abstracts Service: XP002768590 (Oct. 10, 2016), 1 page.
Meryem Köse, et al., "Development of [$^3$H]2-Carboxy-4,6-dichloro-1H-indole-3-propionic Acid ([$^3$H]PSB-12150): A Useful Tool for Studying GPR17," ACS Medicinal Chern. Letters, 5(4):326-330, Apr. 10, 2014.
M. Pailer, et al., "Regarding Sulphurization of Thionaphthene and Methyl-thionaphthenes", Friedl. Fortsehr. Teerfarbenf&br 92(3):677-683 (Jan. 1, 1929) (with English translation of title and summary).
Anonymous: "Substance Record for SID 74606340; N-(4-fluorophenyl)benzothiopene-3-sulfonamide", PubChem pp. 1-5, https://pubchem.ncbi.nlm.nih.gov/substance/74606340#section=Top (Jun. 11, 2009).

* cited by examiner

Figure 1: Effect of Example compounds on myelin expression
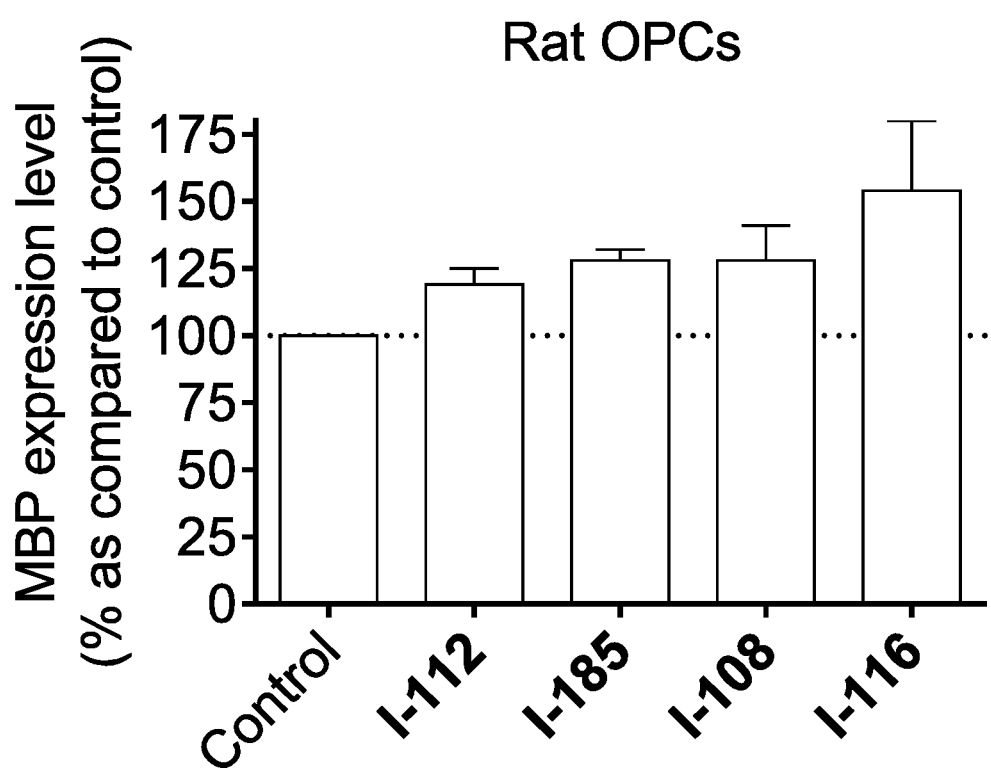

Figure 2: Effect of compound I-116 on myelin sheath length
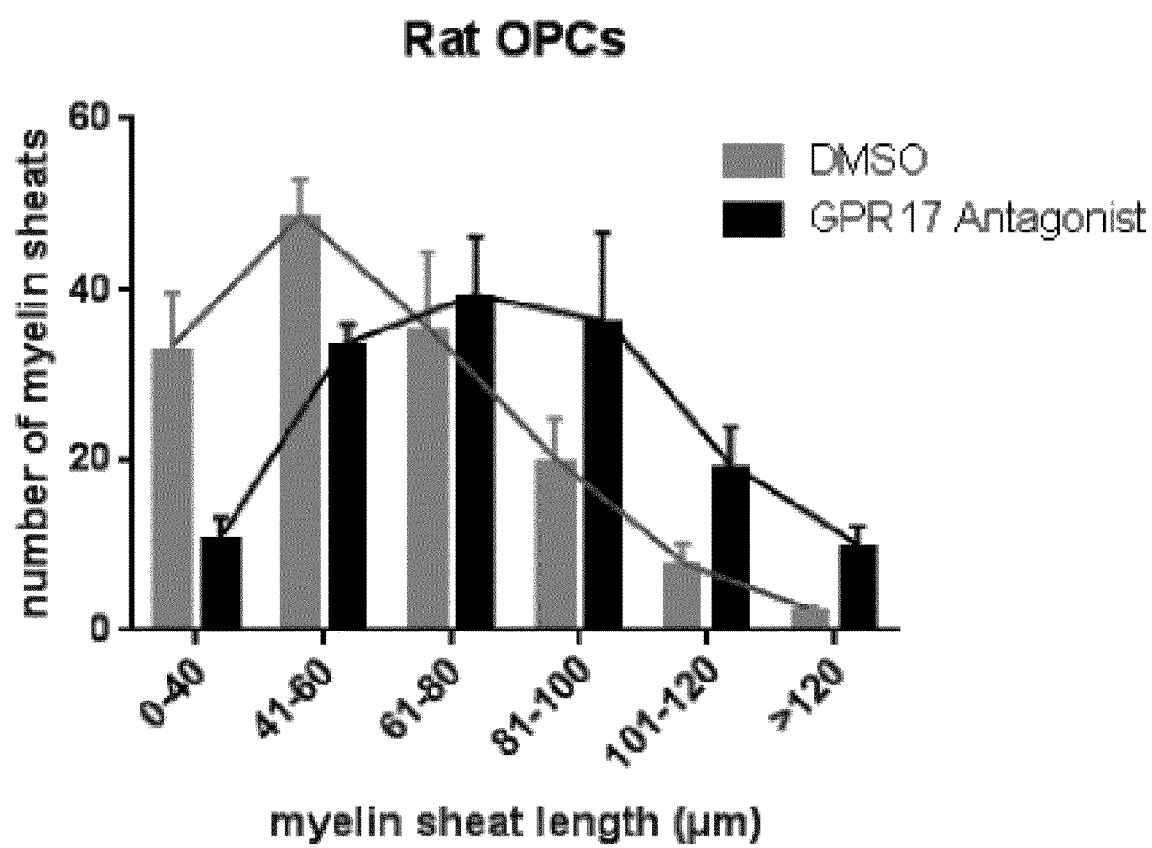

Figure 3: Plasma and brain exposure levels of Example compound I-1
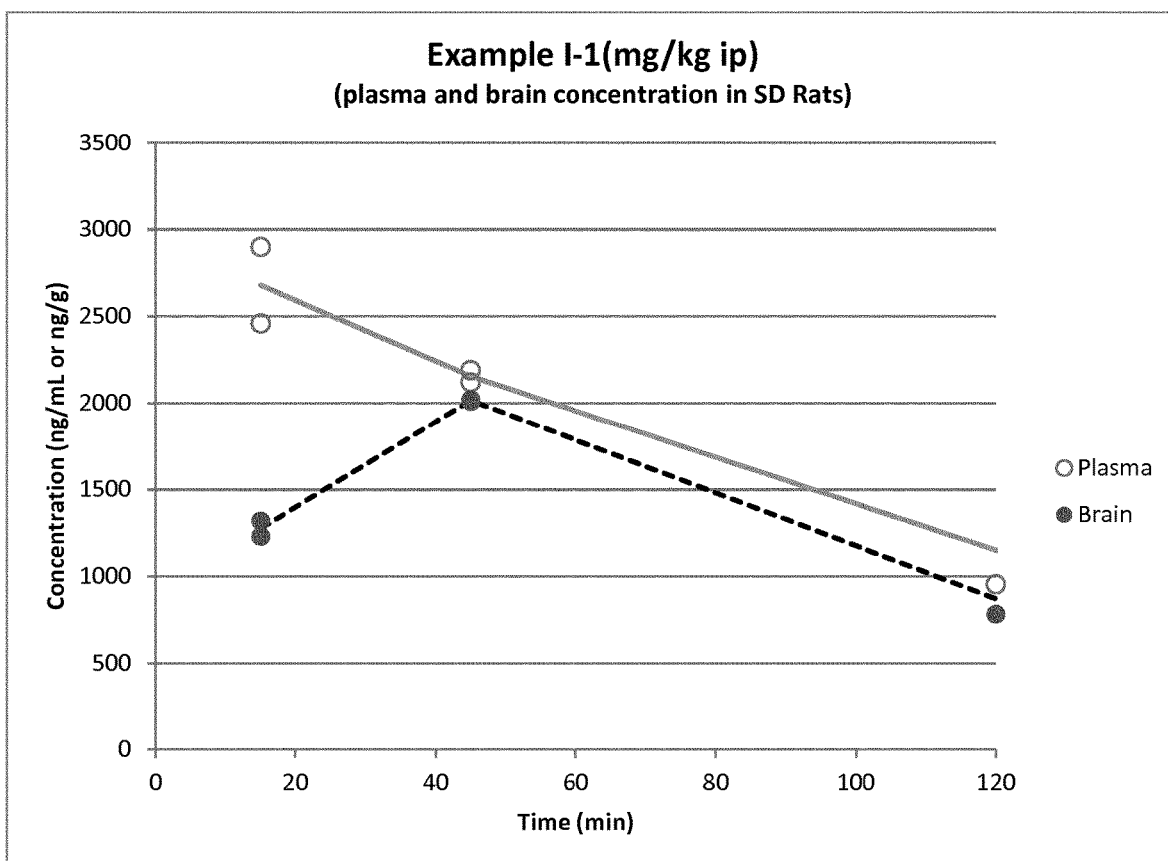

Figure 4: Immunhistochemical staining of PLP in two regions of the mice brain

R 265 (Region 1)

R 285 (Region 2)

Figure 5: Effect of compound I-228 on the expression of PLP after cuprizone treatment
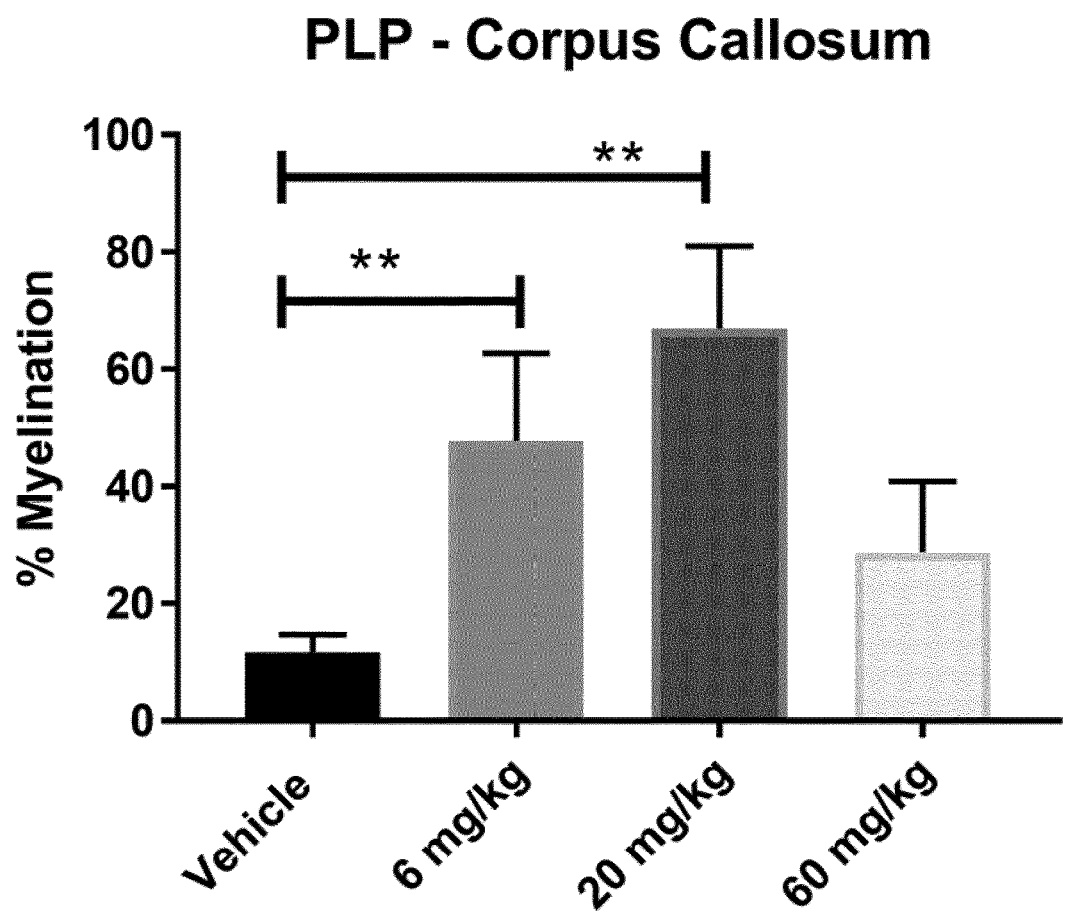

AZA (INDOLE)-, BENZOTHIOPHENE-, AND BENZOFURAN-3-SULFONAMIDES

CROSS REFERENCE TO RELATED APPLICATIONS

This patent application is a U.S. national stage filing under 35 U.S.C. § 371 of International Application No. PCT/EP2017/084602 filed on of 27 Dec. 2017, which claims priority to European Patent Application No. 16207137.7 filed on 28 Dec. 2016. The entire disclosures of each of the above recited applications are incorporated herein by reference.

BACKGROUND

G-protein coupled receptors (GPCRs) constitute the largest family of membrane receptors in the cell. They transduce extracellular signals to intracellular effector systems and are involved in a large variety of physiological phenomena, therefore representing the most common targets of pharmaceutical drugs although only a small percentage of GPCRs are targeted by current therapies.

GPCRs respond to a wide range of ligands. Due to the progress in human genome sequencing, for about 25% out of the more than 400 GPCRs (not including the olfactory GPCRs) that have been identified, a defined physiologically relevant ligand is still lacking. These receptors are known as "orphan GPCRs". "Deorphanization" and identification of their in vivo roles is expected to clarify novel regulatory mechanisms and, therefore, to disclose novel drug targets. Whether GPR17 is such an orphan receptor is still a matter of debate. Phylogenetically, GPR17 is closely related to the nucleotide P2Y receptors and the cysteinylleukotriene (CysLT1, CysLT2) receptors, with an amino acid sequence identity of between about 30 and about 35%, respectively.

Multiple-tissue Northern blot and RT-PCR analyses indicate a predominant expression of GPR17 in the central nervous system (CNS) (Ciana et al., 2006, EMBO J 25(19): 4615; Blasius et al., 1998, J Neurochem 70(4): 1357) and additionally in heart and kidney, i.e. organs typically undergoing ischemic damage. Two human GPR17 isoforms have been identified differing only by the length of their N-terminus. The short GPR17 isoform encodes a 339 amino acid-residue protein with typical rhodopsin type-seven transmembrane motifs. The long isoform encodes a receptor with a 28 amino acid longer N-terminus (Blasius et al., 1998). GPR17 is highly conserved among vertebrate species (~90% identity of amino acid sequence to both mouse and rat orthologs), which may constitute an advantageous feature for development of small molecule ligands and animal models in a drug discovery context.

In the original deorphaning report, GPR17 was identified as a dual receptor for uracil nucleotides and cysteinyl-leukotrienes (cysLTs) LTC4 and LTD4, respectively based on $^{35}$SGTPγS binding and cAMP inhibition assays as well as single cell calcium imaging (Ciana et al., 2006, ibid). Evidence for GPR17 functionality was provided in different cellular backgrounds such as 1321N1, COS7, CHO, and HEK293 cells (Ciana et al., 2006, ibid). Subsequently, an independent study confirmed activation of GPR17 by uracil nucleotides but failed to recapitulate activation by CysLTs (Benned-Jensen and Rosenkilde, 2010, Br J Pharmacol, 159(5): 1092). Yet recent independent reports (Maekawa et al., 2009, PNAS 106(28), 11685; Qi et al., 2013, J Pharmacol Ther 347, 1, 38; Hennen et al., 2013, Sci Signal 6, 298) suggested lack of GPR17 responsiveness to both uracil nucleotides and CysLTs across different cellular backgrounds stably expressing GPR17 (1321N1, CHO, HEK293 cells). A novel regulatory role for GPR17 has also been proposed: GPR17—upon coexpression with the CysLT1 receptor—rendered the CysLT1 receptor unresponsive to its endogenous lipid mediators LTC4 and LTD4. Clearly, additional in vitro investigations are required to probe GPR17 pharmacology and function in more depth.

Drugs modulating the GPR17 activity may have neuroprotective, anti-inflammatory and anti-ischemic effects and may thus be useful for the treatment of cerebral, cardiac and renal ischemia, and stroke (WO 2006/045476), and/or for improving the recovery from these events (Bonfanti et al, Cell Death and Disease, 2017, 8, e2871).

GPR17 modulators are also thought to be involved in food uptake, insulin and leptin responses and are thus claimed to have a role in obesity treatment (WO 2011/113032).

Moreover, there is strong evidence that GPR17 is involved in myelination processes and that negative GPR17 modulators (antagonists or inverse agonists) can be valuable drugs for the treatment or alleviation of myelination disorders such as multiple sclerosis or spinal cord injury (Chen et al, Nature neuroscience 2009, 12(11):1398-406; Ceruti et al; Brain: a journal of neurology 2009 132(Pt 8):2206-18; Hennen et al, Sci Signal, 6, 2013, 298; Simon et al J Biol Chem 291, 2016, 705; Fumagalli et al, Neuropharmacology 104, 2016, 82). Activation of GPR17 has been shown to inhibit oligodendrocyte precursor cells (OPCs) maturation thus preventing effective myelination (Simon et al, supra). The identification of potent and selective GPR17 antagonists or inverse agonists would thus be of significant relevance in the treatment of myelination disorders.

Several serious myelination diseases are known to be caused by disturbances in myelination, either by a loss of myelin (usually called demyelination), and/or by a failure of the body to properly form myelin (sometimes called dysmyelination). The myelination diseases may be idiopathic or secondary to certain trigger events like e.g. traumatic brain injury or viral infection. Myelination diseases may primarily affect the central nervous system (CNS) but may also concern the peripheral nervous system. Myelination diseases include, inter alia, multiple sclerosis, neuromyelitis optica (also known as Devic's disease), leucodystrophies, Guillain-Barre syndrome, and many other diseases as described in more detail further below (see also e.g. Love, J Clin Pathol, 59, 2006, 1151, Fumagalli et al, supra). Neurodegenerative diseases such as Alzheimer's Disease, Huntington's Disease, Parkinson's Disease, amyotropic lateral sclerosis (ALS) and multiple system atrophy (MSA) have been also strongly associated with decreased myelination recently (see e.g. Ettle et al, Mol Neurobiol 53, 2016, 3046; Jellinger and Welling, Movement Disorders, 31, 2016; 1767; Kang et al, Nature Neurosci 6, 2013, 571; Bartzokis, Neurochem Res (2007) 32:1655).

Multiple Sclerosis (MS) is a chronic progressive disorder. It is an inflammatory autoimmune disease causing oligodendrocyte damage, demyelination and ultimately axonal loss, thus leading to a broad spectrum of signs and symptoms of a severe neurological disease, like e.g. fatigue, dizziness, mobility and walking issues, speech and swallowing difficulties, pain and others. MS takes several forms, with new symptoms either occurring in isolated attacks (relapsing forms) or building up over time (progressive forms). While certain symptoms may disappear completely between isolated attacks, severe neurological problems often remain, especially as the disease advances to a more progressive form. According to the Multiple Sclerosis Association of America, approximately 400,000 individuals have been diagnosed with MS in the United States and as many as 2.5 million worldwide, with an estimated 10,000 new cases diagnosed in the United States annually. Multiple sclerosis is two to three times more common in women than in men.

There is no known causal treatment or cure for multiple sclerosis, or many other myelination diseases. Treatments are usually symptomatic and try to improve function after an attack and prevent new attacks, by addressing the inflammatory component of the disease. Such immunomodulatory drugs are usually only modestly effective, in particular if the disease is progressed, but can have side effects and be poorly tolerated. Moreover, most of the available drugs, like ß-interferons, glatiramer acetate, or therapeutic antibodies are only available in injectable form and/or only address the inflammatory component of the disease but not demyelination directly Others drugs, like corticosteroids, show rather unspecific anti-inflammatory and immunosupressive effects thus potentially leading to chronic side effects, such as manifested in Cushing's syndrome, for example.

A strong need therefore exists for a safe and effective drug for the treatment of myelination diseases, like MS, preferably for a drug that is suitable for oral administration. Ideally such a drug would reverse the demyelination process by decreasing demyelination and/or by promoting remyelination of the impacted neurons. A chemical compound which effectively decreases the GPR17 receptor activity could fulfil these requirements.

However, only few chemical compounds are known that effectively modulate GPR17 activity. WO 2005/103291 suggests the endogenous molecules 5 amino levulinic acid (5-ALA) and porphobilinogen (PBG) as activating ligands for GPR17, discloses analgesic effects of a GPR17 agonist and proposes the use of GPR17 agonists for treating neuropathic pain and as tools in GPR17 screening assays. However, the reported affinity of 5-ALA and PBG is quite low and the amounts needed in the assays are significant, namely in the three digit micromolar range for 5-ALA or even in the mM range for PBG, which make both compounds not well suited for use in routine screening assays or even for therapy. Moreover, PBG is a chemically unstable, reactive compound which rapidly decomposes after exposure to air and light, making it impractical to handle on a routine basis. Hence, these compounds do not offer a promising starting point to develop therapeutically effective negative GPR17 modulators.

Montelukast and pranlukast were originally developed as leukotriene receptor antagonists and were recently found to act on the GPR17 receptor as well (Ciana et al, EMBO J. 2006, 25, 4615-4627). However, subsequent results in a functional assay were contradictory for montekulast (Hennen et al, 2013, ibid), while pharmacological inhibition of GPR17 with pranlukast promotes differentiation of primary mouse (Hennen et al., 2013, ibid) and rat (Ou et al., J. Neurosci. 36, 2016, 10560-10573) oligodendrocytes. Pranlukast even phenocopies the effect of GPR17 depression in a lysolecithin model of focal demyelination because both GPR17 knock-out and pranlukast-treated wild-type mice show an earlier onset of remyelination (Ou, ibid). These results strongly support the hypothesis that GPR17 inhibitors offer potential for the treatment of human demyelinating diseases.

However, the affinity of montekulast and pranlukast to GPR17 is only in the high micromolar range (Köse et al, ACS Med. Chem. Lett. 2014, 5, 326-330). Given the high protein binding of both compounds and their poor brain penetration, it is unlikely that they could reach high enough free concentrations to bind to GPR17 receptors in amounts suitable for human therapy. In addition, results obtained in vivo with these compounds are difficult to interpret due to their confounding high affinity for CYSLT1 receptors.

U.S. Pat. No. 8,623,593 discloses certain indole-2-carboxylic acids as GPR17 agonists and their use in screening assays. However, these derivatives are all potent agonists and are not suited to down-regulate GPR17 activity as needed in the treatment of myelination disorders such as MS. Moreover, this class of GPR17 activators does not sufficiently pass the blood-brain barrier due to their easily ionizable carboxyl groups, and were thus no suitable lead compounds to develop negative GPR17 modulators. See also Baqi et al, Med. Chem. Commun., 2014, 5, 86 and Köse et al, 2014, ibid.

WO 2013/167177 suggests certain phenyltriazole and benzodiazepine compounds as GPR17 antagonists. However, the disclosed compounds were selected solely based on in-silico screening results and no biological data at all was provided. The inventors of the present application were unable to confirm the GPR17 antagonist modulating activity of any of purported ligands proposed by the authors of this former patent application so far.

A need therefore exists to identify potent modulators, preferably negative modulators, of GPR17 which are capable of effectively decreasing the GPR17 activity, preferably upon oral administration.

Mehra et al (Eur J Med Chem, 92, 2015, 78-90) disclose a variety of compounds with EColi acetyltransferase inhibiting activity, including four phenyl-substituted pyrrolo[2,3-b]pyridine-3-sulfonamides (compounds 20 [N-(3,4-difluorophenyl 1H-pyrrolo[2,3-b]pyridine-3-sulfonamide], 32 [N-(3,5-dimethoxyphenyl 1H-pyrrolo[2,3-b]pyridine-3-sulfonamide],37 [N-(2,5-difluorophenyl 1H-pyrrolo[2,3-b]pyridine-3-sulfonamide] and 43 [N-(3,5-difluorophenyl 1H-pyrrolo[2,3-b]pyridine-3-sulfonamide] of Table S7). These four azaindole compounds distinguish structurally from the presently disclosed compounds in that the azaindole core in Mehra is not further substituted. Moreover, Mehra et al do not suggest any GPR17 inhibiting property of these compounds and/or any utility of their compounds for treating a myelination disorder. Instead, Mehra et al disclose compounds as potential antibiotics.

FIGURES

FIG. 3 shows the plasma and brain exposure of a compound of the present invention, I-1, after intraperitoneal administration in mice.

Figures 1, 4:
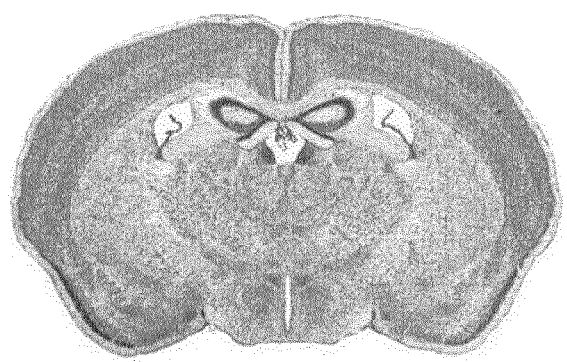
FIG. 1 shows the expression of melin basic protein (MBP) as a marker of oligodendrocyte maturation in a Western Blot assay. After administration to oligodendrocyte progenitor cells (OPCs), the compounds of the present invention, in particular compounds I-112, I-185, I-108 and I-116, stimulated the MBP expression compared to vehicle alone.
FIG. 4 illustrates the distribution of PLP, a myelin marker, in two relevant regions of the mice brain, Region 1 (FIG. 4.1) and Region 2 (FIG. 4.2), after immunohistochemical staining with anti PLP-antibodies. This setup was used to measure the effects of compounds of the present invention in the cuprizone model (results shown in FIG. 5).

FIG. 5 shows the effect of a compound of the present invention (I-228) on the expression of PLP in mice during recovery from cuprizone treatment, as measured by immunohistochemical staining. Following oral administration of I-228 at doses of 6 mg/kg and 20 mg/kg to mice, the myelin-associated protein PLP reappeared significantly quicker in certain mice brain regions than after administration of vehicle only.

DESCRIPTION OF THE INVENTION

The present invention relates to a class of chemical compounds which are negative GPR17 modulators.

These compounds have a general structure according to Formula I:

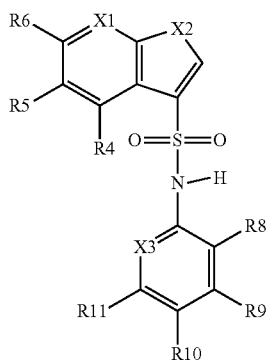

Formula I wherein
X1 is N or C(R7),
X2 is NH, S or O,
X3 is N or C(R12),
R4 is selected from hydrogen, methoxy and halogen including fluoro, and is preferably hydrogen,
R5 is selected from hydrogen, halogen, cyano, $C_{1-6}$ alkyl, $C_{2-3}$ alkenyl, $C_{2-3}$ alkynyl, $C_{1-6}$ alkoxy, $C_{1-3}$ alkylcarbonyl, $C_{1-3}$ alkoxycarbonyl, $C_{1-3}$ alkylsulfinyl, and $C_{1-3}$ alkylsulfonyl, wherein each alkyl or alkoxy may optionally be substituted one or more times selected from halogen, $C_{1-3}$ alkoxy, cyano, azido, hydroxyl, $C_{1-3}$ alkylamino and di($C_{1-3}$ alkyl)amino, and $C_{1-3}$ alkylaminocarbonyl (with preferred optional substitutions of said alkyl and alkoxy groups being halogen and $C_{1-6}$ alkoxy), or R5 forms a ring together with R6 as described herein,
R6 is selected from hydrogen, hydroxy, halogen, cyano, azido, nitro, $C_{1-6}$ alkyl, $C_{2-6}$ alkenyl, $C_{2-6}$ alkynyl, $C_{1-6}$ alkoxy, $C_{3-7}$ cycloalkyl, $C_{3-6}$ cycloalkenyl, $C_{3-7}$ heterocycloalkyl, $C_{3-7}$ heterocycloalkenyl, phenyl, $C_{5-10}$ heteroaryl, $C_{8-10}$ heterocyclyl, —ORx, —SRx, —SORx, $SO_2Rx$, -pentafluorosulfanyl, NRyRzz, —NRyCORx, —NRyCO$_2$Rx, —NRxCONRyRz, —NRySORx, —NRySO$_2$Rx, —CORx, —CO$_2$Rx, —CONRyRz, wherein each alkyl, alkenyl, alkynyl, alkoxy, cycloalkyl, heterocycloalkyl, cycloalkenyl, phenyl, heteroaryl or heterocyclyl group in R6 can be unsubstituted or substituted with one or more residue preferably selected from halogen, hydroxyl, oxo, cyano, azido, nitro, $C_{1-6}$ alkyl, halo($C_{1-6}$)alkyl, $C_{1-6}$ alkoxy($C_{1-3}$)alkyl, $C_{3-7}$ cycloalkyl, $C_{3-7}$ heterocycloalkyl, phenyl, $C_{5-10}$ (preferably $C_{5-6}$) heteroaryl, ORx, —SRx, —SORx, SO$_2$Rx, -pentafluorosulfanyl, NRyRz, —NRyCORx, —NRyCO$_2$Rx, —CORx, —CO$_2$Rx, —CONRyRz, wherein Rx, Ry, Rz and Rzz are independently selected from hydrogen, $C_{1-6}$ alkyl, $C_{3-7}$ cycloalkyl, $C_{3-6}$ cycloalkenyl, $C_{3-7}$ cycloalkyl($C_{1-6}$)alkyl, phenyl, phenyl($C_{1-6}$)alkyl, $C_{3-7}$ heterocycloalkyl, $C_{3-7}$ heterocycloalkyl($C_{1-6}$)alkyl, $C_{5-6}$ heteroaryl or heteroaryl($C_{1-6}$) alkyl, any of which groups can be unsubstituted or substituted with one or more substituents, selected from those described above, and wherein Rzz is preferably different from hydrogen,
or Ry and Rz, or Ry and Rzz together with the amino atom to which they are both attached may form an aromatic or non aromatic, unsubstituted or substituted $C_{5-6}$ heterocycle, wherein any substituent is selected from the substituents described above,
or R6 forms together with R5 or R7 and the carbon atoms to which they are attached a 5 or 6 membered aromatic or non-aromatic ring which may optionally contain one or more heteroatoms selected from S, O, and N, and wherein said ring can be unsubstituted or substituted with one or more substituents,
wherein preferably (i) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl,
wherein each substitution, if present, of a ring formed by R6 and R7, is preferably selected from halogen, hydroxy, cyano, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, $C_{3-7}$ heterocycloalkyl($C_{1-3}$)alkyl and $C_{1-6}$ alkoxy, wherein each alkyl or alkoxy can be unsubstituted or substituted with one or more substituents selected from halogen, hydroxy, and unsubstituted or fluorinated $C_{1-3}$ alkoxy, $C_{3-7}$ cycloalkyl, and $C_{3-7}$ heterocycloalkyl, wherein any substitution of phenyl, pyridyl, cyclopentyl and cyclohexyl are preferably selected from fluoro, chloro, cyano, hydroxy, methyl, fluoromethyl, methoxy and fluoromethoxy,
or (ii) R6 forms together with R5 and the carbon atoms to which R6 and R5 are attached, a 1,3-dioxolane which may be unsubstituted or substituted with one or two substituents selected from fluoro and methyl, or
R7, if present, is selected from hydrogen, halogen, cyano, azido, nitro, amino, $C_{1-6}$ alkyl, $C_{1-6}$ alkoxy, $C_{2-6}$ alkynyl, $C_{2-6}$ alkenyl, $C_{1-6}$ alkylcarbonyl, $C_{1-6}$ alkoxycarbonyl, $C_{1-6}$ alkylsulfonyl, $C_{1-6}$ alkylsulfinyl, $C_{1-6}$ alkylthio, $C_{1-3}$ alkylcarbonylamino, $C_{1-6}$ alkylaminocarbonyl, di($C_{1-3}$)alkylaminocarbonyl, $C_{3-7}$ cycloalkyl, $C_{3-7}$ cycloalkoxy, $C_{3-7}$ heterocycloalkyl, $C_{3-6}$ heterocycloalkoxy, phenyl, phenyloxy, phenyl($C_{1-2}$)alkyl, phenyl($C_{1-2}$)alkoxy, phenylsulfonyl, phenylsulfinyl, $C_{5-6}$ heteroaryl, $C_{5-6}$ heteroaryloxy, $C_{5-6}$ heteroaryl($C_{1-3}$)alkyl, $C_{5-6}$ heteroaryl($C_{1-3}$) alkoxy, $C_{3-6}$cycloalkyl($C_{1-2}$)alkyl, $C_{3-6}$ cycloalkyl($C_{1-3}$)alkoxy, $C_{3-6}$ heterocycloalkyl($C_{1-2}$)alkyl, $C_{3-6}$ heterocycloalkyl($C_{1-2}$) alkoxy, and, wherein each group in R7, in particular each alkyl, alkenyl, alkynyl, alkoxy, cycloalkyl, heterocycloalkyl, phenyl or heteroaryl group, can be unsubstituted or substituted with one or more substituents selected from halogen, hydroxy, cyano, unsubstituted or halogenated $C_{1-6}$ alkyl and unsubstituted or halogenated $C_{1-6}$ alkoxy,
R8 is selected from hydrogen, $C_{1-6}$ alkyl, $C_{2-6}$ alkenyl, $C_{2-6}$ alkynyl, $C_{1-6}$ alkoxy, $C_{1-3}$ alkylsulfinyl, $C_{1-3}$ alkylsulfonyl, $C_{1-3}$ alkylthio, cyano, and halogen, wherein each alkyl or alkoxy can be unsubstituted or substituted with one or more substituents selected from halogen and unsubstituted or fluorinated $C_{1-3}$ alkoxy, or forms a ring system together with R9, as described herein,
R9 is selected from hydrogen, halogen, cyano, azido, $C_{1-6}$ alkyl, $C_{1-6}$ alkoxy, $C_{2-6}$ alkenyl, $C_{2-6}$ alkynyl and halogen, wherein each alkyl or alkoxy can be unsubstituted or substituted with one or more substituents selected from halogen and unsubstituted or fluorinated $C_{1-3}$ alkoxy, or R9 forms together with R8 or R10 and the C atoms to which they are attached a 5 or 6 membered ring which can optionally be further substituted and which may contain one or more ring forming heteroatoms selected from N, S, O, and Se;

wherein the ring formed by R9 together with R8 or R10 and the ring to which they are attached form a bicyclic ring system preferably selected from (a) 2,1,3-benzothiadiazole, (b) 2,1,3-benzoselenadiazole, (c) 2,1,3-benzoxadiazole, (d) 1,3-benzothiazole, (e) 1,3-benzoxazole which may be unsubstituted or may be partially hydrogenated and unsubstituted or substituted with oxo, (f) 1,3-benzodioxole which may be unsubstituted or substituted with one or two substituents selected from fluoro and methyl, (g) benzothiophene, which may be unsubstituted or may be partially hydrogenated and unsubstituted or substituted with one or two substituents selected from oxo, methyl or fluoro, wherein the benzothiophene is preferably partially hydrogenated to 1,3-dihydro-2-benzothiophen which is preferably substituted with two oxos to form 1,1-dioxido-2,3-dihydro-1-benzothiophen, which may be optionally further substituted, (h) benzofuran, which may be unsubstituted or may be partially hydrogenated and unsubstituted or substituted with one or two groups selected from oxo, fluoro and methyl, preferably with one oxo group, wherein the benzofuran is preferably partially hydrogenated to 1,3-dihydro-2-benzofuran which is preferably substituted with oxo to form 3-oxo-1,3 dihydrobenzofuran, which may be optionally further substituted, e.g. with a methyl group, and (i) 2,3-dihydro-1H-isoindol, which is preferably substituted with oxo to give 3-oxo-2,3-dihydro-1H-isoindol, which may be optionally further substituted.

R10 is selected from hydrogen, halogen, $C_{1-6}$ alkyl, $C_{1-6}$alkoxy, $C_{2-6}$ alkenyl, $C_{2-6}$ alkynyl, cyano, cyano($C_{1-6}$)alkyl, cyano($C_{1-6}$)alkyloxy, $C_{1-6}$ alkylcarbonyl, $C_{1-6}$ alkoxycarbonyl, $C_{1-6}$ alkylsulfonyl, $C_{1-6}$ alkylsulfinyl, $C_{1-6}$ alkylthio, $C_{3-6}$cycloalkyl, $C_{3-6}$ cycloalkyloxy, $C_{3-6}$heterocycloalkyl, $C_{3-6}$heterocycloalkyloxy, amino, azido, pentafluorosulfanyl, nitro, $C_{1-5}$ alkylcarbonylamino, $C_{1-5}$ alkylaminocarbonyl, di($C_{1-3}$)alkylaminocarbonyl, $C_{1-3}$ alkylsulfinyl and $C_{1-3}$ alkylsulfonyl, wherein each alkyl, alkenyl, alkynyl or alkoxy can be unsubstituted or substituted with one or more substituents selected from halogen, $C_{1-6}$ alkoxy, halo($C_{1-6}$)alkoxyhydroxy($C_{1-6}$)alkoxy, optionally halogenated $C_{1-6}$ alkylthio, optionally halogenated $C_{1-3}$ alkylcarbonyl, optionally halogenated $C_{1-3}$ alkyloxycarbonyl, optionally halogenated $C_{1-3}$ alkylsulfonyl, optionally halogenated $C_{1-3}$ alkylsulfinyl, $C_{1-3}$ alkylcarbonylamino, $C_{1-3}$ alkylaminocarbonyl, di($C_{1-3}$)alkylaminocarbonyl, hydroxy, cyano, nitro, oxo, $C_{3-6}$cycloalkyl, $C_{3-6}$cycloalkoxy, $C_{3-6}$heterocycloalkyl, $C_{3-6}$heterocycloalkoxy, phenyl, phenyloxy, and $C_{5-6}$heteroaryl, wherein any $C_{3-6}$cycloalkyl, $C_{3-6}$cycloalkoxy, $C_{3-6}$heterocycloalkyl, $C_{3-6}$heterocycloalkoxy, phenyl and heteroaryl may be unsubstituted or substituted with one or more residues selected from halogen, hydroxy, hydroxymethyl, oxo, cyano, nitro, amino, optionally halogenated or hydroxylated $C_{1-3}$alkyl, optionally hydroxylated or halogenated $C_{1-3}$alkoxy, optionally halogenated $C_{1-3}$alkylcarbonyl and optionally halogenated $C_{1-3}$alkoxycarbonyl, any wherein the amino group may be substituted with one or two groups selected from $C_{1-3}$alkyl, $C_{1-3}$alkylsulfonyl, $C_{1-3}$alkylcarbonyl, and $C_{1-3}$alkoxycarbonyl, or R10 forms a ring system together with R9, as described herein, R11 is selected from hydrogen, halogen, cyano, azido, $C_{1-6}$ alkyl, $C_{1-6}$ alkoxy, $C_{1-6}$ alkylcarbonyl, $C_{1-6}$ alkoxycarbonyl, $C_{1-6}$ alkylsulfonyl, and $C_{1-6}$ alkylsulfinyl, $C_{2-6}$ alkenyl, and $C_{2-6}$ alkynyl, wherein each alkyl or alkoxy can be unsubstituted or substituted with one or more substituents selected from halogen and halogenated preferably fluorinated or unsubstituted $C_{1-3}$ alkoxy, R12, if present, is selected from hydrogen, $C_{1-6}$ alkyl, $C_{1-6}$ alkoxy and halogen, wherein each alkyl or alkoxy can be unsubstituted or substituted with one or more substituents selected from halogen and halogenated preferably fluorinated or unsubstituted $C_{1-3}$ alkoxy, and pharmaceutically acceptable salts, solvates, isotopes and co-crystals thereof.

In one embodiment, in the compounds of formula I,

X1 is N or C(R7),

X2 is NH or O,

X3 is N or C(R12),

R4 is selected from hydrogen and fluoro, and is preferably hydrogen,

R5 is selected from hydrogen, halogen, cyano, $C_{1-6}$ alkyl, $C_{1-6}$ alkoxy, $C_{1-3}$ alkylcarbonyl, $C_{1-3}$ alkoxycarbonyl, $C_{1-3}$ alkylsulfinyl, and $C_{1-3}$alkylsulfonyl, wherein each alkyl or alkoxy may optionally be substituted one or more times selected from halogen, $C_{1-3}$ alkoxy, $C_{2-3}$ alkynyl, $C_{2-3}$ alkenyl, cyano, azido, hydroxyl, and optionally $C_{1-3}$ alkylated amino (with preferred optional substitutions of said alkyl and alkoxy groups being halogen and $C_{1-6}$ alkoxy), or R5 forms a ring together with R6 as described herein, R6 is selected from hydrogen, hydroxy, halogen, cyano, azido, $C_{1-6}$ alkyl, $C_{2-6}$ alkenyl, $C_{2-6}$ alkynyl, $C_{1-6}$ alkoxy, $C_{3-7}$ cycloalkyl, $C_{3-6}$ cycloalkenyl, $C_{3-7}$ heterocycloalkyl, $C_{3-7}$ heterocycloalkenyl, phenyl, $C_{5-10}$ heteroaryl, $C_{8-10}$ heterocyclyl, —ORx, —SRx, —SORx, SO$_2$Rx, -pentafluorosulfanyl, NRyRzz, —NRyCORx, —NRyCO$_2$Rx, —NRxCONRyRz, —CORx, —CO$_2$Rx, —CONRyRz, wherein each alkyl, alkenyl, alkynyl, alkoxy, cycloalkyl, heterocycloalkyl, cycloalkenyl, phenyl, heteroaryl or heterocyclyl group in R6 can be unsubstituted or substituted with one or more substituents preferably selected from halogen, hydroxyl, oxo, cyano, azido, nitro, $C_{1-6}$ alkyl, $C_{1-6}$ alkoxy ($C_{1-3}$)alkyl, $C_{3-7}$ cycloalkyl, $C_{3-7}$ heterocycloalkyl, phenyl, $C_{5-10}$ (preferably $C_{5-6}$) heteroaryl, ORx, —SRx, —SORx, SO$_2$Rx, -pentafluorosulfanyl, NRyRz, —NRyCORx, —NRyCO$_2$Rx, —CORx, —CO$_2$Rx, —CONRyRz, wherein Rx, Ry, Rz and Rzz are independently selected from hydrogen, $C_{1-6}$ alkyl, $C_{3-7}$ cycloalkyl, $C_{3-6}$ cycloalkenyl, $C_{3-7}$ cycloalkyl($C_{1-6}$)alkyl, phenyl, phenyl($C_{1-6}$)alkyl, $C_{3-7}$ heterocycloalkyl, $C_{3-7}$ heterocycloalkyl($C_{1-6}$)alkyl, $C_{5-6}$ heteroaryl or heteroaryl($C_{1-6}$) alkyl, any of which groups can be unsubstituted or substituted with one or more substituents, or Ry and Rz, or Ry and Rzz together with the amino atom to which they are both attached may form an aromatic or non aromatic, unsubstituted or substituted $C_{5-6}$ heterocycle, wherein Rzz is preferably different from hydrogen, or R6 forms together with R5 or R7 and the carbon atoms to which they are attached a 5 or 6 membered aromatic or non-aromatic ring which may optionally contain one or more heteroatoms selected from S, O, and N, and wherein said ring can be unsubstituted or substituted with one or more substituents, wherein preferably (i) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl, wherein each substitution, if present, is selected from halogen, $C_{1-3}$ alkyl, $C_{3-7}$ cycloalkyl, $C_{3-7}$ cycloalkyl($C_{1-3}$) alkyl, $C_{3-7}$ heterocycloalkyl($C_{1-3}$) alkyl, $C_{1-3}$ alkoxy, and $C_{1-3}$ alkoxy($C_{1-3}$) alkyl, wherein each alkyl or alkoxy can be unsubstituted or substituted with one or more substituents selected from halogen and $C_{1-3}$ alkoxy, or (ii) R6 forms together with R5 and the carbon atoms to which R6 and R5 are attached, a 1,3-dioxolane which may be unsubstituted or substituted with one or two substituents selected from fluoro and methyl, or R7 is selected from H, halogen, cyano, $C_{1-6}$ alkyl, $C_{1-6}$ alkoxy, $C_{2-6}$ alkynyl, $C_{2-6}$ alkenyl, $C_{1-6}$ alkylcarbonyl, $C_{1-6}$ alkoxycarbonyl, $C_{1-6}$ alkylsulfonyl, $C_{1-6}$ alkylsulfinyl, $C_{3-7}$ cycloalkyl, $C_{3-7}$ heterocycloalkyl, phenyl, $C_{5-6}$ heteroaryl, wherein each alkyl, alkenyl, alkynyl or alkoxy group can be unsubstituted or substituted with one or more substituents selected from halogen, and $C_{1-6}$ alkoxy, R8 is selected from hydrogen, $C_{1-6}$ alkyl, $C_{1-6}$ alkoxy, and halogen, wherein each alkyl or alkoxy can be unsubstituted or substituted with one or more substituents selected from halogen and $C_{1-3}$ alkoxy, or forms a ring system together with R9, as described herein, R9 is selected from hydrogen, halogen, cyano, azido, $C_{1-6}$ alkyl, $C_{1-6}$ alkoxy, $C_{2-6}$ alkenyl, $C_{2-6}$ alkynyl and halogen, wherein each alkyl or alkoxy can be unsubstituted or substituted with one or more substituents selected from halogen and $C_{1-3}$ alkoxy, or R9 forms together with R8 or R10 and the C atoms to which they are attached a 5 or 6 membered ring which can optionally be further substituted and which may contain one or more ring forming heteroatoms selected from N, S, O, and Se;

wherein the ring formed by R9 together with R8 or R10 and the ring to which they are attached are preferably selected from a bicyclic ring system selected from (a) 2,1,3-benzothiadiazole, (b) 2,1,3-benzoselenadiazole, (c) 2,1,3-benzoxadiazole, (d) 1,3-benzothiazole, (e) 1,3-benzoxazole which may be unsubstituted or may be partially hydrogenated and unsubstituted or substituted with oxo, (f) 1,3-benzodioxole which may be unsubstituted or substituted with one or two substituents selected from fluoro and methyl, (g) benzothiophene, which may be unsubstituted or may be partially hydrogenated and unsubstituted or substituted with one or two substituents selected from oxo, methyl or fluoro, or (h) benzofuran, which may be unsubstituted or may be partially hydrogenated and unsubstituted or substituted with one or two groups selected from oxo, fluoro and methyl, preferably with one oxo group, R10 is selected from hydrogen, halogen, $C_{1-6}$ alkyl, $C_{1-6}$alkoxy, $C_{2-6}$ alkenyl, $C_{2-6}$ alkynyl, cyano, cyano($C_{1-6}$) alkyl, $C_{1-6}$ alkylcarbonyl, $C_{1-6}$ alkoxycarbonyl, $C_{1-6}$ alkylsulfonyl, $C_{1-6}$ alkylsulfinyl, azido, pentafluorosulfanyl, and nitro, wherein each alkyl, alkenyl, alkynyl or alkoxy can be unsubstituted or substituted with one or more substituents selected from halogen and $C_{1-6}$ alkoxy, or R10 forms a ring system together with R9, as described herein, R11 is selected from hydrogen, halogen, cyano, azido, $C_{1-6}$ alkyl, $C_{1-6}$ alkoxy, $C_{1-6}$ alkylcarbonyl, $C_{1-6}$ alkoxycarbonyl, $C_{1-6}$ alkylsulfonyl, and $C_{1-6}$ alkylsulfinyl, $C_{2-6}$ alkenyl, and $C_{2-6}$ alkynyl, wherein each alkyl or alkoxy can be unsubstituted or substituted with one or more substituents selected from halogen and $C_{1-3}$ alkoxy, R12 is selected from hydrogen, $C_{1-6}$ alkyl, $C_{1-6}$ alkoxy and halogen, wherein each alkyl or alkoxy can be unsubstituted or substituted with one or more substituents selected from halogen and $C_{1-3}$ alkoxy, and pharmaceutically acceptable salts, solvates, isotopes and co-crystals thereof.

In general, in the compounds of the present invention, where R8 and R9 or R9 and R10 together form a bicyclic ring system such as 2,1,3-benzothiadiazole, 2,1,3-benzoselenadiazole, 2,1,3-benzoxadiazole, dihydro(1,3)-benzoxazole, 1,3-benzothiazole, dihydrobenzothiophene, dihydrobenzofuran, dihydroisoindole, or 1,3-benzodioxole, and the like, as described herein, all phenyl moieties of these bicyclic groups can generally be substituted or unsubstituted as determined by the respective definition of the substituents R8, R10, R11 and R12 herein, whereas the annulated moieties of dihydrobenzothiophene, dihydrobenzofuran, dihydrobenzoxazole, or benzodioxole as formed by R8 and R9, or R9 and R10, respectively, may be optionally substituted as expressly defined herein. By way of non-limiting example, when a 1,3-dihydro-2-benzofuran formed by R8 and R9 or R9 and R10 and the ring to which they are attached, is said to be optionally substituted with one or two groups selected from oxo, fluoro and methyl, then this particular oxo, fluoro or methyl substitution is a substitution of the ring formed by R8 and R9 or R9 and R10, as the case may be, while the phenyl ring to which R8 and R9 or R9 and R10 are attached may be independently further substituted as defined by the residues R8, R10, R11 and R12 herein. Likewise, if, for example, a benzodioxole group would be defined to be unsubstituted, this would refer to the ring formed by R8 and R9 or R9 and R10, whereas the phenyl ring to which they are attached can be substituted in accordance with the definitions of R8, R10, R11 and R12 herein.

In one preferred embodiment, in the compounds of Formula I, if R6 is hydrogen, and X1 is N, then R5 is different from hydrogen; in one preferred embodiment R5 is iodo.

In one embodiment, R5, R6 and R7, if present, are not all hydrogen at the same time In one embodiment, R4, R5, R6 and R7, if present, are not all hydrogen at the same time In one embodiment, R5, R6, R7 (if R7 is present), R8, R9, R10, and R11 are not all hydrogen at the same time.

In one preferred embodiment of the present invention, in a compound of Formula I, either
(a) X1 is CR7 and X2 is NH, S or O, or
(b) X1 is N and X2 is NH, In one embodiment of the present invention, in a compound of Formula I, X2 is NH or O.

In this embodiment, X1 is preferably CR7. In one embodiment of the present invention, in a compound of Formula I, X2 is S. In this embodiment, X1 is preferably CR7

In one embodiment of the present invention, in a compound of Formula I, X2 is NH.

In one embodiment of the present invention, in a compound of Formula I, X2 is O. In this embodiment, X1 is preferably CR7

In one preferred embodiment of the present invention, in a compound of Formula I, if X1 is N, then X2 is also N. In this embodiment, preferably at least one of R4, R5 and R6 is different from hydrogen.

In a preferred embodiment, in the compounds of the present invention, at least one of R8, R9, R10 and R11 is different from hydrogen. In another preferred embodiment, at least one of R8, R9, R10 and R11 is different from hydrogen and unsubstituted alkyl.

In one aspect, the items of the present invention do not include the compounds N-3,4-difluorophenyl 1H-pyrrolo[2,3-b]pyridine-3-sulfonamide, N-(3,5-dimethoxyphenyl 1H-pyrrolo[2,3-b]pyridine-3-sulfonamide, N-(2,5-difluorophenyl 1H-pyrrolo[2,3-b]pyridine-3-sulfonamide, and N-(3,5-difluorophenyl 1H-pyrrolo[2,3-b]pyridine-3-sulfonamide per se, and for use as medicines or as active ingredient in a pharmaceutical composition in general. In one aspect, the invention includes these compounds for use in the prevention and/or treatment of a myelination disorder as further defined herein, in particular in the prevention and/or treatment of multiple sclerosis and/or a method of treating or preventing a GPR17 related disorder, in particular a myelination disorder such as, inter alia, multiple sclerosis.

In one particular aspect, the compounds of the present invention do not include [N-(4-methylphenyl)-1H-pyrrolo[2,3-b]pyridine-3-sulfonamide], [N-[4-methoxy-3-(2-methoxyethoxy)phenyl]-1H-pyrrolo[2,3-b]pyridine-3-sulfonamide], [N-(4-methoxyphenyl)-1H-pyrrolo[2,3-b]pyridine-3-sulfonamide], N-(4-fluoro-2-methylphenyl 1H-pyrrolo[2,3-b]pyridine-3-sulfonamide], [N-(2-chloro-4-fluorophenyl-1H-pyrrolo[2,3-b]pyridine-3-sulfonamide], [N-(6-bromo-2-pyridinyl) 1H-pyrrolo[2,3-b]pyridine-3-sulfonamide], [N-(5-chloro-2-pyridinyl)1H-pyrrolo[2,3-b]pyridine-3-sulfonamide], [N-(2,4-dichlorophenyl)-1H-pyrrolo[2,3-b]pyridine-3-sulfonamide], [N-(3-ethylphenyl)-1H-pyrrolo[2,3-b]pyridine-3-sulfonamide], N-(2,5-dimethylphenyl)-1H-pyrrolo[2,3-b]pyridine-3-sulfonamide], [N-[4-(ethylsulf- onyl]phenyl]-1H-pyrrolo[2,3-b]pyridine-3-sulfonamide], [N-(4-fluorophenyl)-1H-pyrrolo[2,3-b]pyridine-3-sulfonamide], 1 [N-(3-chloro-4-methoxyphenyl)-1H-pyrrolo[2,3-b]pyridine-3-sulfonamide], [N-(2-ethyl-6-methylphenyl)1H-pyrrolo[2,3-b]pyridine-3-sulfonamide], [N-(2,4-difluorophenyl)1H-pyrrolo[2,3-b]pyridine-3-sulfonamide], [N-[2-(trifluoromethoxy)phenyl]-1H-pyrrolo[2,3-b]pyridine-3-sulfonamide], [6-amino-N-(3-bromophenyl)-1H-Indole-3-sulfonamide], [6-amino-N-(2-fluorophenyl)-1H-Indole-3-sulfonamide], [6-amino-N-(3-bromo-2-pyridinyl)-1H-Indole-3-sulfonamide], [N-(4-chloro-2-methylphenyl)-1H-pyrrolo[2,3-b]pyridine-3-sulfonamide], and [N-(4-propylphenyl)-1H-pyrrolo[2,3-b]pyridine-3-sulfonamide per se, while in another aspect, the present invention encompasses these specific compounds for use (a) in therapy and/or diagnosis, (b) in treating or preventing a myelination disorder and/or any other disease or condition associated with a GPR17, such as a GPR17 dysfunction (c) as active ingredient in a pharmaceutical composition along with optional pharmaceutical carriers, and/or (d) in a method of treating or preventing a disorder associated with GPR17, such as a GPR17 dysfunction, in particular a myelination disorder such as, inter alia, multiple sclerosis.

In a further embodiment, in the compound of Formula I, R6 is selected from hydrogen, fluoro, chloro, bromo, iodo, cyano, azido, nitro, unsubstituted or substituted $C_{1-3}$ alkyl, preferably methyl, ethyl, isopropyl, mono-, di-, or trifluoromethyl, unsubstituted or substituted $C_{2-3}$ alkenyl, unsubstituted or substituted $C_{2-3}$ alkynyl, unsubstituted or substituted $C_{1-3}$ alkylcarbonyl, unsubstituted or substituted C-alkoxycarbonyl, unsubstituted or substituted $C_{1-3}$ alkylsulfinyl preferably methylsulfinyl which may by further substituted with one to three fluoros, unsubstituted or substituted $C_{1-3}$ alkylsulfonyl, preferably methylsulfonyl which may by further substituted with one to three fluoros, unsubstituted or substituted benzylsulfonyl, unsubstituted or substituted benzylsulfinyl, unsubstituted or substituted $C_{3-7}$ cycloalkyl preferably cyclopropyl, unsubstituted or substituted $C_{3-7}$ cycloalkyl($C_{1-3}$)alkyl preferably cyclopropylmethyl, unsubstituted or substituted $C_{3-7}$ cycloalkyl($C_{1-3}$)alkyloxy preferably cyclopropylmethoxy, unsubstituted or substituted $C_{3-7}$ heterocycloalkyl preferably tetrahydrofuranyl, unsubstituted or substituted $C_{3-7}$ heterocycloalkyl($C_{1-3}$)alkyl, unsubstituted or substituted $C_{3-7}$ heterocycloalkyl($C_{1-3}$)alkyloxy preferably tetrahydrofuranylmethoxy, unsubstituted or substituted $C_{1-3}$ alkoxy preferably methoxy or ethoxy, each of which may be optionally substituted with one or more halogens preferably with fluoros, unsubstituted or substituted $C_{3-6}$ cycloalkoxy, unsubstituted or substituted $C_{3-6}$ heterocycloalkoxy, unsubstituted or substituted $C_{1-3}$alkoxy($C_{1-3}$)alkoxy, preferably methoxyethoxy, unsubstituted or substituted $C_{1-3}$alkoxy($C_{1-3}$)alkyl, unsubstituted or substituted ($C_{3-6}$)cycloalkyl($C_{1-3}$)alkoxy preferably cyclopropylmethoxy, unsubstituted or substituted ($C_{3-6}$)heterocycloalkyl($C_{1-3}$)alkoxy preferably tetrahydrofuranylmethoxy, unsubstituted or substituted phenyl, unsubstituted or substituted phenyloxy, unsubstituted or substituted thienyl, unsubstituted or substituted pyridyl, preferably unsubstituted pyridyl, unsubstituted or substituted oxazole, unsubstituted or substituted thiazole, unsubstituted or substituted isoxazole, unsubstituted or substituted phenyl($C_{1-3}$)alkoxy preferably benzyloxy, wherein each optional substitution in R6 is preferably selected from fluoro, chloro, bromo, unsubstituted or fluorinated methyl, unsubstituted or fluorinated methoxy, hydroxy, and cyano, or
(i) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl,
wherein each substitution, if present, is selected from halogen, hydroxy, $C_{1-3}$ alkyl, $C_{3-7}$ cycloalkyl, $C_{3-7}$ cycloalkyl($C_{1-3}$) alkyl, $C_{3-7}$ heterocycloalkyl($C_{1-3}$) alkyl, $C_{1-3}$ alkoxy, and $C_{1-3}$ alkoxy($C_{1-3}$)alkyl, wherein each alkyl or alkoxy can be unsubstituted or substituted with one or more substituents selected from halogen and $C_{1-3}$ alkoxy, or
(ii) R6 forms together with R5 and the carbon atoms to which R6 and R5 are attached, a 1,3-dioxolane which may be unsubstituted or substituted with one or two substituents selected from fluoro and methyl,
wherein, preferably, if R6 is hydrogen, and X1 is N, then R5 is preferably different from hydrogen and is more preferably iodo.

In a further embodiment, in the compound of Formula I, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, unsubstituted or substituted $C_{2-3}$ alkenyl, unsubstituted or substituted $C_{2-3}$ alkynyl, unsubstituted or substituted $C_{1-3}$ alkylcarbonyl, unsubstituted or substituted $C_{1-3}$ alkoxycarbonyl, unsubstituted or substituted $C_{1-3}$ alkylsulfinyl preferably methylsulfinyl, unsubstituted or substituted $C_{1-3}$ alkylsulfonyl, preferably methylsulfonyl, unsubstituted or substituted $C_{3-7}$ cycloalkyl preferably cyclopropyl, unsubstituted or substituted $C_{3-7}$ cycloalkyl($C_{1-3}$)alkyl preferably cyclopropylmethyl, unsubstituted or substituted $C_{3-7}$ heterocycloalkyl preferably tetrahydrofuranyl, unsubstituted or substituted $C_{3-7}$ heterocycloalkyl($C_{1-3}$)alkyl, unsubstituted or substituted $C_{1-3}$ alkoxy preferably methoxy, unsubstituted or substituted $C_{3-6}$ cycloalkoxy, unsubstituted or substituted $C_{3-6}$ heterocycloalkoxy, unsubstituted or substituted $C_{1-3}$alkoxy($C_{1-3}$)alkoxy, preferably methoxyethoxy, unsubstituted or substituted ($C_{3-6}$)cycloalkyl($C_{1-3}$)alkoxy preferably cyclopropylmethoxy, unsubstituted or substituted ($C_{3-6}$)heterocycloalkyl($C_{1-3}$)alkoxy preferably tetrahydrofuranylmethoxy, unsubstituted or substituted phenyl, unsubstituted or substituted phenyloxy, unsubstituted or substituted thienyl, unsubstituted or substituted pyridyl, preferably unsubstituted pyridyl, unsubstituted or substituted oxazole, unsubstituted or substituted thiazole, unsubstituted or substituted isoxazole, unsubstituted or substituted phenyl($C_{1-3}$) alkoxy preferably benzyloxy, wherein each optional substitution in R6 is preferably selected from fluoro, chloro, bromo, methyl, methoxy and cyano,
or
(iii) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl,
wherein each substitution, if present, is selected from halogen, $C_{1-3}$ alkyl, $C_{3-7}$ cycloalkyl, $C_{3-7}$ cycloalkyl($C_{1-3}$) alkyl, $C_{3-7}$ heterocycloalkyl($C_{1-3}$)alkyl, $C_{1-3}$ alkoxy, and $C_{1-3}$ alkoxy($C_{1-3}$)alkyl, wherein each alkyl or alkoxy can be unsubstituted or substituted with one or more substituents selected from halogen and $C_{1-3}$ alkoxy,
or
(iv) R6 forms together with R5 and the carbon atoms to which R6 and R5 are attached, a 1,3-dioxolane which may be unsubstituted or substituted with one or two substituents selected from fluoro and methyl,
wherein, preferably, if R6 is hydrogen, and X1 is N, then R5 is preferably different from hydrogen and is more preferably iodo.

In each occurrence, where the compounds of the present invention contain a R6 and a R7 group, which, together with the ring forming atoms of the bicyclic ring system to which they are attached, form another cycle selected from phenyl, pyridyl, cyclopentyl and cyclohexyl, this cycle together with the bicyclic moiety to which it is annulated forms a tricyclic moiety which is preferably selected from 1H-benzo[g]indol-3-yl, 1H-pyrrolo[3,2-h]quinolin-3-yl, 1,6,7,8-tetrahydrocyclopenta[g]indol-3yl, and 6,7,8,9-tetrahydro-1H-benzo[g] indol-3-yl. In one embodiment, any substitution of the 1H-pyrrolo[3,2-h]quinolin-3-yl moiety is preferably in 8 position such as to result in, for example, in 8-(fluoromethyl)-1H-pyrrolo[3,2-h]quinoline.

In one preferred embodiment, in the compounds of Formula I,
X1 is N or C(R7),
X2 is NH, S or O, preferably NH,
X3 is N or C(R12),
R4 is selected from hydrogen, methoxy and halogen and is preferably hydrogen or fluoro, most preferably hydrogen,
R5 is selected from hydrogen, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfinyl, and $C_{1-3}$ akylsulfonyl, wherein each alkyl or alkoxy may optionally be substituted one or more times with a substituent selected from halogen, $C_{1-3}$ alkoxy, cyano, azido, $C_{1-3}$alkylamino and di($C_{1-3}$alkyl)amino, preferably with methoxy or halogen, or R5 forms a ring together with R6 as described below,
R6 is selected from hydrogen, fluoro, chloro, bromo, iodo, cyano, azido, nitro, unsubstituted or substituted $C_{1-3}$ alkyl, preferably methyl, ethyl, isopropyl, or mono-, di- or trifluoromethyl, unsubstituted or substituted $C_{1-3}$ alkoxy preferably methoxy, ethoxy, mono-, di- or trifluoromethoxy, and mono-, di- or trifluoroethoxy, unsubstituted or substituted $C_{2-3}$ alkenyl, unsubstituted or substituted $C_{2-3}$ alkynyl, unsubstituted or substituted $C_{1-3}$ alkylcarbonyl, unsubstituted or substituted $C_{1-3}$ alkoxycarbonyl, unsubstituted or substituted $C_{1-3}$ alkylsulfinyl preferably methylsulfinyl, unsubstituted or substituted $C_{1-3}$ alkylsulfonyl, preferably methylsulfonyl, unsubstituted or substituted benzylsulfonyl, unsubstituted or substituted benzylsulfinyl, unsubstituted or substituted $C_{3-7}$ cycloalkyl preferably cyclopropyl, unsubstituted or substituted $C_{3-7}$ cycloalkyl($C_{1-3}$)alkyl preferably cyclopropylmethyl, unsubstituted or substituted $C_{3-7}$ heterocycloalkyl preferably tetrahydrofuranyl and oxetanyl, unsubstituted or substituted $C_{3-7}$ heterocycloalkyl($C_{1-3}$)alkyl, unsubstituted or substituted $C_{3-6}$ cycloalkoxy, unsubstituted or substituted $C_{3-6}$ heterocycloalkoxy, unsubstituted or substituted $C_{1-5}$alkoxy($C_{1-5}$)alkyl, unsubstituted or substituted $C_{1-3}$alkoxy($C_{1-3}$)alkoxy, preferably methoxyethoxy, unsubstituted or substituted ($C_{3-6}$)cycloalkyl($C_{1-3}$)alkoxy preferably cyclopropylmethoxy, unsubstituted or substituted ($C_{3-6}$)heterocycloalkyl($C_{1-3}$)alkoxy preferably tetrahydrofuranylmethoxy, unsubstituted or substituted phenyl, unsubstituted or substituted phenyloxy, unsubstituted or substituted thienyl, unsubstituted or substituted pyridyl, preferably unsubstituted pyridyl, unsubstituted or substituted oxazole, unsubstituted or substituted thiazole, unsubstituted or substituted isoxazole, unsubstituted or substituted phenyl($C_{1-3}$) alkoxy preferably benzyloxy, wherein each optional substitution in R6 is preferably selected from one or more of the group consisting of fluoro, chloro, bromo, unsubstituted or fluorinated methyl, unsubstituted or fluorinated methoxy, hydroxy, and cyano,
or
(i) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl,
wherein each substitution, if present, is selected from halogen, hydroxy, cyano, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, $C_{3-7}$ heterocycloalkyl($C_{1-3}$)alkyl, $C_{1-6}$ alkoxy, and $C_{1-6}$ alkoxy($C_{1-3}$)alkyl
wherein each alkyl or alkoxy can be unsubstituted or substituted with one or more substituents selected from halogen and $C_{1-3}$ alkoxy,
or
(ii) R6 forms together with R5 and the carbon atoms to which R6 and R5 are attached, a 1,3-dioxolane which may be unsubstituted or substituted with one or two substituents selected from fluoro and methyl,
R7 is selected from H, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfonyl, $C_{1-3}$ alkylsulfinyl, $C_{5-6}$ heteroaryl preferably isoxazol, and $C_{5-6}$ heteroaryl($C_{1-3}$) alkoxy preferably pyridylmethoxy, wherein each alkyl or alkoxy moiety can be substituted with one or more substituents, preferably with halogen, halo($C_{1-6}$)alkoxy, or $C_{1-3}$ alkoxy, and wherein each heteroaryl can be substituted with one or more substituents, preferably with halogen, methyl, hydroxy, or methoxy, or R7 forms a ring together with R6 as described herein,
R8 is selected from hydrogen, $C_{1-3}$ alkyl, $C_{1-3}$ alkoxy, cyano, and halogen, wherein each alkyl or alkoxy can be unsubstituted or substituted with one or more substituents selected from halogen, cyano and methoxy, or R8 forms a ring system together with R9, as described herein,
R9 is selected from hydrogen, $C_{1-3}$ alkyl, $C_{1-3}$ alkoxy, fluoro, chloro, bromo and iodo, wherein each alkyl or alkoxy can be unsubstituted or substituted with one or more substituents selected from halogen and methoxy,
or R9 forms together with R8 or R10 and the ring to which they are attached a bicyclic ring system selected from 2,1,3-benzothiadiazole, 2,1,3-benzoselenadiazole, 2,1,3-benzoxadiazole, 1,3-benzothiazole, 1,3-benzoxazole which may be unsubstituted or may be partially hydrogenated and substituted with oxo to form 2-oxo-2,3-dihydro-1,3-benzoxazol-, 1,3-benzodioxole which may be unsubstituted or substituted with one or two substituents selected from fluoro and methyl to preferably form 2,2-difluoro-1,3-benzodioxol, 2,3-dihydrobenzothiophene, which may be unsubstituted or substituted with one or two oxo groups to preferably form 1,1-dioxido-2,3-dihydro-1-benzothiophen, 1,3-dihydro-2-benzofuran, which may be unsubstituted or substituted with one or two groups selected from oxo, fluoro and methyl, preferably with at least one oxo group to preferably form 3-oxo-1,3-dihydro-2-benzofuran or 1-methyl-3-oxo-1,3-dihydro-2-benzofuran, and dihydroisoindol which may be unsubstituted or substituted with one or more substituents selected from oxo, fluoro and methyl and which preferably is 3-oxo-2,3-dihydro-1H-isoindol, R10 is selected from hydrogen, fluoro, chloro, bromo, iodo, $C_{1-5}$ alkyl preferably $C_{1-3}$ alkyl, $C_{1-5}$ alkoxy preferably $C_{1-3}$ alkoxy, $C_{2-4}$ alkenyl, $C_{2-4}$ alkynyl, $C_{3-4}$ cycloalkyl, $C_{3-4}$ heterocycloalkyl, cyano, cyanomethyl, cyanomethoxy, $C_{1-3}$ alkylcarbonyl, $C_{1-3}$ alkoxycarbonyl, azido, pentafluorosulfanyl, and nitro, wherein each alkyl, alkenyl, alkynyl or alkoxy can be unsubstituted or substituted with one or more substituents selected from halogen, unsubstituted or fluorinated $C_{1-3}$ alkoxy, unsubstituted or fluorinated $C_{1-3}$ alkoxycarbonyl, unsubstituted or fluorinated $C_{1-3}$ alkylcarbonyl, cyano, hydroxy, cyclopropyl and pyridyl, wherein the pyridyl may be optionally substituted with halogen, unsubstituted or fluorinated methyl and/or unsubstituted or fluorinated methoxy, and wherein any cycloalkyl or heterocycloalkyl can be unsubstituted or substituted with a group selected from halogen, cyano, hydroxy($C_{1-2}$)alkyl, $C_{1-2}$alkoxy and $C_{1-2}$alkoxycarbonyl, or R10 forms a ring system together with R9, as described herein, R11 is selected from hydrogen, $C_{1-3}$ alkyl, $C_{1-3}$ alkoxy, fluoro, chloro, bromo, iodo, cyano, $C_{1-3}$ alkylcarbonyl, $C_{1-3}$ alkoxycarbonyl, wherein each alkyl and alkoxy can be unsubstituted or substituted with one or more substituents selected from fluoro, chloro, bromo, iodo and $C_{1-3}$ alkoxy, R12, if present, is selected from hydrogen, $C_{1-3}$ alkyl, $C_{1-3}$ alkoxy, fluoro, chloro, bromo, and iodo, wherein each alkyl and alkoxy can be unsubstituted or substituted with one or more substituents selected from fluoro, chloro, bromo, iodo and $C_{1-3}$ alkoxy, wherein in one preferred embodiment if R6 is hydrogen, and X1 is N, then R5 is different from hydrogen and is particularly preferably iodo, wherein, in a preferred embodiment, at least one of R8, R9, R10 and R11 is different from hydrogen, and more preferably at least one of R8, R9, R10 and R11 is also different from unsubstituted alkyl, and wherein in another preferred embodiment, at least one of R5, R6 and R7, if present, is different from hydrogen, and pharmaceutically acceptable salts, solvates, isotopes and co-crystals thereof.

In one preferred embodiment, in the compounds of Formula I,

X1 is N or C(R7),
X2 is NH or O, preferably NH,
X3 is N or C(R12),
R4 is hydrogen or fluoro, preferably hydrogen,
R5 is selected from hydrogen, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfinyl, and $C_{1-3}$ akylsulfonyl, wherein each alkyl or alkoxy may optionally be substituted one or more times with a substituent selected from halogen, $C_{1-3}$ alkoxy, cyano, azido, and an optionally alkylated amino group, preferably with methoxy or halogen, or R5 forms a ring together with R6 as described below, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, unsubstituted or substituted $C_{1-3}$ alkoxy preferably methoxy, unsubstituted or substituted $C_{2-3}$ alkenyl, unsubstituted or substituted $C_{2-3}$ alkynyl, unsubstituted or substituted $C_{1-3}$ alkylcarbonyl, unsubstituted or substituted $C_{1-3}$ alkoxycarbonyl, unsubstituted or substituted $C_{1-3}$ alkylsulfinyl preferably methylsulfinyl, unsubstituted or substituted $C_{1-3}$ alkylsulfonyl, preferably methylsulfonyl, unsubstituted or substituted $C_{3-7}$ cycloalkyl preferably cyclopropyl, unsubstituted or substituted $C_{3-7}$ cycloalkyl($C_{1-3}$)alkyl preferably cyclopropylmethyl, unsubstituted or substituted $C_{3-7}$ heterocycloalkyl preferably tetrahydrofuranyl, unsubstituted or substituted $C_{3-7}$ heterocycloalkyl($C_{1-3}$)alkyl, unsubstituted or substituted $C_{3-6}$ cycloalkoxy, unsubstituted or substituted $C_{3-6}$ heterocycloalkoxy, unsubstituted or substituted $C_{1-3}$alkoxy($C_{1-3}$)alkoxy, preferably methoxyethoxy, unsubstituted or substituted ($C_{3-6}$)cycloalkyl($C_{1-3}$)alkoxy preferably cyclopropylmethoxy, unsubstituted or substituted ($C_{3-6}$)heterocycloalkyl($C_{1-3}$)alkoxy preferably tetrahydrofuranylmethoxy, unsubstituted or substituted phenyl, unsubstituted or substituted phenyloxy, unsubstituted or substituted thienyl, unsubstituted or substituted pyridyl, preferably unsubstituted pyridyl, unsubstituted or substituted oxazole, unsubstituted or substituted thiazole, unsubstituted or substituted isoxazole, unsubstituted or substituted phenyl($C_{1-3}$) alkoxy preferably benzyloxy, wherein each optional substitution in R6 is preferably selected from fluoro, chloro, bromo, methyl, methoxy and cyano, or (i) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl, wherein each substitution, if present, is selected from halogen, $C_{1-3}$ alkyl, $C_{3-7}$ cycloalkyl, $C_{3-7}$ cycloalkyl ($C_{1-3}$) alkyl, $C_{3-7}$ heterocycloalkyl($C_{1-3}$)alkyl, $C_{1-3}$ alkoxy, and $C_{1-3}$ alkoxy($C_{1-3}$)alkyl, wherein each alkyl or alkoxy can be unsubstituted or substituted with one or more substituents selected from halogen and $C_{1-3}$ alkoxy, or (ii) R6 forms together with R5 and the carbon atoms to which R6 and R5 are attached, a 1,3-dioxolane which may be unsubstituted or substituted with one or two substituents selected from fluoro and methyl, R7 is selected from H, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfonyl, and $C_{1-3}$ alkylsulfinyl, wherein each alkyl or alkoxy moiety can be substituted with one or more substituents, preferably with halogen or $C_{1-3}$ alkoxy, or R7 forms a ring together with R6 as described herein, R8 is selected from hydrogen, $C_{1-3}$ alkyl, $C_{1-3}$ alkoxy, and halogen, wherein each alkyl or alkoxy can be unsubstituted or substituted with one or more substituents selected from halogen, cyano and methoxy, or R8 forms a ring system together with R9, as described herein, R9 is selected from hydrogen, $C_{1-3}$ alkyl, $C_{1-3}$ alkoxy, fluoro, chloro, bromo and iodo, wherein each alkyl or alkoxy can be unsubstituted or substituted with one or more substituents selected from halogen and methoxy, or R9 forms together with R8 or R10 and the ring to which they are attached a bicyclic ring system selected from 2,1,3-benzothiadiazole, 2,1,3-benzoselenadiazole, 2,1,3-benzooxadiazole, 1,3-benzothiazole, 1,3-benzoxazole which may be unsubstituted or may be partially hydrogenated and substituted with oxo, 1,3-benzodioxole which may be unsubstituted or substituted with one or two substituents selected from fluoro and methyl, 2,3-dihydrobenzothiophene, which may be unsubstituted or substituted with one or two oxo groups, and 1,3-dihydro-2-benzofuran, which may be unsubstituted or substituted with one or two groups selected from oxo, fluoro and methyl, preferably with one oxo group, R10 is selected from hydrogen, fluoro, chloro, bromo, iodo, $C_{1-3}$ alkyl, $C_{1-3}$ alkoxy, $C_{2-4}$ alkenyl, $C_{2-4}$ alkynyl, cyano, cyanomethyl, $C_{1-3}$ alkylcarbonyl, $C_{1-3}$ alkoxycarbonyl, azido, pentafluorosulfanyl, and nitro, wherein each alkyl, alkenyl, alkynyl or alkoxy can be unsubstituted or substituted with one or more substituents selected from halogen and $C_{1-3}$ alkoxy, or R10 forms a ring system together with R9, as described herein, R11 is selected from hydrogen, $C_{1-3}$ alkyl, $C_{1-3}$ alkoxy, fluoro, chloro, bromo, iodo, $C_{1-3}$ alkylcarbonyl, $C_{1-3}$ alkoxycarbonyl, wherein each alkyl and alkoxy can be unsubstituted or substituted with one or more substituents selected from fluoro, chloro, bromo, iodo and $C_{1-3}$ alkoxy, R12 is selected from hydrogen, $C_{1-3}$ alkyl, $C_{1-3}$ alkoxy, fluoro, chloro, bromo, and iodo, wherein each alkyl and alkoxy can be unsubstituted or substituted with one or more substituents selected from fluoro, chloro, bromo, iodo and $C_{1-3}$ alkoxy, wherein if R6 is hydrogen, and X1 is N, then R5 is preferably different from hydrogen and is particularly preferably iodo, wherein, in a preferred embodiment, at least one of R8, R9, R10 and R11 is different from hydrogen, and more preferably at least one of R8, R9, R10 and R11 is also different from unsubstituted alkyl, and pharmaceutically acceptable salts, solvates, isotopes and co-crystals thereof.

A further embodiment relates to compounds of Formula I, wherein

X1 is N or C(R7),
X2 is NH, S, or O, preferably NH,
X3 is N or C(R12),
R4 is hydrogen or fluoro, preferably hydrogen,
R5 is selected from hydrogen, fluoro, chloro, bromo, iodo, unsubstituted or fluorinated $C_{1-2}$ alkyl, preferably methyl or trifluoromethyl, unsubstituted or fluorinated $C_{1-2}$ alkyloxy, unsubstituted or fluorinated $C_{1-2}$ alkylcarbonyl, unsubstituted or fluorinated $C_{1-2}$ alkyloxycarbonyl, $C_{1-2}$ alkylsulfinyl preferably methylsulfinyl, and $C_{1-2}$ alkylsulfonyl preferably methylsulfonyl, wherein R5 preferably is preferably selected from hydrogen, methyl, fluoro, chloro, bromo, and iodo, or R5 forms a ring together with R6 as described herein,
R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, unsubstituted or fluorinated $C_{1-3}$ alkylcarbonyl preferably acetyl, unsubstituted or fluorinated $C_{1-3}$ alkoxycarbonyl preferably methoxycarbonyl, unsubstituted or fluorinated($C_{1-3}$) alkylsulfinyl preferably methylsulfinyl, unsubstituted or fluorinated ($C_{1-3}$)alkylsulfonyl preferably methylsulfonyl, unsubstituted or substituted $C_{3-6}$ cycloalkyl preferably cyclopropyl, unsubstituted or substituted $C_{3-6}$ cycloalkyl ($C_{1-3}$))alkyl preferably cyclopropylmethyl, unsubstituted or substituted $C_{3-6}$ heterocycloalkyl, unsubstituted or substituted $C_{3-6}$ cycloalkoxy, unsubstituted or substituted $C_{3-6}$ heterocycloalkoxy, unsubstituted or substituted $C_{1-3}$ alkoxy preferably methoxy, ethoxy, fluoromethoxy, and fluoroethoxy, unsubstituted or substituted $C_{1-3}$alkoxy($C_{1-3}$) alkoxy, preferably methoxyethoxy, unsubstituted or substituted $C_{1-3}$alkoxy($C_{1-3}$)alkyl, unsubstituted or substituted $C_{3-6}$ cycloalkyl($C_{1-3}$)alkoxy preferably cyclopropylmethoxy, unsubstituted or substituted phenyl, unsubstituted or substituted phenyl($C_{1-3}$)alkoxy preferably benzyloxy, unsubstituted or substituted phenyloxy, unsubstituted or substituted phenyl($C_{1-3}$)alkylsulfonyl preferably benzylsulfonyl, unsubstituted or substituted phenyl($C_{1-3}$)alkylsulfinyl preferably benzylsulfinyl, unsubstituted or substituted thienyl, pyridyl, oxazole, thiazole, and isoxazole, and wherein each optional substitution in R6 is preferably selected from fluoro, chloro, unsubstituted or fluorinated methyl, unsubstituted or fluorinated methoxy, hydroxy, and cyano, provided that if R6 is hydrogen, and X1 is N, then R5 is preferably different from hydrogen and is preferably iodo, or
(i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl,
wherein each substitution, if present, is selected from halogen, hydroxy, methyl or methoxy, wherein each methyl or methoxy can be unsubstituted or substituted with one or more substituents selected from halogen preferably fluoro, and methoxy,
or
(ii) R6 forms together with R5 and the carbon atoms to which R6 and R5 are attached, a 1,3-dioxolane which may be unsubstituted or substituted with one or two substituents selected from fluoro and methyl, R7 is selected from hydrogen, fluoro, chloro, bromo, iodo, cyano, $C_{1-3}$ alkyl preferably methyl, $C_{1-3}$ alkyloxy preferably methoxy, fluoro($C_{1-3}$)alkyl preferably mono-, di-, or trifluoromethyl, fluoro($C_{1-3}$)alkoxy preferably mono-, di- or trifluoromethoxy and mono-, di-, and trifluoroethoxy, unsubstituted or fluorinated $C_{1-3}$ alkylcarbonyl, unsubstituted or fluorinated $C_{1-3}$ alkoxycarbonyl, methylsulfinyl, methylsulfonyl, fluorinated methylsulfinyl, fluorinated methylsulfonyl, substituted or unsubstituted $C_{5-6}$ heteroaryl, substituted or unsubstituted $C_{5-6}$ heteroaryloxy, and $C_{5-6}$ heteroarylmethoxy, wherein the heteroaryl is preferably selected from pyridyl, oxazol and isoxazol, and wherein the heteroaryl may be substituted with one or more substituents selected from halogen, unsubstituted or fluorinated methyl, unsubstituted or fluorinated methoxy, or R7 forms a ring together with R6 as described herein, R8 is selected from hydrogen, fluoro, chloro, bromo, iodo, cyano, $C_{1-3}$ alkyloxy preferably methoxy, fluoro($C_{1-3}$) alkoxy, $C_{1-3}$ alkyl preferably methyl, and fluoro($C_{1-3}$)alkyl preferably trifluoromethyl, or R8 forms a ring system together with R9, as described herein, R9 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, cyano, and fluoro($C_{1-3}$)alkyl preferably trifluoromethyl, and is preferably hydrogen, fluoro, chloro, or bromo, or R9 forms together with R8 and the ring to which they are attached a bicyclic ring system selected from 2,1,3-benzothiadiazole, 2,1,3-benzoselenadiazole, 2,1,3-benzoxadiazole, 1,3-benzoxazole which may be unsubstituted or may be partially hydrogenated and substituted with oxo (to give 2-oxo-2,3-dihydro-1,3-benzoxazole) and 1,3-benzodioxole, which is optionally substituted with one or two fluoros, or R9 forms together with R10 and the ring to which they are attached a bicyclic ring system selected from 2,1,3-benzothiadiazole, 2,1,3-benzoselenadiazole, 2,1,3-benzoxadiazole, 1,3-benzothiazole, 3-oxo-2,3-dihydro-1H-isoindol, 2,3-dihydro-1-benzothiophene, which is substituted with one or two oxo (preferably substituted with two oxo to give 1,1-dioxo-2,3-dihydro-1-benzothiophene), 3-oxo-1,3-dihydro-2-benzofuran, which is optionally substituted with methyl to give 1-methyl-3-oxo-1,3-dihydro-2-benzofuran, and 1,3-benzodioxole, which is optionally substituted with one or two fluoros, R10 is selected from hydrogen, fluoro, chloro, bromo, iodo, $C_{1-3}$ alkyl, halo($C_{1-3}$)alkyl, preferably fluoro($C_{1-3}$)alkyl, particularly trifluoromethyl, $C_{2-3}$ alkynyl, $C_{1-3}$ alkyloxy, halo ($C_{1-3}$) alkyloxy, preferably fluoro($C_{1-2}$)alkoxy, cyclopropylcyano, cyanomethyl, cyanoethyl, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro, wherein each alkyl, cyclopropyl, alkoxy, alkenyl or alkynyl in R10, unless otherwise specified, may be optionally further substituted with one or more substituents selected from fluoro, chloro, cyano, hydroxy, $C_{1-3}$ alkoxy preferably methoxy, halo $C_{1-3}$ alkoxy, and unsubstituted or fluorinated $C_{1-3}$ alkoxycarbonyl, wherein each alkyl and alkoxy may also be substituted with cyclopropyl which can be optionally substituted as defined above, or R10 forms a ring system together with R9, as described herein, R11 is selected from hydrogen, fluoro, chloro, bromo, iodo, $C_{1-3}$ alkyl preferably methyl, fluoro($C_{1-3}$)alkyl preferably fluorinated methyl such as trifluoromethyl, $C_{1-3}$ alkyloxy preferably methoxy, fluoro($C_{1-3}$)alkoxy preferably fluoro ($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl, and cyano, and is more preferably hydrogen, fluoro, chloro or bromo, R12, if present, is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro($C_{1-3}$) alkoxy preferably fluoro($C_{1-2}$)alkoxy, and cyano and is more preferably hydrogen, fluoro, chloro, or bromo.

wherein, in a preferred embodiment, at least one of R8, R9, R10 and R11 is different from hydrogen, and more preferably at least one of R8, R9, R10 and R11 is also different from unsubstituted alkyl, and wherein in another preferred embodiment, at least one of R5, R6 and R7, if present, is different from hydrogen, and wherein in one preferred embodiment, if X1 is N, then X2 in NH, and pharmaceutically acceptable salts, solvates, isotopes and co-crystals thereof.

A further embodiment relates to compounds of Formula I, wherein

X1 is N or C(R7),
X2 is NH or O, preferably NH,
X3 is N or C(R12),
R4 is hydrogen,
R5 is selected from hydrogen, fluoro, chloro, bromo, iodo, unsubstituted or fluorinated $C_{1-2}$ alkyl, preferably methyl or trifluoromethyl, unsubstituted or fluorinated $C_{1-2}$ alkyloxy, unsubstituted or fluorinated $C_{1-2}$ alkylcarbonyl, unsubstituted or fluorinated $C_{1-2}$ alkyloxycarbonyl, $C_{1-2}$ alkylsulfinyl preferably methylsulfinyl, and $C_{1-2}$ alkylsulfonyl preferably methylsulfonyl, preferably hydrogen, methyl or iodo, or R5 forms a ring together with R6 as described herein, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, unsubstituted or fluorinated $C_{1-3}$ alkylcarbonyl preferably acetyl, unsubstituted or fluorinated $C_{1-3}$ alkoxycarbonyl preferably methoxycarbonyl, ($C_{1-3}$) alkylsulfinyl preferably methylsulfinyl, ($C_{1-3}$)alkylsulfonyl preferably methylsulfonyl, $C_{3-6}$ cycloalkyl preferably cyclopropyl, $C_{3-6}$ cycloalkyl($C_{1-3}$)) alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, unsubstituted or substituted $C_{1-3}$alkoxy($C_{1-3}$) alkoxy, preferably methoxyethoxy, $C_{3-6}$ cycloalkyl($C_{1-3}$)alkoxy preferably cyclopropylmethoxy, unsubstituted or substituted phenyl, unsubstituted or substituted phenyl($C_{1-3}$)alkoxy preferably benzyloxy, unsubstituted or substituted phenyloxy, unsubstituted or substituted thienyl, pyridyl, oxazole, thiazole, and isoxazole, and wherein each optional substitution in R6 is preferably selected from fluoro, chloro, methyl, methoxy, and cyano, provided that if R6 is hydrogen, and X1 is N, then R5 is preferably different from hydrogen and is preferably iodo, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, methyl or methoxy, wherein each methyl or methoxy can be unsubstituted or substituted with one or more substituents selected from fluoro and methoxy, or (ii) R6 forms together with R5 and the carbon atoms to which R6 and R5 are attached, a 1,3-dioxolane which may be unsubstituted or substituted with one or two substituents selected from fluoro and methyl, R7 is selected from hydrogen, fluoro, chloro, bromo, iodo, cyano, $C_{1-3}$ alkyl, $C_{1-3}$ alkyloxy, fluoro($C_{1-3}$)alkyl preferably trifluoromethyl, fluoro($C_{1-3}$)alkoxy preferably trifluoromethoxy, unsubstituted or fluorinated $C_{1-3}$ alkylcarbonyl, unsubstituted or fluorinated $C_{1-3}$ alkoxycarbonyl, methylsulfinyl, and methylsulfonyl, or R7 forms a ring together with R6 as described herein, R8 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl, or R8 forms a ring system together with R9, as described herein, R9 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, cyano, and fluoro($C_{1-3}$)alkyl preferably trifluoromethyl, and is preferably hydrogen, fluoro, chloro, or bromo, or R9 forms together with R8 and the ring to which they are attached a bicyclic ring system selected from 2,1,3-benzothiadiazole, 2,1,3-benzoselenadiazole, 2,1,3-benzooxadiazole, 1,3-benzoxazole which may be unsubstituted or may be partially hydrogenated and substituted with oxo (to give 2-oxo-2,3-dihydro-1,3-benzoxazole) and 1,3-benzodioxole, which is optionally substituted with one or two fluoros, or R9 forms together with R10 and the ring to which they are attached a bicyclic ring system selected from 2,1,3-benzothiadiazole, 2,1,3-benzoselenadiazole, 2,1,3-benzooxadiazole, 1,3-benzothiazole, 2,3-dihydro-1-benzothiophene, which is substituted with one or two oxo (preferably substituted with two oxo to give 1,1-dioxo-2,3-dihydro-1-benzothiophene), 3-oxo-1,3-dihydro-2-benzofuran, and 1,3-benzodioxole, which is optionally substituted with one or two fluoros, R10 is selected from hydrogen, fluoro, chloro, bromo, iodo, $C_{1-3}$ alkyl, halo($C_{1-3}$)alkyl, preferably fluoro($C_{1-3}$)alkyl, particularly trifluoromethyl, $C_{2-3}$ alkynyl, $C_{1-3}$ alkyloxy, halo ($C_{1-3}$) alkyloxy, preferably fluoro($C_{1-2}$)alkoxy, cyano, cyanomethyl, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro, or R10 forms a ring system together with R9, as described herein, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$)alkoxy preferably fluoro($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl, and cyano, and is more preferably hydrogen, fluoro, chloro or bromo, R12 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy preferably fluoro($C_{1-2}$)alkoxy, and cyano and is more preferably hydrogen, fluoro, chloro, or bromo.

wherein, in a preferred embodiment, at least one of R8, R9, R10 and R11 is different from hydrogen, and more preferably at least one of R8, R9, R10 and R11 is also different from unsubstituted alkyl, and pharmaceutically acceptable salts, solvates, isotopes and co-crystals thereof.

In one preferred embodiment, in the compounds of Formula I as described herein, if X2 is O, then X1 is C(R7).

A further embodiment relates to compounds of Formula I, wherein

X1 is N or C(R7),

X2 is NH, S or O provided that if X1 is N, then X2 is preferably also N,

X3 is N or C(R12),

R4 is hydrogen or fluoro, preferably hydrogen,

R5 is selected from hydrogen, methyl, fluoro, chloro and bromo, or R5 forms a ring together with R6 as described herein, R6 is selected from hydrogen, halogen, cyano, nitro, azido, $C_{1-3}$ alkyl, $C_{1-3}$alkylsulfinyl preferably methylsulfinyl, $C_{1-3}$alkylsulfonyl preferably methylsulfonyl, cyclopropyl, cyclopropylmethyl, cyclopropyloxy, $C_{1-3}$ alkoxy preferably methoxy or ethoxy, phenyl, phenyloxy, benzyl, phenyl ($C_{1-3}$)alkoxy preferably benzyloxy, benzylsulfinyl, benzylsulfonyl, tetrahydrofuranyl, and a 5-6 membered heteroaryl, preferably selected from thienyl, pyridyl, oxazole, and isoxazole, and wherein each alkyl, alkoxy, cyclopropyl, tetrahydrofuranyl, phenyl or heteroaryl group can be optionally substituted one or more times with substituents selected from fluoro, chloro, hydroxy, unsubstituted or fluorinated $C_{1-2}$ alkyl, unsubstituted or fluorinated $C_{1-2}$ alkoxy, and cyano, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, hydroxy, methyl or methoxy, wherein each methyl or methoxy can be unsubstituted or substituted with one or more substituents selected from halogen, preferably fluoro, and methoxy, or (ii) R6 forms together with R5 and the carbon atoms to which R6 and R5 are attached, a 1,3-dioxolane which may be unsubstituted or substituted with one or two substituents selected from fluoro and methyl, R7 is selected from hydrogen, halogen, cyano, $C_{1-3}$ alkyl, $C_{1-3}$ alkyloxy, fluoro($C_{1-3}$)alkyl preferably mono-, di-, and trifluoromethyl, fluoro($C_{1-3}$)alkoxy preferably mono-, di-, and trifluoromethoxy or mono-, di-, and trifluoroethoxy, unsubstituted or fluorinated methylsulfinyl, unsubstituted or fluorinated methylsulfonyl, $C_{5-6}$ heteroaryl, $C_{5-6}$ heteroaryloxy, $C_{5-6}$ heteroarylmethyl and $C_{5-6}$ heteroarylmethoxy, wherein the heteroaryl (in each occurrence in R7) is preferably selected from pyridyl, oxazol and isoxazol, and wherein the heteroaryl is unsubstituted or substituted with one or more substituents selected from halogen, cyano, unsubstituted or fluorinated methyl, and unsubstituted or fluorinated methoxy, or R7 forms a ring together with R6 as described herein, R8 is selected from hydrogen, fluoro, chloro, bromo, $C_{1-3}$ alkyloxy preferably methoxy, fluoro($C_{1-3}$)alkoxy preferably fluoromethoxy, and unsubstituted or fluorinated $C_{1-3}$alkyl preferably fluoromethyl, or R8 forms a ring system together with R9, as described herein, R9 is selected from hydrogen, fluoro, chloro, methoxy, fluromethoxy, methyl and fluoromethyl, or R9 forms together with R8 and the ring to which they are attached a bicyclic ring system selected from 2,1,3-benzothiadiazole, 2,1,3-benzoselenadiazole, 2,1,3-benzoxadiazole, 1,3-benzoxazole which may be unsubstituted or may be partially hydrogenated and substituted with oxo (to give 2-oxo-2,3-dihydro-1,3-benzoxazole) and 1,3-benzodioxole, which is optionally substituted with one or two fluoros, or R9 forms together with R10 and the ring to which they are attached a bicyclic ring system selected from 2,1,3-benzothiadiazole, 2,1,3-benzoselenadiazole, 2,1,3-benzoxadiazole, 1,3-benzothiazole, 3-oxo-2,3-dihydro-1H-isoindol, 2,3-dihydro-1-benzothiophene, which is substituted with one or two oxo (preferably substituted with two oxo to give 1,1-dioxo-2,3-dihydro-1-benzothiophene), 3-oxo-1,3-dihydro-2-benzofuran, which is optionally substituted with methyl to give 1-methyl-3-oxo-1,3-dihydro-2-benzofuran, and 1,3-benzodioxole, which is optionally substituted with one or two fluoros, R10 is selected from hydrogen, halogen, cyano, azido, pentafluorosulfanyl, nitro, $C_{1-3}$ alkyl, $C_{2-3}$ alkenyl, $C_{2-3}$ alkynyl, $C_{1-3}$ alkyloxy, $C_{1-3}$ alkylcarbonyl preferably acetyl, $C_{3-6}$cycloalkyl preferably cycloalkyl, $C_{3-6}$ cycloalkyloxy preferably cycloalkyloxy, $C_{3-6}$hetero cycloalkyl, $C_{3-6}$heterocycloalkyloxy, wherein each cycloalkyl is optionally substituted by one or more substituents selected from fluoro, cyano, unsubstituted or fluorinated $C_{1-2}$alkoxy, and unsubstituted or fluorinated $C_{1-2}$alkoxycarbonyl, and wherein each alkyl, alkoxy, alkenyl or alkynyl in R10 may be optionally further substituted with one or more substituents selected from cyclopropyl, halogen preferably fluoro, cyano, hydroxy, $C_{1-3}$ alkoxy, halo($C_{1-3}$)alkoxy preferably fluoro ($C_{1-3}$)alkoxy, unsubstituted or fluorinated $C_{1-3}$ alkylcarbonyl, and unsubstituted or fluorinated $C_{1-3}$ alkoxycarbonyl, or R10 forms a ring system together with R9, as described herein, R11 is selected from hydrogen, fluoro, chloro, bromo, $C_{1-3}$ alkyl preferably methyl, fluoro($C_{1-3}$)alkyl preferably fluoromethyl, $C_{1-3}$ alkyloxy preferably methoxy, fluoro($C_{1-3}$) alkoxy preferably fluoromethoxy, and cyano, R12, if present, is selected from hydrogen, fluoro, chloro, bromo, methyl, fluoromethyl, methoxy and fluoromethoxy, wherein preferably, R12 is hydrogen or fluoro, and pharmaceutically acceptable salts, solvates, isotopes and co-crystals thereof;

wherein, in a preferred embodiment, at least one, more preferably two of R8, R10 and R11 are different from hydrogen, and more preferably at least one of R8, R10 and R11 is also different from unsubstituted alkyl, and wherein in another preferred embodiment, at least one of R5, R6 and R7, if present, is different from hydrogen, A further embodiment relates to compounds of Formula I, wherein X1 is N or C(R7),
X2 is NH, S or O, preferably NH or O,
X3 is N or C(R12),
R4 is hydrogen,
R5 is selected from hydrogen, fluoro, chloro and bromo,
R6 is selected from fluoro, chloro, bromo, iodo, cyano, azido, amino, nitro, methyl, ethyl, n-propyl, isopropyl, trifluoromethyl, ethenyl, ethynyl, propargyl, methylsulfinyl, methylsulfonyl, cyclopropyl, cyclopropyloxy, cyclopropylmethyl, methoxy, ethoxy, propoxy, methoxyethoxy, ethoxymethoxy, cyclopropylmethoxy, oxetanyl, oxetanylmethoxy, tetrahydrofuranyl, tetrahydrofuranylmethoxy, phenyl, benzyloxy, phenyloxy, benzylsulfinyl, thienyl, pyridyl, oxazole, thiazole, and isoxazole, wherein each phenyl, thienyl, pyridyl, oxazol, thiazole and isoxazol can be optionally substituted one or more times, preferably with a substitution selected from halogen, methoxy, and methyl, and wherein each alkyl, alkenyl, alkynyl and alkoxy group can be substituted one or more times with halogen preferably fluoro, methoxy, fluoromethoxy, and hydroxy, or R6 forms together with R7 and the carbon atoms to which R6 and R7 are attached, a ring selected from phenyl, pyridyl, cyclohexyl, and cyclopentyl, each of which can be unsubstituted or further substituted with one or more residues selected from halogen, hydroxy, unsubstituted or fluorinated methyl, and unsubstituted or fluorinated methoxy, R7 is selected from hydrogen, fluoro, chloro, bromo, iodo, cyano, methylsulfinyl, methylsulfonyl, methoxy, fluoromethoxy, fluoroethoxy, methyl, fluoromethyl, and fluoroethyl, or R7 forms a ring together with R6 as described herein, R8 is selected from hydrogen, fluoro, chloro, bromo, iodo, methoxy, fluoromethoxy, cyano, methyl, and fluoromethyl, or R8 forms a ring system together with R9, as described herein, R9 is selected from hydrogen, fluoro and chloro and is preferably hydrogen, or R9 forms together with R8 or R10 and the ring to which they are attached a bicyclic ring system selected from 2,1,3-benzothiadiazole, 2,1,3-benzoxadiazole, 2-oxo-2,3-dihydro-1,3-benzoxazole and 1,3-benzodioxole, which is optionally substituted with two fluoros, or R9 forms together with R10 and the ring to which they are attached a bicyclic ring system selected from 3-oxo-2,3-dihydro-1H-isoindol, 2,3-dihydro-1-benzothiophene, which is substituted with one or two oxo (preferably substituted with two oxo to give 1,1-dioxo-2,3-dihydro-1-benzothiophene), and optionally methylated 3-oxo-1,3-dihydro-2-benzofuran, R10 is selected from hydrogen, fluoro, chloro, bromo, iodo, methyl, ethyl, n-propyl, isopropyl, ethenyl, n-propenyl, isopropenyl, ethynyl, propargyl, fluoro($C_{1-3}$)alkyl preferably trifluoromethyl, methoxy, ethoxy, propoxy, fluoro($C_{1-3}$) alkoxy $C_{1-3}$alkoxy($C_{1-3}$)alkyl, $C_{1-3}$alkoxy($C_{1-3}$)alkoxy, $C_{1-3}$alkoxy($C_{2-3}$)alkenyl, $C_{1-3}$alkoxy($C_{2-3}$)alkynyl, $C_{1-3}$alkoxycarbonyl($C_{1-3}$)alkyl, $C_{1-3}$alkylcarbonyl($C_{1-3}$)alkyl, $C_{1-3}$ alkylcarbonyl($C_{1-3}$)alkyloxy, cyano, acetyl, azido, nitro, pentafluorosulfanyl, cyclopropyl, cyclopropyloxy, cyclopropylmethoxy, and $C_{1-3}$alkoxycarbonyl including methoxycarbonyl, wherein each alkyl, alkenyl, alkynyl and alkoxy group in R10 can be unsubstituted or substituted with one or more residues selected from halogen preferably fluoro, cyano and/or hydroxy, and wherein the cyclopropyl is optionally substituted with one or more residues selected from cyano, optionally fluorinated $C_{1-2}$ alkoxy and optionally fluorinated $C_{1-2}$alkoxycarbonyl, or R10 forms a ring system together with R9, as described herein, R11 is selected from hydrogen, fluoro, chloro, bromo, cyano, methyl, fluoromethyl, methoxy and fluoromethoxy, R12, if present, is selected from hydrogen, fluoro, chloro, and bromo, and is preferably hydrogen or fluoro.

wherein, in a preferred embodiment, at least one of R8, R9, R10 and R11, more preferably at least one or at least two, most preferably all of R8, R10 and R11, are different from hydrogen and at least one, preferably at least two of R8, R10 and R11, are preferably also different from unsubstituted alkyl, and pharmaceutically acceptable salts, solvates, isotopes and co-crystals thereof.

A further embodiment relates to compounds of Formula I, wherein

X1 is N or C(R7),
X2 is NH, S or O, preferably NH or O,
X3 is N or C(R12),
R4 is hydrogen,
R5 is selected from hydrogen, fluoro, chloro and bromo,
R6 is selected from fluoro, chloro, bromo, azido, nitro, methyl, ethyl, isopropyl, trifluoromethyl, methylsulfinyl, methylsulfonyl, cyclopropyl, methoxy, phenyl, benzyloxy, phenylsulfinyl, benzylsulfinyl, thiophen-2-yl, and thiophen-3-yl, wherein each alkyl and alkoxy group in R6 can be substituted one or more times with fluoro, methoxy, cyano and hydroxy, or R6 forms together with R7 and the carbon atoms to which R6 and R7 are attached, a ring selected from phenyl, pyridyl, cyclohexyl, and cyclopentyl, each of which can be optionally substituted one or more times with a group selected from methyl, fluorinated methyl, methoxy, fluorinated methoxy and fluoro, R7 is selected from hydrogen, fluoro, chloro, bromo, cyano, methyl, ethyl, methylsulfonyl, methylsulfinyl, methoxy, ethoxy, mono-, di-, and trifluoromethoxy, mono-, di-, and trifluoroethoxy, mono-, di-, and trifluoromethyl, mono-, di-, and trifluoroethyl, or R7 forms a ring together with R6 as described herein, R8 is selected from hydrogen, fluoro, chloro, bromo, methoxy, cyano, and mono-, di-, and trifluoromethyl, or R8 forms a ring system together with R9, as described herein, R9 is hydrogen or fluoro, preferably hydrogen, or R9 forms together with R8 or R10 and the ring to which they are attached a bicyclic ring system selected from 2,1,3-benzothiadiazole, 2,1,3-benzoxadiazole, 1,3-benzodioxole, or 2,2-difluoro-1,3-benzodioxole, or R9 forms together with R10 and the ring to which they are attached a bicyclic ring system selected from 3-oxo-2,3-dihydro-1H-isoindol, 3-oxo-1,3-dihydro-2-benzofuran, and 1-methyl-3-oxo-1,3-dihydro-2-benzofuran, R10 is selected from hydrogen, fluoro, chloro, bromo, iodo, methyl, ethyl, propyl, ethenyl, propenyl, ethynyl, propargyl, methoxy, ethoxy, propyloxy, cyano, cyanomethyl, cyanoethyl, cyanomethoxy, fluoro($C_{1-3}$)alkyl including trifluoromethyl, fluorinated and/or hydroxylated $C_{1-3}$alkoxy preferably fluoro($C_{1-2}$)alkoxy, unsubstituted or fluorinated and/or hydroxylated $C_{1-2}$alkoxy($C_{1-3}$)alkyl preferably methoxypropyl, ethoxyethyl, and fluoromethoxymethyl, unsubstituted or fluorinated and/or hydroxylated $C_{1-2}$alkoxy($C_{1-3}$)alkoxy preferably fluoromethoxyethoxy, unsubstituted or fluorinated and/or hydroxylated $C_{1-2}$alkoxy($C_{2-3}$)alkenyl preferably methoxypropenyl and ethoxyethenyl, $C_{1-2}$alkoxycyclopropyl, $C_{1-2}$alkoxycarbonylcyclopropyl, cyclopropyl($C_{1-2}$)alkoxy, acetyl, azido, and pentafluorosulfanyl, or R10 forms a ring system together with R9, as described herein, and wherein, in a preferred embodiment, R8 and R10 are not both hydrogen,
R11 is selected from hydrogen, fluoro, fluoromethyl, chloro, methoxy and fluoromethoxy,
R12, if present, is selected from hydrogen and fluoro,
and pharmaceutically acceptable salts, solvates, isotopes and co-crystals thereof,
wherein in one preferred embodiment, if R9 does not form a ring with R8, then R10 is different from hydrogen.

One embodiment relates to compounds of Formula I,
wherein
X1 is N or C(R7),
X2 is NH, S or O, preferably NH or O, preferably NH,
R4 is hydrogen,
R5 is selected from hydrogen, fluoro, chloro and bromo,
R6 is selected from fluoro, bromo, chloro, nitro, azido, cyano, methyl, fluoromethyl, ethyl, fluoroethyl, isopropyl, cyclopropyl, cyclopropylmethyl, cyclopropylmethoxy, methoxy, ethoxy, fluoromethoxy, fluoroethoxy, methylsulfinyl, methylsulfonyl, benzyloxy, thienyl, and and is preferably chloro,
R7 is selected from hydrogen, methoxy, fluoro, chloro, bromo, cyano, fluoromethoxy, fluoroethoxy, and mono-, di- and trifluoromethyl,
X3 is N or C(R12),
R8 is selected from hydrogen, fluoro, chloro, and methoxy,
R9 is hydrogen or fluoro, preferably hydrogen,
R10 is selected from fluoro, chloro, bromo, cyano, cyanomethyl, cyanoethyl, cyanomethoxy, azido, methyl, ethyl, propyl, ethenyl, propenyl, ethynyl, propargyl, mono-, di-, and trifluoromethyl, cyclopropylmethoxy, methoxycyclopropyl, ethoxycyclopropyl, methoxycarbonylcyclopropyl, ethoxycarbonylcyclopropyl, mono-, di- and trifluoromethoxy, mono-, di-, and trifluoroethoxy, ethoxymethyl, methoxyethyl, ethoxyethyl, methoxypropyl, fluoroethoxymethyl, fluoromethoxyethyl, fluoroethoxyethyl, fluoromethoxypropyl, ethoxymethoxy, methoxyethoxy, methoxypropoxy, fluoroethoxymethoxy, fluoromethoxyethoxy, fluoromethoxypropoxy, methoxyethenyl, methoxypropenyl, fluoromethoxyethenyl, ethynyl, propargyl, and pentafluorosulfanyl,
R11 is selected from hydrogen, fluoro, chloro, fluoromethyl, methoxy, and fluoromethoxy,
R12, if present, is hydrogen or fluoro, preferably hydrogen
wherein, in a preferred embodiment, at least one of R8, and R11 is different from hydrogen,
and pharmaceutically acceptable salts, solvates, isotopes and co-crystals thereof.

One preferred embodiment relates to compounds of Formula I,
wherein
X1 is N, or C(R7),
X2 is NH, S or O, preferably NH,
R4 and R5 are both hydrogen,
R6 is methoxy, chloro or bromo, preferably chloro,
R7 is hydrogen, methoxy, fluoroor trifluoromethyl,
X3 is N or C(R12),
R9 forms together with R8 and the phenyl ring to which R8 and R9 are attached a 2,1,3-benzothiadiazole, a 1,3-benzodioxole, or a 2,2-difluoro-1,3-benzodioxole,
R10 is hydrogen or fluoro,
R11 is selected from hydrogen, fluoro, cyano and methoxy, and is preferably hydrogen,
R12, if present, is hydrogen or fluoro, preferably hydrogen,
and pharmaceutically acceptable salts, solvates, isotopes and co-crystals thereof.

One preferred embodiment relates to compounds of Formula I,
wherein
X1 is N or C(R7),
X2 is NH, S or O,
R4 and R5 are both hydrogen,
R6 is, selected from fluoro, chloro, bromo, cyano, azido, methyl, ethyl, isopropyl, fluoromethyl, cyclopropyl, methoxy, fluoromethoxy, methylsulfinyl, methylsulfonyl, thien-2-yl, thien-3-yl, and benzyloxy and is preferably chloro or bromo,
R7 is selected from hydrogen, methoxy, fluoro, chloro, bromo, cyano, mono-, di-, and trifluoromethyl, methylsulfinyl, methylsulfonyl, and fluoro($C_{1-2}$)alkoxy,
X3 is N or C(R12),
R8 is selected from fluoro and methoxy,
R9 is hydrogen,
R10 is selected from fluoro, chloro, bromo, azido, cyano, cyanomethyl, cyanoethyl, cyanomethoxy, cyclopropyl($C_{1-2}$)alkyl, cyclopropyl($C_{1-2}$)alkoxy, $C_{1-2}$alkoxycyclopropyl, $C_{1-2}$ alkoxycarbonylcyclopropyl, unsubstituted or fluorinated $C_{1-3}$ alkyl, preferably methyl, ethyl and fluoromethyl, unsubstituted or fluorinated $C_{1-3}$ alkoxy, preferably methoxy, difluoromethoxy, difluoroethoxy and trifluoroethoxy, unsubstituted or fluorinated $C_{2-3}$ alkenyl, unsubstituted or fluorinated $C_{2-3}$ alkynyl, unsubstituted or fluorinated $C_{1-3}$ alkoxy($C_{1-3}$)alkyl, preferably methoxypropyl, ethoxyethyl, and fluoromethoxymethyl, unsubstituted or fluorinated $C_{1-3}$ alkoxy($C_{1-3}$)alkoxy, preferably methoxyethoxy and fluoromethoxyethoxy, unsubstituted or fluorinated $C_{1-3}$ alkoxy($C_{2-3}$)alkenyl, preferably methoxypropenyl, ethoxyethenyl and fluoromethoxypropenyl, and pentafluorosulfanyl,
R11 is selected from hydrogen, fluoro and methoxy,
R12, if present, is hydrogen,
and pharmaceutically acceptable salts, solvates, isotopes and co-crystals thereof.

A further embodiment relates to compounds of Formula I,
wherein
X1 is N or C(R7),
X2 is NH or O,
X3 is N or C(R12),
R4 and R5 are both hydrogen,
R6 is selected from fluoro, chloro, bromo, iodo, cyano, azido, methyl, ethyl, isopropyl, trifluoromethyl, methylsulfinyl, methylsulfonyl, cyclopropyl, cyclopropylmethyl, methoxy, ethoxy, methoxyethoxy, cyclopropylmethoxy, phenyl, benzyloxy, phenyloxy, thienyl, pyridyl, oxazole, thiazole, and isoxazole,
or R6 forms together with R7 and the carbon atoms to which R6 and R7 are attached, a ring selected from phenyl, pyridyl, and cyclopentyl,
R7 is selected from hydrogen, fluoro, chloro, bromo, iodo, methoxy, difluoromethoxy, trifluoromethoxy, methyl, difluoromethyl, and trifluoromethyl, or R7 forms a ring together with R6 as described herein, R8 is selected from hydrogen, fluoro, chloro, bromo, iodo, methyl, methoxy, methyl, and trifluoromethyl, or R8 forms a ring system together with R9, as described herein,
R9 is selected from hydrogen, fluoro and chloro and is preferably hydrogen,
or R9 forms together with R8 or R10 and the ring to which they are attached a bicyclic ring system selected from 2,1,3-benzothiadiazole, 2,1,3-benzooxadiazole, 2-oxo-2,3-dihydro-1,3-benzoxazole and 1,3-benzodioxole, which is optionally substituted with two fluoros,
R10 is selected from hydrogen, fluoro, chloro, bromo, iodo, methyl, ethynyl, propargyl, fluoro($C_{1-2}$)alkyl preferably trifluoromethyl, methoxy, fluoro($C_{1-2}$)alkoxy, cyano, cyanomethyl, acetyl, azido, pentafluorosulfanyl, and methoxycarbonyl, or R10 forms a ring system together with R9, as described herein,
R11 is selected from hydrogen, fluoro, chloro, bromo, and methoxy,
R12 is selected from hydrogen, fluoro, chloro, or bromo.
wherein, in a preferred embodiment, at least one of R8, R9, R10 and R11 is different from hydrogen and unsubstituted alkyl,
and pharmaceutically acceptable salts, solvates, isotopes and co-crystals thereof.

A further embodiment relates to compounds of Formula I, wherein
X1 is N or C(R7),
X2 is NH or O,
X3 is N or C(R12),
R4 and R5 are both hydrogen,
R6 is selected from fluoro, chloro, bromo, azido, methyl, isopropyl, trifluoromethyl, methylsulfonyl, cyclopropyl, methoxy, phenyl, benzyloxy, thiophen-2-yl, and thiophen-3-yl,
or R6 forms together with R7 and the carbon atoms to which R6 and R7 are attached, a ring selected from phenyl, pyridyl, and cyclopentyl,
R7 is selected from hydrogen, fluoro, chloro, and methoxy, or R7 forms a ring together with R6 as described herein,
R8 is selected from hydrogen, fluoro, chloro, bromo, methoxy, and trifluoromethyl, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzooxadiazole, 1,3-benzodioxole, or 2,2-difluoro-1,3-benzodioxole, R10 is selected from hydrogen, fluoro, chloro, bromo, iodo, ethynyl, propargyl, methoxy, cyano, cyanomethyl, trifluoromethyl, fluoro ($C_{1-2}$)alkoxy, acetyl, azido, and pentafluorosulfanyl, or R10 forms a ring system together with R9, as described herein, and wherein, in a preferred embodiment, R8 and R10 are not both hydrogen,
R11 is selected from hydrogen, fluoro, chloro, and methoxy,
R12 is selected from hydrogen, and fluoro, and pharmaceutically acceptable salts, solvates, isotopes and co-crystals thereof.

One embodiment relates to compounds of Formula I, wherein
X1 is N or C(R7),
X2 is NH or O, preferably NH,
R4 and R5 are both hydrogen,
R6 is bromo or chloro, preferably chloro,
R7 is hydrogen, methoxy, fluoro or trifluoromethyl,
X3 is N or C(R12),
R8 is selected from hydrogen, fluoro, chloro, and methoxy,
R9 is hydrogen of fluoro, preferably hydrogen,
R10 is selected from fluoro, chloro, bromo, cyano, cyanomethyl, trifluoromethyl, difluoroethoxy, trifluoroethoxy, and pentafluorosulfanyl,
R11 is selected from hydrogen, fluoro, chloro, and methoxy,
R12 is hydrogen or fluoro, preferably hydrogen,
wherein, in a preferred embodiment, at least one of R8, R9, R10 and R11 is different from hydrogen,
and pharmaceutically acceptable salts, solvates, isotopes and co-crystals thereof.

One preferred embodiment relates to compounds of Formula I,
wherein
X1 is N, or C(R7),
X2 is NH or O, preferably NH,
R4 and R5 are both hydrogen,
R6 is chloro or bromo, preferably chloro,
R7 is hydrogen, methoxy, fluoro or trifluoromethyl,
X3 is N or C(R12),
R9 forms together with R8 and the phenyl ring to which R8 and R9 are attached a 2,1,3-benzothiadiazole or a 2,2-difluoro-1,3-benzodioxole,
R10 is hydrogen, or fluoro,
R11 is selected from hydrogen, fluoro and methoxy,
R12 is hydrogen or fluoro preferably hydrogen,
and pharmaceutically acceptable salts, solvates, isotopes and co-crystals thereof.

One preferred embodiment relates to compounds of Formula I,
wherein
X1 is N or C(R7),
X2 is NH,
R4 and R5 are both hydrogen,
R6 is chloro or bromo, preferably chloro,
R7 is hydrogen, methoxy, fluoro or trifluoromethyl,
X3 is N or C(R12),
R8 is selected from fluoro and methoxy,
R9 is hydrogen,
R10 is selected from fluoro, chloro, bromo, cyano, cyanomethyl, trifluoromethyl, difluoroethoxy, trifluoroethoxy, and pentafluorosulfanyl,
R11 is selected from hydrogen, fluoro and methoxy,
R12 is hydrogen,
and pharmaceutically acceptable salts, solvates, isotopes and co-crystals thereof.

One embodiment of the present invention relates to compounds of the general Formula I-2,

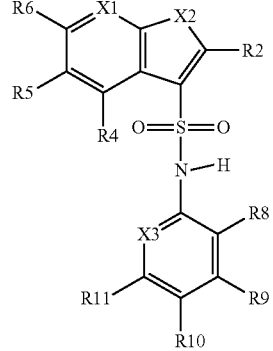

Formula I-2 wherein
R2 is selected from hydrogen, fluoro, chloro, bromo, iodo and methoxy, preferably from hydrogen and fluoro, and wherein R4, R5, R6, R7 if present, R8, R9, R10, R11, X1, X2, and X3 are as described for the compounds of Formula I herein.

One embodiment relates to compounds of Formula I-2, wherein
X1 is N or C(R7),
X2 is NH, S or O, preferably NH or O, more preferably NH,
R2 is hydrogen or fluoro,
R4 is hydrogen or fluoro,
R5 is selected from hydrogen and halogen,
R6 is selected from hydrogen, fluoro, chloro, bromo, iodo, cyano, azido, nitro, unsubstituted or fluorinated $C_{1-3}$alkyl, unsubstituted or fluorinated $C_{1-3}$alkoxy, methylsulfinyl, methylsulfonyl, cyclopropyl, cyclopropylmethyl, cyclopropylmethoxy, benzyloxy, benzylsulfinyl, thienyl and pyridyl, and is preferably chloro or bromo,
R7 is selected from hydrogen, fluoro, chloro, bromo, cyano, methyl, methoxy, fluoromethyl, fluoromethoxy, methylsulfinyl and methylsulfonyl,
X3 is N or C(R12),
R8 is selected from hydrogen, fluoro, chloro, cyano, methoxy and fluoromethoxy,
R9 is hydrogen or fluoro, preferably hydrogen,
R10 is selected from fluoro, chloro, bromo, iodo, azido, cyano, oxetanyl, cyano($C_{1-2}$)alkyl, cyano($C_{1-2}$)alkoxy, cyclopropyl($C_{1-2}$)alkyl, cyclobutyl($C_{1-2}$)alkyl, cyclopropyl($C_{1-2}$)alkoxy, optionally fluorinated $C_{1-2}$alkoxycyclopropyl, optionally fluorinated $C_{1-2}$alkoxycarbonylcyclopropyl, unsubstituted or fluorinated $C_{1-3}$ alkyl, preferably methyl, ethyl and fluoromethyl, unsubstituted or fluorinated $C_{1-3}$ alkoxy, preferably methoxy, difluoromethoxy, difluoroethoxy and trifluoroethoxy, unsubstituted or fluorinated $C_{2-3}$ alkenyl, unsubstituted or fluorinated $C_{2-3}$ alkynyl, unsubstituted or fluorinated $C_{1-3}$ alkoxy($C_{1-3}$)alkyl, preferably methoxypropyl, ethoxyethyl, and fluoromethoxymethyl, unsubstituted or fluorinated $C_{1-3}$ alkoxy($C_{1-3}$)alkoxy, preferably methoxyethoxy and fluoromethoxyethoxy, unsubstituted or fluorinated $C_{1-3}$ alkoxy($C_{2-3}$)alkenyl, preferably methoxypropenyl, ethoxyethenyl and fluoromethoxypropenyl, and pentafluorosulfanyl,
R11 is selected from hydrogen, fluoro, chloro, methoxy, fluoromethoxy and fluoromethyl.
R12, if present, is hydrogen or fluoro, preferably hydrogen
wherein, in a preferred embodiment, at least one of R8 and R11 is different from hydrogen,
wherein, in another preferred embodiment, R6 is not hydrogen,
and pharmaceutically acceptable salts, solvates, isotopes and co-crystals thereof.

One preferred embodiment relates to compounds of Formula I-2,
wherein
X1 is N, or C(R7),
X2 is NH, S or O, preferably NH,
R2 is hydrogen,
R4 is selected from hydrogen and fluoro,
R5 is selected from hydrogen, fluoro, chloro, and bromo,
R6 is selected from halogen, azido, cyano, benzyloxy, thienyl preferably thien-2-yl, unsubstituted or fluorinated $C_{1-3}$ alkyl preferably isopropyl and fluoromethyl, cyclopropyl, cyclopropylmethyl, cyclopropylmethoxy, unsubstituted or fluorinated $C_{1-3}$ alkoxy preferably methoxy, fluoromethoxy and fluoroethoxy, methylsulfinyl and methylsulfonyl, wherein R6 is preferably chloro or bromo,
R7 is selected from hydrogen, fluoro, bromo, chloro, cyano, methyl, fluoromethyl, methoxy, fluoromethoxy, fluoroethoxy, methylsulfinyl and methylsulfonyl,
X3 is N or C(R12),
R8 is selected from hydrogen, fluoro, methoxy and fluoromethoxy, and is preferably fluoro or methoxy,
R9 selected from hydrogen, fluoro and methoxy and is preferably hydrogen,
R10 is selected from fluoro, chloro, bromo, iodo, cyano, azido, nitro, pentafluorosulfanyl, $C_{1-3}$alkyl, $C_{1-3}$alkoxy, $C_{2-3}$alkenyl, $C_{2-3}$alkynyl, cyclopropyl, cyclopropylmethoxy and cyclopropylethoxy, wherein each alkyl, alkenyl and alkoxy group in R10 can be substituted with one or more residues selected from fluoro, chloro, cyano, $C_{1-3}$alkyloxy and fluoro($C_{1-3}$)alkyloxy, and wherein each cycloalkyl may be unsubstituted or substituted with a residue selected from fluoro, methyl, $C_{1-2}$ alkoxy, $C_{1-2}$ alkoxycarbonyl and cyano,
R11 is selected from hydrogen, fluoro, methyl, fluoromethyl, methoxy, and fluoromethoxy,
R12, if present, is hydrogen or fluoro, preferably hydrogen, and pharmaceutically acceptable salts, solvates, isotopes and co-crystals thereof,
wherein in a preferred embodiment, if X1 is N, then X2 is also N, and
wherein in another preferred embodiment, at least one of R8 and R11 is different from hydrogen.

One preferred embodiment relates to compounds of Formula I-2,
wherein
X1 is N or C(R7),
X2 is NH,
R2, R4 and R5 are all hydrogen,
R6 is selected from fluoro, chloro, bromo, azido, isopropyl, cyclopropyl, methoxy, fluoromethyl, fluormethoxy, methylsulfonyl, methylsulfinyl and benzyloxy and is preferably chloro or bromo,
R7 is selected from hydrogen, fluoro, chloro, bromo, cyano, methyl, ethyl, fluoromethyl, fluoroethyl, methoxy, fluoromethoxy, fluoroethoxy, methylsulfinyl and methylsulfonyl,
X3 is N or C(R12),
R8 is selected from fluoro and methoxy,
R9 is hydrogen,
R10 is selected from fluoro, chloro, bromo, iodo, cyano, azido, cyanomethyl, cyanoethyl, cyanomethoxy, cyanoethoxy, methyl, ethyl, propyl, cyclopropyl, cyclopropylmethyl, cyclopropylethyl, methoxymethyl, methoxyethyl, methoxypropyl, ethoxymethyl, ethoxyethyl, methoxy, ethoxy, propoxy, cyclopropylmethoxy, cyclopropylethoxy, methoxymethoxy, methoxyethoxy, methoxypropoxy, ethoxymethoxy, ethoxyethoxy, propoxymethoxy, ethenyl, propenyl, methoxyethenyl, methoxypropenyl, ethynyl, propynyl, methoxycarbonylethyl, ethoxycarbonylethyl, methoxycarbonylethenyl, ethoxycarbonylethenyl, and pentafluorosulfanyl, wherein each alkyl or alkoxy group in R10 can be fluorinated and/or hydroxylated, preferably fluorinated, one or more times, and wherein each cyclopropyl group may be substituted with a substituent selected from fluoro, $C_{1-2}$ alkoxy and $C_{1-2}$ alkoxycarbonyl,
R11 is selected from hydrogen, fluoro, chloro, fluoromethyl, methoxy and fluoromethoxy,
R12, if present, is hydrogen or fluoro,
and pharmaceutically acceptable salts, solvates, isotopes and co-crystals thereof.

One embodiment relates to compounds of Formula I or I-2, wherein
X1 is N or C(R7),
X2 is NH, S or O and is preferably NH,
X3 is N or CR12,
R2, if present, R4, R5 and R9 are all hydrogen,
R6 is selected from halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro and unsubstituted or fluorinated $C_{1-3}$alkoxy, R7 is selected from hydrogen, halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro and unsubstituted or fluorinated $C_{1-3}$alkoxy, R8 is selected from fluoro, methoxy and fluoromethoxy, preferably from fluoro and methoxy, R10 is selected from halogen, $C_{1-4}$alkoxy, $C_{1-4}$alkyl, $C_{2-3}$alkenyl $C_{2-3}$alkynyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro, cyano and unsubstituted or fluorinated $C_{1-3}$alkoxy, R11 is selected from hydrogen, fluoro, methoxy and fluoromethoxy, preferably from fluoro and methoxy, and R12, if present is selected from hydrogen, fluoro, fluoromethyl, methoxy and fluoromethoxy.

One embodiment of the present invention relates to compounds of Formula I, wherein X1 is CR7 and X2 is NH, thus having the structure of Formula II Formula II wherein R4, R5, R6, R7, R8, R9, R10, R11, R12, if present, and X3 are as described as for Formula I herein and pharmaceutically acceptable salts, solvates, isotopes and co-crystals thereof.

Another embodiment relates to compounds of Formula I, wherein X1 is N and X2 is NH, thus having the structure of Formula III Formula III wherein R4, R5, R6, R8, R9, R10, R11, R12, if present, and X3 are as described as for Formula I herein and pharmaceutically acceptable salts, solvates, isotopes and co-crystals thereof.

Another embodiment relates to compounds of Formula I, wherein X2 is O and X1 is C(R7), thus having the structure of Formula IV Formula IV wherein R4, R5, R6, R7, R8, R9, R10, R11, R12, if present, and X3 are as described as for Formula I herein and pharmaceutically acceptable salts, solvates, isotopes and co-crystals thereof.

Another embodiment relates to compounds of Formula I, wherein X2 is S and X1 is C(R7), thus having the structure of Formula V Formula V wherein R4, R5, R6, R7, R8, R9, R10, R11, R12, if present, and X3 are as described as for Formula I herein and pharmaceutically acceptable salts, solvates, isotopes and co-crystals thereof.

It is to be understood that subsequently in any definition of the substituents of compounds of Formula II, III, IV and V, the potential reference to R7 only applies to compounds of Formula II, IV and V, whereas the other substitutions apply to compounds of Formula III as well.

In one embodiment of the compounds of Formula I, II, III, IV and V, X3 is C(R12).

In one embodiment of the compounds of Formula I, II, III, IV and V, X3 is N.

In one embodiment, in the compounds having Formula III, at least one of R4, R5 and R6 is different from hydrogen, in particular at least one of R5 and R6 is different from hydrogen.

In one embodiment, in the compounds of Formula III, if R6 is hydrogen, then R5 is halogen; in one particular embodiment, R5 is iodo.

In one embodiment, in the compounds of Formula I, II, IV and/or V, at least one of R5, R6 and R7 is different from hydrogen.

In one embodiment, in the compounds of Formula I, II, III, IV and/or V, if R6 is hydrogen, then R7 is different from hydrogen, and is preferably selected from fluoro, chloro, bromo, cyano, methoxy, unsubstituted or fluorinated $C_{1-2}$alkyl, unsubstituted or fluorinated $C_{1-2}$ alkoxy, unsubstituted or fluorinated methylsulfonyl, and unsubstituted or fluorinated methylsulfinyl, and is preferably selected from fluoro, chloro, bromo, methyl, methoxy, fluoromethyl, fluoromethoxy, fluoroethoxy, methylsulfonyl and methylsulfinyl.

In one preferred embodiment, in the compounds of Formula I, II, III, IV and V, if R10 is hydrogen, then R8 and R11 are both different from hydrogen.

A further embodiment relates to compounds of Formula II, III, IV or V,
wherein
X3 is N or C(R12),
R4 is hydrogen,
R5 is selected from hydrogen, fluoro, chloro and bromo,
R6 is selected from fluoro, chloro, bromo, iodo, cyano, azido, nitro, methyl, ethyl, n-propyl, isopropyl, trifluoromethyl, methylsulfinyl, methylsulfonyl, cyclopropyl, cyclopropylmethyl, methoxy, ethoxy, methoxymethoxy, methoxyethoxy, ethoxymethoxy, cyclopropylmethoxy, phenyl, benzyloxy, phenyloxy, benzylsulfinyl, benzylsulfonyl, thienyl, pyridyl, oxazole, thiazole, and isoxazole, wherein each alkyl and alkoxy group in R6 can be substituted with one or more residues selected from fluoro, cyano, and hydroxy and wherein each phenyl, thienyl, pyridyl, oxazol, thiazole and isoxazol can be optionally substituted one or more times, preferably with a substitution selected from halogen, methoxy, fluoromethoxy, methyl and fluoromethyl, or, in the compounds of Formula II, IV or V, in particular in the compounds of formula II, R6 may form together with R7 and the carbon atoms to which R6 and R7 are attached, a ring selected from phenyl, pyridyl, cycloxhexyl and cyclopentyl, each of which can be unsubstituted or substituted one or more times with a group selected from methyl, fluorinated methyl, methoxy, fluorinated methoxy, hydroxy, chloro and fluoro,
R7 is selected from hydrogen, fluoro, chloro, bromo, iodo, cyano, methoxy, ethoxy, methylsulfinyl, methylsulfonyl, methyl, ethyl, fluoromethyl, fluoroethyl, and fluoro($C_{1-2}$) alkoxy, or R7 forms a ring together with R6 as described herein,
R8 is selected from hydrogen, fluoro, chloro, bromo, iodo, methoxy, fluoromethyl and fluoromethoxy, or R8 forms a ring system together with R9, as described herein,
R9 is selected from hydrogen, methyl, methoxy, fluoro and chloro and is preferably hydrogen,
or R9 forms together with R8 or R10 and the ring to which they are attached a bicyclic ring system selected from 2,1,3-benzothiadiazole, 2,1,3-benzoxadiazole, 2-oxo-2,3-dihydro-1,3-benzoxazole and 1,3-benzodioxole, which is optionally substituted with two fluoros,
or R9 forms together with R10 and the ring to which they are attached a bicyclic ring system selected from 3-oxo-2,3-dihydro-1H-isoindol, 1,1-dioxo-2,3-dihydro-1-benzothiophene, 3-oxo-1,3-dihydro-2-benzofuran which can be optionally methylated in 1 position,
R10 is selected from hydrogen, fluoro, chloro, bromo, iodo, unsubstituted or fluorinated $C_{1-3}$alkenyl including ethenyl and propenyl, unsubstituted or fluorinated $C_{1-3}$alkynyl including ethynyl and propargyl, unsubstituted or fluorinated and/or hydroxylated $C_{1-3}$alkyl including methyl, ethyl, isopropyl and trifluoromethyl, unsubstituted or fluorinated and/or hydroxylated $C_{1-3}$alkoxy including methoxy and fluoro($C_{1-2}$)alkoxy, cyano, cyanomethyl, cyanomethoxy, cyclopropyl, cyclopropylmethoxy, cyclopropylethoxy, acetyl, azido, nitro, pentafluorosulfanyl, unsubstituted or fluorinated and/or hydroxylated $C_{1-3}$alkoxy($C_{1,3}$)alkyl, preferably methoxypropyl and ethoxyethyl, unsubstituted or fluorinated and/or hydroxylated $C_{1,3}$alkoxy($C_{1-3}$)alkoxy, preferably methoxyethoxy and fluoromethoxyethoxy, unsubstituted or fluorinated and/or hydroxylated $C_{1-3}$alkoxy ($C_{2-3}$)alkenyl, preferably methoxypropenyl and ethoxyethenyl, unsubstituted or fluorinated and/or hydroxylated $C_{1-3}$alkoxy($C_{2-3}$)alkynyl, unsubstituted or fluorinated and/or hydroxylated $C_{1-3}$alkoxycarbonyl($C_{1-3}$)alkyl preferably ethoxycarbonylethyl, and unsubstituted or fluorinated and/or hydroxylated $C_{1-3}$alkoxycarbonyl($C_{1-3}$)alkenyl preferably ethoxycarbonylethenyl, wherein each cyclopropyl group in R10 may be unsubstituted or further substituted with one or more substituents selected from fluoro, chloro, cyano, optionally fluorinated $C_{1-2}$alkoxy and optionally fluorinated $C_{1-2}$alkoxycarbonyl or R10 forms a ring system together with R9, as described herein,
R11 is selected from hydrogen, fluoro, chloro, bromo, unsubstituted or fluorinated methyl, and unsubstituted or fluorinated methoxy,
R12, if present, is selected from hydrogen, fluoro, chloro, or bromo, and is preferably hydrogen or fluoro;
wherein, in a preferred embodiment, at least one, preferably two of R8, R10 and R11, are different from hydrogen and unsubstituted alkyl,
and wherein in one embodiment the residues in R10 are preferably unsubstituted or fluorinated,
and pharmaceutically acceptable salts, solvates, isotopes and co-crystals thereof.

One embodiment relates to compounds of Formula II, III IV and V, wherein
X3 is N or C(R12),
R4 is hydrogen,
R5 is selected from hydrogen, fluoro, chloro and bromo, R6 is selected from fluoro, chloro, bromo, azido, cyano, methyl, ethyl, n-propyl, isopropyl, trifluoromethyl, methylsulfinyl, methylsulfonyl, cyclopropyl, methoxy, phenyl, benzyloxy, thiophen-2-yl, and thiophen-3-yl, wherein each alkyl and alkoxy group in R6 can be unsubstituted or substituted with one or more residues selected from fluoro, cyclopropyl and methoxy, preferably with fluoro,
R7 is selected from hydrogen, fluoro, chloro, bromo, cyano, methyl, ethyl, methylsulfinyl, methylsulfonyl, fluoromethyl, fluoroethyl, methoxy, fluoromethoxy, fluoroethoxy, and fluoropropoxy,
R8 is selected from hydrogen, fluoro, chloro, bromo, methoxy, fluoromethyl and fluoromethoxy, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzoxadiazole, 2-oxo-2,3-dihydro-1,3-benzoxazole, 1,3-benzodioxole, or 2,2-difluoro-1,3-benzodioxole, or R9 forms together with R10 and the ring to which they are attached a bicyclic ring system selected from 3-oxo-2,3-dihydro-1H-isoindol, 1,1-dioxo-2,3-dihydro-1-benzothiophene, 3-oxo-1,3-dihydro-2-benzofuran and 1-methyl-3-oxo-1,3-dihydro-2-benzofuran,
R10 is selected from hydrogen, fluoro, chloro, bromo, iodo, methyl, ethyl, propyl, ethenyl, propenyl, ethynyl, propargyl, fluoro($C_{1-3}$) alkyl preferably trifluoromethyl, methoxy, ethoxy, fluoro($C_{1-3}$)alkoxy, cyano, cyanomethyl, cyanoethyl, cyanomethoxy, acetyl, azido, unsubstituted or fluorinated $C_{1-3}$alkoxy($C_{1-3}$)alkyl, unsubstituted or fluorinated $C_{1-3}$ alkoxy($C_{1-3}$)alkoxy, unsubstituted or fluorinated $C_{1-3}$alkoxy($C_{2-3}$)alkenyl, unsubstituted or fluorinated $C_{1-3}$alkoxy($C_{2-3}$)alkynyl, unsubstituted or fluorinated $C_{1-3}$ alkoxycyclopropyl, unsubstituted or fluorinated $C_{1-3}$ alkoxycarbonylcyclopropyl, and pentafluorosulfanyl, or R10 forms a ring system together with R9, as described herein, and wherein, in a preferred embodiment, R8 and R10 are not both hydrogen,
R11 is selected from hydrogen, fluoro, chloro, fluorinated methyl, and unsubstituted or fluorinated methoxy,
R12, if present, is selected from hydrogen and fluoro,
and pharmaceutically acceptable salts, solvates, isotopes and co-crystals thereof.

A further embodiment relates to compounds of Formula II, III or IV,
wherein
X3 is N or C(R12),
R4 and R5 are both hydrogen,
R6 is selected from fluoro, chloro, bromo, iodo, cyano, azido, methyl, ethyl, isopropyl, trifluoromethyl, acetyl, methylsulfinyl, methylsulfonyl, cyclopropyl, cyclopropylmethyl, methoxy, ethoxy, methoxyethoxy, cyclopropylmethoxy, phenyl, benzyloxy, phenyloxy, thienyl, pyridyl, oxazole, thiazole, and isoxazole,
or R6 forms together with R7 and the carbon atoms to which R6 and R7 are attached, a ring selected from phenyl, pyridyl, and cyclopentyl, R7 is selected from hydrogen, fluoro, chloro, bromo, iodo, methoxy, ethoxy, methyl, trifluoromethyl and fluoro($C_{1-2}$)alkoxy, or R7 forms a ring together with R6 as described herein,
R8 is selected from hydrogen, fluoro, chloro, bromo, iodo, methoxy, methyl, and trifluoromethyl, or R8 forms a ring system together with R9, as described herein,
R9 is selected from hydrogen, fluoro and chloro and is preferably hydrogen,
or R9 forms together with R8 or R10 and the ring to which they are attached a bicyclic ring system selected from 2,1,3-benzothiadiazole, 2,1,3-benzooxadiazole, 2-oxo-2,3-dihydro-1,3-benzoxazole and 1,3-benzodioxole, which is optionally substituted with two fluoros, R10 is selected from hydrogen, fluoro, chloro, bromo, iodo, ethynyl, propargyl, trifluoromethyl, methoxy, fluoro($C_{1-2}$)alkoxy, cyano, cyanomethyl, acetyl, azido, pentafluorosulfanyl, and methoxycarbonyl, or R10 forms a ring system together with R9, as described herein,
R11 is selected from hydrogen, fluoro, chloro, bromo, and methoxy,
R12 is selected from hydrogen, fluoro, chloro, or bromo.
wherein, in a preferred embodiment, at least one of R8, R9, R10 and R11 is different from hydrogen and unsubstituted alkyl,
and pharmaceutically acceptable salts, solvates, isotopes and co-crystals thereof.

One embodiment relates to compounds of Formula II, III and IV, wherein
X3 is N or C(R12),
R4 and R5 are both hydrogen,
R6 is selected from fluoro, chloro, bromo, azido, methyl, isopropyl, trifluoromethyl, methylsulfonyl, cyclopropyl, methoxy, phenyl, benzyloxy, thiophen-2-yl, and thiophen-3-yl,
R7 is selected from hydrogen, fluoro, chloro, and methoxy,
R8 is selected from hydrogen, fluoro, chloro, bromo, methoxy, and trifluoromethyl, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzooxadiazole, 2-oxo-2,3-dihydro-1,3-benzoxazole, 1,3-benzodioxole, or 2,2-difluoro-1,3-benzodioxole,
R10 is selected from hydrogen, fluoro, chloro, bromo, iodo, methyl, ethynyl, trifluoromethyl, methoxy, fluoro($C_{1-2}$) alkoxy, cyano, cyanomethyl, acetyl, azido, and pentafluorosulfanyl, or R10 forms a ring system together with R9, as described herein, and wherein, in a preferred embodiment, R8 and R10 are not both hydrogen,
R11 is selected from hydrogen, fluoro, chloro, and methoxy,
R12 is selected from hydrogen, and fluoro, and pharmaceutically acceptable salts, solvates, isotopes and co-crystals thereof.

One embodiment relates to compounds of Formula II, III IV or V,
wherein
R4 and R5 are both hydrogen,
R6 is methoxy, trifluoromethyl, bromo or chloro, preferably chloro,
R7 is hydrogen, fluoro, methoxy, or trifluoromethyl,
X3 is C(R12),
R9 forms together with R8 or R10 and the phenyl ring to which R8 and R9, or R9 and R10 are attached, a 2,1,3-benzothiadiazole or 2,2-difluoro-1,3-benzodioxole,
R10 is selected from hydrogen and fluoro,
R11 is selected from hydrogen, fluoro and methoxy, and is preferably hydrogen, and
R12, if present, is hydrogen or fluoro,
and pharmaceutically acceptable salts, solvates, isotopes and co-crystals thereof.

One embodiment relates to compounds of Formula II, III or IV,
wherein
R4 and R5 are both hydrogen,
R6 is bromo or chloro, preferably chloro,
R7 is hydrogen, fluoro, methoxy, or trifluoromethyl,
X3 is C(R12),
R9 forms together with R8 or R10 and the phenyl ring to which R8 and R9, or R9 and R10 are attached, a 2,1,3-benzothiadiazole or 2,2-difluoro-1,3-benzodioxole,
R10 is selected from hydrogen and fluoro,
R11 is selected from hydrogen, fluoro and methoxy, and
R12 is hydrogen,
and pharmaceutically acceptable salts, solvates, isotopes and co-crystals thereof.

One preferred embodiment relates to compounds of Formula I,
wherein
R 4 and R5 are both hydrogen,
R6 is chloro or bromo, preferably chloro,
R7 is hydrogen, fluoro, methoxy, or trifluoromethyl,
X3 is N or C(R12),
R8 is selected from fluoro, chloro and methoxy,
R9 is hydrogen, R10 is selected from fluoro, chloro, bromo, cyano, cyanomethyl, trifluoromethyl and pentafluorosulfanyl,
R11 is selected from hydrogen, fluoro and methoxy,
R12 is hydrogen
and pharmaceutically acceptable salts, solvates, isotopes and co-crystals thereof.

One preferred embodiment of the present invention relates to compound of Formula II, III IV or V, wherein
X3 is N or C(R12),
R4 is hydrogen or fluoro, preferably hydrogen,
R5 is selected from hydrogen, fluoro, chloro, bromo, iodo, methyl, methoxy, and fluorinated $C_{1-2}$ alkyl, including trifluoromethyl, preferably hydrogen, methyl, fluoro, chloro, bromo or iodo, or R5 forms a ring together with R6 as described herein,
R6 is selected from hydrogen, fluoro, chloro, bromo, iodo, cyano, azido, unsubstituted or substituted $C_{1-3}$ alkyl, preferably methyl, ethyl, isopropyl, difluoromethyl, difluoroethyl, trifluoroethyl and/trifluoromethyl, unsubstituted or substituted $C_{2-3}$ alkenyl, unsubstituted or substituted $C_{2-3}$ alkynyl, unsubstituted or unsubstituted or substituted $(C_{1-3})$ alkylsulfinyl preferably methylsulfinyl, unsubstituted or unsubstituted or substituted $C_{1-3}$ alkylsulfonyl preferably methylsulfonyl, unsubstituted or substituted $C_{3-6}$ cycloalkyl preferably cyclopropyl, unsubstituted or substituted $C_{3-6}$ cycloalkyl($C_{1-3}$)alkyl preferably cyclopropylmethyl, unsubstituted or substituted $C_{3-6}$ cycloalkyl($C_{1-3}$)alkyloxy preferably cyclopropylmethoxy, unsubstituted or substituted $C_{3-6}$ heterocycloalkyl, unsubstituted or substituted $C_{3-6}$ heterocycloalkyl($C_{1-3}$)alkyloxy preferably heterocyclopropylmethoxy unsubstituted or substituted $C_{3-6}$ cycloalkoxy, unsubstituted or substituted $C_{3-6}$ heterocycloalkoxy, unsubstituted or substituted $C_{1-3}$ alkoxy preferably methoxy, difluoromethoxy, trifluoromethoxy, difluoroethoxy, trifluoroethoxy unsubstituted or substituted $C_{1-3}$alkoxy($C_{1-3}$)alkoxy, preferably methoxyethoxy, unsubstituted or substituted $C_{1-3}$alkoxy($C_{1-3}$)alkyl, $C_{3-6}$ cycloalkyl($C_{1-3}$)alkoxy preferably cyclopropylmethoxy, unsubstituted or substituted phenyl, unsubstituted or substituted phenyl($C_{1-3}$)alkyl preferably benzyl, unsubstituted or substituted phenyl($C_{1-3}$)alkoxy preferably benzyloxy, unsubstituted or substituted phenyloxy, unsubstituted or substituted phenyl($C_{1-3}$)alkylsulfonyl preferably benzylsulfonyl, unsubstituted or substituted phenyl($C_{1-3}$)alkylsulfinyl preferably benzylsulfinyl, unsubstituted or substituted thienyl, unsubstituted or substituted pyridyl, unsubstituted or substituted oxazole, unsubstituted or substituted thiazole, and unsubstituted or substituted isoxazole, and wherein each optional substitution in R6 is preferably selected from fluoro, chloro, unsubstituted or fluorinated methyl, unsubstituted or fluorinated methoxy, hydroxy, and cyano,
provided that in the compounds of Formula III, if R6 is hydrogen, then at least one of R5 and R7 is different from hydrogen, wherein R5 is preferably iodo,
or
(i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl,
wherein each substitution, if present, is selected from halogen, hydroxy, methyl or methoxy, wherein each methyl or methoxy can be unsubstituted or substituted with one or more substituents selected from halogen, preferably fluoro, and methoxy,
or
(ii) R6 forms together with R5 and the carbon atoms to which R6 and R5 are attached, a 1,3-dioxolane which may be unsubstituted or substituted with one or two substituents selected from fluoro and methyl,
R7 is selected hydrogen, fluoro, chloro, bromo, iodo, cyano, $C_{1-3}$ alkyl, $C_{1-3}$ alkyloxy preferably methoxy, fluoro($C_{1-3}$)alkyl preferably difluoromethyl or trifluoromethyl, fluoro($C_{1-3}$)alkoxy preferably difluoromethoxy, difluoroethoxy, trifluoroethoxy and trifluoromethoxy, methylsulfinyl, methylsulfonyl, fluorinated methylsulfinyl, fluorinated methylsulfonyl, substituted or unsubstituted $C_{3-6}$ cycloalkyl, substituted or unsubstituted $C_{3-6}$ heterocycoalkyl, substituted or unsubstituted $C_{3-6}$ cycloalkyloxy, substituted or unsubstituted $C_{3-6}$ heterocycoalkyloxy, substituted or unsubstituted $C_{5-6}$ heteroaryl, substituted or unsubstituted $C_{3-6}$ heteroaryloxy, and $C_{5-6}$ heteroarylmethoxy, wherein the heteroaryl is preferably selected from pyridyl, oxazol and isoxazol, and wherein the heteroaryl may be substituted with one or more substituents selected from halogen, unsubstituted or fluorinated methyl, unsubstituted or fluorinated methoxy, or R7 forms a ring together with R6 as described herein,
R8 is selected from hydrogen, fluoro, chloro, bromo, iodo, cyano, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl,
R9 is selected from hydrogen, fluoro, chloro, bromo, iodo, cyano, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl, and is preferably hydrogen, methoxy, or fluoro,
R10 is selected from hydrogen, fluoro, chloro, bromo, iodo, $C_{1-3}$ alkyl, halo($C_{1-3}$)alkyl, preferably fluoro(C-s)alkyl preferably trifluoromethyl, $C_{2-3}$ alkenyl, $C_{2-3}$ alkynyl, $C_{1-3}$ alkyloxy, halo($C_{1-3}$)alkyloxy preferably fluoro($C_{1-3}$)alkoxy, cyano, cyanomethyl, cyanoethyl, unsubstituted or fluorinated $C_{1-3}$ alkylcarbonyl preferably acetyl, unsubstituted or fluorinated $C_{1-3}$ alkoxycarbonyl preferably methoxycarbonyl, cyclopropyl, cyclopropyloxy, azido, pentafluorosulfanyl, and nitro, wherein any cyclopropyl residue is preferably substituted with a group selected from fluoro, cyano, $C_{1-3}$alkoxy and $C_{1-3}$alkoxycarbonyl, and wherein each alkyl, alkoxy, alkenyl or alkynyl in R10 can be optionally further substituted with one or more substituents selected from cyclopropyl, fluoro, chloro, bromo, iodo, cyano, hydroxy, halo($C_{1-3}$)alkoxy and $C_{1-3}$ alkoxy, preferably with fluoro, methoxy, fluoromethoxy or fluoroethoxy,
R11 is selected from hydrogen, fluoro, chloro, cyano, $C_{1-3}$ alkyl preferably methyl, fluoro($C_{1-3}$)alkyl preferably fluoromethyl, $C_{1-3}$ alkyloxy preferably methoxy, fluoro($C_{1-3}$) alkoxy preferably fluoro($C_{1-2}$)alkoxy, and is more preferably hydrogen, fluoro, chloro, methoxy, fluoromethoxy or fluoromethyl,
R12, if present, is selected from hydrogen, fluoro, chloro, bromo, iodo, $C_{1-3}$ alkyloxy preferably methoxy, fluoro($C_{1-3}$) alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, or fluoromethyl,
wherein, in a preferred embodiment, at least one of R8, R10 and R11 is different from hydrogen, and more preferably at least one of R8, R10 and R11 is also different from unsubstituted alkyl,
and wherein, preferably, in the compounds of Formula II, at least one of R5, R6 and R7, if present, is not hydrogen,
and pharmaceutically acceptable salts, solvates, isotopes and co-crystals thereof.

One preferred embodiment of the present invention relates to compound of Formula II, III or IV, wherein X3 is N or C(R12), R4 is hydrogen, R5 is selected from hydrogen, fluoro, chloro, bromo, iodo, methyl, methoxy, acetyl, methoxycarbonyl and trifluoromethyl, preferably hydrogen, methyl or iodo, or R5 forms a ring together with R6 as described herein, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, unsubstituted or fluorinated $C_{1-2}$ alkylcarbonyl, unsubstituted or fluorinated $C_{1-2}$ alkoxycarbonyl, $(C_{1-3})$alkylsulfinyl preferably methylsulfinyl, $C_{1-3}$ alkylsulfonyl preferably methylsulfonyl, $C_{3-6}$ cycloalkyl preferably cyclopropyl, $C_{3-6}$ cycloalkyl$(C_{1-3})$alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, unsubstituted or substituted $C_{1-3}$alkoxy$(C_{1-3})$alkoxy, preferably methoxyethoxy, $C_{3-6}$ cycloalkyl$(C_{1-3})$alkoxy preferably cyclopropylmethoxy, unsubstituted or substituted phenyl, unsubstituted or substituted phenyl$(C_{1-3})$alkoxy preferably benzyloxy, unsubstituted or substituted phenyloxy, thienyl, pyridyl, oxazole, thiazole, and isoxazole, and wherein each optional substitution in R6 is preferably selected from fluoro, chloro, methyl, methoxy, and cyano, provided that in the compounds of Formula III, if R6 is hydrogen, then R5 is different from hydrogen, and is preferably iodo, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, methyl or methoxy, wherein each methyl or methoxy can be unsubstituted or substituted with one or more substituents selected from fluoro and methoxy, or (ii) R6 forms together with R5 and the carbon atoms to which R6 and R5 are attached, a 1,3-dioxolane which may be unsubstituted or substituted with one or two substituents selected from fluoro and methyl, R7 is selected hydrogen, fluoro, chloro, bromo, iodo, cyano, $C_{1-3}$ alkyl, $C_{1-3}$ alkyloxy, fluoro$(C_{1-3})$alkyl preferably trifluoromethyl, fluoro$(C_{1-3})$alkoxy preferably trifluoromethoxy, unsubstituted or fluorinated $C_{1-2}$ alkylcarbonyl, unsubstituted or fluorinated $C_{1-2}$ alkoxycarbonyl, methylsulfinyl, and methylsulfonyl, or R7 forms a ring together with R6 as described herein, R8 is selected from hydrogen, fluoro, chloro, bromo, iodo, $C_{1-3}$ alkyloxy preferably methoxy, fluoro$(C_{1-3})$alkoxy, $C_{1-3}$ alkyl preferably methyl, and fluoro$(C_{1-3})$alkyl preferably trifluoromethyl, R9 is selected from hydrogen, fluoro, chloro, bromo, iodo, cyano, $C_{1-3}$ alkyloxy preferably methoxy, fluoro$(C_{1-3})$alkoxy, $C_{1-3}$ alkyl preferably methyl, and fluoro$(C_{1-3})$alkyl preferably trifluoromethyl, and is preferably hydrogen fluoro, chloro, or bromo, R10 is selected from hydrogen, fluoro, chloro, bromo, iodo, $C_{1-3}$ alkyl, halo$(C_{1-3})$alkyl, preferably fluoro$(C_{1-3})$alkyl, particularly trifluoromethyl, $C_{2-3}$ alkynyl, $C_{1-3}$ alkyloxy, halo$(C_{1-3})$ alkyloxy, preferably fluoro$(C_{1-2})$alkoxy, cyano, cyanomethyl, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro, R11 is selected from hydrogen, fluoro, chloro, bromo, iodo, $C_{1-3}$ alkyl preferably methyl, fluoro$(C_{1-3})$alkyl preferably trifluoromethyl, $C_{1-3}$ alkyloxy preferably methoxy, fluoro$(C_{1-3})$alkoxy, preferably fluoro$(C_{1-2})$alkoxy, unsubstituted or fluorinated $C_{1-3}$ alkylcarbonyl preferably acetyl, unsubstituted or fluorinated $C_{1-3}$ alkoxycarbonyl preferably methoxycarbonyl and cyano, and, and is more preferably hydrogen, fluoro, chloro or bromo, R12 is selected from hydrogen, fluoro, chloro, bromo, iodo, $C_{1-3}$ alkyloxy preferably methoxy, fluoro$(C_{1-3})$alkoxy preferably fluoro$(C_{1-2})$alkoxy, $C_{1-3}$ alkyl preferably methyl, and fluoro$(C_{1-3})$alkyl preferably trifluoromethyl, and is more preferably hydrogen, fluoro, chloro, or bromo, wherein, in a preferred embodiment, at least one of R8, R9, R10 and R11 is different from hydrogen, and more preferably at least one of R8, R9, R10 and R11 is also different from unsubstituted alkyl, and pharmaceutically acceptable salts, solvates, isotopes and co-crystals thereof One preferred embodiment of the present invention relates to compounds of Formula II, III IV or V, wherein R4 is hydrogen or fluoro, more preferably hydrogen, R5 is selected from hydrogen, fluoro, bromo, chloro, iodo and methyl, R6 is selected from hydrogen, fluoro, chloro, bromo, iodo, methyl, ethyl, propyl preferably isopropyl, acetyl, cyano, nitro, azido, methylsulfonyl, methylsulfinyl, fluoro$(C_{1-2})$ alkyl, methoxy, ethoxy, fluoro$(C_{1-2})$alkoxy, $C_{1-2}$alkoxymethoxy, fluorinated $(C_{1-2})$alkoxymethoxy, fluorinated $(C_{1-2})$alkoxymethyl, phenyl, phenoxy, benzyloxy, benzylsulfinyl, pyrid-3-yl, thien-2-yl, thien-3-yl, cyclopropyl, cyclopropyloxy, cyclopropylmethyl, and cyclopropylmethoxy, wherein each phenyl, thienyl, pyridyl, and cyclopropyl can be optionally substituted one or more times with methoxy, fluoro and/or chloro, and wherein R6 is preferably not hydrogen, or, in compounds of Formula II, R6 may form, together with R7 and the carbon atoms to which R6 and R7 are attached a ring selected from an unsubstituted or substituted phenyl, unsubstituted or substituted pyridyl, and unsubstituted or substituted cyclohexyl, and unsubstituted or substituted cyclopentyl, wherein any substitution of such phenyl, pyridyl and cyclopentyl is selected from fluoro, chloro, hydroxy, fluorinated or unsubstituted methoxy and fluorinated or unsubstituted methyl, wherein the ring is preferably selected from unsubstituted phenyl, pyridyl or cyclopentyl, R7 is selected from hydrogen, fluoro, chloro, bromo, cyano, methyl, methoxy, methylsulfonyl, methylsulfinyl, fluoromethyl, fluoroethyl, fluoromethoxy, fluoroethoxy, and optionally methylated isoxazol which is preferably 3,5-dimethyl-1,2-oxazol, X3 is N or C(R12), and is preferably C(R12), R8 is selected from hydrogen, methoxy, fluoromethoxy, cyano, chloro and fluoro, and is preferably fluoro, methoxy or fluoromethoxy, R9 is selected from hydrogen, methoxy, and fluoro, R10 is selected from hydrogen, ethenyl, propenyl, ethynyl, propargyl, cyano, cyanomethyl, acetyl, fluoro, chloro, bromo, iodo, azido, nitro, unsubstituted or fluorinated $C_{1-3}$alkyl, preferably methyl and trifluoromethyl, hydroxy$(C_{1-3})$alkoxy preferably hydroxyethoxy, cyano$(C_{1-3})$alkoxy preferably cyanomethoxy, cyclopropyl$(C_{1-2})$alkyl, cyclopropyl$(C_{1-3})$alkoxy preferably cyclopropylmethoxy, unsubstituted or fluorinated $C_{1-3}$ alkoxy preferably difluoroethoxy and trifluoroethoxy, unsubstituted or fluorinated $C_{1-2}$alkoxy $(C_{1-3})$alkyl preferably methoxypropyl and ethoxyethyl, unsubstituted or fluorinated $C_{1-2}$alkoxy$(C_{1-3})$alkoxy preferably methoxyethoxy and fluoromethoxyethoxy, unsubstituted or fluorinated $C_{1-2}$alkoxy($C_{2-3}$)alkenyl preferably methoxypropenyl, unsubstituted or fluorinated $C_{1-2}$alkoxy ($C_{2-3}$)alkynyl, and pentafluorosulfanyl, $C_{1-2}$alkoxycyclopropyl and $C_{1-2}$alkoxycarbonylcyclopropyl, R11 is selected from hydrogen, fluoro, chloro, cyano, fluoromethyl, methoxy and fluoromethoxy, R12 is hydrogen or fluoro, and wherein at least one, preferably at least two of R8, R10 and R11 are different from hydrogen, and pharmaceutically acceptable salts, solvates, isotopes and co-crystals thereof.

One preferred embodiment of the present invention relates to compounds of Formula II, III or IV, wherein R4 is hydrogen or fluoro, more preferably hydrogen, R5 is hydrogen, iodo, or methyl, R6 is selected from hydrogen, fluoro, chloro, bromo, iodo, methyl, ethyl, isopropyl, acetyl, trifluoromethyl, methoxy, ethoxy, fluoro($C_{1-2}$)alkoxy, ($C_{1-2}$)alkoxymethoxy, cyanomethylsulfonyl, phenyl, phenoxy, benzyloxy, 2-pyridyl, 3-pyridyl, 4-pyridyl, 2-thienyl, 3-thienyl, cyclopropyl, cyclopropyloxy, and cyclopropylmethoxy, or R6 forms, together with R7 and the carbon atoms to which R6 and R7 are attached a ring selected from an unsubstituted or substituted phenyl, unsubstituted or substituted pyridyl, and unsubstituted or substituted cyclopentyl, wherein any substitution is selected from fluoro, methoxy and methyl, wherein the ring is preferably selected from unsubstituted phenyl, pyridyl or cyclopentyl, and wherein in Formula II, if R6 is hydrogen, then R5 is iodo, R7 is selected from hydrogen, methyl, methoxy, trifluoromethyl, fluoro, chloro and bromo, X3 is N or C(R12), and is preferably C(R12), R8 is selected from hydrogen, methoxy, cyano, chloro and fluoro, R9 is selected from hydrogen and fluoro, R10 is selected from hydrogen, ethynyl, cyano, cyanomethyl, acetyl, fluoro, chloro, bromo, iodo, azido, nitro, trifluoromethyl, difluoroethoxy, trifluoroethoxy, and pentafluorosulfanyl, R11 is selected from hydrogen, fluoro, chloro, and methoxy, R12 is hydrogen or fluoro and wherein at least one of R8, R9, R10 and R11 is different from hydrogen and pharmaceutically acceptable salts, solvates, isotopes and co-crystals thereof.

One preferred embodiment of the present invention relates to compound of Formula II, III IV or V, particularly preferably of Formula II or III, wherein R4 is hydrogen, R5 is selected from hydrogen, fluoro, chloro and bromo, and is preferably hydrogen, R6 is selected from fluoro, chloro, bromo, cyano, methyl, ethyl, propyl preferably isopropyl, methylsulfinyl, methylsulfonyl, cyclopropyl, cyclopropyloxy, benzyloxy, thienyl, methoxy, ethoxy, fluoro($C_{1-3}$)alkoxy and fluoro($C_{1-3}$)alkyl preferably trifluoromethyl, R7 is selected from hydrogen, methoxy, fluoro, chloro, bromo, cyano, methylsulfinyl, methylsulfonyl, $C_{1-3}$alkoxy, fluoro($C_{1-3}$)alkoxy, $C_{1-3}$alkyl and fluoro($C_{1-3}$)alkyl preferably trifluoromethyl, or, in compounds of Formula II, R6 and R7, together with the ring-forming C atoms to which they are attached, may form a ring selected from phenyl, cyclopentyl and pyridyl, each of which may be unsubstituted or substituted with one or more residues selected from fluoro, chloro, hydroxy, fluorinated or unsubstituted methoxy and fluorinated or unsubstituted methyl, wherein the phenyl, cyclopentyl and cyclohexyl rings are preferably unsubstituted and wherein the pyroidyl ring is preferably unsubstituted or substituted in 8-position, X3 is —C(R12)- or N, R8 is hydrogen, fluoro, methoxy or fluoromethoxy, and is preferably fluoro or methoxy, R9 is hydrogen, R10 is selected from halogen, azido, nitro, cyano, $C_{1-3}$alkyl, $C_{2-3}$alkenyl, $C_{2-3}$alkynyl, $C_{1-3}$ alkoxy, $C_{3-5}$cycloalkyl preferably cyclopropyl, $C_{3-5}$cycloalkyloxy and pentafluorosulfanyl, wherein each alkyl, alkenyl, alkynyl and alkoxy can be unsubstituted or substituted with one or more residues selected from halogen preferably fluoro, cyano, cyclopropyl, $C_{1-3}$alkoxy, and fluoro$C_{1-3}$alkoxy, and wherein any cycloalkyl moiety can be unsubstituted or substituted with one or more residues selected from fluoro, cyano, unsubstituted or fluorinated $C_{1-3}$alkoxy and unsubstituted or fluorinated $C_{1-3}$alkoxycarbonyl, R11 is selected from hydrogen, fluoro, chloro, cyano, methoxy, fluoromethoxy, and fluoromethyl, and R12 is selected from hydrogen and fluoro, wherein preferably at least one of R8 and R11 is different from hydrogen, and wherein preferably at least one of R8 and R11 is selected from fluoro, chloro and methoxy, and pharmaceutically acceptable salts, solvates, isotopes and co-crystals thereof.

One embodiment relates to compounds of Formula II, III IV and V, preferably of Formula II and III;

wherein

R4 and R5 are both hydrogen,

R6 is selected from methyl, ethyl, propyl, methylsulfonyl, methylsulfinyl, methoxy, mono-, di- and trifluoromethyl, mono-, di- and trifluoroethyl, mono-, di- and trifluoromethoxy, mono-, di- and trifluoroethoxy, cyano, azido, fluoro, bromo and chloro, and is preferably selected from chloro and bromo, R7, if present, is selected from hydrogen, fluoro, chloro, bromo, cyano, methoxy, fluoromethoxy, fluoroethoxy, methyl, fluoromethyl, methylsulfinyl and methylsulfonyl, X3 is C(R12), R8 is selected from hydrogen, fluoro, chloro and methoxy, or forms a ring with R9 as described herein, R9 forms together with R8 or R10 and the phenyl ring to which R8 and R9, or R9 and R10 are attached, a 2,1,3-benzothiadiazole or 1,3-benzodioxole which is optionally substituted with two fluoros, R10 is selected from hydrogen and fluoro, or R10 forms a ring together with R9 as described above, R11 is selected from hydrogen, fluoro and methoxy, R12 is hydrogen and pharmaceutically acceptable salts, solvates, isotopes and co-crystals thereof.

One preferred embodiment of the present invention relates to compound of Formula II, III IV or V, particularly preferably of Formula II or III, wherein R4, R5 are both hydrogen, R6 is selected from fluoro, chloro, bromo, methoxy, fluoromethoxy and fluoromethyl, R7 is selected from hydrogen, methoxy, fluoro, chloro, bromo, fluoromethyl preferably trifluoromethyl, fluoromethoxy, fluoroethoxy, methylsulfinyl and methylsulfonyl, X3 is N or CR12, R8 is fluoro or methoxy, R9 is hydrogen, R10 is selected from fluoro, chloro, bromo, cyano, cyanomethyl, cyanoethyl, cyanomethoxy, unsubstituted or fluorinated $C_{1-3}$ alkyl preferably methyl, ethyl and fluoromethyl, unsubstituted or fluorinated $C_{1-3}$ alkoxy preferably fluoromethoxy and fluoroethoxy, unsubstituted or fluorinated $C_{1-2}$alkoxy($C_{1-3}$)alkyl preferably methoxypropyl, fluorinated methoxypropyl, ethoxyethyl, and fluorinated methoxymethyl, unsubstituted or fluorinated $C_{1-2}$alkoxy ($C_{2-3}$)alkenyl including methoxypropenyl and ethoxyethenyl, unsubstituted or fluorinated $C_{1-2}$alkoxy($C_{1-3}$)alkoxy preferably methoxyethoxy, pentafluorosulfanyl and cycloalkyl, which is substituted with a substituent selected from $C_{1-2}$alkoxy, fluoro($C_{1-2}$)alkoxy, $C_{1-2}$alkoxycarbonyl and fluoro($C_{1-2}$)alkoxycarbonyl R11 is selected from hydrogen, methoxy, fluoromethoxy, fluoromethyl, and fluoro, R12, if present, is hydrogen or fluoro, and pharmaceutically acceptable salts, solvates, isotopes and co-crystals thereof.

One preferred embodiment of the present invention relates to compound of Formula II, III or IV, particularly preferably of Formula II or III, wherein R4 and R5 are both hydrogen, R6 is selected from fluoro, chloro, bromo, isopropyl, benzyloxy, and trifluoromethyl, R7 is hydrogen, methoxy, fluoro, or bromo, preferably hydrogen, or R6 and R7, together with the ring-forming C atoms to which they are attached, form a ring selected from phenyl, cyclopentyl and pyridyl, X3 is —C(R12)-, R8 is fluoro, hydrogen, or methoxy, R9 is hydrogen, R10 is ethynyl, trifluoromethyl, difluoroethoxy, cyano, chloro, bromo, or iodo, R11 is selected from hydrogen and fluoro, and R12 is selected from hydrogen and fluoro, and pharmaceutically acceptable salts, solvates, isotopes and co-crystals thereof.

One embodiment relates to compounds of Formula II, III and IV, preferably of Formula II and III;

wherein

R4 and R5 are both hydrogen,

R6 is bromo or chloro, preferably chloro,

R7 is hydrogen, methoxy, fluoro or trifluoromethyl,

X3 is C(R12),

R8 is selected from hydrogen, fluoro, and methoxy, or forms a ring with R9 as described herein, R9 forms together with R8 or R10 and the phenyl ring to which R8 and R9, or R9 and R10 are attached, a 2,1,3-benzothiadiazole or 1,3-benzodioxole which is optionally substituted with two fluoros, R10 is selected from hydrogen and fluoro, or R10 forms a ring together with R9 as described above, R11 is selected from hydrogen, fluoro and methoxy, R12 is hydrogen and pharmaceutically acceptable salts, solvates, isotopes and co-crystals thereof.

One preferred embodiment of the present invention relates to compound of Formula II, III or IV, particularly preferably of Formula II or III, wherein R4, R5 are hydrogen, R6 is bromo, chloro, or trifluoromethyl, R7 is hydrogen, methoxy, fluoro, or trifluoromethyl, R8 is fluoro or methoxy, R9 is hydrogen, R10 is selected from fluoro, chloro, bromo, cyano, cyanomethyl, trifluoromethyl, difluoroethoxy, and pentafluorosulfanyl, R11 is selected from hydrogen, methoxy and fluoro, and pharmaceutically acceptable salts, solvates, isotopes and co-crystals thereof.

One embodiment of the present invention relates to compounds of Formula II, III, IV or V, preferably of Formula II or III, wherein X3 is C(R12), R4 is hydrogen or fluoro, preferably hydrogen, R5 is selected from hydrogen, fluoro, chloro, bromo, iodo, methyl, and trifluoromethyl, preferably hydrogen, or R5 forms a ring together with R6 as described herein, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, $C_{1-2}$ alkylcarbonyl, $C_{1-2}$ alkoxycarbonyl, ($C_{1-3}$)alkylsulfinyl preferably methylsulfinyl, ($C_{1-3}$)alkylsulfonyl, preferably methylsulfonyl, unsubstituted or substituted benzylsulfonyl, unsubstituted or substituted benzylsulfinyl, $C_{3-6}$ cycloalkyl preferably cyclopropyl, $C_{3-6}$ cycloalkyl($C_{1-3}$)alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, mono di- and trifluoroethoxy, unsubstituted or substituted $C_{1-3}$alkoxy ($C_{1-3}$)alkoxy, preferably methoxyethoxy, unsubstituted or substituted $C_{1-3}$alkoxy($C_{1-3}$)alkyl, ($C_{3-6}$)cycloalkyl($C_{1-3}$) alkoxy preferably cyclopropylmethoxy, unsubstituted or substituted phenyl, unsubstituted or substituted phenyl ($C_{1-3}$)alkoxy preferably benzyloxy, unsubstituted or substituted phenyloxy, thienyl, pyridyl, oxazole, thiazole, and isoxazole, and wherein each optional substitution in R6 is preferably selected from fluoro, chloro, unsubstituted or fluorinated methyl, unsubstituted or fluorinated methoxy, hydroxy, and cyano, provided that in the compounds of Formula III, if R6 is hydrogen, then R5 is preferably iodo, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, hydroxy, methyl or methoxy, wherein each methyl or methoxy can be unsubstituted or substituted with one or more substituents selected from halogen, preferably fluoro, and methoxy, or (ii) R6 forms together with R5 and the carbon atoms to which R6 and R5 are attached, a 1,3-dioxolane which may be unsubstituted or substituted with one or two substituents selected from fluoro and methyl, R7 is selected from hydrogen, fluoro, chloro, bromo, iodo, cyano, $C_{1-3}$ alkyl, $C_{1-3}$ alkyloxy, fluoro($C_{1-3}$)alkyl preferably trifluoromethyl, fluoro($C_{1-3}$)alkoxy preferably fluoromethoxy or fluoroethoxy, $C_{1-2}$ alkylcarbonyl, $C_{1-2}$alkoxycarbonyl, methylsulfinyl, and methylsulfonyl, or R7 forms a ring together with R6 as described herein, R8 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl, R9 forms together with R10 and the ring to which they are attached a bicyclic ring system selected from 2,1,3-benzothiadiazole, 2,1,3-benzoselenadiazole, 2,1,3-benzoxadiazole, 2-oxo-2,3-dihydro-1,3-benzoxazole, 1,3-benzothiazole, 2,3-dihydro-1-benzothiophene, which is substituted with one or two oxo (preferably substituted with two oxo to give 1,1-dioxo-2,3-dihydro-1-benzothiophene), 3-oxo-1,3-dihydro-2-benzofuran-5-yl, which may be unsubstituted or substituted with one or two groups selected from oxo, fluoro and methyl, preferably with at least one oxo group to preferably form 3-oxo-1,3-dihydro-2-benzofuran or 1-methyl-3-oxo-1,3-dihydro-2-benzofuran, and dihydroisoindol which may be unsubstituted or substituted with one or more substituents selected from oxo, fluoro and methyl and which preferably is 3-oxo-2,3-dihydro-1H-isoindol, and 1,3-benzodioxole, which is optionally substituted with one or two fluoros to preferably form 2,2-difluoro-1,3-benzodioxol, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy, preferably fluoro($C_{1-2}$)alkoxy, cyano, and, and is more preferably hydrogen, fluoro, chloro or bromo, R12 is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo, and pharmaceutically acceptable salts, solvates, isotopes and co-crystals thereof.

One embodiment of the present invention relates to compounds of Formula II, III, or IV, preferably of Formula II or III, wherein X3 is C(R12), R4 is hydrogen, R5 is selected from hydrogen, fluoro, chloro, bromo, iodo, methyl, and trifluoromethyl, preferably hydrogen or iodo, or R5 forms a ring together with R6 as described herein, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, $C_{1-2}$ alkylcarbonyl, $C_{1-2}$ alkoxycarbonyl, ($C_{1-3}$)alkylsulfinyl preferably methylsulfinyl, ($C_{1-3}$)alkylsulfonyl, preferably methylsulfonyl, $C_{3-6}$ cycloalkyl preferably cyclopropyl, $C_{3-6}$ cycloalkyl($C_{1-3}$)alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, unsubstituted or substituted $C_{1-3}$alkoxy($C_{1-3}$)alkoxy, preferably methoxyethoxy, ($C_{3-6}$)cycloalkyl($C_{1-3}$)alkoxy preferably cyclopropylmethoxy, unsubstituted or substituted phenyl, unsubstituted or substituted phenyl($C_{1-3}$)alkoxy preferably benzyloxy, unsubstituted or substituted phenyloxy, thienyl, pyridyl, oxazole, thiazole, and isoxazole, and wherein each optional substitution in R6 is preferably selected from fluoro, chloro, methyl, methoxy, and cyano, provided that in the compounds of Formula II, if R6 is hydrogen, then R5 is preferably iodo, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, methyl or methoxy, wherein each methyl or methoxy can be unsubstituted or substituted with one or more substituents selected from fluoro and methoxy, or (ii) R6 forms together with R5 and the carbon atoms to which R6 and R5 are attached, a 1,3-dioxolane which may be unsubstituted or substituted with one or two substituents selected from fluoro and methyl, R7 is selected from hydrogen, fluoro, chloro, bromo, iodo, cyano, $C_{1-3}$ alkyl, $C_{1-3}$ alkyloxy, fluoro($C_{1-3}$)alkyl preferably trifluoromethyl, fluoro($C_{1-3}$)alkoxy preferably trifluoromethoxy, $C_{1-2}$ alkylcarbonyl, $C_{1-2}$ alkoxycarbonyl, methylsulfinyl, and methylsulfonyl, or R7 forms a ring together with R6 as described herein, R8 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl, or R9 forms together with R10 and the ring to which they are attached a bicyclic ring system selected from 2,1,3-benzothiadiazole, 2,1,3-benzoselenadiazole, 2,1,3-benzooxadiazole, 2-oxo-2,3-dihydro-1,3-benzoxazole, 1,3-benzothiazole, 2,3-dihydro-1-benzothiophene, which is substituted with one or two oxo (preferably substituted with two oxo to give 1,1-dioxo-2,3-dihydro-1-benzothiophene), 3-oxo-1,3-dihydro-2-benzofuran-5-yl, and 1,3-benzodioxole, which is optionally substituted with one or two fluoros, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy, preferably fluoro($C_{1-2}$)alkoxy, cyano, and, and is more preferably hydrogen, fluoro, chloro or bromo, R12 is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo, and pharmaceutically acceptable salts, solvates, isotopes and co-crystals thereof.

One preferred embodiment of the present invention relates to compound of Formula II, III or Formula IV, particularly preferably of Formula II or III, wherein X3 is C(R12), R4, R5 are both hydrogen, R6 is selected from fluoro, chloro, bromo, methoxy, trifluoromethyl, methylsulfonyl, and cyano, or R6 forms, together with R7 and the carbon atoms to which R6 and R7 are attached a ring selected from an unsubstituted or substituted phenyl, unsubstituted or substituted pyridyl, unsubstituted or substituted cyclohexyl, and unsubstituted or substituted cyclopentyl, wherein any substitution is selected from fluoro, methoxy and methyl, and wherein the ring is preferably selected from unsubstituted phenyl, pyridyl, cyclohexyl or cyclopentyl, R7 is selected from hydrogen, methyl, fluoromethyl preferably trifluoromethyl, methoxy, fluoro, chloro and bromo, preferably from hydrogen, fluoro and trifluoromethyl, or R7 forms a ring together with R6 as described herein, R8 is hydrogen or fluoro, R9 together with R10 and the C atoms to which they are attached form a ring selected from 2,1,3-benzothiadiazole, 2,1,3-benzoxadiazole, 3-oxo-2,3-dihydro-1H-isoindol, 3-oxo-1,3-dihydro-2-benzofuran, 1-methyl-3-oxo-1,3-dihydro-2-benzofuran, and 2,2 difluoro-substituted 1,3-benzodioxole, preferably a 2,1,3-benzothiadiazole, R11 is hydrogen or fluoro, preferably hydrogen, and R12 is hydrogen or fluoro, and pharmaceutically acceptable salts, solvates, isotopes and co-crystals thereof.

One preferred embodiment of the present invention relates to compound of Formula II, III or Formula IV, particularly preferably of Formula II or III, wherein X3 is C(R12), R4, R5 are both hydrogen, R6 is fluoro, chloro, bromo, trifluoromethyl, methylsulfonyl, or cyano, or R6 forms, together with R7 and the carbon atoms to which R6 and R7 are attached a ring selected from an unsubstituted or substituted phenyl, unsubstituted or substituted pyridyl, and unsubstituted or substituted cyclopentyl, wherein any substitution is selected from fluoro, methoxy and methyl, and wherein the ring is preferably selected from unsubstituted phenyl, pyridyl or cyclopentyl, R7 is selected from hydrogen, methyl, trifluoromethyl, methoxy, fluoro, chloro and bromo, preferably from hydrogen and bromo, or R7 forms a ring together with R6 as described herein, R8 is hydrogen or fluoro, R9 together with R10 and the C atoms to which they are attached form a ring selected from an 2,1,3-benzothiadiazole, 2,1,3-benzooxadiazole, and 2,2 difluoro-substituted 1,3-benzodioxole, preferably a 2,1,3-benzothiadiazole, R11 is hydrogen or fluoro, and R12 is hydrogen or fluoro, and pharmaceutically acceptable salts, solvates, isotopes and co-crystals thereof.

A further embodiment relates to compounds of Formula II, III IV or V, wherein

X3 is C(R12),

R4 is hydrogen or fluoro, preferably hydrogen,

R5 is selected from hydrogen, fluoro, chloro, bromo, iodo, methyl, and fluoromethyl, preferably hydrogen, or R5 forms a ring together with R6 as described herein, R6 is selected from hydrogen, fluoro, chloro, bromo, iodo, cyano, azido, unsubstituted or substituted $C_{1-3}$ alkyl, preferably methyl, ethyl, propyl, mono-, di- and trifluoromethyl, unsubstituted or substituted $C_{1-2}$ alkylcarbonyl, unsubstituted or substituted $C_{1-2}$ alkoxycarbonyl, $(C_{1-3})$ alkylsulfinyl preferably methylsulfinyl, $(C_{1-3})$alkylsulfonyl, preferably methylsulfonyl, $C_{3-6}$ cycloalkyl preferably cyclopropyl, $C_{3-6}$ cycloalkyl($C_{1-3}$)alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, mono-, di- and trifluoromethoxy, mono-, di- and trifluoroethoxy, unsubstituted or substituted $C_{1-3}$alkoxy($C_{1-3}$) alkoxy, preferably methoxyethoxy, unsubstituted or substituted $C_{1-3}$alkoxy($C_{1-3}$)alkyl, $(C_{3-6})$cycloalkyl($C_{1-3}$)alkoxy preferably cyclopropylmethoxy, unsubstituted or substituted phenyl, unsubstituted or substituted phenyl($C_{1-3}$)alkoxy preferably benzyloxy, unsubstituted or substituted phenyloxy, thienyl, pyridyl, oxazole, thiazole, and isoxazole, and wherein each optional substitution in R6 is preferably selected from fluoro, chloro, methyl, methoxy, and cyano, provided that in the compounds of Formula III, if R6 is hydrogen, then R5 is preferably iodo, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, hydroxy, methyl or methoxy, wherein each methyl or methoxy can be unsubstituted or substituted with one or more substituents selected from fluoro and methoxy, or (ii) R6 forms together with R5 and the carbon atoms to which R6 and R5 are attached, a 1,3-dioxolane which may be unsubstituted or substituted with one or two substituents selected from fluoro and methyl, R7, if present, is selected from hydrogen, fluoro, chloro, bromo, iodo, cyano, $C_{1-3}$ alkyl, $C_{1-3}$ alkyloxy, fluoro($C_{1-3}$) alkyl preferably trifluoromethyl, fluoro($C_{1-3}$)alkoxy preferably fluoromethoxy or fluoroethoxy, unsubstituted or fluorinated $C_{1-2}$ alkylcarbonyl, unsubstituted or fluorinated $C_{1-2}$ alkoxycarbonyl, methylsulfinyl, pyridylmethoxy, isoxazol and methylsulfonyl, or R7 forms a ring together with R6 as described herein, R9 forms together with R8 and the ring to which they are attached a bicyclic ring system selected from 2,1,3-benzothiadiazole, 2,1,3-benzoselenadiazole, 2,1,3-benzoxadiazole, 2-oxo-2,3-dihydro-1,3-benzoxazole, and 1,3-benzodioxole, which is optionally substituted with one or two fluoros, R10 is selected from hydrogen, fluoro, chloro, bromo, iodo, $C_{1-3}$ alkyl, halo($C_{1-3}$)alkyl, preferably fluoro($C_{1-2}$)alkyl, halogenated preferably fluorinated or unsubstituted $C_{1-3}$alkoxy($C_{1-3}$)alkyl, $C_{2-3}$ alkynyl, halogenated preferably fluorinated or unsubstituted $C_{1-3}$alkoxy($C_{1-3}$)alkenyl, methoxy, ethoxy, halo($C_{1-3}$)alkyloxy preferably fluoro($C_{1-2}$) alkoxy, halogenated preferably fluorinated or unsubstituted $C_{1-3}$alkoxy($C_{1-3}$)alkoxy, cyano, cyanomethyl, cyanoethyl, unsubstituted or fluorinated $C_{1-3}$ alkylcarbonyl preferably acetyl, unsubstituted or fluorinated $C_{1-3}$ alkoxycarbonyl preferably methoxycarbonyl, cyclopropylmethoxy, $(C_{1-2})$ alkoxycyclopropyl, $(C_{1-2})$alkoxycarbonylcyclopropyl, azido, pentafluorosulfanyl, and nitro, and wherein in one embodiment, R10 is hydrogen, methoxy or halogen, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy, preferably fluoro($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl and cyano, and is more preferably hydrogen, fluoro, chloro or bromo, R12 is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo.

and pharmaceutically acceptable salts, solvates, isotopes and co-crystals thereof.

A further embodiment relates to compounds of Formula II, III or IV, wherein

X3 is C(R12),

R4 is hydrogen,

R5 is selected from hydrogen, fluoro, chloro, bromo, iodo, methyl, and trifluoromethyl, preferably hydrogen or iodo, or R5 forms a ring together with R6 as described herein, R6 is selected from hydrogen, fluoro, chloro, bromo, iodo, cyano, azido, unsubstituted or substituted $C_{1-3}$ alkyl, preferably methyl, ethyl, isopropyl, or trifluoromethyl, unsubstituted or substituted $C_{1-2}$ alkylcarbonyl, unsubstituted or substituted $C_{1-2}$ alkoxycarbonyl, $(C_{1-3})$ alkylsulfinyl preferably methylsulfinyl, $(C_{1-3})$alkylsulfonyl, preferably methylsulfonyl, $C_{3-6}$ cycloalkyl preferably cyclopropyl, $C_{3-6}$ cycloalkyl($C_{1-3}$)alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, unsubstituted or substituted $C_{1-3}$alkoxy($C_{1-3}$) alkoxy, preferably methoxyethoxy, $(C_{3-6})$cycloalkyl($C_{1-3}$)alkoxy preferably cyclopropylmethoxy, unsubstituted or substituted phenyl, unsubstituted or substituted phenyl($C_{1-3}$)alkoxy preferably benzyloxy, unsubstituted or substituted phenyloxy, thienyl, pyridyl, oxazole, thiazole, and isoxazole, and wherein each optional substitution in R6 is preferably selected from fluoro, chloro, methyl, methoxy, and cyano, provided that in the compound of Formula II, if R6 is hydrogen, then R5 is preferably iodo,
or
(iii) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl,
wherein each substitution, if present, is selected from halogen, methyl or methoxy, wherein each methyl or methoxy can be unsubstituted or substituted with one or more substituents selected from fluoro and methoxy,
or
(iv) R6 forms together with R5 and the carbon atoms to which R6 and R5 are attached, a 1,3-dioxolane which may be unsubstituted or substituted with one or two substituents selected from fluoro and methyl,
R7 is selected from hydrogen, fluoro, chloro, bromo, iodo, cyano, $C_{1-3}$ alkyl, $C_{1-3}$ alkyloxy, fluoro($C_{1-3}$)alkyl preferably trifluoromethyl, fluoro($C_{1-3}$)alkoxy preferably trifluoromethoxy, unsubstituted or fluorinated $C_{1-2}$ alkylcarbonyl, unsubstituted or fluorinated $C_{1-2}$ alkoxycarbonyl, methylsulfinyl, and methylsulfonyl, or R7 forms a ring together with R6 as described herein,
R9 forms together with R8 and the ring to which they are attached a bicyclic ring system selected from 2,1,3-benzothiadiazole, 2,1,3-benzoselenadiazole, 2,1,3-benzooxadiazole, 2-oxo-2,3-dihydro-1,3-benzoxazole, and 1,3-benzodioxole, which is optionally substituted with one or two fluoros,
R10 is selected from hydrogen, fluoro, chloro, bromo, iodo, $C_{1-3}$ alkyl, halo($C_{1-3}$)alkyl, preferably fluoro($C_{1-2}$)alkyl, $C_{2-3}$ alkynyl, methoxy, ethoxy, halo($C_{1-3}$)alkyloxy, preferably fluoro($C_{1-2}$)alkoxy, cyano, cyanomethyl, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro, and wherein in one embodiment, R10 is hydrogen, methoxy or halogen,
R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy, preferably fluoro($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl and cyano, and is more preferably hydrogen, fluoro, chloro or bromo,
R12 is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo.
and pharmaceutically acceptable salts, solvates, isotopes and co-crystals thereof.

Another embodiment relates to compounds of Formula II, III IV or V, particularly preferably of Formula II or III, wherein
X3 is C(R12),
R4 and R5 are both hydrogen,
R6 is selected from fluoro, chloro, bromo, methoxy, fluoromethoxy, methylsulfinyl, methylsulfonyl, and fluoromethyl, and is preferably chloro, bromo or fluoromethyl,
or R6 forms, together with R7 and the carbon atoms to which R6 and R7 are attached, a ring selected from an unsubstituted or substituted phenyl, unsubstituted or substituted pyridyl, unsubstituted or substituted cyclohexyl, and unsubstituted or substituted cyclopentyl, wherein any substitution is selected from fluoro, fluorinated or unsubstituted methoxy and fluorinated or unsubstituted methyl, and wherein the ring is preferably selected from unsubstituted phenyl, pyridyl, cycloxexyl or cyclopentyl,
R7 is selected from hydrogen, fluoro, chloro, bromo, methoxy, methyl, acetyl, cyano, fluoromethyl, fluoromethoxy and fluoroethoxy, preferably from hydrogen and trifluoromethyl, or R7 forms a ring together with R6 as described herein,
R8 together with R9 and the C atoms to which they are attached form a ring selected from 2,1,3-benzoselenadiazole, 2,1,3-benzothiadiazole, 2,1,3-benzoxadiazole, unsubstituted 1,3-benzodioxole, 2-oxo-2,3-dihydro-1,3-benzoxazole, and 2,2-difluoro-1,3-benzodioxole,
R10 is selected from hydrogen, fluoro, chloro, bromo and fluoromethyl,
R11 is selected from hydrogen, cyano, fluoro and chloro, and is preferably hydrogen, and
R12 is selected from hydrogen, fluoro, chloro and fluoromethyl,
and pharmaceutically acceptable salts, solvates, isotopes and co-crystals thereof.

Another embodiment relates to compounds of Formula II, III or IV, particularly preferably of Formula II or III, wherein
X3 is C(R12),
R4 and R5 are both hydrogen,
R6 is selected from fluoro, chloro, bromo, and trifluoromethyl,
or R6 forms, together with R7 and the carbon atoms to which R6 and R7 are attached a ring selected from an unsubstituted or substituted phenyl, unsubstituted or substituted pyridyl, and unsubstituted or substituted cyclopentyl, wherein any substitution is selected from fluoro, methoxy and methyl, and wherein the ring is preferably selected from unsubstituted phenyl, pyridyl or cyclopentyl,
R7 is selected from hydrogen, fluoro, chloro, bromo, methoxy, methyl, acetyl and trifluoromethyl, preferably from hydrogen and trifluoromethyl, or R7 forms a ring together with R6 as described herein,
R8 together with R9 and the C atoms to which they are attached form a ring selected from 2,1,3-benzothiadiazole, 2,1,3-benzooxadiazole, unsubstituted 1,3-benzodioxole, 2-oxo-2,3-dihydro-1,3-benzoxazole, and 2,2-difluoro-1,3-benzodioxole,
R10 is hydrogen, or fluoro,
R11 is selected from hydrogen, fluoro, chloro, bromo and cyano, and
R12 is hydrogen, fluoro, chloro, and trifluoromethyl and pharmaceutically acceptable salts, solvates, isotopes and co-crystals thereof.

Another embodiment relates to compounds of Formula II, III IV or V, particularly preferably of Formula II or III, wherein X3 is C(R12),
R4 and R5 are both hydrogen,
R6 is selected from fluoro, chloro, bromo, and fluoromethyl, or R6 forms, together with R7 and the carbon atoms to which R6 and R7 are attached, a ring selected phenyl, pyridyl, cyclohexyl and cyclopentyl,
R7, if present, is selected from hydrogen, fluoro, chloro, bromo, methoxy, methyl, fluoromethyl, fluoromethoxy and fluoroethoxy, preferably from hydrogen, fluoro and trifluoromethyl, or R7 forms a ring together with R6 as described herein, R8 together with R9 and the C atoms to which they are attached form a ring selected from 2,1,3-benzothiadiazole, 2,1,3-benzoxadiazole, and 2,2-difluoro-1,3-benzodioxole, R10 is hydrogen or fluoro, R11 is selected from hydrogen, fluoro and cyano, and R12 is selected from hydrogen, fluoro and fluoromethyl, and pharmaceutically acceptable salts, solvates, isotopes and co-crystals thereof.

One embodiment relates to compounds of the general formula II, III, IV and V which are optionally substituted in 2-position of the upper bicyclic ring, thus having structures according to the general formula II-2, III-2, IV-2 and V-2 as depicted below:

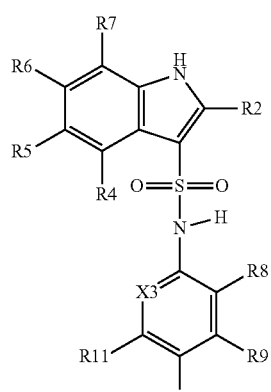

Formula II-2

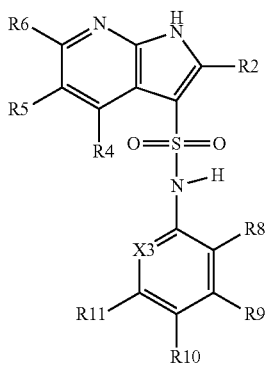

Formula III-2

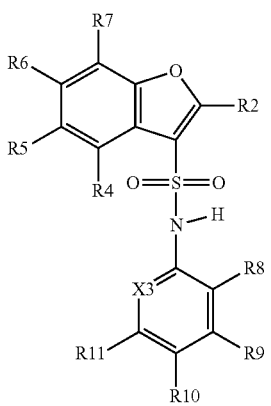

Formula IV-2

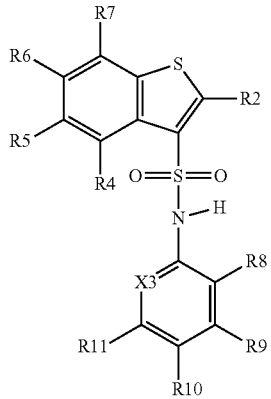

Formula V-2 wherein R2 is selected from hydrogen, fluoro, chloro, bromo, iodo and methoxy, and is preferably hydrogen or fluoro, particularly preferably hydrogen, and wherein R4, R5, R6, R7, if present, R8, R9, R10, R11 and X3 are as described for the respective corresponding compounds of formula II, III, IV and V herein.

In one preferred embodiment of the present invention, in the compounds of Formula II, II-2, III, III-2, IV, IV-2, V and V-2, X3 is N or CR12, R2, if present, R4, R5 and R9 are all hydrogen, R6 is selected from halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro and unsubstituted or fluorinated $C_{1-3}$alkoxy, R7 is selected from hydrogen, halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro and unsubstituted or fluorinated $C_{1-3}$alkoxy, R8 is selected from fluoro, methoxy and fluoromethoxy, preferably from fluoro and methoxy, R10 is selected from halogen, $C_{1-4}$alkoxy, $C_{1-4}$alkyl, $C_{2-3}$alkenyl $C_{2-3}$alkynyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro, cyano and unsubstituted or fluorinated $C_{1-3}$alkoxy, and R11 is selected from hydrogen, fluoro, methoxy and fluoromethoxy, preferably from fluoro and methoxy, and R12, if present is selected from hydrogen, fluoro, fluoromethyl, methoxy and fluoromethoxy.

In a further embodiment, the compounds of the present invention are represented by one of the following Formulae IIa-IIc:

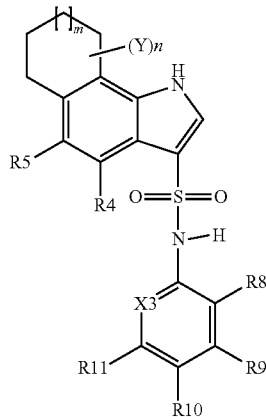

Formula IIa

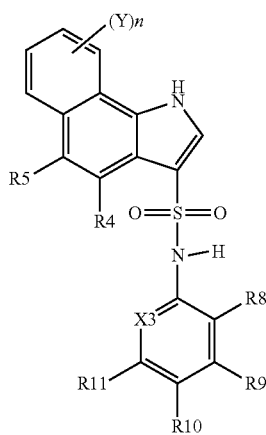

Formula IIb

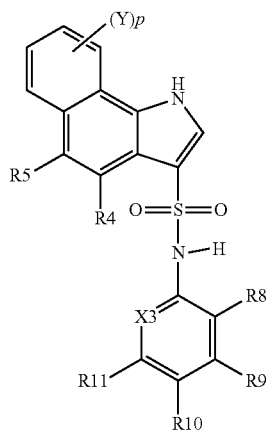

Formula IIc wherein
n is any number from 0 to 4,
m is 0 or 1,
p is any number from 0 to 3,
and
any Y is an independently selected substitution selected from the group consisting of halogen, hydroxy, cyano, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, $C_{3-7}$ heterocycloalkyl($C_{1-3}$)alkyl, $C_{1-6}$ alkoxy, and $C_{1-6}$ alkoxy($C_{1-3}$)alkyl wherein each alkyl or alkoxy can be unsubstituted or substituted with one or more substituents selected from halogen and $C_{1-3}$ alkoxy,
R4, R5, X3, R8, R9, R10, R11 and R12 are as described in the compounds of Formula I, and II herein.

According to one embodiment, in the compounds of Formula II(a) to II(c)
m is 0 or 1, preferably 0,
n is any number from 0 to 4, preferably from 0 to 2, more preferably 0 or 1,
p is any number from 0 to 3, preferably from 0 to 2, more preferably 0 or 1,
any Y is an independently selected substitution selected from the group of halogen, hydroxy, cyano, $C_{1-3}$ alkyl, $C_{1-3}$ alkoxy, and $C_{1-3}$alkoxy($C_{1-3}$)alkyl wherein each alkyl or alkoxy can be unsubstituted or substituted with one or more substituents selected from halogen and $C_{1-3}$ alkoxy,
R4 is hydrogen or fluoro, preferably hydrogen,
R5 is selected from hydrogen, halogen, $C_{1-3}$ alkyl, and $C_{1-3}$ alkoxy, wherein each alkyl or alkoxy may optionally be substituted one or more times, preferably with methoxy or halogen,
X3 is N or C(R12),
R8 is selected from hydrogen, $C_{1-3}$ alkyl, $C_{1-3}$ alkoxy, and halogen, wherein each alkyl or alkoxy can be unsubstituted or substituted with one or more substituents selected from halogen, cyano and methoxy, or R8 forms a ring system together with R9, as described herein,
R9 is selected from hydrogen, $C_{1-3}$ alkyl, $C_{1-3}$ alkoxy, fluoro, chloro, bromo and iodo, wherein each alkyl or alkoxy can be unsubstituted or substituted with one or more substituents selected from halogen and methoxy, and wherein R9 is preferably hydrogen,
or R9 forms together with R8 or R10 and the ring to which they are attached a bicyclic ring system selected from 2,1,3-benzothiadiazole, 2,1,3-benzoselenadiazole, 2,1,3-benzoxadiazole, 1,3-benzoxazole which may optionally be partially hydrogenated and 2-oxo-substituted, 1,3-benzodioxole which may be unsubstituted or substituted with one or two substituents selected from fluoro and methyl, 1,3-benzothiazole, 2,3-dihydro-1-benzothiophene, which is substituted with one or two oxo(preferably substituted with two oxo to give 1,1-dioxo-2,3-dihydro-1-benzothiophene), 3-oxo-2,3-dihydro-1H-isoindol, or 1,3 dihydro-2-benzofuran, which may be unsubstituted or substituted with one or two groups selected from oxo, fluoro and methyl, preferably with one oxo group, or with one oxo and one methyl group,
R10 is selected from hydrogen, fluoro, chloro, bromo, iodo, $C_{1-3}$ alkyl, $C_{1-3}$ alkoxy, $C_{2-4}$ alkenyl, $C_{2-4}$ alkynyl, cyano, cyanomethyl, cyanoethyl, cyanomethoxy, $C_{1-3}$ alkylcarbonyl, $C_{1-3}$ alkoxycarbonyl, azido, pentafluorosulfanyl, and nitro, wherein each alkyl, alkenyl, alkynyl or alkoxy can be unsubstituted or substituted with one or more substituents selected from halogen, cyano, hydroxy, fluoro($C_{1-3}$)alkoxy and $C_{1-3}$ alkoxy, or R8 forms a ring system together with R9, as described herein,
R11 is selected from hydrogen, $C_{1-3}$ alkyl, $C_{1-3}$ alkoxy, $C_{1-3}$ alkylcarbonyl, $C_{1-3}$ alkoxycarbonyl, fluoro, chloro, bromo, and iodo, wherein each alkyl and alkoxy can be unsubstituted or substituted with one or more substituents selected from fluoro, chloro, bromo, iodo and $C_{1-3}$ alkoxy,
R12, if present, is selected from hydrogen, $C_{1-3}$ alkyl, $C_{1-3}$ alkoxy, fluoro, chloro, bromo, and iodo, wherein each alkyl and alkoxy can be unsubstituted or substituted with one or more substituents selected from fluoro, chloro, bromo, iodo and $C_{1-3}$ alkoxy,
wherein, in a preferred embodiment, at least one of R8, R10 and R11 is different from hydrogen, and more preferably at least one of R8, R9, R10 and R11 is also different from unsubstituted alkyl, and pharmaceutically acceptable salts, solvates, isotopes and co-crystals thereof.

In one preferred embodiment, in the compounds having a structure of Formula IIa, IIb, and IIc, Y is selected from hydrogen, halogen, hydroxy, unsubstituted or fluorinated methyl and unsubstituted or fluorinated methoxy. In one embodiment, Y is fluoro, chloro, methoxy or trifluoromethyl. In one preferred embodiment, the values for n and p are independently 0, 1 or 2.

In another preferred embodiment, in the compounds having a structure of Formula IIa, IIb, or IIc, the values for m, n and p are all 0.

In a particularly preferred embodiment of the compounds of Formula IIa, IIb and IIc,
m is 0 or 1,
n and p are independently 0, 1 or 2,
Y is selected from halogen, hydroxy, fluorinated methyl and unsubstituted or fluorinated methoxy,
R4 is hydrogen,
R5 is hydrogen, methyl, methoxy, or halogen, preferably hydrogen,
X3 is N or C(R12),
R8 is selected from hydrogen, fluoro, chloro, bromo, methoxy, fluoromethoxy, and fluoromethyl, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzoxadiazole, 1,3-benzodioxole, 2-oxo-2,3-dihydro-1,3-benzoxazole, 2,2-difluoro-1,3-benzodioxole and 4-methyl-2-oxodihydrobenzofuran,
R10 is selected from hydrogen, fluoro, chloro, bromo, iodo, methyl, cyano, cyanomethyl, cyanoethyl, cyanomethoxy, ethenyl, propenyl, ethynyl, propargyl, pentafluorosulfanyl, unsubstituted, fluorinated or hydroxylated $C_{1-3}$alkyloxy including mono-, di- and trifluoromethoxy and mono-, di- and trifluoroethoxy, unsubstituted or fluorinated $C_{1-3}$alkyloxy($C_{1-3}$)alkyl, unsubstituted or fluorinated $C_{1-3}$alkyloxy ($C_{1-3}$)alkyloxy, unsubstituted or fluorinated $C_{1-3}$alkyloxy ($C_{2-3}$)alkenyl, unsubstituted or fluorinated $C_{1-3}$alkyloxy($C_{2-3}$)alkynyl, unsubstituted or fluorinated $C_{1-3}$alkyl including trifluoromethyl, and cyclopropyl which is substituted with a substituent selected from hydroxy, hydroxymethyl, $C_{1-2}$ alkoxy and $C_{1-2}$ alkoxycarbonyl,
or R10 forms a ring system together with R9, as described herein,
R11 is selected from hydrogen, fluoro, chloro, and methoxy,
R12, if present, is selected from hydrogen, and fluoro,
and pharmaceutically acceptable salts, solvates, isotopes and co-crystals thereof,
wherein in one preferred embodiment, if R9 does not form a ring with R8 or R10, then R10 is not hydrogen, and, more preferably, R8 and R10 are both not hydrogen.

In a particularly preferred embodiment of the compounds of Formula IIa, IIb and IIc, the values for m, n and p are all 0,
R4 is hydrogen,
R5 is hydrogen, methyl, methoxy, or halogen, preferably hydrogen,
X3 is N or C(R12),
R8 is selected from hydrogen, fluoro, chloro, bromo, methoxy, fluoromethoxy, and mono-, di-, and trifluoromethyl, and is preferably selected from fluoro and methoxy, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzoxadiazole, 1,3-benzodioxole, 2-oxo-2,3-dihydro-1,3-benzoxazole, or 2,2-difluoro-1,3-benzodioxole,
R10 is selected from hydrogen, fluoro, chloro, bromo, iodo, cyano, cyanomethyl, cyanoethyl, cyanomethoxy, pentafluorosulfanyl, fluoro($C_{1-2}$)alkoxy preferably difluoroethoxy or trifluoroethoxy, and fluoro($C_{1-2}$)alkyl preferably trifluoromethyl, or R10 forms a ring system together with R9, as described herein,
R11 is selected from hydrogen, fluoro, chloro, methoxy and fluoromethoxy, preferably from fluoro and methoxy,
R12, if present, is selected from hydrogen, methoxy and fluoro, and pharmaceutically acceptable salts, solvates, isotopes and co-crystals thereof, wherein in one preferred embodiment, if R9 does not form a ring with R8, then R10 is not hydrogen, and more preferably, R8 and R10 are both not hydrogen.

In a particularly preferred embodiment of the compounds of Formula IIa, IIb and IIc, the values for m, n and p are all 0,
R4 is hydrogen,
R5 is hydrogen, methyl, methoxy, or halogen, preferably hydrogen,
R8 is selected from hydrogen, fluoro, chloro, bromo, methoxy, and trifluoromethyl, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzooxadiazole, 1,3-benzodioxole, 2-oxo-2,3-dihydro-1,3-benzoxazole, or 2,2-difluoro-1,3-benzodioxole, R10 is selected from hydrogen, fluoro, chloro, bromo, cyano, cyanomethyl, pentafluorosulfanyl, difluoroethoxy, trifluoroethoxy, and trifluoromethyl, or R10 forms a ring system together with R9, as described herein, wherein, in a preferred embodiment, R8 and R10 are not both hydrogen,
R11 is selected from hydrogen, fluoro, chloro, and methoxy,
R12 is selected from hydrogen, and fluoro,
and pharmaceutically acceptable salts, solvates, isotopes and co-crystals thereof.

A further embodiment relates to compounds of Formula IIa to IIc, wherein
m is 0 or 1, preferably 0,
n is any number from 0 to 3, and is preferably 0 or 1,
p is any number from 0 to 2, and is preferably 0 or 1, any Y is a substitution independently selected from the group of halogen, hydroxy, $C_{1-3}$ alkyl, $C_{1-3}$ alkoxy, wherein each alkyl or alkoxy can be unsubstituted or substituted with one or more substituents selected from halogen and $C_{1-3}$ alkoxy,
R4 is hydrogen,
R5 is selected from hydrogen, fluoro, chloro, bromo, iodo, methyl, methoxy, and trifluoromethyl, and is preferably hydrogen,
X3 is N or C(R12),
R8 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl,
R9 is selected from hydrogen, fluoro, chloro, or bromo, and is preferably hydrogen,
R10 is selected from hydrogen, fluoro, chloro, bromo, iodo, $C_{1-3}$ alkyl, $C_{2-3}$ alkenyl, $C_{2-3}$ alkynyl, $C_{1-3}$ alkyloxy, cyano, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro, wherein each alkyl, alkoxy, alkenyl or alkynyl can be optionally substituted with one or more substituents selected from halogen, cyano, hydroxy, and unsubstituted or fluorinated and/or hydroxylated $C_{1-3}$ alkoxy, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy preferably fluoro($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl and cyano, and is more preferably hydrogen, fluoro, chloro or bromo, R12, if present, is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo.

wherein, in a preferred embodiment, at least one of R8, R10 and R11 is different from hydrogen, and preferably at least one of R8, R10 and R11 is also different from unsubstituted alkyl, wherein, in one preferred embodiment, R10 is different from hydrogen, and in a particularly preferred embodiment R10 and R8 are both not hydrogen, and pharmaceutically acceptable salts, solvates, isotopes and co-crystals thereof.

A further embodiment relates to compounds of Formula IIa to IIc, wherein m is 0 or 1, preferably 0,
n is any number from 0 to 3, and is preferably 0 or 1,
p is any number from 0 to 2, and is preferably 0 or 1,
any Y is a substitution independently selected from the group of halogen, $C_{1-3}$ alkyl, $C_{1-3}$ alkoxy, wherein each alkyl or alkoxy can be unsubstituted or substituted with one or more substituents selected from halogen and $C_{1-3}$ alkoxy,
R4 is hydrogen,
R5 is selected from hydrogen, fluoro, chloro, bromo, iodo, methyl, methoxy, and trifluoromethyl, preferably hydrogen or iodo, and is preferably hydrogen,
X3 is N or C(R12),
R8 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl,
R9 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, cyano, and fluoro($C_{1-3}$)alkyl preferably trifluoromethyl, and is preferably hydrogen fluoro, chloro, or bromo,
R10 is selected from hydrogen, fluoro, chloro, bromo, iodo, $C_{1-3}$ alkyl, halo($C_{1-3}$)alkyl, preferably fluoro($C_{1-3}$)alkyl, particularly trifluoromethyl, $C_{2-3}$ alkynyl, $C_{1-3}$ alkyloxy, halo ($C_{1-3}$) alkyloxy, preferably fluoro($C_{1-2}$)alkoxy, cyano, cyanomethyl, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro or R10 forms a ring system together with R9, as described herein,
R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$) alkoxy, preferably fluoro($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl and cyano, and is more preferably hydrogen, fluoro, chloro or bromo, R12 is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo.

wherein, in a preferred embodiment, at least one of R8, R9, R10 and R11 is different from hydrogen, and more preferably at least one of R8, R9, R10 and R11 is also different from unsubstituted alkyl, and pharmaceutically acceptable salts, solvates, isotopes and co-crystals thereof.

Another preferred embodiment relates to compounds having a structure of Formula IIa, IIb, or IIc, wherein m is 0 or 1,
n is 0, 1 or 2, and is preferably 0 or 1,
p is 0 or 1
any Y is selected from hydrogen, halogen, hydroxy, unsubstituted or fluorinated methyl and unsubstituted or fluorinated methoxy,
R4 and R5 are both hydrogen,
R8 is selected from hydrogen, methoxy, fluoromethoxy, fluoro, and chloro, and is preferably fluoro,
X3 is N or C(R12),
R9 is selected from hydrogen, methoxy, fluoro and chloro, and is preferably hydrogen,
R10 is selected from hydrogen, ethynyl, cyano, cyanomethyl, cyanoethyl, cyanomethoxy, ethynyl, fluoro, chloro, bromo, iodo, azido, trifluoromethyl, trifluoromethoxy, difluoroethoxy, trifluoroethoxy and pentafluorosulfanyl,
R11 is selected from hydrogen, fluoro, chloro, and methoxy, and
R12, if present, is hydrogen or fluoro,
and wherein at least one of R8, R9, R10 and R11 is different from hydrogen, and wherein, in a preferred embodiment, at least R10 is different from hydrogen and wherein in a particularly preferred embodiment, R8 and R10 are both different from hydrogen, and pharmaceutically acceptable salts, solvates, isotopes and co-crystals thereof.

Another preferred embodiment relates to compounds having a structure of Formula IIa, IIb, or IIc, wherein m is 0 or 1,
n is 0, 1 or 2, and is preferably 0 or 1,
p is 0, 1 or 2,
any Y is selected from hydrogen, halogen, hydroxy, unsubstituted or fluorinated methyl and unsubstituted or fluorinated methoxy,
R4 and R5 are both hydrogen,
R8 is fluoro or methoxy,
X3 is N or C(R12),
R9 is selected from hydrogen, methoxy, fluoro and chloro, and is preferably hydrogen,
R10 is selected from halogen, ethynyl, propynyl, cyano, cyanomethyl, cyanoethyl, cyanomethoxy, unsubstituted or fluorinated ($C_{1-3}$)alkyl, unsubstituted or fluorinated ($C_{2-3}$) alkenyl, unsubstituted or fluorinated ($C_{2-3}$)alkynyl, unsubstituted or fluorinated $C_{1-3}$ alkyloxy, unsubstituted or fluorinated methoxy($C_{1-3}$)alkyl, unsubstituted or fluorinated methoxy($C_{1-3}$)alkyloxy, unsubstituted or fluorinated methoxy($C_{2-3}$)alkenyl, unsubstituted or fluorinated methoxy ($C_{2-3}$)alkynyl and pentafluorosulfanyl,
R11 is selected from hydrogen, fluoro, and methoxy, and
R12, if present, is hydrogen or fluoro,
and pharmaceutically acceptable salts, solvates, isotopes and co-crystals thereof.

In one preferred embodiment of the compounds of formula IIc, p is 1, and Y is attached to the 8-position of the tricyclic ring system to give a compound of formula II-c1, wherein Y is preferably selected from halogen, methyl, fluoromethyl, methoxy, fluoromethoxy and hydroxy, and wherein X3, R4, R5, R8, R9, R10, and R11 are as described for the compounds of Formula II-c herein.

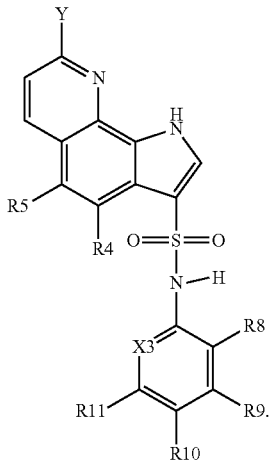

Formula IIc-1

Another preferred embodiment relates to compounds having a structure of Formula IIa, IIb, or IIc, wherein
m is 0 or 1,
n is 0, 1 or 2, and is preferably 0 or 1,
p is 0 or 1 or 2,
any Y is selected from hydrogen, halogen, hydroxy, unsubstituted or fluorinated methyl and unsubstituted or fluorinated methoxy,
R4 and R5 are both selected from hydrogen and fluoro,
R8 is fluoro or methoxy,
X3 is N,
R9 is selected from hydrogen, methoxy, fluoro and chloro, and is preferably hydrogen,
R10 is selected from fluoro, chloro, bromo, ethynyl, propynyl, cyano, cyanomethyl, cyanoethyl, cyanomethoxy, unsubstituted or fluorinated $(C_{1-3})$alkyl, unsubstituted or fluorinated $(C_{2-3})$alkenyl, $C_{2-3}$alkynyl, unsubstituted or fluorinated $C_{1-3}$ alkyloxy, unsubstituted or fluorinated $C_{1-2}$alkoxy$(C_{1-3})$alkyl, unsubstituted or fluorinated $C_{1-2}$alkoxy$(C_{1-3})$alkyloxy, unsubstituted or fluorinated $C_{1-2}$alkoxy$(C_{2-3})$alkenyl and pentafluorosulfanyl,
R11 is selected from hydrogen, fluoro, chloro, methoxy, fluoromethoxy and fluoromethyl,
and pharmaceutically acceptable salts, solvates, isotopes and co-crystals thereof,
wherein in a preferred embodiment, R10 is selected from chloro, bromo, cyanomethyl, cyanoethyl, cyanomethoxy, unsubstituted or fluorinated $(C_{1-3})$alkyl, unsubstituted or fluorinated $C_{1-3}$ alkyloxy, unsubstituted or fluorinated $C_{1-2}$alkoxy$(C_{1-2})$alkyloxy and unsubstituted or fluorinated methoxy$(C_{1-3})$alkyl, and is, in another preferred embodiment, chloro.

Another preferred embodiment relates to compounds having a structure of Formula IIa, IIb, or IIc, wherein R10 is selected from halogen, cyano, cyanomethyl, and cyanoethyl.

Another preferred embodiment relates to compounds having a structure of Formula IIa, IIb, or IIc, wherein
m is 0 or 1,
n is any number from 0 to 3, and is preferably 0 or 1,
p is any number from 0 to 2, and is preferably 0 or 1,
any Y is a substitution independently selected from the group of halogen, hydroxy, cyano, $C_{1-3}$ alkyl, $C_{1-3}$ alkoxy, wherein each alkyl or alkoxy can be unsubstituted or substituted with one or more substituents selected from halogen, hydroxy and $C_{1-3}$ alkoxy,
X3 is C(R12),
R4 is hydrogen,
R5 is selected from hydrogen, fluoro, chloro, bromo, iodo, methyl, methoxy, and trifluoromethyl, preferably hydrogen or iodo,
R8 is selected from hydrogen, fluoro, chloro, bromo, iodo, $C_{1-3}$ alkyl, preferably methyl, and $C_{1-3}$ alkoxy, wherein R8 is preferably selected from fluoro and methoxy,
or R9 forms together with R10 and the ring to which they are attached a bicyclic ring system selected from 2,1,3-benzothiadiazole, 2,1,3-benzoselenadiazole, 2,1,3-benzoxadiazole, 1,3-benzothiazole, 2,3-dihydro-1-benzothiophene, which is substituted with one or two oxo (preferably substituted with two oxo to give 1,1-dioxo-2,3-dihydro-1-benzothiophene), optionally methylated 3-oxo-1,3-dihydro-2-benzofuran-5-yl, and 1,3-benzodioxole, which is optionally substituted with one or two fluoros,
R11 is selected from hydrogen, fluoro, chloro, bromo, iodo and methoxy, and
R12 is selected from hydrogen, fluoro, chloro, bromo, methoxy, fluoromethoxy, methyl, and fluoromethyl.

Another preferred embodiment relates to compounds having a structure of Formula IIa, IIb, or IIc, wherein
m is 0 or 1,
n is 0, 1 or 2, and is preferably 0,
p is 0 or 1, preferably 0,
any Y is selected from hydrogen, halogen, unsubstituted or fluorinated methyl and unsubstituted or fluorinated methoxy,
R4, R5 are both hydrogen,
X3 is C(R12),
R8 is hydrogen, methoxy or fluoro, and is preferably hydrogen,
R9 together with R10 and the C atoms to which they are attached form a ring selected from an 2,1,3-benzothiadiazole, 2,1,3-benzoxadiazole, and 2,2-difluoro-1,3-benzodioxole, preferably 2,1,3-benzothiadiazole,
R11 is hydrogen or fluoro, and
R12 is hydrogen or fluoro
and pharmaceutically acceptable salts, solvates, isotopes and co-crystals thereof.

Another preferred embodiment relates to compounds having a structure of Formula IIa, IIb, or IIc, wherein
m is 0 or 1,
n is any number from 0 to 3, and is preferably 0 or 1,
p is any number from 0 to 2, and is preferably 0 or 1,
any Y is a substitution independently selected from the group of halogen, hydroxy, $C_{1-3}$ alkyl, $C_{1-3}$ alkoxy, wherein each alkyl or alkoxy can be unsubstituted or substituted with one or more substituents selected from halogen and $C_{1-3}$ alkoxy,
X3 is C(R12),
R4 is hydrogen,
R5 is selected from hydrogen, fluoro, chloro, bromo, iodo, methyl, methoxy, and trifluoromethyl, preferably hydrogen or iodo,
R9 forms together with R8 and the ring to which they are attached a bicyclic ring system selected from 2,1,3-benzothiadiazole, 2,1,3-benzoselenadiazole, 2,1,3-benzoxadiazole, 2-oxo-2,3-dihydro-1,3-benzoxazole, and 1,3-benzodioxole, which is optionally substituted with one or two fluoros,
R10 is selected from hydrogen, fluoro, chloro, bromo, iodo, $C_{1-3}$ alkyl, halo$(C_{1-3})$alkyl, preferably fluoro$(C_{1-3})$alkyl, particularly trifluoromethyl, $C_{2-3}$ alkynyl, $C_{1-3}$ alkyloxy, halo$(C_{1-3})$ alkyloxy, preferably fluoro$(C_{1-2})$alkoxy, cyano, cyanomethyl, cyanoethyl, cyanomethoxy, unsubstituted or fluorinated $C_{1-3}$ alkylcarbonyl preferably acetyl, unsubstituted or fluorinated $C_{1-3}$ alkoxycarbonyl preferably methoxycarbonyl, azido, pentafluorosulfanyl, and nitro, wherein R10 is preferably hydrogen, fluoro, chloro or bromo, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-3}$)alkoxy, preferably fluoro($C_{1-2}$)alkoxy, unsubstituted or fluorinated $C_{1-3}$ alkylcarbonyl preferably acetyl, unsubstituted or fluorinated $C_{1-3}$ alkoxycarbonyl preferably methoxycarbonyl and cyano, and is more preferably hydrogen, fluoro, chloro or bromo, R12 is selected from hydrogen, fluoro, chloro, bromo, iodo, $C_{1-3}$ alkyloxy preferably methoxy, fluoro($C_{1-3}$)alkoxy preferably fluoro($C_{1-2}$)alkoxy, $C_{1-3}$ alkyl preferably methyl, and fluoro($C_{1-3}$)alkyl preferably trifluoromethyl, and is more preferably hydrogen, fluoro, chloro, or bromo, and pharmaceutically acceptable salts, solvates, isotopes and co-crystals thereof.

Another preferred embodiment relates to compounds having a structure of Formula IIa, IIb, or IIc, wherein m is 0 or 1,
n is 0, 1 or 2, and is preferably 0,
p is 0 or 1 and is preferably 0,
any Y is selected from hydrogen, halogen, unsubstituted or fluorinated methyl and unsubstituted or fluorinated methoxy
X3 is C(R12)
R4 and R5 are both hydrogen,
R8 together with R9 and the ring to which they are attached form a bicyclic ring system selected from 2,1,3-benzothiadiazole, 2,1,3-benzoxadiazole, 2,1,3-benzoselanadiazole, 2-oxo-2,3-dihydro-1,3-benzoxazole, unsubstituted 1,3-benzodioxole and 2,2-difluoro-1,3-benzodioxole,
R10 is selected from the group of hydrogen, fluoro, chloro, bromo, trifluoromethyl, trifluoromethoxy, difluoroethoxy, trifluoroethoxy, and cyano, and is preferably hydrogen or fluoro,
R11 is selected from hydrogen, methoxy, fluoro, chloro, bromo and cyano, and is preferably hydrogen or fluoro,
R12 is hydrogen, fluoro, chloro, and trifluoromethyl,
and pharmaceutically acceptable salts, solvates, isotopes and co-crystals thereof.

Another preferred embodiment relates to compounds having a structure of Formula II,

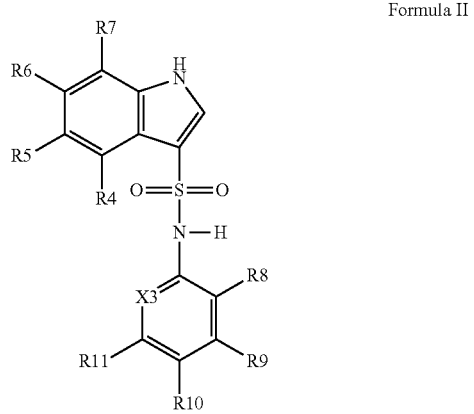

Formula II wherein
R4 and R5 are both hydrogen or fluoro;
R6 is selected from fluoro, chloro, bromo, amino, nitro, cyano, azido, unsubstituted or fluorinated $C_{1-3}$alkyl preferably selected from methyl, ethyl, propyl preferably isopropyl, fluoromethyl preferably trifluoromethyl, unsubstituted or fluorinated methylsulfonyl, unsubstituted or fluorinated methylsulfinyl, unsubstituted or fluorinated $C_{1-3}$alkyloxy preferably selected from methoxy, fluoromethoxy and fluoroethoxy, unsubstituted or fluorinated $C_{1-2}$alkyloxy($C_{1-2}$) alkyloxy including methoxyethoxy, cyclopropyl, cyclopropylmethoxy, phenyl, phenoxy, benzyloxy, benzylsulfinyl, 2-thienyl, 3-thienyl, 3-pyridyl, 4-pyridyl, tetrahydrofuranyl, tetrahydrofuranylmethoxy and dimethyloxazole, wherein each phenyl, phenoxy, benzyloxy, 2-thienyl, 3-thienyl, 3-pyridyl, 4-pyridyl residue may be optionally substituted with one or more of fluoro, chloro, unsubstituted or fluorinated methyl or unsubstituted or fluorinated methoxy, X3 is C(R12) or N,
R7 is selected from hydrogen, methyl, fluoro($C_{1-2}$)alkyl preferably mono-, di- or trifluoromethyl, methylsulfonyl, methylsulfinyl, methoxy, fluoro($C_{1-2}$)alkoxy, cyano, pyridyl, pyridylmethoxy, phenoxy, oxazol, isoxazol, cyano, fluoro, chloro or bromo, and is preferably hydrogen, methoxy, fluoro, or bromo, wherein each pyridyl, isoxazol and phenyl residue may be optionally substituted with one or more of fluoro, chloro, unsubstituted or fluorinated methyl or unsubstituted or fluorinated methoxy;

R8 and R11 are independently selected from hydrogen, fluoro, chloro, and unsubstituted or fluorinated methoxy;
R9 is hydrogen,
R10 is selected from fluoro, chloro, bromo, iodo, acetyl, azido, nitro, cyano, cyanomethyl, cyanothyl, cyanomethoxy, unsubstituted or fluorinated $C_{1-2}$alkoxycyclopropyl, unsubstituted or fluorinated $C_{1-2}$alkoxycarbonylcyclopropyl, cyclopropylmethoxy, cyclopropylmethyl, unsubstituted or fluorinated $C_{1-3}$alkyl preferably selected from methyl and trifluoromethyl, unsubstituted or fluorinated and/or hydroxylated $C_{1-3}$alkoxy preferably selected from methoxy, difluoromethoxy, trifluoromethoxy, difluoroethoxy, and trifluoroethoxy, unsubstituted or fluorinated $C_{1-2}$ alkoxy($C_{1-3}$) alkyl preferably unsubstituted or fluorinated methoxypropyl, unsubstituted or fluorinated $C_{1-2}$ alkoxy($C_{1-3}$)alkoxy including fluoromethoxyethoxy, unsubstituted or fluorinated $C_{2-3}$alkenyl, unsubstituted or fluorinated $C_{2-3}$alkynyl, preferably ethynyl unsubstituted or fluorinated $C_{1-2}$ alkoxy ($C_{2-3}$)alkenyl preferably methoxypropenyl, unsubstituted or fluorinated $C_{1-2}$ alkoxy($C_{2-3}$)alkynyl and pentafluorosulfanyl;

R12, if present, is hydrogen or fluoro,
and pharmaceutically acceptable salts, solvates, isotopes and co-crystals thereof.

Another preferred embodiment relates to compounds having a structure of Formula II wherein R4 and R5 are both hydrogen; R6 is selected from fluoro, chloro, bromo, methyl, ethyl, isopropyl, trifluoromethyl, methylsulfonyl, methoxy, cyclopropyl, cyclopropylmethoxy, phenyl, phenoxy, benzyloxy, 2-thienyl, 3-thienyl, 3-pyridyl, 4-pyridyl, tetrahydrofuranyl and dimethyloxazole, X3 is C(R12), R9 is hydrogen;
R7 is selected from hydrogen, methyl, trifluoromethyl, methoxy, fluoro, chloro or bromo, and is preferably hydrogen, methoxy, or bromo; R8 and R11 are independently selected from hydrogen, fluoro, chloro, and methoxy; R10 is fluoro, chloro, bromo, iodo, acetyl, azido, ethynyl, cyano, cyanomethyl, trifluoromethyl, difluoroethoxy, trifluoroethoxy, or pentafluorosulfanyl; R12 is hydrogen or fluoro, and pharmaceutically acceptable salts, solvates, isotopes and co-crystals thereof Another embodiment relates to compounds of formula II, wherein
R4 is hydrogen or fluoro, preferably hydrogen;
R5 is selected from hydrogen, fluoro, chloro, bromo, methoxy and fluoromethoxy,
R6 is selected from halogen, cyano, amino, nitro, unsubstituted or fluorinated methylsulfonyl, unsubstituted or fluorinated methylsulfinyl, $C_{1-3}$alkyl, $C_{1-3}$alkyloxy, $C_{2-3}$ alkenyl, cyclopropyl, phenyl, phenoxy, benzyloxy, benzylsulfinyl, 2-thienyl, 3-thienyl, 3-pyridyl, and 4-pyridyl, wherein each phenyl, phenoxy, benzyloxy, 2-thienyl, 3-thienyl, 3-pyridyl, 4-pyridyl may be optionally substituted with one or more of fluoro, chloro, unsubstituted or fluorinated methyl or unsubstituted or fluorinated methoxy, and wherein each alkyl, alkenyl and alkoxy group can be unsubstituted or substituted with one or more group selected from halogen, methoxy, fluoromethoxy, cyano, cyclopropyl, and halogen, X3 is C(R12) or N, R7 is selected from hydrogen, cyano, fluoro, chloro, bromo, unsubstituted or fluorinated $C_{1-3}$alkyl preferably selected from methyl, fluoromethyl and fluoroethyl, and unsubstituted or fluorinated $C_{1-3}$alkyloxy preferably selected from methoxy, fluoromethoxy and fluoroethoxy, R8 and R11 are independently selected from hydrogen, fluoro, chloro, cyano, methyl, fluoromethyl, methoxy and fluoromethoxy;

R9 is hydrogen or fluoro, preferably hydrogen,

R10 is selected from halogen, azido, cyano, cyclopropyl, nitro, $C_{1-3}$alkyl, $C_{1-3}$alkoxy, $C_{2-3}$ alkenyl, $C_{2-3}$ alkynyl, $C_{1-3}$alkylcarbonyl($C_{1-3}$)alkyl, $C_{1-3}$alkoxycarbonyl($C_{1-3}$)alkyl and pentafluorosulfanyl, wherein each alkyl, alkenyl, alkynyl and alkoxy group can be unsubstituted or substituted with one or more residues selected from fluoro, chloro, cyano, cyclopropyl and unsubstituted or fluorinated and/or hydroxylated $C_{1-3}$alkoxy, and wherein each cyclopropyl group can be substituted with one or more residues selected from halogen, hydroxy, hydroxymethyl, $C_{1-3}$alkoxy, $C_{1-3}$alkoxycarbonyl and cyano, R12, if present, is hydrogen or fluoro, and pharmaceutically acceptable salts, solvates, isotopes and co-crystals thereof.

Another embodiment relates to compounds of Formula II wherein

R4 is hydrogen,

R5 is selected from hydrogen, fluoro, chloro and bromo,

R6 is selected from fluoro, chloro, bromo, iodo, cyano, nitro, methyl, ethyl, isopropyl, fluoromethyl preferably trifluoromethyl, fluoroethyl, methoxy, fluoromethoxy, fluoroethoxy, cyano, methylsulfinyl, methylsulfonyl, cyclopropyl, phenyl, benzyloxy, 2-thienyl and 3-thienyl, R7 is selected from hydrogen, fluoro, chloro, bromo, cyano, fluoro($C_{1-2}$)alkyl preferably trifluoromethyl, and fluoro($C_{1-2}$)alkoxy, and is preferably selected from hydrogen, fluoro, methoxy, fluoromethoxy and fluoroethoxy, X3 is C(R12), R8 and R11 are independently selected from hydrogen, fluoro, chloro, cyano, fluoromethyl, methoxy and fluoromethoxy, R9 is hydrogen, R10 is selected from fluoro, chloro, bromo, iodo, azido, unsubstituted or fluorinated $C_{1-3}$alkyl preferably trifluoromethyl, unsubstituted or fluorinated $C_{1-3}$alkyloxy preferably selected from difluoroethoxy, trifluoromethoxy and trifluoroethoxy, unsubstituted or fluorinated $C_{1-3}$alkoxy($C_{1-3}$)alkyl, unsubstituted or fluorinated $C_{1-3}$alkoxy($C_{1-3}$)alkoxy, unsubstituted or fluorinated $C_{1-3}$alkoxy($C_{2-3}$)alkenyl, pentafluorosulfanyl, ethynyl, propynyl, cyano, cyanomethoxy, and cyanomethyl, and R12 is hydrogen and fluoro, wherein preferably at least one of R8 and R11 is fluoro or chloro, preferably fluoro.

Another embodiment relates to compounds of Formula II wherein R4 and R5 are both hydrogen, R6 is selected from fluoro, chloro, bromo, iodo, methyl, isopropyl, trifluoromethyl, methylsulfonyl, cyclopropyl, phenyl, benzyloxy, 2-thienyl and 3-thienyl, X3 is C(R12), R7 is selected from hydrogen, methyl, methoxy, fluoro, chloro, bromo and trifluoromethyl, preferably from hydrogen, fluoro, and bromo, R8 and R11 are independently selected from hydrogen, fluoro, chloro and methoxy, R9 is hydrogen, R10 is selected from hydrogen, fluoro, chloro, bromo, iodo, azido, trifluoromethyl, difluoroethoxy, trifluoromethoxy, trifluoroethoxy, pentafluorosulfanyl, ethynyl, cyano and cyanomethyl, R12 is hydrogen and fluoro, wherein preferably at least one of R8 and R11 is fluoro or chloro, preferably fluoro.

Another embodiment relates to compounds of Formula II wherein R4 and R5 are both hydrogen, R6 is selected from fluoro, chloro, bromo, isopropyl, trifluoromethyl, cyclopropyl, methoxy, fluoromethoxy, fluoroethoxy, methylsulfinyl, and benzyloxy, R7 is hydrogen, methyl, methoxy, fluoromethoxy, fluoroethoxy, fluoromethyl, cyano, bromo, or fluoro, X3 is C(R12), R9 is hydrogen, R10 is selected from fluoro, bromo, chloro, iodo, methyl, fluoromethyl preferably trifluoromethyl, fluoro($C_{1-2}$)alkoxy preferably difluoroethoxy and trifluoromethoxy, pentafluorosulfanyl, cyano, cyanomethoxy, cyanomethyl and cyanoethyl, R12 is hydrogen or fluoro, and R8 and R11 are independently selected from hydrogen, fluoro, chloro, methoxy and fluoromethoxy, and are, in one preferred embodiment, both different from hydrogen.

Another embodiment relates to compounds of Formula II wherein R4, and R5 are both hydrogen, R6 is selected from fluoro, chloro, bromo, isopropyl, trifluoromethyl, cyclopropyl, and benzyloxy, R7 is hydrogen, methoxy, or fluoro, X3 is C(R12), R9 is hydrogen, R10 is selected from fluoro, bromo, chloro, iodo, trifluoromethyl, difluoroethoxy, trifluoromethoxy, pentafluorosulfanyl, cyano, and cyanomethyl, R12 is hydrogen or fluoro, and R8 and R11 are both different from hydrogen and are preferably fluoro, chloro, methoxy or cyano, more preferably fluoro.

Another preferred embodiment relates to compounds of Formula II wherein R4 and R5 are both hydrogen, R6 is selected from fluoro, chloro, bromo, isopropyl, fluoromethyl, methoxy, fluoromethoxy and phenyloxy, R7 is hydrogen, methoxy, fluoromethoxy, fluoroethoxy, cyano, fluoro or chloro, X3 is C(R12), R9 is hydrogen or fluoro, R10 is hydrogen, R12 is hydrogen or fluoro, and R8 and R11 are both independently selected from fluoro, chloro and methoxy.

Another preferred embodiment relates to compounds of Formula II wherein R4, and R5 are both hydrogen, R6 is selected from fluoro, chloro, bromo, isopropyl, trifluoromethyl, and phenyloxy, R7 is hydrogen, methoxy or fluoro, X3 is C(R12), R9 is hydrogen or fluoro, R10 is hydrogen, R12 is hydrogen or fluoro, and R8 and R11 are both independently selected from fluoro, chloro and cyano.

Another preferred embodiment relates to compounds of Formula II wherein R4 and R5 are both hydrogen, R6 is selected from fluoro, chloro, bromo, iodo, methyl, ethyl, isopropyl, fluoromethyl preferably trifluoromethyl, methoxy, methylsulfinyl, methylsulfonyl, cyclopropyl, phenyl, benzyloxy, 2-thienyl and 3-thienyl, and preferably from fluoro, chloro, bromo, and trifluoromethyl, R7 is hydrogen, methoxy or fluoro, preferably hydrogen, X3 is C(R12), R8 is hydrogen, R9 and R10, together with the C atoms to which they are attached form a 2,1,3-benzothiadiazole, 3-oxo-1,3-dihydro-2-benzofuran, or 1-methyl-3-oxo-1,3-dihydro-2-benzofuran and R11 and R12 are independently selected from hydrogen and fluoro.

Another embodiment relates to compounds of Formula II wherein R4, and R5 are both hydrogen, R6 is selected from fluoro, chloro, bromo and methylsulfonyl, R7 is selected from hydrogen, fluoro, bromo, chloro, methoxy, and trifluoromethyl, X3 is C(R12), R8 and R9 together with the ring to which they are attached form a 2,1,3-benzothiadiazole, 2,1,3-benzoselenadiazole, 2,1,3-benzoxadiazole or optionally 2,2-fluoro-substituted 1,3-benzodioxole, R10 is hydrogen, fluoro, or bromo, R11 is selected from hydrogen, fluoro and cyano, and R12 is hydrogen, fluoro or trifluoromethyl.

Another embodiment relates to compounds of Formula II wherein R4 is hydrogen, R5 is selected from hydrogen and fluoro, R6 is selected from fluoro, chloro, bromo, methoxy and trifluoromethyl, R7 is selected from hydrogen, halogen, methylsulfonyl, methoxy, fluoromethoxy, fluoroethoxy and fluoromethyl preferably trifluoromethyl, X3 is N, R8 is fluoro, chloro or methoxy, R9 is selected from hydrogen, fluoro, chloro, methyl and methoxy and is preferably hydrogen, R10 is selected from fluoro, chloro, bromo, cyano, cyanomethyl, cyanoethyl, pentafluorosulfanyl, mono-, di- and trifluoromethyl, mono-, di- and trifluoromethoxy, mono-, di- and trifluoroethoxy, unsubstituted or fluorinated $C_{1-2}$ alkoxy($C_{1-3}$)alkyl, unsubstituted or fluorinated $C_{1-2}$alkoxy($C_{1-2}$)alkoxy, ethynyl and cyanomethyl, and R11 is selected from hydrogen, fluoro, chloro, fluoromethyl, methoxy and fluoromethoxy.

Another embodiment relates to compounds of Formula II wherein R4, R5 are both hydrogen, R6 is selected from fluoro, chloro, bromo and methoxy, R7 is selected from, hydrogen, fluoro, chloro, bromo, fluorometyl, methoxy and fluoromethoxy, X3 is N, R8 is fluoro or methoxy, R9 is hydrogen, R10 is selected from fluoro, chloro, bromo, cyano, cyanomethyl, acetyl, methyl, ethyl, ethoxyethyl, methoxypropyl, fluorinated methoxypropyl, fluoromethyl, fluoromethoxymethyl, methoxycarbonylcyclopropyl, ethoxycarbonylcyclopropyl, ethenyl, ethoxyethenyl, methoxy, fluoromethoxy, fluoroethoxy, fluoropropoxy, methoxyethoxy, fluorinated methoxyethoxy, ethoxyethoxy, fluorinated ethoxyethoxy, methoxypropoxy, fluorinated methoxypropoxy, methoxypropenyl, and fluoromethoxypropenyl, and R11 is hydrogen, methoxy, fluoro or chloro.

Another embodiment relates to compounds of Formula II wherein R4 and R5 are both hydrogen, R6 is chloro or bromo, R7 is selected from hydrogen, fluoro, chloro, bromo and methoxy, and X3 is C(R12) or N, R8 is fluoro, chloro or methoxy, R9 is hydrogen or fluoro, preferably hydrogen, R10 is selected from fluoro, chloro, bromo, cyano, $C_{1-3}$alkyl, $C_{2-3}$alkenyl and $C_{1-3}$alkoxy, wherein each alkyl, alkenyl and alkoxy can be unsubstituted or substituted with one or more substituents selected from halogen, preferably fluoro, cyano, $C_{1-2}$alkoxy and fluoro($C_{1-2}$)alkoxy, and R11 is hydrogen, fluoro or methoxy.

Another embodiment relates to compounds having Formula II(d), II(e), II(f) and II(g),

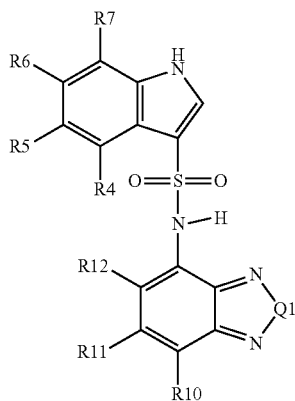

Formula II(d)

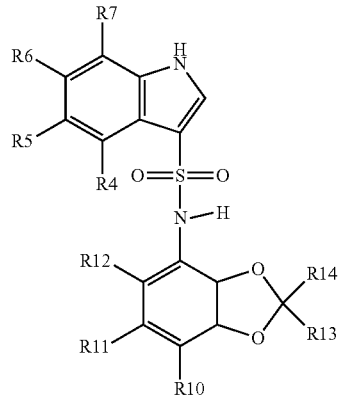

Formula II(e)

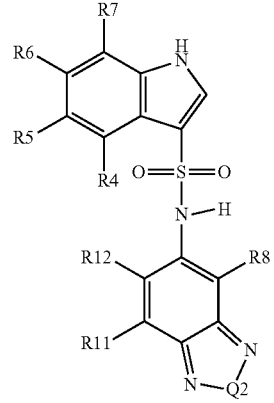

Formula II(f)

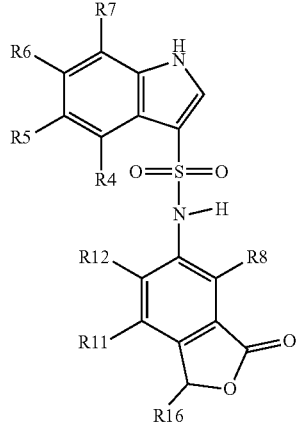

Formula II(g)

wherein R4, R5, R6, R7, R8, R10, R11 and R12 are as otherwise described for Formulae I and II herein, wherein in Formula II(d), Q1 is S or O, and wherein in Formula II(e), R13 and R14 are selected from the group of hydrogen, methyl and fluoro and are preferably either both hydrogen or both fluoro, wherein in Formula II(f), Q2 is S or O, preferably S, and wherein in Formula II(g), R16 is selected from hydrogen, fluoro, hydroxy, methyl, fluoromethyl, methoxy and fluoromethoxy, and is preferably selected from hydrogen and methyl, and pharmaceutically acceptable salts, solvates, isotopes and co-crystals thereof.

One embodiment relates to compounds according to Formulae II(d), II(e), II(f) and II(g),
wherein
wherein in Formula II(d), Q1 is S or O, and
wherein in Formula II(e), R13 and R14 are both selected from hydrogen and fluoro,
wherein in Formula II(f), Q2 is S or O, preferably S,
wherein in Formula II(g), R16 is selected from hydrogen and methyl,
R4 is hydrogen,
R5 is selected from hydrogen, fluoro, chloro and bromo, and is preferably hydrogen,
R6 is selected from fluoro, chloro, bromo, methyl, methoxy, methylsulfonyl, methylsulfinyl, fluoromethyl, fluoromethoxy, cyano, and benzyloxy, preferably from fluoro, chloro, bromo and fluoromethyl,
R7 is selected from hydrogen, fluoro, chloro, bromo, methoxy, cyano, methyl, and fluoromethyl, preferably from hydrogen and mono-, di-, and trifluoromethyl,
R8, if present, is selected from hydrogen and halogen, preferably from hydrogen and fluoro, and is more preferably hydrogen,
R10, if present, is selected from hydrogen, fluoro, chloro, bromo, and cyano, preferably hydrogen or fluoro,
R11 is selected from hydrogen, halogen, methoxy, fluoromethoxy, fluoromethyl and cyano, and is preferably hydrogen or fluoro,
R12 is selected from hydrogen, halogen, methoxy, fluoromethyl, preferably from hydrogen, fluoro, and fluoromethyl,
and pharmaceutically acceptable salts, solvates, isotopes and co-crystals thereof.

In a preferred embodiment of the compounds of Formula IId and IIe,
R4 and R5 are both hydrogen,
R6 is selected from fluoro, chloro, bromo, trifluoromethyl, and phenyl,
R7 is hydrogen, fluoro, bromo, methoxy, or trifluoromethyl, preferably hydrogen or trifluoromethyl,
R10 is selected from hydrogen and halogen, preferably from hydrogen, fluoro and chloro,
R11 is selected from hydrogen, halogen, trifluoromethyl and cyano, preferably from fluoro and hydrogen,
R12 is selected from hydrogen, halogen and trifluoromethyl, preferably from fluoro and hydrogen,
R13 and R14, in formula IIe, are both selected from hydrogen and fluoro, and pharmaceutically acceptable salts, solvates, isotopes and co-crystals thereof.

In a preferred embodiment of the compounds of Formula II(f),
R4 and R5 are both hydrogen,
R6 is selected from fluoro, chloro, bromo, trifluoromethyl and phenyl,
R7 is selected from hydrogen, methoxy, fluoro, and trifluoromethyl,
R8 is selected from hydrogen and halogen, preferably from hydrogen and fluoro,
R11 is selected from hydrogen, halogen, trifluoromethyl and cyano, and is preferably hydrogen,
R12 is selected from hydrogen, halogen and trifluoromethyl, preferably from fluoro and hydrogen,
and pharmaceutically acceptable salts, solvates, isotopes and co-crystals thereof.

One embodiment relates to compounds of subformula IIa, IIb, IIc, IId, IIe, IIf, and IIg, which are additionally substituted with a group R2, as depicted for the general Formula II-2 above, thus leading to the respective corresponding compounds having subformula II-2a, II-2b, II-2c, II-2d, II-2e, II-2f, and II-2g, wherein R2 is selected from hydrogen, fluoro, chloro, bromo, iodo and methoxy, and wherein R2 is preferably hydrogen or fluoro, and particularly preferably hydrogen, and wherein the other residues are as defined in the formula II-2a, II-2b, II-2c, II-2d, II-2e, II-2f, and II-2g, herein. By way of non-limiting example, Formula II-2d and II-2f are depicted below:

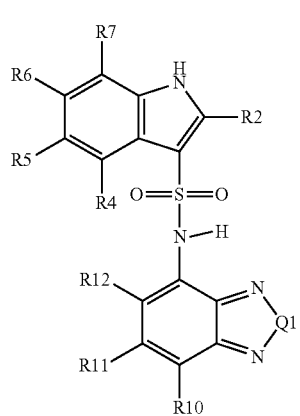

Formula II-2(d)

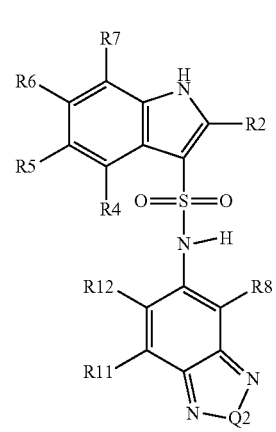

Formula II-2(f)

Another preferred embodiment relates to compounds having a structure of Formula III,

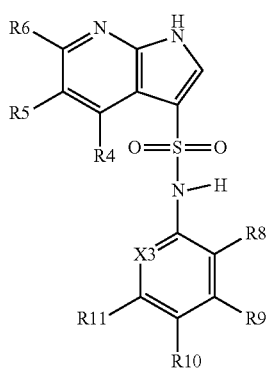

Formula III wherein R4 and R5 are both hydrogen,
R6 is selected from hydrogen, fluoro, chloro, bromo, fluoromethyl, methoxy, fluoromethoxy, and cyclopropyl,
X3 is C(R12) or N,
R8 is selected from hydrogen, methoxy, and halogen, particularly preferably from fluoro, chloro, methoxy and hydrogen,
R9 is hydrogen,
R10 is selected from fluoro, bromo, chloro, iodo, methyl, fluoro($C_{1-3}$)alkyl preferably trifluoromethyl, unsubstituted or fluorinated methoxy($C_{1-3}$)alkyl, unsubstituted or fluorinated $C_{1-3}$alkyloxy preferably mono-, di- and trifluoromethoxy and mono-, di- and trifluoroethoxy, unsubstituted or fluorinated methoxy($C_{1-3}$)alkyloxy, unsubstituted or fluorinated $C_{2-3}$alkenyl, unsubstituted or fluorinated methoxy ($C_{2-3}$)alkenyl, ethynyl, propargyl, unsubstituted or fluorinated methoxy($C_{2-3}$)alkynyl, azido, pentafluorosulfanyl, cyanomethyl, cyanoethyl, and cyano,
R11 is hydrogen, fluoro, chloro, or methoxy, particularly preferably hydrogen or fluoro,
R12, if present, is hydrogen or fluoro,
and pharmaceutically acceptable salts, solvates, isotopes and co-crystals thereof.

Another embodiment relates to compounds of Formula III, wherein R4 and R5 are both hydrogen, R6 is chloro or bromo, X3 is C(R12), R12 is hydrogen or fluoro, R8 is selected from hydrogen, methoxy, and halogen, particularly preferably from fluoro and hydrogen, R9 is hydrogen, R10 is selected from fluoro, bromo, chloro, iodo, trifluoromethyl, difluoroethoxy, trifluoromethoxy, trifluoroethoxy, ethynyl, azido, acetyl, pentafluorosulfanyl, cyanomethyl, and cyano, R11 is hydrogen, fluoro, chloro, or methoxy, particularly preferably hydrogen or fluoro, and pharmaceutically acceptable salts, solvates, isotopes and co-crystals thereof.

Another particularly preferred embodiment relates to a compound of Formula III, wherein R4 and R5 are both hydrogen, R6 is selected from methyl, fluoromethyl, methoxy, fluoromethoxy, chloro or bromo, X3 is C(R12), R8 is hydrogen, methoxy, or fluoro and is preferably fluoro, R9 is hydrogen, R10 is selected from fluoro, bromo, chloro, iodo, mono-, di- and trifluoromethyl, mono-, di- and trifluoromethoxy, mono-, di-, and trifluoroethoxy, pentafluorosulfanyl, ethynyl and cyano, and R11 and R12 are independently selected from hydrogen and fluoro.

Another preferred embodiment relates to compounds of Formula III, wherein R4 and R6 are hydrogen, R5 is iodo, X3 is C(R12) or N, R8 and R11 are both independently selected from hydrogen or fluoro, R10 is selected from fluoro, bromo, chloro, iodo, mono-, di- and trifluoromethyl, mono-, di-, and trifluoromethoxy, mono-, di-, and trifluoroethoxy, pentafluorosulfanyl, and cyano, R9 is hydrogen, and R12, if present, is hydrogen or fluoro, Another preferred embodiment relates to a compound of Formula III, wherein R4 and R5 are both hydrogen, R6 is chloro or bromo, X3 is C(R12), R8 is hydrogen, R9 and R10, together with the phenyl ring to which they are attached, form a 2,1,3-benzothiadiazole ring system, R11 is hydrogen and R12 is fluoro or hydrogen.

Another preferred embodiment relates to a compound of Formula III, wherein R4 and R5 are both hydrogen, R6 is chloro or bromo, X3 is C(R12), R8 and R9, together with the phenyl ring to which they are attached, form a 2,1,3-benzothiadiazole, 2,1,3-benzoxadiazole, unsubstituted 1,3-benzoxolane, or 2,3,-difluoro-1,3-benzoxalane group, R10 and R11 are independently selected from hydrogen, methoxy, cyano and halogen, preferably from hydrogen and fluoro, and R12 is fluoro, trifluoromethyl or hydrogen.

Another embodiment relates to compounds of Formula III, wherein R4 and R5 are both hydrogen, R6 is selected from fluoro, chloro, bromo and mono-, di-, and trifluoromethyl, X3 is N, R8 is fluoro, chloro or methoxy, R9 is selected from hydrogen, fluoro, chloro, and methoxy, and is preferably hydrogen, R10 is selected from fluoro, chloro, bromo, iodo, cyano, mono-, di and trifluoromethyl, mono-, di-, and trifluoromethoxy, mono-, di-, and trifluoroethoxy, ethynyl and cyanomethyl, and R11 is hydrogen, fluoro or chloro.

Another embodiment relates to compounds of Formula III, wherein R4 and R5 are both hydrogen, R6 is selected from chloro, bromo, methoxy, mono-, di-, and trifluoromethyl, X3 is C(R12) or N, R8 is selected from hydrogen, fluoro, chloro, methoxy and fluoromethoxy, R9 is hydrogen, R10 is selected from fluoro, chloro, bromo, cyano, cyanomethyl, cyanoethyl, cyanomethoxy, mono-, di-, and trifluoromethyl, mono-, di-, and trifluoromethoxy, mono-, di-, and trifluoroethoxy, unsubstituted or fluorinated $C_{1-2}$alkoxy($C_{1-3}$)alkoxy, unsubstituted or fluorinated $C_{1-2}$alkoxy($C_{1-3}$)alkyl, unsubstituted or fluorinated $C_{2-3}$alkenyl, unsubstituted or fluorinated $C_{1-2}$alkoxy($C_{2-3}$)alkenyl, and $C_{2-3}$alkynyl, R11 is hydrogen, methoxy. fluoro, or chloro and R12, if present, is hydrogen or fluoro.

In one embodiment, the compounds have a structure selected from Formula III(a) to III(c)

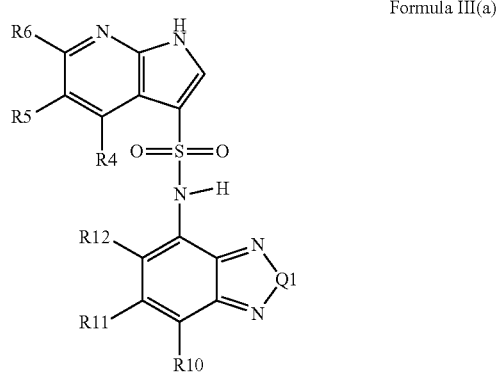

Formula III(a)

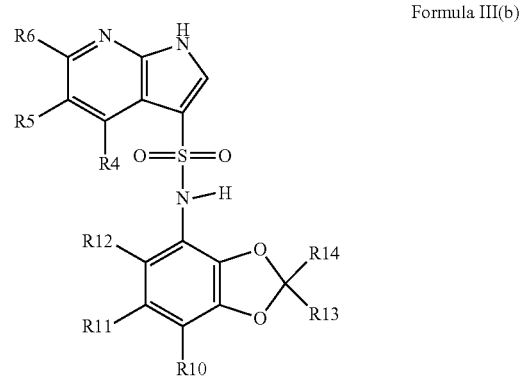

Formula III(b)

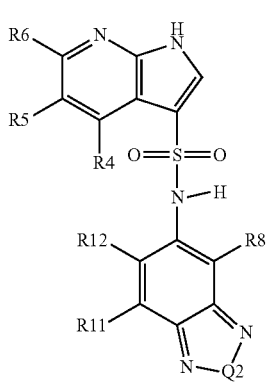

Formula III(c)

wherein R4, R5, R6, R8, R10, R11 and R12 are as otherwise described for Formulae I and III herein,
wherein in Formula III(a), Q1 is S or O, and
wherein in Formula III(b), R13 and R14 are selected from the group of hydrogen, methyl and fluoro and are preferably either both hydrogen or both fluoro, and
wherein in Formula III(c), Q2 is S or O, preferably S,
and pharmaceutically acceptable salts, solvates, isotopes and co-crystals thereof.

In a preferred embodiment of the compounds of Formula III(a) to III(c),
R4 and R5 are both hydrogen,
R6 is selected from fluoro, chloro, bromo, mono-, di-, and trifluoromethyl, methoxy and fluoromethoxy,
R8, if present, is hydrogen or fluoro, preferably hydrogen,
R10, if present, is selected from hydrogen and halogen, preferably from hydrogen, fluoro and chloro,
R11 is selected from hydrogen, halogen, trifluoromethyl and cyano, preferably from fluoro and hydrogen,
R12 is selected from hydrogen, halogen and trifluoromethyl, preferably from hydrogen and fluoro.
One embodiment refers to compounds of Formula IId, IIe, IIIa and IIIb
wherein R4 and R5 are both hydrogen,
R6 is selected from fluoro, chloro, bromo, mono-, di-, and trifluoromethyl, and methoxy,
R10 is selected from hydrogen and halogen, preferably from hydrogen, fluoro and chloro,
R11 is selected from hydrogen, halogen, trifluoromethyl and cyano, preferably from fluoro and hydrogen,
R12 is selected from hydrogen, halogen and trifluoromethyl,
wherein in the compounds of Formula II(d) and III(a), Q1 is S or O, and
wherein in Formula II(e) and III(b), R13 and R14 are selected from hydrogen and fluoro and are preferably either both hydrogen or both fluoro.

One embodiment refers to compounds of Formula IIf and IIIc,
wherein R4 and R5 are both hydrogen,
R6 is selected from fluoro, chloro, bromo, methylsulfonyl, mono-, di-, and trifluoromethyl and phenyl,
R7, if present, is selected from hydrogen, methoxy, fluoro, and trifluoromethyl,
R8 is selected from hydrogen and halogen, preferably from hydrogen and fluoro,
R11 is selected from hydrogen, halogen, trifluoromethyl and cyano, and is preferably hydrogen,
R12 is selected from hydrogen, halogen and trifluoromethyl, preferably from fluoro and hydrogen,
Q2 is O or S, and is preferably S.

One embodiment relates to compounds of subformula IIIa, IIIb, and IIIc, which are additionally substituted with a group R2, as depicted for the general Formula III-2 above, thus leading to the respective corresponding compounds having subformula III-2a, III-2b, and III-2c, wherein R2 is selected from hydrogen, fluoro, chloro, bromo, iodo and methoxy, and wherein R2 is preferably hydrogen or fluoro, and particularly preferably hydrogen, and wherein the other residues are as defined in the formula IIIa, IIIb, and IIIc herein.

By way of example, if a compound of formula III-c also carries a R2 group, the resulting compound of Formula III-2c is as follows:

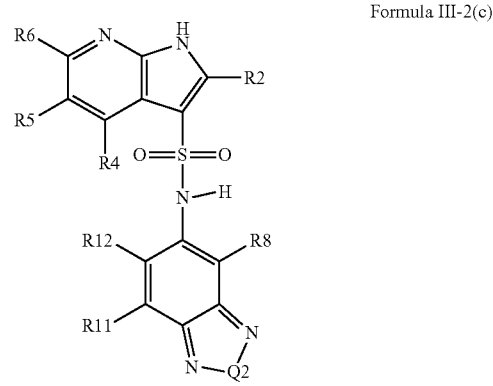

Formula III-2(c)

Another aspect of the present invention relates to compounds having the general formula VI, and pharmaceutically acceptable salts, solvates, isotopes and co-crystals thereof,

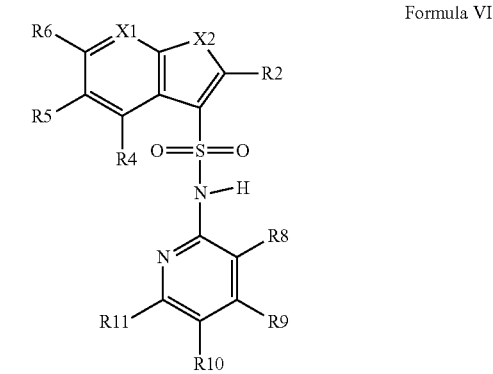

Formula VI wherein X1, X2, R2, R4, R5, R6, R8, R9, R10 and R11 have the meaning as described for the compounds of formula I-2, II-2, III-2, IV-2 or V-2 hereinbefore, and wherein R2 is selected from hydrogen, fluoro, chloro, bromo, iodo and methoxy, preferably from hydrogen and fluoro; more preferably, R2 is hydrogen.

One embodiment relates to a compound of Formula VI, wherein
X1 is C—R7 or N
X2 is NH, S or O, wherein if X1 is N, then X2 is preferably NH,
R2 is hydrogen or fluoro, preferably hydrogen,
R4 is hydrogen or fluoro,
R5 is selected from hydrogen, halogen, cyano, unsubstituted or fluorinated $C_{1-3}$ alkyl, unsubstituted or fluorinated $C_{1-3}$ alkoxy, unsubstituted or fluorinated $C_{1-3}$ alkylcarbonyl, unsubstituted or fluorinated $C_{1-3}$ alkylsulfinyl, and unsubstituted or fluorinated $C_{1-3}$ alkylsulfonyl, wherein R5 is preferably selected from hydrogen, halogen, cyano, methyl, methoxy, fluoromethyl and fluoromethoxy, and is more preferably selected from hydrogen, fluoro, chloro and bromo, or R5 forms a ring together with R6 as described herein, R6 is selected from hydrogen, fluoro, chloro, bromo, iodo, cyano, azido, nitro, amino, $C_{1-3}$alkyl, $C_{2-3}$alkenyl, $C_{2-3}$alkynyl, $C_{1-3}$alkoxy, $C_{3-6}$ cycloalkyl, $C_{3-6}$ heterocycloalkyl, phenyl, $C_{5-6}$heteroaryl, $C_{3-6}$ cycloalkyloxy, $C_{3-6}$ heterocycloalkyloxy, phenyloxy, $C_{5-6}$heteroaryloxy, $C_{1-3}$alkylsulfinyl, phenylsulfinyl, $C_{1-3}$alkylsulfonyl, phenylsulfonyl, benzylsulfonyl, $C_{1-3}$ alkylcarbonyl, $C_{1-3}$ alkoxycarbonyl, $C_{1-3}$ alkylaminocarbonyl, di($C_{1-3}$)alkylaminocarbonyl, $C_{3-6}$cycloalkyl($C_{1-2}$)alkyl, heterocycloalkyl($C_{1-2}$)alkyl, phenyl($C_{1-2}$)alkyl, $C_{5-6}$ heteroaryl(C1-2)alkyl, $C_{3-6}$ cycloalkyl($C_{1-3}$)alkoxy, $C_{3-6}$ heterocycloalkyl($C_{1-2}$)alkyloxy, phenyl($C_{1-2}$)alkoxy $C_{5-6}$heteroaryl($C_{1-2}$)alkoxy, phenyl($C_{1-2}$)alkylsulfinyl, phenyl($C_{1-2}$)alkylsulfonyl and wherein each group in R6 can be unsubstituted or substituted with one or more groups selected from fluoro, chloro, bromo, fluorinated or unsubstituted $C_{1-3}$alkyl, fluorinated or unsubstituted $C_{1-3}$alkyloxy, hydroxy, and cyano, or (i) R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from hydroxy, halogen, methyl or methoxy, wherein each methyl or methoxy can be unsubstituted or substituted with one or more substituents selected from halogen and methoxy, or (ii) R6 forms together with R5 and the carbon atoms to which R6 and R5 are attached, a 1,3-dioxolane which may be unsubstituted or substituted with one or two substituents selected from fluorine and methyl, R7, if present, is selected from hydrogen, fluoro, chloro, bromo, iodo, cyano, $C_{1-3}$alkyl, $C_{1-3}$ alkoxy, $C_{2-3}$alkynyl, $C_{2-3}$alkenyl, $C_{1-3}$alkylcarbonyl, $C_{1-3}$alkoxycarbonyl, $C_{1-3}$alkylsulfinyl, $C_{1-3}$alkylsulfonyl, $C_{1-3}$alkylthio, $C_{3-6}$cycloalkyl, $C_{3-6}$ cycloalkyloxy, $C_{3-6}$heterocycloalkyl, $C_{3-6}$heterocycloalkyloxy, phenyl, phenoxy, phenylsulfonyl, phenylsulfinyl, $C_{5-6}$heteroaryl, $C_{5-6}$ heteroaryloxy, $C_{5-6}$heteroaryl($C_{1-2}$)alkyl, and $C_{5-6}$heteroaryl($C_{1-2}$)alkoxy, $C_{3-6}$cycloalkyl($C_{1-2}$)alkyl, $C_{3-6}$ cycloalkyl($C_{1-3}$)alkoxy, $C_{3-6}$ heterocycloalkyloxy, $C_{3-6}$ heterocycloalkyl($C_{1-2}$)alkyl, heterocycloalkyl($C_{1-2}$)alkyloxy, phenyl($C_{1-2}$)alkyl, phenyl($C_{1-2}$)alkoxy, and wherein each group in R7 can be unsubstituted or substituted with one or more groups selected from fluoro, chloro, bromo, fluorinated or unsubstituted $C_{1-3}$alkyl, fluorinated or unsubstituted $C_{1-3}$alkyloxy, hydroxy, and cyano, or R7 forms a ring together with R6 as described herein, R8 is selected from hydrogen, optionally halogenated preferably fluorinated or nsubstituted $C_{1-3}$ alkyl, optionally halogenated preferably fluorinated or unsubstitued $C_{1-3}$ alkyloxy, cyano and halogen, R9 is selected from hydrogen, fluoro, chloro, bromo, iodo, $C_{1-3}$ alkyl, fluoro($C_{1-3}$)alkyl, $C_{1-3}$ alkoxy and fluoro($C_{1-3}$) alkoxy, wherein R9 is preferably hydrogen or fluoro, R10 is selected from hydrogen, halogen, $C_{1-3}$alkyl, $C_{1-3}$alkoxy, $C_{2-3}$alkenyl, $C_{2-3}$alkynyl, cyano, $C_{1-3}$alkylcarbonyl, $C_{1-3}$alkoxycarbonyl, $C_{1-3}$ alkylsulfinyl, $C_{1-3}$ alkylsulfonyl, $C_{1-3}$ alkylthio, $C_{3-6}$cycloalkyl, $C_{3-6}$cycloalkyloxy $C_{3-6}$heterocycloalkyl, $C_{3-6}$heterocycloalkyloxy, azido, pentafluorosulfanyl, nitro, $C_{1-3}$alkylaminocarbonyl, and di($C_{1-3}$)alkylaminocarbonyl, wherein each alkyl, alkenyl, alkynyl or alkoxy in R10 can be unsubstituted or substituted with one or more substituents selected from halogen, unsubstituted or halogenated $C_{1-3}$alkoxy, unsubstituted or halogenated $C_{1-3}$alkylthio, unsubstituted or halogenated $C_{1-3}$ alkylcarbonyl, unsubstituted or halogenated $C_{1-3}$ alkyloxycarbonyl, unsubstituted or halogenated $C_{1-3}$ alkylaminocarbonyl, unsubstituted or halogenated di($C_{1-3}$)alkylaminocarbonyl, hydroxy, cyano, $C_{3-6}$cycloalkyl, $C_{3-6}$heterocycloalkyl, phenyl, and $C_{5-6}$heteroaryl, wherein any cycloalkyl, heterocycloalkyl, phenyl and heteroaryl may be unsubstituted or substituted with one or more residues selected from halogen, hydroxy, hydroxymethyl, cyano, nitro, unsubstituted or halogenated $C_{1-3}$alkyl, unsubstituted or halogenated $C_{1-3}$alkoxy, unsubstituted or halogenated $C_{1-3}$alkylcarbonyl and unsubstituted or halogenated $C_{1-3}$alkoxycarbonyl, and wherein any halogenated substituent in R10 is preferably fluorinated and wherein R8 and R10 are preferably not hydrogen, R11 is selected from hydrogen, fluoro, chloro, bromo, iodo, cyano, unsubstituted or fluorinated $C_{1-3}$ alkyl, and unsubstituted or fluorinated $C_{1-3}$alkyloxy, and is preferably selected from hydrogen, fluoro, chloro, methyl, fluoromethyl, methoxy and fluoromethoxy, and pharmaceutically acceptable salts, solvates, isotopes and co-crystals thereof.

One embodiment relates to a compound of formula VI, wherein

X1 is C—R7 or N,

X2 is NH, S or O, wherein X2 is preferably NH

R2 and R4 are both hydrogen,

R5 is selected from hydrogen, fluoro, chloro and bromo,

R6 is selected from hydrogen, fluoro, chloro, bromo, cyano, azido, nitro, $C_{1-3}$alkyl, $C_{1-3}$alkyloxy, cyclopropyl, cyclopropyloxy, oxetanyl, tetrahydrofuranyl, methylsulfonyl, methylsulfinyl, thienyl, pyridyl, and benzyloxy, wherein each alkyl or alkoxy group in R6 can be unsubstituted or substituted with one or more groups selected from fluoro, chloro, bromo, unsubstituted or fluorinated $C_{1-2}$alkyloxy and cyclopropyl and wherein each cyclopropyl, thienyl, pyridyl and phenyl group in R6 can be substituted with one or more groups selected from halogen, methoxy, fluoromethoxy, methyl, fluoromethyl and cyano, or R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution of a ring formed by R6 and R7 is selected from hydroxy, halogen, cyano, methyl or methoxy, wherein each methyl or methoxy can be unsubstituted or fluorinated, R7, if present, is selected from hydrogen, halogen, cyano, $C_{1-3}$alkyl, $C_{1-3}$alkoxy, methylsulfinyl and methylsulfonyl, wherein alkyl or alkoxy group in R7 can be unsubstituted or substituted with one or more groups selected from fluoro, chloro, cyano, and unsubstituted or fluorinated $C_{1-2}$alkyloxy, or R7 forms a ring together with R6 as described herein, R8 is selected from hydrogen, fluoro, chloro, unsubstituted or fluorinated methyl, and unsubstituted or fluorinated methoxy, R9 is selected from hydrogen, fluoro, methyl, fluoromethyl, methoxy, and fluoromethoxy, and is preferably hydrogen, R10 is selected from hydrogen, halogen, $C_{1-3}$alkyl, $C_{1-3}$alkyloxy, $C_{2-3}$alkenyl, $C_{2-3}$alkynyl, $C_{1-3}$ alkylcarbonyl, $C_{3-4}$cycloalkyl and cyano, wherein each alkyl, alkenyl, alkynyl or alkoxy can be unsubstituted or substituted with one or more substituents selected from fluoro, chloro, bromo, fluorinated or unsubstituted $C_{1-3}$alkyloxy, fluorinated or unsubstituted $C_{1-3}$alkylcarbonyl, fluorinated or unsubstituted $C_{1-3}$alkoxycarbonyl, $C_{3-5}$cycloalkyl, $C_{3-5}$cycloalkyloxy, $C_{3-5}$heterocycloalkyl, $C_{3-5}$heterocycloalkyloxy, hydroxy and cyano, wherein any cycloalkyl, heterocycloalkyl, cycloalkyloxy and heterocycloalkyloxy may be unsubstituted or substituted with one or more residues selected from halogen, hydroxy, hydroxymethyl, cyano, fluorinated or unsubstituted methyl, fluorinated or unsubstituted $C_{1-3}$alkyloxy, fluorinated or unsubstituted $C_{1-3}$alkyloxycarbonyl and fluorinated or unsubstituted $C_{1-3}$alkyloxy($C_{1-3}$)alkyloxy, R11 is selected from hydrogen, fluoro, chloro, bromo, unsubstituted or fluorinated $C_{1-3}$ alkyl, and unsubstituted or fluorinated $C_{1-3}$ alkyloxy, and pharmaceutically acceptable salts, solvates, isotopes and co-crystals thereof.

In one preferred embodiment of the compounds of Formula VI, R6 is not hydrogen; in a more preferred embodiment at least one of, preferably two of R8, R10 and R11 are also different from hydrogen. In one embodiment, R6 and R10 are both not hydrogen.

In one preferred embodiment of the present invention, in a compound of Formula VI, either (a) X1 is CR7 and X2 is NH, S or O, or (b) X1 is N and X2 is NH, Hence, preferred substructures of Formula VI are those of Formula VIa, VIb, VIc and VId as follows:

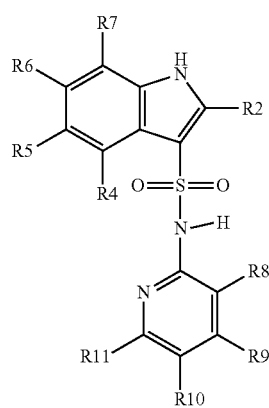

Formula VIa

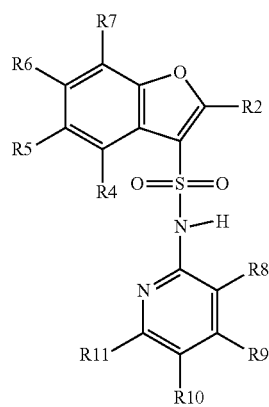

Formula VIb

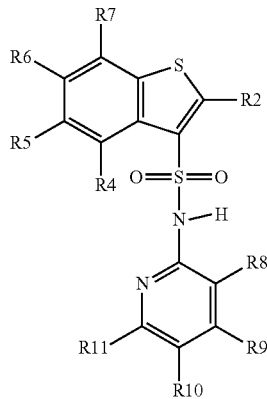

Formula VIc

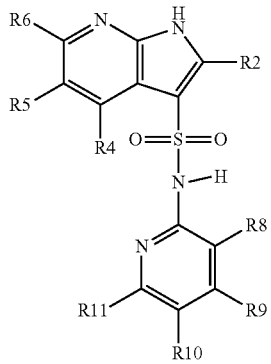

Formula VId wherein any R2, R4, R5, R6, R7, if present, R8, R9, R10 and R11 are as described as for compounds of formula I-2, II-2, III-2, IV-2, V-2 and VI herein.

In one preferred embodiment of the invention, in the compounds of formula VI and VIa-d, R2 is hydrogen or fluoro, R4 is selected from hydrogen, methoxy and fluoro, and is preferably hydrogen or fluoro, more preferably hydrogen, R5 is selected from hydrogen, halogen, cyano, $C_{1-3}$alkoxy, $C_{1-3}$ alkylcarbonyl, $C_{1-3}$alkoxycarbonyl, $C_{1-3}$alkylsulfinyl, and $C_{1-3}$alkylsulfonyl, wherein each alkyl or alkoxy may optionally be substituted one or more times with a group selected from halogen, $C_{1-3}$ alkoxy, halo($C_{1-3}$)alkoxy, cyano, hydroxyl, and $C_{1-3}$ alkylamino, with preferred optional substitutions of said alkyl and alkoxy groups being halogen and $C_{1-6}$ alkoxy, or R5 forms a ring together with R6 as described herein, R6 is selected from hydrogen, hydroxy, halogen, cyano, azido, nitro, $C_{1-6}$ alkyl, $C_{2-6}$ alkenyl, $C_{2-6}$ alkynyl, $C_{1-6}$ alkoxy, $C_{3-7}$ cycloalkyl, $C_{3-6}$ cycloalkenyl, $C_{3-7}$ heterocycloalkyl, $C_{3-7}$ heterocycloalkenyl, phenyl, $C_{5-10}$heteroaryl preferably $C_{5-6}$heteroaryl, $C_{8-10}$ heterocyclyl, —ORx, —SRx, —SORx, $SO_2Rx$, -pentafluorosulfanyl, NRyRzz, —NRyCORx, —NRyCO$_2$Rx, —NRxCONRyRz, —CORx, —CO$_2$Rx, —CONRyRz, wherein each alkyl, alkenyl, alkynyl, alkoxy, cycloalkyl, heterocycloalkyl, cycloalkenyl, heterocycloalkenyl, phenyl, heteroaryl or heterocyclyl group in R6 can be unsubstituted or substituted with one or more substituents preferably selected from halogen, hydroxyl, oxo, cyano, azido, nitro, $C_{1-6}$ alkyl, $C_{1-6}$ alkoxy($C_{1-3}$)alkyl, $C_{3-7}$ cycloalkyl, $C_{3-7}$ heterocycloalkyl, phenyl, $C_{5-10}$ (preferably $C_{5-6}$) heteroaryl, ORx, —SRx, —SORx, SO$_2$Rx, -pentafluorosulfanyl, NRyRz, —NRyCORx, —NRyCO$_2$Rx, —CORx, —CO$_2$Rx, —CONRyRz, wherein Rx, Ry, Rz and Rzz are independently selected from hydrogen, $C_{1-6}$ alkyl, $C_{3-7}$ cycloalkyl, $C_{3-6}$ cycloalkenyl, $C_{3-7}$ cycloalkyl($C_{1-6}$)alkyl, phenyl, phenyl($C_{1-6}$)alkyl, $C_{3-7}$ heterocycloalkyl, $C_{3-7}$ heterocycloalkyl($C_{1-6}$)alkyl, $C_{5-6}$ heteroaryl or heteroaryl($C_{1-6}$) alkyl, any of which groups can be unsubstituted or substituted with one or more substituents, or Ry and Rz, or Ry and Rzz together with the amino atom to which they are both attached may form an aromatic or non aromatic, unsubstituted or substituted $C_{5-6}$ heterocycle, wherein Rzz is preferably different from hydrogen, or in the compounds of formula VI, VIa, VIb or VIc R6 may form together with R5 or R7 and the carbon atoms to which they are attached a 5 or 6 membered aromatic or non-aromatic ring which may optionally contain one or more heteroatoms selected from S, O, and N, and wherein said ring can be unsubstituted or substituted with one or more substituents, wherein preferably R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl, wherein each substitution, if present, is selected from halogen, hydroxy, cyano, $C_{1-3}$ alkyl, $C_{3-7}$ cycloalkyl, $C_{3-7}$ cycloalkyl($C_{1-3}$) alkyl, $C_{3-7}$ heterocycloalkyl($C_{1-3}$)alkyl, $C_{1-3}$ alkoxy, and $C_{1-3}$ alkoxy($C_{1-3}$) alkyl, wherein each alkyl or alkoxy can be unsubstituted or substituted with one or more substituents selected from halogen and $C_{1-3}$ alkoxy, or (ii) R6 forms together with R5 and the carbon atoms to which R6 and R5 are attached, a 1,3-dioxolane which may be unsubstituted or substituted with one or two substituents selected from fluoro and methyl, or R7, if present, is selected from H, halogen, cyano, $C_{1-6}$ alkyl, $C_{1-6}$ alkoxy, $C_{2-6}$ alkynyl, $C_{2-6}$ alkenyl, $C_{1-6}$ alkylcarbonyl, $C_{1-6}$ alkoxycarbonyl, $C_{1-6}$ alkylcarbonylamino, $C_{1-5}$ alkylaminocarbonyl, di($C_{1-3}$)alkylaminocarbonyl, $C_{1-6}$ alkylsulfonyl, $C_{1-6}$ alkylsulfinyl, $C_{3-7}$ cycloalkyl, $C_{3-7}$ heterocycloalkyl, phenyl, $C_{5-6}$ heteroaryl, $C_{5-6}$ heteroaryl($C_{1-3}$) alkyl and $C_{5-6}$ heteroaryl($C_{1-3}$) alkoxy, wherein each alkyl, alkenyl, alkynyl or alkoxy group can be unsubstituted or substituted with one or more substituents selected from halogen, halo($C_{1-6}$)alkoxy preferably fluro($C_{1-3}$)alkoxy and $C_{1-6}$ alkoxy, R8 is selected from hydrogen, $C_{1-6}$ alkyl, $C_{1-6}$ alkoxy, and halogen, wherein each alkyl or alkoxy can be unsubstituted or substituted with one or more substituents selected from halogen and optionally fluorinated $C_{1-3}$ alkoxy, R9 is selected from hydrogen, halogen, cyano, azido, $C_{1-6}$ alkyl, $C_{1-6}$ alkoxy, $C_{2-6}$ alkenyl, $C_{2-6}$ alkynyl and halogen, wherein each alkyl or alkoxy can be unsubstituted or substituted with one or more substituents selected from halogen and $C_{1-3}$ alkoxy, R10 is selected from hydrogen, halogen, $C_{1-6}$ alkyl, $C_{1-6}$alkoxy, $C_{2-6}$ alkenyl, $C_{2-6}$ alkynyl, cyano, $C_{1-6}$ alkylcarbonyl, $C_{1-6}$ alkoxycarbonyl, $C_{1-6}$ alkylsulfonyl, $C_{1-6}$ alkylsulfinyl, $C_{1-6}$ alkylthio, $C_{1-5}$ alkylcarbonylamino, $C_{1-5}$ alkylaminocarbonyl, di($C_{1-3}$)alkylaminocarbonyl, $C_{3-6}$cycloalkyl, hetero($C_{3-6}$)cycloalkyl, azido, pentafluorosulfanyl, and nitro, wherein each alkyl, alkenyl, alkynyl or alkoxy can be unsubstituted or substituted with one or more substituents selected from halogen, $C_{1-6}$ alkoxy, halo($C_{1-6}$)alkoxy, unsubstituted or fluorinated $C_{1-3}$ alkoxycarbonyl, unsubstituted or fluorinated $C_{1-3}$ alkylcarbonyl, $C_{1-6}$ alkylthio, unsubstituted or fluorinated $C_{1-3}$ alkylcarbonylamino, unsubstituted or fluorinated $C_{1-3}$ alkylaminocarbonyl, unsubstituted or fluorinated di($C_{1-3}$)alkylaminocarbonyl, unsubstituted or fluorinated $C_{1-3}$ alkylsulfonyl, unsubstituted or fluorinated $C_{1-3}$ alkylsulfinyl, hydroxy, cyano, cyclo ($C_{3-6}$)alkyl, phenyl, and $C_{5-6}$heteroaryl, wherein any cycloalkyl, heterocycloalkyl, phenyl and heteroaryl may be unsubstituted or substituted with one or more residues selected from halogen, hydroxy, cyano, unsubstituted or fluorinated $C_{1-3}$ alkyl, unsubstituted or fluorinated $C_{1-3}$alkoxy, and unsubstituted or fluorinated $C_{1-3}$alkoxycarbonyl, R11 is selected from hydrogen, halogen, cyano, azido, $C_{1-6}$ alkyl, $C_{1-6}$ alkoxy, $C_{1-6}$ alkylcarbonyl, $C_{1-6}$ alkoxycarbonyl, $C_{1-6}$ alkylsulfonyl, and $C_{1-6}$ alkylsulfinyl, $C_{2-6}$ alkenyl, and $C_{2-6}$ alkynyl, wherein each alkyl or alkoxy can be unsubstituted or substituted with one or more substituents selected from halogen and $C_{1-3}$ alkoxy, and pharmaceutically acceptable salts, solvates, isotopes and co-crystals thereof.

In one embodiment, in the compounds of Formula VI and VIa-d, at least one of the group R5, R6 and R7, if present, and at least one, preferably two of the group R8, R10 and R11 are different from hydrogen, wherein more preferably at least one substituent is selected from fluoro, chloro and bromo.

In one embodiment, in the compounds of Formula VI and VIa-d,

X1, if present, is N or CR7,

X2, if present, is NH, S or O, wherein if X1 is N, then X2 is preferably NH,

R2 is hydrogen or fluoro, preferably hydrogen,

R4 is hydrogen or fluoro, preferably hydrogen,

R5 is selected from hydrogen, halogen, cyano, $C_{1-2}$ alkyl, and $C_{1-2}$ alkyloxy, wherein R5 is preferably hydrogen, methyl or halogen, or R5 forms a ring together with R6 as described herein, R6 is selected from hydrogen, halogen, cyano, nitro, amino, azido, $C_{1-3}$alkyl, $C_{2-3}$alkenyl, $C_{2-3}$alkynyl, $C_{1-3}$alkyloxy, $C_{1-3}$ alkylcarbonyl, $C_{1-3}$ alkoxycarbonyl, $C_{1-3}$ alkylcarbonylamino, $C_{1-3}$ alkylaminocarbonyl, di($C_{1-3}$)alkylaminocarbonyl, ($C_{1-3}$)alkylsulfinyl, ($C_{1-3}$)alkylsulfonyl, $C_{3-6}$ cycloalkyl, $C_{3-6}$ cycloalkyloxy, $C_{3-6}$ cycloalkyl($C_{1-2}$)alkyl, $C_{3-6}$ cycloalkyl($C_{1-3}$)alkoxy, $C_{3-6}$ heterocycloalkyl, $C_{3-6}$ heterocycloalkyloxy, $C_{3-6}$ heterocycloalkyl($C_{1-2}$)alkyl, heterocycloalkyl($C_{1-2}$)alkyloxy, phenyl, phenyloxy, phenyl($C_{1-2}$)alkyl, phenyl($C_{1-2}$)alkoxy, phenylsulfonyl, phenylsulfinyl, phenyl($C_{1-2}$)alkylsulfonyl, phenyl($C_{1-2}$)alkylsulfinyl, $C_{5-6}$heteroaryl, $C_{5-6}$heteroaryloxy, $C_{5-6}$heteroaryl($C_{1-2}$)alkyl, and $C_{5-6}$heteroaryl($C_{1-2}$)alkoxy and wherein each group in R6 can be unsubstituted or substituted with one or more groups selected from fluoro, chloro, bromo, fluorinated or unsubstituted $C_{1-3}$alkyl, fluorinated or unsubstituted $C_{1-3}$alkyloxy, hydroxy, and cyano, or (i) wherein in the compounds of formula VI, VIa, VIb or VIc R6 may form together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from hydroxy, halogen, methyl or methoxy, wherein each methyl or methoxy can be unsubstituted or substituted with one or more substituents selected from halogen, preferably fluoro, and methoxy, or (ii) R6 forms together with R5 and the carbon atoms to which R6 and R5 are attached, a 1,3-dioxolane which may be unsubstituted or substituted with one or two substituents selected from fluoro and methyl, R7, if present, is selected from hydrogen, fluoro, chloro, bromo, iodo, cyano, azido, nitro, amino, $C_{1-3}$alkyl, $C_{2-3}$alkenyl, $C_{2-3}$alkynyl, $C_{1-3}$alkyloxy, $C_{1-3}$ alkylcarbonyl, $C_{1-3}$ alkoxycarbonyl, $C_{1-3}$ alkylcarbonylamino, $C_{1-3}$ alkylaminocarbonyl, di($C_{1-3}$)alkylaminocarbonyl, $C_{1-3}$alkylsulfinyl, $C_{1-3}$alkylsulfonyl, $C_{1-3}$alkylthio, $C_{3-6}$ cycloalkyl, $C_{3-6}$ cycloalkyloxy, $C_{3-6}$ cycloalkyl($C_{1-2}$)alkyl, $C_{3-6}$ cycloalkyl($C_{1-3}$)alkoxy, $C_{3-6}$ heterocycloalkyl, $C_{3-6}$ heterocycloalkyloxy, $C_{3-6}$ heterocycloalkyl($C_{1-2}$)alkyl, heterocycloalkyl($C_{1-2}$)alkyloxy, phenyl, phenyloxy, phenyl($C_{1-2}$)alkyl, phenyl($C_{1-2}$)alkoxy, phenylsulfonyl, phenylsulfinyl, $C_{5-6}$ heteroaryl, $C_{5-6}$heteroaryloxy, $C_{5-6}$heteroaryl($C_{1-2}$)alkyl, and $C_{5-6}$heteroaryl($C_{1-2}$)alkoxy and wherein each group in R7 can be unsubstituted or substituted with one or more groups selected from fluoro, chloro, bromo, fluorinated or unsubstituted $C_{1-3}$alkyl, fluorinated or unsubstituted $C_{1-3}$alkyloxy, hydroxy, and cyano, or R7 forms a ring together with R6 as described herein, R8 is selected from hydrogen, halogen, cyano, optionally halogenated $C_{1-3}$ alkyloxy, optionally halogenated $C_{1-3}$ alkyl, optionally halogenated ($C_{1-3}$)alkylsulfinyl, optionally halogenated ($C_{1-3}$)alkylsulfonyl and optionally halogenated ($C_{1-3}$)alkylthio, R9 is selected from hydrogen, fluoro, chloro, bromo, iodo, $C_{1-3}$alkyloxy, fluoro($C_{1-3}$)alkoxy, $C_{1-3}$ alkyl, and fluoro ($C_{1-3}$)alkyl, and is preferably hydrogen, R10 is selected from hydrogen, fluoro, chloro, bromo, iodo, cyano, nitro, amino, azido, pentafluorosulfanyl, $C_{1-3}$alkyl, $C_{2-3}$alkenyl, $C_{2-3}$alkynyl, $C_{1-3}$alkyloxy, $C_{1-3}$ alkylcarbonyl, $C_{1-3}$ alkoxycarbonyl, $C_{1-3}$ alkylaminocarbonyl, di($C_{1-3}$)alkylaminocarbonyl, ($C_{1-3}$)alkylsulfinyl, ($C_{1-3}$)alkylsulfonyl, ($C_{1-3}$)alkylthio, $C_{3-6}$ cycloalkyl, $C_{3-6}$ cycloalkyloxy, $C_{3-6}$ cycloalkyl($C_{1-2}$)alkyl, $C_{3-6}$ cycloalkyl($C_{1-3}$)alkoxy, $C_{3-6}$ heterocycloalkyl, $C_{3-6}$ heterocycloalkyloxy, $C_{3-6}$ heterocycloalkyl($C_{1-2}$)alkyl, $C_{3-6}$ heterocycloalkyl($C_{1-2}$)alkyloxy, and wherein each group in R10 can be unsubstituted or substituted with one or more groups selected from fluoro, chloro, bromo, fluorinated or unsubstituted $C_{1-3}$alkyl, fluorinated or unsubstituted $C_{1-3}$alkyloxy, fluorinated or unsubstituted $C_{1-3}$alkoxycarbonyl, fluorinated or unsubstituted $C_{1-3}$alkylcarbonyl, $C_{1-3}$ alkylaminocarbonyl, di($C_{1-3}$)alkylaminocarbonyl, hydroxy, and cyano, R11 is selected from hydrogen, fluoro, chloro, bromo, iodo, $C_{1-3}$ alkyl, fluoro($C_{1-3}$)alkyl, $C_{1-3}$ alkyloxy, fluoro($C_{1-3}$) alkoxy, unsubstituted or fluorinated $C_{1-3}$ alkylcarbonyl, unsubstituted or fluorinated $C_{1-3}$ alkoxycarbonyl, and cyano, and pharmaceutically acceptable salts, solvates, isotopes and co-crystals thereof.

In one preferred embodiment, R6 and R10 are both different from hydrogen and are independently selected from a group as further defined herein.

In one embodiment, in the compounds of Formula VI and VIa-d,

R2 and R4 are both hydrogen,

R5 is selected from hydrogen, fluoro, chloro and bromo,

R6 is selected from fluoro, chloro, bromo, azido, cyano, benzyloxy, methylsulfonyl, methylsulfinyl, $C_{1-3}$alkyl, $C_{1-3}$alkyloxy, cyclopropyl, cyclopropyloxy and cyclopropylmethoxy, wherein each alkyl, alkoxy and cyclopropyl group in R6 can be unsubstituted or substituted with one or more groups selected from fluoro, chloro, bromo and unsubstituted or fluorinated $C_{1-2}$alkyloxy, wherein R6 is preferably selected from fluoro, chloro, bromo, fluorinated methyl, and unsubstituted or fluorinated methoxy, or in the compounds of formula VI, VIa, VIb or VIc, R6 may form together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution in R7, if present, is selected from hydroxy, halogen, cyano, methyl or methoxy, wherein each methyl or methoxy can be unsubstituted or fluorinated and/or hydroxylated, R7, if present, is selected from hydrogen, halogen, cyano, $C_{1-3}$alkyl, $C_{1-3}$alkyloxy, $C_{3-6}$ cycloalkyl, $C_{3-6}$ cycloalkyloxy, methylsulfinyl and methylsulfonyl, wherein each alkyl, alkoxy or cycloalkyl group in R7 can be unsubstituted or substituted with one or more groups selected from fluoro, chloro, cyano and unsubstituted or fluorinated $C_{1-2}$alkyloxy, or R7 forms a ring together with R6 as described herein, R8 is selected from hydrogen, fluoro, chloro, unsubstituted or fluorinated methoxy and unsubstituted or fluorinated methyl, R9 is selected from hydrogen, fluoro, methyl and methoxy, and is preferably hydrogen, R10 is selected from hydrogen, halogen, cyano, $C_{1-3}$alkyl, $C_{2-3}$alkenyl, $C_{2-3}$alkynyl, $C_{1-3}$alkyloxy, $C_{3-4}$cycloalkyl, $C_{3-4}$cycloalkyloxy, $C_{3-4}$heterocycloalkyl, and $C_{3-4}$heterocycloalkyloxy, wherein each alkyl, alkenyl, alkynyl and alkyloxy group in R10 can be unsubstituted or substituted with one or more groups selected from fluoro, chloro, bromo, fluorinated or unsubstituted $C_{1-3}$alkyloxy, fluorinated or unsubstituted $C_{1-3}$alkylcarbonyl, fluorinated or unsubstituted $C_{1-3}$alkoxycarbonyl, $C_{3-4}$cycloalkyl, $C_{3-4}$cycloalkyloxy, $C_{3-4}$heterocycloalkyl, $C_{3-4}$heterocycloalkyloxy, hydroxy, and cyano, and wherein each cycloalkyl and heterocycloalkyl group in R10 can be substituted with a residue selected from fluoro, chloro, bromo, hydroxy, hydroxymethyl, fluorinated or unsubstituted $C_{1-3}$alkyl, fluorinated or unsubstituted $C_{1-3}$alkyloxy, fluorinated or unsubstituted $C_{1-2}$alkyloxy$C_{1-2}$alkyloxy and fluorinated or unsubstituted $C_{1-3}$alkoxycarbonyl, R11 is selected from hydrogen, fluoro, chloro, bromo, unsubstituted or fluorinated $C_{1-3}$ alkyl preferably fluoromethyl, and unsubstituted or fluorinated $C_{1-3}$ alkyloxy preferably methoxy and fluoromethoxy, wherein R11 is preferably selected from hydrogen, fluoro, chloro, methoxy and fluoromethyl, and pharmaceutically acceptable salts, solvates, isotopes and co-crystals thereof.

In one preferred embodiment of the compounds of Formula VI, R2 is hydrogen.

In one preferred embodiment of the compounds of Formula VI and VIa-d, R4 is hydrogen or fluoro, particularly preferably hydrogen.

In one preferred embodiment of the compounds of Formula VI and VIa-d, R5 is selected from hydrogen, fluoro, chloro, bromo, iodo, and unsubstituted or fluorinated methyl. In a particularly preferred embodiment, R5 is selected from hydrogen, fluoro, chloro, bromo and methyl, and particularly preferably from hydrogen, fluoro, chloro and bromo. In one preferred embodiment of the compounds of Formula VI and VIa-d, if R6 is not hydrogen, then R5 is hydrogen.

In one embodiment of the compounds of Formula VIa-c, in particular in the compounds of Formula VIa, R6 forms a ring together with R7 and the C-atoms atoms to which R6 and R7 are attached, wherein the ring is preferably selected from phenyl, pyridyl, cyclopentyl and cyclohexyl, each of which may be unsubstituted or substituted with one or more substituents selected from halogen, hydrogen, oxo, $C_{1-3}$ alkyl $C_{1-3}$alkoxy, fluoro $C_{1-3}$ alkoxy, fluoro $C_{1-3}$ alkyl, amino, cyano, di($C_{1-3}$ alkyl)amino, acetyl, $C_{1-3}$ alkylsulfonyl, $C_{1-3}$ alkylsulfanyl, $C_{1-3}$alkylthio, and wherein the substitution is preferably selected from fluoro, chloro, bromo, cyano, hydroxy, methyl, fluoromethyl, methoxy and fluoromethoxy. In a preferred embodiment, in the compounds of formula VIa, R6 and R7 form a ring which, together with the annulated bicyclic ring, give a tricyclic moiety selected from 1H-benzo[g]indol-3-yl, 1H-pyrrolo[3,2-h]quinolin-3-yl, 1,6,7,8-tetrahydrocyclopenta[g]indol-3-yl, and 6,7,8,9-tetrahydro-1H-benzo[g]indol-3-yl. In one embodiment, if R6 and R7 form a pyridyl ring to give 1H-pyrrolo[3,2-h]quinolin-3-yl, the tricycle may be further substituted with a substituent selected from fluoro, chloro, bromo, hydroxy, methoxy, fluoromethyl and flurometoxy, preferably at the 8-position to give, for example, 8-hydroxy-1H-pyrrolo[3,2-h]quinoline, 8-(difluoromethyl)-1H-pyrrolo[3,2-h]quinoline or 8-(trifluoromethoxy)-1H-pyrrolo[3,2-h]quinoline. In one embodiment of the compounds of Formula VIa-c, in particular in the compounds of Formula VIa, R6 forms a ring together with R7 and the C-atoms atoms to which R6 and R7 are attached, wherein the ring is selected from phenyl, pyridyl, cyclopentyl and cyclohexyl, which are unsubstituted or substituted with one or more substituents selected from fluoro, chloro, fluoromethyl and fluoromethoxy, wherein, in one preferred embodiment, the ring is unsubstituted.

In one preferred embodiment of the compounds of Formula VIa-c, if R6 and R7 form an optionally substituted ring selected from phenyl, pyridyl, cyclopentyl and cyclohexyl, then R4 and R5 are preferably both hydrogen, R8 is hydrogen, halogen or unsubstituted or fluorinated methoxy, preferably fluoro or methoxy, R9 is hydrogen or fluoro preferably hydrogen, R10 is selected from halogen, cyano, cyanomethyl, cyanoethyl, cyanomethoxy, nitro, azido, pentafluorosulfanyl, unsubstituted or fluorinated and/or hydroxylated, preferably unsubstituted or fluorinated $C_{1-3}$ alkyl, unsubstituted or fluorinated and/or hydroxylated, preferably unsubstituted or fluorinated $C_{1-3}$ alkylcarbonyl, unsubstituted or fluorinated and/or hydroxylated, preferably unsubstituted or fluorinated $C_{1-3}$ alkoxy, unsubstituted or fluorinated $C_{2-3}$ alkenyl, $C_{2-3}$ alkynyl, unsubstituted or fluorinated and/or hydroxylated, preferably unsubstituted or fluorinated $C_{1-2}$ alkoxy($C_{1-3}$)alkyl, unsubstituted or fluorinated and/or hydroxylated, preferably unsubstituted or fluorinated $C_{1-2}$ alkoxy($C_{1-3}$)alkoxy, R11 is selected from hydrogen, fluoro, chloro, bromo, unsubstituted or fluorinated methoxy and unsubstituted or fluorinated methyl.

In one embodiment, in the compounds of formula VIa, R6 and R7 form a pyridine and the tricyclic ring system formed is optionally substituted 1H-pyrrolo[3,2-h]quinolin-3-yl, preferably 8-substituted 1H-pyrrolo[3,2-h]quinoline.

In one preferred embodiment of the compounds of Formula VIa, R6 and R7 form an optionally substituted ring selected from phenyl, pyridyl (to preferably form optionally 8-substituted 1H-pyrrolo[3,2-h]quinolin-3-yl), cyclopentyl and cyclohexyl, R4 and R5 are both hydrogen, R8 is fluoro or unsubstituted or fluorinated methoxy, R9 is hydrogen or fluoro, preferably hydrogen, R10 is selected from fluoro, chloro, bromo, iodo, cyano, cyanomethyl, cyanoethyl, cyanomethoxy, unsubstituted or fluorinated $C_{1-3}$ alkyl, unsubstituted or fluorinated $C_{1-3}$ alkoxy, unsubstituted or fluorinated $C_{2-3}$ alkenyl, $C_{2-3}$ alkynyl, unsubstituted or fluorinated $C_{1-2}$ alkoxy($C_{1-3}$)alkyl and unsubstituted or fluorinated $C_{1-2}$ alkoxy($C_{1-3}$)alkoxy, R11 is selected from hydrogen, fluoro, chloro, bromo, unsubstituted or fluorinated methoxy and unsubstituted or fluorinated methyl.

In one preferred embodiment of the compounds of Formula VI and VIa-d, R6 is selected from fluoro, chloro, bromo, iodo, cyano, azido, amino, nitro, $C_{1-3}$alkyl, $C_{2-3}$alkenyl, $C_{2-3}$alkynyl, $C_{1-3}$alkyloxy, $C_{1-3}$ alkylcarbonylamino, $C_{1-3}$ alkylaminocarbonyl, di($C_{1-3}$)alkylaminocarbonyl, ($C_{1-3}$)alkylsulfinyl, ($C_{1-3}$)alkylsulfonyl, $C_{3-6}$ cycloalkyl, $C_{3-6}$ cycloalkyloxy, $C_{3-6}$ cycloalkyl($C_{1-2}$)alkyl, $C_{3-6}$ cycloalkyl($C_{1-3}$)alkoxy, $C_{3-6}$ heterocycloalkyl, $C_{3-6}$ heterocycloalkyloxy, $C_{3-6}$ heterocycloalkyl($C_{1-2}$)alkyl, heterocycloalkyl($C_{1-2}$)alkyloxy, phenyl, phenyloxy, phenyl($C_{1-2}$)alkyl, phenyl($C_{1-2}$)alkoxy, phenylsulfonyl, benzylsulfonyl, phenylsulfinyl, benzylsulfinyl, $C_{5-6}$heteroaryl, $C_{5-6}$heteroaryloxy, $C_{5-6}$heteroaryl($C_{1-2}$)alkyl, and $C_{5-6}$heteroaryl($C_{1-2}$) alkoxy and wherein each group in R6 can be unsubstituted or substituted with one or more groups selected from fluoro, chloro, bromo, fluorinated or unsubstituted $C_{1-2}$alkyl, fluorinated or unsubstituted $C_{1-2}$alkoxy, hydroxy, and cyano.

In one preferred embodiment of the compounds of Formula VI and VIa-d, R6 is selected from fluoro, chloro, bromo, cyano, cyanomethyl, cyanomethoxy, nitro, azido, cyclopropyl, cyclopropyloxy, cycopropylmethoxy, unsubstituted or substituted $C_{1-3}$alkyl, unsubstituted or substituted $C_{1-3}$alkyloxy, methylsulfinyl, methylsulfonyl, pyridyl, optionally halogenated thienyl, and benzyloxy, wherein each substitution in R6 is selected from halo, methoxy and fluoromethoxy, and is preferably fluoro. In one preferred embodiment, R6 is selected from chloro, bromo, azido, cyano, cyclopropyl, methylsulfinyl, methylsulfonyl, mono-, di- and trifluoromethyl, methoxy, mono-, di- and trifluoromethoxy, and mono-, di- and trifluoroethoxy. In a particularly preferred embodiment, R6 is selected from fluoro, chloro, bromo, methoxy, fluoromethoxy, fluoroethoxy and fluoromethyl, and most preferably from fluoro, chloro, bromo and methoxy.

In one preferred embodiment of the compounds of Formula Via-c, R7 is selected from hydrogen, fluoro, chloro, bromo, iodo, cyano, nitro, $C_{1-3}$alkyl, $C_{1-3}$alkyloxy, $C_{1-3}$alkylsulfinyl, $C_{1-3}$alkylsulfonyl, $C_{1-3}$alkylthio, $C_{3-6}$cycloalkyl, $C_{3-6}$cycloalkyloxy, $C_{3-6}$heterocycloalkyl, $C_{3-6}$heterocycloalkyloxy, phenyl, phenyloxy, phenyl($C_{1-2}$)alkyl, phenyl($C_{1-2}$) alkoxy, phenylsulfonyl, phenylsulfinyl, $C_{5-6}$heteroaryl, $C_{5-6}$heteroaryloxy, $C_{5-6}$heteroaryl($C_{1-2}$)alkyl, and $C_{5-6}$heteroaryl($C_{1-2}$)alkoxy, wherein each group in R7 can be unsubstituted or substituted with one or more residues selected from fluoro, chloro, bromo, fluorinated or unsubstituted methyl, fluorinated or unsubstituted $C_{1-3}$alkyloxy, hydroxy, and cyano, and wherein the $C_{5-6}$heteroaryl is preferably selected from pyridyl, oxazol and isoxazol, each of which may be substituted as described above. In one preferred embodiment, R7 is selected from hydrogen, fluoro, chloro, bromo, methyl, fluoromethyl, methoxy, fluoromethoxy, fluoroethoxy, methylsulfinyl, methylsulfonyl and optionally substituted isoxazol. In one preferred embodiment, R7 is selected from hydrogen, fluoro, chloro, bromo, methyl, fluoromethyl, methoxy, fluoromethoxy and methylsulfonyl.

In a preferred embodiment, in the compounds of Formula VI and VIa-d, R8 is selected from hydrogen, halogen, cyano, unsubstituted or fluorinated $C_{1-3}$ alkyl and unsubstituted or fluorinated $C_{1-3}$ alkyloxy, preferably from fluoro, chloro, bromo, methyl, fluoromethyl, methoxy and fluoromethoxy. In one preferred embodiment, R8 is selected from fluoro, methoxy and fluoromethoxy, and in a particularly preferred embodiment, R8 is fluoro or methoxy.

In one preferred embodiment, in the compounds of Formula VI and VIa-d, R9 is selected from hydrogen, fluoro, chloro, methyl, fluoromethyl, methoxy and fluoromethoxy.

In one preferred embodiment, R9 is selected from hydrogen, fluoro, methoxy and fluoromethoxy, and is more preferably hydrogen or fluoro and particularly preferably hydrogen, In one embodiment, in the compounds of Formula VI and VIa-d, R10 is selected from hydrogen, fluoro, chloro, bromo, iodo, cyano, nitro, amino, azido, pentafluorosulfanyl, $C_{1-3}$alkyl, $C_{2-3}$alkenyl, $C_{2-3}$alkynyl, $C_{1-3}$alkyloxy, $C_{1-3}$ alkylcarbonyl, $C_{1-3}$ alkoxycarbonyl, $C_{1-3}$ alkylcarbonylamino, $C_{1-3}$ alkylaminocarbonyl, di($C_{1-3}$)alkylaminocarbonyl, ($C_{1-3}$)alkylsulfinyl, ($C_{1-3}$)alkylsulfonyl, ($C_{1-3}$)alkylthio, $C_{3-4}$ cycloalkyl, $C_{3-4}$ cycloalkyloxy, $C_{3-4}$ heterocycloalkyl, $C_{3-4}$ heterocycloalkyloxy, $C_{3-4}$ heterocycloalkyl($C_{1-2}$)alkyl, $C_{3-4}$heterocycloalkyl($C_{1-2}$)alkoxy, $C_{5-6}$heteroaryl($C_{1-2}$)alkyl, and $C_{5-6}$heteroaryl($C_{1-2}$)alkoxy and wherein each alkyl, alkenyl, alkynyl and alkoxy group in R10 can be unsubstituted or substituted with one or more groups selected from fluoro, chloro, bromo, fluorinated or unsubstituted $C_{1-3}$alkyloxy, $C_{1-3}$ alkyloxycarbonyl, phenyl, phenyloxy, $C_{3-6}$ cycloalkyl, $C_{3-6}$ cycloalkyloxy, $C_{3-6}$ heterocycloalkyl, $C_{3-6}$ heterocycloalkyloxy, hydroxy, and cyano, and wherein each cyclic group in R10 can be unsubstituted or substituted with one or more residues selected from fluoro, chloro, bromo, fluorinated or unsubstituted $C_{1-3}$alkyl, fluorinated or unsubstituted $C_{1-3}$alkyloxy, fluorinated or unsubstituted $C_{1-3}$alkyloxycarbonyl, hydroxy, hydroxymethyl, and cyano.

In one embodiment, in the compounds of Formula VI and VIa-d, R10 is selected from hydrogen, fluoro, chloro, bromo, iodo, cyano, nitro, amino, azido, pentafluorosulfanyl, $C_{1-3}$alkyl, $C_{2-3}$alkenyl, $C_{2-3}$alkynyl, $C_{1-3}$alkyloxy, $C_{1-3}$ alkylcarbonyl, $C_{1-3}$ alkoxycarbonyl, ($C_{1-3}$)alkylsulfinyl, ($C_{1-3}$)alkylsulfonyl, ($C_{1-3}$)alkylthio, $C_{1-3}$alkyloxycyclopropyl and $C_{1-3}$ alkyloxycarbonylcyclopropyl, wherein each alkyl, alkoxy, alkenyl and alkynyl group in R10 can be unsubstituted or substituted with one or more groups selected from fluoro, chloro, bromo, fluorinated or unsubstituted $C_{1-3}$alkyl, fluorinated or unsubstituted $C_{1-3}$alkyloxy, fluorinated or unsubstituted $C_{1-3}$alkyloxycarbonyl, $C_{3-6}$ cycloalkyl and cyano.

In one preferred embodiment, R10 is selected from hydrogen, fluoro, chloro, bromo, iodo, cyano, cyanomethyl, cyanoethyl, cyanomethoxy, cyanoethoxy, nitro, azido, pentafluorosulfanyl, $C_{1-3}$alkyl, $C_{2-3}$alkenyl, $C_{2-3}$alkynyl, $C_{1-3}$alkyloxy, $C_{1-2}$alkylcarbonyl and substituted cyclopropyl, wherein each group in R10 can be unsubstituted or substituted with one or more groups selected from fluoro, unsubstituted or fluorinated and/or hydroxylated, preferably unsubstituted or fluorinated $C_{1-2}$alkyloxy, unsubstituted or fluorinated and/or hydroxylated, preferably unsubstituted or fluorinated $C_{1-2}$alkyloxycarbonyl, unsubstituted or substituted cyclopropyl and hydroxy, provided that any substitution of cycopropyl is selected from the group of halogen, cyano, hydroxymethyl, optionally fluorinated $C_{1-2}$alkoxy and optionally fluorinated $C_{1-2}$alkoxycarbonyl.

In one preferred embodiment, in the compound of the present invention, including but not limited to the compounds of Formula VI and VIa-d, R10 is selected from hydrogen, fluoro, chloro, bromo, iodo, cyano, cyanomethyl, cyanoethyl, cyanomethoxy, cyanoethoxy, nitro, azido, pentafluorosulfanyl, methyl, ethyl, propyl, fluoromethyl, fluoroethyl, fluoropropyl, methoxymethyl, fluoromethoxymethyl, methoxyethyl, fluoromethoxyethyl, methoxypropyl, fluoromethoxypropyl, ethoxymethyl, fluoroethoxymethyl, ethoxyethyl, fluoroethoxyethyl, propoxymethyl, fluoropropoxymethyl, methoxy, ethoxy, propoxy, fluoromethoxy, fluoroethoxy, fluoropropoxy, methoxymethoxy, fluoromethoxymethoxy, methoxyethoxy, fluoromethoxyethoxy, methoxypropoxy, fluoromethoxypropoxy, ethoxymethoxy, fluoroethoxymethoxy, ethoxyethoxy, fluoroethoxyethoxy, propoxymethoxy, fluoropropoxymethoxy, ethenyl, propenyl, fluoroethenyl, fluoropropenyl, methoxyethenyl, fluoromethoxyethenyl, methoxypropenyl, fluoromethoxypropenyl, ethoxyethenyl, fluoroethoxyethenyl, ethynyl, propynyl, methoxyethynyl, fluoromethoxyethynyl, methoxypropynyl, fluoromethoxypropynyl and cyclopropylmethoxy, wherein in one embodiment, each group in R10 may be further suitably substituted with hydroxy.

In one preferred embodiment, R10 is a cyclic group selected from $C_{3-5}$ cycloalkyl, $C_{3-5}$ cycloalkyloxy, $C_{3-5}$ cycloalkyl($C_{1-3}$)alkyl preferably cycloalkylmethyl, $C_{3-5}$ cycloalkyl($C_{1-3}$)alkoxy preferably cycloalkylmethoxy, $C_{3-5}$ heterocycloalkyl, $C_{3-5}$ heterocycloalkyloxy, $C_{3-5}$ heterocycloalkyl($C_{1-3}$)alkyl preferably heterocycloalkylmethyl, and $C_{3-5}$ heterocycloalkyl($C_{1-3}$)alkoxy preferably heterocycloalkylmethoxy, wherein each cyclic group may be unsubstituted or substituted with one or more substituents selected from halogen preferably fluoro, cyano, hydroxymethyl, optionally fluorinated $C_{1-3}$alkoxy, optionally fluorinated $C_{1-2}$alkoxy($C_{1-2}$)alkyl, optionally fluorinated $C_{1-2}$alkoxy($C_{1-2}$)alkoxy, and optionally fluorinated $C_{1-2}$alkoxycarbonyl. In one preferred embodiment, the substitution is preferably selected from fluoro, cyano and optionally fluorinated $C_{1-3}$alkoxy, wherein the cyclic group is preferably cyclopropyl.

In one preferred embodiment, in the compound of the present invention, including but not limited to the compounds of formula VI and VIa-d, R10 is selected from fluoro, chloro, bromo, iodo, cyano, cyanomethyl, cyanoethyl, cyanomethoxy, cyanoethoxy, pentafluorosulfanyl, methyl, ethyl, propyl, butyl, fluoromethyl, fluoroethyl, fluoropropyl, methoxymethyl, fluoromethoxymethyl, methoxyethyl, fluoromethoxyethyl, methoxypropyl, fluoromethoxypropyl, ethoxymethyl, fluoroethoxymethyl, ethoxyethyl, fluoroethoxyethyl, methoxy, ethoxy, propoxy, butyloxy, fluoromethoxy, fluoroethoxy, fluoropropoxy, methoxymethoxy, fluoromethoxymethoxy, methoxyethoxy, fluoromethoxyethoxy, methoxypropoxy, fluoromethoxypropoxy, ethoxymethoxy, fluoroethoxymethoxy, ethoxyethoxy, fluoroethoxyethoxy, ethenyl, propenyl, fluoroethenyl, fluoropropenyl, methoxyethenyl, fluoromethoxyethenyl, methoxypropenyl, fluoromethoxypropenyl, ethoxyethenyl, fluoroethoxyethenyl, ethynyl, propynyl, ethoxycyclopropyl, ethoxycarbonylcyclopropyl and cyclopropylmethoxy.

In one preferred embodiment, in the compound of the present invention, including but not limited to the compounds of formula VI and VIa-d, R10 is selected from fluoro, chloro, bromo, cyano, cyanomethyl, cyanoethyl, methyl, mono-, di-, and trifluoromethyl, ethyl, mono-, di-, and trifluoroethyl, propyl, mono-, di-, and trifluoropropyl, methoxy, mono-, di-, and trifluoromethoxy, ethoxy, mono-, di-, and trifluoroethoxy, propyloxy, mono-, di-, and trifluoropropyloxy, methoxymethyl, mono-, di-, and trifluoromethoxymethyl, methoxyethyl, mono-, di-, and trifluoromethoxyethyl, methoxypropyl, mono-, di-, and trifluoromethoxypropyl, methoxymethoxy, mono-, di-, and trifluoromethoxymethoxy, methoxyethoxy, mono-, di-, and trifluoromethoxyethoxy, methoxypropyloxy, mono-, di-, and trifluoromethoxypropyloxy ethoxymethoxy, mono-, di-, and trifluoroethoxymethoxy, methoxypropenyl, and mono-, di-, and trifluoromethoxypropenyl.

In one preferred embodiment, R10 is selected from fluoro, chloro, bromo, iodo, cyano, cyanomethyl, cyanoethyl, cyanomethoxy, cyanoethoxy, unsubstituted or fluorinated $C_{1-3}$alkyl, unsubstituted or fluorinated $C_{1-3}$alkoxy, unsubstituted or fluorinated $C_{1-2}$alkoxy($C_{1-3}$)alkyl, unsubstituted or fluorinated $C_{1-2}$alkoxy($C_{1-3}$)alkoxy, and unsubstituted or fluorinated $C_{1-2}$alkoxy($C_{2-3}$)alkenyl.

In one preferred embodiment, R10 is selected from halogen, $C_{1-4}$alkoxy, $C_{1-4}$alkyl, $C_{2-4}$alkenyl, $C_{2-4}$alkynyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$cheterocycloalkyloxy, each of which can be optionally substituted with a residue selected from cyano, fluoro and unsubstituted or fluorinated $C_{1-3}$alkoxy.

In one embodiment, in the compounds of formula VI and VIa-d, R11 is selected from hydrogen, fluoro, chloro, bromo, iodo, $C_{1-3}$ alkyl, fluoro($C_{1-3}$)alkyl, $C_{1-3}$ alkyloxy, fluoro($C_{1-3}$)alkoxy, unsubstituted or fluorinated $C_{1-3}$ alkylcarbonyl, and cyano. In a preferred embodiment, R11 is selected from hydrogen, fluoro, chloro, methyl, fluoromethyl, methoxy, fluoromethoxy and cyano, more preferably from hydrogen, fluoro, floromethyl, methoxy and fluoromethoxy.

In one preferred embodiment, in the compounds of Formula VI and VIa-d,
R2, R4, R5 and R9 are all hydrogen,
R6 is selected from halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-4}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro and unsubstituted or fluorinated $C_{1-3}$alkoxy,
R7 is selected from hydrogen, halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro and unsubstituted or fluorinated $C_{1-3}$alkoxy,
R8 is selected from fluoro, methoxy and fluoromethoxy, preferably from fluoro and methoxy,
R10 is selected from halogen, $C_{1-4}$alkoxy, $C_{1-4}$alkyl, $C_{2-3}$alkenyl $C_{2-3}$alkynyl, $C_{3-4}$cycloalkyl preferably $C_{3-4}$cycloalkyl, $C_{3-6}$cycloalkyloxy preferably $C_{3-4}$cycloalkyloxy, $C_{3-6}$heterocycloalkyl preferably $C_{3-4}$heterocycloalkyl, and $C_{3-6}$heterocycloalkyloxy preferably $C_{3-4}$heterocycloalkyloxy, each of which can be optionally substituted with a residue selected from fluoro, cyano and unsubstituted or fluorinated $C_{1-3}$alkoxy, and
R11 is selected from hydrogen, fluoro, methoxy and fluoromethoxy, preferably from fluoro and methoxy.

In a preferred embodiment, in the compounds of formula VI and VIa-d,
R2 is hydrogen,
R4 is hydrogen or fluoro, more preferably hydrogen;
R5 is selected from hydrogen, fluoro, chloro and bromo;
R6 is selected from fluoro, chloro, bromo, azido, cyclopropyl, cyclopropyloxy, cycopropylmethoxy, unsubstituted or fluorinated $C_{1-3}$alkyl, unsubstituted or fluorinated $C_{1-3}$alkyloxy, methylsulfinyl, methylsulfonyl, pyridyl, optionally halogenated thienyl and benzyloxy;
R7, if present, is selected from hydrogen, fluoro, chloro, bromo, methyl, fluoromethyl, methoxy, fluoromethoxy, fluoroethoxy, methylsulfinyl, and methylsulfonyl;
R8 is selected from hydrogen, fluoro, chloro, bromo, methyl, fluoromethyl, methoxy and fluoromethoxy;
R9 is selected from hydrogen, fluoro, chloro, methyl, flurometyl, methoxy and fluoromethoxy, and is preferably hydrogen,
R10 is selected from hydrogen, fluoro, chloro, bromo, iodo, cyano, nitro, azido, pentafluorosulfanyl, $C_{1-3}$alkyl, $C_{2-3}$alkenyl, $C_{2-3}$alkynyl, $C_{1-3}$alkyloxy, $C_{1-3}$alkylcarbonyl, $C_{1-3}$alkoxycarbonyl and cyclopropyl, wherein the cyclopropyl is optionally substituted with a residue selected from cyano, $C_{1-2}$alkoxy, fluoro($C_{1-2}$)alkoxy, $C_{1-2}$alkoxy($C_{1-2}$)alkoxy, fluoro($C_{1-2}$)alkoxy($C_{1-2}$)alkoxy, $C_{1-2}$alkoxycarbonyl and fluoro($C_{1-2}$)alkoxycarbonyl, and wherein each alkyl, alkoxy, alkenyl and alkynyl group in R10 can be unsubstituted or substituted with one or more groups selected from halogen, fluorinated or unsubstituted $C_{1-2}$alkyloxy, cyano, cyclopropyl and hydroxy, wherein such substitution is preferably selected from fluoro, fluorinated or unsubstituted $C_{1-2}$alkyloxy and cyano;
and R11 is selected from hydrogen, fluoro, chloro, methyl, fluoromethyl, methoxy, fluoromethoxy and cyano,
and pharmaceutically acceptable salts, solvates, isotopes and co-crystals thereof.

In one preferred embodiment, in the compounds of formula VI and VIa-d, R2, if present, is hydrogen, R4 is hydrogen or fluoro, more preferably hydrogen; R5 is selected from hydrogen, fluoro, chloro and bromo and is preferably hydrogen; R6 is selected from fluoro, chloro, bromo, azido, methylsulfinyl, methylsulfonyl, methyl, mono-, di- and trifluoromethyl, methoxy, mono-, di- and trifluoromethoxy, and mono-, di- and trifluoroethoxy; R7, if present, is selected from hydrogen, fluoro, chloro, bromo, methyl, fluoromethyl, methoxy, fluoromethoxy, fluoroethoxy, methylsulfinyl and methylsulfonyl, R8 is selected from hydrogen, fluoro, chloro, bromo, methyl, fluoromethyl, methoxy and fluoromethoxy and is preferably fluoro or methoxy; R9 is selected from hydrogen, fluoro, methoxy and fluoromethoxy, and is preferably hydrogen; R10 is selected from hydrogen, fluoro, chloro, bromo, iodo, cyano, cyanomethyl, cyanoethyl, cyanomethoxy, cyanoethoxy, unsubstituted or fluorinated $C_{1-3}$alkyl, unsubstituted or fluorinated $C_{1-3}$alkyloxy, unsubstituted or fluorinated $C_{1-2}$alkyloxy($C_{1-3}$)alkyl, unsubstituted or fluorinated $C_{1-2}$alkyloxy($C_{1-3}$)alkyloxy, unsubstituted or fluorinated $C_{1-2}$alkyloxy($C_{2-3}$)alkenyl, cyclopropyl, cyclopropyloxy and cyclopropylmethoxy, wherein any cyclopropyl moiety is optionally substituted with a residue selected from fluoro, cyano, $C_{1-2}$alkoxy, fluoro($C_{1-2}$)alkoxy, $C_{1-2}$alkoxy($C_{1-2}$)alkoxy, fluoro($C_{1-2}$)alkoxy($C_{1-2}$)alkoxy, $C_{1-2}$alkoxycarbonyl, fluoro($C_{1-2}$)alkoxycarbonyl; and R11 is selected from hydrogen, fluoro, chloro, methyl, fluoromethyl, methoxy and fluoromethoxy, wherein preferably at least one, preferably two and more preferably all substituents in R8, R10 and R11 are different from hydrogen, and wherein in one particularly preferred embodiment R8 and R11 are both independently selected from fluoro and methoxy.

Another embodiment relates to compounds of Formula VI and VIa-d, wherein R2, if present, is hydrogen, R4 and R5 are both hydrogen, R6 is selected from fluoro, chloro, bromo, methylsulfinyl, fluoromethyl, methoxy and fluoromethoxy, R7 is selected from hydrogen, fluoro, chloro, bromo, unsubstituted or fluorinated $C_{1-2}$alkyl, unsubstituted or fluorinated $C_{1-2}$alkoxy, methylsulfinyl, and methylsulfonyl, R8 is selected from hydrogen, fluoro, chloro methoxy and fluoromethoxy, R9 is hydrogen, methoxy or fluoro, preferably hydrogen, R10 is selected from fluoro, chloro, bromo, iodo, cyano, cyanomethyl, cyanoethyl, unsubstituted or fluorinated and/or hydroxylated $C_{1-3}$alkyl, unsubstituted or fluorinated and/or hydroxylated $C_{1-3}$alkoxy, unsubstituted or fluorinated and/or hydroxylated $C_{1-2}$alkoxy($C_{1-3}$)alkyl, unsubstituted or fluorinated and/or hydroxylated $C_{1-2}$alkoxy($C_{1-3}$)alkoxy, unsubstituted or fluorinated and/or hydroxylated C$_{1-2}$alkoxy(C$_{2-3}$)alkenyl and unsubstituted or fluorinated C$_{1-2}$alkoxycarbonylcyclopropyl, and is preferably selected from fluoro, chloro, bromo, iodo, cyano, cyanomethyl, cyanoethyl, unsubstituted or fluorinated C$_{1-3}$alkyl, unsubstituted or fluorinated C$_{1-3}$alkoxy, unsubstituted or fluorinated C$_{1-2}$alkoxy(C$_{1-3}$)alkyl, unsubstituted or fluorinated C$_{1-2}$alkoxy(C$_{1-3}$)alkoxy, unsubstituted or fluorinated C$_{1-2}$alkoxy(C$_{2-3}$)alkenyl, unsubstituted or fluorinated C$_{1-2}$alkoxycarbonylcyclopropyl and unsubstituted or fluorinated C$_{1-3}$alkoxycyclopropyl, and R11 is selected from hydrogen, fluoro, chloro, fluoromethyl, methoxy, and fluoromethoxy, wherein in a particular preferably embodiment, at least one, more preferably both of R8 and R11 are different from hydrogen.

A further embodiment relates to compounds of Formula VI and VIa-d,
wherein
R2, R4 and R9 are all hydrogen,
R5 is hydrogen, fluoro, chloro or bromo, and is preferably hydrogen,
R6 is selected from fluoro, chloro, bromo, methoxy, fluoromethoxy, fluoromethyl and azido, or in the compounds of formula VI, VIa, VIb or VIc R6 may form together with R7 and the carbon atoms to which R6 and R7 are attached, a ring selected from phenyl, pyridyl, cyclohexyl and cyclopentyl, each of which may be unsubstituted or substituted with one or two substituents selected from fluoro, chloro, hydroxy, cyano, methoxy, fluoromethoxy and fluoromethyl,
R7 is selected from hydrogen, fluoro, chloro, bromo, unsubstituted or fluorinated methyl, unsubstituted or fluorinated methoxy and methylsulfinyl,
R8 is selected from fluoro, chloro, methoxy and fluoromethoxy,
R10 is selected from fluoro, chloro, bromo, iodo, cyano, cyanomethyl, cyanoethyl, cyanomethoxy, unsubstituted or fluorinated C$_{1-3}$alkyl, unsubstituted or fluorinated C$_{1-3}$alkoxy, unsubstituted or fluorinated C$_{1-2}$alkoxy(C$_{1-3}$)alkyl, unsubstituted or fluorinated C$_{1-2}$alkoxy(C$_{1-3}$)alkoxy, and unsubstituted or fluorinated C$_{1-2}$alkoxy(C$_{2-3}$)alkenyl, wherein R10 is preferably selected from fluoro, chloro, bromo, cyanomethyl, cyanoethyl, unsubstituted or fluorinated C$_{1-3}$alkyl, unsubstituted or fluorinated C$_{1-3}$alkoxy, unsubstituted or fluorinated C$_{1-2}$alkoxy(C$_{1-3}$)alkyl, unsubstituted or fluorinated C$_{1-2}$alkoxy(C$_{1-3}$)alkoxy, unsubstituted or fluorinated C$_{1-2}$alkoxy(C$_{2-3}$)alkenyl, unsubstituted or fluorinated C$_{1-3}$alkoxycyclopropyl, unsubstituted or fluorinated C$_{1-3}$alkoxycarbonylcyclopropyl and unsubstituted or fluorinated C$_{1-2}$alkoxy(C$_{1-2}$)alkoxycyclopropyl,
R11 is selected from hydrogen, fluoro, chloro, methyl, fluoromethyl, fluoromethoxy and methoxy,
and pharmaceutically acceptable salts, solvates, isotopes and co-crystals thereof.

In one preferred embodiment, in the compounds of Formula VI and VIa-d, R6 and R10 are different from hydrogen and are independently selected from a group as further defined herein.

In one preferred embodiment, in the compounds of Formula VI and VIa-d, R6, R8 and R10 are all different from hydrogen and are independently selected from a group as further defined herein In one preferred embodiment, in the compounds of Formula VI and VIa-d, R6, R8, R10 and R11 are all different from hydrogen and are independently selected from a group as further defined herein.

In one embodiment, in the compounds of Formula VI and VIa-c, R7 is not hydrogen.

In one preferred embodiment of the compounds of Formula VI and VIa-d, R6, R8 and at least one of R10 and R11 are all different from hydrogen, and are independently selected from a group as further defined herein In one embodiment, in the compounds of Formula VI and VIa, R6 and R7 form a ring selected from phenyl, pyridyl, cyclopentyl and cyclohexyl to give the formula VIe to VIg below:

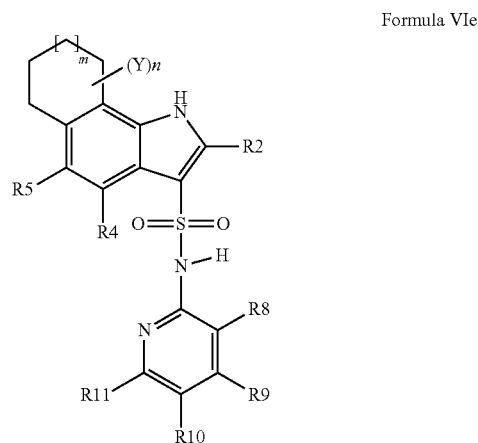

Formula VIe

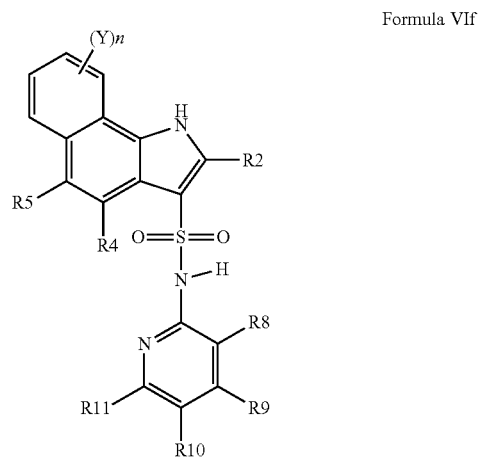

Formula VIf

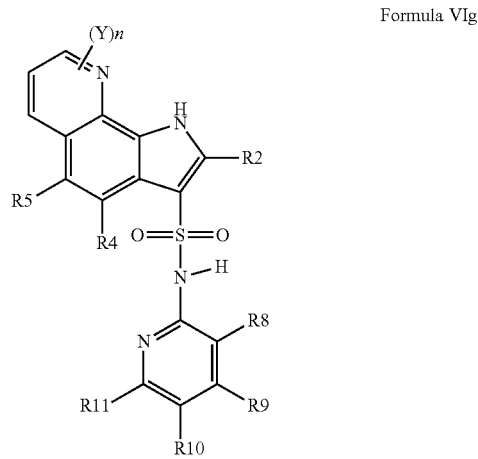

Formula VIg wherein m is 0 or 1, n is any number from 0 to 4, preferably from 0 to 2, more preferably 0 or 1, p is any number from 0 to 3, preferably from 0 to 2, more preferably 0 or 1, Y is selected from hydrogen, fluoro, chloro, bromo, iodo, cyano, hydroxy, methyl and methoxy, wherein the methoxy and methyl group are optionally substituted with one or more substituents selected from fluoro, chloro, bromo, hydroxy, methoxy and fluoromethoxy, R2 and R4 are both hydrogen, R5 is selected from hydrogen, fluoro, and chloro, more preferably hydrogen, R8 is selected from fluoro, fluoromethyl, methoxy and fluoromethoxy, R9 is hydrogen or fluoro, R10 is selected from hydrogen, fluoro, chloro, bromo, iodo, cyano, cyanomethyl, cyanoethyl, cyanopropyl, cyanomethoxy, cyanoethoxy, nitro, azido, pentafluorosulfanyl, $C_{1-3}$alkyl, $C_{2-3}$alkenyl, $C_{2-3}$alkynyl, $C_{1-3}$alkyloxy, $C_{1-2}$alkylcarbonyl, cycylopropyl, cyclopropylmethyl, and cyclopropylmethoxy, wherein each group in R10 can be unsubstituted or substituted with one or more groups selected from fluoro, fluorinated or unsubstituted $C_{1-2}$alkyloxy, fluorinated or unsubstituted $C_{1-2}$alkyloxycarbonyl and hydroxy, R11 is selected from hydrogen, fluoro, chloro, fluoromethyl, methoxy and fluoromethoxy, and pharmaceutically acceptable salts, solvates, isotopes and co-crystals thereof.

In one preferred embodiment, in the compounds of Formula VI e, m is 0 or 1, n is 0 or 1, preferably 0, Y is selected from fluoro, chloro, cyano, hydroxy, methyl and methoxy, wherein the methoxy and methyl group are optionally substituted with one or more substituents selected from fluoro, chloro, bromo, hydroxy, methoxy and fluoromethoxy, R2 and R4 are hydrogen, R5 is hydrogen, fluoro, or chloro, preferably hydrogen, R8 is selected from fluoro, fluoromethyl, methoxy and fluoromethoxy, preferably from fluoro and methoxy, R9 is hydrogen or fluoro, preferably hydrogen, R10 is selected from hydrogen, fluoro, chloro, bromo, iodo, cyano, cyanomethyl, cyanoethyl, pentafluorosulfanyl, $C_{1-3}$alkyl, $C_{2-3}$alkenyl, $C_{2-3}$alkynyl, $C_{1-3}$alkyloxy, $C_{1-2}$alkylcarbonyl and cyclopropyl, wherein each alkyl, alkenyl, alkynyl, alkyloxy and cyclopropyl group in R10 can be unsubstituted or suitably substituted with one or more groups selected from fluoro, fluorinated or unsubstituted $C_{1-2}$alkyloxy, fluorinated or unsubstituted $C_{1-2}$alkyloxycarbonyl and hydroxy, wherein said substituent is preferably selected from fluoro and fluorinated or unsubstituted $C_{1-2}$alkyloxy, R11 is selected from hydrogen, fluoro, chloro, fluoromethyl, methoxy and fluoromethoxy, and pharmaceutically acceptable salts, solvates, isotopes and co-crystals thereof.

In one preferred embodiment, in the compounds of Formula VI(f), n is 0 or 1, preferably 0, Y is selected from fluoro, chloro, cyano, hydroxy, methyl and methoxy, wherein the methoxy and methyl group are optionally substituted with one or more substituents selected from fluoro, chloro, bromo, hydroxy, methoxy and fluoromethoxy, R2 and R4 are both hydrogen, R5 is hydrogen, fluoro, or chloro, preferably hydrogen, R8 is selected from fluoro, fluoromethyl, methoxy and fluoromethoxy, R9 is hydrogen or fluoro, preferably hydrogen, R10 is selected from hydrogen, fluoro, chloro, bromo, iodo, cyano, cyanomethyl, cyanoethyl, pentafluorosulfanyl, $C_{1-3}$alkyl, $C_{2-3}$alkenyl, $C_{2-3}$alkynyl, $C_{1-3}$alkyloxy, $C_{1-2}$alkylcarbonyl and cyclopropyl, wherein each alkyl, alkenyl, alkynyl, alkyloxy and cyclopropyl group in R10 can be unsubstituted or suitably substituted with one or more groups selected from fluoro, fluorinated or unsubstituted $C_{1-2}$alkyloxy, fluorinated or unsubstituted $C_{1-2}$alkyloxycarbonyl and hydroxy, wherein said substituent is preferably selected from fluoro and fluorinated or unsubstituted $C_{1-2}$alkyloxy, R11 is selected from hydrogen, fluoro, chloro, fluoromethyl, methoxy and fluoromethoxy, and pharmaceutically acceptable salts, solvates, isotopes and co-crystals thereof.

In one preferred embodiment, in the compounds of Formula VI g, p is 0 or 1,

Y is selected from fluoro, chloro, cyano, hydroxy, methyl and methoxy, wherein the methoxy and methyl group are optionally substituted with one or more substituents selected from fluoro, chloro, bromo, hydroxy, methoxy and fluoromethoxy, R4 is hydrogen, R5 is hydrogen or fluoro, preferably hydrogen, R8 is selected from fluoro, fluoromethyl, methoxy and fluoromethoxy, R9 is hydrogen or fluoro, R10 is selected from hydrogen, fluoro, chloro, bromo, iodo, cyano, cyanomethyl, cyanoethyl, pentafluorosulfanyl, $C_{1-3}$alkyl, $C_{2-3}$alkenyl, $C_{2-3}$alkynyl, $C_{1-3}$alkyloxy, $C_{1-2}$alkylcarbonyl and cyclopropyl, wherein each alkyl, alkenyl, alkynyl, alkyloxy and cyclopropyl group in R10 can be unsubstituted or suitably substituted with one or more groups selected from fluoro, fluorinated or unsubstituted $C_{1-2}$alkyloxy, fluorinated or unsubstituted $C_{1-2}$alkyloxycarbonyl and hydroxy, wherein said substituent is preferably selected from fluoro and fluorinated or unsubstituted $C_{1-2}$alkyloxy, R11 is selected from hydrogen, fluoro, chloro, fluoromethyl, methoxy and fluoromethoxy, and pharmaceutically acceptable salts, solvates, isotopes and co-crystals thereof.

In one preferred embodiment of the compounds of formula VIe-g, R10 is selected from chloro, cyano, cyanomethyl, cyanoethyl, $C_{1-3}$alkyl and $C_{1-3}$alkoxy, wherein each alkyl and alkoxy can be unsubstituted or substituted with one or more substituents selected from fluoro, methoxy, fluoromethoxy, ethoxy and fluoroethoxy, wherein in one embodiment R10 is selected from chloro, bromo, unsubstituted or fluorinated $C_{1-3}$alkoxy, cyano, cyanomethyl and cyanoethyl. In one preferred embodiment of the compounds of formula VIe-g, R10 is chloro.

In one preferred embodiment of the compounds of formula VIe-g, Y, if present, is selected from fluoro, chloro, cyano, hydroxy, methyl, fluoromethyl, hydroxymethyl, methoxy and fluoromethoxy. In one preferred embodiment of the compounds of formula VIg, Y is selected from fluoro, hydroxy, fluoromethyl, methoxy and fluoromethoxy.

In one preferred embodiment, in the compounds or Formula VIe to VIg, R10 is selected from fluro, chloro, bromo, fluromethyl, fluoroethyl, fluoromethoxy, fluoroethoxy, cyano and cyanomethyl, and is particularly preferably chloro.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, wherein R4 is hydrogen, and the other substitutions are as disclosed herein.

Another embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, wherein R5 is selected from hydrogen, halogen, cyano, azido, unsubstituted or fluorinated $C_{1-2}$ alkyl, preferably methyl or trifluoromethyl, unsubstituted or fluorinated $C_{1-2}$ alkyloxy, unsubstituted or fluorinated $C_{1-2}$ alkylcarbonyl, unsubstituted or fluorinated $C_{1-2}$ alkyloxycarbonyl, $C_{1-2}$ alkylsulfinyl preferably methylsulfinyl, and $C_{1-2}$ alkylsulfonyl preferably methylsulfonyl, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, wherein R5 is selected from hydrogen, fluoro, chloro, bromo, iodo, methyl, trifluoromethyl, methoxy and trifluoromethoxy, and is particularly preferably selected from hydrogen, fluoro, chloro and bromo, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, wherein R5 is iodo and R6 is hydrogen, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, wherein R5 is hydrogen, and the other substitutions are as disclosed herein Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7, if present, is hydrogen, and the other substitutions are as disclosed herein.

Another preferred embodiment relates to compounds of the present invention including but not limited to those having a structure of Formula I1, I-2, II, II-2, IId, II-2d, IIe, II-2e, IIf, II-2f, IIg, II-2g, IV, IV-2, V, V-2, VI, VIa, VIb, or VIc, wherein R7, if present, is fluoro, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7, if present, is $C_{1-3}$ alkoxy or fluoro($C_{1-3}$) alkoxy, preferably mono-, di- or trifluoromethoxy, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7, if present, is methoxy, and the other substitutions are as disclosed herein.

Another preferred embodiment relates to compounds of the present invention, including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc wherein R7, if present, is selected from hydrogen, cyano, fluoro, chloro, bromo, methoxy, ethoxy, fluoromethoxy, fluoroethoxy, methyl, ethyl, fluoromethyl, fluoroethyl, methylsulfinyl, fluoromethylsulfinyl, methylsulfonyl and fluoromethylsulfonyl, and the other substitutions are as disclosed herein.

Another preferred embodiment relates to compounds of the present invention, including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7, if present, is methylsulfonyl, fluoromethylsulfonyl, methylsulfinyl, or fluoromethylsulfinyl, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7 is trifluoromethyl, and the other substitutions are as disclosed herein.

Another preferred embodiment relates to compounds of the present invention, including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7, if present, is cyano, cyanomethyl, or cyanomethoxy, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, or VIc, wherein R7 is bromo or chloro, preferably bromo, and the other substitutions are as disclosed herein.

Another preferred embodiment relates to compounds of the present invention including but not limited to those having a structure of Formula I, I-2, II, II-2, IIc, II-2c, IId, II-2d, IIe, II-2e, IIf, II-2f, IIg, II-2g, III, III-2, IV, IV-2, V, V-2, VI, VIa, VIb, VIc, VId, VIe, Vhf, or VIg, wherein R8 is selected from hydrogen, fluoro, chloro, bromo, iodo, methoxy, methyl, and trifluoromethyl and the other substitutions are as disclosed herein.

Another preferred embodiment relates to compounds of the present invention including but not limited to those having a structure of Formula I, I-2, II, II-2, IIc, II-2c, IId, II-2d, IIe, II-2e, IIf, II-2f, IIg, II-2g, III, III-2, IV, IV-2, V, V-2, VI, VIa, VIb, VIc, VId, VIe, Vhf, or VIg, wherein R8 is selected from fluoro, chloro, cyano, methoxy and fluoromethoxy, and the other substitutions are as disclosed herein.

Another preferred embodiment relates to compounds of the present invention including but not limited to those having a structure of Formula I, I-2, II, II-2, IIc, II-2c, IId, II-2d, IIe, II-2e, III, III-2, IV, IV-2, V, V-2, VI, VIa, VIb, VIc, VId, VIe, Vhf, or VIg, wherein R9 is selected from hydrogen, fluoro, chloro, bromo, iodo, methoxy, methyl, cyano, and trifluoromethyl, and is preferably hydrogen, fluoro, chloro, or bromo and the other substitutions are as disclosed herein.

Another preferred embodiment relates to compounds of the present invention including but not limited to those having a structure of Formula I, I-2, II, II-2, IIc, II-2c, IId, II-2d, IIe, II-2e, III, III-2, IV, IV-2, V, V-2, VI, VIa, VIb, VIc, VId, VIe, VIf, or VIg, wherein R9 is hydrogen, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, wherein R11 is selected from hydrogen, fluoro, chloro, bromo, iodo, methoxy, fluoromethoxy, methyl, cyano, and fluoromethyl preferably trifluoromethyl, and is more preferably selected from hydrogen, methoxy, fluoromethoxy, fluoromethyl, fluoro, chloro and bromo, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, or V-2, wherein X3 is C—R12 and R12 is selected from hydrogen, fluoro, chloro, bromo, iodo, methoxy, methyl, and fluoro ($C_{1-3}$)alkyl preferably trifluoromethyl, and is more preferably hydrogen, fluoro, chloro, or bromo, and the other substitutions are as disclosed herein. In a particularly preferred embodiment, R12 is hydrogen or fluoro.

Another preferred embodiment relates to compounds of the present invention including but not limited to those having a structure of Formula I, I-2, II, II-2, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, and VId, wherein R6 is different from hydrogen, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, and VId, wherein R6 is selected from the group of halogen, cyclopropyl, cyclopropyloxy, cyclopropylmethyl, unsubstituted or fluorinated $C_{1-3}$ alkyl, unsubstituted or fluorinated $C_{1-3}$ alkyloxy, unsubstituted or fluorinated phenyl, benzyloxy, thiophene, methylsulfinyl, methylsulfonyl, and cyclopropyl, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, and VId, wherein R6 is selected from fluoro, chloro, bromo, methoxy, methyl, ethyl, isopropyl, cyclopropyl, phenyl, benzyloxy, 2-thiophene, 3-thiophene, trifluoromethyl, and the other substitutions are as disclosed herein.

Another preferred embodiment relates to compounds of the present invention including but not limited to having a structure of Formula I, I-2, II, II-2, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, and VId, wherein R6 is chloro or bromo, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc and VId, wherein R6 is chloro, and the other substitutions are as disclosed herein.

Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, VIc and VId, wherein R6 is selected from halogen, cyano, $C_{1-3}$alkyl, $C_{1-3}$alkyloxy, $C_{3-6}$ cycloalkyl and $C_{3-6}$ cycloalkyloxy, each of which can be optionally substituted with a residue selected from fluoro and unsubstituted or fluorinated $C_{1-3}$alkoxy.

Another preferred embodiment relates to compounds of the present invention including but not limited to those having a structure of Formula I, I-2, II, II-2, IId, II-2d, IIe, II-2e, IIf, II-2f, IIg, II-2g, IV, IV-2, V, V-2, VI, VIa, VIb, VIc, wherein R7 is selected from hydrogen, halogen, cyano, $C_{1-3}$alkyl, $C_{1-3}$alkyloxy, $C_{3-6}$ cycloalkyl and $C_{3-6}$ cycloalkyloxy, each of which can be optionally substituted with a residue selected from fluoro and unsubstituted or fluorinated $C_{1-3}$alkoxy.

Another preferred embodiment relates to compounds of the present invention including but not limited to those having a structure of Formula I, I-2, II, II-2, IIa, II-2a, IIb, II-2b, IIc, II-2c, III, III-2, IV, IV-2, V and V-2, wherein X3 is C(R12), and the other substitutions are as disclosed herein.

Another preferred embodiment relates to compounds of the present invention including but not limited to those structure of Formula I, I-2, II, II-2, IIa, II-2a, IIb, II-2b, IIc, II-2c, III, III-2, IV, IV-2, V and V-2, wherein X3 is N and the other substitutions are as disclosed herein.

Another preferred embodiment relates to compounds of the present invention including but not limited to those having a structure of Formula I, II, IIa, IIb, IIc, III, or IV, wherein at least one of R8, R10 and R11 is different from hydrogen and unsubstituted alkyl.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is selected from hydrogen, fluoro, chloro, bromo, iodo, $C_{1-3}$ alkyl, halo($C_{1-3}$)alkyl preferably fluoro($C_{1-2}$)alkyl, $C_{2-3}$ alkynyl, methoxy, ethoxy, propoxy, halo($C_{1-3}$)alkyloxy preferably fluoro($C_{1-2}$)alkyloxy, unsubstituted or fluorinated ($C_{1-2}$)alkoxy($C_{1-3}$)alkoxy, cyano, cyanomethyl, azido, pentafluorosulfanyl, and nitro, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is selected from halogen, cyano, $C_{1-3}$alkyl, $C_{2-3}$alkenyl, $C_{2-3}$alkynyl, $C_{1-3}$alkyloxy, $C_{3-6}$ cycloalkyl and $C_{3-6}$ cycloalkyloxy, each of which can be optionally substituted with a residue selected from fluoro, cyano and optionally fluorinated $C_{1-3}$alkoxy.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is selected from the group of cyano, cyanomethyl, halogen, azido, ethynyl, pentafluorosulfanyl, acetyl, difluoroethoxy, trifluoroethoxy, trifluoromethoxy and trifluoromethyl, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is cyano, cyanomethyl, cyanoethyl, or cyanomethoxy and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is fluoro, and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg wherein R10 is chloro and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is bromo and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is mono-, di- or trifluoromethyl and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is difluoroethoxy (—OCH$_3$CHF$_2$) and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is trifluoroethoxy (—OCH$_3$CF$_3$) and the other substitutions are as disclosed herein.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, III, III-2, IIIa, III-2a, IIIb, III-2b, IV, IV-2, V, V-2, VI, VIa, VIb, VIc, VId, VIe, VIf, or VIg, wherein R10 is ethynyl and the other substitutions are as disclosed herein.

Another preferred embodiment relates to compounds of the present invention, wherein R10 is selected from methoxymethyl, methoxyethyl, methoxypropyl, ethoxymethyl, ethoxyethyl, ethoxypropyl, propoxymethyl, methoxyethenyl, methoxypropenyl, ethoxyethenyl, ethoxypropenyl, methoxyethynyl, methoxypropynyl, methoxymethoxy, methoxyethoxy, methoxypropoxy, ethoxymethoxy, ethoxyethoxy, ethoxypropoxy and propoxymethoxy, each of which may be unsubstituted or fluorinated up to three times, and the other substitutions are as disclosed herein.

Another preferred embodiment relates to compounds of the present invention, wherein R10 is methoxypropyl or fluorinated methoxypropyl, and the other substitutions are as disclosed herein.

Another particularly preferred embodiment relates to compounds of the present invention, as further described herein, wherein R8, R10 and R11 are all different from hydrogen, and the other substitutions are as disclosed herein.

Another particularly preferred embodiment relates to compounds of the present invention including but not limited to those having a structure of Formula I, II, III, or IV, as further described herein, wherein R6, R8, and R10 are all different from hydrogen and the other substitutions are as disclosed herein.

Another particularly preferred embodiment relates to compounds of the present invention including but not limited to those having a structure of Formula I, II, III, or IV, as further described herein, wherein R6, R8, R10 and R11 are all different from hydrogen, and the other substitutions are as disclosed herein.

Another embodiment relates to compounds of the present invention, as further described herein, wherein at least one of R5, R6 and R7 is different from hydrogen and the other substitutions are as disclosed herein.

Another embodiment relates to compounds of the present invention as further described herein, wherein at least one of R6 and R7 is different from hydrogen and the other substitutions are as disclosed herein.

Another embodiment relates to compounds having a structure of Formula III, as further described herein, wherein at least one of R6 and R5 is different from hydrogen and the other substitutions are as disclosed herein.

In one preferred embodiment, in the compounds of the present invention, R10 and at least one of R5, R6 and R7 are different from hydrogen and are independently selected from a group as further defined herein.

In one preferred embodiment, in the compounds of the present invention, R6 and R10 are different from hydrogen and are independently selected from a group as further defined herein.

In one preferred embodiment, in the compounds of the present invention, R6, R10 and at least one of R8 and R11 are different from hydrogen and are independently selected from a group as further defined herein.

In one preferred embodiment, in the compounds of the present invention, R6, R8 and R11 are all different from hydrogen, and are independently selected from a group as further defined herein.

In one preferred embodiment, in the compounds of the present invention
  (a) at least one of R5, R6 and R7, if R7 is present, and
  (b) at least one of R8, R10 and R11
is different from hydrogen.

In one preferred embodiment, in the compounds of the present invention, R6, R7, if present, R8, R10 and R11 are all different from hydrogen and are independently selected from a group as further defined herein.

In one preferred embodiment, in the compounds of the present invention, R4 is hydrogen, and R6, R8, R10 and R11 are all different from hydrogen and are independently selected from a group as further defined herein.

In one preferred embodiment, in the compounds of the present invention, R4, R5 and R9 are all hydrogen, and R6, R8, and R10 are all different from hydrogen and are independently selected from a group as further defined herein In one preferred embodiment, in the compounds of the present invention, R4, R5, R9 and R12, if present, are all hydrogen, and R6, R8, and R10 are all different from hydrogen and are independently selected from a group as further defined herein.

In one preferred embodiment, in the compounds of the present invention, R4 and R12, if present, are both hydrogen, R5 and R9 are independently hydrogen or fluoro, and R6, R8, R10 and R11 are all different from hydrogen and are independently selected from a group as further defined herein.

In one preferred embodiment, in the compounds of the present invention, R4, R5, R9 and R12, if present, are all hydrogen, and R6, R8, R10 and R11 are all different from hydrogen and are independently selected from a group as further defined herein In one preferred embodiment, in the compounds of the present invention, R4 and R12, if present, are both hydrogen, R5 and R9 are independently hydrogen or fluoro, and R6, R7, R8, R10 and R11 are all different from hydrogen and are independently selected from a group as further defined herein In one preferred embodiment, in the compounds of the present invention, R2, R4, R5, R9 and R12, if present, are all hydrogen, and R6, R7, R8, R10 and R11 are all different from hydrogen and are independently selected from a group as further defined herein.

Another preferred embodiment relates to compounds of the present invention including but not limited to those having a structure of Formula I, II, III, or IV, wherein R4 and R5 are both hydrogen, R6 is chloro or bromo, X3 is CR12, R8 and R11 are both selected from halogen preferably fluoro and methoxy, R10 is selected from the group of fluoro, chloro, bromo, iodo, cyano, cyanomethyl, azido, acetyl, ethynyl, difluoroethoxy, trifluoroethoxy, and trifluoromethyl, and R9 and R12 are both hydrogen.

Another particularly preferred embodiment relates to compounds of the present invention including but not limited to those having a structure of Formula I, II, Ia, Ib, IIc, III, or IV, as further described herein, wherein R8 and R9 together with the ring to which they are attached form a 2,1,3 benzothiadiazole and the other substitutions are as disclosed herein. In one aspect of this embodiment, R10, R11 and R12 are all hydrogen.

Another particularly preferred embodiment relates to compounds of the present invention including but not limited to those having a structure of Formula I, II, IIa, IIb, IIc, III, or IV, as further described herein, wherein R10 and R9 together with the ring to which they are attached form a 2,1,3 benzothiadiazole and the other substitutions are as disclosed herein. In one aspect of this embodiment, R10 and R11 are both hydrogen and R12 is hydrogen, fluoro or chloro.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg, and comprising at least one $^{18}$F isotope, preferably in the position of a fluoro atom as indicated in one of the compounds disclosed herein. By way of non-limiting example, in the compound 6-chloro-N-[2-fluoro-4-(pentafluorosulfanyl) phenyl]-1H-pyrrolo[2,3-b]pyridine-3-sulfonamide, disclosed herein, at least one of the six fluoros may be represented by or may comprise a suitable amount of the $^{18}$F isotope. As another example, the fluoro in the compound 7-bromo-6-chloro-N-[5-(cyanomethyl)-3-fluoro-6-methoxypyridin-2-yl]-1H-indole-3-sulfonamide may be represented by or include an amount of $^{18}$F that is measurable by a suitable PET equipment. This applies likewise to other fluoro containing compounds described herein. These $^{18}$F containing compounds can preferably be used as PET tracers.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, VIf, or VIg and comprising at least one $^{11}$C isotope preferably in the position of a carbon atom as indicated herein. These $^{11}$C containing compounds can preferably be used as PET tracers.

Another preferred embodiment relates to compounds of the present invention including but not limited to those having a structure of Formula I, I-2, II, II-2, IIa, II-2a, IIb, II-2b, IIc, II-2c, IId, II-2d, IIe, II-2e, IIf, II-2f, IIg, II-2g, III, III-2, IIIa, III-2a, IIIb, III-2b, IIIc, III-2c, IV, IV-2, V, V-2, VI, VIa, VIb, VIc, VId, VIe, Vhf, or VIg, and comprising at least one $^{123}$I, $^{125}$I or $^{131}$I isotope, preferably in the position of a iodine atom as indicated herein. By way of non-limiting example, in the compound N-(4-cyanophenyl)-5-iodo-1H-pyrrolo[2,3-b]pyridine-3-sulfonamide, disclosed herein, the iodine may be represented by a $^{123}$I, $^{125}$I or $^{131}$I isotope. This applies likewise to other iodine containing compounds described herein. These $^{123}$I $^{125}$I or $^{131}$I containing compounds can preferably be used as SPECT tracers.

One embodiment relates to any one of the compounds of the invention which is specifically disclosed herein.

A preferred embodiment relates to a compound selected from the list of:
6-chloro-N-(4-ethynylphenyl)-1H-indole-3-sulfonamide
6-chloro-N-(5-cyanopyridin-2-yl)-1H-indole-3-sulfonamide
7-chloro-N-(4-chloro-2,5-difluorophenyl)-6-(methylsulfinyl)-1H-indole-3-sulfonamide
6-chloro-N-[3-fluoro-5-(methoxymethyl)pyridin-2-yl]-1H-indole-3-sulfonamide
6-chloro-N-(5-iodo-3-methylpyridin-2-yl)-1H-indole-3-sulfonamide
N-(4-chloro-2-fluorophenyl)-6-(trifluoromethyl)-1H-indole-3-sulfonamide
N-(2,5-difluorophenyl)-6-methyl-1H-indole-3-sulfonamide
N-(4-chloro-2-fluorophenyl)-6-(tetrahydrofuran-3-yl)-1H-pyrrolo[2,3-b]pyridine-3-sulfonamide
6-chloro-N-(4-chloro-2,5-difluorophenyl)-7-(pyridin-3-yl)-1H-indole-3-sulfonamide
N-(2,2,6-trifluoro-1,3-benzodioxol-5-yl)-1H-pyrrolo[3,2-h]quinoline-3-sulfonamide
6-cyano-N-(2,2,6-trifluoro-1,3-benzodioxol-5-yl)-1H-indole-3-sulfonamide
6-chloro-N-(7-cyano-2,1,3-benzothiadiazol-4-yl)-1H-indole-3-sulfonamide
N-(2,1,3-benzothiadiazol-4-yl)-7-bromo-1H-indole-3-sulfonamide
N-(2,1,3-benzothiadiazol-4-yl)-6-methoxy-1H-indole-3-sulfonamide
6-chloro-N-[2,5-difluoro-4-(pyridin-2-ylmethoxy)phenyl]-1H-indole-3-sulfonamide
6-chloro-N-(3-fluoro-5-methylpyridin-2-yl)-1H-pyrrolo[2,3-b]pyridine-3-sulfonamide N-(4-chloro-2-fluorophenyl)-6-(3-hydroxyprop-1-en-2-yl)-1H-pyrrolo[2,3-b]pyridine-3-sulfonamide
6-chloro-N-(7-fluoro-2,1,3-benzoxadiazol-4-yl)-1H-indole-3-sulfonamide
N-(2,5-difluorophenyl)-6-(methylsulfonyl)-1H-indole-3-sulfonamide
N-(4-cyano-2,5-difluorophenyl)-6-(2-methoxyethoxy)-1H-indole-3-sulfonamide
N-(4-chloro-2,5-difluorophenyl)-6,7,8,9-tetrahydro-1H-benzo[g]indole-3-sulfonamide
6-chloro-N-{2-fluoro-4-[(1E)-3-methoxyprop-1-en-1-yl]phenyl}-1H-indole-3-sulfonamide
N-(2,2-difluoro-1,3-benzodioxol-4-yl)-5-iodo-1H-pyrrolo[2,3-b]pyridine-3-sulfonamide
6-chloro-N-(4,6-dichloropyridin-2-yl)-1H-indole-3-sulfonamide
6-chloro-N-(2,3-difluorophenyl)-1H-indole-3-sulfonamide
N-(2-fluoro-4-iodophenyl)-6-(trifluoromethyl)-1H-indole-3-sulfonamide
N-(1,3-benzodioxol-4-yl)-6-methyl-1H-indole-3-sulfonamide
6-chloro-N-(2-chlorophenyl)-1H-indole-3-sulfonamide
5-bromo-N-(4-cyanophenyl)-1H-indole-3-sulfonamide
N-(4-bromo-2,5-difluorophenyl)-6-chloro-1H-indole-3-sulfonamide
6-bromo-N-(4-cyano-2,5-difluorophenyl)-1H-indole-3-sulfonamide
6-chloro-N-[5-(cyanomethyl)-3-fluoro-6-methoxypyridin-2-yl]-1H-indole-3-sulfonamide
N-(4-chloro-2,5-difluorophenyl)-1H-pyrrolo[3,2-h]quinoline-3-sulfonamide
N-(4-bromo-2,5-difluorophenyl)-1H-pyrrolo[3,2-h]quinoline-3-sulfonamide
6-chloro-N-(4-chloro-2,5-difluorophenyl)-1H-indole-3-sulfonamide
6-chloro-N-[4-(difluoromethoxy)-2,5-difluorophenyl]-1H-indole-3-sulfonamide
N-[4-(cyanomethyl)-2,5-difluorophenyl]-1H-pyrrolo[3,2-h]quinoline-3-sulfonamide
6-bromo-N-[3,6-difluoro-5-(3-methoxypropyl)pyridin-2-yl]-1H-indole-3-sulfonamide
N-(5-bromo-3,6-difluoropyridin-2-yl)-6-chloro-1H-indole-3-sulfonamide
N-(4-bromo-2,5-difluorophenyl)-6-chloro-1H-pyrrolo[2,3-b]pyridine-3-sulfonamide
6-chloro-N-(5-chloro-3-fluoro-6-methoxypyridin-2-yl)-7-fluoro-1H-indole-3-sulfonamide
N-(4-cyano-2-fluorophenyl)-1H-benzo[g]indole-3-sulfonamide
6-chloro-N-[3,6-difluoro-5-(3-methoxypropyl)pyridin-2-yl]-1H-indole-3-sulfonamide
5-bromo-6-chloro-N-[5-(cyanomethyl)-3-fluoro-6-methoxypyridin-2-yl]-1H-indole-3-sulfonamide
6-chloro-N-(5-chloro-3,6-difluoropyridin-2-yl)-1H-indole-3-sulfonamide
6-chloro-N-(4-chloro-2,5-difluorophenyl)-7-fluoro-1H-indole-3-sulfonamide
N-(4-cyano-2,5-difluorophenyl)-1H-benzo[g]indole-3-sulfonamide
N-(5-chloro-3-fluoro-6-methoxypyridin-2-yl)-1H-benzo[g]indole-3-sulfonamide
7-bromo-6-chloro-N-(5-chloro-3-fluoro-6-methoxypyridin-2-yl)-1H-indole-3-sulfonamide
6-chloro-N-[4-(cyanomethoxy)-2,5-difluorophenyl]-1H-indole-3-sulfonamide
N-(5-chloro-3-fluoro-6-methoxypyridin-2-yl)-1H-pyrrolo[3,2-h]quinoline-3-sulfonamide
6-chloro-N-(4-cyano-5-fluoro-2-methoxyphenyl)-1H-indole-3-sulfonamide
6-chloro-N-(5-chloro-3-fluoro-6-methoxypyridin-2-yl)-1H-indole-3-sulfonamide
6-chloro-N-(5-ethyl-3,6-difluoropyridin-2-yl)-1H-indole-3-sulfonamide
6-chloro-N-{5-[(E)-2-ethoxyethenyl]-3,6-difluoropyridin-2-yl}-1H-indole-3-sulfonamide
6-chloro-N-(4-chloro-2,5-difluorophenyl)-7-methoxy-1H-indole-3-sulfonamide
6-chloro-N-(4-chloro-2-fluorophenyl)-1H-indole-3-sulfonamide
ethyl 3-(6-{[(6-chloro-1H-indol-3-yl)sulfonyl]amino}-2,5-difluoropyridin-3-yl)propanoate
6-chloro-N-[2,5-difluoro-4-(trifluoromethyl)phenyl]-1H-indole-3-sulfonamide
6-bromo-N-{3,6-difluoro-5-[(1E)-3-methoxyprop-1-en-1-yl]pyridin-2-yl}-1H-indole-3-sulfonamide
6-chloro-N-[5-(cyanomethyl)-3-fluoro-6-methoxypyridin-2-yl]-1-benzothiophene-3-sulfonamide
N-(2,1,3-benzothiadiazol-4-yl)-6-bromo-1H-indole-3-sulfonamide
6-chloro-N-[4-(2,2-difluoroethoxy)-2,5-difluorophenyl]-1H-indole-3-sulfonamide ethyl (2E)-3-(6-{[(6-chloro-1H-indol-3-yl)sulfonyl]amino}-2,5-difluoropyridin-3-yl)prop-2-enoate
N-(5-chloro-3-fluoropyridin-2-yl)-1H-benzo[g]indole-3-sulfonamide
N-(4-chloro-2,5-difluorophenyl)-8-(difluoromethyl)-1H-pyrrolo[3,2-h]quinoline-3-sulfonamide
6-chloro-N-(4-chloro-2,5-difluorophenyl)-1H-pyrrolo[2,3-b]pyridine-3-sulfonamide
6-chloro-N-(5-chloro-3-fluoro-6-methoxypyridin-2-yl)-7-methoxy-1H-indole-3-sulfonamide
6-chloro-N-[5-(cyanomethyl)-3-fluoro-6-methoxypyridin-2-yl]-7-fluoro-1H-indole-3-sulfonamide
6-chloro-N-(2,5-difluoro-4-iodophenyl)-1H-indole-3-sulfonamide
N-(4-cyano-5-fluoro-2-methoxyphenyl)-1H-benzo[g]indole-3-sulfonamide
N-[4-(cyanomethoxy)-2,5-difluorophenyl]-1H-pyrrolo[3,2-h]quinoline-3-sulfonamide
N-(4-cyano-2,5-difluorophenyl)-6-(trifluoromethyl)-1H-indole-3-sulfonamide
6-chloro-N-(6-fluoro-2,1,3-benzothiadiazol-5-yl)-1H-indole-3-sulfonamide
6-chloro-N-[4-(difluoromethoxy)-2,5-difluorophenyl]-1H-pyrrolo[2,3-b]pyridine-3-sulfonamide
N-(2,1,3-benzoselenadiazol-4-yl)-6-chloro-1H-indole-3-sulfonamide
6-chloro-N-[2,5-difluoro-4-(trifluoromethyl)phenyl]-1H-pyrrolo[2,3-b]pyridine-3-sulfonamide
6-chloro-N-{3,6-difluoro-5-[(1E)-3-methoxyprop-1-en-1-yl]pyridin-2-yl}-1H-indole-3-sulfonamide
6-chloro-N-(4-cyano-2-fluorophenyl)-1H-indole-3-sulfonamide
6-chloro-N-(2,5-difluoro-4-methylphenyl)-1H-indole-3-sulfonamide
6-chloro-N-[5-(2-ethoxyethyl)-3,6-difluoropyridin-2-yl]-1H-indole-3-sulfonamide
6-chloro-N-(5-chloro-3,6-difluoropyridin-2-yl)-7-methoxy-1H-indole-3-sulfonamide
N-(4-cyano-2-fluorophenyl)-6-(thiophen-2-yl)-1H-indole-3-sulfonamide
6-chloro-N-(4-ethynyl-2-fluorophenyl)-1H-indole-3-sulfonamide 6-chloro-N-[3-fluoro-5-(trifluoromethyl)pyridin-2-yl]-1H-indole-3-sulfonamide
6-chloro-N-[2-fluoro-4-(trifluoromethyl)phenyl]-1H-indole-3-sulfonamide
7-bromo-6-chloro-N-(4-cyano-2-fluorophenyl)-1H-indole-3-sulfonamide
6-bromo-N-(4-cyano-2-fluorophenyl)-1H-pyrrolo[2,3-b]pyridine-3-sulfonamide
6-chloro-N-(4-cyano-2,5-difluorophenyl)-1H-indole-3-sulfonamide
6-bromo-N-(2-fluoro-4-iodophenyl)-1H-pyrrolo[2,3-b]pyridine-3-sulfonamide
N-(5-bromo-6-fluoro-3-methoxypyridin-2-yl)-6-chloro-1H-indole-3-sulfonamide
6-chloro-N-(2-fluoro-4-iodophenyl)-1H-indole-3-sulfonamide
6-chloro-N-[5-(cyanomethyl)-6-fluoro-3-methoxypyridin-2-yl]-1H-indole-3-sulfonamide
6-bromo-7-chloro-N-(4-chloro-2,5-difluorophenyl)-1H-indole-3-sulfonamide
6-bromo-N-(6-fluoro-2,1,3-benzothiadiazol-5-yl)-1H-indole-3-sulfonamide
N-(4-bromo-2,5-difluorophenyl)-6-methoxy-1H-indole-3-sulfonamide
6-bromo-N-(4-cyano-2-fluorophenyl)-1H-indole-3-sulfonamide
6-chloro-N-(4-cyano-2-fluoro-5-methoxyphenyl)-1H-indole-3-sulfonamide
N-(5-chloro-3,6-difluoropyridin-2-yl)-1H-benzo[g]indole-3-sulfonamide
6-azido-N-[5-(cyanomethyl)-3-fluoro-6-methoxypyridin-2-yl]-1H-indole-3-sulfonamide
6-chloro-N-[3,6-difluoro-5-(2-fluoroethoxy)pyridin-2-yl]-1H-indole-3-sulfonamide
6-chloro-N-(6-fluoro-1-methyl-3-oxo-1,3-dihydro-2-benzofuran-5-yl)-1H-indole-3-sulfonamide
N-(4-chloro-2,5-difluorophenyl)-5H-[1,3]dioxolo[4,5-f]indole-7-sulfonamide
6-bromo-N-(5-chloro-3-fluoropyridin-2-yl)-1H-indole-3-sulfonamide
N-[4-(cyanomethoxy)-2,5-difluorophenyl]-6-(difluoromethyl)-1H-indole-3-sulfonamide
N-(2,1,3-benzothiadiazol-4-yl)-1H-benzo[g]indole-3-sulfonamide
6-bromo-N-(4-chloro-2-fluorophenyl)-1H-pyrrolo[2,3-b]pyridine-3-sulfonamide
6-chloro-N-(4-chloro-2,5-difluorophenyl)-7-(2,2-difluoroethoxy)-1H-indole-3-sulfonamide
6-bromo-N-(4-cyanophenyl)-1H-indole-3-sulfonamide
N-(2,1,3-benzothiadiazol-5-yl)-6-bromo-1H-indole-3-sulfonamide
N-(4-cyano-2-fluorophenyl)-6-(propan-2-yl)-1H-indole-3-sulfonamide
N-(4-cyano-2-fluorophenyl)-6-(trifluoromethyl)-1H-indole-3-sulfonamide
N-(4-cyano-2,5-difluorophenyl)-6-methoxy-1H-indole-3-sulfonamide
N-(4-bromo-2,5-difluorophenyl)-6-methoxy-1H-pyrrolo[2,3-b]pyridine-3-sulfonamide
6-chloro-N-(5-ethenyl-3,6-difluoropyridin-2-yl)-1H-indole-3-sulfonamide
N-(4-bromo-2,5-difluorophenyl)-6-(methylsulfinyl)-1H-indole-3-sulfonamide
N-(4-bromo-2,5-difluorophenyl)-6-chloro-1-benzofuran-3-sulfonamide
N-[4-(difluoromethoxy)-2,5-difluorophenyl]-6-(methylsulfinyl)-1H-indole-3-sulfonamide
6-chloro-N-(2,4,5-trifluorophenyl)-1H-indole-3-sulfonamide
N-(4-chloro-2,5-difluorophenyl)-8-hydroxy-1H-pyrrolo[3,2-h]quinoline-3-sulfonamide
6-chloro-N-(2,5-difluoro-4-methylphenyl)-1H-pyrrolo[2,3-b]pyridine-3-sulfonamide
6-chloro-N-(4-chloro-2,5-difluorophenyl)-7-cyano-1H-indole-3-sulfonamide
6-chloro-N-[5-(cyanomethyl)-3-methoxypyridin-2-yl]-1H-indole-3-sulfonamide
N-[4-(2-cyanoethyl)-2,5-difluorophenyl]-1H-pyrrolo[3,2-h]quinoline-3-sulfonamide
6-chloro-N-[4-(cyanomethyl)-2-fluorophenyl]-1H-indole-3-sulfonamide
N-(4-cyano-2-fluorophenyl)-1,6,7,8-tetrahydrocyclopenta[g]indole-3-sulfonamide
N-(2,1,3-benzothiadiazol-4-yl)-1H-pyrrolo[3,2-h]quinoline-3-sulfonamide
N-(4-chloro-2,5-difluorophenyl)-6-(trifluoromethyl)-1H-pyrrolo[2,3-b]pyridine-3-sulfonamide
N-(4-ethynyl-2-fluorophenyl)-1H-pyrrolo[3,2-h]quinoline-3-sulfonamide
N-(4-bromo-2-fluorophenyl)-6-chloro-1H-indole-3-sulfonamide
6-bromo-N-(5-chloro-3-fluoropyridin-2-yl)-7-methyl-1H-indole-3-sulfonamide
6-chloro-N-[4-chloro-5-(difluoromethoxy)-2-fluorophenyl]-1H-indole-3-sulfonamide
N-(2,1,3-benzoxadiazol-5-yl)-6-chloro-1H-indole-3-sulfonamide
5-bromo-6-chloro-N-(4-cyano-2-fluorophenyl)-1H-indole-3-sulfonamide
6-(benzyloxy)-N-(4-cyano-2,5-difluorophenyl)-1H-indole-3-sulfonamide
N-(6-fluoro-2,1,3-benzothiadiazol-5-yl)-1H-benzo[g]indole-3-sulfonamide
N-(2,1,3-benzothiadiazol-4-yl)-6-chloro-1H-indole-3-sulfonamide
6-chloro-N-(3,6-difluoro-5-methylpyridin-2-yl)-1H-indole-3-sulfonamide
6-chloro-N-(4-cyanophenyl)-1H-indole-3-sulfonamide
6-chloro-N-(5-chloro-3-fluoropyridin-2-yl)-1H-indole-3-sulfonamide
N-(4-chloro-2,5-difluorophenyl)-6-methoxy-1H-indole-3-sulfonamide
N-(4-chloro-2,5-difluorophenyl)-6-(difluoromethyl)-1H-pyrrolo[2,3-b]pyridine-3-sulfonamide
6-chloro-N-(3-chloro-4-cyanophenyl)-1H-indole-3-sulfonamide
7-chloro-N-(5-chloro-3-fluoro-6-methoxypyridin-2-yl)-6-fluoro-1H-indole-3-sulfonamide
6-chloro-N-[2-fluoro-4-(pentafluoro-lambda~6~-sulfanyl)phenyl]-1H-pyrrolo[2,3-b]pyridine-3-sulfonamide
N-(4-cyanophenyl)-1H-benzo[g]indole-3-sulfonamide
N-(4-chloro-2-fluorophenyl)-1H-pyrrolo[3,2-h]quinoline-3-sulfonamide
6-chloro-N-(5-chloro-3-fluoro-6-methoxypyridin-2-yl)-5,7-difluoro-1H-indole-3-sulfonamide
N-[5-(cyanomethyl)-3-fluoro-6-methoxypyridin-2-yl]-6-nitro-1H-indole-3-sulfonamide
6-chloro-N-[2-fluoro-4-(trifluoromethyl)phenyl]-1H-pyrrolo[2,3-b]pyridine-3-sulfonamide
6-chloro-N-[4-(cyanomethoxy)-2,5-difluorophenyl]-1-benzofuran-3-sulfonamide
N-(4-chloro-2,5-difluorophenyl)-6-cyano-1H-indole-3-sulfonamide 6-chloro-N-(2,2-difluoro-1,3-benzodioxol-4-yl)-1H-indole-3-sulfonamide
6-chloro-N-(4-chloro-2,5-difluorophenyl)-7-(methylsulfinyl)-1H-indole-3-sulfonamide
6-chloro-N-[3,6-difluoro-5-(propan-2-yl)pyridin-2-yl]-1H-indole-3-sulfonamide
6-chloro-N-(4-chloro-2,5-difluorophenyl)-1-benzofuran-3-sulfonamide
7-chloro-N-(4-chloro-2,5-difluorophenyl)-6-(methylsulfanyl)-1H-indole-3-sulfonamide
N-(2,1,3-benzothiadiazol-4-yl)-6-chloro-1H-pyrrolo[2,3-b]pyridine-3-sulfonamide
6-chloro-N-{5-[(difluoromethoxy)methyl]-3-fluoropyridin-2-yl}-1H-indole-3-sulfonamide
N-(1,3-benzodioxol-4-yl)-6-chloro-1H-indole-3-sulfonamide
6-(benzyloxy)-N-(4-cyano-2-fluorophenyl)-1H-indole-3-sulfonamide
6-chloro-N-(3,6-difluoro-5-methylpyridin-2-yl)-7-fluoro-1H-indole-3-sulfonamide
N-(4-cyanophenyl)-6-cyclopropyl-1H-indole-3-sulfonamide
6-chloro-N-(5-chloro-3-fluoro-6-methoxypyridin-2-yl)-5-fluoro-1H-indole-3-sulfonamide
7-chloro-N-(5-chloro-3-fluoro-6-methoxypyridin-2-yl)-6-methoxy-1H-indole-3-sulfonamide
6-chloro-N-(4-cyano-5-fluoro-2-methoxyphenyl)-1H-pyrrolo[2,3-b]pyridine-3-sulfonamide
6-chloro-N-(6-fluoro-3-oxo-1,3-dihydro-2-benzofuran-5-yl)-1H-indole-3-sulfonamide ethyl 2-(6-{[(6-chloro-1H-indol-3-yl)sulfonyl]amino}-2,5-difluoropyridin-3-yl)cyclopropanecarboxylate
N-(2,1,3-benzoxadiazol-4-yl)-6-chloro-1H-indole-3-sulfonamide
6-chloro-N-(4-cyanophenyl)-1H-pyrrolo[2,3-b]pyridine-3-sulfonamide
6-chloro-N-(4-chloro-2-fluorophenyl)-1H-pyrrolo[2,3-b]pyridine-3-sulfonamide
N-(2,1,3-benzoxadiazol-4-yl)-1H-pyrrolo[3,2-h]quinoline-3-sulfonamide
6-chloro-N-(4-chloro-5-fluoro-2-methoxyphenyl)-1H-indole-3-sulfonamide
6-chloro-N-(4-chloro-2,5-difluorophenyl)-1-benzothiophene-3-sulfonamide
6-chloro-N-[4-(cyanomethoxy)-2,5-difluorophenyl]-1-benzothiophene-3-sulfonamide
N-(2,1,3-benzothiadiazol-4-yl)-6-bromo-1H-pyrrolo[2,3-b]pyridine-3-sulfonamide
6-bromo-N-(4-cyanophenyl)-1H-pyrrolo[2,3-b]pyridine-3-sulfonamide
6-chloro-N-(4-cyano-2,6-difluorophenyl)-1H-indole-3-sulfonamide
6-chloro-N-(5-chloro-3-fluoro-6-methoxypyridin-2-yl)-1H-pyrrolo[2,3-b]pyridine-3-sulfonamide
N-(5-bromo-3-fluoropyridin-2-yl)-6-chloro-1H-indole-3-sulfonamide
6-chloro-N-(4-cyano-2-fluorophenyl)-5-fluoro-1H-indole-3-sulfonamide
N-(2,2-difluoro-1,3-benzodioxol-4-yl)-1H-pyrrolo[3,2-h]quinoline-3-sulfonamide
N-(5-chloro-3,6-difluoropyridin-2-yl)-1H-pyrrolo[3,2-h]quinoline-3-sulfonamide
N-(4-bromo-2-fluorophenyl)-6-methyl-1H-indole-3-sulfonamide
6-bromo-N-(4-chloro-2,5-difluorophenyl)-4-fluoro-1H-indole-3-sulfonamide
N-(2,1,3-benzothiadiazol-5-yl)-6-chloro-1H-indole-3-sulfonamide
N-(4-cyano-2-fluorophenyl)-6-methoxy-1H-indole-3-sulfonamide
N-(4-chloro-2,5-difluorophenyl)-6-methoxy-1H-pyrrolo[2,3-b]pyridine-3-sulfonamide
6-cyano-N-[4-(difluoromethoxy)-2,5-difluorophenyl]-1H-indole-3-sulfonamide
N-(4-chloro-2,5-difluorophenyl)-6-(methylsulfinyl)-1H-indole-3-sulfonamide
6-chloro-N-(6-fluoro-2,1,3-benzoxadiazol-5-yl)-1H-indole-3-sulfonamide
6-chloro-N-(3,5-difluoro-6-methoxypyridin-2-yl)-1H-indole-3-sulfonamide
N-(4-cyano-5-fluoro-2-methoxyphenyl)-6-methoxy-1H-indole-3-sulfonamide
N-[4-(difluoromethoxy)-2,5-difluorophenyl]-6-(difluoromethyl)-1H-pyrrolo[2,3-b]pyridine-3-sulfonamide
N-(4-cyano-2-fluorophenyl)-6-(thiophen-3-yl)-1H-indole-3-sulfonamide
N-(4-azido-2-fluorophenyl)-6-chloro-1H-indole-3-sulfonamide
6-chloro-N-[2-fluoro-4-(trifluoromethoxy)phenyl]-1H-pyrrolo[2,3-b]pyridine-3-sulfonamide
6-chloro-N-(2-fluoro-4-iodophenyl)-1H-pyrrolo[2,3-b]pyridine-3-sulfonamide
N-(5-bromo-6-chloropyridin-2-yl)-6-chloro-1H-indole-3-sulfonamide
N-(5-bromo-3-methoxypyridin-2-yl)-6-chloro-1H-indole-3-sulfonamide
6-chloro-N-[3-methoxy-5-(trifluoromethyl)pyridin-2-yl]-1H-indole-3-sulfonamide
6-chloro-N-(2,5-difluorophenyl)-1H-indole-3-sulfonamide
6-chloro-N-(5-chloro-3-fluoro-6-methoxypyridin-2-yl)-1-benzothiophene-3-sulfonamide
6-chloro-N-(4-chloro-2,5-difluorophenyl)-7-(methylsulfonyl)-1H-indole-3-sulfonamide
6-chloro-N-(4-chloro-2,5-difluorophenyl)-5-fluoro-1H-indole-3-sulfonamide
N-(2-fluoro-4-iodophenyl)-5H-[1,3]dioxolo[4,5-f]indole-7-sulfonamide
N-[4-(cyanomethoxy)-2,5-difluorophenyl]-6-fluoro-1H-indole-3-sulfonamide
N-[2-fluoro-4-(trifluoromethyl)phenyl]-6-methoxy-1H-indole-3-sulfonamide
6-chloro-N-[2-fluoro-4-(pentafluoro-lambda~6~sulfanyl)phenyl]-1H-indole-3-sulfonamide
6-bromo-N-(2,4,5-trifluorophenyl)-1H-pyrrolo[2,3-b]pyridine-3-sulfonamide
N-(2-fluoro-4-iodophenyl)-6-(methylsulfonyl)-1H-indole-3-sulfonamide
6-chloro-N-(7-fluoro-2,1,3-benzothiadiazol-4-yl)-1H-indole-3-sulfonamide
6-chloro-N-(3,6-difluoro-5-methylpyridin-2-yl)-7-(trifluoromethyl)-1H-indole-3-sulfonamide
6-chloro-N-(3,5-difluoro-6-methoxypyridin-2-yl)-7-fluoro-1H-indole-3-sulfonamide
6-chloro-N-[2-fluoro-4-(trifluoromethoxy)phenyl]-1H-indole-3-sulfonamide
6-chloro-N-(5-chloro-3-fluoro-6-methoxypyridin-2-yl)-1-benzofuran-3-sulfonamide
6-chloro-N-(5-chloro-3-fluoro-6-methylpyridin-2-yl)-1H-indole-3-sulfonamide
N-(5-chloro-3-fluoro-6-methoxypyridin-2-yl)-6,7,8,9-tetrahydro-1H-benzo[g]indole-3-sulfonamide
6-bromo-N-(4-ethynylphenyl)-1H-pyrrolo[2,3-b]pyridine-3-sulfonamide 6-chloro-N-(2,2,6-trifluoro-1,3-benzodioxol-5-yl)-1H-indole-3-sulfonamide
6-chloro-N-(4-chloro-2,5-difluorophenyl)-7-(3,5-dimethyl-1,2-oxazol-4-yl)-1H-indole-3-sulfonamide
6-chloro-N-[5-chloro-3-fluoro-6-(fluoromethyl)pyridin-2-yl]-1H-indole-3-sulfonamide
6-chloro-N-(3-fluoro-5-methylpyridin-2-yl)-1H-indole-3-sulfonamide
6-chloro-N-(2,5-difluoro-4-methoxyphenyl)-1H-indole-3-sulfonamide
N-(4-chloro-2-fluorophenyl)-6-methyl-1H-indole-3-sulfonamide
N-(5-chloro-3,6-difluoropyridin-2-yl)-1,6,7,8-tetrahydrocyclopenta[g]indole-3-sulfonamide
5-bromo-6-chloro-N-(4-chloro-2,5-difluorophenyl)-1H-indole-3-sulfonamide
6-chloro-N-(5-chloro-3,6-difluoropyridin-2-yl)-7-(3,5-dimethyl-1,2-oxazol-4-yl)-1H-indole-3-sulfonamide
6-bromo-N-(2-chloro-3-fluorophenyl)-1H-pyrrolo[2,3-b]pyridine-3-sulfonamide
6-chloro-N-(5-chloro-3,6-difluoropyridin-2-yl)-1H-pyrrolo[2,3-b]pyridine-3-sulfonamide
6-azido-N-(4-cyano-2-fluorophenyl)-1H-indole-3-sulfonamide
6-(methylsulfonyl)-N-(2,2,6-trifluoro-1,3-benzodioxol-5-yl)-1H-indole-3-sulfonamide
6-chloro-N-[3,6-difluoro-5-(prop-1-en-2-yl)pyridin-2-yl]-1H-indole-3-sulfonamide
N-(5-chloro-3-fluoropyridin-2-yl)-1H-pyrrolo[3,2-h]quinoline-3-sulfonamide
N-(2,1,3-benzothiadiazol-4-yl)-6-fluoro-1H-indole-3-sulfonamide
6-chloro-N-(5-chloro-2-fluorophenyl)-1H-indole-3-sulfonamide
N-(4-chloro-5-fluoro-2-methoxyphenyl)-1H-benzo[g]indole-3-sulfonamide
6-chloro-7-(difluoromethoxy)-N-(3,5-difluoro-6-methoxypyridin-2-yl)-1H-indole-3-sulfonamide
N-(4-chloro-2-fluorophenyl)-6-(methylsulfonyl)-1H-indole-3-sulfonamide
6-bromo-N-(2,5-difluorophenyl)-1H-pyrrolo[2,3-b]pyridine-3-sulfonamide
N-(1,3-benzodioxol-4-yl)-6-bromo-1H-pyrrolo[2,3-b]pyridine-3-sulfonamide
N-(2,1,3-benzothiadiazol-4-yl)-6-(trifluoromethyl)-1H-indole-3-sulfonamide
6-chloro-N-(2-chloro-3,5-difluorophenyl)-1H-indole-3-sulfonamide
6-amino-N-[5-(cyanomethyl)-3-fluoro-6-methoxypyridin-2-yl]-1H-indole-3-sulfonamide
6-amino-N-[5-(cyanomethyl)-3-fluoro-6-methoxypyridin-2-yl]-1H-indole-3-sulfonamide
6-(benzylsulfinyl)-N-(4-chloro-2,5-difluorophenyl)-1H-indole-3-sulfonamide
6-chloro-N-(3,6-difluoropyridin-2-yl)-1H-indole-3-sulfonamide
6-chloro-N-(2-fluoro-4-methylphenyl)-1H-indole-3-sulfonamide
N-(4-bromo-2-fluorophenyl)-6-methoxy-1H-indole-3-sulfonamide
N-(4-cyano-2-fluorophenyl)-6-(2,2,2-trifluoroethoxy)-1H-indole-3-sulfonamide
N-(4-cyanophenyl)-6-(methylsulfonyl)-1H-indole-3-sulfonamide
N-(2,4,5-trifluorophenyl)-1H-pyrrolo[3,2-h]quinoline-3-sulfonamide
6-chloro-N-(5-iodopyridin-2-yl)-1H-indole-3-sulfonamide
N-(4-cyano-2-fluorophenyl)-6-(cyclopropylmethoxy)-1H-indole-3-sulfonamide
N-(4-ethynyl-2-fluorophenyl)-6-methoxy-1H-pyrrolo[2,3-b]pyridine-3-sulfonamide
6-fluoro-N-(2-fluoro-4-iodophenyl)-1H-indole-3-sulfonamide
6-chloro-N-(5-chloropyridin-2-yl)-1H-indole-3-sulfonamide
6-chloro-N-(4-cyano-2-fluorophenyl)-1H-pyrrolo[2,3-b]pyridine-3-sulfonamide
6-chloro-N-(4-cyano-2-methoxyphenyl)-1H-indole-3-sulfonamide
6-chloro-N-(3,5-difluoro-6-methoxypyridin-2-yl)-7-(trifluoromethyl)-1H-indole-3-sulfonamide
N-(4-cyano-2-fluorophenyl)-6-(pyridin-3-yl)-1H-indole-3-sulfonamide
N-(2,1,3-benzothiadiazol-4-yl)-5-iodo-1H-pyrrolo[2,3-b]pyridine-3-sulfonamide
N-(4-chloro-2,5-difluorophenyl)-6-(2,2,2-trifluoroethoxy)-1H-indole-3-sulfonamide
6-chloro-N-(2-oxo-2,3-dihydro-1,3-benzoxazol-7-yl)-1H-indole-3-sulfonamide
6-chloro-N-(2,2,6-trifluoro-1,3-benzodioxol-5-yl)-1H-pyrrolo[2,3-b]pyridine-3-sulfonamide
N-(2,4,5-trifluorophenyl)-1H-benzo[g]indole-3-sulfonamide
6-chloro-N-(6-methoxy-2,1,3-benzoxadiazol-5-yl)-1H-indole-3-sulfonamide
N-(2,1,3-benzothiadiazol-5-yl)-6-chloro-1H-pyrrolo[2,3-b]pyridine-3-sulfonamide
N-(4-ethynyl-2-fluorophenyl)-6-methoxy-1H-indole-3-sulfonamide
6-chloro-N-[3,6-difluoro-5-(2-methoxyethoxy)pyridin-2-yl]-1H-indole-3-sulfonamide
6-chloro-N-[4-(cyclopropylmethoxy)-2,5-difluorophenyl]-1H-indole-3-sulfonamide
N-(4-acetyl-2-fluorophenyl)-6-chloro-1H-indole-3-sulfonamide
6-chloro-N-(4-cyano-3-methoxyphenyl)-1H-indole-3-sulfonamide
6-chloro-N-(3,5-difluoropyridin-2-yl)-1H-indole-3-sulfonamide
6-chloro-N-(6-cyano-2,2-difluoro-1,3-benzodioxol-4-yl)-1H-indole-3-sulfonamide
N-(4-chloro-2,5-difluorophenyl)-2-fluoro-6-methoxy-1H-indole-3-sulfonamide
N-(4-chloro-2,5-difluorophenyl)-2-fluoro-6-methoxy-1H-indole-3-sulfonamide
6-chloro-N-(2,2-difluoro-1,3-benzodioxol-4-yl)-1H-pyrrolo[2,3-b]pyridine-3-sulfonamide
N-(4-cyano-2-fluorophenyl)-6-phenyl-1H-indole-3-sulfonamide
N-(1,3-benzodioxol-4-yl)-6-chloro-1H-pyrrolo[2,3-b]pyridine-3-sulfonamide
6-chloro-N-(4-cyanophenyl)-1-benzothiophene-3-sulfonamide
6-chloro-N-(4-nitrophenyl)-1H-indole-3-sulfonamide
N-(4-cyanophenyl)-6-(methylsulfinyl)-1H-indole-3-sulfonamide
6-(methylsulfonyl)-N-(2,4,5-trifluorophenyl)-1H-indole-3-sulfonamide
N-(4-cyanophenyl)-5-iodo-1H-pyrrolo[2,3-b]pyridine-3-sulfonamide
6-chloro-N-(2,4,5-trifluorophenyl)-1H-pyrrolo[2,3-b]pyridine-3-sulfonamide
6-chloro-N-(6-fluoro-3-oxo-1,3-dihydro-2-benzofuran-5-yl)-1H-pyrrolo[2,3-b]pyridine-3-sulfonamide 6-chloro-N-(5-fluoro-1,3-benzothiazol-6-yl)-1H-indole-3-sulfonamide
6-chloro-N-(7-fluoro-2,1,3-benzothiadiazol-4-yl)-1H-pyrrolo[2,3-b]pyridine-3-sulfonamide
N-(4-chloro-2,5-difluorophenyl)-6-(thiophen-3-yl)-1H-indole-3-sulfonamide
6-chloro-N-(2,4-difluorophenyl)-1H-indole-3-sulfonamide
6-chloro-N-[3,6-difluoro-5-(3-hydroxypropyl)pyridin-2-yl]-1H-indole-3-sulfonamide
6-chloro-N-(2,5-difluorophenyl)-1H-pyrrolo[2,3-b]pyridine-3-sulfonamide
N-(4-chloro-2-fluorophenyl)-6-methoxy-1H-indole-3-sulfonamide
6-chloro-N-(5-fluoro-1,1-dioxido-2,3-dihydro-1-benzothiophen-6-yl)-1H-indole-3-sulfonamide
N-(2,2-difluoro-1,3-benzodioxol-4-yl)-6-(methylsulfonyl)-1H-indole-3-sulfonamide
6-bromo-N-(2,4-difluorophenyl)-1H-pyrrolo[2,3-b]pyridine-3-sulfonamide
6-chloro-N-(3,5-dichloropyridin-2-yl)-1H-indole-3-sulfonamide
6-chloro-N-(6-fluoro-3-oxo-2,3-dihydro-1H-isoindol-5-yl)-1H-indole-3-sulfonamide
N-(5-bromo-3-methoxypyridin-2-yl)-6-chloro-1H-pyrrolo[2,3-b]pyridine-3-sulfonamide
N-(4-chloro-2-fluorophenyl)-6-cyano-1H-indole-3-sulfonamide
6-chloro-N-(2,4,5-trifluorophenyl)-1-benzofuran-3-sulfonamide
6-chloro-N-(2,2-difluoro-1,3-benzodioxol-4-yl)-1-benzofuran-3-sulfonamide
6-chloro-N-(4-cyanophenyl)-1-benzofuran-3-sulfonamide
6-chloro-N-(3-oxo-1,3-dihydro-2-benzofuran-5-yl)-1H-indole-3-sulfonamide
6-chloro-N-(2-cyano-5-fluorophenyl)-1H-indole-3-sulfonamide
6-chloro-N-(5-chloro-4-methoxypyridin-2-yl)-1H-indole-3-sulfonamide
6-chloro-N-(3,5-dimethoxypyridin-2-yl)-1H-indole-3-sulfonamide
6-chloro-N-[5-(difluoromethoxy)-3,6-difluoropyridin-2-yl]-1H-indole-3-sulfonamide
N-(2,1,3-benzothiadiazol-5-yl)-6-(trifluoromethyl)-1H-indole-3-sulfonamide
6-bromo-N-[5-(cyanomethyl)-3-fluoro-6-methoxypyridin-2-yl]-1H-indole-3-sulfonamide
N-(4-cyano-2,5-difluorophenyl)-1,6,7,8-tetrahydrocyclopenta[g]indole-3-sulfonamide
7-bromo-6-chloro-N-[5-(cyanomethyl)-3-fluoro-6-methoxypyridin-2-yl]-1H-indole-3-sulfonamide
N-(4-cyano-2,5-difluorophenyl)-6-fluoro-1H-indole-3-sulfonamide
N-(4-cyanophenyl)-6-(trifluoromethyl)-1H-indole-3-sulfonamide
N-(4-cyano-2,5-difluorophenyl)-6-methyl-1H-indole-3-sulfonamide
6-bromo-N-(2,2-difluoro-1,3-benzodioxol-4-yl)-1H-pyrrolo[2,3-b]pyridine-3-sulfonamide
N-(2,1,3-benzoselenadiazol-5-yl)-6-chloro-1H-indole-3-sulfonamide
N-(4-cyanophenyl)-6-methyl-1H-indole-3-sulfonamide
6-chloro-N-(6-fluoro-2,1,3-benzothiadiazol-5-yl)-1H-pyrrolo[2,3-b]pyridine-3-sulfonamide
7-bromo-N-(4-cyano-2,5-difluorophenyl)-1H-indole-3-sulfonamide
6-chloro-N-(3,6-difluoro-5-methylpyridin-2-yl)-1H-pyrrolo[2,3-b]pyridine-3-sulfonamide
N-(2,5-difluoro-4-methylphenyl)-6-(methylsulfinyl)-1H-indole-3-sulfonamide
6-fluoro-N-(6-fluoro-2,1,3-benzothiadiazol-5-yl)-1H-indole-3-sulfonamide
6-chloro-N-(4-cyano-2,5-difluorophenyl)-1H-pyrrolo[2,3-b]pyridine-3-sulfonamide
N-(4-chloro-2-fluorophenyl)-6-cyclopropyl-1H-pyrrolo[2,3-b]pyridine-3-sulfonamide
N-(2,1,3-benzothiadiazol-4-yl)-6-chloro-7-(trifluoromethyl)-1H-indole-3-sulfonamide
N-(2,1,3-benzothiadiazol-5-yl)-1H-benzo[g]indole-3-sulfonamide
N-(4-cyano-3-fluorophenyl)-1,6,7,8-tetrahydrocyclopenta[g]indole-3-sulfonamide
6-bromo-N-(4-cyanophenyl)-5-methyl-1H-indole-3-sulfonamide
N-(4-cyano-2-fluorophenyl)-4,6-difluoro-1H-indole-3-sulfonamide
N-(4-cyano-2,5-difluorophenyl)-1H-indole-3-sulfonamide
6-chloro-N-(4-cyano-3-methylphenyl)-1H-indole-3-sulfonamide
N-(4-cyanophenyl)-6-fluoro-1H-indole-3-sulfonamide
N-(2,1,3-benzothiadiazol-5-yl)-6-fluoro-1H-indole-3-sulfonamide
N-(2,1,3-benzothiadiazol-5-yl)-1,6,7,8-tetrahydrocyclopenta[g]indole-3-sulfonamide
6-chloro-N-[5-(cyanomethyl)-3-fluoro-6-methylpyridin-2-yl]-1H-indole-3-sulfonamide
7-chloro-N-(4-cyano-2,5-difluorophenyl)-1H-indole-3-sulfonamide
6-chloro-N-(4-chloro-2,5-difluorophenyl)-7-(pyridin-2-ylmethoxy)-1H-indole-3-sulfonamide
N-(4-chloro-2-fluorophenyl)-8-(difluoromethyl)-1H-pyrrolo[3,2-h]quinoline-3-sulfonamide
N-(4-cyanophenyl)-5H-[1,3]dioxolo[4,5-f]indole-7-sulfonamide
N-(5-bromo-4-chloro-2-fluorophenyl)-6-chloro-1H-indole-3-sulfonamide
6-chloro-N-(4-chloro-2,5-difluorophenyl)-7-phenoxy-1H-indole-3-sulfonamide
N-(4-cyano-2-fluorophenyl)-6-phenoxy-1H-indole-3-sulfonamide
6-chloro-N-[4-(2,2-difluoroethoxy)-2-fluorophenyl]-1H-indole-3-sulfonamide
N-(4-chloro-2-fluorophenyl)-5H-[1,3]dioxolo[4,5-f]indole-7-sulfonamide
N-(4-bromo-2-fluoro-5-methylphenyl)-6-chloro-1H-indole-3-sulfonamide
N-(4-chloro-2-fluorophenyl)-6-(oxetan-3-yl)-1H-pyrrolo[2,3-b]pyridine-3-sulfonamide
N-(4-cyano-2-fluorophenyl)-6-(3,5-dimethyl-1,2-oxazol-4-yl)-1H-indole-3-sulfonamide
N-(4-cyano-2-fluorophenyl)-6-(pyridin-4-yl)-1H-indole-3-sulfonamide
N-(7-bromo-2,2-difluoro-1,3-benzodioxol-4-yl)-6-chloro-1H-indole-3-sulfonamide
N-(2,5-difluorophenyl)-5-iodo-1H-pyrrolo[2,3-b]pyridine-3-sulfonamide
6-chloro-N-(2-chloro-3-fluorophenyl)-1H-indole-3-sulfonamide
N-(4-cyano-2,5-difluorophenyl)-4,6-difluoro-1H-indole-3-sulfonamide
N-(4-cyano-2-fluorophenyl)-1H-indole-3-sulfonamide
N-(5-chloro-3-fluoropyridin-2-yl)-6-methoxy-1H-indole-3-sulfonamide
N-(4-chloro-2-fluorophenyl)-8-hydroxy-1H-pyrrolo[3,2-h]quinoline-3-sulfonamide N-(4-cyano-2-fluorophenyl)-6-(tetrahydrofuran-2-yl-methoxy)-1H-indole-3-sulfonamide
N-(2,2-difluoro-1,3-benzodioxol-5-yl)-6-(methylsulfonyl)-1H-indole-3-sulfonamide
6-(5-chlorothiophen-2-yl)-N-(4-cyano-2-fluorophenyl)-1H-indole-3-sulfonamide
6-chloro-N-(2,2,7-trifluoro-1,3-benzodioxol-4-yl)-1H-indole-3-sulfonamide
6-chloro-7-methoxy-N-(2,4,5-trifluorophenyl)-1H-indole-3-sulfonamide
6-chloro-N-(4-chloro-2-fluoro-5-methylphenyl)-1H-indole-3-sulfonamide
N-(4-chloro-2-fluorophenyl)-6-fluoro-1H-indole-3-sulfonamide
N-(4-ethynylphenyl)-6-(methylsulfonyl)-1H-indole-3-sulfonamide The compounds of the present invention can be prepared according to the methods disclosed in the experimental section of this application.

Therapeutic and Diagnostic Application

In one aspect, the invention relates to any one of the compounds described herein, for use in therapy or diagnosis, particularly in the therapy of animals, most preferably humans.

Because of their GPR17 modulating properties, the compounds of the present invention can be used as medicine, and may be used for the treatment and/or prevention of various diseases of the CNS system.

One embodiment of the present disclosure is thus a compound as described herein for use as a medicine, in particular for use as a medicine for the treatment and/or prevention of a GPR17-associated disease, i.e. a disease which is associated with a dysfunction of the GPR17 signaling system such as, for example, an overexpression and/or overactivity of GPR17 receptors. Without wished to be bound by any theory, the activity of GPR17 may be increased, extended or otherwise altered in certain tissues, for example in oligodendrocyte progenitor cells (OPCs) or during maturation of oligondendrocytes, potentially due to activating endogenous stimuli such as, for example, inflammation factors. This may prevent the differentiation of oligodendrocytes and an efficient myelination thus promoting the emergence or further development of a myelination disease (see Chen et al, supra). Negative GPR17 modulators may thus promote myelination by decreasing or turning off GPR17 activity and by supporting OPC maturation into myelin-producing oligondendrocytes (see e.g. Simon et al, supra).

In one preferred aspect, the invention relates to any one of the compounds described herein, for use in therapy or diagnosis for use in the prevention, or treatment of a disorder or syndrome selected from and/or associated with a myelination disorder, particularly of the central nervous system.

Myelination disorders may be classified in three broad categories:
    demyelination disorders wherein the myelin is initially normal but is destroyed or degraded for certain reasons,
    dysmyelination disorders wherein the formed myelin is abnormal and dysfunctional (e.g. because of mutations affecting the structure of myelin) and may degenerate, and
    hypomyelination disorders, which are characterized by abnormal low amounts of myelin.

An example of a dysmyelination disorder is metachromatic leukodystrophy.
An example of a hypomyelination disorders is Pelizaeus Merzbacher disease.

A demyelination disorder describes a loss of myelin around axons due to the damage or degradation of otherwise functioning myelin. The causes for degradation can be multifold and can be based on e.g. inflammatory and/or autoimmune processes (such as e.g. multiple sclerosis), infections (such as e.g. progressive multifocal leukoencephalopathy caused by a papovavirus), metabolic disorders (e.g. central pontine myelinolysis), toxic or mechanic traumata and ischemic states. Demylination disorders may occur in central and peripheral tissues.

Neurodegenerative disorders have been recently associated strongly with a loss of myelination. It is believed that preserved oligodendroglial and myelin functionality is a crucial prerequisite for the prevention of axonal and neuronal degeneration (see e.g. Ettle et al, supra). Negative GPR17 modulators may thus represent an excellent treatment option for any demyelination disorders, including but not limited to neurodegenerative diseases associated with demyelination and/or impacted myelination such as e.g. ALS, MSA, Alzheimer's disease, Huntington Disease or Parkinson's Disease.

In a particularly preferred aspect, the compounds of the present invention can thus be used in the prevention and/or treatment of a peripheral or central myelination disorder, preferably of a demyelination disorder, and particularly preferably of a demyelination disorder of the central nervous system. In one aspect, the compounds of the present invention are used in the treatment and/or prevention and/or diagnosis of a myelination disorder, preferably a demyelination disorder, by oral administration.

Examples of such myelination disorders to be treated and/or prevented by the presently disclosed compounds are, in particular,
    multiple sclerosis (MS) including its various subforms,
    neuromyelitis optica (also known as Devic's disease),
    chronic relapsing inflammatory optic neuritis, acute disseminated encephalomyelitis,
    acute haemorrhagic leucoencephalitis (AHL),
    periventricular leukomalacia
    demyelination due to viral infections, e.g. by HIV or progressive multifocal leucoencephalopathy,
    myelopathies such as e.g. tabes dorsalis (syphilitic myelopathy)
    central pontine and extrapontine myelinolysis,
    demyelination due to traumatic brain tissue damage, including compression-induced demyelination, e.g. by tumors
    demyelination in response to hypoxia, stroke or ischaemia or other cardiovascular diseases,
    demyelination due to exposure to carbon dioxide, cyanide, or other CNS toxins
    Schilder's disease,
    Balo concentric sclerosis,
    Perinatal encephalopathy,
    Neurodegenerative Diseases including, in particular,
        Amyotrophic lateral sclerosis (ALS).
        Alzheimer's disease (AD).
        Multiple system atrophy
        Parkinson's Disease
        Spinocerebellar ataxia (SCA), also known as spinocerebellar atrophy
        Huntington's Disease
    psychiatric disorders such as schizophrenia and bipolar disorder (see e.g. Fields, Trends Neurosci 31, 2008, 361; Tkachev et al, Lancet 362, 2003, 798).

peripheral myelination diseases such as leukodystrophies, peripheral demyelinating neuropathies, Dejerine-Sottas syndrome or Charcot-Marie-Tooth disease Moreover, the compounds of the present invention may be used for the treatment of prevention of the dysfunction of tissues where GPR17 is expressed such as e.g. heart or kidney, including but not limited to treating or preventing ischaemic disorders of kidney and heart.

The treatment or prevention of a CNS disease such as, in particular, a myelination disease, preferably a demyelination disease, also includes the treatment of the signs and symptoms associated with such a disease. Hence, the compounds of the present invention may also be used to treat a disorder or syndrome associated with brain tissue damage, a cerebrovascular disorder, and certain neurodegenerative diseases underlying or associated with a demyelination disorder.

In one embodiment, the use of the compounds of the present invention for the treatment and/or prevention of MS also includes the treatment and/or prevention of the signs and symptoms associated with MS such as negative effects on optic nerves (vision loss, double vision), dorsal columns (loss of sensation), corticospinal tract (spastic weakness), cerebellar pathways (incoordination, dysarthria, vertigo, cognitive impairment), medial longitudinal fasciculus (double vision on lateral gaze), spinal trigeminal tract (face numbness or pain), muscle weakness (impaired swallowing, control of the bladder or gut, spasms), or psychological effects associated with the underlying disease such as depression, anxiety or other mood disorders, general weakness or sleeplessness.

Hence, the compounds of the present invention are for use in treating signs and symptoms of a myelination disease, such as multiple sclerosis, wherein such signs and symptoms include but are not limited to the group of vision loss, vision impairment, double vision, loss or impairment of sensation, weakness such as spastic weakness, motor incoordination, vertigo, cognitive impairment, face numbness, face pain, impaired swallowing, impaired speech, impaired control of bladder and/or gut, spasms, depression, anxiety, mood disorders, sleeplessness, and fatigue.

In one preferred embodiment, the compounds of the present invention are for use in treating multiple sclerosis. MS is a heterogeneous myelination disease and can manifest itself in a variety of different forms and stages, including but not limited to Relapsing-Remitting MS, Secondary-Progressive MS, Primary Progressive MS, Progressive Relapsing MS, each depending on activity and disease progression.

In another aspect, the compound of the present invention may be used in the prevention and treatment of a spinal cord injury, perinatal encephalopathy, stroke, ischemia, or a cerebrovascular disorder, or for improving the recovery following these events.

In one aspect, the invention relates to a method for the prevention and/or treatment of a syndrome or disorder associated with a myelination disorder, or with a disorder or syndrome associated with a brain tissue damage, which comprises administering to a patient in need thereof a therapeutically effective amount of a compound as described herein. A patient in need of such a treatment can be any patient who suffered brain tissue damage such as by mechanical, chemical, viral, or other trauma.

In one aspect, the invention relates to a method for the prevention and/or treatment of a syndrome or disorder associated with a myelination disorder, preferably with a demyelination disorder, or with a disorder or syndrome associated with stroke or other brain ischemia, which comprises administering to a patient in need thereof a therapeutically effective amount of a compound as described herein. A patient in need thereof may be any patient that recently experienced a cerebral ischemia/stroke which may have been caused, for example, by the occlusion of a cerebral artery either by an embolus or by local thrombosis.

In one aspect, the compounds of the present invention are for use in the treatment/or prevention of Neuromyelitis optica (also known as Devic's disease or Devic's syndrome).

Neuromyelitis optica is a heterogeneous disorder characterized by inflammation and demyelination of the optic nerve and the spinal cord. Many of the associated symptoms are similar to MS and include muscle weakness, in particular of the limbs, reduced sensation and loss of bladder control.

In one aspect, the compounds of the present invention are for use in preventing and/or treating ALS. ALS has been associated recently with oligodendrocyte degeneration and increased demyelination, suggesting ALS as a target disease for negative GPR17 modulators (Kang et al, supra; Fumagalli et al, Neuropharmacology 104, 2016, 82).

In one aspect, the compounds of the present invention are for use in prevention and/or treating Huntington Disease. Huntington is well described to be associated with impacted myelination, (Bartzokis et al, supra; Huang et al, Neuron 85, 2015, 1212).

In one aspect, the compounds of the present invention are for use in prevention and/or treating multiple system atrophy. MSA was associated strongly with demelination recently (Ettle supra, Jellinger supra) suggesting remyelination strategies to treat or prevent MSA.

In one aspect, the compounds of the present invention are for use in prevention and/or treating Alzheimer's Disease. AD has been recently observed to be associated with increased cell death of oligodendronecytes and focal demyelination and to represent a pathological process in AD (Mitew et al, Acta Neuropathol 119, 2010, 567), One aspect of the present invention relates to a method of treatment of any one of the diseases or disorders described herein, in particular of a myelination disease such as MS, Neuromyeltis optica, ALS or others, by administering to a subject in need thereof, including a human patient, a therapeutically effective amount of a compound of the present invention.

GPR17 has been recently also associated with food uptake, insulin control and obesity. According to various reports, negative modulators of GPR17 may be helpful for controlling food uptake and for treating obesity (see e.g. Ren et al, Diabetes 64, 2015; 3670.) Hence, one embodiment of the present invention relates to the use of the compounds herein for the prevention and/or treatment of obesity, and methods of treating obesity.

The treatments according to the present invention may comprise the administration of one of the presently disclosed compounds as "stand alone" treatment of a CNS disease, in particular of a myelination disease or disorder such as MS or ALS. Alternatively, a compound disclosed herein may be administered together with other useful drugs in a combination therapy.

In a non-limiting example, a compound according to the present invention is combined with another medicament for treating a myelination disease, such as MS, said other medicament having a different mode of action, such as e.g. an anti-inflammatory drug. Likewise, a compound of the present invention can be combined with an analgesic drug if a painful myelination condition is to be treated. Also, a compound of the present disclosure may be used in combination with an antidepressant to co-treat psychological effects associated with the underlying myelination disease to be treated.

In combination therapies, the two or more active principles may be provided via the same formulation or as a "kit of parts", i.e. in separate galenic units to be used in combination. Also, the two or more active principles, including the compounds of the present invention, may be administered to the patient at the same time or subsequently, e.g. in an interval therapy. The additional drug may be administered by the same mode or a different mode of administration. For example, the GPR17 modulator of the present invention may be administered orally, while the second medicament may be administered by subcutaneous injection.

The second medicament for the treatment of MS may be selected from, for example, corticosteroids (e.g. prednisone, declamethasone), dalfampridine, interferon beta-1a, interferon beta-1b, glatiramer acetate, peginterferon beta-1a, daclizumab, teriflunomide, fingolimod, siponimod, dimethylfumarate, alemtuzumab, mitoxantrone, ocrelizumab, natalizumab and bioequivalents or biosimilars thereof.

In one aspect, the compounds of the present invention may be used for the diagnosis and/or monitoring of a GPR17-related disease, as further described herein, in particular of a demyelinating disease, as disclosed herein, preferably in the diagnosis and monitoring of multiple sclerosis.

In one aspect, the compounds of the present invention can be used to diagnose and/or monitor the expression, distribution and/or activation of the GPR17 receptor either in-vivo, e.g. directly in a subject, such as using molecular imaging techniques, or in-vitro, such as e.g. by examining any samples such as body fluids or tissues taken from a subject. Any such determination of the GPR17 activity, expression and/or distribution may be used to predict, diagnose and/or monitor (a) the status and progression of a GPR17-associated disease as described herein, in particular a myelination disease including but not limited to, for example, multiple sclerosis, and/or (b) the efficacy and/or applicability and/or proper dosing of a treatment associated with any such GPR17-associated disease.

In one aspect, the compounds of the present invention may be used as PET or SPECT tracers, as further disclosed herein, in order to perform in-vivo diagnosis and/or disease monitoring. By this, the expression, activation and/or distribution of a GPR17 receptor may be directly measured in a subject, e.g. by imaging of a human patient after the administration of a GPR17 PET or SPECT tracer of the present invention. This may facilitate a proper diagnosis of the disease, may help to determine applicable treatment options and/or may be used to monitor disease progression and/or to monitor or predict the success of a medical intervention, including the selection and proper administration and/or dosing of a therapeutic drug.

Hence, one embodiment of the present invention is the use of a PET or SPECT tracer of the present invention in a diagnostically effective amount for the diagnosis of a GPR17-associated disorder, preferably of a myelination disease, including not limited to MS.

One embodiment of the present invention relates to a method of diagnosing a GPR17-associated disorder, preferably a myelination disorder including but not limited MS, said method including the steps of (a) administering a PET or SPECT tracer of the present invention in a diagnostically effective amount to a subject (b) determining the amount and/or distribution of GPR17 in the subject by its binding to the PET or SPECT tracer administered and (c) comparing the results with results of a comparative subject or group of subjects.

In one embodiment, the PET or SPECT tracers of the present invention may be used in conjunction with a therapeutic drug, i.e. as a Companion Diagnostic, in order to monitor and/or predict the efficacy and/or safety of said therapeutic drug in a particular subject, or to estimate a drug's proper dosage.

One embodiment relates to a PET or SPECT tracer of the present invention for use as a Companion Drug in conjunction with a therapeutic drug. The therapeutic drug to be used with the PET or SPECT tracer of the present invention may be selected from the group of (a) an unlabeled compound of the present invention, (b) a GPR17 modulating compound which is different from the compounds of the present invention and (c) a drug for the treatment of a myelination disease, including but not limited to a drug for use in multiple sclerosis treatment, which is not a GPR17 modulator.

One embodiment relates to a kit comprising
(a) as a first component, a PET or SPECT tracer of the present invention, in particular a PET or PET tracer based on a compound of the present invention including but not limited to those having a structure according to any one of Formula I, II, IIa, IIb, IIc, IId, IIe, IIf, III, IIIa, IIIb, IIIc, or IV, as further defined herein, or having a structure of any one of the compounds disclosed herein, but having incorporated at least one radionuclide which is suitable for PET or SPECT imaging, preferably a radionuclide selected from $^{18}$F, $^{11}$C, $^{123}$I, $^{125}$I and $^{131}$I,
(b) as a second component, a therapeutic drug selected from among
 i. a compound of the present invention including but not limited to those having a structure according to anyone of Formula I, II, IIa, IIb, IIc, IId, IIe, IIf, III, IIIa, IIIb, IIIc, or IV, as further defined herein, or having a structure of any one of the individual compounds disclosed herein, and having no radionuclide incorporated,
 ii. a GPR17 modulating compound which is different from the compounds of the present invention as defined in (i), and
 iii. a drug for the treatment of a myelination disease, including but not limited to a drug for use in multiple sclerosis treatment, but having no GPR17 modulating activity Alternatively, the compounds of the present invention may be used in an in-vitro diagnostic assay, for example for the examination of suitable body fluids of a subject such as e.g. blood, plasma, urine, saliva, or cerebrospinal fluid for any level of GPR17 expression, activity and/or distribution.

One embodiment relates to a method of treating a GPR17-associated disease, in particular a myelination disease, preferably a demyelination disorder, including but not limited to multiple sclerosis, wherein said method includes the steps of (a) determining the expression, activity and/or distribution of the GPR17 receptor of a subject, (b) comparing the expression, activity and/or distribution of the GPR17 receptor in said subject with the expression, activity and/or distribution of the GPR17 receptor in one or more healthy subjects or a population, (c) determining the need for medical treatment or prophylaxis of said subject based on a deviation of expression, activity and/or distribution of GPR17 of said subject from healthy subjects or a population and (d) treating the subject having the deviation of expression, activity and/or distribution of the GPR17 receptor by administering a therapeutic drug to said individual, which drug is suitable for the treatment of GPR17-associated diseases or disorders, in particular by administering a GPR17 modulator, preferably by administering one of more of the compounds of the present invention. In one embodiment, the determination (a) of the expression, activity and/or distribution of GPR17 will be conducted using one of the compounds of the present invention, in particular with a PET or SPECT tracer of the present invention, or by an in vitro examination of body fluids or tissue of said subject using a PET or SPECT tracer of the present invention.

In one preferred aspect, the invention relates to a pharmaceutical composition comprising a compound as described herein, and a pharmaceutical acceptable carrier.

For the administration as a medicinal drug, the compounds may be used in pharmaceutical composition comprising a compound of the present disclosure, and a pharmaceutically acceptable carrier, as further defined herein. Such a pharmaceutical composition can be adapted, for example, for oral, intravenous, intramuscular, subcutaneous, nasal, rectal, buccal or transdermal administration and may comprise pharmaceutically acceptable carriers, adjuvants, diluents, stabilizers and the like.

In one embodiment, the compounds of the present invention may be administered orally, e.g. in the form of a tablet, a capsule, a dragee, a powder, a granulate, or in form of a liquid or a semi-solid, including e.g. syrups, suspensions, emulsions or solutions, by way of non-limiting example.

For instance, the compounds of the present invention may be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

A tablet may provide an immediate release or sustained release of the compounds of the present invention.

Oral formulations, such as tablets, may contain, without limitation, sustained release agents, disintegrants, fillers, lubricants, stabilizers, antioxidants, flavours, dispersion agents, electrolytes, buffers, dyes, or conservation agents. Suitable excipients and formulations are known to those skilled in the art and are disclosed in standard monographs such as like Remington ("The science and practice of pharmacy", Lippincott, Williams & Wilkins, 2000).

Non-limiting examples of disintegrants include pregelatinised starch, sodium starch glycolate, microcrystalline cellulose, carboxymethylcellulose sodium (CMC-Na), cross-linked CMC-Na, and low-substituted hydroxypropylcellulose, as well as mixtures thereof.

Suitable fillers and binders include without limitation microcrystalline cellulose, powdered cellulose, lactose (anhydrous or monohydrate), compressible sugar, starch (e.g. corn starch or potato starch), pregelatinised starch, fructose, sucrose, dextrose, dextrans, other sugars such as mannitol, maltitol, sorbitol, lactitol and saccharose, siliconised microcrystalline cellulose, calcium hydrogen phosphate, calcium hydrogen phosphate dihydrate, dicalciumphosphate dihydrate, tricalciumphosphate, calcium lactate or mixtures thereof.

Lubricants, antiadherents and/or glidants include stearic acid, magnesium stearate, calcium stearate, sodium lauryl sulphate, hydrogenated vegetable oil, hydrogenated castor oil, sodium stearyl fumarate, macrogols, glycerol dibehenate, talc, corn starch, silicon dioxide, and the like, including mixtures.

Typical sustained release agents are for example those that swell upon contact with water such as polyvinylpyrrolidone, hydroxyethylcellulose, hydroxypropylcellulose, other cellulose ethers, starch, pregelatinised starch, polymethacrylate, polyvinylacetate, microcrystalline cellulose, dextrans, and mixtures of these. Other sustained release agents may be those that can be incorporated in a functional coating, which prevents the rapid disintegration and/or release of the active ingredient from the tablet core. Examples of agents that can be used in a functional coating are e.g. acrylic resins, cellulose derivatives such as hydroxypropylmethylcellulose acetate phthalate, hydroxypropylcellulose, or ethylcellulose, vinyl acetate derivatives, polyvinyl pyrrolidone, polyvinyl acetate, shellac, methacrylate polymers or methacrylate copolymers.

A tablet can, for example, be prepared by mixing at least one compound of the present invention with at least one non-toxic pharmaceutically acceptable excipient, such as e.g. binder, filler/diluents, disintegrant agents, plastisizer, and the like, and an optional solvent (aqueous or non-aqueous), and by subsequent processing the mixture to a tablet by a process including but not limited to dry compression, dry granulation, wet granulation, spray drying, or melt extrusion. A tablet can either be uncoated, or coated by known techniques to either mask the bad taste of an unpleasant tasting drug, or delay disintegration and absorption of the active ingredient in the gastrointestinal tract.

The compound of the present invention may also be formulated for parenteral administration by injection, e.g. by bolus injection or infusion. The compositions for injection may be provided ready to use and may take such forms as suspensions, solutions, or emulsions in oily or aqueous vehicles, and may contain excipients such as suspending, stabilising, preserving and/or dispersing agents. Alternatively, the active ingredient may be in powder form for constitution with a suitable vehicle, e.g. sterile pyrogen-free water or saline, before use.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

For ophthalmic administration, the compounds for use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration, the compounds for use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

In one embodiment, the compounds may be administered transdermally. This mode of administration prevents the so-called 1$^{st}$ pass effect of oral administration and moreover allows providing more constant plasma levels which is of particular advantage in some instances. The design of transdermal forms such as ointments or creams or other transdermal systems such as e.g. patches or electrophoretic devices is generally known from the art, see e.g. Prausnitz and Langer, Nat Biotechnology 2008, Vol 26.11 p 1261; WO 2001/47503; WO2009/000262; WO99/49852.

The preferable dose level of the compounds according to the present invention depends upon a variety of factors including the condition and body weight of the patient, severity of the particular disease, dosage form, and route and period of administration, but may appropriately be chosen by those skilled in the art. In various embodiments, the compounds are administered in an amount ranging from 0.001 to 10 mg/kg of body weight per day, or from 0.03 to 1 mg/kg of body weight per day. Individual doses may range from about 0.1 to 1000 mg of active ingredient per day, from about 0.2 to 750 mg/day, from about 0.3 to 500 mg/day, from 0.5 to 300 mg/day, or from 1 to 100 mg/day. Doses may be administered once a day, or several times a day, preferably with each divided portions.

Another aspect of the present invention is a Kit comprising a medicine or a pharmaceutical composition as described herein, and instructions for its use.

DEFINITIONS

Any reference to a compound according to the present invention also includes pharmaceutically acceptable salts, solvates, isotopes and co-crystals of such compounds unless expressly indicated otherwise. The "compounds of the present invention" include the compounds referred to and disclosed in the general Formula I, I-2, II, IIa, IIb, IIc, IId, IIe, IIf, IIg, II-2, II-2a, II-2b, II-2c, II-2d, II-2e, II-2f, II-2g, III, IIIa, IIIb, IIIc, III-2, III-2a, III-2b, III-2c, IV, IV-2, V, V-2, VI, VIa, VIb, VIc, VId, VIe, VIf and VIg as well as the individual compounds specifically disclosed in the specification and/or the experimental part. In any instance where a specific substitution is defined in relation to the "compounds of the present invention", it is to be understood that this only refers to those compounds carrying the respective substituent. For example, any definition of R12 in the "compounds of the present invention" of course does not apply to compounds wherein R12 does not exist per se, such as, for example, in compounds of formula VI and its corresponding subformula.

The term "pharmaceutically acceptable salts" relates to any salts that the compounds of the present invention may form and which are suitable for administration to subjects, in particular human subjects. Such salts include but are not limited to acid addition salts, formed either with inorganic acids such as hydrochloric acid, hydrobromic acid, sulfuric acid, nitric acid, phosphoric acid, and the like, or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-6arboxyic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. Other salts include 2,2-dichloroacetate, adipate, alginate, ascorbate, aspartate, 2-acetamidobenzoate, caproate, caprate, camphorate, cyclamate, laurylsulfate, edisilate, esylate, isethionate, formate, galactarate, gentisate, gluceptate, glucuronate, oxoglutarate, hippurate, lactobionate, napadisilate, xinafoate, nicotinate, oleate, orotate, oxalate, palmitate, embonate, pidolate, p-aminosalicylate, sebacate, tannate, rhodanide, undecylenate, and the like; or salts formed when an acidic proton present in the parent compound is replaced, such as with ammonia, arginine, benethamine, benzathine, calcium, choline, deanol, diethanolamine, diethylamine, ethanolamine, ethylendiamine, meglumine, glycine, hydrabamine, imidazole, lysine, magnesium, hydroxyethylmorpholine, piperazine, potassium, epolamine, sodium, trolamine, tromethamine or zinc.

The present invention includes within its scope solvates of the compounds as defined herein. "Solvates" are crystals formed by an active compound and a second component (solvent) which, in isolated form, is liquid at room temperature. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds herein may be formed with water, in which case they will be hydrates.

The present invention also includes co-crystals within its scope. The term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity. Examples of co-crystal formers, which may be present in the co-crystal alongside the active pharmaceutical ingredient, include L-ascorbic acid, citric acid, glutaric acid, cinnamic acid, mandelic acid, urea and nicotinamide.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature with the more abundant isotope(s) being preferred. Examples of isotopes that can be incorporated into compounds of the invention include isotopes of hydrogen, carbon, nitrogen, oxygen, sulphur, fluoro and chloro such as $^{2}$H, $^{3}$H, $^{11}$C, $^{13}$C, $^{14}$C, $^{15}$N, $^{17}$O, $^{18}$O, $^{35}$S, $^{18}$F, and $^{36}$Cl, respectively. It is to be understood that for any isotop that is present in measurable amounts in nature, like e.g. deuterium, the amount of the corresponding radionuclide that may be introduced into the compounds of the present invention to modulate its properties, will advantageously exceed its natural abundance in nature. Hence, for example, the rate of deuterium introduced in the deuterated compounds of the present invention is typically higher than the amount of deuterium to be naturally expected in said compound. Certain isotopic variations of the invention, for example, those in which a radioactive isotope such as $^{3}$H or $^{14}$C is incorporated, are useful in drug and/or substrate tissue distribution studies. Tritiated, i.e., $^{3}$H, and carbon-14, i.e., $^{14}$C, isotopes are particularly preferred for their ease of preparation and detectability. Further, substitution with isotopes such as deuterium, i.e., $^{2}H$, may afford certain therapeutic advantages resulting form greater metabolic stability, for example, increased in vivo half-life, reduced dosage requirements and hence may be preferred in some circumstances. Isotopic variations of the compounds of the invention can generally be prepared by conventional procedures using appropriate isotopic variations of suitable reagents.

Also part of the invention are those compounds wherein at least one atom has been replaced by a radioisotope (radionuclide) of the same or a different atom that can be used in vivo imaging techniques such as single-photon emission computed tomography (SPECT), positron emission tomography (PET), magnetic resonance spectroscopy (MRS) or magnetic resonance imaging (MRI).

Examples for such radioactive GPR17 modulator derivatives usable in SPECT studies (such compounds herein "SPECT tracers") are compounds wherein a $^{99m}Tc$, $^{111}In$, $^{82}Rb$, $^{137}Cs$ $^{123}I$, $^{125}I$, $^{131}I$, $^{67}Ga$, $^{192}Ir$ or $^{201}Tl$, and preferably $^{123}I$ has been introduced. For example, in order for the compounds of the present invention to be used as SPECT tracers, a $^{123}I$ isotope may be introduced into a GPR17 modulator as disclosed herein. By way of a non-limiting example, in order for a compound to be used as SPECT tracer, a radionuclide selected from $^{123}I$, $^{125}I$ and $^{131}I$, preferably $^{123}I$, may be introduced into a compound of the present invention. In one embodiment, a SPECT tracer of the present invention may be based on the structure of a iodine-containing GPR17 modulator disclosed herein, wherein one of the radionuclides $^{123}I$, $^{125}I$ and $^{131}I$, preferably $^{123}I$, has been introduced into the position of the iodine atom.

Accordingly, the term "SPECT tracer of the present invention", relates to compounds of the present invention including those having a structure according to any one of Formula I, I-2, II, IIa, IIb, IIc, IId, IIe, IIf, IIg, II-2, II-2a, II-2b, II-2c, II-2d, II-2e, II-2f, II-2g, III, IIIa, IIIb, IIIc, III-2, III-2a, III-2b, III-2c, IV, IV-2, V, V-2, VI, VIa, VIb, VIc, VId, VIe, VIf and VIg as further defined herein, or as otherwise individually disclosed herein, wherein at least one radioisotope has been introduced in an amount which is suitable for SPECT imaging. This includes but is not limited to $^{99m}Tc$, $^{111}In$, $^{82}Rb$, $^{137}Cs$, $^{123}I$, $^{125}I$, $^{131}I$, $^{67}Ga$, $^{192}IR$ or $^{201}Tl$, and is preferably $^{123}I$.

Examples for GPR17 modulator derivatives usable in PET applications (herein "PET tracers") are compounds wherein $^{11}C$, $^{13}N$, $^{15}O$, $^{18}F$, $^{76}Br$ or $^{124}I$ have been introduced. For example, in order for a compound to be used as a PET tracer, an $^{18}F$ isotope may be introduced into a compound of the present invention in an amount which is suitable for PET imaging. In one embodiment, a PET tracer may be based on the structure of a fluoro-containing GPR17 modulator disclosed herein, wherein the respective radionuclide $^{18}F$ has been introduced into the position of the fluoro atom. In another embodiment, an $^{18}F$ isotope may be introduced into a compound of the present invention instead of a hydroxy group. This likewise applies to the introduction of at least one $^{11}C$, $^{13}N$, $^{15}O$, $^{76}Br$ or $^{124}I$, instead of an "unlabelled" carbon, nitrogen, oxygen, bromine, or iodine atom, respectively, or instead of any other atom or group which may be found suitable for replacement by the respective radionuclide. (see e.g. Pimlott and Sutherland, Chem Soc Rev 2011, 40, 149).

Accordingly, the term "PET tracer of the present invention", relates to compounds as described in the present patent application and having a structure according to any one of the compounds of the present invention including those of Formula I, I-2, II, IIa, IIb, IIc, IId, IIe, IIf, IIg, II-2, II-2a, II-2b, II-2c, II-2d, II-2e, II-2f, II-2g, III, IIIa, IIIb, IIIc, III-2, III-2a, III-2b, III-2c, IV, IV-2, V, V-2, VI, VIa, VIb, VIc, VId, VIe, VIf and VIg as further defined herein, or as otherwise individually disclosed herein, wherein at least one radioisotope has been introduced which is suitable for PET imaging. This includes but is not limited to $^{11}C$, $^{13}N$, $^{15}O$, $^{18}F$, $^{76}Br$ or $^{124}I$, and is preferably $^{18}F$.

Compounds for use in MRI and MRS are preferably compounds of the present invention having a suitable amount of a magnetic radioisotope incorporated. Those include $^{13}C$, $^{1}H$, $^{18}F$, $^{19}F$, $^{14}N$, $^{17}O$, $^{31}P$, and $^{33}S$, wherein $^{19}F$ or $^{13}C$ are preferred.

The present invention includes within its scope prodrugs of the compounds of the present invention. In general, such prodrugs will be functional derivatives of the compounds described herein which are readily convertible in vivo, e.g. by endogenous enzymes in the gut or the blood, into the required GPR17 modulating compounds described herein. Conventional procedures for the selection and preparation of suitable prodrug derivatives are described, for example, in Design of Prodrugs, ed. H. Bundgaard, Elsevier, 1985. For example, a prodrug may have a suitable ester group incorporated which will be cleaved by esterases to release an active GPR17 antagonist according to the present invention.

Depending on its substitution pattern, the compounds of the present invention may or may not have one or more optical stereocenters, and may or may not exist as different enantiomers or diastereomers. Any such enantiomers, diastereomers or other optical isomers are encompassed by the scope of the invention.

The compound of the present invention may also exist in different crystal forms, i.e. as polymorphs, all of which are encompassed by the present invention.

The compounds of the present invention may be included in a pharmaceutical composition which may also include a pharmaceutically acceptable carrier.

"Pharmaceutically acceptable carrier" refers to a diluent, adjuvant, excipient, or carrier, or other ingredient with which a compound of the invention is administered and which a person of skilled in the art would understand to be pharmaceutically acceptable but whitself is typically not biodynamically active.

The compounds of the present invention are useful in the prevention and/or treatment of certain diseases or disorders in animals, in particular in humans, as described herein.

"Preventing" or "prevention" refers to a reduction in risk of acquiring a disease or disorder (i. e., causing at least one of the clinical symptoms of the disease not to develop in a subject, in particular a human subject, that may be exposed to or predisposed to the disease but does not yet experience or display symptoms of the disease).

"Treating" or "treatment" of any disease or disorder includes, in one embodiment, to improve the disease or disorder (i. e., arresting or reducing the development of the disease or at least reducing one of the clinical symptoms of the disease). In another embodiment "treating" or "treatment" refers to improve at least one physical parameter, which may or may not be discernible by the subject, in particular a human subject, but which is based on or associated with the disease or disorder to be treated. In yet another embodiment, "treating" or "treatment" refers to modulating the disease or disorder, either physically (e. g. stabilization of a discernible on non-discernible symptom), physiologically (e. g. stabilization of a physiological parameter), or both. In yet another embodiment, "treating" or "treatment" refers to delaying the onset or progression of the disease or disorder. Accordingly, "treating" or "treatment"

includes any causal treatment of the underlying disease or disorder (i.e. disease modification), as well as any treatment of signs and symptoms of the disease or disorder (whether with or without disease modification), as well as any alleviation or amelioration of the disease or disorder, or its signs and symptoms.

"Diagnosis", "diagnoses" or "diagnosing" of a disease or disorder include, in one embodiment, the identification and measurement of signs and symptoms which are associated with said disease. "Diagnosis", "diagnoses" or "diagnosing" include but are not limited to the detection and/or measurement of decreased, increased, or otherwise incorrectly (e.g. as to time or place) expressed, activated, or distributed GPR17 receptors as indicator of a GPR17-related disease or disorder, as compared to healthy subjects. In one example, GPR17 ligands may be used in the form of PET or SPECT tracers for such a diagnosis, including a diagnosis of a myelination disease.

The terms "disease(s)" and "disorder(s)" are used largely interchangeably herein.

"Monitoring" refers to the observation of a disease, condition or at least one medical parameter over a certain period of time. "Monitoring" also includes the observations of the effects of a therapeutic drug with the assistance of a "Companion Drug"

"Companion Diagnostic" as used herein refers to a compound that can be used in conjunction to a therapeutic drug with the aim to determine the applicability (e.g. in terms of safety and efficacy) of said therapeutic drug to a specific patient. The use of a "Companion Diagnostic" may include diagnostic and monitoring steps.

The term "animal(s)" and "subject(s)" includes humans. The terms "human," "patient" and "human subject" are used interchangeably herein.

The invention also relates to methods of treating an animal disease or disorder, as described in more detail herein, in particular a human disease or disorder, which includes the administration of the compounds of the present invention in therapeutically effective amounts. "Therapeutically effective amount" means the amount of a compound that, when administered to a subject, in particular a human subject, for treating a disease, is sufficient to effect such treatment for the disease. The "therapeutically effective amount" can vary depending on the compound, the disease and its severity, and the condition, age, weight, gender etc. of the subject, in particular a human subject, to be treated.

"Diagnostically effective amount" means the amount of a compound that, when administered to a subject, in particular a human subject, for diagnosing a disease, is sufficient to effect such diagnosis for the disease.

The term "multiple sclerosis" as used herein refers to the disease as classified in Section G35 of the 2016/7 ICD-10-CM diagnosis code.

The term "myelination disorder" includes demyelination disorders, dysmyelination disorders and hypomyelination disorders, as further described herein. A preferred subclass of myelination disorder for the treatment with or diagnosis by the compounds of the present invention are demyelination disorders, particularly of the central nervous system. A particularly preferred myelination disorder for treatment with or diagnosis by the compounds of the present invention is multiple sclerosis.

The term "GPR17modulators" as used herein are meant to describe compounds that are capable of modulating the activity of the GPR17 receptor, in particular compounds that are capable of decreasing the GPR17 activity. Such "negative GPR17modulators" include GPR17 antagonists which are capable of blocking the effects of GPR17 agonists, as well as GPR17 inverse agonists which are also capable of inhibiting constitutional active GPR17 receptors or receptor variants.

Whenever numbers appear in subscript following a "C", these numbers (whether in brackets or not) refer to the range of carbon atoms comprised by the respective group directly following the numbers. For example, "$C_{1-6}$" and "$(C_{1-6})$" both refer to a group, as further specified herein, which comprises from 1 to 6 C-Atoms.

"Alkyl" includes saturated aliphatic hydrocarbyl groups. The hydrocarbon chain may be either straight-chained or branched. Examples of "alkyl" include those with 1-6 carbon atoms ("$C_{1-6}$alkyl"), those with 1-5 carbon atoms ("$C_{1-5}$ alkyl"), 1-4 carbon atoms ("$C_{1-4}$ alkyl"), or only 1-3 carbon atoms ("$C_{1-3}$ alkyl"). This term is exemplified by groups such as methyl, ethyl, n-propyl, isopropyl, n-butyl, sec-butyl, isobutyl, tert-butyl, t-amyl, and the like. Any numbers of C atoms in alkyls or other groups may be indicated herein in brackets or without brackets.

"Alkenyl" includes monovalent aliphatic hydrocarbyl groups comprising at least one double bond. Alkenyls may be branched or straight-chained. Examples of "alkenyl" include those with 2-3 carbon atoms ("$C_{2-3}$ alkenyl") or 2-6 carbon atoms ("$C_{2-6}$ alkenyl"). This term is exemplified by groups such as vinyl (ethenyl), allyl or butenyl. The term "propenyl" refers to alkenyls with three chain forming carbon atoms and includes linear (n-propenyl) as well as branched (isopropenyl/methylethenyl) groups.

"Alkynyl" includes monovalent aliphatic hydrocarbyl groups comprising at least one triple bond. Alkynyls may be branched or straight-chained. Examples of "alkynyl" include those with 2-6 carbon atoms ("$C_{2-6}$alkynyl"). This term is exemplified by groups such as ethynyl, propargyl and 2-butynyl.

"Alkyloxy" and "alkoxy", as used interchangeably herein (together alk(yl)oxy), include the group —OR wherein R is "alkyl" as defined and exemplified further herein. Particular alk(yl)oxy groups include, by way of example, meth(yl)oxy, eth(yl)oxy, n-prop(yl)oxy, isoprop(yl)oxy, n-but(yl)oxy, tert-but(yl)oxy, sec-but(yl)oxy, isobut(yl)oxy, n-pent(yl)oxy, 1,2-dimethylbut(yl)oxy, and the like.

"Halogen" includes fluoro, chloro, bromine, and iodine atoms.

"Azido" refers to the group —N=N=N.

"Cyanomethyl" refers to —$CH_2$—C≡N.

The term "haloalkyl" as used herein refers to an "alkyl" as described herein (and wherein the numbers indicate the numbers of C-atoms in the alkyl part), which is substituted with one or more halogen atoms. Representative examples of "halo($C_{1-3}$)alkyl" groups include, but are not limited to —$CF_3$, —$CCl_3$, —$CFCl_2$, —$CH_2CH_2CF_3$ and —$CH_2CF_3$.

The term "fluorinated" refers to a group wherein one or more hydrogens are replaced with fluoros. For example, an alkyl or alkoxy group, respectively, which is said to be unsubstituted or fluorinated comprises a "fluoroalkyl" or "fluoroalk(yl)oxy", respectively, as defined herein. Likewise, a fluorinated alkoxyalkyl group comprises the groups fluoroalkoxyalkyl and alkoxyfluoroalkyl.

The term "fluoroalkyl" as used refers to an "alkyl" as described herein, which is substituted with one or more fluoro atoms. Representative examples of fluoro($C_{1-3}$)alkyl groups include, but are not limited to —$CF_3$, —$CH_2CHF_2$ and —$CH_2CF_3$. Preferred "fluoroalkyl" groups are those wherein terminal methyl groups are substituted with one or more fluoro atoms; hence, a particularly preferred monofluoroethyl group is —$CH_2CH_2F$, a particularly preferred difluoroethyl group is the group —CH$_2$CHF$_2$, a particularly preferred trifluoroethyl group is the group —CH$_2$CF$_3$, a particularly preferred monofluoropropyl group is —CH$_2$CH$_2$CH$_2$F, a particularly preferred difluoropropyl is —CH$_2$CH$_2$CHF$_2$, and, a particularly preferred trifluoropropyl group is —CH$_2$CH$_2$CF$_3$.

The term "mono-, di- and trifluoro" as prefix to chemical groups such as alkyl or alkoxy represents an abbreviation of the respective fluorinated groups. For example, the term "mono-, di- and trifluoroethyl" refers to the group of monofluoroethyl, difluoroethyl and trifluoroethyl.

The term "haloalk(yl)oxy" as used herein refers to an "alk(yl)oxy" as described herein, which is substituted with one or more halogen atoms. Representative examples of halo(C$_{1-3}$)alkyloxy groups include, but are not limited to, —OCF$_3$, —OCCl$_3$, —OCFCl$_2$, and —OCH$_2$CF$_3$.

The terms "fluoroalkyloxy" or "fluoroalkoxy" as interchangeably used herein refer to an "alk(yl)oxy" as described herein, which is substituted with one or more fluoro atoms. Representative examples of fluoro(C$_{1-3}$)alk(yl)oxy groups include, but are not limited to —OCF$_3$, —OCH$_2$CHF$_2$ and —OCF$_2$CHF$_2$. A preferred "monofluoroethoxy" group is the group —OCH$_2$CH$_2$F. A preferred difluoroethoxy is the group —OCH$_2$CHF$_2$. A preferred trifluoroethoxy group is the group —OCH$_2$CF$_3$. A preferred monofluoropropyloxy group is the group —OCH$_2$CH$_2$CH$_2$F. A preferred difluoropropyloxy group is the group —OCH$_2$CH$_2$CHF$_2$, and a preferred trifluoropropyloxy group is the group —OCH$_2$CH$_2$CF$_3$.

The term "fluoroalk(yl)oxyalkyl" or "fluoroalkoxyalkyl" as interchangeably used herein refers to a group comprising an alkyl group which is substituted with an alk(yl)oxy group, wherein the terminal alkoxy group is substituted with one or more fluoro atoms.

Representative examples include, but are not limited to —CH$_2$CH$_2$OCF$_3$, —CH$_2$OCF$_2$CH$_3$, and —CH$_2$OCHFCHF$_2$.

The term "fluoroalkyloxyalkyloxy" or "fluoroalkoxyalkoxy" as interchangeably used herein refers to a group, wherein an alkoxy group is substituted with another alkoxy group, wherein the terminal alkoxy group is substituted with one or more fluoro atoms. Representative examples include, but are not limited to —OCH$_2$OCH$_2$CF$_3$, —OCH$_2$OCF$_2$CH$_3$, and —OCH$_2$CH$_2$OCHF$_2$.

"Alkylcarbonyl" refers to the group —C(=O)-alkyl, wherein alkyl is as defined herein. Typical examples are C$_{1-6}$ alkylcarbonyl and C$_{1-3}$ alkylcarbonyl, and in particular acetyl (—C(=O)CH$_3$).

"Alk(yl)oxycarbonyl" refers to the radical —C(=O)—O-alkyl, wherein the alkyl group is as defined herein. Typical examples are C$_{1-6}$alkoxycarbonyl and C$_{1-3}$alkoxycarbonyl, and in particular methoxycarbonyl (—C(=O)OCH$_3$).

"Alkylsulfinyl" refers to the radical —S(=O)-alkyl wherein alkyl is as defined herein. A typical example is C$_{1-3}$ alkylsulfinyl, and in particular methylsulfinyl (—S(=O)CH$_3$).

"Alkylsulfonyl" refers to the radical —S(=O)$_2$-alkyl wherein alkyl is as defined herein. A typical example is C$_{1-3}$ alkylsulfonyl, and in particular methylsulfonyl (—S(=O)$_2$CH$_3$).

"C$_{1-3}$ alkoxy(C$_{1-3}$)alkyl" refers to the group —C$_{1-3}$ alkyl-O—(C$_{1-3}$)alkyl, wherein alkyl is as defined herein "C$_{1-3}$ alkoxy(C$_{1-3}$)alkoxy" refers to the group —O—C$_{1-3}$ alkyl —O—(C$_{1-3}$)alkyl, wherein alkyl is as defined herein The term "cycloalkyl" as used herein refers to a monovalent group derived from a saturated hydrocarbon, which may be unsubstituted or substituted with one or more substituents as further indicated herein. The "cycloalkyl" is comprised of at least three up to, for example, 7 ring forming carbon atoms ("C$_{3-7}$ cycloalkyl"), or 6 ring forming atoms ("C$_{3-6}$ cycloalkyl"). Suitable cycloalkyl groups include cyclopropyl, cyclobutyl, cyclopentyl, cyclohexyl and cycloheptyl. Cycloalkyls are preferably monocyclic but may also include bridged bicyclic groups like, e.g. norbornanyl. A cycloalkyl group may be a terminal group that may be bound to e.g. a ring system via a methylene or methoxy group, in which case it would be called "cyclopropylmethyl" or "cyclopropylmethoxy", respectively. Alternatively, a cyclopropyl group may be substituted, for example, via a terminal alkoxy or alkoxycarbonyl group, in which case it is called "alkoxycyclopropyl or "alkoxycarbonylcyclopropyl" group. For example, an "ethoxycarbonylcyclopropyl" has the structure CH$_3$CH$_2$—O—C(=O)-cyclopropyl-, whereas a cyclopropylmethoxy group has the structure cyclopropyl-CH$_2$—O—.

The term "C$_{3-7}$ cycloalkenyl" as used herein refers to monovalent groups of 3 to 7 carbon atoms derived from a hydrocarbon which includes at least one double bond.

The term "heterocycloalkyl" as used herein refers to saturated ring containing at least two ring forming carbon atoms and at least one ring forming heteroatom preferably selected from oxygen, sulphur and nitrogen, wherein each ring which may be unsubstituted or further substituted with one or more substituents as described herein. Suitable heterocycloalkyl groups include oxetanyl, azetidinyl, tetrahydrofuranyl, dioxolanyl, pyrrolidinyl, oxazolidinyl, thiazolidinyl, isothiazolidinyl, imidazolidinyl, tetrahydropyranyl, tetrahydrothiopyranyl, piperidinyl, piperazinyl, morpholinyl, thiomorpholinyl, azepanyl, oxazepanyl, diazepanyl, thiadiazepanyl and azocanyl. The term "C$_{3-7}$ heterocycloalkyl" refers to a heterocycloalkyl comprising between three to seven ring forming atoms. Heterocycloalkyls are preferably monocyclic but may also include bridged bicyclic molecules like, e.g. tropanyl.

The term "heterocycloalkenyl" as used herein refers to rings containing at least one double bond, at least two ring forming carbon atoms and at least one ring-forming heteroatom preferably selected from oxygen, sulphur and nitrogen, wherein each ring which may be unsubstituted or substituted with one or more substituents as further defined herein. Suitable heterocycloalkenyl groups include thiazolinyl, isothiazolinyl, imidazolinyl, dihydrofuranyl, dihydropyranyl, and dihydrothiopyranyl. The term "C$_{3-7}$ heterocycloalkenyl" refers to a heterocycloalkenyl comprising between three to seven ring forming atoms. Heterocycloalkenyls herein are preferably monocyclic.

The term "heteroaryl" as used herein refers to monovalent aromatic groups containing at least five ring-forming atoms derived from a single ring with e.g. up to six atoms (e.g. "C$_{5-6}$ heteroaryl") or multiple condensed rings with e.g. up to 10 ring forming atoms (e.g. "C$_{5-6}$ heteroaryl"), wherein one or more carbon atoms have been replaced by one or more heteroatoms preferably selected from oxygen, sulphur and nitrogen. Suitable heteroaryl groups include furyl, benzofuryl, thienyl, benzothienyl, thieno[2,3-c]pyrazolyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, benzoxadiazolyl, benzoselenathiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2- a]pyrazinyl, oxadiazolyl, thiadiazolyl, triazolyl, [1,2,4]triazolo[1,5-a]-5-pyrimidinyl, benzotriazolyl, tetrazolyl, pyridinyl, quinolinyl, isoquinolinyl, pyridazinyl, cinnolinyl, phthalazinyl, pyrimidinyl, quinazolinyl, pyrazinyl, quinoxalinyl, pteridinyl, and triazinyl. As indicated above, the term "$C_{5-6}$ heteroaryl" refers to a heteroaryl with 5- or 6-ring forming atoms although some of the ring forming atoms are no carbon atoms but heteroatoms.

The term "$C_{8-10}$ heterocyclyl" as used herein refers to bicyclic groups containing 8 to 10 ring-forming atoms, wherein one or more ring forming carbon atoms have been replaced by one or more heteroatoms preferably selected from oxygen, sulphur and nitrogen, and wherein one of said rings is aromatic, and the other one is non-aromatic. Suitable C8-10 heterocyclyl are benzodioxolyl, dihydrobenzofuranyl, dihydrobenzothienyl, tetrahydroquinolinyl, tetrahydroisoquinolinyl, tetrahydroquinoxaline, and the like.

The terms "$C_{3-7}$cycloalkyl($C_{1-6}$)alkyl" or $C_{3-7}$heterocycloalkyl($C_{1-6}$)alkyl" refer to a terminal "$C_{3-7}$cycloalkyl" or "$C_{3-7}$heterocycloalkyl", respectively, as defined herein, which are attached to $C_{1-6}$ alkyl as defined herein.

The terms "$C_{3-7}$cycloalkyl($C_{1-6}$)alkoxy" or $C_{3-7}$heterocycloalkyl($C_{1-6}$)alkoxy" refer to a terminal "$C_{3-7}$cycloalkyl" or "$C_{3-7}$heterocycloalkyl", respectively, as defined herein, which are attached to a "$C_{1-6}$alkoxy" as defined herein.

The term "phenyl($C_{1-6}$)alkyl" refers to a $C_{1-6}$alkyl as defined herein, substituted with a phenyl. Examples are benzyl or phenylethyl.

"Phenyl($C_{1-6}$)alkoxy" refers to a "$C_{1-6}$alkyloxy" group substituted with a phenyl. Examples of phenylalkyloxy groups are phenylethyloxy and, in particular, benzyloxy.

The terms "pyridyl" and "pyridinyl" are used interchangeably herein.

The term "isoxazol" refers to 1,2 oxazol.
The present disclosure is further illustrated by the following non-limiting items:
1. A compound having a structure according to Formula I:

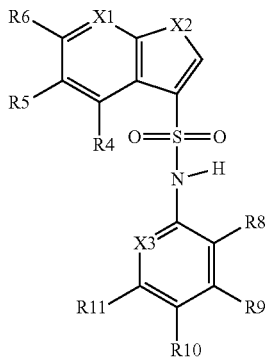

wherein
X1 is N or C(R7),
X2 is NH or O,
X3 is N or C(R12),
R4 is selected from hydrogen and fluoro,
R5 is selected from hydrogen, halogen, cyano, $C_{1-6}$ alkyl, $C_{1-6}$ alkoxy, $C_{1-3}$ alkylcarbonyl, $C_{1-3}$ alkoxycarbonyl, $C_{1-3}$ akylsulfinyl, and $C_{1-3}$ akylsulfonyl, wherein each alkyl or alkoxy may optionally be substituted one or more times selected from halogen, $C_{1-3}$ alkoxy, $C_{2-3}$ alkynyl, $C_{2-3}$ alkenyl, cyano, azido, hydroxyl, amino, and $C_{1-3}$ alkyl amino or R5 forms a ring together with R6 as described herein, R6 is selected from hydrogen, hydroxy, halogen, cyano, azido, $C_{1-6}$ alkyl, $C_{2-6}$ alkenyl, $C_{2-6}$ alkynyl, $C_{1-6}$ alkoxy, $C_{3-7}$ cycloalkyl, $C_{3-6}$ cycloalkenyl, $C_{3-7}$ heterocycloalkyl, $C_{3-7}$ heterocycloalkenyl, phenyl, $C_{5-10}$ heteroaryl, $C_{8-10}$ heterocyclyl, —ORx, —SRx, —SORx, SO$_2$Rx, -pentafluorosulfanyl, NRyRzz, —NRyCORx, —NRyCO$_2$Rx, —NRxCONRyRz, —CORx, —CO$_2$Rx, —CONRyRz, wherein each alkyl, alkenyl, alkynyl, alkoxy, cycloalkyl, heterocycloalkyl, cycloalkenyl, phenyl, heteroaryl or heterocyclyl group in R6 can be unsubstituted or substituted with one or more substituents preferably selected from halogen, hydroxyl, oxo, cyano, azido, nitro, $C_{1-6}$ alkyl, $C_{1-6}$ alkoxy ($C_{1-3}$)alkyl, $C_{3-7}$ cycloalkyl, $C_{3-7}$ heterocycloalkyl, phenyl, $C_{5-10}$ (preferably $C_5$-6) heteroaryl, ORx, —SRx, —SORx, SO$_2$Rx, -pentafluorosulfanyl, NRyRz, —NRyCORx, —NRyCO$_2$Rx, —CORx, —CO$_2$Rx, —CONRyRz,
wherein Rx, Ry, Rz and Rzz are independently selected from hydrogen, $C_{1-6}$ alkyl, $C_{3-7}$ cycloalkyl, $C_{3-6}$ cycloalkenyl, $C_{3-7}$ cycloalkyl($C_{1-6}$)alkyl, phenyl, phenyl($C_{1-6}$)alkyl, $C_{3-7}$ heterocycloalkyl, $C_{3-7}$ heterocycloalkyl($C_{1-6}$)alkyl, $C_{5-6}$ heteroaryl or heteroaryl($C_{1-6}$) alkyl, any of which groups can be unsubstituted or substituted with one or more substituents, or Ry and Rz, or Ry and Rzz together with the amino atom to which they are both attached may form an aromatic or non-aromatic, unsubstituted or substituted $C_{5-6}$ heterocycle, and wherein Rzz is different from hydrogen,
or R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl, wherein each substitution, if present, is selected from halogen, $C_{1-3}$ alkyl, $C_{3-7}$cycloalkyl, $C_{3-7}$ cycloalkyl ($C_{1-3}$) alkyl, $C_{3-7}$ heterocycloalkyl($C_{1-3}$)alkyl, $C_{1-3}$ alkoxy, and $C_{1-3}$ alkoxy($C_{1-3}$) alkyl, wherein each alkyl or alkoxy can be unsubstituted or substituted with one or more substituents selected from halogen and $C_{1-3}$ alkoxy,
or R6 forms together with R5 and the carbon atoms to which R6 and R5 are attached, a 1,3-dioxolane which may be unsubstituted or substituted with one or two substituents selected from fluoro and methyl, or
R7 is selected from H, halogen, cyano, $C_{1-6}$ alkyl, $C_{1-6}$ alkoxy, $C_{2-6}$ alkynyl, $C_{2-6}$ alkenyl, $C_{1-6}$ alkylcarbonyl, $C_{1-6}$ alkoxycarbonyl, $C_{1-6}$ alkylsulfonyl, $C_{1-6}$ alkylsulfinyl, $C_{3-7}$ cycloalkyl, $C_{3-7}$ heterocycloalkyl, phenyl, $C_{5-6}$ heteroaryl, wherein each alkyl, alkenyl, alkynyl or alkoxy group can be unsubstituted or substituted with one or more substituents selected from halogen, and $C_{1-6}$ alkoxy,
R8 is selected from hydrogen, $C_{1-6}$ alkyl, $C_{1-6}$ alkoxy, and halogen, wherein each alkyl or alkoxy can be unsubstituted or substituted with one or more substituents selected from halogen and $C_{1-3}$ alkoxy, or forms a ring system together with R9, as described herein,
R9 is selected from hydrogen, halogen, cyano, azido, $C_{1-6}$ alkyl, $C_{1-6}$ alkoxy, $C_{2-6}$ alkenyl, $C_{2-6}$ alkynyl, and halogen, wherein each alkyl or alkoxy can be unsubstituted or substituted with one or more substituents selected from halogen and $C_{1-3}$ alkoxy,
or R9 forms together with R8 or R10 and the ring to which they are attached are preferably selected from a bicyclic ring system selected from (a) 2,1,3-benzothiadiazole, (b) 2,1,3-benzoselenadiazole, (c) 2,1,3-benzoxadiazole, (d) 1,3-benzothiazole, (e) 1,3-benzoxazole which may be unsubstituted or may be partially hydrogenated and unsubstituted or substituted with oxo, (f) 1,3-benzodioxole which may be unsubstituted or substituted with one or two substituents selected from fluoro and methyl, (g) benzothiophene, which may be unsubstituted or may be partially hydrogenated and unsubstituted or substituted with one or two substituents selected from oxo, methyl or fluoro, or (h) benzofuran, which may be unsubstituted or may be partially hydrogenated and unsubstituted or substituted with one or two groups selected from oxo, fluoro and methyl, preferably with one oxo group, R10 is selected from hydrogen, halogen, $C_{1-6}$ alkyl, $C_{1-6}$alkoxy, $C_{2-6}$ alkenyl, $C_{2-6}$ alkynyl, cyano, cyano($C_{1-6}$) alkyl, $C_{1-6}$ alkylcarbonyl, $C_{1-6}$ alkoxycarbonyl, $C_{1-6}$ alkylsulfonyl, $C_{1-6}$ alkylsulfinyl, azido, pentafluorosulfanyl, and nitro, wherein each alkyl, alkenyl, alkynyl or alkoxy can be unsubstituted or substituted with one or more substituents selected from halogen and $C_{1-6}$ alkoxy, or R10 forms a ring system together with R9, as described herein, R11 is selected from hydrogen, halogen, cyano, azido, $C_{1-6}$ alkyl, $C_{1-6}$ alkoxy, $C_{1-6}$ alkylcarbonyl, $C_{1-6}$ alkoxycarbonyl, $C_{1-6}$ alkylsulfonyl, and $C_{1-6}$ alkylsulfinyl, $C_{2-6}$ alkenyl, and $C_{2-6}$ alkynyl, wherein each alkyl or alkoxy can be unsubstituted or substituted with one or more substituents selected from halogen and $C_{1-3}$ alkoxy, R12 is selected from hydrogen, $C_{1-6}$ alkyl, $C_{1-6}$ alkoxy and halogen, wherein each alkyl or alkoxy can be unsubstituted or substituted with one or more substituents selected from halogen and $C_{1-3}$ alkoxy, and pharmaceutically acceptable salts, solvates, isotopes and co-crystals thereof.

2) A compound according to item 1,
wherein
R4 is hydrogen
R5 is selected from hydrogen, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfinyl, and $C_{1-3}$ akylsulfonyl, wherein each alkyl or alkoxy may optionally be substituted one or more times with a substituent selected from halogen, $C_{1-3}$ alkoxy, cyano, azido, and an optionally alkylated amino group, or R5 forms a ring together with R6 as described below, R6 is selected from hydrogen, fluoro, chloro, bromo, iodo, cyano, azido, unsubstituted or substituted $C_{1-3}$ alkyl, unsubstituted or substituted $C_{1-3}$ alkoxy unsubstituted or substituted $C_{2-3}$ alkenyl, unsubstituted or substituted $C_{2-3}$ alkynyl, unsubstituted or substituted $C_{1-3}$ alkylcarbonyl, unsubstituted or substituted $C_{1-3}$ alkoxycarbonyl, unsubstituted or substituted $C_{1-3}$ alkylsulfinyl, unsubstituted or substituted $C_{1-3}$ alkylsulfonyl, unsubstituted or substituted $C_{3-7}$ cycloalkyl, unsubstituted or substituted $C_{3-7}$ cycloalkyl($C_{1-3}$)alkyl unsubstituted or substituted $C_{3-7}$ heterocycloalkyl unsubstituted or substituted $C_{3-7}$ heterocycloalkyl($C_{1-3}$)alkyl, unsubstituted or substituted $C_{3-6}$ cycloalkoxy, unsubstituted or substituted $C_{3-6}$ heterocycloalkoxy, unsubstituted or substituted $C_{1-3}$alkoxy($C_{1-3}$)alkoxy, unsubstituted or substituted ($C_{3-6}$)cycloalkyl($C_{1-3}$)alkoxy unsubstituted or substituted ($C_{3-6}$)heterocycloalkyl($C_{1-3}$)alkoxy, unsubstituted or substituted phenyl, unsubstituted or substituted phenyloxy, unsubstituted or substituted thienyl, unsubstituted or substituted pyridyl, unsubstituted or substituted oxazole, unsubstituted or substituted thiazole, unsubstituted or substituted isoxazole, unsubstituted or substituted phenyl($C_{1-3}$)alkoxy preferably benzyloxy, wherein each optional substitution in R6 is selected from fluoro, chloro, bromo, methyl, methoxy and cyano, or R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl, wherein each substitution, if present, is selected from halogen, $C_{1-3}$ alkyl, $C_{3-7}$cycloalkyl, $C_{3-7}$ cycloalkyl ($C_{1-3}$) alkyl, $C_{3-7}$ heterocycloalkyl($C_{1-3}$)alkyl, $C_{1-3}$ alkoxy, and $C_{1-3}$ alkoxy($C_{1-3}$)alkyl, wherein each alkyl or alkoxy can be unsubstituted or substituted with one or more substituents selected from halogen and $C_{1-3}$ alkoxy, or R6 forms together with R5 and the carbon atoms to which R6 and R5 are attached a 1,3-dioxolane, which may be unsubstituted or substituted with one or two substituents selected from fluoro and methyl, R7 is selected from H, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfonyl, and $C_{1-3}$ alkylsulfinyl, wherein each alkyl or alkoxy moiety can be substituted with one or more substituents, preferably with halogen or $C_{1-3}$ alkoxy, or R7 forms a ring together with R6 as described herein, R8 is selected from hydrogen, $C_{1-3}$ alkyl, $C_{1-3}$ alkoxy, and halogen, wherein each alkyl or alkoxy can be unsubstituted or substituted with one or more substituents selected from halogen, cyano and methoxy, or R8 forms a ring system together with R9, as described herein, R9 is selected from hydrogen, $C_{1-3}$ alkyl, $C_{1-3}$ alkoxy, fluoro, chloro, bromo and iodo, wherein each alkyl or alkoxy can be unsubstituted or substituted with one or more substituents selected from halogen and methoxy, or R9 forms together with R8 or R10 and the ring to which they are attached a bicyclic ring system selected from 2,1,3-benzothiadiazole, 2,1,3-benzoselenadiazole, 2,1,3-benzoxadiazole, 1,3-benzothiazole, 1,3-benzoxazole which may be unsubstituted or may be partially hydrogenated and substituted with oxo, 1,3-benzodioxole which may be unsubstituted or substituted with one or two substituents selected from fluoro and methyl, 2,3-dihydrobenzothiophene, which may be unsubstituted or substituted with one or two oxo groups, and 1,3-dihydro-2-benzofuran, which may be unsubstituted or substituted with one or two groups selected from oxo, fluoro and methyl, preferably with one oxo group, R10 is selected from hydrogen, fluoro, chloro, bromo, iodo, $C_{1-3}$ alkyl, $C_{1-3}$ alkoxy, C2-C4 alkenyl, $C_{2-4}$ alkynyl, cyano, cyanomethyl, $C_{1-3}$ alkylcarbonyl, $C_{1-3}$ alkoxycarbonyl, azido, pentafluorosulfanyl, and nitro, wherein each alkyl, alkenyl, alkynyl or alkoxy can be unsubstituted or substituted with one or more substituents selected from halogen and $C_{1-3}$ alkoxy, or R10 forms a ring system together with R9, as described herein, R11 is selected from hydrogen, $C_{1-3}$ alkyl, $C_{1-3}$ alkoxy, fluoro, chloro, bromo, iodo, $C_{1-3}$ alkylcarbonyl, $C_{1-3}$ alkoxycarbonyl, wherein each alkyl and alkoxy can be unsubstituted or substituted with one or more substituents selected from fluoro, chloro, bromo, iodo and $C_{1-3}$ alkoxy, R12 is selected from hydrogen, $C_{1-3}$ alkyl, $C_{1-3}$ alkoxy, fluoro, chloro, bromo, and iodo, wherein each alkyl and alkoxy can be unsubstituted or substituted with one or more substituents selected from fluoro, chloro, bromo, iodo and $C_{1-3}$ alkoxy, wherein if R6 is hydrogen, and X1 is N, then R5 is different from hydrogen and is preferably iodo, and pharmaceutically acceptable salts, solvates, isotopes and co-crystals thereof.

3) A compound according to item 1,
wherein
X1 is N or C(R7),
X2 is NH,
X3 is N or C(R12),
R4 is hydrogen,
R5 is selected from hydrogen, fluoro, chloro, bromo, iodo, unsubstituted or fluorinated $C_{1-2}$ alkyl, preferably methyl or trifluoromethyl, unsubstituted or fluorinated $C_{1-2}$ alkyloxy, unsubstituted or fluorinated $C_{1-2}$ alkylcarbonyl, unsubstituted or fluorinated $C_{1-2}$ alkyloxycarbonyl, methylsulfinyl, and methylsulfonyl, or R5 forms a ring together with R6 as described herein, R6 is selected from hydrogen, fluoro, chloro, bromo, iodo, cyano, azido, unsubstituted or substituted $C_{1-3}$ alkyl, trifluoromethyl, unsubstituted or fluorinated $C_{1-3}$ alkylcarbonyl preferably acetyl, unsubstituted or fluorinated $C_{1-3}$ alkoxycarbonyl, methylsulfinyl, methylsulfonyl, $C_{3-6}$ cycloalkyl preferably cyclopropyl, $C_{3-6}$ cycloalkyl($C_{1-3}$))alkyl preferably cyclopropylmethyl, $C_{3-6}$ heterocycloalkyl, $C_{3-6}$ cycloalkoxy, $C_{3-6}$ heterocycloalkoxy, unsubstituted or substituted $C_{1-3}$ alkoxy preferably methoxy, unsubstituted or substituted $C_{1-3}$alkoxy($C_{1-3}$) alkoxy cyclopropylmethoxy, unsubstituted or substituted phenyl, unsubstituted or substituted phenyl($C_{1-3}$)alkoxy preferably benzyloxy, unsubstituted or substituted phenyloxy, unsubstituted or substituted thienyl, pyridyl, oxazole, thiazole, and isoxazole, and wherein each optional substitution in R6 is preferably selected from fluoro, chloro, methyl, methoxy, and cyano, provided that if R6 is hydrogen, and X1 is N, then R5 is preferably different from hydrogen and is preferably iodo, or R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution, if present, is selected from halogen, methyl or methoxy, wherein each methyl or methoxy can be unsubstituted or substituted with one or more substituents selected from fluoro and methoxy, or R6 forms together with R5 and the carbon atoms to which R6 and R5 are attached, a 1,3-dioxolane which may be unsubstituted or substituted with one or two substituents selected from fluoro and methyl, R7 is selected from hydrogen, fluoro, chloro, bromo, iodo, cyano, $C_{1-3}$ alkyl, $C_{1-3}$ alkyloxy, fluoro($C_{1-3}$)alkyl preferably trifluoromethyl, fluoro($C_{1-3}$)alkoxy preferably trifluoromethoxy, unsubstituted or fluorinated $C_{1-3}$ alkylcarbonyl, unsubstituted or fluorinated $C_{1-3}$ alkoxycarbonyl, methylsulfinyl, and methylsulfonyl, or R7 forms a ring together with R6 as described herein, R8 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, and fluoro($C_{1-3}$)alkyl preferably trifluoromethyl, or R8 forms a ring system together with R9, as described herein, R9 is selected from hydrogen, fluoro, chloro, bromo, iodo, $C_{1-3}$ alkyloxy preferably methoxy, fluoro($C_{1-3}$)alkoxy, $C_{1-3}$ alkyl preferably methyl, cyano, and fluoro($C_{1-3}$)alkyl preferably trifluoromethyl, or R9 forms together with R8 and the ring to which they are attached a bicyclic ring system selected from 2,1,3-benzothiadiazole, 2,1,3-benzoselenadiazole, 2,1,3-benzoxadiazole, 1,3-benzoxazole which may be unsubstituted or may be partially hydrogenated and substituted with oxo (to give 2-oxo-2,3-dihydro-1,3-benzoxazole and 1,3-benzodioxole, which is optionally substituted with one or two fluoros, or R9 forms together with R10 and the ring to which they are attached a bicyclic ring system selected from 2,1,3-benzothiadiazole, 2,1,3-benzoselenadiazole, 2,1,3-benzoxadiazole, 1,3-benzothiazole, 2,3-dihydro-1-benzothiophene, which is substituted with one or two oxo (preferably substituted with two oxo to give 1,1-dioxo-2,3-dihydro-1-benzothiophene), 3-oxo-1,3-dihydro-2-benzofuran-5-yl, and 1,3-benzodioxole, which is optionally substituted with one or two fluoros, R10 is selected from hydrogen, fluoro, chloro, bromo, iodo, $C_{1-3}$ alkyl, fluoro($C_{1-3}$)alkyl, preferably trifluoromethyl, $C_{2-3}$ alkynyl, $C_{1-3}$ alkyloxy, fluoro($C_{1-2}$)alkoxy, cyano, cyanomethyl, unsubstituted or fluorinated $C_{1-3}$ alkylcarbonyl preferably acetyl, unsubstituted or fluorinated $C_{1-3}$ alkoxycarbonyl azido, pentafluorosulfanyl, and nitro, or R10 forms a ring system together with R9, as described herein, R11 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-2}$)alkoxy, unsubstituted or fluorinated $C_{1-3}$ alkylcarbonyl, unsubstituted or fluorinated $C_{1-3}$ alkoxycarbonyl and cyano, R12 is selected from hydrogen, fluoro, chloro, bromo, iodo, $C_{1-3}$ alkyl preferably methyl, fluoro($C_{1-3}$)alkyl preferably trifluoromethyl, $C_{1-3}$ alkyloxy preferably methoxy, fluoro ($C_{1-2}$)alkoxy, and cyano.

and pharmaceutically acceptable salts, solvates, isotopes and co-crystals thereof.

4) A compound according to any one of the preceding items, wherein

X1 is N or C(R7),

X2 is NH or O,

X3 is N or C(R12),

R4 and R5 are both hydrogen,

R6 is selected from fluoro, chloro, bromo, iodo, cyano, azido, methyl, ethyl, isopropyl, trifluoromethyl, methylsulfinyl, methylsulfonyl, cyclopropyl, cyclopropylmethyl, methoxy, ethoxy, methoxyethoxy, cyclopropylmethoxy, phenyl, benzyloxy, phenyloxy, thienyl, pyridyl, oxazole, thiazole, and isoxazole, or R6 forms together with R7 and the carbon atoms to which R6 and R7 are attached, a ring selected from phenyl, pyridyl, and cyclopentyl, R7 is selected from hydrogen, fluoro, chloro, bromo, iodo, methoxy, difluoromethoxy, trifluoromethoxy, methyl, difluoromethyl, and trifluoromethyl, or R7 forms a ring together with R6 as described herein, R8 is selected from hydrogen, fluoro, chloro, bromo, iodo, methoxy, methyl, and trifluoromethyl, or R8 forms a ring system together with R9, as described herein, R9 is selected from hydrogen, fluoro and chloro and is preferably hydrogen, or R9 forms together with R8 or R10 and the ring to which they are attached a bicyclic ring system selected from 2,1,3-benzothiadiazole, 2,1,3-benzoxadiazole, 2-oxo-2,3-dihydro-1,3-benzoxazole, 3-oxo-1,3-dihydro-2-benzofuran-5-yl, and 1,3-benzodioxole, which is optionally substituted with two fluoros, R10 is selected from hydrogen, fluoro, chloro, bromo, iodo, methyl, ethynyl, propargyl, fluoro($C_{1-2}$)alkyl preferably trifluoromethyl, methoxy, fluoro($C_{1-2}$)alkoxy, cyano, cyanomethyl, acetyl, azido, pentafluorosulfanyl, and methoxycarbonyl, or R10 forms a ring system together with R9, as described herein, R11 is selected from hydrogen, fluoro, chloro, bromo, and methoxy, R12 is selected from hydrogen, fluoro, chloro, or bromo.

wherein at least one of R8, R9, R10 and R11 is different from hydrogen and unsubstituted alkyl, and pharmaceutically acceptable salts, solvates, isotopes and co-crystals thereof.

5) A compound according to any one of the preceding items, wherein
X1 is N or C(R7),
X2 is NH,
X3 is N or C(R12),
R4 and R5 are both hydrogen,
R6 is selected from fluoro, chloro, bromo, azido, methyl, ethyl, isopropyl, trifluoromethyl, methylsulfonyl, cyclopropyl, methoxy, ethoxy, trifluoromethoxy, phenyl, benzyloxy, thiophen-2-yl, and thiophen-3-yl,
or R6 forms together with R7 and the carbon atoms to which R6 and R7 are attached, a ring selected from phenyl, pyridyl, and cyclopentyl,
R7 is selected from hydrogen, fluoro, chloro, and methoxy, or R7 forms a ring together with R6 as described herein,
R8 is selected from hydrogen, fluoro, chloro, bromo, methoxy, and trifluoromethyl, or R8 forms a ring system together with R9, as described herein,
R9 is hydrogen or fluoro, preferably hydrogen,
or R9 forms together with R8 or R10 and the ring to which they are attached a bicyclic ring system selected from 2,1,3-benzothiadiazole, 2,1,3-benzoxadiazole, 1,3-benzodioxole, or 2,2-difluoro-1,3-benzodioxole,
R10 is selected from hydrogen, fluoro, chloro, bromo, iodo, ethynyl, propargyl, methoxy, cyano, cyanomethyl, trifluoromethyl, fluoro($C_{1-2}$)alkoxy, acetyl, azido, and pentafluorosulfanyl, or R10 forms a ring system together with R9, as described herein, and wherein, in a preferred embodiment, R8 and R10 are not both hydrogen,
R11 is selected from hydrogen, fluoro, chloro, and methoxy,
R12 is selected from hydrogen, and fluoro, and pharmaceutically acceptable salts, solvates, isotopes and co-crystals thereof.
6) A compound according to any one of the preceding items wherein
X1 is N or C(R7),
X2 is NH,
R4 and R5 are both hydrogen,
R6 is bromo or chloro,
R7 is hydrogen, methoxy, fluoro or trifluoromethyl,
X3 is N or C(R12),
R8 is selected from hydrogen, fluoro, chloro, and methoxy,
R9 is hydrogen or fluoro,
R10 is selected from fluoro, chloro, bromo, cyano, cyanomethyl, trifluoromethyl, difluoroethoxy, trifluoroethoxy, and pentafluorosulfanyl,
R11 is selected from hydrogen, fluoro, chloro, and methoxy,
R12 is hydrogen or fluoro, wherein at least one of R8, R9, R10 and R11 is different from hydrogen,
and pharmaceutically acceptable salts, solvates, isotopes and co-crystals thereof.
7) A compound according to any one of the preceding items wherein
X1 is N, or C(R7),
X2 is NH,
R4 and R5 are both hydrogen,
R6 is chloro or bromo,
R7 is hydrogen, methoxy, fluoro or trifluoromethyl,
X3 is N or C(R12),
R9 forms together with R8 and the phenyl ring to which R8 and R9 are attached a 2,1,3-benzothiadiazole or a 2,2-difluoro-1,3-benzodioxole,
R10 is hydrogen or fluoro,
R11 is selected from hydrogen, fluoro and methoxy,
R12 is hydrogen or fluoro,
and pharmaceutically acceptable salts, solvates, isotopes and co-crystals thereof.

8) A compound according to any one of the preceding items wherein
X1 is N or C(R7),
X 2 is NH,
R4 and R5 are both hydrogen,
R6 is chloro or bromo, preferably chloro,
R7 is hydrogen, methoxy, fluoro or trifluoromethyl,
X3 is N or C(R12),
R8 is selected from fluoro and methoxy,
R9 is hydrogen,
R10 is selected from fluoro, chloro, bromo, iodo, cyano, cyanomethyl, difluoromethyl, trifluoromethyl, difluoroethoxy, trifluoroethoxy, and pentafluorosulfanyl,
R11 is selected from hydrogen, fluoro and methoxy,
R12 is hydrogen,
and pharmaceutically acceptable salts, solvates, isotopes and co-crystals thereof.
9) A compound according to any one of the preceding items, represented by Formula II or III,

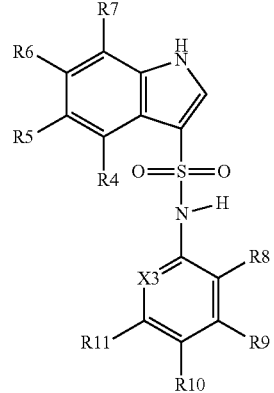

Formula II

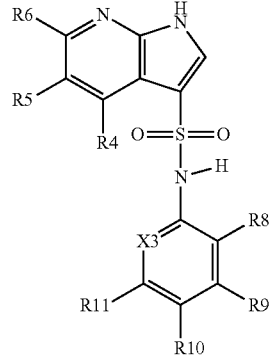

Formula III wherein R4, R5, R6, R7, if present, R8, R9, R10, R11 and X3 are as defined in any one of the preceding items.
10) A compound according to item 9, wherein
R4 is hydrogen,
R5 is hydrogen, iodo, or methyl,
R6 is selected from hydrogen, fluoro, chloro, bromo, iodo, methyl, ethyl, isopropyl, acetyl, trifluoromethyl, methoxy, ethoxy, fluoro($C_{1-2}$)alkoxy, ($C_{1-2}$)alkoxymethoxy, cyanomethylsulfonyl, phenyl, phenoxy, benzyloxy, 2-pyridyl, 3-pyridyl, 4-pyridyl, 2-thienyl, 3-thienyl, cyclopropyl, cyclopropyloxy, and cyclopropylmethoxy,
R7, in Formula II, is selected from hydrogen, methyl, methoxy, trifluoromethyl, fluoro, chloro and bromo,
X3 is N or C(R12), and is preferably C(R12), R8 is selected from hydrogen, methoxy, cyano, chloro and fluoro,
R9 is selected from hydrogen and fluoro,
R10 is selected from hydrogen, ethynyl, cyano, cyanomethyl, acetyl, fluoro, chloro, bromo, iodo, azido, nitro, trifluoromethyl, difluoroethoxy, trifluoroethoxy, and pentafluorosulfanyl,
R11 is selected from hydrogen, fluoro, chloro, and methoxy,
R12 is hydrogen or fluoro,
wherein at least one of R8, R9, R10 and R11 is different from hydrogen,
and pharmaceutically acceptable salts, solvates, isotopes and co-crystals thereof.

11) A compound according to item 9,
wherein
R4 and R5 are both hydrogen,
R6 is selected from fluoro, chloro, bromo, isopropyl, benzyloxy, and trifluoromethyl,
R7, in Formula II, is hydrogen, methoxy, fluoro, or bromo, preferably hydrogen,
X3 is —C(R12)-, or N,
R8 is fluoro, hydrogen, or methoxy,
R9 is hydrogen,
R10 is ethynyl, trifluoromethyl, difluoroethoxy, cyano, chloro, bromo, or iodo,
R11 is selected from hydrogen and fluoro, and
R12 is selected from hydrogen and fluoro,
and pharmaceutically acceptable salts, solvates, isotopes and co-crystals thereof.

12) A compound according to item 9.
wherein
R4, R5 are both hydrogen,
R6 is bromo, chloro, or trifluoromethyl,
R7 is hydrogen, methoxy, fluoro, or trifluoromethyl,
R8 is fluoro or methoxy,
R9 is hydrogen,
R10 is selected from fluoro, chloro, bromo, cyano, cyanomethyl, trifluoromethyl, difluoroethoxy, and pentafluorosulfanyl,
R11 is selected from hydrogen, methoxy and fluoro,
and pharmaceutically acceptable salts, solvates, isotopes and co-crystals thereof.

13) A compound according to any one of items 1 to 5, represented by one of the following Formulae IIa-IIc:

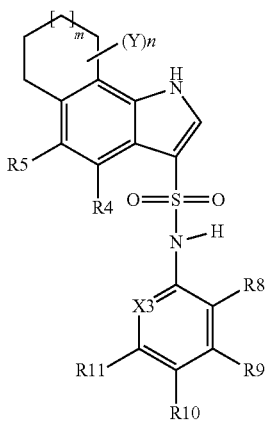
(IIa)

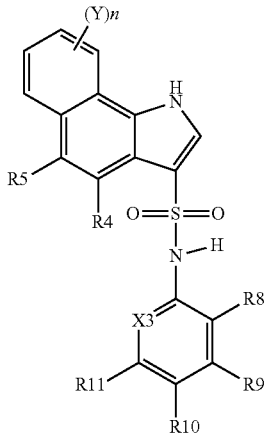
(IIb)

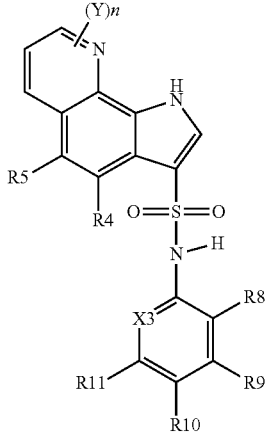
(IIc)

wherein
n is any number from 0 to 4, preferably 0, 1 or 2,
m is 0 or 1, p is any number from 0 to 3, preferably 0, 1 or 2,
any Y is an independently selected substitution from the group of halogen, cyano, $C_{1-6}$ alkyl, $C_{2-6}$ alkenyl, $C_{2-6}$ alkynyl, $C_{3-7}$cycloalkyl, $C_{3-7}$cycloalkyl($C_{1-3}$) alkyl, $C_{3-7}$ heterocycloalkyl($C_{1-3}$)alkyl, $C_{1-6}$ alkoxy, and $C_{1-6}$alkoxy($C_{1-3}$)alkyl wherein each alkyl or alkoxy can be unsubstituted or substituted with one or more substituents selected from halogen and $C_{1-3}$ alkoxy, and
R4, R5, X3, R8, R9, R10, R11 and R12 are as described in any one of items 1 to 5,
and pharmaceutically acceptable salts, solvates, isotopes and co-crystals thereof.

14) A compound according to item 13
wherein
m is 0, n is 0 or 1, p is 0 or 1,
any Y is selected from hydrogen, halogen, unsubstituted or fluorinated methyl and unsubstituted or fluorinated methoxy,
R4 and R5 are both hydrogen,
R8 is selected from hydrogen, methoxy, fluoro, and chloro,
X3 is N or C(R12),
R9 is selected from hydrogen, methoxy, fluoro and chloro, and is preferably hydrogen,
R10 is selected from hydrogen, ethynyl, cyano, cyanomethyl, fluoro, chloro, bromo, iodo, azido, trifluoromethyl, trifluoromethoxy, difluoroethoxy, trifluoroethoxy and pentafluorosulfanyl, R11 is selected from hydrogen, fluoro, chloro, and methoxy, and R12 is hydrogen or fluoro, and wherein at least one of R8, R9, R10 and R11 is different from hydrogen, and pharmaceutically acceptable salts, solvates, isotopes and co-crystals thereof.

15) A compound according to item 13 and pharmaceutically acceptable salts, solvates, isotopes and co-crystals thereof, wherein m is 0, n is 0 or 1, p is 0 or 1, any Y is selected from hydrogen, halogen, unsubstituted or fluorinated methyl and unsubstituted or fluorinated methoxy X3 is C(R12)

R4 and R5 are both hydrogen, and either (a) R8 together with R9 and the ring to which they are attached form a bicyclic ring system selected from 2,1,3-benzothiadiazole, 2,1,3-benzoxadiazole, 2,1,3-benzoselanadiazole, 2-oxo-2,3-dihydro-1,3-benzoxazole, unsubstituted 1,3-benzodioxole and 2,2-difluoro-1,3-benzodioxole, R10 is selected from the group of hydrogen, fluoro, chloro, bromo, trifluoromethyl, trifluoromethoxy, difluoroethoxy, trifluoroethoxy, and cyano, and is preferably hydrogen or fluoro, R11 is selected from hydrogen, methoxy, fluoro, chloro, bromo and cyano, and R12 is hydrogen, fluoro, chloro, and trifluoromethyl, or (b) R8 is hydrogen, methoxy or fluoro, R9 together with R10 and the C atoms to which they are attached form a ring selected from an 2,1,3-benzothiadiazole, 2,1,3-benzoxadiazole, and 2,2-difluoro-1,3-benzodioxole, R11 is hydrogen or fluoro, and R12 is hydrogen or fluoro.

16) A compound according to any one of items 1 to 5, represented by one of the following Formulae II(d), II(e), II(f), III(a), III(b) or III(c)

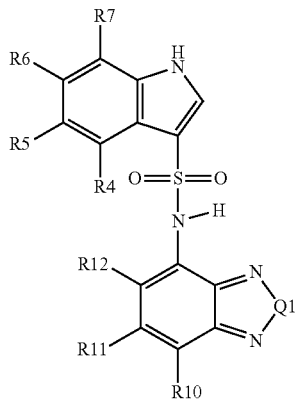

Formula II(d)

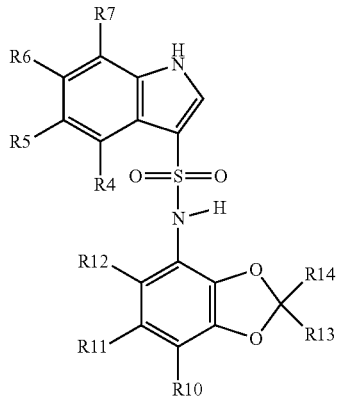

Formula II(e)

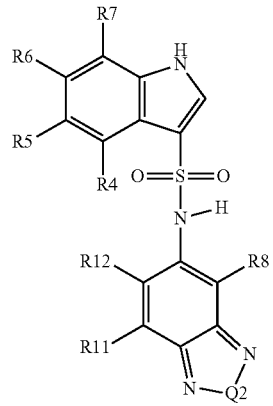

Formula II(f)

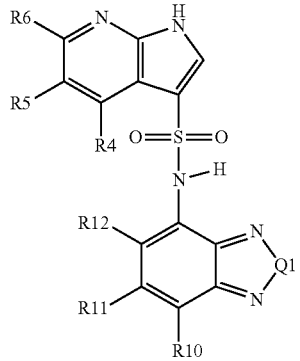

Formula III(a)

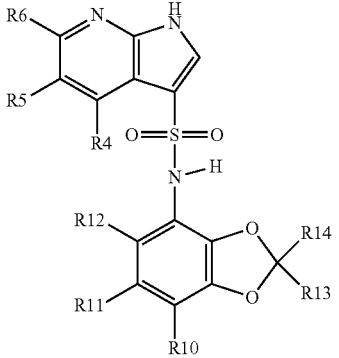

Formula III(b)

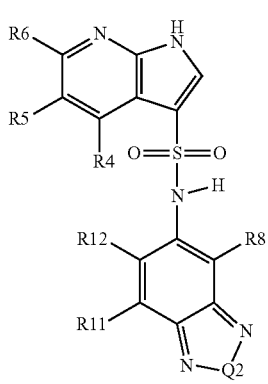

Formula III(c)

wherein
R4, R5, R6, R7, R8, R10, R11 and R12 are as described in any one of items 1 to 5,
in Formulae II(d) and III(a) Q1 is S or O,
in Formulae II(e) and III(b), R13 and R14 are selected from the group of hydrogen, methyl
and fluoro and are preferably either both hydrogen or both fluoro, and
in Formulae II(f) and III(c), Q2 is S or O, preferably S,
and pharmaceutically acceptable salts, solvates, isotopes and co-crystals thereof.
17) A compound according to item 16 represented by one of the Formulae IId, IIe, IIIa and IIIb, wherein
Q1 is S or O,
R13 and R14 are selected from hydrogen and fluoro,
R4 and R5 are both hydrogen,
R6 is selected from fluoro, chloro, bromo, trifluoromethyl, and phenyl,
R7, if present, is hydrogen, fluoro, bromo, methoxy, or trifluoromethyl, preferably hydrogen or trifluoromethyl,
R10 is selected from hydrogen and halogen, preferably from hydrogen, fluoro and chloro,
R11 is selected from hydrogen, halogen, trifluoromethyl and cyano, preferably from fluoro and hydrogen,
R12 is selected from hydrogen, halogen and trifluoromethyl.
18) A compound according to item 16, represented by one of the Formulae IIf and IIIc,
wherein
Q2 is S or O,
R4 and R5 are both hydrogen,
R6 is selected from fluoro, chloro, bromo, trifluoromethyl and phenyl,
R7, if present, is selected from hydrogen, methoxy, fluoro, and trifluoromethyl,
R8 is selected from hydrogen and halogen, preferably from hydrogen and fluoro,
R11 is selected from hydrogen, halogen, trifluoromethyl and cyano, and is preferably hydrogen,
R12 is selected from hydrogen, halogen and trifluoromethyl, preferably from fluoro and hydrogen,
19) A compound according to one of the preceding items comprising at least one istope selected from $^{123}$I, $^{125}$I, $^{131}$I, $^{11}$C, $^{14}$C, $^{13}$N, $^{15}$O, $^{18}$F, $^{76}$Br, $^{124}$I, $^2$H and $^3$H in an enriched amount, exceeding the natural abundance if said isotope is naturally occurring
20) The use of a compound according to item 19, wherein the isotope is selected from $^{123}$I, $^{125}$I, $^{131}$I, $^{11}$C, $^{13}$N, $^{15}$O, $^{18}$F, $^{76}$Br and $^{124}$I and is present in an amount suitable for PET and/or SPECT imaging, in diagnosis and/or in PET or SPECT imaging.

21) A compound according to any one of the preceding items, for use in therapy.
22) A compound according to any one of the preceding items for use in the prevention, treatment of a disorder or syndrome selected from a myelination disorder and a disorder or syndrome associated with brain tissue damage.
23) A compound according to item 22, wherein the syndrome or disorder is selected from the group of multiple sclerosis (MS) including its various subforms, neuromyelitis optica (Devic's disease), chronic relapsing inflammatory optic neuritis, acute disseminated encephalomyelitis, acute haemorrhagic leucoencephalitis (AHL), periventricular leukomalacia, demyelination due to viral infections, central pontine and extrapontine myelinolysis, demyelination due to traumatic brain tissue damage, demyelination in response to hypoxia, stroke or ischaemia or other cardiovascular diseases, demyelination due to exposure to carbon dioxide, cyanide, or other CNS toxins, Schilder disease, Balo concentric sclerosis, perinatal encephalopathy, neurodegenerative diseases including amyotrophic lateral sclerosis (ALS). Alzheimer's disease (AD). multiple system atrophy, Parkinson's Disease, spinocerebellar ataxia (SCA) and Huntington's Disease, psychiatric disorders such as schizophrenia and bipolar disorder and peripheral myelination diseases including leukodystrophies, peripheral neuropathies, Dejerine-Sottas syndrome or Charcot-Marie-Tooth disease
24) A compound according to any one of the preceding items for use in the prevention and/or treatment of multiple sclerosis (MS).
25) A method for the prevention, and/or treatment of a syndrome or disorder selected from a myelination disorder and a disorder or syndrome associated with a brain tissue damage, which comprises administering to a patient in need thereof a therapeutically effective amount of a compound according to any one of the preceding items.
26) A method according to item 25, wherein the symptom or disorder is associated with a myelination disorder, selected from the group of multiple sclerosis (MS) including its various subforms, neuromyelitis optica (Devic's disease), chronic relapsing inflammatory optic neuritis, acute disseminated encephalomyelitis, acute haemorrhagic leucoencephalitis (AHL), periventricular leukomalacia, demyelination due to viral infections, central pontine and extrapontine myelinolysis, demyelination due to traumatic brain tissue damage, demyelination in response to hypoxia, stroke or ischaemia or other cardiovascular diseases, demyelination due to exposure to carbon dioxide, cyanide, or other CNS toxins, Schilder's disease, Balo concentric sclerosis, perinatal encephalopathy, neurodegenerative diseases including amyotrophic lateral sclerosis (ALS). Alzheimer's disease (AD), multiple system atrophy, Parkinson's Disease, spinocerebellar ataxia (SCA) and Huntington Disease, psychiatric disorders such as schizophrenia and bipolar disorder and peripheral myelination diseases including leukodystrophies, peripheral neuropathies, Dejerine-Sottas syndrome or Charcot-Marie-Tooth disease.
27) A pharmaceutical composition comprising a compound according to any one of the preceding items, and a pharmaceutical acceptable carrier.

EXPERIMENTAL PART

A. Chemistry

The compounds of the present inventions and their syntheses routes are described in more detail below.

It is to be understood that 1H-pyrrolo[2,3-b]pyridines and 1H indoles as well as their aniline precursors typically contain a hydrogen attached to the nitrogen atom in the 5 ring even though this hydrogen is not always expressly indicated in the drawings herein.

A-I General Methods of Making the Compounds

The compounds of Formula I according to the invention can be prepared analogously to conventional methods as understood by the person skilled in the art of synthetic organic chemistry.

Any reference to the synthesis of compounds of general Formula I herein likewise apply to the applicable compounds of the subgeneric Formula II, IIa, IIb, IIc, IId, IIe, IIf, III, IIIa, IIIb, IIIc and IV, and the specific Example compounds disclosed herein.

According to one embodiment, some compounds of general Formula I may be prepared by reaction of a compound of Formula XI with an aniline of Formula X according to the equation:

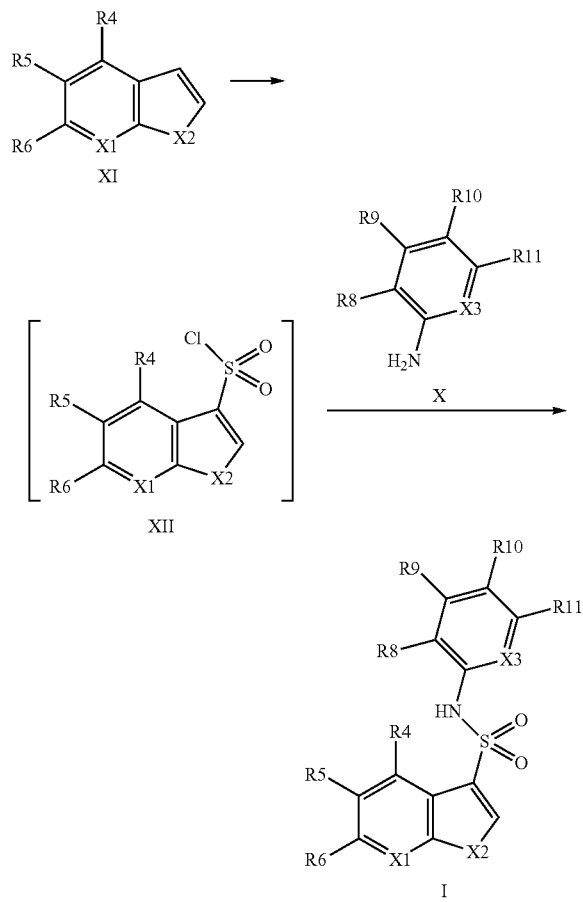

This reaction may be performed with chlorosulfonic acid to form the non-isolated sulfonyl chloride intermediate XII at a temperature ranging from 60 to 120° C. in a polar solvent such as acetonitrile. Intermediate XII is then directly reacted with an aniline X in the presence of a base such as pyridine with or without a catalytic amount of 4-dimethylaminopyridine (DMAP), in a polar solvent such as acetonitrile at a temperature preferably ranging from 60 to 80° C.

Alternatively, the sulfonyl chloride intermediate XII may be formed starting from compound XI, in the presence of pyridine-sulfur trioxide complex in pyridine, at reflux temperature. The intermediate sulfonic acid salt may be chlorinated in the presence of a chlorinating agent such as triphenylphosphine/trichloroacetonitrile in a solvent such as dichloromethane at reflux temperature.

Alternatively, some compounds of general Formula I may be prepared by reaction of a sulfonyl chloride of Formula XII with an aniline of Formula X according to the equation:

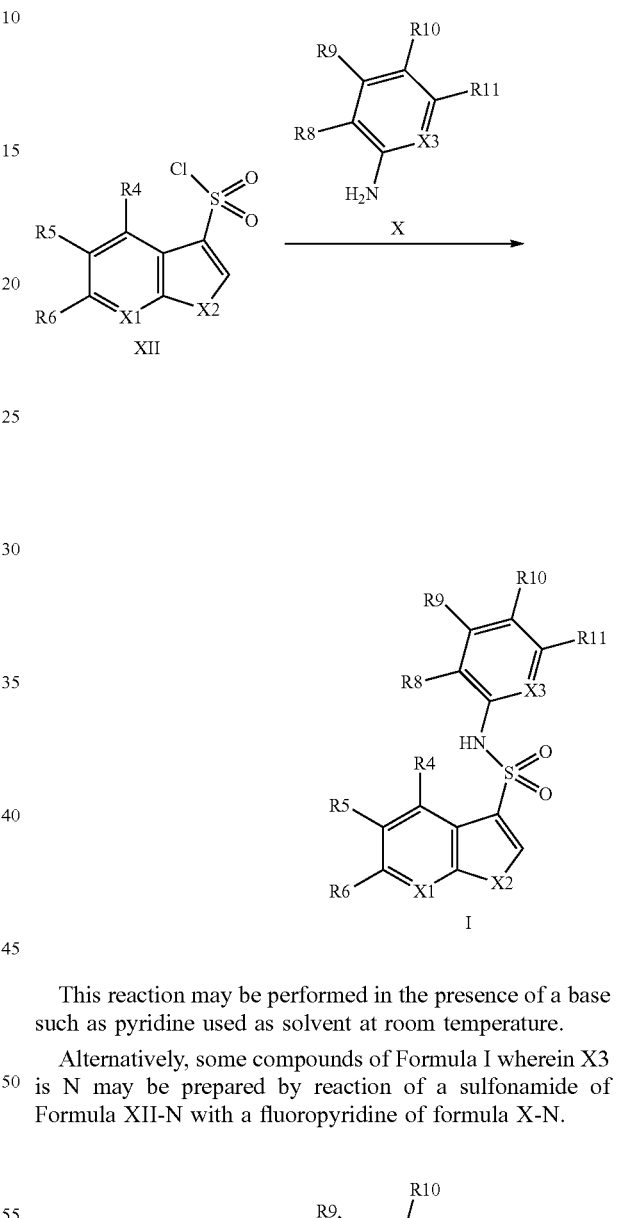

This reaction may be performed in the presence of a base such as pyridine used as solvent at room temperature.

Alternatively, some compounds of Formula I wherein X3 is N may be prepared by reaction of a sulfonamide of Formula XII-N with a fluoropyridine of formula X-N.

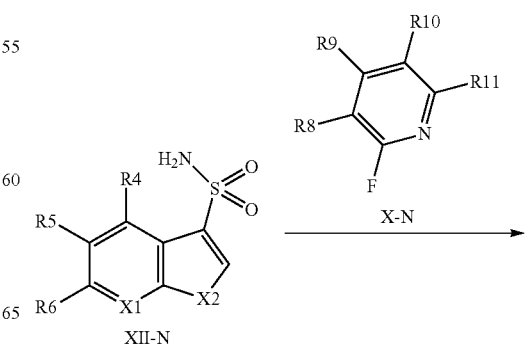

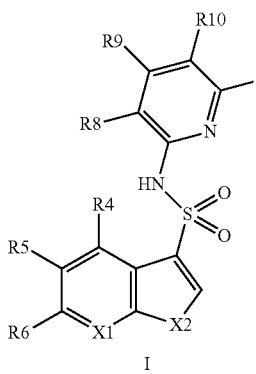

I

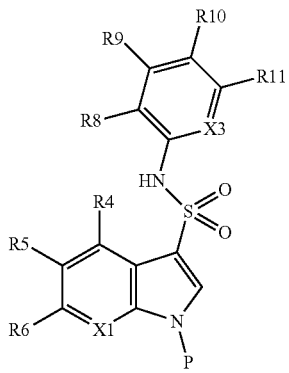

I-P

This reaction may be performed in the presence of a base such as potassium carbonate in a polar solvent such as dioxane at high temperature.

Compounds of formula XII-N may be prepared by ammonolysis of sulfonyl chlorides of formula XII.

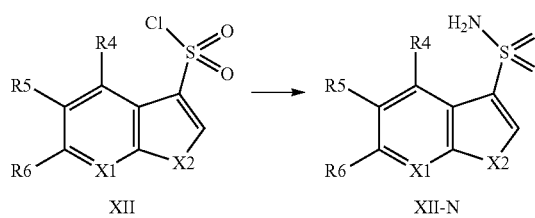

XII → XII-N

This reaction may be performed with gaseous ammonia in a polar solvent such as tetrahydrofuran at room temperature.

Alternatively, some compounds of general Formula I wherein X2=NH may be prepared by deprotection of a compound of Formula I-P wherein P is a protecting group such as phenylsulfonyl (PhSO$_2$) according to the equation:

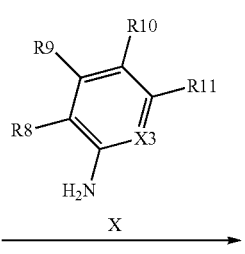

XII-P

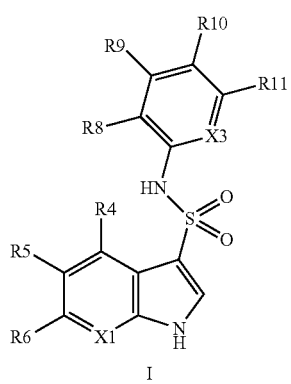

I

This reaction may be performed in the presence of a weak base such as potassium carbonate in a protic solvent mixture such as methanol and water at room temperature.

Compounds of Formula I-P may be prepared by reaction of a sulfonyl chloride of Formula XII-P with an aniline of Formula X. This reaction may be performed in the presence of a base such as pyridine used as solvent at room temperature.

Compounds of Formula XII may be prepared by chlorination of a compound of Formula IX according to the equation:

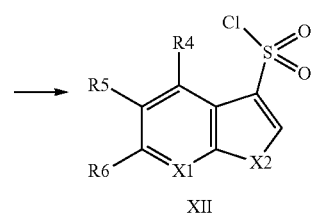

IX → XII

This reaction may be performed in the presence of a chlorinating agent such as phosphorus oxychloride or thionyl chloride in a polar solvent such as acetonitrile at a temperature ranging from 50 to 100° c.

Compounds of Formula IX wherein may be prepared by sulfonylation of a compound of Formula XI according to the equation:

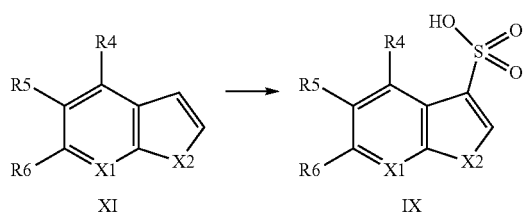

This reaction may be performed in the presence of a sulfonylating agent such as pyridine-sulfur trioxide complex in the presence of a base such as pyridine used as a solvent at reflux temperature.

Alternatively, some compounds of Formula XII wherein X2=O may be prepared by chlorosulfonylation of a compound of Formula XI wherein X2=O according to the equation:

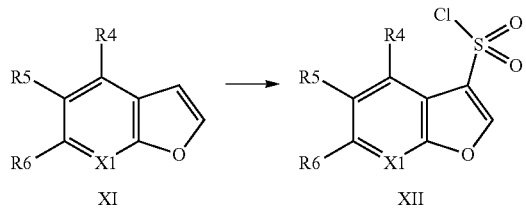

This reaction may be performed in the presence of a sulfonylating agent such as sulfur trioxide-dimethyl formamide complex in a solvent such as 1,2-dichloroethane at reflux temperature, followed by the addition of a chlorinating agent such as thionyl chloride at a temperature ranging from 60 to 80° C.

Alternatively, some compounds of Formula XII wherein X2=S may be prepared by chlorosulfonylation of a compound of Formula XI wherein X2=S according to the equation:

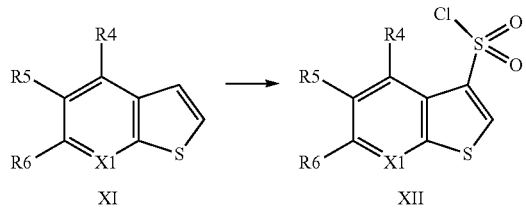

This reaction may be performed in the presence of a sulfonylating agent such as chlorosulfonic acid in a solvent such as dichloromethane at room temperature.

Compounds of Formula XII-P wherein P is a protecting group such as phenylsulfonyl may be prepared by chlorosulfonylation of a compound of Formula XI-P according to the equation:

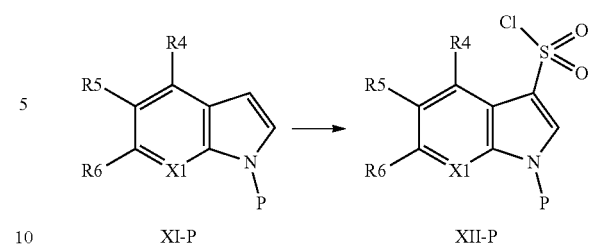

This reaction may be performed in the presence of chlorosulfonic acid in a polar solvent such as acetonitrile at room temperature.

Compounds of Formula XI-P wherein P is a protecting group such as phenylsulfonyl may be prepared by protection of a compound of Formula XI according to the equation:

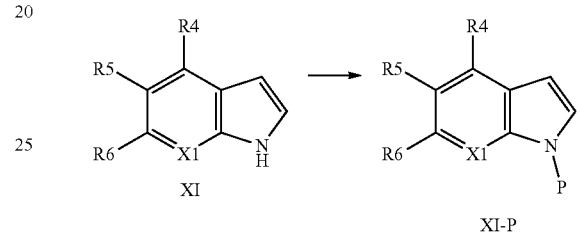

This reaction may be performed according to any method known to the person skilled in the art.

Anilines of Formula X are commercially available or may be prepared according to any method known to the person skilled in the art or using procedures described in literature. Alternatively, some anilines of Formula X may be prepared by reduction of a compound VIII according to the equation:

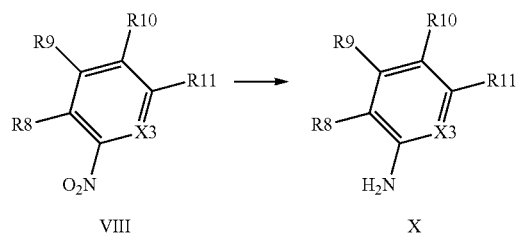

This reaction may be performed using any reducing agent such as tin dichloride in the presence of a strong acid such as concentrated hydrochloric acid or hydrogen in the presence of a catalytic amount of palladium on charcoal in a protic solvent such as ethanol or according to any method known to the person skilled in the art.

Compounds of Formula VIII are commercially available or may be prepared according to literature procedures or any other methods known to the person skilled in the art.

Compounds of Formula XI are commercially available or may be prepared by suitable methods well known by the person skilled in the art.

Alternatively, some compounds of Formula XI wherein X1=C—R7 and wherein R7 is not an hydrogen may be prepared by reaction of a ortho-substituted nitroarene XII with a vinyl Grignard reagent XIII (Bartoli indole synthesis) according to the equation:

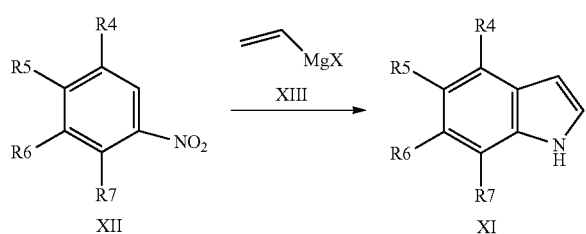

This reaction may be performed using a vinyl Grignard reagent such as vinyl magnesium bromide in a polar solvent such as tetrahydrofuran at low temperature such as −20° C.

Alternatively, some compounds having the general Formula I may be prepared by functional group conversion on already assembled analogs of compounds having the general Formula I using procedures described in the literature or known to the person skilled in the art.

In particular, some compounds of Formula I wherein R6 is an aryl or an heteroaryl group may be prepared by Suzuki-type coupling starting from a compound of Formula I wherein R5 is a halogen atom, preferentially bromine, in the presence of the corresponding boronic acid, a palladium salt such as [1,1′-bis(diphenylphosphino)ferrocene]dichloropalladium and a base such as potassium carbonate in a polar solvent such as dioxane according to methods known to the person skilled in the art.

Alternatively, some compounds of Formula I wherein R6 is an alkylsulfonyl group such as methylsulfonyl may be prepared starting from a compound of Formula I wherein R5 is a halogen atom, preferentially bromine, in the presence of an alkyl sulfinate salt such as sodium methane sulfinate and a copper salt such as copper iodide in a polar solvent such as dimethylsulfoxide at 130° C.

Alternatively, compounds of Formula I wherein R6 is —S(O)Rx, and Rx is a $C_{1-6}$ alkyl may be prepared by oxidation of a compound of Formula I wherein R6 is SRx, Rx having the same definition as above, according to any method known to the person skilled in the art. Compound of Formula I wherein R6 is SRx may be prepared starting from a compound of Formula I wherein R6 is a halogen atom, preferentially bromine, in the presence of an alkyl thiolate salt, a palladium salt such as tris(dibenzylideneacetone)dipalladium(0), a phosphine ligand such as xantphos in a polar solvent such as N,N-dimethylformamide under microwave heating at high temperature.

A-II. Abbreviations/Recurrent Reagents

Ac: acetyl
ACN: Acetonitrile
Brine: Saturated aqueous sodium chloride solution
nBu: n-butyl
tBu: tert-butyl
Cy: Cyclohexyl
dba: dibenzylideneacetone
DCM: Dichloromethane
DIPEA: N,N-diisopropylethylamine
DMAC: N,N-dimethylacetamide
DMAP: 4-dimethylaminopyridine
DMF: N,N-Dimethylformamide
DMSO: Dimethylsulfoxide
DPPA: Diphenylphosphoryl azide
dppf: 1,1′-bis(diphenylphosphino)ferrocene
ES+: Electrospray Positive Ionization
ES−: Electrospray Negative Ionization
ESI: Electrospray Ionization
EtOAc: Ethyl acetate
h: Hour
LC: Liquid Chromatography
LCMS: Liquid Chromatography Mass Spectrometry
Me: Methyl
MeOH: Methanol
min.: minutes
MOM: methoxymethyl
mw: microwave oven
NBS: N-Bromosuccinimide
NMR: Nuclear magnetic resonance
Pin: pinacolato
PMA: Phosphomolybdic acid
PMB: para-methoxybenzyl
rt: room temperature
TBAHSA: Tetrabutylammonium hydrogen sulfate
TBAF: Tetrabutylammonium fluoride
TBS: tert-butyldimethylsilyl
TEA: Triethylamine
TFA: Trifluoroacetic acid
THF: Tetrahydrofuran
TLC: Thin Layer Chromatography
Xantphos: 4,5-Bis(diphenylphosphino)-9,9-dimethylxanthene A-III. Analytical Methods Commercial solvents and reagents were generally used without further purification, including anhydrous solvents when appropriate (generally Sure-Sea™ products from Aldrich Chemical Company or AcroSeal™ from ACROS Organics). In general reactions were followed by thin layer chromatography or Liquid Chromatography Mass Spectrometry analyses.

Mass spectrometric measurements in LCMS mode are performed using different methods and instrument as follows:

Basic LCMS Method 1:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an basic elution. The reverse phase separation is carried out at 45° C. on a Waters Acquity UPLC BEHC18 1.7 μm (2.1×50 mm) column for basic elution. Gradient elution is done with water/ACN/ammonium formate (95/5/63 mg/L) (solvent A) and ACN/water/ammonium formate (95/5/63 mg/L) (solvent B). Injection volume: 1 μL. Full flow in MS.

Basic Program "4 Min" (Table 1)

TABLE 1

| Time (min) | A (%) | B (%) | Flow (mL/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

Basic LCMS Method 2:

Mass spectrometry (MS) spectra were recorded on an LCMS-2010EV mass spectrometer (Shimadzu) with electrospray ionization (ESI) coupled to an HPLC modular Prominence (Shimadzu) using Xbridge C18-2.1×30 mm, 2.5

μm (Waters) column. A volume of 3 μL of sample solution with a concentration of approx. 1 mg/mL was injected. The mobile phase for basic conditions was a mixture of A) 5 mM ammonium formate +0.1% ammonia in water B) 5% mobile phase A+ 0.1% ammonia in acetonitrile. The gradient used was as follows-5:95 (B/A) to 95:5 (B/A) in 4 min and hold 95:5 (B/A) for next 1 min.

Neutral LCMS Method 3:

Mass spectrometry (MS) spectra were recorded on an LCMS instrument (Applied Biosystems API 2000 LC/MS/MS, HPLC Agilent 1100) using the following procedure: dissolving of the compounds at a concentration of 1.0 mg mL-1 in ACN (Solvent A) or water (containing 2 mM ammonium acetate):MeOH 90:10 (Solvent B), and if necessary sonicated until completely dissolved. Then, 10 μL of the solution was injected into a Phenomenex Luna C18 HPLC column (50×2.00 mm, particle size 3 μm) and elution was performed with a gradient of water:ACN (Gradient A) or water:MeOH (Gradient B) from 90:10 to 0:100 within 10 min, starting the gradient after 1 min, followed by elution in pure organic solvent for 10 min at a flow rate of 300 μL min-1. UV absorption was detected from 220 to 400 nm using a diode array detector (DAD).

Crude materials could be purified by normal phase chromatography, (acidic or basic) reverse phase chromatography or recrystallization.

Normal phase chromatography was performed using silica gel columns (100:200 mesh silica gel or cartridges for flash chromatography systems such as Isolera™ Four from Biotage® or Teledyne Isco CombiFlash®).

Preparative reverse phase chromatography was performed with two different instruments and according to the methods as follows:

Basic Prep LCMS Method 1:

LCMS purification is using an SQD or QM Waters triple quadrupole mass spectrometer for MS detection. This spectrometer is equipped with an ESI source and a Prep LC controller Waters quaternary pump with diode array detector (210 to 400 nm).

MS parameters: ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC parameters: The reverse phase separation is carried out at rt on an XBridge prep OBD C18 column (5 μm, 30×50 mm) (basic elution). Gradient elution is done with water (solvent A), ACN (solvent B), ammonium bicarbonate in water 8 g/L+500 μL/L NH$_4$OH 30% (solvent C) (pH~8.5). HPLC flow rate: 35 mL/min to 60 mL/min, injection volume: 1 mL. The splitting ratio is set at +/−1/6000 to MS (table 2).

TABLE 2

| Time (min) | A (%) | B (%) | C (%) | Flow (mL/min) |
|---|---|---|---|---|
| 0 | 85 | 5 | 10 | 35 |
| 1 | 85 | 5 | 10 | 35 |
| 7 | 5 | 85 | 10 | 35 |
| 9 | 5 | 95 | 0 | 60 |
| 12 | 5 | 95 | 0 | 60 |
| 12.5 | 85 | 5 | 10 | 35 |
| 16 | 85 | 5 | 10 | 35 |

Neutral RP-HPLC Method 2:

HPLC purification of final products was performed on a Knauer Smartline 1050 HPLC system using a RP-HPLC column (Knauer 20 mm i.d., Eurospher-100 C18). The product was dissolved in methanol (20 mg per 8 mL) and subjected to reversed-phase HPLC applying a gradient of methanol/water (70:30 to 100:0 over 24 min).

NMR spectra were recorded on different instruments:
- a BRUKER AVANCEIII 400 MHz-Ultrashield NMR Spectrometer fitted with a Windows 7 Professional workstation running Topspin 3.2 software and a 5 mm Double Resonance Broadband Probe (PABBI 1H/19F-BB Z-GRD Z82021/0075) or a 1 mm Triple Resonance Probe (PATXI 1H/D-13C/15N Z-GRD Z868301/004).
- a Varian 400 MHz NMR spectrometer with acquisition time (at)=2.0 sec, relaxation delay (d1)=2.0 sec and line broadening (lb)=0.5 Hz.
- a Bruker Avance DRX 500 MHz NMR spectrometer
- a Bruker Avance III 600 MHz NMR spectrometer Chemical shifts are referenced to signals deriving from residual protons of the deuterated solvents (DMSO-d$_6$, Benzene-d$_6$ or CDCl$_3$). Chemical shifts are given in parts per million (ppm) and coupling constants (J) in Hertz (Hz). Spin multiplicities are given as broad (br), singlet (s), doublet (d), triplet (t), quartet (q) and multiplet (m).

Products were generally dried under vacuum before final analyses and submission to biological testing A-IV: Example Compounds and Synthesis The names of the following compounds are IUPAC names generated by Biovia Draw Version 16.1 for Intermediates of Formula X, XI, XII and by ACDlabs version 14.03 for Example compounds of Formula I.

Intermediates

A. Synthesis of intermediates of Formula X

A.1. Synthesis of 4-fluoro-2,1,3-benzothiadiazol-7-amine X-1

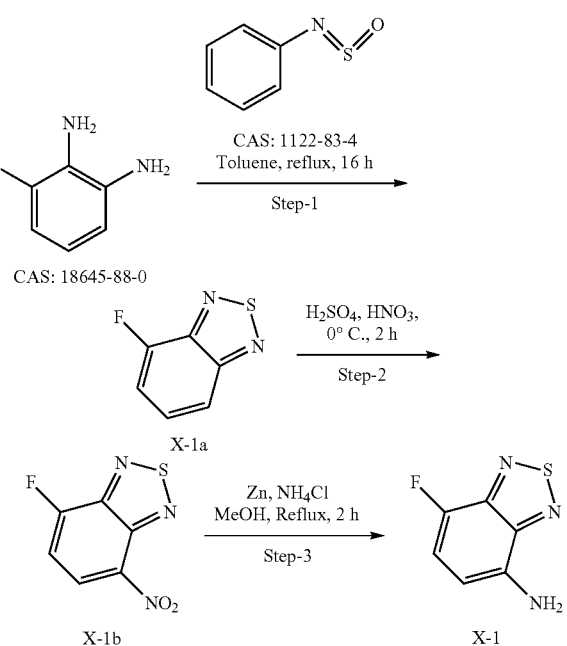

Step-1: Synthesis of 4-fluoro-2,1,3-benzothiadiazole X-1a

To a solution of 3-fluorobenzene-1,2-diamine (1.00 g, 7.94 mmol) in toluene (20 mL) was added (sulfinylamino)benzene (10 mL) and the reaction mixture was heated to reflux for 16 h. Progress of the reaction was monitored by TLC. After completion, the reaction mixture was concentrated under vacuum. The crude mixture obtained was purified by column chromatography (silica, 100-200 mesh, 2% EtOAc in hexanes) to afford 4-fluoro-2,1,3-benzothiadiazole X-1a (1.06 g) as a light yellow liquid.

Yield: 87%.

$^1$H NMR (400 MHz, CDCl$_3$) δ 7.21-7.25 (m, 1H) 7.52-7.61 (m, 1H) 7.83 (d, J=8.80 Hz, 1H).

Step-2: Synthesis of 4-fluoro-7-nitro-2,1,3-benzothiadiazole X-1b

To H$_2$SO$_4$ (12.0 mL) was added fuming HNO$_3$ (8.00 mL) dropwise at 0° C. and the reaction mixture was stirred at same temperature for 10 min. This nitrating mixture was added dropwise to 4-fluoro-2,1,3-benzothiadiazole X-1a (0.80 g, 5.19 mmol) at 0° C. The reaction mixture was stirred at 0° C. for 2 h. Progress of the reaction was monitored by TLC. After completion, the reaction mixture was quenched with ice, filtered, washed with H$_2$O (250 mL) and dried under vacuum to afford 4-fluoro-7-nitro-2,1,3-benzothiadiazole X-1b (0.80 g crude) as a yellow solid.

This compound was used as such for the next reaction without further purification.

$^1$H NMR (400 MHz, CDCl$_3$) δ 7.43 (t, J=8.56 Hz, 1H) 8.69 (dd, J=8.31, 3.91 Hz, 1H).

Step-3: Synthesis of 4-fluoro-2,1,3-benzothiadiazol-7-amine X-1

To a solution of 4-fluoro-7-nitro-2,1,3-benzothiadiazole X-1b (0.50 g, 2.51 mmol) in MeOH (50 mL) was added Zn (0.82 g, 12.5 mmol) followed by NH$_4$Cl (1.34 g, 25.1 mmol). The reaction mixture was heated to reflux for 2 h. Progress of the reaction was monitored by TLC and LCMS. After completion, the reaction mixture was filtered through a Celite pad and the filtrate was concentrated under vacuum. The crude obtained was purified by column chromatography (silica, 100-200 mesh, 10% EtOAc in hexanes) to afford 0.13 g of 4-fluoro-2,1,3-benzothiadiazol-7-amine X-1 as a yellow solid.

Yield: 30%.

Basic LCMS Method 2 (ES$^+$): 169.85 (M+H)$^+$, 97% purity.

$^1$H NMR (400 MHz, CDCl$_3$) δ 4.53 (brs, 2H) 6.52 (dd, J=8.07, 3.67 Hz, 1H) 7.05-7.14 (m, 1H).

A.2. Synthesis of 7-bromo-2,2-difluoro-1,3-benzodioxol-4-amine X-2

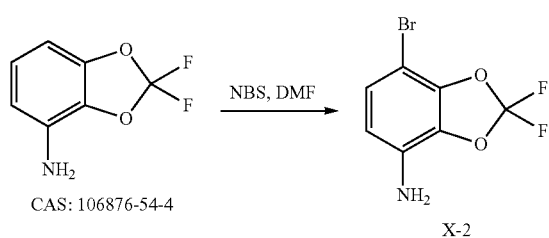

To a solution of 2,2-difluoro-1,3-benzodioxol-4-amine (0.11 g, 0.66 mmol) in DMF (15 mL) was added N-bromosuccinimide (0.10 g, 0.59 mmol) portionwise at 0° C. and the reaction mixture was stirred at room temperature for 1 h. Progress of the reaction was monitored by TLC and LCMS. After completion, the reaction mixture was quenched with cold H$_2$O (15 mL) and extracted with EtOAc (3×10 mL). The organic layer was separated, dried over anhydrous Na$_2$SO$_4$ and concentrated under vacuum. The crude obtained was purified by column chromatography (silica, 100-200 mesh, 2% EtOAc in hexanes) to afford 0.1 g of 7-bromo-2,2-difluoro-1,3-benzodioxol-4-amine X-2 as a brown solid.

Yield: 60%.

Basic LCMS Method 2 (ES$^-$): 250.00 (M−H)$^-$, 99% purity.

A.3. Synthesis of 5-fluorobenzo[c][1,2,5]thiadiazol-4-amine X-3

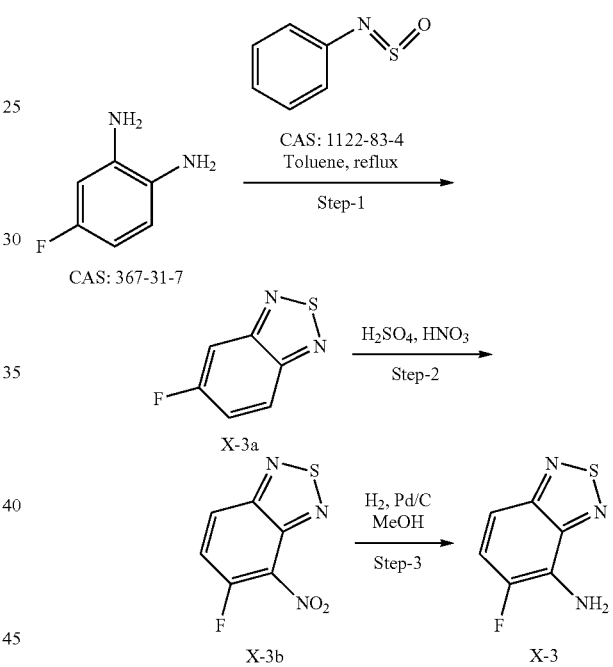

Step-1: Synthesis of 5-fluorobenzo[c][1,2,5]thiadiazole X-3a

To a solution of 4-fluorobenzene-1,2-diamine (1.50 g, 11.9 mmol) in toluene (20 mL) was added (sulfinylamino)benzene (0.40 mL, 35.7 mmol) and the reaction mixture was heated to reflux for 16 h. Progress of the reaction was monitored by TLC and LCMS. After completion, the reaction mixture was concentrated under vacuum. The residue was diluted with H$_2$O (150 mL) and extracted with EtOAc (3×150 mL). The organic layer was separated, dried over anhydrous Na$_2$SO$_4$ and concentrated under vacuum. The crude obtained was purified by flash column chromatography (0 to 3% EtOAc in hexanes) to afford 1.36 g of 5-fluoro-2,1,3-benzothiadiazole X-3a as a light yellow liquid.

Yield: 74%.

$^1$H NMR (400 MHz, DMSO-d$_6$) δ 7.67-7.73 (m, 1H) 7.92-7.95 (m, 1H) 8.15-8.19 (m, 1H).

Step-2: Synthesis of 5-fluoro-4-nitro-2,1,3-benzothiadiazole X-3b

To a solution of 5-fluoro-2,1,3-benzothiadiazole X-3a (1.00 g, 6.49 mmol) in concentrated $H_2SO_4$ (2 mL) was added nitrating mixture (1 mL) at −10° C. and the reaction mixture was stirred at room temperature for 3 h. Progress of the reaction was monitored by TLC and LCMS. After completion, the reaction mixture was poured in to ice-cold $H_2O$ (50 mL) and extracted with EtOAc (3×50 mL). The organic layer was separated, dried over anhydrous $Na_2SO_4$ and concentrated under vacuum. The crude obtained was purified by flash column chromatography (0 to 8% EtOAc in hexanes) to afford 0.66 g of 5-fluoro-4-nitro-2,1,3-benzothiadiazole X-3b as a brown solid.

Yield: 51%.

$^1$H NMR (400 MHz, DMSO-$d_6$) δ 7.56 (d, J=9.78 Hz, 1H) 8.20 (d, J=9.29 Hz, 1H).

Step-3: Synthesis of 5-fluoro-2,1,3-benzothiadiazol-4-amine X-3

To a solution of 5-fluoro-4-nitro-2,1,3-benzothiadiazole X-3b (0.65 g, 3.26 mmol) in MeOH (20 mL) was added Pd/C (0.30 g) and the reaction mixture was stirred at room temperature for 16 h under hydrogen pressure. Progress of the reaction was monitored by TLC. After completion, the reaction mixture was filtered through a celite pad and the filtrate was concentrated under vacuum to afford 0.27 g of 5-fluoro-2,1,3-benzothiadiazol-4-amine X-3 as an orange solid.

Yield: 50%.

$^1$H NMR (400 MHz, DMSO-$d_6$) δ 6.09 (brs, 2H) 7.16-7.20 (m, 1H) 7.56 (t, J=10.52 Hz, 1H).

A.4. Synthesis of 7-amino-2,2-difluoro-1,3-benzodioxole-5-carbonitrile X-4

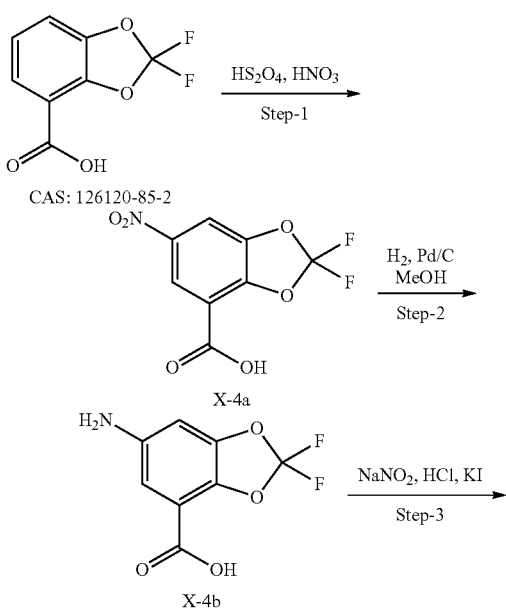

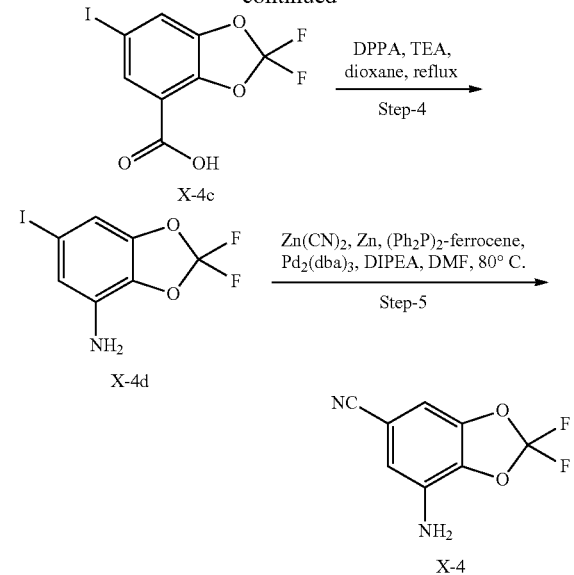

Step-1: Synthesis of 2,2-difluoro-6-nitro-1,3-benzodioxole-4-carboxylic acid X-4a To a solution of 2,2-difluoro-1,3-benzodioxole-4-carboxylic acid (10.0 g, 49.5 mmol) in concentrated $H_2SO_4$ (70 mL) was added nitrating mixture (Conc. $H_2SO_4$:Conc. $HNO_3$, 6:5, 55 mL) at 0° C. and the reaction mixture was stirred at 0° C. for 3 h. Progress of the reaction was monitored by TLC and LCMS. After completion, the reaction mixture was poured into crushed ice, filtered, washed with $H_2O$ (200 mL) and dried in vacuum to afford 2,2-difluoro-6-nitro-1,3-benzodioxole-4-carboxylic acid X-4a (9.80 g crude) as an off-white solid used in the next step without further purification.

Basic LCMS Method 2 (ES$^-$): 245.75 (M−H)$^-$, 73% purity.

$^1$H NMR (400 MHz, DMSO-$d_6$) δ 8.42 (d, J=2.45 Hz, 1H) 8.62 (d, J=2.45 Hz, 1H) 14.34 (brs, 1H).

Step-2: Synthesis of 6-amino-2,2-difluoro-1,3-benzodioxole-4-carboxylic acid X-4b To a solution of 2,2-difluoro-6-nitro-1,3-benzodioxole-4-carboxylic acid X-4a (1.00 g, 4.04 mmol) in MeOH (25 mL) was added Pd/C (0.10 g) and the reaction mixture was stirred at room temperature for 2 h under hydrogen pressure. Progress of the reaction was monitored by TLC and LCMS. After completion, the reaction mixture was filtered through a celite pad, washed with MeOH (40 mL) and the filtrate was concentrated in vacuum to afford 6-amino-2,2-difluoro-1,3-benzodioxole-4-carboxylic acid X-4b (0.76 g crude) as an off-white solid.

Basic LCMS Method 2 (ES$^-$): 216.00 (M−H)$^-$, 97% purity.

$^1$H NMR (400 MHz, DMSO-$d_6$) δ 5.16 (brs, 1H) 6.48 (s, 1H) 6.70 (s, 1H) 7.28 (brs, 2H).

Step-3: Synthesis of 2,2-difluoro-6-iodo-1,3-benzodioxole-4-carboxylic acid X-4c To a solution of 6-amino-2,2-difluoro-1,3-benzodioxole-4-carboxylic acid X-4b (0.75 g, 3.45 mmol) in 6N HCl (25 mL) was added NaNO$_2$ (0.75 g, 10.3 mmol) solution in H$_2$O (10 mL) at 0° C. and the reaction mixture was stirred at same temperature for 30 min. KI (3.40 g, 20.7 mmol) solution in H$_2$O (5 mL) was added dropwise at 0° C. and the reaction mixture was stirred at same temperature for 40 min. The reaction mixture was stirred at room temperature for 16 h. Progress of the reaction was monitored by TLC. After completion, the reaction mixture was extracted with EtOAc (2×25 mL). The organic layer was separated, washed with saturated Na$_2$S$_2$O$_3$ solution (2×20 mL), dried over anhydrous Na$_2$SO$_4$ and concentrated in vacuum to afford 2,2-difluoro-6-iodo-1,3-benzodioxole-4-carboxylic acid X-4c (0.41 g) as a pale yellow solid.

This compound was used as such for the next reaction without further purification.

Yield: 36%.

$^1$H NMR (400 MHz, DMSO-d$_6$) δ 7.70 (d, J=1.60 Hz, 1H) 7.91 (d, J=1.60 Hz, 1H).

Step-4: Synthesis of 2,2-difluoro-6-iodo-1,3-benzodioxol-4-amine X-4d

To a solution of 2,2-difluoro-6-iodo-1,3-benzodioxole-4-carboxylic acid X-4c (0.40 g, 1.21 mmol) in dioxane (5 mL) was added triethylamine (0.50 mL, 3.65 mmol) followed by addition of diphenylphosphorylazide (0.78 mL, 3.65 mmol). The reaction mixture was heated to reflux for 1 h. Progress of the reaction was monitored by TLC and LCMS. After completion, the reaction mixture was diluted with H$_2$O (20 mL), stirred for 30 min and extracted with EtOAc (2×25 mL). The organic layer was separated, dried over anhydrous Na$_2$SO$_4$ and concentrated under vacuum. The crude mixture obtained was purified by column chromatography (silica, 100-200 mesh, 5% EtOAc in hexanes) to afford 0.21 g of 2,2-difluoro-6-iodo-1,3-benzodioxol-4-amine X-4d as a colorless semi solid.

Yield: 57%.

Basic LCMS Method 2 (ES$^-$): 298.00 (M−H)$^-$, 84% purity.

Step-5: Synthesis of 7-amino-2,2-difluoro-1,3-benzodioxole-5-carbonitrile X-4

To a solution of 2,2-difluoro-6-iodo-1,3-benzodioxol-4-amine X-4d (5, 0.20 g, 0.66 mmol) in DMF (3 mL) was added Zn (0.002 g, 0.03 mmol), Zn(CN)$_2$ (0.08 g, 0.73 mmol), (Ph$_2$P)$_2$ferrocene (0.04 g, 0.06 mmol) and DIPEA (0.11 mL, 0.66 mmol) and the reaction mixture was purged with argon for 10 min. Pd$_2$(dba)$_3$ (0.03 g, 0.04 mmol) was added and the reaction mixture was heated at 80° C. for 2 h. Progress of the reaction was monitored by TLC. After completion, the reaction mixture was diluted with EtOAc (25 mL), filtered through a celite pad and washed with H$_2$O (2×25 mL). The organic layer was separated, dried over anhydrous Na$_2$SO$_4$ and concentrated under vacuum. The crude obtained was passed through silica (100-200 mesh) by using 20% EtOAc in hexanes to afford 0.07 g of 7-amino-2,2-difluoro-1,3-benzodioxole-5-carbonitrile X-4 as a pale yellow solid.

Yield: 53%.

$^1$H NMR (400 MHz, DMSO-d$_6$) δ 3.72 (s, 2H) 7.80 (s, 1H) 7.87 (s, 1H).

A.5. Synthesis of 5-fluoro-2,1,3-benzothiadiazol-6-amine X-5

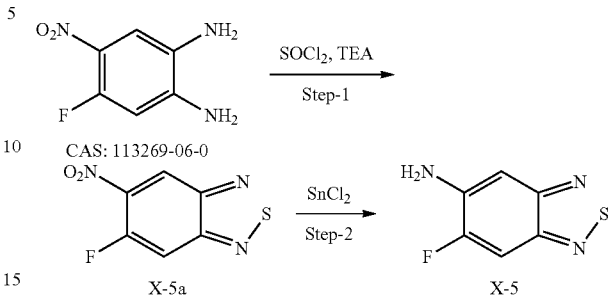

Step-1: Synthesis of 5-fluoro-6-nitro-2,1,3-benzothiadiazole X-5a

To a round-bottom flask were added 4-fluoro-5-nitrobenzene-1,2-diamine (0.40 g, 2.30 mmol), anhydrous DCM (10 mL) and triethylamine (TEA, 1.4 mL, 1.00 mmol). The solution was stirred until the diamine was completely dissolved. Thionyl chloride (1 mL, 13.70 mmol) was added dropwise at 0° C. Then the reaction mixture was heated to 40° C. for 3 h. The mixture was then cooled to room temperature and concentrated under reduced pressure. Water was added and the mixture was subsequently extracted with DCM (20 mL×3). The organic layers were combined and dried over MgSO$_4$. The solvent was evaporated and 5-fluoro-6-nitro-2,1,3-benzothiadiazole X-5a was obtained as a yellow solid (0.37 g).

Yield: 95%.

Neutral LCMS Method 3 (ES$^+$): 200.0 (M+H)$^+$, 89% purity

Step-2: Synthesis of 5-fluoro-2,1,3-benzothiadiazol-6-amine X-5

To a solution of 5-fluoro-6-nitro-2,1,3-benzothiadiazole X-5a (0.35 g, 1.75 mmol) in a mixture of dioxane (7 mL) and ethanol (7 mL) at rt was added solid SnCl$_2$ (1.8 g, 9.50 mmol) followed by water (0.35 mL). The reaction mixture was warmed up to 50° C. and stirred for 30 min, cooled to room temperature, concentrated and partitioned between ethyl acetate and 1N NaOH. The organic layer was washed with 1N NaOH, water, and brine, and then dried over MgSO$_4$. The solvent was evaporated and the residue was purified over silica gel eluting with petroleum ether/EtOAc (3/1) to afford 5-fluoro-2,1,3-benzothiadiazol-6-amine X-5 as a yellow powder (0.21 g).

Yield: 68%.

Neutral LCMS Method 3 (ES$^+$): 170.1 (M+H)$^+$, 93% purity.

A.6. Synthesis of 4-amino-2,1,3-benzoselenodiazole X-6

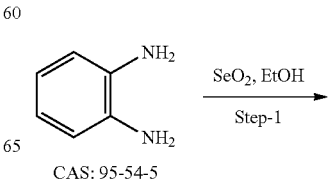

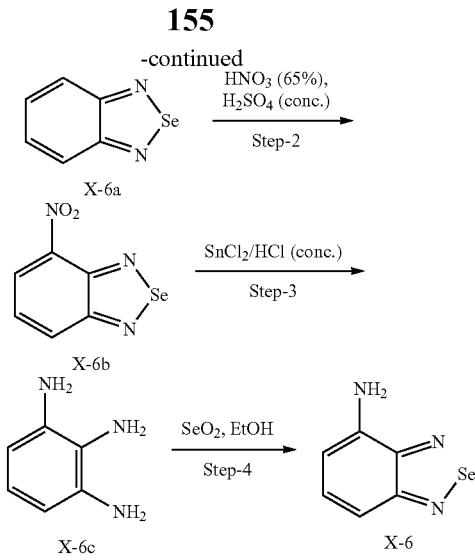

Step-1: Synthesis of 2,1,3-benzoselenadiazole X-6a

A mixture of o-phenylendiamine (10.5 g, 97.1 mmol) and selenium dioxide (11.85 g, 106.8 mmol) in ethanol (100 mL) was refluxed for 10 min. The reaction mixture was cooled to room temperature and ca. 90% of the solvent was evaporated under reduced pressure. Subsequently, 2,1,3-benzoselenadiazole X-6a was precipitated by adding water (50 mL) and filtered off under reduced pressure to afford 17.8 g of a beige solid.

Yield: 85%.
$^1$H NMR: (500 MHz, DMSO-$d_6$) δ: 7.99-7.69 (m, 2H), 7.60-7.43 (m, 2H).
Purity>95%, calculated from $^1$H NMR data.

Step-2: Synthesis of 4-nitro-2,1,3-benzoselenadiazole X-6b 2,1,3-Benzoselenadiazole X-6a (6.7 g, 36.6 mmol) was dissolved in concentrated sulfuric acid and cooled to 0° C. Subsequently, a mixture of 65% nitric acid (3.8 mL) and concentrated sulfuric acid (7.23 mL) was added. The solution was stirred for 30 min at room temperature and then diluted with an excess of ice water. The yellow precipitate (4-nitro-2,1,3-benzoselenadiazole) X-6b was filtered off and washed with water. It was obtained in quantitative yield.

Yield: 100%. $^1$H NMR (500 MHz, DMSO-$d_6$) δ: 8.44 (d, J=7.3 Hz, 1H), 8.27 (d, J=8.8 Hz, 1H), 7.77-7.68 (m, 1H).
Purity: 80%, calculated from $^1$H NMR data.

Step-3: Synthesis of 1,2,3-triaminobenzene X-6c

Tin(II) chloride dihydrate (2.22 g, 9.84 mmol) was suspended in concentrated hydrochloric acid. To this suspension 4-nitro-2,1,3-benzoselenadiazole X-6b (200 mg, 1.11 mmol) was added in portions. After the addition was completed the mixture was refluxed for 5 h. Subsequently, elemental selenium was filtered off while hot. The filtrate was cooled to room temperature. The formed yellowish crystals (1,2,3-triaminobenzene dihydrochloride X-6c) were filtered under reduced pressure, washed with ethanol and dried to afford 1.11.g. The product was directly used for the next step without further characterization.

Yield: 58%.

Step-4: Synthesis of 4-amino-2,1,3-benzoselenodiazole X-6

To a solution of 1 g (5.0 mmol) of 1,2,3-triaminobenzene dihydrochloride X-6c in water (10 mL) was added a solution of SeO$_2$ (555 mg, 5.0 mmol) in water (15 mL) at room temperature. After the addition was finished the reaction mixture was stirred for 15 min and then alkalized with a 30% aq. NaOH solution while cooling on an ice bath. The resulting orange needles were filtered off under reduced pressure, washed with water and dried. Additional purification by column chromatography (eluent: pure dichloromethane) yielded 560 mg of 4-amino-2,1,3-benzoselenodiazole.

Yield: 56%.
$^1$H NMR (600 MHz, DMSO-$d_6$) δ: 7.26 (dd, J=8.9, 7.2 Hz, 1H), 6.93 (d, J=8.8 Hz, 1H), 6.35 (d, J=7.3 Hz, 1H), 5.98 (s, 2H, NH$_2$).
Purity>95%, calculated from $^1$H NMR data.

A.7. Synthesis of 2-(4-amino-3-fluoro-phenyl)acetonitrile X-7

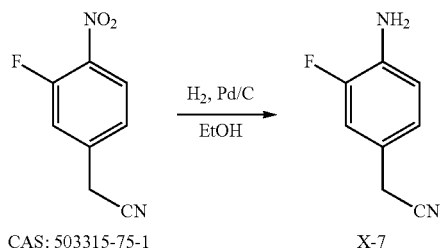

To a round-bottom flask, EtOH (5 mL) and 3-fluoro-4-nitrophenylacetonitrile (0.05 g, 0.28 mmol) and 10% of palladium-charcoal (8 mg) were added at room temperature. The reaction mixture was treated with H$_2$ at 35 psi for 2 h and subsequently filtered through a Celite pad and washed with EtOH. The filtrate was concentrated in vacuum. The crude product 2-(4-amino-3-fluoro-phenyl)acetonitrile X-7 was used in the next step without further purification.

Yield: 100%.
Neutral LCMS Method 3 (ES$^+$): 151.10 (M+H)$^+$, 98% purity.

A.8. Synthesis of 2-(4-amino-3-fluoro-phenyl)propanenitrile X-8

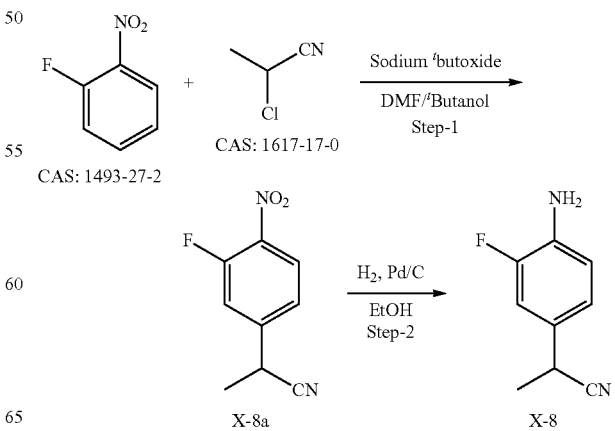

Step-1: Synthesis of 2-(3-fluoro-4-nitro-phenyl)propanenitrile X-8a

Into a dried flask were placed 2.35 g (24.45 mmol) of sodium tert-butoxide, 5 mL of tert-butanol and 5 mL of DMF. The resulting solution was cooled in an ice water bath. A solution of 1.24 g (8.85 mmol) of 2-fluoronitrobenzene and 1.10 g (12.30 mmol) of 2-chloropropionitrile in 3 mL of DMF was added dropwise to the cold solution. The resulting mixture was allowed to react for 30 minutes at −10° C. and was then poured into 50 mL of 1N aq. HCl solution. The aqueous mixture was extracted with ethyl acetate (50 mL×3), and dried over magnesium sulfate. After evaporation of the solvent the residue was purified over silica gel eluting with petroleum ether/EtOAc (95/5) to give 2-(4-amino-3-fluorophenyl)propionitrile (0.65 g).

$^1$H NMR (600 MHz, DMSO-d$_6$) δ 8.22 (t, J=8.2 Hz, 2H), 7.69 (d, J=14.0 Hz, 1H) 7.52 (d, J=8.5 Hz, 1H), 4.52 (q, J=7.2 Hz, 2H), 1.59 (d, J=7.3 Hz, 5H).

Purity>95% calculated from $^1$HNMR data.

Step-2: Synthesis of 2-(4-amino-3-fluoro-phenyl)propanenitrile X-8

2-(4-amino-3-fluoro-phenyl)propanenitrile X-8 was synthesized according to the method described for X-7.

Yield: quantitative yield %.

Neutral LCMS Method 3 (ES$^+$): 165.1 (M+H)$^+$, 95% purity.

A.9. Synthesis of 3-amino-6-cyanobenzo-2,1,3-thiadiazole X-9

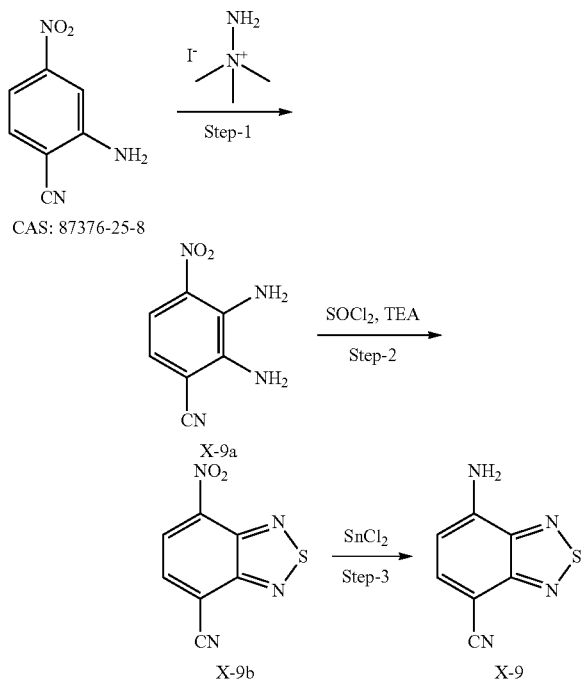

Step-1: Synthesis of 2,3-diamino-4-nitro-benzonitrile X-9a

To a stirred solution of 2-amino-4-nitrobenzonitrile (0.1 g, 0.613 mmol) in DMSO (6 mL) at room temperature was added 1,1,1-trimethylhydrazinium iodide (0.124 g, 0.613 mmol) in one portion, followed by portionwise addition of potassium tert-butoxide (0.21 g, 1.84 mmol). The reaction mixture was stirred at room temperature under argon overnight. The reaction mixture was poured into ice/water, acidified to pH 3 with 10% aq. HCl solution and extracted with DCM (20 mL×3). The combined organic layers were dried over MgSO$_4$ and evaporation of the solvent and the residue was purified over silica eluting with petroleum ether/EtOAc (2/1) to give 2,3-diamino-4-nitro-benzonitrile X-9a as a white powder (0.06 g).

Yield: 58%.

Neutral LCMS Method 3 (ES$^+$): 179.1 (M+H)$^+$, 98% purity.

Step-2 and 3: 4-amino-2,1,3-benzothiadiazole-7-carbonitrile X-9

4-amino-2,1,3-benzothiadiazole-7-carbonitrile X-9 was synthesized according to the method described for X-5.

Yield: 42%.

Neutral LCMS Method 3 (ES$^+$): 176.9 (M+H)$^+$, 98% purity.

A.10. Synthesis of 2,1,3-benzoselenadiazol-5-amine X-10

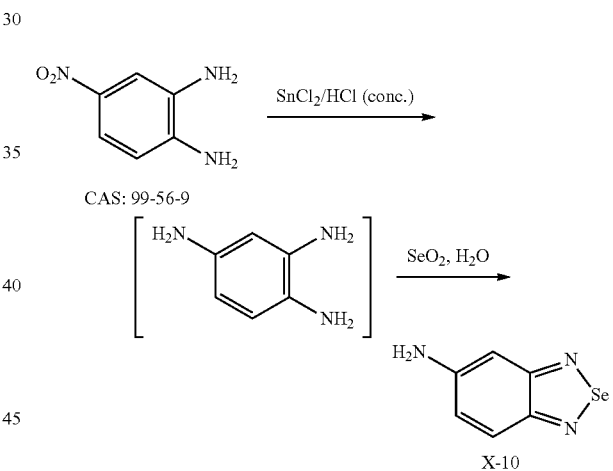

To a solution of SnCl$_2$ (5.6 g, 30 mmol) in 10 mL of concentrated HCl was added 4-nitro-ortho-phenylenediamine (1.0 g, 6.53 mmol) at 50° C. The mixture was stirred at 50° C. for 0.5 h and cooled to room temperature. Subsequently, a solution of SeO$_2$ (0.73 g, 6.53 mmol) in water was added under vigorous stirring. The resulting orange suspension was neutralized with a conc. NaHCO$_3$ solution (ca. 250 mL) and extracted with DCM (5 times, 100 mL each). The combined organic extracts were dried over MgSO$_4$, filtered and concentrated under reduced pressure. The residue was purified by column chromatography on silica gel 60 (eluent: DCM:MeOH=9.5:0.5) and subsequent crystallization from diethyl ether yielding 912 mg of 2,1,3-benzoselenadiazol-5-amine X-10 as orange needles.

Yield: 71%

$^1$H NMR (500 MHz, DMSO-d$_6$) δ: 7.51 (d, J=9.4 Hz, 1H), 7.12 (dd, J=9.5, 2.2 Hz, 1H), 6.52 (d, J=2.2 Hz, 1H), 6.01 (s, 2H, NH$_2$).

A.11. Synthesis of 2-(6-amino-5-methoxy-3-pyridyl)acetonitrile X-11

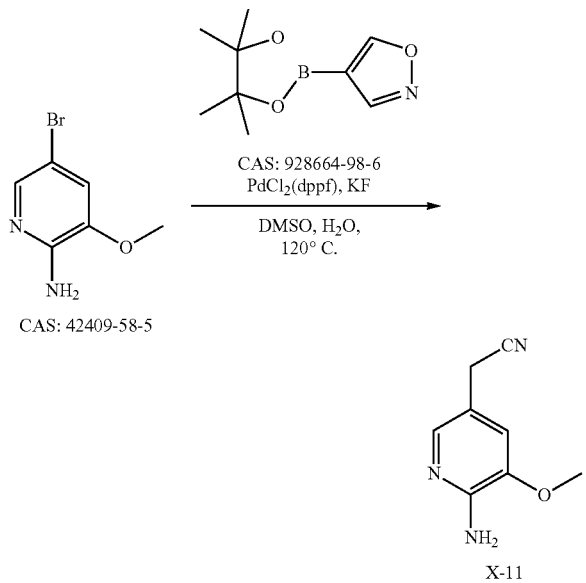

To a solution of 5-bromo-3-methoxy-pyridin-2-amine (0.20 g, 0.98 mmol) and 4-(4,4,5,5-tetramethyl-1,3,2-dioxaborolan-2-yl)isoxazole (0.23 g, 1.18 mmol) in DMSO (4.8 mL) was added KF (0.17 g, 2.96 mmol) solution in H$_2$O (2.9 mL). The reaction mixture was purged with argon for 15 min followed by addition of PdCl$_2$(dppf) (0.14 g, 0.19 mmol). The reaction mixture was heated at 120° C. for 16 h. Progress of the reaction was monitored by TLC and LCMS. After completion, the reaction mixture was filtered through a Celite pad and filtrate was diluted with an aqueous NaCl (20 mL) solution. The aqueous layer was extracted with EtOAc (2×60 mL). The organic layer was separated, dried over anhydrous Na$_2$SO$_4$ and concentrated under vacuum to afford 2-(6-amino-5-methoxy-3-pyridyl)acetonitrile X-11 (0.15 g) as a brown solid.

Yield: 94%

Basic LC-MS Method 2 (ES$^-$): 164 (M−H)$^-$, 58% purity.

A.12. Synthesis of 4-chloro-5-(difluoromethoxy)-2-fluoro-aniline X-12

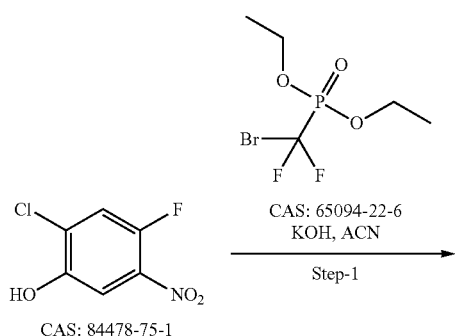

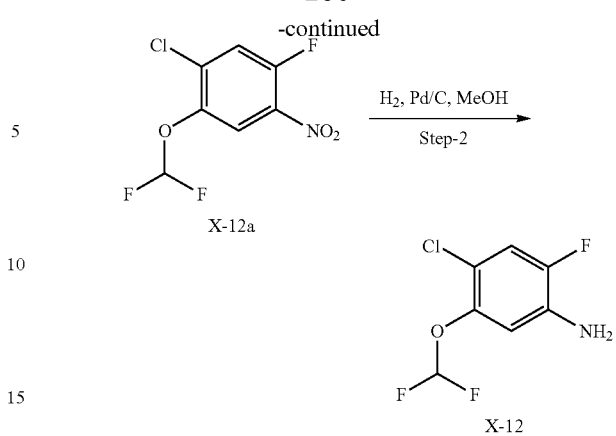

Step-1: Synthesis of 1-chloro-2-(difluoromethoxy)-5-fluoro-4-nitro-benzene X-12a To a solution of 2-chloro-4-fluoro-5-nitro-phenol (0.50 g, 2.61 mmol) in CH$_3$CN (10 mL) was added KOH (0.73 g, 13.0 mmol) at 0° C. and the reaction mixture was stirred at same temperature for 30 min. 1-[[bromo(difluoro)methyl]-ethoxy-phosphoryl]oxyethane (3.48 g, 13.0 mmol) was added dropwise at 0° C. and the reaction mixture was stirred at room temperature for 3 h. Progress of the reaction was monitored by TLC and LCMS. After completion, the reaction mixture was diluted with H$_2$O (20 mL) and extracted with EtOAc (20 mL). The organic layer was separated, dried over anhydrous Na$_2$SO$_4$ and concentrated under vacuum. The crude obtained was purified by column chromatography (silica, 100-200 mesh, 0 to 6% EtOAc in hexanes) to afford 1-chloro-2-(difluoromethoxy)-5-fluoro-4-nitro-benzene X-12a (0.46 g) as a colourless oil.

Yield: 73%

$^1$H NMR (400 MHz, DMSO-d$_6$) δ 7.41 (t, J=72 Hz, 1H) 8.15 (d, J=6.80 Hz, 1H) 8.21 (d, J=6.80 Hz, 1H).

Step-2: Synthesis of 4-chloro-5-(difluoromethoxy)-2-fluoro-aniline X-12

To a solution of 1-chloro-2-(difluoromethoxy)-5-fluoro-4-nitro-benzene X-12a (0.15 g, 0.59 mmol) in MeOH (7 mL) was added Pd/C (0.026 g, 0.24 mmol) and the reaction mixture was stirred at room temperature for 30 min under hydrogen pressure. Progress of the reaction was monitored by TLC and LCMS. After completion, the reaction mixture was filtered through celite celite and washed with MeOH (10 mL). The filtrate was concentrated under vacuum to afford 4-chloro-5-(difluoromethoxy)-2-fluoro-aniline X-12 (0.13 g) as a brown semi solid. This compound was used as such for the next reaction without further purification.

Yield: 80%

Basic LC-MS Method 2 (ES$^-$): 210 (M−H)$^-$, 78% purity.

A.13. Synthesis of 4-fluoro-2,1,3-benzoxadiazol-7-amine X-13

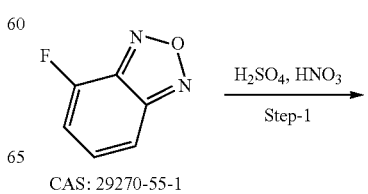

Step-1

Step-1: Synthesis of 4-fluoro-7-nitro-2,1,3-benzoxadiazole X-13a

To a solution of 4-fluoro-2,1,3-benzoxadiazole (1.00 g, 7.24 mmol) in Conc. H$_2$SO$_4$ (8 mL) was added nitrating mixture (H$_2$SO$_4$:HNO$_3$, 3:1, 2.40 mL) dropwise at −10° C. The reaction mixture was stirred at the same temperature for 1 h. Progress of the reaction was monitored by TLC and LCMS. After completion, the reaction mixture was quenched with H$_2$O (250 mL) and extracted with EtOAc (2×250 mL). The organic layer was separated, dried over anhydrous Na$_2$SO$_4$ and concentrated under vacuum. The crude obtained was purified by flash column chromatography (0 to 10% EtOAc in hexanes) to afford 4-fluoro-7-nitro-2,1,3-benzoxadiazole X-13a (0.39 g) as a yellow solid.

Yield: 30%

$^1$H NMR (400 MHz, DMSO-d$_6$) δ 7.70 (d, J=8.40 Hz, 1H) 8.77-8.80 (m, 1H).

Step-2: Synthesis of 4-fluoro-2,1,3-benzoxadiazol-7-amine X-13

To a solution of 4-fluoro-7-nitro-2,1,3-benzoxadiazole X-13a (0.13 g, 0.71 mmol) in MeOH (12 mL) was added Pd/C (0.04 g) at 0° C. and the reaction mixture was stirred at room temperature for 1 h under hydrogen pressure. Progress of the reaction was monitored by TLC and LCMS. After completion, the reaction mixture was filtered through a Celite bed, washed with MeOH (3×10 mL). The filtrate was concentrated under vacuum to afford 4-fluoro-2,1,3-benzoxadiazol-7-amine X-13 (0.12 g crude) as a brown semi solid.

This compound was used as such for the next reaction without further purification.

Basic LC-MS Method 2 (ES$^−$): 152 (M−H)$^−$, 80% purity.

$^1$H NMR (400 MHz, DMSO-d$_6$) δ 6.18 (d, J=8.00 Hz, 1H), 6.40 (brs, 2H), 7.14-7.20 (m, 1H).

A.14. Synthesis of 5-chloro-3,6-difluoro-pyridin-2-amine X-14

To a solution of 3-chloro-2,5,6-trifluoro-pyridine (0.50 g, 2.98 mmol) in DMSO (10 mL) was added 25% aqueous NH$_3$ (4 mL) and the reaction mixture was heated in steel bumb at 100° C. for 12 h. Progress of the reaction was monitored by TLC and LCMS. After completion, the reaction mixture was diluted with H$_2$O (200 mL) and extracted with EtOAc (400 mL). The organic layer was separated, dried over anhydrous Na$_2$SO$_4$ and concentrated under vacuum to afford 5-chloro-3,6-difluoro-pyridin-2-amine X-14 (0.41 g crude) as a yellow solid.

This compound was used as such for the next reaction without further purification.

$^1$H NMR (400 MHz, DMSO-d$_6$) δ 6.85 (s, 2H), 7.80-7.85 (m, 1H).

A.15. Synthesis of 3,6-difluoropyridin-2-amine X-15

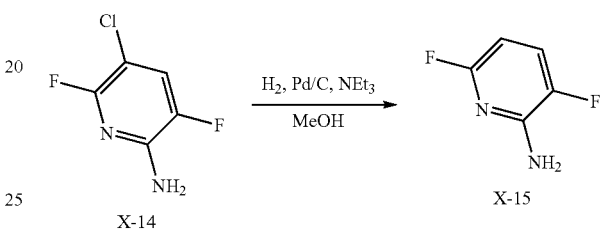

To a solution of 5-chloro-3,6-difluoro-pyridin-2-amine X-14 (0.50 g, 3.03 mmol) in MeOH (100 mL) was added triethylamine (5 mL) and Pd/C (0.40 g) and the reaction mixture was stirred at room temperature under hydrogen pressure in parr shaker for 10 h. Progress of the reaction was monitored by TLC and LCMS. After completion, the reaction mixture was filtered through celite, and filtrate was concentrated under vacuum. The residue was diluted with H$_2$O (200 mL) and extracted with 10% MeOH in DCM (200 mL). The organic layer was separated, dried over anhydrous Na$_2$SO$_4$ and concentrated under vacuum to afford 3,6-difluoropyridin-2-amine X-15 (0.21 g crude) as an off-white solid.

This compound was used as such for the next reaction without further purification.

Basic LC-MS Method 2 (ES$^+$): 130 (M)$^+$, 91% purity.

$^1$H NMR (400 MHz, DMSO-d$_6$) δ 6.09-6.11 (m, 1H) 6.57 (brs, 2H) 7.44-7.50 (m, 1H).

A.16. Synthesis of 5-bromo-3,6-difluoro-pyridin-2-amine X-16

To a solution of 3,6-difluoropyridin-2-amine X-15 (0.60 g, 4.19 mmol) in CH$_3$CN (40 mL) was added NBS (0.52 g, 2.93 mmol) and the reaction mixture was stirred in absence of light at room temperature for 30 min. NBS (0.52 g, 2.93 mmol) solution in CH$_3$CN (10 mL) was added and the reaction mixture was stirred at room temperature for 30 min.

Progress of the reaction was monitored by TLC and LCMS. After completion, the reaction mixture was diluted with H$_2$O (100 mL) and extracted with EtOAc (160 mL). The organic layer was separated, dried over anhydrous Na$_2$SO$_4$ and concentrated under vacuum. The crude obtained was purified by column chromatography (silica, 100-200 mesh, 5 to 10% EtOAc in hexanes) to afford 5-bromo-3,6-difluoropyridin-2-amine X-16 (0.70 g) as an off-white solid.

Yield: 79%

Basic LC-MS Method 2 (ES$^-$): 207 (M–H)$^-$, 98% purity.
$^1$H NMR (400 MHz, DMSO-d$_6$) δ 6.86 (brs, 2H) 7.82-7.91 (m, 1H).

A.17. Synthesis of 6-amino-5-fluoro-3H-isobenzofuran-1-one X-17

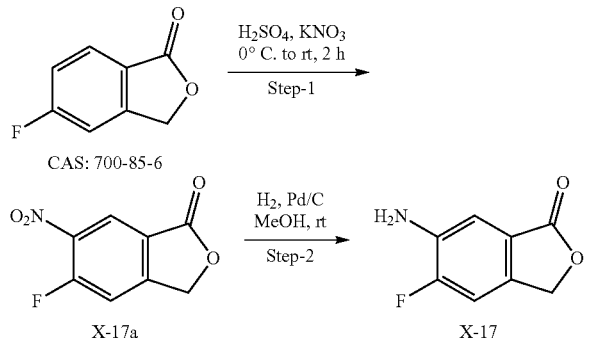

Step-1: Synthesis of 5-fluoro-6-nitro-3H-isobenzofuran-1-one X-17a

To a solution of 5-fluoro-3H-isobenzofuran-1-one (0.10 g, 0.65 mmol) in concentrated H$_2$SO$_4$ (1 mL) was added KNO$_3$ (0.13 g, 1.31 mmol) at 0° C. The reaction mixture was stirred at room temperature for 2 h. Progress of the reaction was monitored by TLC and LCMS. After completion, the reaction mixture was quenched with ice and extracted with EtOAc (3×30 mL). The organic layer was separated, dried over anhydrous Na$_2$SO$_4$ and concentrated under vacuum. The crude obtained was purified by combi-flash column chromatography (15 to 20% EtOAc in hexanes) to afford 5-fluoro-6-nitro-3H-isobenzofuran-1-one X-17a (0.063 g) as an off-white solid.

Yield: 48%

Basic LC-MS Method 2 (ES$^-$): 196 (M–H)$^-$, 99% purity.
$^1$H NMR (400 MHz, DMSO-d$_6$) δ 5.51 (s, 2H) 7.95 (d, J=10.27 Hz, 1H) 8.54 (d, J=6.85 Hz, 1H).

Step-2: Synthesis of 6-amino-5-fluoro-3H-isobenzofuran-1-one X-17

To a solution of 5-fluoro-6-nitro-3H-isobenzofuran-1-one X-17a (0.06 g, 0.30 mmol) in MeOH (10 mL) was added Pd/C (0.015 g, 0.02 mmol) and the reaction mixture was stirred at room temperature for 2 h under hydrogen pressure. Progress of the reaction was monitored by TLC and LCMS. After completion, the reaction mixture was filtered through celite, washed with MeOH (3×10 mL). The filtrate was concentrated under vacuum to 6-amino-5-fluoro-3H-isobenzofuran-1-one X-17 (0.054 g crude) as an off-white solid.

This compound was used as such for the next reaction without further purification.

Basic LC-MS Method 2 (ES$^-$): 166 (M–H)$^-$, 95% purity.
$^1$H NMR (400 MHz, DMSO-d$_6$) δ 5.20 (s, 2H) 5.59 (s, 2H) 7.12 (d, J=7.83 Hz, 1H) 7.32 (d, J=10.76 Hz, 1H).

A.18. Synthesis of 4-(2,2-difluoroethoxy)-2,5-difluoro-aniline X-18

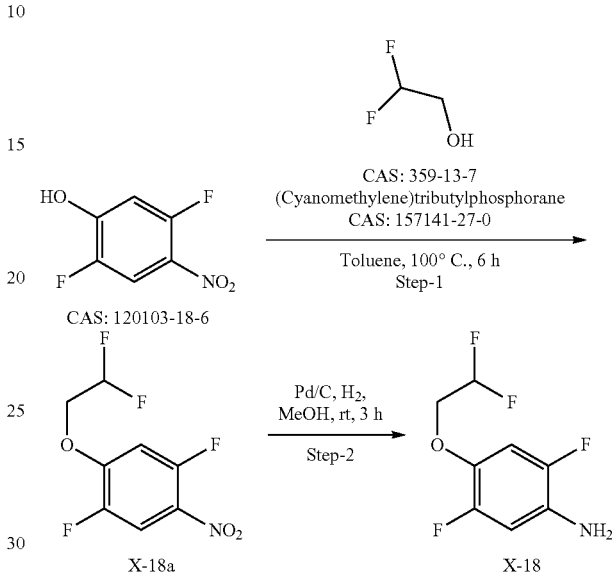

Step-1: Synthesis of 1-(2,2-difluoroethoxy)-2,5-difluoro-4-nitro-benzene X-18a To a solution of 2,5-difluoro-4-nitro-phenol (0.30 g, 1.71 mmol) and 2,2-difluoroethanol (0.28 g, 3.43 mmol) in toluene (4 mL) was added (cyanomethylene)tributylphosphorane (0.49 g, 2.06 mmol) and the reaction mixture was heated in a sealed tube at 100° C. for 6 h. Progress of the reaction was monitored by TLC and LCMS. After completion, the reaction mixture was diluted with H$_2$O (30 mL) and extracted with EtOAc (2×30 mL). The organic layer was separated, washed with brine (20 mL), dried over anhydrous Na$_2$SO$_4$ and concentrated under vacuum. The crude obtained was purified by column chromatography (silica, 100-200 mesh, 10% EtOAc in hexanes) to afford 1-(2,2-difluoroethoxy)-2,5-difluoro-4-nitro-benzene X-18a (0.20 g) as a pale brown liquid.

Yield: 39%

$^1$H NMR (400 MHz, DMSO-d$_6$) δ 4.54-4.68 (m, 2H) 6.48 (t, J=54 Hz, 1H) 7.65 (m, 1H) 8.19-8.28 (m, 1H).

Step-2: Synthesis of 4-(2,2-difluoroethoxy)-2,5-difluoro-aniline X-18

To a solution of 1-(2,2-difluoroethoxy)-2,5-difluoro-4-nitro-benzene X-18a (0.20 g, 0.67 mmol) in MeOH (6 mL) was added Pd/C (0.014 g, 0.13 mmol) and the reaction mixture was stirred at room temperature for 3 h under hydrogen pressure. Progress of the reaction was monitored by TLC and LCMS. After completion, the reaction mixture was filtered through celite, washed with MeOH (2×20 mL) and filtrate was concentrated under vacuum to afford 4-(2,2-difluoroethoxy)-2,5-difluoro-aniline X-18 (0.16 g) as a pale yellow liquid.

This compound was used as such for the next reaction without further purification.

Yield: 78%

Basic LC-MS Method 2 (ES$^+$): 210 (M+H)$^+$, 68% purity.

A.19. Synthesis of 3,6-difluoro-5-[(E)-3-methoxy-prop-1-enyl]pyridin-2-amine X-19

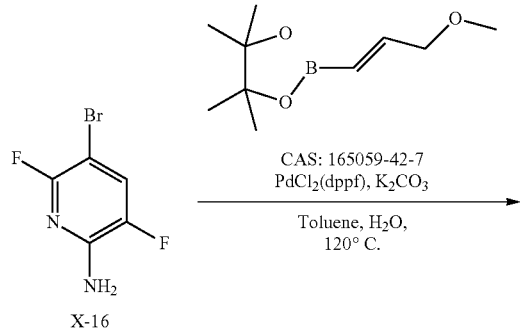

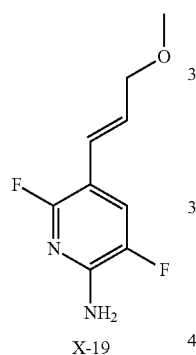

To a solution of 5-bromo-3,6-difluoropyridin-2-amine X-16 (1.00 g, 4.68 mmol) in toluene (26 mL) and H$_2$O (4 mL) was added TRANS-3-METHOXY-1-PROPENYLBORONIC ACID PINACOL ESTER (1.39 g, 7.02 mmol) and K$_2$CO$_3$ (1.94 g, 14.0 mmol). The reaction mixture was purged with argon for 20 min followed by addition of PdCl$_2$(dppf) (0.34 g, 0.47 mmol). The reaction mixture was heated at 120° C. for 16 h. Progress of the reaction was monitored by TLC and LCMS. After completion, the reaction mixture was diluted with H$_2$O (250 mL) and extracted with EtOAc (500 mL). The organic layer was separated, dried over anhydrous Na$_2$SO$_4$ and concentrated under vacuum. The crude obtained was purified by column chromatography (silica, 100-200 mesh, 40% EtOAc in hexanes) to afford 3,6-difluoro-5-[(E)-3-methoxyprop-1-enyl]pyridin-2-amine X-19 (0.803 g) as an off-white solid.

Yield: 82%

Basic LC-MS Method 2 (ES$^+$): 201 (M+H)$^+$, 95% purity.

$^1$H NMR (400 MHz, DMSO-d$_6$) δ 3.24 (s, 3H) 3.98 (dd, J=5.62, 1.22 Hz, 2H) 6.14-6.21 (m, 1H) 6.41 (dd, J=16.14, 0.98 Hz, 1H) 6.74 (s, 2H) 7.76-7.82 (m, 1H).

A.20. Synthesis of 3,6-difluoro-5-(3-methoxypropyl)pyridin-2-amine X-20

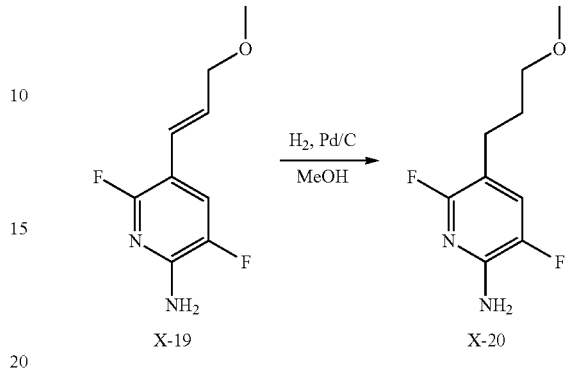

To a solution of 3,6-difluoro-5-[(E)-3-methoxyprop-1-enyl]pyridin-2-amine X-19 (0.39 g, 1.87 mmol) in MeOH (15 mL) was added Pd/C (0.10 g, 0.94 mmol) and the reaction mixture was stirred at room temperature for 6 h under hydrogen pressure. Progress of the reaction was monitored by TLC and LCMS. After completion, the reaction mixture was filtered through celite, washed with MeOH (20 mL) and filtrate was concentrated under vacuum to afford 3,6-difluoro-5-(3-methoxypropyl)pyridin-2-amine X-20 (0.368 g) as yellow liquid.

This compound was used as such for the next reaction without further purification.

Yield: 89%

Basic LC-MS Method 2 (ES$^+$): 203 (M+H)$^+$, 91% purity.

A.21. Synthesis of 5-chloro-3-fluoro-6-methoxy-pyridin-2-amine X-21

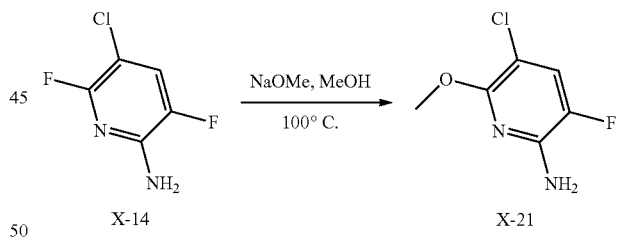

To a solution of 5-chloro-3,6-difluoro-pyridin-2-amine X-14 (0.50 g, 2.97 mmol) in MeOH (25 mL) was added NaOMe (0.48 g, 8.92 mmol) and the reaction mixture was heated at 100° C. for 24 h. Progress of the reaction was monitored by TLC and LCMS. After completion, the reaction mixture was concentrated under vacuum. The residue was diluted with H$_2$O (100 mL) and extracted with DCM (200 mL). The organic layer was separated, dried over anhydrous Na$_2$SO$_4$ and concentrated under vacuum to afford 5-chloro-3-fluoro-6-methoxy-pyridin-2-amine X-21 (0.40 g) as an off-white solid.

This compound was used as such for the next reaction without further purification.

Yield: 72%

$^1$H NMR (400 MHz, DMSO-d$_6$) δ 3.80 (s, 3H) 6.35 (s, 2H) 7.58 (d, J=9.78 Hz, 1H).

A.22. Synthesis of 2-(6-amino-5-fluoro-2-methoxy-3-pyridyl)acetonitrile X-22

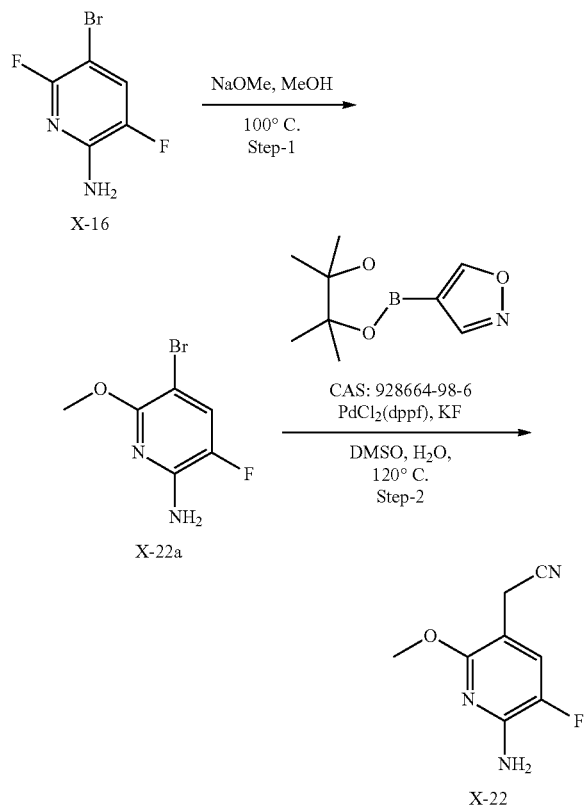

Step-1: Synthesis of 5-bromo-3-fluoro-6-methoxypyridin-2-amine X-22a

To a solution of 5-bromo-3,6-difluoropyridin-2-amine X-16 (0.50 g, 2.34 mmol) in MeOH (25 mL) was added NaOMe (0.38 g, 7.02 mmol) and the reaction mixture was heated at 100° C. for 18 h. Progress of the reaction was monitored by TLC and LCMS. After completion, the reaction mixture was concentrated under vacuum. The residue was diluted with H₂O (100 mL) and extracted with DCM (200 mL). The organic layer was separated, dried over anhydrous Na₂SO₄ and concentrated under vacuum. The crude obtained was purified by column chromatography (silica, 100-200 mesh, 5 to 10% EtOAc in hexanes) to afford 5-bromo-3-fluoro-6-methoxypyridin-2-amine X-22a (0.403 g) as an off-white solid.

Yield: 71%

Basic LC-MS Method 2 (ES⁺): 221 (M+H)⁺, 91% purity.

1H NMR (400 MHz, DMSO-d6) δ 3.79 (s, 3H) 6.39 (s, 2H) 7.63-7.69 (m, 1H).

Step-2: Synthesis of 2-(6-amino-5-fluoro-2-methoxy-3-pyridyl)acetonitrile X-22

To a solution of 5-bromo-3-fluoro-6-methoxypyridin-2-amine X-22a (0.37 g, 1.52 mmol) and 4-(4,4,5,5-tetramethyl-1,3,2-dioxaborolan-2-yl)isoxazole (0.39 g, 1.97 mmol) in DMSO (8 mL) and H₂O (4.54 mL) was added KF (0.27 g, 4.56 mmol) and the reaction mixture was purged with argon for 20 min. PdCl₂(dppf) (0.22 g, 0.30 mmol) was added and the reaction mixture was heated at 110° C. for 16 h. Progress of the reaction was monitored by TLC and LCMS. After completion, the reaction mixture was diluted with H₂O (100 mL) and extracted with EtOAc (200 mL). The organic layer was separated, dried over anhydrous Na₂SO₄ and concentrated under vacuum. The crude obtained was purified by column chromatography (silica, 100-200 mesh, 40% EtOAc in hexanes) to afford 2-(6-amino-5-fluoro-2-methoxy-3-pyridyl)acetonitrile X-22 (0.135 g) as a pale yellow solid.

Yield: 48%

Basic LC-MS Method 2 (ES⁺): 182 (M+H)⁺, 97% purity.

1H NMR (400 MHz, DMSO-d6) δ 3.61 (s, 2H) 3.79 (s, 3H) 6.22 (s, 2H) 7.36 (d, J=10.34 Hz, 1H).

A.23. Synthesis of 2-(4-amino-2,5-difluorophenoxy)acetonitrile X-23

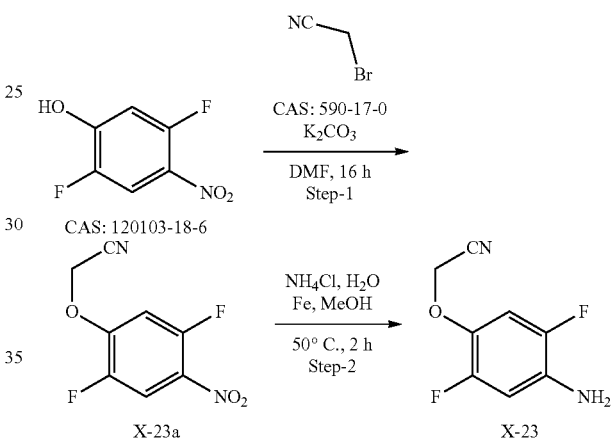

Step-1: Synthesis of 2-(2,5-difluoro-4-nitro-phenoxy)acetonitrile X-23a

To a solution of 2,5-difluoro-4-nitro-phenol (0.60 g, 3.43 mmol) in DMF (6 mL) was added K₂CO₃ (0.95 g, 6.85 mmol). The reaction mixture was cooled at 0 to 5° C. followed by slowly addition of bromoacetonitrile (0.29 mL, 4.11 mmol). The reaction mixture was stirred at room temperature for 16 h. Progress of the reaction was monitored by TLC and LCMS. After completion, the reaction mixture was poured in to ice-cold H₂O (35 mL) and extracted with EtOAc (2×50 mL). The organic layer was separated, dried over anhydrous Na₂SO₄ and concentrated under vacuum to afford 2-(2,5-difluoro-4-nitro-phenoxy)acetonitrile X-23a (0.51 g) as a brown solid.

This compound was used as such for the next reaction without further purification.

Yield: 70%

¹H NMR (400 MHz, DMSO-d₆) δ 5.93 (s, 2H) 7.66-7.70 (m, 1H) 8.23-8.27 (m, 1H)

Step-2: Synthesis of 2-(4-amino-2,5-difluorophenoxy)acetonitrile X-23

To a suspension of NH₄Cl (0.63 g, 11.7 mmol) and Fe (0.39 g, 7.01 mmol) in H₂O (15 mL) was added solution of 2-(2,5-difluoro-4-nitro-phenoxy)acetonitrile X-23a (0.50 g, 2.34 mmol) in MeOH (28 mL). The reaction mixture was heated at 50° C. for 2 h. Progress of the reaction was monitored by TLC. After completion, the reaction mixture was filtered, washed with MeOH (20 mL) and filtrate was concentrated under vacuum. The residue was extracted with EtOAc (2×25 mL). The organic layer was separated, dried over anhydrous Na$_2$SO$_4$ and concentrated under vacuum. The crude obtained was purified by column chromatography (silica, 100-200 mesh, 30% EtOAc in hexanes) to afford 2-(4-amino-2,5-difluorophenoxy)acetonitrile X-23 (0.17 g) as pale yellow solid.

Yield: 40%

$^1$H NMR (400 MHz, DMSO-d$_6$) δ 5.04 (s, 2H) 5.22 (s, 2H) 6.62-6.67 (m, 1H) 7.12-7.17 (m, 1H)

A.24. Synthesis of 4-(cyclopropylmethoxy)-2,5-difluoroaniline X-24

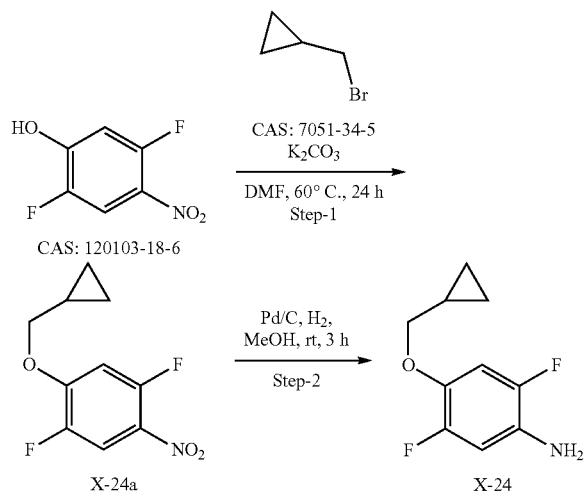

Step-1: Synthesis of 1-(cyclopropylmethoxy)-2,5-difluoro-4-nitrobenzene X-24a

To a solution of 2,5-difluoro-4-nitro-phenol (0.50 g, 2.86 mmol) in DMF (3 mL) was added K$_2$CO$_3$ (1.97 g, 14.3 mmol) and the reaction mixture was stirred at room temperature for 20 min. Cyclopropylmethyl bromide (0.77 g, 5.71 mmol) was added at 0° C. and the reaction mixture was heated at 60° C. for 24 h. Progress of the reaction was monitored by TLC and LCMS. After completion, the reaction mixture was diluted with H$_2$O (60 mL) and extracted with EtOAc (3×30 mL). The organic layer was separated, washed with brine (2×30 mL), dried over anhydrous Na$_2$SO$_4$ and concentrated under vacuum to afford 1-(cyclopropylmethoxy)-2,5-difluoro-4-nitrobenzene X-24a (0.584 g) as a yellow liquid.

This compound was used as such for the next reaction without further purification.

Yield: 89%

$^1$H NMR (400 MHz, DMSO-d$_6$) δ 0.32-0.41 (m, 2H) 0.59-0.66 (m, 2H) 1.22-1.34 (m, 1H) 4.07 (d, J=7.34 Hz, 2H) 7.46 (dd, J=13.21, 6.85 Hz, 1H) 8.16 (dd, J=11.00, 7.58 Hz, 1H).

Step-2: Synthesis of 4-(cyclopropylmethoxy)-2,5-difluoroaniline X-24

To a solution of 1-(cyclopropylmethoxy)-2,5-difluoro-4-nitrobenzene X-24a (0.20 g, 0.87 mmol) in MeOH (10 mL) was added Pd/C (0.05 g, 0.09 mmol) and the reaction mixture was stirred at room temperature for 3 h under hydrogen pressure. Progress of the reaction was monitored by TLC and LCMS. After completion, the reaction mixture was filtered through celite, washed with MeOH (3×15 mL) and filtrate was concentrated under vacuum. The crude obtained was purified by combi-flash column chromatography (5 to 10% EtOAc in hexanes) to afford 4-(cyclopropylmethoxy)-2,5-difluoroaniline X-24 (0.127 g) as a brown solid.

Yield: 62%

Basic LC-MS Method 2 (ES$^+$): 200 (M+H)$^+$, 84% purity.

A.25. Synthesis of 3,5-dimethoxypyridin-2-amine X-25

To a solution of 5-bromo-3-methoxy-pyridin-2-amine (0.50 g, 2.46 mmol), 1,10-phenanthroline (0.13 g, 0.74 mmol) and CuBr (0.21 g, 1.48 mmol) in MeOH (25 mL) was added Cs$_2$CO$_3$ (1.61 g, 4.93 mmol). The reaction mixture was heated at 120° C. for 24 h. Progress of the reaction was monitored by TLC and LCMS. After completion, the reaction mixture was concentrated under vacuum. The residue was diluted with H$_2$O (50 mL) and extracted with EtOAc (2×40 mL). The organic layer was separated, dried over anhydrous Na$_2$SO$_4$ and concentrated under vacuum. The crude obtained was purified by column chromatography (silica, 100-200 mesh, 1 to 5% MeOH in DCM) to afford 3,5-dimethoxypyridin-2-amine X-25 (0.27 g) as a pale brown liquid.

Yield: 57%

Basic LC-MS Method 2 (ES$^+$): 155 (M+H)$^+$, 80% purity.

A.26. Synthesis of 6-amino-5-fluoro-isoindolin-1-one X-26

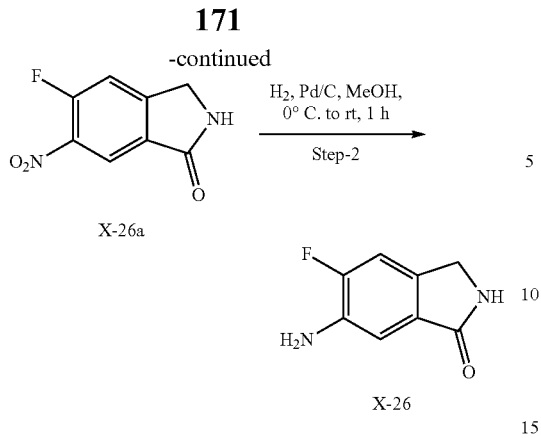

Step-1: Synthesis of 5-fluoro-6-nitroisoindolin-1-one X-26a

To a solution of 5-fluoroisoindolin-1-one (1.00 g, 6.62 mmol) in $H_2SO_4$ (15 mL) was added $KNO_3$ (1.00 g, 9.92 mmol) at 0° C. and the reaction mixture was stirred at same temperature for 1 h. Progress of the reaction was monitored by TLC and LCMS. After completion, the reaction mixture was diluted with cold $H_2O$ (250 mL) and extracted with EtOAc (250 mL). The organic layer was separated, dried over anhydrous $Na_2SO_4$ and concentrated under vacuum. The crude obtained was purified by washing with DCM (4 mL) and pentane (10 mL) and dried under vacuum to afford 5-fluoro-6-nitroisoindolin-1-one X-26a (0.60 g) as an off-white solid.

Yield: 46%
Basic LC-MS Method 2 (ES$^-$): 195 (M−H)$^-$, 99% purity.
$^1$H NMR (400 MHz, DMSO-d$_6$) δ 4.51 (s, 2H) 7.86 (d, J=10.88 Hz, 1H) 8.29 (d, J=6.85 Hz, 1H) 8.95 (brs, 1H).

Step-2: Synthesis of 6-amino-5-fluoro-isoindolin-1-one X-26

To a solution of 5-fluoro-6-nitroisoindolin-1-one X-26a (0.20 g, 1.02 mmol) in MeOH (10 mL) was added Pd/C (0.05 g, 0.47 mmol) and the reaction mixture was stirred at room temperature for 2 h under hydrogen pressure. Progress of the reaction was monitored by TLC and LCMS. After completion, the reaction mixture was filtered through celite, washed with MeOH (10 mL) and filtrate was concentrated under vacuum to afford 6-amino-5-fluoro-isoindolin-1-one X-26 (0.155 g) as an off-white solid.

This compound was used as such for the next reaction without further purification.

Yield: 89%
Basic LCMS Method 2 (ES$^+$): 167 (M+H)$^+$, 97% purity.
$^1$H NMR (400 MHz, DMSO-d$_6$) δ 4.17 (s, 2H) 5.32 (s, 2H) 7.02 (d, J=8.31 Hz, 1H) 7.19 (d, J=10.76 Hz, 1H) 8.33 (brs, 1H).

A.27. Synthesis of 6-amino-5-fluoro-3-methyl-3H-isobenzofuran-1-one X-27

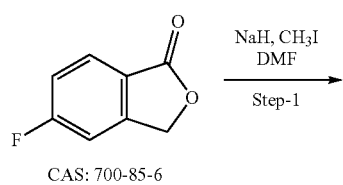

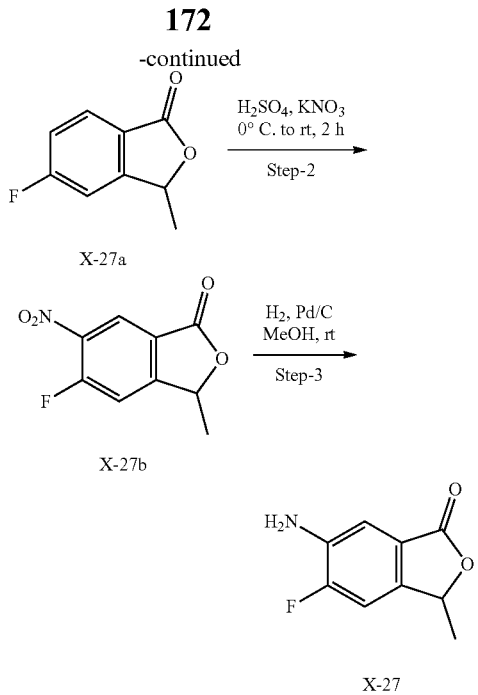

Step-1: Synthesis of 5-fluoro-3-methyl-3H-isobenzofuran-1-one X-27a

To a solution of 5-fluoro-3H-isobenzofuran-1-one (1.00 g, 6.57 mmol) in DMF (5 mL) was added CH$_3$I (0.82 mL, 13.1 mmol) at −20° C. followed by addition of NaH (0.34 g, 7.89 mmol) portion wise. The reaction mixture was stirred at room temperature for 3 h. Progress of the reaction was monitored by TLC and LCMS. After completion, the reaction mixture was diluted with ice-cold saturated aqueous NH$_4$Cl solution (50 mL) and extracted with EtOAc (2×30 mL). The organic layer was separated, dried over anhydrous Na$_2$SO$_4$ and concentrated under vacuum. The crude obtained was purified by combi-flash column chromatography (4% EtOAc in hexanes) to afford 5-fluoro-3-methyl-3H-isobenzofuran-1-one X-27a (0.44 g) an as an off-white solid.

Yield: 35%
Basic LCMS Method 2 (ES$^+$): 167 (M+H)$^+$, 87% purity.
$^1$H NMR (400 MHz, DMSO-d$_6$) δ 1.56 (d, J=6.36 Hz, 3H) 5.68 (q, J=6.36 Hz, 1H) 7.41-7.48 (m, 1H) 7.62 (dd, J=8.80, 1.96 Hz, 1H) 7.87-7.93 (m, 1H).

Step-2: Synthesis of 5-fluoro-6-nitro-3-methyl-3H-isobenzofuran-1-one X-27b

To a solution of 5-fluoro-3-methyl-3H-isobenzofuran-1-one X-27a (0.40 g, 2.10 mmol) in Conc. H$_2$SO$_4$ (4 mL) was added KNO$_3$ (0.26 g, 2.52 mmol) at 0° C. and the reaction mixture was stirred at room temperature for 2 h. Progress of the reaction was monitored by TLC. After completion, the reaction mixture was diluted with ice-cold H$_2$O (25 mL) and extracted with EtOAc (2×20 mL). The organic layer was separated, washed with cold saturated NaHCO$_3$ (25 mL) solution, dried over anhydrous Na$_2$SO$_4$ and concentrated under vacuum. The crude obtained was purified by combi-flash column chromatography (12 to 15% EtOAc in hexanes) to afford 5-fluoro-6-nitro-3-methyl-3H-isobenzofuran-1-one X-27b (0.145 g, 33%) as an off-white solid.

Yield: 33%
$^1$H NMR (400 MHz, DMSO-d$_6$) δ 1.61 (d, J=6.85 Hz, 3H) 5.82 (q, J=6.85 Hz, 1H) 8.03-8.07 (m, 1H) 8.53 (d, J=6.85 Hz, 1H).

Step-3: Synthesis of 6-amino-5-fluoro-3-methyl-3H-isobenzofuran-1-one X-27

To a solution of 5-fluoro-6-nitro-3-methyl-3H-isobenzofuran-1-one X-27b (0.14 g, 0.66 mmol) in MeOH (5 mL) was added Pd/C (0.02 g) and the reaction mixture was stirred at room temperature for 2 h under hydrogen pressure. Progress of the reaction was monitored by TLC. After completion, the reaction mixture was filtered through celite, washed with EtOAc (2×10 mL) and filtrate was concentrated under vacuum to afford 6-amino-5-fluoro-3-methyl-3H-isobenzofuran-1-one X-27 (0.11 g, 92%) as an off-white solid.

This compound was used as such for the next reaction without further purification.

Yield: 92%

$^1$H NMR (400 MHz, DMSO-$d_6$) δ 1.48 (d, J=6.85 Hz, 3H) 5.49 (q, J=6.52 Hz, 1H) 5.60 (s, 2H) 7.09 (d, J=7.82 Hz, 1H) 7.36 (d, J=10.27 Hz, 1H).

A.28. Synthesis of 3-methoxy-5-(trifluoromethyl)pyridin-2-amine X-28

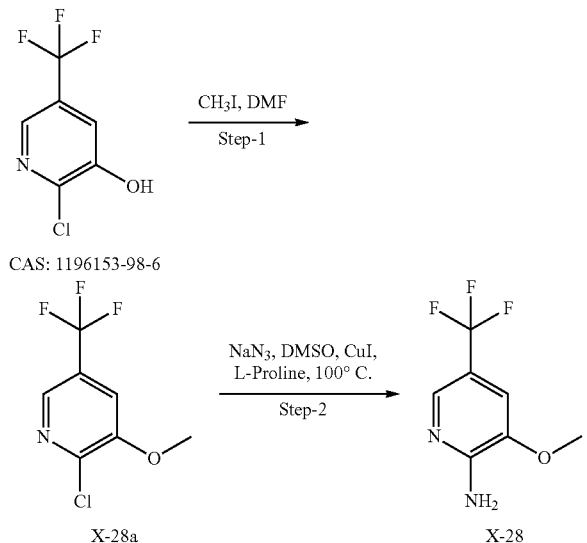

Step-1: Synthesis of 2-chloro-3-methoxy-5-(trifluoromethyl)pyridine X-28a

To a solution of 2-chloro-5-(trifluoromethyl)pyridin-3-ol (0.75 g, 3.80 mmol) in DMF (15 mL) was added NaH (0.26 g, 6.45 mmol) slowly at 0° C. and the reaction mixture was stirred at same temperature for 15 min. CH$_3$I (0.40 mL, 6.45 mmol) was added at 0° C. and the reaction mixture was stirred at same temperature for 15 min. The reaction mixture was stirred at room temperature for 30 min. Progress of the reaction was monitored by TLC and LCMS. After completion, the reaction mixture was quenched with ice-cold H$_2$O (100 mL) and extracted with EtOAc (250 mL). The organic layer was separated, dried over anhydrous Na$_2$SO$_4$ and concentrated under vacuum. The crude obtained was purified by flash column chromatography (silica, 230-400 mesh, 15% EtOAc in hexanes) to afford 2-chloro-3-methoxy-5-(trifluoromethyl)pyridine X-28a (0.403 g) as a pale yellow liquid.

Yield: 50%

Basic LCMS Method 2 (ES$^+$): 212 (M+H)$^+$, 100% purity.

$^1$H NMR (400 MHz, DMSO-$d_6$) δ 4.01 (s, 3H) 7.91 (s, 1H) 8.40 (s, 1H).

Step-2: Synthesis of 3-methoxy-5-(trifluoromethyl)pyridin-2-amine X-28

To a solution of 2-chloro-3-methoxy-5-(trifluoromethyl) pyridine X-28a (0.35 g, 1.65 mmol) in DMSO (10 mL) was added NaN$_3$ (0.33 g, 5.08 mmol) and the reaction mixture was purged with argon for 10 min. CuI (0.09 g, 0.46 mmol) and L-Proline (0.09 g, 0.76 mmol) were added and the reaction mixture was heated at 100° C. for 16 h. Progress of the reaction was monitored by TLC and LCMS. After completion, the reaction mixture was diluted with H$_2$O (200 mL) and extracted with EtOAc (300 mL). The organic layer was separated, dried over anhydrous Na$_2$SO$_4$ and concentrated under vacuum. The crude obtained was purified by column chromatography (silica, 100-200 mesh, 40% EtOAc in hexanes) to afford 3-methoxy-5-(trifluoromethyl)pyridin-2-amine X-28 (0.173 g) as a pale brown solid.

Yield: 54%

Basic LCMS Method 2 (ES$^+$): 193 (M+H)$^+$, 99% purity.

$^1$H NMR (400 MHz, DMSO-$d_6$) δ 3.84 (s, 3H) 6.54 (brs, 2H) 7.16 (s, 1H) 7.84 (s, 1H).

A.29. Synthesis of 3,5-difluoro-6-methoxy-pyridin-2-amine X-29

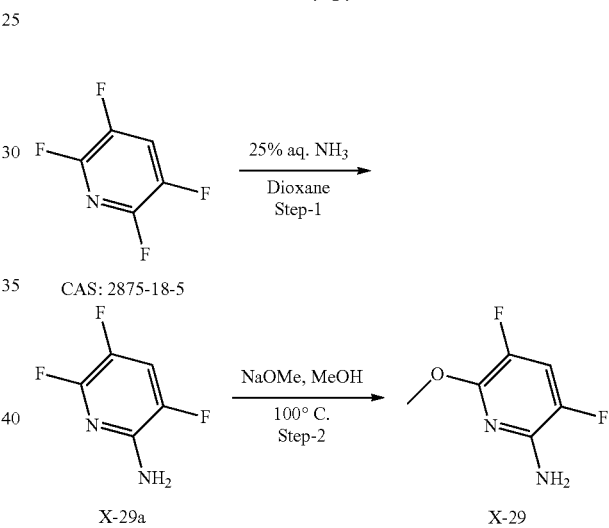

Step-1: Synthesis of 2-chloro-3-methoxy-5-(trifluoromethyl)pyridine X-28a

To a solution of 2,3,5,6-tetrafluoropyridine (2.00 g, 13.2 mmol) in Dioxane (100 mL) was added NH$_4$OH (25% in water, 40 mL). The reaction mixture was heated at 60° C. for 48 h. Progress of the reaction was monitored by TLC. After completion, the reaction mixture was concentrated under vacuum. The reaction was diluted with H$_2$O (100 mL) and extracted with diethyl ether (2×150 mL). The organic layers were separated, dried over anhydrous Na$_2$SO$_4$ and concentrated under vacuum to afford 1.30 g of 3,5,6-trifluoropyridin-2-amine X-29a as an off white solid.

This compound was used as such for the next reaction without further purification.

Yield: 65%

Basic LCMS Method 2 (ES$^-$): 147 (M–H)$^-$, 99% purity.

$^1$H NMR (400 MHz, DMSO-$d_6$) δ 6.52 (br s, 2H) 7.85-7.94 (m, 1H).

Step-2: Synthesis of
3,5-difluoro-6-methoxy-pyridin-2-amine X-29

To a solution 3,5,6-trifluoropyridin-2-amine X-29a (500 mg, 3.38 mmol) in methanol (15 mL), sodium methoxide (547 mg, 10.1 mmol) was added. The reaction mixture was heated at 90-100° C. for 24 h. Progress of the reaction was monitored by TLC. After completion, the reaction mixture was concentrated under vacuum. The residue was diluted with H$_2$O (20 mL) and extracted with EtOAc (50 mL). The organic layer was separated, dried over anhydrous Na$_2$SO$_4$ and concentrated under vacuum to afford 310 mg of 3,5-difluoro-6-methoxy-pyridin-2-amine X-29 as an off white solid.
Yield: 52%
Basic LCMS Method 2 (ES$^+$): 161 (M+H)$^+$, 90% purity.
$^1$H NMR (400 MHz, DMSO-d$_6$) δ 3.81 (s, 3H) 6.00 (s, 2H) 7.59 (t, J=10.03 Hz, 1H)

A.30. Synthesis of
3,6-difluoro-5-methyl-pyridin-2-amine X-30

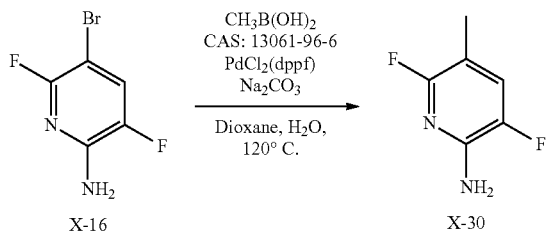

To a stirred solution of 5-bromo-3,6-difluoropyridin-2-amine X-16 (0.40 g, 1.91 mmol) in dioxane (12 mL) was added CH$_3$B(OH)$_2$ (0.23 g, 3.82 mmol), Na2CO3 (0.51 g, 4.78 mmol) solution in H$_2$O (3 mL). The reaction mixture was purged with argon for 20 min followed by addition of PdCl$_2$(dppf) (0.28 g, 0.38 mmol). The reaction mixture was purged with argon for 10 min and heated at 120° C. for 3 h. Progress of reaction was monitored by TLC and LCMS. After completion, the reaction mixture was cooled to room temperature, filtered through Celite, washed with EtOAc (2×30 mL) and the filtrate was concentrated under vacuum. The crude obtained was diluted with H$_2$O (30 mL) and extracted with EtOAc (3×25 mL). The organic layer was separated, washed with brine (2×30 mL), dried over anhydrous Na$_2$SO$_4$ and concentrated under vacuum. The crude obtained was purified by column chromatography (silica, 100-200 mesh, 3% of EtOAc in hexanes) to afford 3,6-difluoro-5-methyl-pyridin-2-amine X-30 (0.145 g) as an off-white solid.
Yield: 32%
Basic LC-MS Method 2 (ES$^+$): 145 (M+H)$^+$, 60% purity.
$^1$H NMR (400 MHz, DMSO-d$_6$) δ 3.79 (s, 3H) 6.39 (s, 2H) 7.63-7.69 (m, 1H).

A.31. Synthesis of
5-bromo-6-fluoro-3-methoxy-pyridin-2-amine X-31

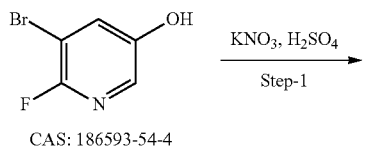
CAS: 186593-54-4

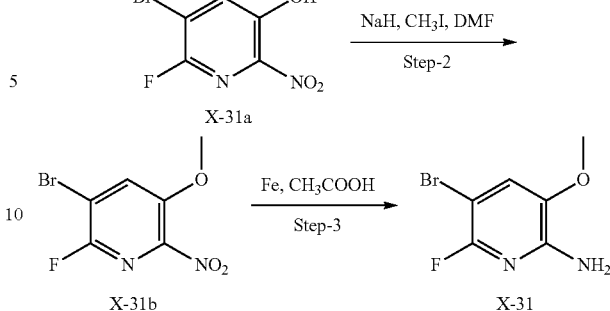

Step 1—Synthesis of
5-bromo-6-fluoro-2-nitro-pyridin-3-ol X-31a

To a solution of H$_2$SO$_4$ (15 mL) was added KNO$_3$ (0.63 g, 6.28 mmol) and the reaction mixture was stirred at room temperature for 20 min. 5-bromo-6-fluoro-pyridin-3-ol (0.60 g, 3.14 mmol) was added and the reaction mixture was stirred at room temperature for 16 h. Progress of reaction was monitored by TLC. After completion, the reaction mixture was poured into ice (100 mL) and extracted with EtOAc (3×80 mL). The organic layer was separated, washed with brine (120 mL), dried over anhydrous Na$_2$SO$_4$ and concentrated under vacuum to afford 5-bromo-6-fluoro-2-nitro-pyridin-3-ol X-31a (0.60 g) as an off-white solid.
Yield: 56%
$^1$H NMR (400 MHz, DMSO-d$_6$) δ 8.11 (d, J=7.2 Hz, 1H) 11.83 (brs, 1H).

Step 2—Synthesis of 3-bromo-2-fluoro-5-methoxy-6-nitro-pyridine X-31b

To a stirred suspension of NaH (0.11 g, 2.65 mmol) in DMF (8 mL) was added 5-bromo-6-fluoro-2-nitro-pyridin-3-ol X-31a (0.60 g, 1.77 mmol in DMF 4 mL) at 0° C. and the reaction mixture was stirred at same temperature for 30 min. CH$_3$I (0.76 g, 5.32 mmol) was added at 0° C. and the reaction mixture was stirred at room temperature for 16 h. Progress of reaction was monitored by TLC. After completion, the reaction mixture was quenched with ice, diluted with H$_2$O (60 mL) and extracted with EtOAc (3×40 mL). The organic layer was separated, washed with brine (60 mL), dried over anhydrous Na$_2$SO$_4$ and concentrated under vacuum. The crude obtained was purified by flash column chromatography (12 to 20% EtOAc in hexanes) to afford 3-bromo-2-fluoro-5-methoxy-6-nitro-pyridine X-31b (0.30 g) as a pale yellow liquid.
Yield: 67%
$^1$H NMR (400 MHz, CDCl$_3$) δ 4.02 (s, 3H) 7.86 (d, J=6.4 Hz, 1H).

Step 3—Synthesis of
5-bromo-6-fluoro-3-methoxy-pyridin-2-amine X-31

To a solution of 3-bromo-2-fluoro-5-methoxy-6-nitro-pyridine X-31b (0.25 g, 1.00 mmol) in CH$_3$COOH (10 mL) was added Fe (0.45 g, 7.97 mmol) and the reaction mixture was stirred at room temperature for 2 h. Progress of reaction was monitored by TLC and LCMS. After completion, the reaction mixture was filtered through a pad of celite, washed with EtOAc (220 mL) and filtrate was concentrated under vacuum. The residue was poured into aqueous saturated NaHCO$_3$ (150 mL) and extracted with EtOAc (2×125 mL). The organic layer was separated, dried over anhydrous Na₂SO₄ and concentrated under vacuum to afford 5-bromo-6-fluoro-3-methoxy-pyridin-2-amine X-31 (0.21 g) as an off-white solid.

This compound was used as such for the next reaction without further purification.

Yield: 87%

Basic LC-MS Method 2 (ES⁺): 221 (M+H)⁺, 91% purity.

$^1$H NMR (400 MHz, CDCl$_3$) δ 3.78 (s, 3H) 6.39 (brs, 2H) 7.32 (d, J=6.8 Hz, 1H).

A.32. Synthesis of 2-(6-amino-2-fluoro-5-methoxy-3-pyridyl)acetonitrile X-32

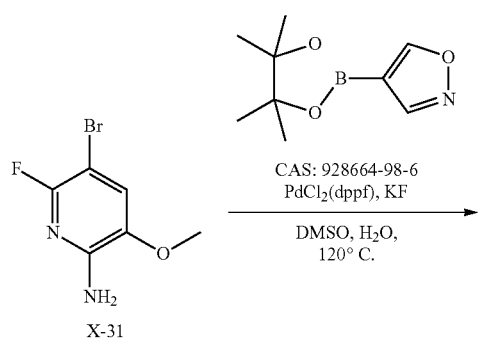

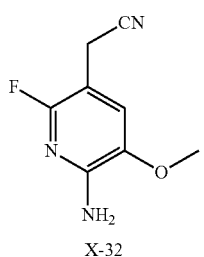

To a solution of 5-bromo-6-fluoro-3-methoxy-pyridin-2-amine X-31 (0.24 g, 1.02 mmol) and 4-(4,4,5,5-tetramethyl-1,3,2-dioxaborolan-2-yl)isoxazole (0.24 g, 1.22 mmol) in DMSO (12 mL) was added KF (0.18 g, 3.05 mmol) solution in H₂O (3.05 mL). The reaction mixture was purged with argon for 15 min followed by addition of PdCl₂(dppf) (0.15 g, 0.20 mmol). The reaction mixture was heated at 120° C. for 16 h. Progress of reaction was monitored by TLC and LCMS. After completion, the reaction mixture was filtered, filtrate was diluted with brine (40 mL) and extracted with EtOAc (2×70 mL). The organic layer was separated, washed with H₂O (70 mL), dried over anhydrous Na₂SO₄ and concentrated under vacuum. The crude obtained was purified by flash chromatography (40 to 55% EtOAc in hexanes) to afford 2-(6-amino-2-fluoro-5-methoxy-3-pyridyl)acetonitrile X-32 (0.10 g) as an off-white solid.

Yield: 54%

Basic LC-MS Method 2 (ES⁻): 180 (M–H)⁻, 99% purity.

$^1$H NMR (400 MHz, DMSO-d$_6$) δ 3.77 (s, 5H) 6.24 (brs, 2H) 7.16 (s, 1H).

A.33. Synthesis of 2-(4-amino-2,5-difluoro-phenyl)acetonitrile X-33

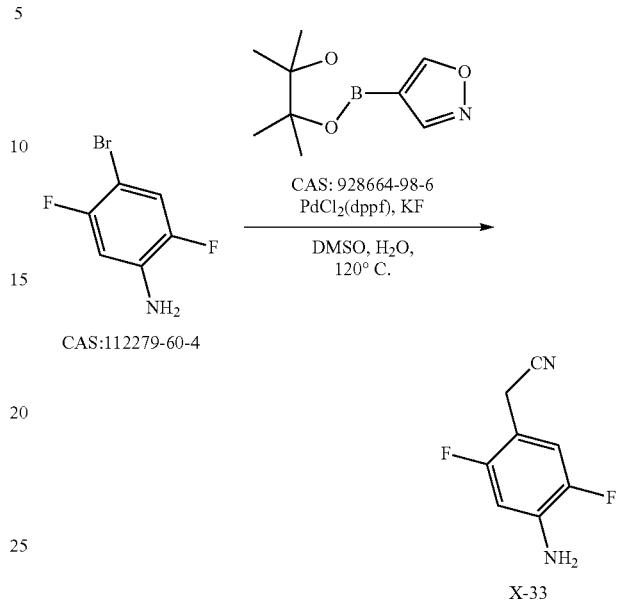

4-bromo-2,5-difluoroaniline (300 mg, 1.44 mmol) and 4-(4,4,5,5-tetramethyl-1,3,2-dioxaborolan-2-yl)isoxazole (338 mg, 1.731 mmol) were placed in dimethyl sulfoxide (10 mL) in a vial. Then potassium fluoride (251 mg, 4.326 mmol) and water (78 μL, 4.32 mmol) were added. This suspension was degassed for 10 min of fast argon bubbling in an ultrasound bath. Then [1,1'-bis(diphenylphosphino)ferrocene]dichloropalladium(II) (106 mg, 1.144 mmol) was added and the reaction mixture was heated to 120° C. under argon atmosphere for 19 h. It was then filtered over celite and brine was added to the filtrate which was extracted three times with ethyl acetate, dried over magnesium sulfate and evaporated to dryness. The crude residue was purified by column chromatography (SiO₂, 5% to 15% EtOAc in petroleum ether) to afford 2-(4-amino-2,5-difluoro-phenyl)acetonitrile X-33 (87 mg) as a light orange oil.

Yield: 36%

$^1$H NMR (400 MHz, DMSO-d$_6$) δ 7.06 (dd, J=11.4, 6.9 Hz, 1H), 6.58 (dd, J=11.6, 7.5 Hz, 1H), 5.53 (s, 2H), 3.80 (s, 2H).

A.34. Synthesis of 3-(4-amino-2,5-difluoro-phenyl)propanenitrile X-34

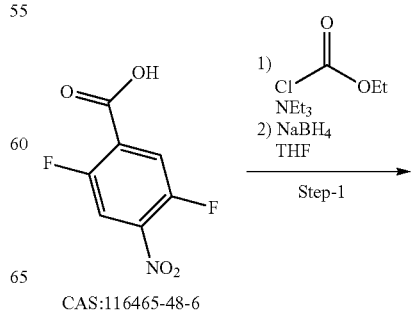

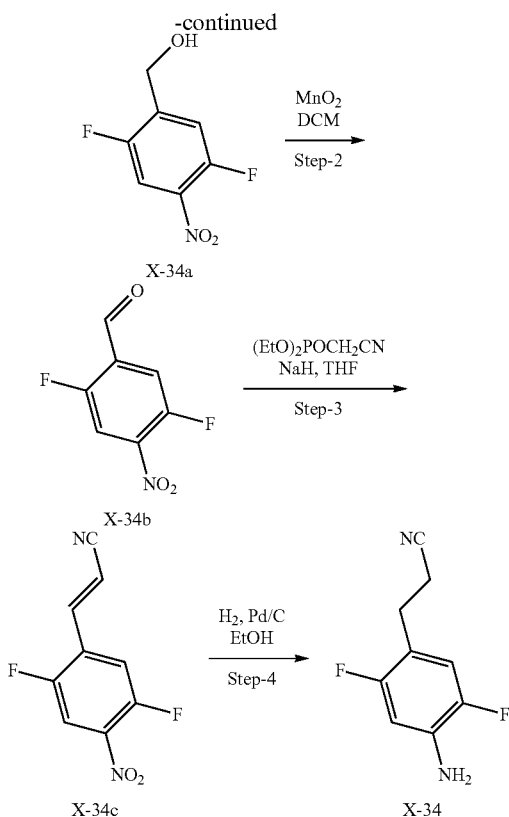

Step-1: Synthesis of
(2,5-difluoro-4-nitrophenyl)methanol X-34a 2,5-Difluoro-4-nitrobenzoic acid (2.5 g, 12.3 mmol) was placed in dry tetrahydrofuran (10 mL) under argon atmosphere. Then triethylamine (1.7 mL, 12.3 mmol) was added and the solution was cooled to 0° C. A solution of ethyl chloroformate (1.2 mL, 12.9 mmol) in dry tetrahydrofuran (15 mL) was added over 15 min and the reaction mixture was stirred overnight at room temperature. The precipitated triethylammonium chloride was filtered off and, while stirring, sodium borohydride (1.4 g, 3.69 mmol) was added portionwise to the filtrate. Next, methanol (15 mL) was added dropwise and the reaction mixture was stirred overnight at room temperature. It was then acidified with 1N HCl until pH=2 and the tetrahydrofuran was removed under vacuum. The residue was taken up in ethyl acetate and washed with a saturated sodium hydrogen carbonate solution. The aqueous phase was then extracted three times with ethyl acetate. The combined organic phases were washed with brine, dried over magnesium sulfate and evaporated to dryness. The crude residue was purified by column chromatography (SiO$_2$, DCM) to afford (2,5-difluoro-4-nitrophenyl)methanol X-34a (1.61 g) as an orange solid.
Yield: 70%.
$^1$H NMR (400 MHz, DMSO-d$_6$) δ 7.77 (dd, J=8.8, 5.8 Hz, 1H), 7.51 (dd, J=11.0, 5.7 Hz, 1H), 4.86 (s, 2H), 2.19 (s, 1H).

Step-2: Synthesis of
2,5-difluoro-4-nitrobenzaldehyde X-34b (2,5-Difluoro-4-nitrophenyl)methanol X-34a (320 mg, 1.69 mmol) was stirred in dichloromethane (10 mL) with activated manganese oxide (163 g, 169.2 mmol) at room temperature. After two days the reaction mixture was filtered over celite and evaporated to dryness to afford 2,5-difluoro-4-nitrobenzaldehyde X-34b (231 mg) as an orange solid.
Yield: 73%.
$^1$H NMR (400 MHz, DMSO-d$_6$) δ 10.36 (d, J=2.6 Hz, 1H), 7.93 (dd, J=8.7, 5.4 Hz, 1H), 7.80 (dd, J=9.7, 5.4 Hz, 1H).

Step-3: Synthesis of (E)-3-(2,5-difluoro-4-nitrophenyl)acrylonitrile X-34c

Diethyl cyanomethylphosphonate (227 mg, 1.238 mmol) was placed in dry tetrahydrofuran (2 mL) under argon atmosphere. At 0° C., sodium hydride (60% dispersion in mineral oil, 77 mg, 1.925 mmol) was added. The mixture was stirred for 15 min at room temperature and 2,5-difluoro-4-nitrobenzaldehyde X-34b (240 mg, 1.238 mmol) in solution in dry tetrahydrofuran (3 mL) was added slowly at 0° C. After 1.5 h, the reaction mixture was quenched with a saturated sodium hydrogen carbonate solution. The product was next extracted with ethyl acetate, and the organic phase was washed once with a saturated sodium hydrogen carbonate solution. The combined aqueous layers were extracted three times with ethyl acetate. The combined organic phases were washed brine, dried over magnesium sulfate and evaporated to dryness. The crude residue was purified by column chromatography (SiO$_2$, CombiFlash 24 g, 2% to 15% EtOAc in petroleum ether) to afford the desired product (E)-3-(2,5-difluoro-4-nitrophenyl)acrylonitrile X-34c (40 mg) as a yellow solid.
Yield: 15%.
$^1$H NMR (400 MHz, DMSO-d$_6$) δ 8.24 (dd, J=9.8, 6.2 Hz, 1H), 8.11 (dd, J=11.8, 5.9 Hz, 1H), 7.72 (d, J=16.7 Hz, 1H), 6.77 (d, J=16.7 Hz, 1H).

Step-4: Synthesis of
3-(4-amino-2,5-difluoro-phenyl)propanenitrile X-34

(E)-3-(2,5-Difluoro-4-nitrophenyl)acrylonitrile X-34c (65 mg, 0.309 mmol) was dissolved in absolute ethanol (8 mL) under argon atmosphere. Then palladium on carbon (10 wt. % loading, 16 mg, 0.015 mmol) was added and the flask was flushed with argon, and then hydrogen. The reaction mixture was stirred for 4 h under hydrogen atmosphere. It was then filtered over celite and evaporated to dryness. The crude residue was purified by column chromatography (SiO$_2$, CombiFlash 4 g, 2% to 20% EtOAc in petroleum ether) to afford 3-(4-amino-2,5-difluoro-phenyl)propanenitrile X-34 (35 mg) as a yellow oil that crystalizes on standing.
Yield: 63%.
$^1$H NMR (400 MHz, DMSO-d$_6$) δ 7.01 (dd, J=11.7, 6.9 Hz, 1H), 6.52 (dd, J=11.6, 7.6 Hz, 1H), 5.34 (br s, 2H), 2.75-2.69 (m, 4H).

A.35. Synthesis of
3,6-difluoro-5-(2-fluoroethoxy)pyridin-2-amine
X-35

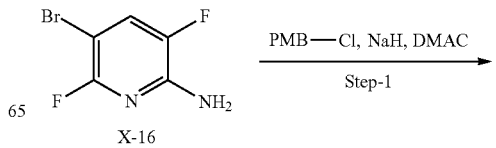

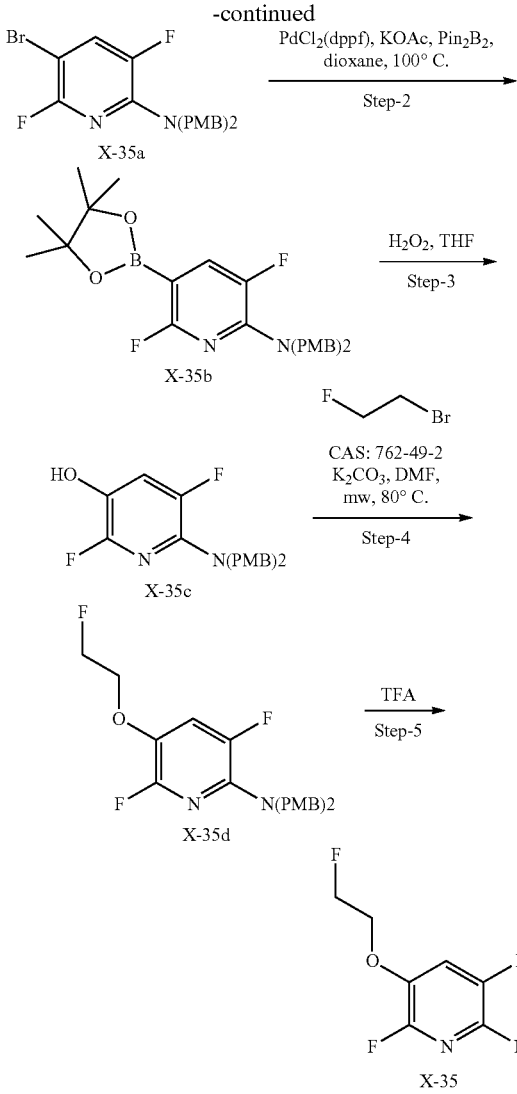

Step-1: Synthesis of 5-bromo-3,6-difluoro-N,N-bis[(4-methoxyphenyl)methyl]pyridin-2-amine X-35a To a solution of 5-bromo-3,6-difluoropyridin-2-amine X-16 (4.00 g, 19.0 mmol) in DMAC (40 mL) was added NaH (2.29 g, 57.1 mmol) portion wise at 0° C. and the reaction was stirred at the same temperature for 30 min. Para-methoxybenzyl chloride (5.19 mL, 38.1 mmol) was added dropwise at 0° C. and the reaction mixture was stirred at room temperature for 2 h. Progress of the reaction was monitored by TLC. After completion, the reaction mixture was cooled to 0° C., quenched with saturated NH$_4$Cl (20 mL), poured into H$_2$O (60 mL) and extracted with EtOAc (3×60 mL). The organic layer was separated, washed with brine (2×80 mL), dried over anhydrous Na$_2$SO$_4$ and concentrated under vacuum. The crude obtained was purified by column chromatography (silica, 100-200 mesh, 4% EtOAc in hexanes) to afford 5-bromo-3,6-difluoro-N,N-bis[(4-methoxyphenyl)methyl]pyridin-2-amine X-35a (8.2 g, 96%) as an off-white solid.

Yield: 96%.

$^1$H NMR (400 MHz, DMSO-d$_6$) δ 3.72 (s, 6H) 4.57 (s, 4H) 6.87-6.89 (m, 4H) 7.16-7.18 (m, 4H) 7.99-8.07 (m, 1H).

Step-2: Synthesis of 3,6-difluoro-N,N-bis[(4-methoxyphenyl)methyl]-5-(4,4,5,5-tetramethyl-1,3,2-dioxaborolan-2-yl)pyridin-2-amine X-35b To a solution of 5-bromo-3,6-difluoro-N,N-bis[(4-methoxyphenyl)methyl]pyridin-2-amine X-35a (4.00 g, 8.90 mmol) in dioxane (160 mL) was added Bis(pinacolato)diboron (4.52 g, 17.8 mmol) and KOAc (3.06 g, 31.2 mmol) at room temperature and the reaction mixture was purged with argon for 20 min followed by addition of PdCl$_2$(dppf) (0.65 g, 0.89 mmol). The reaction mixture was purged with argon for 10 min and heated at 100° C. for 16 h. Progress of the reaction was monitored by TLC. After completion, the reaction mixture was cooled, filtered through a pad of celite and washed with EtOAc (2×80 mL). The filtrate was concentrated under vacuum, the residue was diluted with H$_2$O (100 mL) and extracted with EtOAc (2×80 mL). The organic layer was separated, washed with brine (2×100 mL), dried over anhydrous Na$_2$SO$_4$ and concentrated under vacuum. The crude obtained was purified by column chromatography (silica, 100-200 mesh, 8% EtOAc in hexanes) to afford 3,6-difluoro-N,N-bis[(4-methoxyphenyl)methyl]-5-(4,4,5,5-tetramethyl-1,3,2-dioxaborolan-2-yl)pyridin-2-amine X-35b (2.60 g) as an off-white solid.

Yield: 59%.

$^1$H NMR (400 MHz, DMSO-d$_6$) δ 1.26 (s, 12H) 3.73 (s, 6H) 4.64 (s, 4H) 6.89 (d, J=8.31 Hz, 4H) 7.17 (d, J=8.80 Hz, 4H) 7.51-7.56 (m, 1H).

Step-3: Synthesis of 6-[bis[(4-methoxyphenyl)methyl]amino]-2,5-difluoro-pyridin-3-ol X-35c To a solution of 3,6-difluoro-N,N-bis[(4-methoxyphenyl)methyl]-5-(4,4,5,5-tetramethyl-1,3,2-dioxaborolan-2-yl)pyridin-2-amine X-35b (2.50 g, 5.04 mmol) in THF (30 mL) was added 30% H$_2$O$_2$ solution in H$_2$O (10 mL) at 0° C. and the reaction mixture was stirred at same temperature for 15 min. The reaction mixture was stirred at room temperature for 1.5 h. Progress of the reaction was monitored by TLC and LCMS. The reaction mixture was poured into 5% Na$_2$S2O$_3$ solution in cold H$_2$O (250 mL) at 0° C., diluted with H$_2$O (100 mL) and extracted with EtOAc (2×100 mL). The organic layer was separated, dried over anhydrous Na$_2$SO$_4$ and concentrated under vacuum to afford 6-[bis[(4-methoxyphenyl)methyl]amino]-2,5-difluoro-pyridin-3-ol X-35c (1.74 g crude) as a yellow semi solid.

This compound was used as such for the next reaction without further purification.

Basic LC-MS Method 2 (ES$^+$): 387 (M+H)$^+$, 93% purity.

$^1$H NMR (400 MHz, DMSO-d$_6$) δ 3.71 (s, 6H) 4.32 (s, 4H) 6.86 (d, J=8.80 Hz, 4H) 7.14 (d, J=8.31 Hz, 4H) 7.22-7.27 (m, 1H) 9.84 (s, 1H).

Step-4: Synthesis of 3,6-difluoro-5-(2-fluoroethoxy)-N,N-bis[(4-methoxyphenyl)methyl]pyridin-2-amine X-35d To a solution of 6-[bis[(4-methoxyphenyl)methyl]amino]-2,5-difluoro-pyridin-3-ol X-35c (0.70 g, 1.68 mmol) in DMF (13 mL) was added K$_2$CO$_3$ (0.70 g, 5.04 mmol) and 1-bromo-2-fluoroethane (0.43 g, 3.36 mmol) at room temperature. The reaction mixture was heated in microwave at 80° C. for 15 min. Progress of the reaction was monitored by TLC and LCMS. After completion, the reaction mixture was cooled to room temperature, poured into H$_2$O (30 mL) and extracted with EtOAc (3×25 mL). The organic layer was separated, washed with brine (2×30 mL), dried over anhydrous Na$_2$SO$_4$ and concentrated under vacuum. The crude obtained was purified by column chromatography (silica, 100-200 mesh, 25% EtOAc in hexanes) to afford 3,6-difluoro-5-(2-fluoroethoxy)-N,N-bis[(4-methoxyphenyl)methyl]pyridin-2-amine X-35d (0.52 g) as a brown liquid.

Yield: 71%.

Basic LC-MS Method 2 (ES$^+$): 433 (M+H)$^+$, 99% purity.

$^1$H NMR (400 MHz, DMSO-d$_6$) δ 3.72 (s, 6H) 4.21-4.25 (m, 1H) 4.29-4.32 (m, 1H) 4.42 (s, 4H) 4.63-4.66 (m, 1H) 4.75-4.78 (m, 1H) 6.87 (d, J=8.86 Hz, 4H) 7.15 (d, J=8.37 Hz, 4H) 7.69-7.76 (m, 1H).

Step-5: Synthesis of 3,6-difluoro-5-(2-fluoroethoxy)pyridin-2-amine X-35

To 3,6-difluoro-5-(2-fluoroethoxy)-N,N-bis[(4-methoxyphenyl)methyl]pyridin-2-amine X-35d (0.50 g, 1.15 mmol) was added TFA (5 mL) at 0° C. and the reaction mixture was stirred at same temperature for 30 min. The reaction mixture was stirred at room temperature for 2 h. Progress of the reaction was monitored by TLC and LCMS. After completion, the reaction mixture was concentrated under vacuum. The residue was diluted with H$_2$O (25 mL), basified with aqueous NaHCO$_3$ solution (10 mL) and extracted with EtOAc (2×25 mL). The organic layer was separated, washed with brine (2×40 mL), dried over anhydrous Na$_2$SO$_4$ and concentrated under vacuum. The crude obtained was purified by triturating with Et$_2$O (10 mL) and dried under vacuum to afford 3,6-difluoro-5-(2-fluoroethoxy)pyridin-2-amine X-35 (0.258 g) as an off-white solid.

Yield: 80%.

Basic LC-MS Method 2 (ES$^+$): 193 (M+H)$^+$, 69% purity.

$^1$H NMR (400 MHz, DMSO-d$_6$) δ 4.13-4.17 (m, 1H) 4.20-4.25 (m, 1H) 4.59-4.64 (m, 1H) 4.71-4.76 (m, 1H) 6.10 (s, 2H) 7.57-7.62 (m, 1H).

A.36. Synthesis of 3,6-difluoro-5-(2-methoxyethoxy)pyridin-2-amine X-36

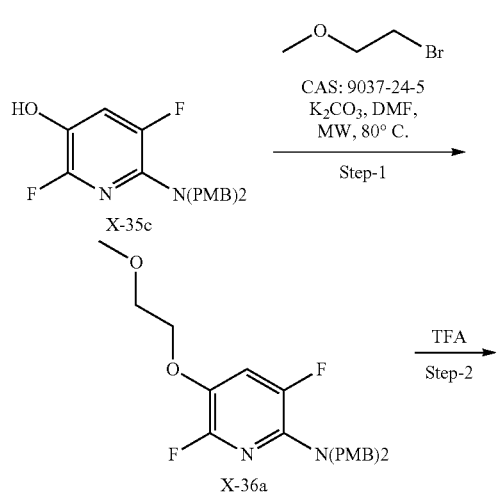

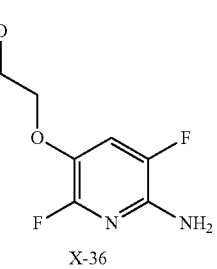

Step-1: Synthesis of 3,6-difluoro-5-(2-methoxyethoxy)-N,N-bis[(4-methoxyphenyl)methyl]pyridin-2-amine X-36a To a solution of 6-[bis[(4-methoxyphenyl)methyl]amino]-2,5-difluoro-pyridin-3-ol X-35c (0.60 g, 1.44 mmol) and 2-bromoethyl methyl ether (0.70 g, 5.04 mmol) in DMF (10 mL) was added K$_2$CO$_3$ (0.90 g, 6.48 mmol) and the reaction mixture was heated in microwave at 80° C. for 30 min. The reaction mixture was stirred at room temperature for 16 h. Progress of the reaction was monitored by TLC and LCMS. After completion, the reaction mixture was diluted with H$_2$O (100 mL) and extracted with EtOAc (200 mL). The organic layer was separated, dried over anhydrous Na$_2$SO$_4$ and concentrated under vacuum. The crude obtained was purified by column chromatography (silica, 100-200 mesh, 2% EtOAc in hexanes) to afford 3,6-difluoro-5-(2-methoxyethoxy)-N,N-bis[(4-methoxyphenyl)methyl]pyridin-2-amine X-36a (0.205 g) as a brown semi solid.

Yield: 31%.

Basic LC-MS Method 2 (ES$^+$): 445 (M+H)$^+$, 96% purity.

$^1$H NMR (400 MHz, DMSO-d$_6$) δ 3.28 (s, 3H) 3.59-3.63 (m, 2H) 3.71 (s, 6H) 4.09-4.14 (m, 2H) 4.40 (s, 4H) 6.85-6.89 (m, 4H) 7.15 (d, J=8.31 Hz, 4H) 7.66-7.71 (m, 1H).

Step-2: Synthesis of 3,6-difluoro-5-(2-methoxyethoxy)pyridin-2-amine X-36

To 3,6-difluoro-5-(2-methoxyethoxy)-N,N-bis[(4-methoxyphenyl)methyl]pyridin-2-amine X-36a (0.20 g, 0.43 mmol) was added TFA (6 mL) at 0° C. and the reaction mixture was stirred at room temperature for 2 h. Progress of the reaction was monitored by TLC. After completion, the reaction mixture was concentrated under vacuum. The residue was diluted with H$_2$O (100 mL), basified with saturated NaHCO$_3$ solution (50 mL) and extracted with EtOAc (200 mL). The organic layer was separated, dried over anhydrous Na$_2$SO$_4$ and concentrated under vacuum to afford 3,6-difluoro-5-(2-methoxyethoxy)pyridin-2-amine X-36 (0.15 g crude) as a brown semi solid.

This compound was used as such for the next reaction without further purification.

$^1$H NMR (400 MHz, DMSO-d$_6$) δ 3.29 (s, 3H) 3.53-3.59 (m, 2H) 4.00-4.04 (m, 2H) 6.01 (s, 2H) 7.51-7.57 (m, 1H).

B. Synthesis of Intermediates of Formula XI

B.1. Synthesis of 6-cyclopropyl-1H-indole XI-1

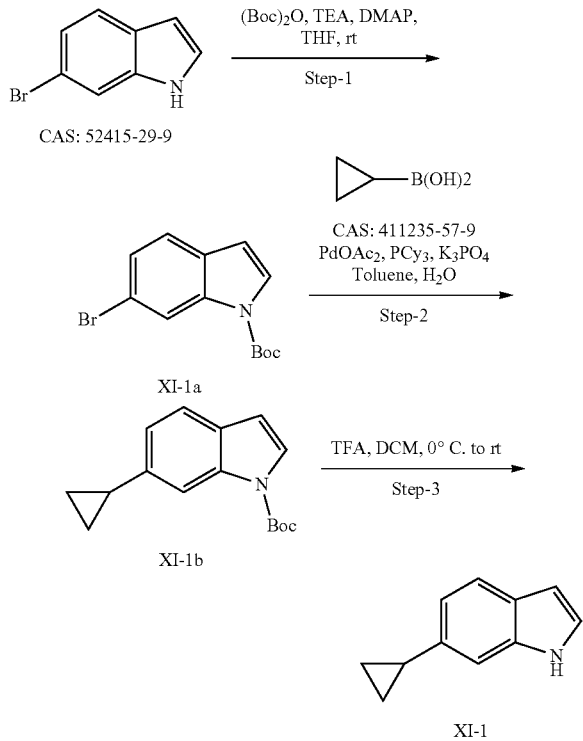

Step 1: Synthesis of tert-butyl 6-bromoindole-1-carboxylate XI-1a

To a solution of 6-bromo-1H-indole (2.70 g, 13.8 mmol) in THF (30 mL) was added triethylamine (2.80 g, 27.6 mmol) at 0° C. and the reaction mixture was stirred at same temperature for 5 min. DMAP (0.84 g, 6.90 mmol) and (Boc)$_2$O (4.50 g, 20.7 mmol) were added at 0° C. and the reaction mixture was stirred at room temperature for 3 h. Progress of the reaction was monitored by TLC. After completion, the reaction mixture was quenched with ice and concentrated under vacuum. The residue was diluted with H$_2$O (100 mL) and extracted with EtOAc (3×100 mL). The organic layer was separated, dried over anhydrous Na$_2$SO$_4$ and concentrated under vacuum. The crude obtained was purified by column chromatography (silica, 100-200 mesh, 1% EtOAc in hexanes) to afford 3.8 g of tert-butyl 6-bromoindole-1-carboxylate XI-1a as a light yellow solid.

Yield: 92%.

$^1$H NMR (400 MHz, DMSO-d$_6$) δ 1.65 (s, 9H) 6.73 (d, J=3.42 Hz, 1H) 7.20-7.27 (m, 1H) 7.60 (d, J=8.31 Hz, 1H) 7.69 (d, J=3.42 Hz, 1H) 8.23 (s, 1H).

Step-2: Synthesis of tert-butyl 6-cyclopropylindole-1-carboxylate XI-1b

To a solution of tert-butyl 6-bromoindole-1-carboxylate XI-1a (0.70 g, 2.36 mmol) and cyclopropylboronic acid (0.30 g, 3.55 mmol) in toluene (15 mL) was added K$_3$PO$_4$ (1.00 g, 4.72 mmol), tricyclohexylphosphine (PCy$_3$) (0.13 g, 0.47 mmol) and H$_2$O (0.70 mL). The reaction mixture was purged with argon for 15 min followed by addition of Pd(OAc)$_2$ (0.05 g, 0.24 mmol). The reaction mixture was heated at 100° C. for 8 h. Progress of the reaction was monitored by TLC. After completion, the reaction mixture was diluted with H$_2$O (20 mL) and extracted with EtOAc (2×20 mL). The organic layer was separated, dried over anhydrous Na$_2$SO$_4$ and concentrated in vacuum. The crude obtained was purified by column chromatography (silica, 100-200 mesh, 0.5 to 0.8% EtOAc in hexanes) to afford 0.5 g of tert-butyl 6-cyclopropylindole-1-carboxylate XI-1b as a colourless liquid.

Yield: 83%.

$^1$H NMR (400 MHz, CDCl$_3$) δ 0.70-0.78 (m, 2H) 0.96-1.03 (m, 2H) 1.67 (s, 9H) 1.98-2.10 (m, 1H) 6.50 (s, 1H) 6.99 (d, J=7.82 Hz, 1H) 7.42 (d, J=8.31 Hz, 1H) 7.50 (d, J=3.42 Hz, 1H) 7.90 (brs, 1H).

Step-3: Synthesis of 6-cyclopropyl-1H-indole XI-1

To a solution of tert-butyl 6-cyclopropylindole-1-carboxylate XI-1b (1.30 g, 5.10 mmol) in DCM (25 mL) was added TFA (2.5 mL) dropwise at 0° C. The reaction mixture was stirred at room temperature for 3 h. Progress of the reaction was monitored by TLC. After completion, the reaction mixture was concentrated in vacuum. The residue was diluted with DCM (80 mL) and neutralised with triethylamine (4 mL) at 0° C. The organic layer was separated, washed with cold brine (20 mL), dried over anhydrous Na$_2$SO$_4$ and concentrated in vacuum. The crude obtained was purified by column chromatography (silica, 100-200 mesh, 4 to 5% EtOAc in hexanes) to afford 0.32 g of 6-cyclopropyl-1H-indole XI-1 as a colourless liquid.

Yield: 41%.

$^1$H NMR (400 MHz, CDCl$_3$) δ 0.71-0.76 (m, 2H) 0.93-1.00 (m, 2H) 1.98-2.08 (m, 1H) 6.51 (s, 1H) 6.90 (d, J=8.31 Hz, 1H) 7.13-7.18 (m, 2H) 7.52-7.58 (m, 1H) 8.03 (brs, 1H).

B.2. Synthesis of 6-chloro-benzofuran XI-2

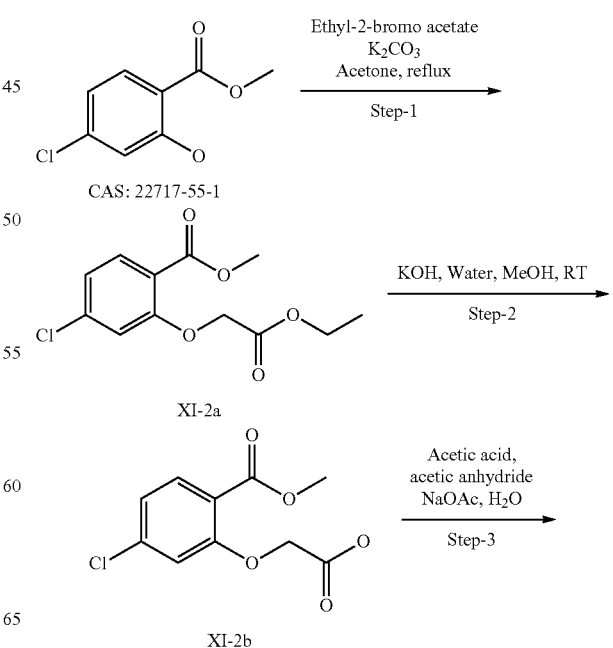

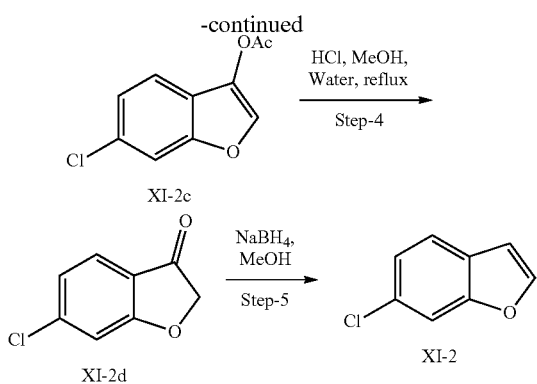

Step-1: Synthesis of methyl 4-chloro-2-(2-ethoxy-2-oxoethoxy)benzoate XI-2a

To a solution of methyl 4-chloro-2-hydroxy-benzoate (5.00 g, 26.7 mmol) in acetone (60 mL) was added ethyl-2-bromo acetate (6.72 g, 40.2 mmol) and $K_2CO_3$ (5.56 g, 40.2 mmol). The reaction mixture was heated to reflux for 16 h. Progress of the reaction was monitored by TLC. After completion, the reaction mixture was concentrated under vacuum. The residue was dissolved in petroleum ether (80 mL), filtered and the filtrate was concentrated under vacuum. The crude obtained was purified by column chromatography (silica, 100-200 mesh, 20% EtOAc in hexanes) to afford methyl 4-chloro-2-(2-ethoxy-2-oxoethoxy)benzoate XI-2a (6.80 g) as a red semi solid.

The product was confirmed by TLC analysis only.
Yield: 93%.

Step-2: Synthesis of 2-(5-chloro-2-(methoxycarbonyl)phenoxy)acetic acid XI-2b To a solution of XI-2a (6.80 g, 24.9 mmol) in MeOH (180 mL) was added KOH (3.13 g, 55.8 mmol) solution in $H_2O$ (40 mL) at 0° C. and the reaction mixture was stirred at room temperature for 2 h. Progress of the reaction was monitored by TLC and LCMS. After completion, the reaction mixture was concentrated under vacuum. The residue was dissolved in $H_2O$ (100 mL) and acidified to pH 2 with 2N HCl. The precipitated solid was filtered, dried under vacuum to afford 2-(5-chloro-2-(methoxycarbonyl)phenoxy)acetic acid XI-2b (3.80 g) as a white solid.
Yield: 66%.
Basic LCMS Method 2 (ES$^+$): 245.00 (M+H)$^+$, 16% purity.

Step-3: Synthesis of 6-chlorobenzofuran-3-yl acetate XI-2c

To a solution of XI-2b (3.80 g, 16.4 mmol) in $CH_3COOH$ (75 mL) was added $Ac_2O$ (95 mL) followed by addition of NaOAc (3.19 g, 37.7 mmol). The reaction mixture was heated at 140° C. for 5 h. Progress of the reaction was monitored by TLC. After completion, the reaction mixture was diluted with $H_2O$ (300 mL) and extracted with EtOAc (60 mL). The organic layer was separated, washed with saturated $NaHCO_3$ (20 mL), dried over anhydrous $Na_2SO_4$ and concentrated under vacuum to afford 6-chlorobenzofuran-3-yl acetate XI-2c (3.00 g, 87%) as a red liquid.

This compound was used as such for the next reaction without further purification.
$^1$H NMR (400 MHz, DMSO-d$_6$) δ 2.37 (s, 3H) 7.34-7.40 (m, 1H) 7.60 (s, 1H) 7.78-7.82 (m, 1H) 8.24 (s, 1H).

Step-4: Synthesis of 6-chlorobenzofuran-3(2H)-one XI-2d

To a solution of XI-2c (3.00 g, 1.42 mmol) in MeOH (150 mL) was added concentrated. HCl (4 mL) and $H_2O$ (35 mL) and the reaction mixture was heated at reflux for 3 h. Progress of the reaction was monitored by TLC. After completion, the reaction mixture was cooled to room temperature, diluted with $H_2O$ (20 mL) and filtered. The crude obtained was washed with $H_2O$ (20 mL) and dried under vacuum to afford 6-chlorobenzofuran-3(2H)-one XI-2d (2.20 g, 92%) as a red solid.
$^1$H NMR (400 MHz, DMSO-d$_6$) δ 2.34 (s, 2H) 7.23 (d, J=7.83 Hz, 1H) 7.38 (d, J=7.83 Hz, 1H) 7.70 (t, J=9.05 Hz, 1H).

Step-5: Synthesis of 6-chlorobenzofuran XI-2

To a solution of XI-2d (2.20 g, 13.0 mmol) in MeOH (75 mL) was added NaBH$_4$ (1.08 g, 28.7 mmol) portion wise at 0° C. The reaction mixture was stirred at room temperature for 4 h. Progress of the reaction was monitored by TLC. After completion, the reaction mixture was quenched with acetone (20 mL), diluted with 3 N HCl (35 mL) and stirred for 1 h. The reaction mixture was extracted with EtOAc (50 mL), dried over anhydrous $Na_2SO_4$ and concentrated under vacuum to afford 6-chlorobenzofuran XI-2 (1.60 g) as a colourless liquid.

This compound was used as such for the next reaction without further purification.
Yield: 80%.
$^1$H NMR (400 MHz, DMSO-d$_6$) δ 6.99 (d, J=0.98 Hz, 1H) 7.30 (d, J=8.31 Hz, 1H) 7.67 (d, J=8.31 Hz, 1H) 7.77 (s, 1H) 8.04 (d, J=1.96 Hz, 1H).

B.3. Synthesis of 6-(2-methoxyethoxy)-1H-indole XI-3

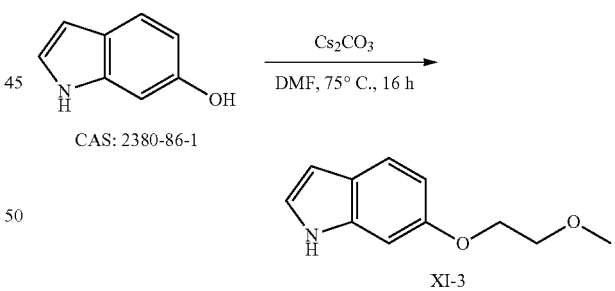

A solution of 1H-indol-6-ol (0.95 g, 7.12 mmol) in DMF (12 mL) was treated with cesium carbonate (2.79 g, 8.59 mmol) and stirred at 75° C. for 16 h (TLC control). Subsequently, the solvent was evaporated and the residue was diluted with ethyl acetate, washed with 1 N NaOH solution, water and brine. The combined organic extracts were dried over MgSO$_4$, filtered and evaporated. The residue was purified by column chromatography (cyclohexane/ethyl acetate=4:1) and afforded 0.88 g of 6-(2-methoxyethoxy)-1H-indole XI-3 as a white solid.

Yield: 65%.
Neutral LCMS Method 3 (ES$^+$): 192.0 (M+H)$^+$, 96% purity.

B.4. Synthesis of 6-chloro-7-methoxy-1H-indole XI-4

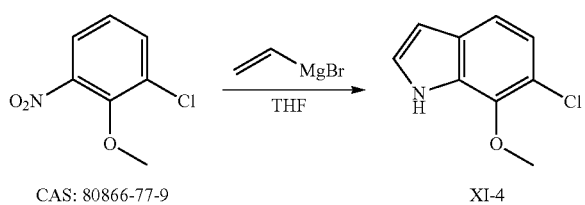

CAS: 80866-77-9    XI-4

To a solution of 1-chloro-2-methoxy-3-nitro-benzene (1.00 g, 5.34 mmol) in THF (20 mL) was added vinyl magnesium bromide (16.0 mL, 16.0 mmol) at −20° C. and the reaction mixture was stirred at room temperature for 3 h. Progress of the reaction was monitored by TLC and LCMS. After completion, the reaction mixture was quenched with ice and extracted with EtOAc (100 mL). The organic layer was separated, dried over anhydrous $Na_2SO_4$ and concentrated under vacuum. The crude obtained was purified by column chromatography (silica, 100-200 mesh, 5 to 10% EtOAc in hexanes) to afford 6-chloro-7-methoxy-1H-indole XI-4 (0.50 g) as a viscous oil.

Yield: 51%

$^1$H NMR (400 MHz, DMSO-$d_6$) δ 3.91 (s, 3H) 6.47 (s, 1H) 6.99 (d, J=8.40 Hz, 1H) 7.29 (d, J=8.00 Hz, 1H) 7.35 (s, 1H) 11.46 (brs, 1H).

B.5. Synthesis of 6-chloro-7-fluoro-1H-indole XI-5

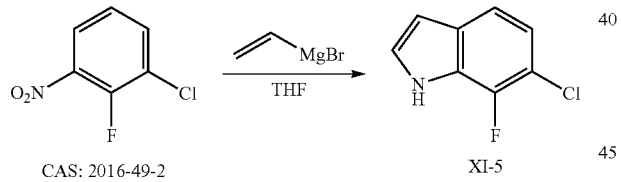

CAS: 2016-49-2    XI-5

To a solution of 1-chloro-2-fluoro-3-nitro-benzene (2.50 g, 14.2 mmol) in THF (50 mL) was added vinyl magnesium bromide (5.61 g, 42.7 mmol) at −78° C. and the reaction mixture was stirred at same temperature for 1 h. Progress of the reaction was monitored by TLC and LCMS. After completion, the reaction mixture was quenched with saturated $NH_4Cl$ (100 mL), diluted with $H_2O$ (400 mL) and extracted with EtOAc (500 mL). The organic layer was separated, dried over anhydrous $Na_2SO_4$ and concentrated under vacuum. The crude obtained was purified by column chromatography (silica, 100-200 mesh, 5% EtOAc in hexanes) to afford 6-chloro-7-fluoro-1H-indole XI-5 (0.60 g) as a red liquid.

Yield: 17%

Basic LCMS Method 2 (ES$^-$): 168.00 (M−H)$^-$, 66% purity.

B.6. Synthesis of 6-(trifluoromethyl)-1H-pyrrolo[2,3-b]pyridine XI-6

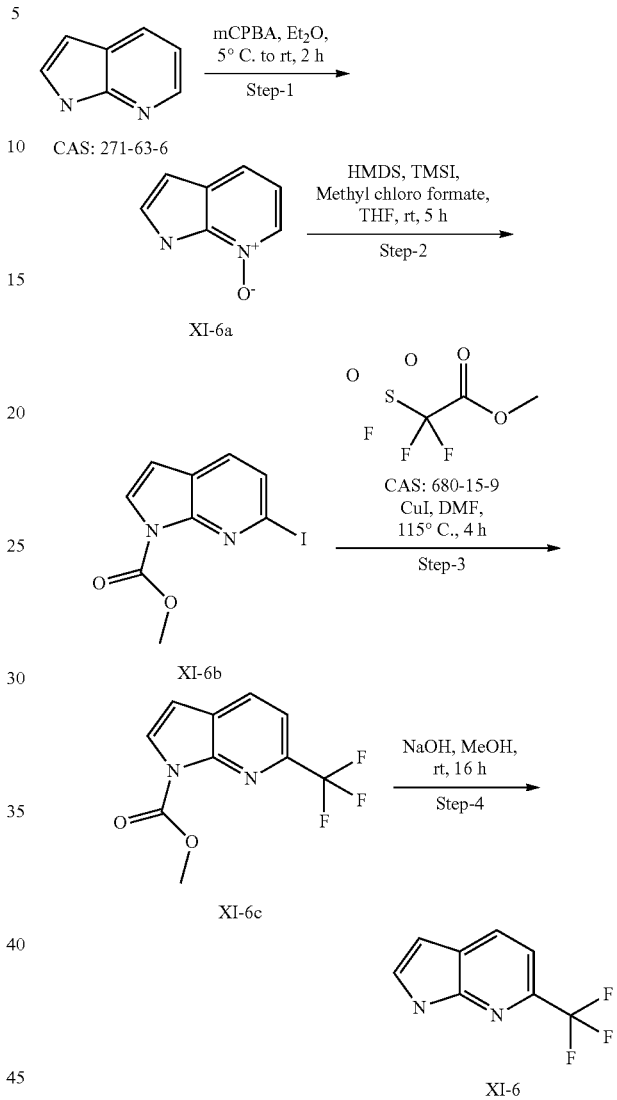

Step-1: Synthesis of 7-oxido-1H-pyrrolo[2,3-b]pyridin-7-ium XI-6a

To a solution of 1H-pyrrolo[2,3-b]pyridine (2.00 g, 16.9 mmol) in $Et_2O$ (50 mL) was added m-CPBA (3.80 g, 22.0 mmol) portion wise at 5° C. and the reaction mixture was stirred at room temperature for 2 h. Progress of the reaction was monitored by TLC and LCMS. After completion, the reaction mixture was filtered, washed with $Et_2O$ (12 mL) and dried under vacuum to afford 7-oxido-1H-pyrrolo[2,3-b]pyridin-7-ium XI-6a (3.75 g) as an off-white solid.

This compound was used as such for the next reaction without further purification.

Yield: 89%

Basic LCMS Method 2 (ES$^+$): 135 (M+H)$^+$, 54% purity.

Step-2: Synthesis of methyl 6-iodopyrrolo[2,3-b]pyridine-1-carboxylate XI-6b To a solution of 7-oxido-1H-pyrrolo[2,3-b]pyridin-7-ium XI-6a (1.60 g, 11.9 mmol) in THF (100 mL) was added hexamethyldisilazane (2.31 g, 14.3 mmol) and trimethylsilyl iodide (4.77 g, 23.9 mmol) dropwise followed by dropwise addition of methyl chloroformate (2.25 g, 23.9 mmol). The reaction mixture was stirred at room temperature for 5 h. Progress of the reaction was monitored by TLC and LCMS. After completion, the reaction mixture was concentrated under vacuum. The residue was diluted with EtOAc (150 mL) and washed with saturated NaHCO$_3$ (100 mL). The organic layer was separated, dried over anhydrous Na$_2$SO$_4$ and concentrated under vacuum. The crude obtained was purified by column chromatography (silica, 100-200 mesh, 10% EtOAc in hexanes) to afford methyl 6-iodopyrrolo[2,3-b]pyridine-1-carboxylate XI-6b (1.00 g) as a brown solid.

Yield: 26%

Basic LCMS Method 2 (ES$^+$): 303 (M+H)$^+$, 95% purity.

$^1$H NMR (400 MHz, DMSO-d$_6$) δ 4.12 (s, 3H) 6.55 (d, J=3.91 Hz, 1H) 7.54-7.58 (m, 1H) 7.61-7.65 (m, 1H) 7.69 (d, J=3.91 Hz, 1H).

Step-3: Synthesis of methyl 6-(trifluoromethyl)pyrrolo[2,3-b]pyridine-1-carboxylate XI-6c To a solution of methyl 6-iodopyrrolo[2,3-b]pyridine-1-carboxylate XI-6b (1.00 g, 3.14 mmol) in DMF (16.7 mL) was added methyl 2,2-difluoro-2-fluorosulfonyl-acetate (2.41 g, 12.6 mmol) and CuI (0.12 g, 0.62 mmol) and the reaction mixture was heated at 115° C. for 4 h. Progress of the reaction was monitored by TLC and LCMS. After completion, the reaction mixture was diluted with EtOAc (60 mL). The organic layer was separated, washed with H$_2$O (25 mL), NH4Cl (25 mL) and brine (25 mL), dried over anhydrous Na$_2$SO$_4$ and concentrated under vacuum. The crude obtained was purified by column chromatography (silica, 100-200 mesh, 10% EtOAc in hexanes) to afford methyl 6-(trifluoromethyl)pyrrolo[2,3-b]pyridine-1-carboxylate XI-6c (0.65 g) as an off-white solid.

Yield: 71%

Basic LCMS Method 2 (ES$^+$): 245 (M+H)$^+$, 84% purity.

$^1$H NMR (400 MHz, CHLOROFORM-d) δ 4.14 (s, 3H) 6.68 (d, J=3.42 Hz, 1H) 7.63 (d, J=8.31 Hz, 1H) 7.94 (d, J=2.93 Hz, 1H) 8.06 (d, J=7.83 Hz, 1H).

Step-4: Synthesis of 6-(trifluoromethyl)-1H-pyrrolo[2,3-b]pyridine XI-6

To a solution of methyl 6-(trifluoromethyl)pyrrolo[2,3-b]pyridine-1-carboxylate XI-6c (0.65 g, 2.23 mmol) in MeOH (33 mL) was added 1 M NaOH (0.26 g, 6.68 mmol) solution and the reaction mixture was stirred at room temperature for 16 h. Progress of the reaction was monitored by TLC and LCMS. After completion, the reaction mixture was concentrated under vacuum. The residue was extracted with DCM (3×15 mL). The organic layer was separated, dried over anhydrous Na$_2$SO$_4$ and concentrated under vacuum to afford 6-(trifluoromethyl)-1H-pyrrolo[2,3-b]pyridine XI-6 (0.45 g) as an off-white solid.

This compound was used as such for the next reaction without further purification.

Yield: 97%

Basic LCMS Method 2 (ES$^+$): 187 (M+H)$^+$, 89% purity.

$^1$H NMR (400 MHz, DMSO-d$_6$) δ 6.61 (t, J=2.00 Hz, 1H) 7.52 (d, J=7.82 Hz, 1H) 7.77 (t, J=2.93 Hz, 1H) 8.21 (d, J=8.31 Hz, 1H) 12.16 (brs, 1H).

B.7. Synthesis of 7-bromo-6-chloro-1H-indole XI-7

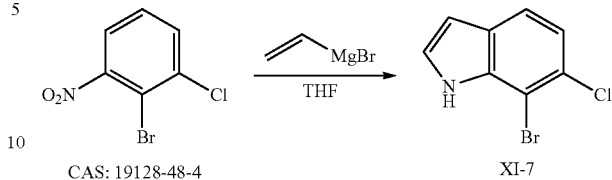

To a solution of 2-bromo-1-chloro-3-nitro-benzene (4.50 g, 19.0 mmol) in THF (90 mL) was added vinyl magnesium bromide (9.99 g, 76.1 mmol) dropwise at −78° C. and the reaction mixture was stirred at the same temperature for 2 h. Progress of the reaction was monitored by TLC and LCMS. The reaction was repeated at 4.5 g scale and the crude mixture of 2 reactions was clubbed. After completion, the reaction mixture was quenched with saturated NH$_4$Cl (500 mL), diluted with H$_2$O (500 mL) and extracted with EtOAc (1000 mL). The organic layer was separated, dried over anhydrous Na$_2$SO$_4$ and concentrated under vacuum. The crude obtained was purified by column chromatography (silica, 100-200 mesh, 2% EtOAc in hexanes) to afford 7-bromo-6-chloro-1H-indole XI-7 (3.05 g) as a yellow solid.

Yield: 33%

Basic LCMS Method 2 (ES$^-$): 228.00 (M−H)$^-$, 96% purity.

$^1$H NMR (400 MHz, DMSO-d$_6$) δ 6.59 (d, J=1.96 Hz, 1H) 7.18 (d, J=8.31 Hz, 1H) 7.41-7.45 (m, 1H) 7.57 (d, J=8.31 Hz, 1H) 11.48 (brs, 1H)

B.8. Synthesis of 6-chloro-7-(2,2-difluoroethoxy)-1H-indole XI-8

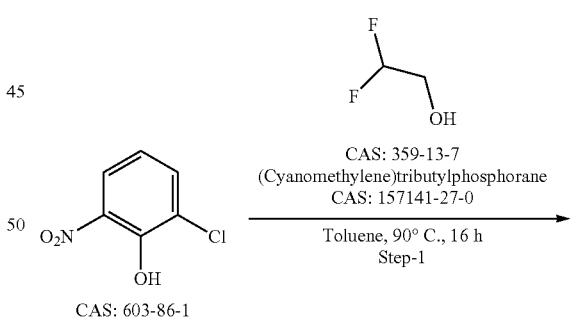

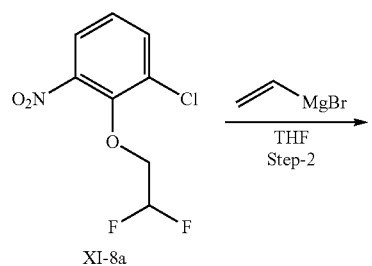

B.9. Synthesis of 6-chlorobenzothiophene XI-9

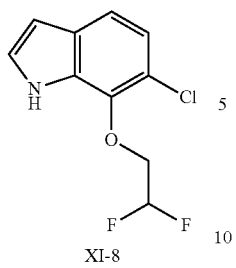

XI-8

Step-1: Synthesis of 1-chloro-2-(2,2-difluoroethoxy)-3-nitrobenzene XI-8a

To a solution of 2-chloro-6-nitro-phenol (0.50 g, 2.88 mmol) in toluene (15 mL) was added 2,2-difluoroethanol (0.37 mL, 5.76 mmol) followed by addition of (cyanomethylene)tributylphosphorane (0.91 mL, 3.46 mmol). The reaction mixture was heated at 90° C. for 16 h. Progress of the reaction was monitored by TLC and LCMS. After completion, the reaction mixture was diluted with $H_2O$ (50 mL) and extracted with EtOAc (3×25 mL). The organic layer was separated, washed with brine (30 mL), dried over anhydrous $Na_2SO_4$ and concentrated under vacuum. The crude obtained was purified by column chromatography (silica, 100-200 mesh, 10% EtOAc in hexanes) to afford 1-chloro-2-(2,2-difluoroethoxy)-3-nitrobenzene XI-8a (0.60 g) as a pale yellow solid.

Yield: 86%

$^1$H NMR (400 MHz, DMSO-$d_6$) δ 4.39-4.43 (m, 2H) 6.21-6.53 (m, 1H) 7.41-7.47 (m, 1H) 7.90-7.94 (m, 1H) 7.98 (dd, J=8.31, 1.47 Hz, 1H).

Step-2: Synthesis of 6-chloro-7-(2,2-difluoroethoxy)-1H-indole XI-8

To a solution of 1-chloro-2-(2,2-difluoroethoxy)-3-nitrobenzene XI-8a (0.60 g, 2.46 mmol) in THF (40 mL) was added 1 M vinylmagnesium bromide (1.29 g, 9.86 mmol) dropwise at −78° C. and the reaction mixture was stirred at same temperature for 1 h. The reaction mixture was then stirred at −40° C. for 1 h. Progress of the reaction was monitored by TLC and LCMS. After completion, the reaction mixture was quenched with saturated $NH_4Cl$ (35 mL) and extracted with EtOAc (2×50 mL). The organic layer was separated, dried over anhydrous $Na_2SO_4$ and concentrated under vacuum. The crude obtained was purified by column chromatography (silica, 100-200 mesh, 10% EtOAc in hexanes) to afford 6-chloro-7-(2,2-difluoroethoxy)-1H-indole XI-8 (0.13 g) as a pale yellow solid.

Yield: 23%

Basic LCMS Method 2 (ES$^-$): 230 (M−H)$^-$, 67% purity.

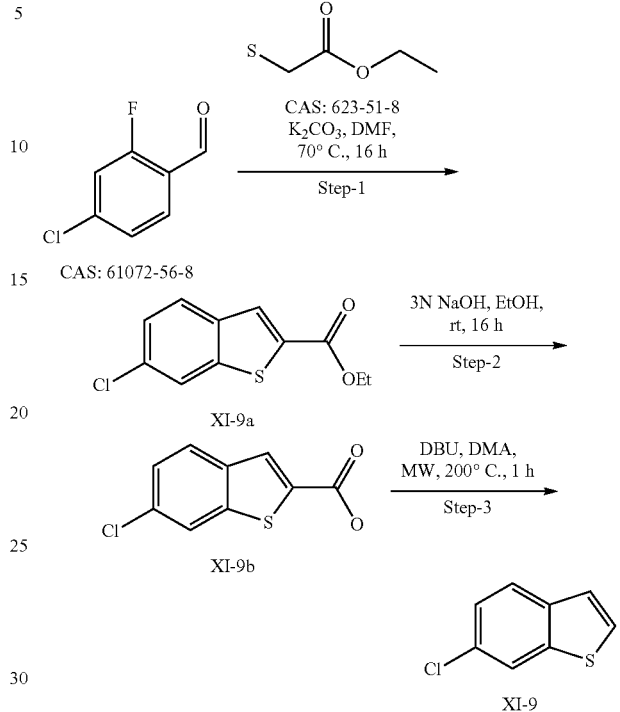

Step-1: Synthesis of ethyl 6-chlorobenzothiophene-2-carboxylate XI-9a

To a solution of 4-chloro-2-fluorobenzaldehyde (10.0 g, 63.0 mmol) in DMF (100 mL) was added ethyl thioglycolate (11.3 g, 94.6 mmol) followed by addition of $K_2CO_3$ (26.1 g, 189 mmol). The reaction mixture was heated at 70° C. for 16 h. Progress of the reaction was monitored by TLC. After completion, the reaction mixture was diluted with $H_2O$ (300 mL) and extracted with EtOAc (2×300 mL). The organic layer was separated, dried over anhydrous $Na_2SO_4$ and concentrated under vacuum to afford ethyl 6-chlorobenzothiophene-2-carboxylate XI-9a (9.10 g) as an off-white solid.

This compound was used as such for the next reaction without further purification.

Yield: 60%

$^1$H NMR (400 MHz, DMSO-$d_6$) δ 1.33 (t, J=7.09 Hz, 3H) 4.35 (q, J=7.01 Hz, 2H) 7.51 (dd, J=8.56, 1.71 Hz, 1H) 8.04 (d, J=8.80 Hz, 1H) 8.20 (s, 1H) 8.25 (d, J=0.98 Hz, 1H).

Step-2: Synthesis of 6-chlorobenzothiophene-2-carboxylic acid XI-9b

To a solution of ethyl 6-chlorobenzothiophene-2-carboxylate XI-9a (9.00 g, 37.5 mmol) in EtOH was added 3 N NaOH (24.9 mL, 74.7 mmol) and the reaction mixture was stirred at room temperature for 16 h. Progress of the reaction was monitored by TLC. After completion, the reaction mixture was concentrated under vacuum. The residue was diluted with $H_2O$ (200 mL), acidified with 2 N HCl and extracted with EtOAc (2×300 mL). The organic layer was separated, dried over anhydrous $Na_2SO_4$ and concentrated under vacuum to afford 6-chlorobenzothiophene-2-carboxylic acid XI-9b (6.10 g) as an off-white solid.

This compound was used as such for the next reaction without further purification.

Yield: 77%

$^1$H NMR (400 MHz, DMSO-$d_6$) δ 8.00 (d, J=8.31 Hz, 2H) 8.10 (s, 1H) 8.21 (s, 1H) 13.52 (brs, 1H).

Step-3: Synthesis of 6-chlorobenzothiophene XI-9

To a solution of 6-chlorobenzothiophene-2-carboxylic acid XI-9b (1.00 g, 4.70 mmol) in DMA (5 mL) was added DBU (2.86 g, 18.8 mmol) and reaction mixture was heated in microwave at 200° C. for 1 h. Progress of the reaction was monitored by TLC. After completion, the reaction mixture was diluted with H$_2$O (30 mL) and extracted with EtOAc (3×20 mL). The organic layer was separated, dried over anhydrous Na$_2$SO$_4$ and concentrated under vacuum to afford 6-chlorobenzothiophene XI-9 (0.51 g) as an off-white solid.

This compound was used as such for the next reaction without further purification.

Yield: 65%

$^1$H NMR (400 MHz, DMSO-$d_6$) δ 7.41 (dd, J=8.56, 1.71 Hz, 1H) 7.47 (d, J=5.38 Hz, 1H) 7.80 (d, J=5.38 Hz, 1H) 7.89 (d, J=8.80 Hz, 1H) 8.17 (d, J=0.98 Hz, 1H).

B.10. Synthesis of 6-chloro-5,7-difluoro-1H-indole XI-10

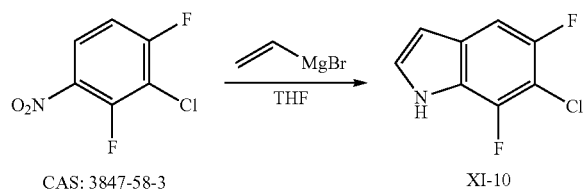

To a solution of 2-chloro-1,3-difluoro-4-nitro-benzene (6 g, 31 mmol) in THF (120 mL) was added vinyl magnesium bromide (105 mL, 1 M, 105 mmol) dropwise at −78° C. and the reaction mixture was stirred at the same temperature for 2 h. Progress of the reaction was monitored by TLC and LCMS. After completion, the reaction mixture was quenched with saturated NH$_4$Cl (200 mL), diluted with H$_2$O (300 mL) and extracted with EtOAc (500 mL). The organic layer was separated, dried over anhydrous Na$_2$SO$_4$ and concentrated under vacuum. The crude obtained was purified by column chromatography (silica, 100-200 mesh, 10% EtOAc in hexanes) to afford 6-chloro-5,7-difluoro-1H-indole XI-10 (0.71 g) as a brown solid.

Yield: 12%

Basic LCMS Method 2 (ES$^-$): 186 (M−H)$^-$, 96% purity.

$^1$H NMR (400 MHz, DMSO-$d_6$) δ 6.54-6.60 (m, 1H) 7.44 (d, J=9.78 Hz, 1H) 7.54 (t, J=2.69 Hz, 1H) 11.92 (br s, 1H)

B.11. Synthesis of 6-bromo-7-chloro-1H-indole XI-11

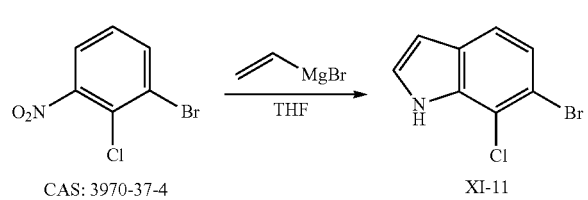

To a solution of 1-bromo-2-chloro-3-nitro-benzene (500 mg, 1.9 mmol) in THF (6 mL) was added vinyl magnesium bromide (7.6 mL, 1 M, 7.6 mmol) dropwise at −78° C. and the reaction mixture was stirred at −78° C. for 3 h. Progress of the reaction was monitored by TLC and LCMS. After completion, the reaction mixture was quenched with saturated NH$_4$Cl (60 mL) and extracted with EtOAc (3×50 mL). The organic layer was separated, dried over anhydrous Na$_2$SO$_4$ and concentrated under vacuum. The crude obtained was purified by column chromatography (silica, 100-200 mesh, 2-5% EtOAc in hexanes) to afford 6-bromo-7-chloro-1H-indole XI-11 (0.15 g) as an off-white solid.

Yield: 32%

Basic LCMS Method 2 (ES$^-$): 228 (M−H)$^-$, 95% purity.

$^1$H NMR (400 MHz, DMSO-$d_6$) δ 6.59-6.60 (m, 1H) 7.26 (t, J=2.4 Hz, 1H) 7.34 (d, J=8.4 Hz, 1H) 7.42 (d, J=8.4 Hz, 1H) 8.41 (brs, 1H).

B.12. Synthesis of 7-chloro-6-methoxy-1H-indole XI-12

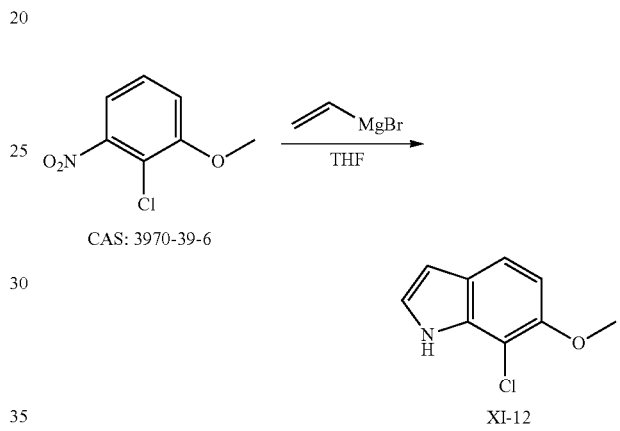

To a solution of 2-chloro-1-methoxy-3-nitro-benzene (500 mg, 2.67 mmol) in THF (10.0 mL) was added bromo(vinyl)magnesium (1.00 M, 8.00 mL, 8.00 mmol) at −78° C. The reaction mixture was stirred at same temperature for 3 h. Progress was monitored by TLC. The reaction mixture was quenched with the addition of a saturated NH$_4$Cl solution (15 mL) and extracted with ethyl acetate (3×30 mL). The organic layer was washed with a brine solution (30 mL), separated and concentrated under reduced pressure. The crude compound was purified by column chromatography (silica gel, 100-200 mesh, in 2% EtOAc in hexanes) to afford 7-chloro-6-methoxy-1H-indole XI-12 (0.15 g) as a white solid.

Yield: 30%

$^1$H NMR (400 MHz, DMSO-$d_6$) δ 3.86 (s, 3H) 6.44 (s, 1H) 6.92 (d, J=8.80 Hz, 1H) 7.26 (s, 1H) 7.45 (d, J=8.80 Hz, 1H) 11.15 (br s, 1H)

B.13. Synthesis of 7-chloro-6-fluoro-1H-indole XI-13

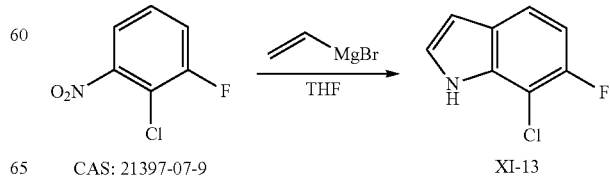

To a solution of 2-chloro-1-fluoro-3-nitro-benzene (4.00 g, 22.8 mmol) in anhydrous tetrahydrofuran (40.0 ml) under inert atmosphere, cooled to −78° C. was slowly added vinylmagnesium bromide (1.00 M, 91.1 mL, 91.1 mmol). The reaction mixture was stirred at −78° C. for 3 h. The reaction was monitored by TLC. On completion, the reaction mixture was quenched by adding it to a cold saturated aqueous NH$_4$Cl solution (80 mL). The aqueous layer was extracted with ethyl acetate (50 mL×2). The organic layer was separated, dried over anhydrous Na$_2$SO$_4$, filtered and concentrated under reduced pressure. The crude product was purified by silica gel (100-200 mesh) column chromatography with 5% ethyl acetate in n-hexane to afford 7-chloro-6-fluoro-1H-indole XI-13 (2.0 g) as a pale yellow solid.

Yield: 45%

$^1$H NMR (400 MHz, DMSO-d$_6$) δ 6.52-6.54 (m, 1H) 7.00-7.07 (m, 1H) 7.42 (t, J=2.69 Hz, 1H) 7.49-7.55 (m, 1H) 11.60 (br s, 1H).

B.14. Synthesis of 6-(difluoromethyl)-1H-pyrrolo[2,3-b]pyridine XI-14

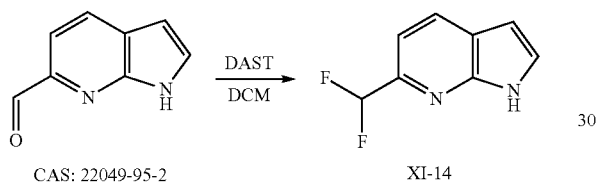

To a solution of 1H-pyrrolo[2,3-b]pyridine-6-carbaldehyde (196 mg, 1.26 mmol) in dichloromethane (4 mL) was added, at 0° C., diethylaminosulfur trifluoride (260 µL, 1.91 mmol). The reaction mixture was stirred 4 h at room temperature. Pour the reaction on a mixture of ice and NaHCO$_3$ and extract 3 times with DCM. Dry the organic phase on Na$_2$SO$_4$ and concentrate the solvents to get 6-(difluoromethyl)-1H-pyrrolo[2,3-b]pyridine XI-14 (96 mg) as a brown solid Yield: 45%.

Basic LCMS Method 1 (ES$^+$): 169 (M+H)$^+$, 82% purity.

B.15. Synthesis of 6-chloro-7-(difluoromethoxy)-1H-indole XI-15

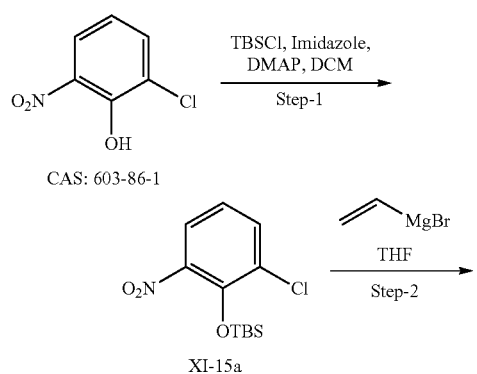

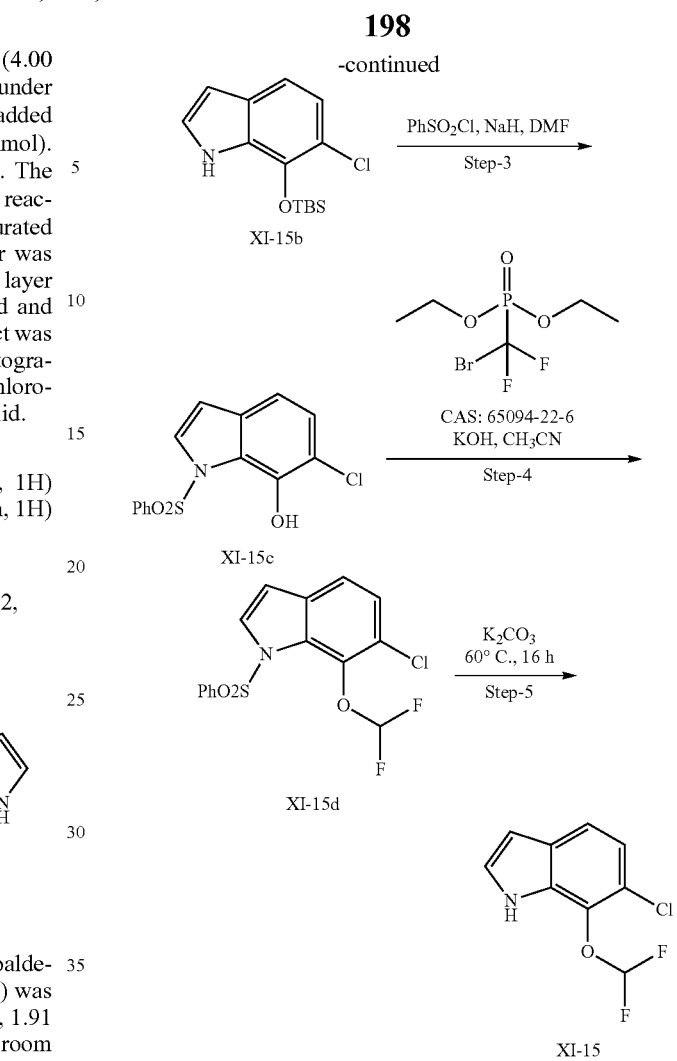

Step-1: Synthesis of tert-butyl(2-chloro-6-nitrophenoxy)dimethylsilane XI-15a

To a solution of 2-chloro-6-nitro-phenol (4.00 g, 23.0 mmol) in DCM (40 mL) was added imidazole (4.71 g, 69.1 mmol) and TBSCl (3.82 g, 25.4 mmol). The reaction mixture was stirred at room temperature for 4 h. Progress of the reaction was monitored by TLC. After completion, the reaction mixture was diluted with H$_2$O (100 mL) and extracted with DCM (2×120 mL). The organic layer was separated, washed with a saturated NaHCO$_3$ solution (2×100 mL), dried over anhydrous Na$_2$SO$_4$ and concentrated under vacuum to afford tert-butyl(2-chloro-6-nitrophenoxy)dimethylsilane XI-15a (7.50 g crude) as a pale brown liquid.

This compound was used as such for the next reaction without further purification.

$^1$H NMR (400 MHz, DMSO-d$_6$) δ 0.15 (s, 6H) 0.97 (s, 9H) 7.21 (t, J=8.40 Hz, 1H) 7.81-7.89 (m, 2H).

Step-2: Synthesis of 7-((tert-butyldimethylsilyl)oxy)-6-chloro-1H-indole XI-15b

To a solution of tert-butyl(2-chloro-6-nitrophenoxy)dimethylsilane XI-15a (7.49 g, 26.0 mmol) in THF (60 mL) was added vinylmagnesium bromide (1 M, 104 mL, 104 mmol)

dropwise at −78° C. and the reaction was stirred at same temperature for 3 h. The reaction mixture was then stirred at room temperature for 16 h. Progress of the reaction was monitored by TLC and LCMS. After completion, the reaction mixture was quenched with saturated NH₄Cl (150 mL) and extracted with EtOAc (3×120 mL). The organic layer was separated, dried over anhydrous Na₂SO₄ and concentrated under vacuum. The crude obtained was purified by flash chromatography (1.3% EtOAc in hexanes) to afford 7-((tert-butyldimethylsilyl)oxy)-6-chloro-1H-indole XI-15b (2.00 g) as a pale yellow liquid.

Yield: 21%.

Basic LCMS Method 2 (ES⁻): 280 (M–H)⁻, 77% purity.
¹H NMR (400 MHz, DMSO-d₆) δ 0.21 (s, 6H) 1.05 (s, 9H) 6.43 (dd, J=2.93, 1.96 Hz, 1H) 6.96 (d, J=8.31 Hz, 1H) 7.17 (d, J=8.31 Hz, 1H) 7.30 (t, J=2.69 Hz, 1H) 10.60 (brs, 1H).

Step-3: Synthesis of 6-chloro-1-(phenylsulfonyl)-1H-indol-7-ol XI-15c

To a solution of 7-((tert-butyldimethylsilyl)oxy)-6-chloro-1H-indole XI-15b (1.69 g, 4.60 mmol) in DMF (40 mL) was added NaH (0.92 g, 23.0 mmol) portion wise at 0° C. and the reaction was stirred at same temperature for 30 min. PhSO₂Cl (0.98 g, 5.53 mmol) was added and the reaction mixture was stirred at room temperature for 8 h. Progress of the reaction was monitored by TLC and LCMS. After completion, the reaction mixture was slowly poured into ice-cold H₂O (100 mL) and extracted with EtOAc (2×80 mL). The organic layer was separated, washed with H₂O (2×70 mL), dried over anhydrous Na₂SO₄ and concentrated under vacuum. The crude obtained was purified by column chromatography (silica, 100-200 mesh, 5 to 8% EtOAc in hexanes) to afford 6-chloro-1-(phenylsulfonyl)-1H-indol-7-ol XI-15c (0.71 g) as an off-white solid.

Yield: 41%.

Basic LCMS Method 2 (ES⁻): 306 (M–H)⁻, 81% purity.
¹H NMR (400 MHz, DMSO-d₆) δ 6.77 (d, J=3.2 Hz, 1H) 7.07 (d, J=8.4 Hz, 1H) 7.16 (d, J=8.4 Hz, 1H) 7.55-7.60 (m, 2H) 7.65-7.70 (m, 1H) 7.82 (d, J=3.2 Hz, 1H) 7.85-7.88 (m, 2H) 9.70 (brs, 1H).

Step-4: Synthesis of 6-chloro-7-(difluoromethoxy)-1-(phenylsulfonyl)-1H-indole XI-15d To a solution of 6-chloro-1-(phenylsulfonyl)-1H-indol-7-ol XI-15c (0.70 g, 1.85 mmol) in CH₃CN (20 mL) was added KOH (0.52 g, 9.23 mmol) solution in H₂O (4 mL) at 0° C. and stirred at same temperature for 15 min. Bromodifluoromethyl diethylphosphonate (1.64 mL, 9.23 mmol) was added dropwise at 0° C. and the reaction mixture was stirred at room temperature for 16 h. Progress of the reaction was monitored by TLC. After completion, the reaction mixture was diluted with H₂O (60 mL) and extracted with EtOAc (2×50 mL). The organic layer was separated, dried over anhydrous Na₂SO₄ and concentrated under vacuum. The crude obtained was purified by flash chromatography (2 to 6% EtOAc in hexanes) to afford 6-chloro-7-(difluoromethoxy)-1-(phenylsulfonyl)-1H-indole XI-15d (0.41 g) as an off-white solid.

Yield: 53%.

Basic LCMS Method 2 (ES⁻): 356 (M–H)⁻, 86% purity.
¹H NMR (400 MHz, DMSO-d₆) δ 6.97 (d, J=4.0 Hz, 1H) 7.19 (t, J=74 Hz, 1H) 7.42 (d, J=8.0 Hz, 1H) 7.54-7.61 (m, 3H), 7.69 (t, J=7.2 Hz, 1H) 7.77-7.80 (m, 2H) 7.94 (d, J=3.2 Hz, 1H).

Step-5: Synthesis of 6-chloro-7-(difluoromethoxy)-1H-indole XI-15

To a solution of 6-chloro-7-(difluoromethoxy)-1-(phenylsulfonyl)-1H-indole XI-15d (0.41 g, 0.97 mmol) in MeOH (6 mL) was added a K₂CO₃ (0.27 g, 1.95 mmol) solution in H₂O (2 mL) and the reaction mixture was heated at 60° C. for 16 h. Progress of the reaction was monitored by TLC and LCMS. The reaction mixture was concentrated under vacuum. The residue was diluted with H₂O (40 mL) and extracted with EtOAc (3×30 mL). The organic layer was separated, dried over anhydrous Na₂SO₄ and concentrated under vacuum. The crude obtained was purified by flash chromatography (1 to 3% EtOAc in hexanes) to afford 6-chloro-7-(difluoromethoxy)-1H-indole XI-15 (0.205 g, 91%) as an off-white solid.

Yield: 91%.

Basic LCMS Method 2 (ES⁻): 216 (M–H)⁻, 93% purity.
¹H NMR (400 MHz, DMSO-d₆) δ 6.53-6.55 (m, 1H) 7.11 (d, J=8.00 Hz, 1H) 7.17 (t, J=74 Hz, 1H) 7.42 (d, J=2.40 Hz, 1H) 7.51 (d, J=8.00 Hz, 1H) 11.52 (brs, 1H).

B.16. Synthesis of 6-chloro-7-(trifluoromethyl)-1H-indole XI-16

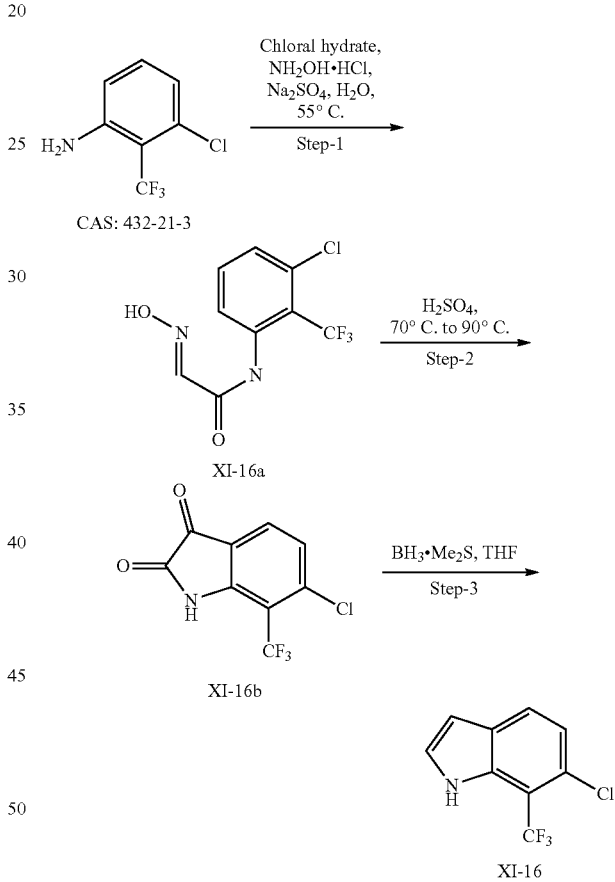

Step 1—Synthesis of (E)-N-(3-chloro-2-(trifluoromethyl)phenyl)-2-(hydroxyimino)acetamide XI-16a To a stirred solution of chloral hydrate (2.54 g, 15.3 mmol) in H₂O (30 mL) was added Na₂SO₄ (0.87 g, 6.14 mmol) and 3-chloro-2-(trifluoromethyl)aniline (2.00 g, 10.2 mmol) followed by addition of NH₂OH·HCl (2.13 g, 30.7 mmol) at room temperature. The reaction mixture was heated at 55° C. for 16 h. Progress of reaction was monitored by TLC and LCMS. After completion, the reaction mixture was diluted with H₂O (100 mL) and extracted with EtOAc (2×40 mL). The organic layer was separated, dried over anhydrous Na₂SO₄ and concentrated under vacuum. The crude obtained was purified by combi-flash chromatography (10 to 20% EtOAc in hexanes) to (E)-N-(3-chloro-2-(trifluoromethyl)phenyl)-2-(hydroxyimino)acetamide XI-16a (1.25 g) as an off-white solid.

Yield: 44%.

Basic LCMS Method 2 (ES⁻): 265 (M−H)⁻, 97% purity.

$^1$H NMR (400 MHz, DMSO-d$_6$) δ 7.48 (d, J=7.82 Hz, 1H) 7.61 (s, 1H) 7.62-7.68 (m, 2H) 10.10 (s, 1H) 12.36 (s, 1H).

Step 2—Synthesis of 6-chloro-7-(trifluoromethyl)indoline-2,3-dione XI-16b

To a stirred solution of H$_2$SO$_4$ (25 mL) was added (E)-N-(3-chloro-2-(trifluoromethyl)phenyl)-2-(hydroxyimino)acetamide XI-16a (2.50 g, 8.92 mmol) portion wise at 70° C. and the reaction mixture was heated at 90° C. for 3 h. Progress of reaction was monitored by TLC and LCMS. After completion, reaction mixture was poured into crushed ice (150 mL) and extracted with EtOAc (2×40 mL). The organic layer was separated, dried over anhydrous Na$_2$SO$_4$ and concentrated under vacuum to afford 6-chloro-7-(trifluoromethyl)indoline-2,3-dione XI-16b (2.31 g crude) as a pale yellow solid.

This compound was used as such for the next reaction without further purification.

Basic LCMS Method 2 (ES⁻): 248 (M−H)⁻, 97% purity.

$^1$H NMR (400 MHz, DMSO-d$_6$) δ 7.34 (d, J=7.82 Hz, 1H) 7.72 (d, J=7.82 Hz, 1H) 11.20 (brs, 1H).

Step 3—Synthesis of 6-chloro-7-(trifluoromethyl)-1H-indole XI-16

To a stirred solution of 6-chloro-7-(trifluoromethyl)indoline-2,3-dione XI-16b (0.90 g, 3.49 mmol) in THF (20 mL) was added BH$_3$.Me$_2$S (2 M, 5.23 mL, 10.5 mmol) at 0° C. and the reaction mixture was stirred at room temperature for 16 h. Progress of reaction was monitored by TLC and LCMS. After completion, the reaction mixture was quenched with 2N HCl (20 mL), diluted with H$_2$O (60 mL) and extracted with EtOAc (3×40 mL). The organic layer was separated, dried over anhydrous Na$_2$SO$_4$ and concentrated under vacuum. The reaction was repeated on 0.90 g and the crude obtained from 2 reactions was clubbed in DCM (50 mL) and purified by combi-flash chromatography (0 to 5% EtOAc in hexanes) to afford 6-chloro-7-(trifluoromethyl)-1H-indole XI-16 (0.844 g) as a pale yellow liquid.

Yield: 53%.

Basic LCMS Method 2 (ES⁻): 218 (M−H)⁻, 97% purity.

$^1$H NMR (400 MHz, DMSO-d$_6$) δ 6.64-6.65 (m, 1H) 7.26 (d, J=8.37 Hz, 1H) 7.48-7.50 (m, 1H) 7.85 (d, J=8.37 Hz, 1H) 11.38 (brs, 1H).

C. Synthesis of Intermediates of Formula XII

C.1. Method A. Synthesis of 1H-pyrrolo[3,2-h]quinoline-3-sulfonic acid XII-1

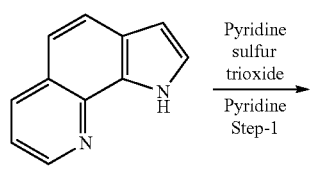

CAS: 233-88-5

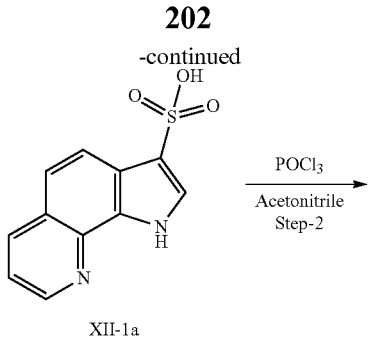

XII-1a

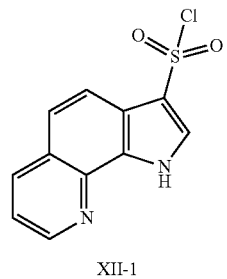

XII-1

Step-1: Synthesis of 1H-pyrrolo[3,2-h]quinoline-3-sulfonic acid XII-1a

To a solution of 1H-pyrrolo[3,2-H]quinoline (400 mg, 2.3 mmol) in pyridine (6 mL) at 0° C., was added pyridine-sulfur trioxide complex (1.2 g, 3.5 mmol). The reaction mixture was then heated at 120° C. under stirring for 2 h, cooled to room temperature and evaporated to dryness. The beige solid was dissolved in water and the aqueous phase washed with chloroform (3×). A precipitate formed on standing in the aqueous fraction and was filtered, rinsed with water and dried under vacuum at 35° C. to afford 470 mg of 1H-pyrrolo[3,2-H]quinoline-3-sulfonic acid XII-1a as a beige solid.

Yield: 79%.

Basic LCMS Method 1 (ES⁺): 249 (M+H)⁺, 100% purity.

Step 2: Synthesis of 1H-pyrrolo[3,2-h]quinoline-3-sulfonyl chloride XII-1

To a solution of 1H-pyrrolo[3,2-h]quinoline-3-sulfonic acid XII-1a (855 mg, 3.44 mmol) in acetonitrile (8.5 mL), under Argon, cooled to 0° C., was added dropwise phosphorus oxychloride (1.06 g, 6.88 mmol). The reaction mixture was then heated to 70° C. under stirring overnight. After cooling to room temperature, ice water was carefully added under vigorous stirring. A solid precipitated and was filtered, rinsed with water and dried under vacuum at 35° C., affording 284 mg of 1H-pyrrolo[3,2-h]quinoline-3-sulfonyl chloride XII-1 as a beige solid.

Yield: 27%.

Basic LCMS Method 1 (ES⁺): 275 (M+H)⁺, after quenching aliquot with ethylamine prior to the analysis The following intermediates may be synthesized according a method analogous to Method A. When commercially available, starting materials are identified by their CAS Register Numbers.

TABLE 3

| No | Indoles XI | Conditions, Time (Step-1) | Yield (%) | Conditions, Time (Step-2) | Yield (%) |
|---|---|---|---|---|---|
| XII-2 | 169674-01-5 | 130° C., 48 h | 91 (crude) | ACN/sulfolane 1/1, 70° C., 1 h | 58 (crude) |
| XII-3 | 233-34-1 | 125° C., 5 h | 64 (crude) | 70° C., 1 h | 60 (crude) |
| XII-4 | 17422-33-2 | Reflux, 16 h | 100 (crude) | ACN/sulfolane 1/1, 70° C., 3 h | 62 |
| XII-5 | XI-1 | Reflux, 16 h | 100 (crude) | ACN/sulfolane 1/1, 80° C., 2 h | 25 |
| XII-6 | 52415-29-9 | Reflux, 48 h | 76 | ACN/sulfolane 1/1, 70° C., 1 h | crude |
| XII-7 | 55052-27-2 | Reflux, 2 h | 81 | ACN/sulfolane 1/1, 70° C., 1 h | 68 |
| XII-8 | 120-72-9 | Reflux, 2 h | 84 | ACN/sulfolane 1/1, 70° C., 1 h | 65 |
| XII-9 | XI-3 | Reflux, 2 h | 87 | ACN/sulfolane 1/1, 70° C., 1 h | 53 |
| XII-10 | 129848-59-5 | Reflux, 2 h | 91 | ACN/sulfolane 1/1, 70° C., 1 h | 78 |
| XII-11 | 15903-94-3 | Reflux, 2 h | 95 | ACN/sulfolane 1/1, 70° C., 1 h | 88 |
| XII-12 | <u>199526-97-1</u> | Reflux, 2 h | 90 | ACN/sulfolane 1/1, 70° C., 1 h | 77 |
| XII-13 | 399-51-9 | Reflux, 2 h | 88 | ACN/sulfolane 1/1, 70° C., 1 h | 82 |
| XII-14 | 51417-51-7 | Reflux, 2 h | 93 | ACN/sulfolane 1/1, 70° C., 1 h | 85 |
| XII-15 | 32996-24-0 | Reflux, 2 h | 94 | ACN/sulfolane 1/1, 70° C., 1 h | 62 |
| XII-16 | 3420-02-8 | Reflux, 2 h | 92 | ACN/sulfolane 1/1, 70° C., 1 h | 81 |
| XII-17 | 143468-13-7 | Reflux, 2 h | 86 | ACN/sulfolane 1/1, 70° C., 1 h | 85 |
| XII-18 | 13544-43-9 | Reflux, 2 h | crude | ACN/sulfolane 1/1, 70° C., 1 h | 68 |

5,6-difluoro-1H-indole-3-sulfonyl chloride XII-2

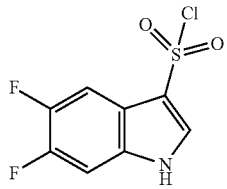

Basic LCMS Method 2 (ES⁻): 250 (M−H)⁻

1H-benzo[g]indole-3-sulfonyl chloride XII-3

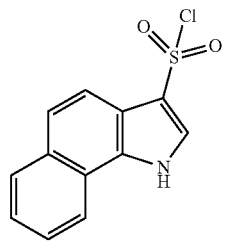 [SMILES: O=S(=O)(Cl)c1c[nH]c2c1ccc1ccccc12]

Basic LCMS Method 1 (ES⁻): 246 (M−H)⁻

6-chloro-1H-indole-3-sulfonyl chloride XII-4

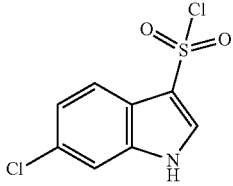 [SMILES: O=S(=O)(Cl)c1c[nH]c2cc(Cl)ccc12]

$^1$H NMR (400 MHz, DMSO-d$_6$) δ 7.32 (dd, J=8.56, 1.22 Hz, 1H) 7.71 (s, 1H) 8.03 (d, J=8.80 Hz, 1H) 8.45 (d, J=2.93 Hz, 1H) 12.38 (brs, 1H).

6-cyclopropyl-1H-indole-3-sulfonyl chloride XII-5

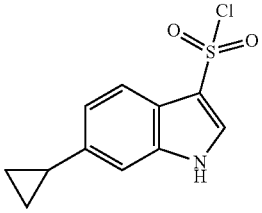 [SMILES: O=S(=O)(Cl)c1c[nH]c2cc(C3CC3)ccc12]

$^1$H NMR (400 MHz, DMSO-d$_6$) δ 0.71 (m, 2H) 0.92 (m, 2H) 1.96-2.01 (m, 1H) 7.27 (brs, 1H) 7.31 (s, 1H) 7.60 (d, J=8.31 Hz, 1H) 7.69 (d, J=8.31 Hz, 1H) 10.85 (brs, 1H).

6-bromo-1H-indole-3-sulfonyl chloride XII-6

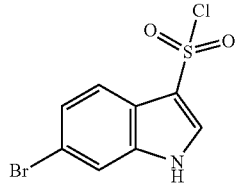

Not characterized.

6-chloro-1H-pyrrolo[2,3-b]pyridine-3-sulfonyl chloride XII-7

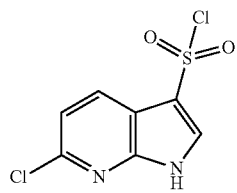 [SMILES: O=S(=O)(Cl)c1c[nH]c2nc(Cl)ccc12]

$^1$H NMR (500 MHz, DMSO-d$_6$) δ: 11.88 (s, 1H), 8.09 (d, J=8.2 Hz, 1H), 7.51 (s, 1H), 7.17 (d, J=8.2 Hz, 1H).

1H-indole-3-sulfonyl chloride XII-8

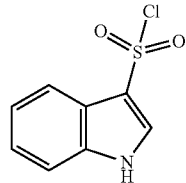 [SMILES: O=S(=O)(Cl)c1c[nH]c2ccccc12]

Not characterized.

6-(2-methoxyethoxy)-1H-indole-3-sulfonyl chloride XII-9

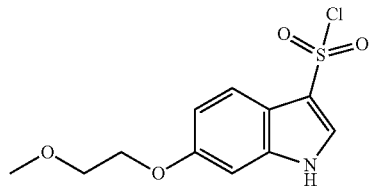 [SMILES: COCCOc1ccc2c(S(=O)(=O)Cl)c[nH]c2c1]

Not characterized.

1,6,7,8-tetrahydrocyclopenta[g]indole-3-sulfonyl chloride XII-10

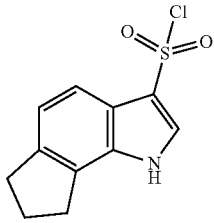 [SMILES: O=S(=O)(Cl)c1c[nH]c2c3c(ccc12)CCC3]

$^1$H NMR (600 MHz, Benzene-d$_6$) δ :8.05 (d, J=8.2 Hz, 1H), 7.16 (s, 1H), 7.02 (d, J=8.1 Hz, 1H), 6.43 (s, 1H), 2.71 (t, J=7.4 Hz, 2H), 2.38 (t, J=7.4 Hz, 2H), 1.82-1.85 (m, 2H).

6-benzyloxy-1H-indole-3-sulfonyl chloride XII-11

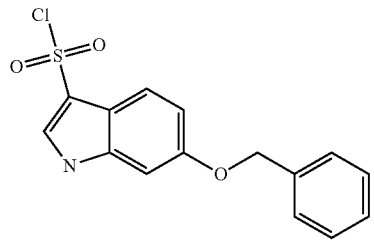 [SMILES: O=S(=O)(Cl)c1c[nH]c2cc(OCc3ccccc3)ccc12]

Not characterized.

4,6-difluoro-1H-indole-3-sulfonyl chloride XII-12

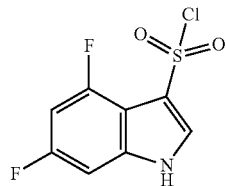 [SMILES: O=S(=O)(Cl)c1c[nH]c2cc(F)cc(F)c12]

$^1$H NMR (600 MHz, Benzene-d$_6$) δ: 7.54 (d, J=8.8 Hz, 1H), 7.04-6.88 (m, 1H), 6.73 (s, 1H), 6.46 (s, 1H).

6-fluoro-1H-indole-3-sulfonyl chloride XII-13

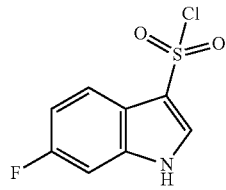 [SMILES: O=S(=O)(Cl)c1c[nH]c2cc(F)ccc12]

$^1$H NMR (600 MHz, Benzene-d$_6$) δ: 7.85 (dd, J=8.9, 5.1 Hz, 1H), 6.87 (d, J=3.2 Hz, 1H), 6.77-6.78 (m, 1H), 6.37 (dd, J=8.8, 2.2 Hz, 1H), 6.32-6.10 (m, 1H).

7-bromo-1H-indole-3-sulfonyl chloride XII-14

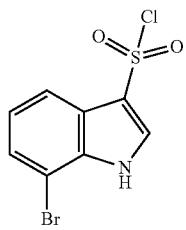 [SMILES: O=S(=O)(Cl)c1c[nH]c2c(Br)cccc12]

¹H NMR (600 MHz, Benzene-d₆) δ: 8.03 (dd, J=8.8, 5.3 Hz, 1H), 7.33 (d, J=2.9 Hz, 1H), 6.88-6.89 (m, 1H), 6.44 (dd, J=9.1, 2.3 Hz, 1H), 6.36 (s, 1H).

6-isopropyl-1H-indole-3-sulfonyl chloride XII-15

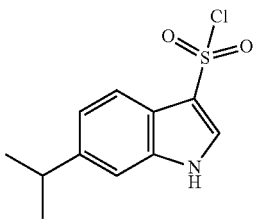 [SMILES: CC(C)c1ccc2c(S(=O)(=O)Cl)c[nH]c2c1]

¹H NMR (600 MHz, Benzene-d₆) δ: 8.10 (d, J=8.3 Hz, 1H), 7.16 (s, 1H), 6.98-6.97 (m, 1H), 6.62 (d, J=1.4 Hz, 1H), 6.50 (s, 1H), 2.75 (sept, J=6.9 Hz, 1H), 1.15 (d, J=6.9 Hz, 6H).

6-methyl-1H-indole-3-sulfonyl chloride XII-16

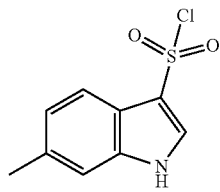

Not characterized.

6-bromo-1H-pyrrolo[2,3-b]pyridine-3-sulfonyl chloride XII-17

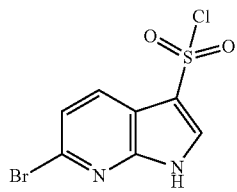

¹H NMR (500 MHz, DMSO-d₆) δ: 11.86 (s, 1H, NH), 8.09 (d, J=8.2 Hz, 1H), 7.50 (s, 1H), 7.16 (d, J=8.2 Hz, 1H).

6-trifluoromethyl-1H-indole-3-sulfonyl chloride XII-18

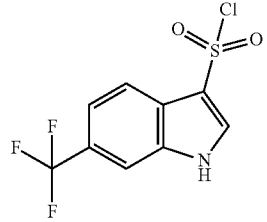 [SMILES: O=S(=O)(Cl)c1c[nH]c2cc(C(F)(F)F)ccc12]

Not characterized.

C.2. Synthesis of 1-(benzenesulfonyl)-6-chloro-indole XII-19

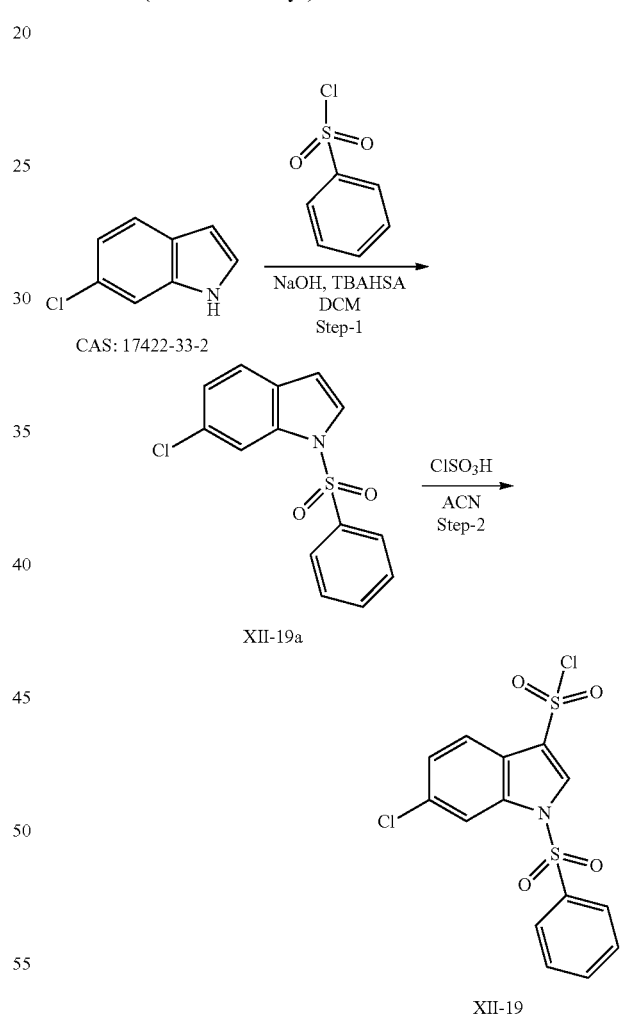

Step-1: Synthesis of 1-(benzenesulfonyl)-6-chloro-indole XII-19a

A suspension of finely powdered sodium hydroxide (24.5 g, 613 mmol) in dichloromethane (300 mL) was stirred in an ice bath and 6-chloroindole (30 g, 197 mmol) was added in one portion followed by tetrabutylammonium hydrogen sulfate (1.75 g, 5.15 mmol). Then benzenesulfonyl chloride (2.2 mL, 218 mmol) was added dropwise over 20 min and the reaction mixture was stirred at 0° C. for 1 h. The ice bath was then removed and the mixture was stirred for a further 1 h at room temperature. When LC/MS showed completion of reaction, the reaction mixture was filtered through a celite pad and the latter was washed with DCM, combined filtrate and washings were evaporated to dryness. The product was triturated in ether, filtered, washed with small amount of ether then hexane and dried, the filtrate was concentrated to give a second crop with a total of 50.54 g of 1-(benzenesulfonyl)-6-chloro-indole XII-19a as light brown solid.

Yield: 88%.

$^1$H NMR (400 MHz, CDCl$_3$) δ 8.04 (dd, J=1.8, 0.9 Hz, 1H), 7.91 (t, J=1.4 Hz, 1H), 7.89 (t, J=1.8 Hz, 1H), 7.67-7.54 (m, 2H), 7.53-7.48 (m, 2H), 7.48-7.42 (m, 1H), 7.23 (dd, J=8.4, 1.9 Hz, 1H), 6.65 (dd, J=3.7, 0.9 Hz, 1H).

Step-2: Synthesis of 1-(benzenesulfonyl)-6-chloro-indole-3-sulfonyl chloride XII-19

A solution of 1-(benzenesulfonyl)-6-chloro-indole XII-19a (50 g, 171.4 mmol) in acetonitrile (500 mL) was stirred in an ice bath and chlorosulfonic acid (100.8 g, 856.8 mmol) was added dropwise over 20 min and the reaction mixture was stirred for 5 days at room temperature. It was then slowly poured with stirring into ice-water (2.2 L) for 20 min, filtered, washed several times with water and dried by suction to give 63.77 g of 1-(benzenesulfonyl)-6-chloro-indole-3-sulfonyl chloride XII-19 as light brown solid.

Yield: 95%.

$^1$H NMR (400 MHz, CDCl$_3$) δ 8.36 (s, 1H), 8.07 (d, J=1.8 Hz, 1H), 8.04 (t, J=1.3 Hz, 1H), 8.02 (d, J=1.5 Hz, 1H), 7.91 (d, J=8.6 Hz, 1H), 7.79-7.70 (m, 1H), 7.68-7.59 (m, 2H), 7.47 (dd, J=8.6, 1.8 Hz, 1H).

C.3. Synthesis of 1-(benzenesulfonyl)-6-chloro-pyrrolo[2,3-b]pyridine-3-sulfonyl chloride XII-20

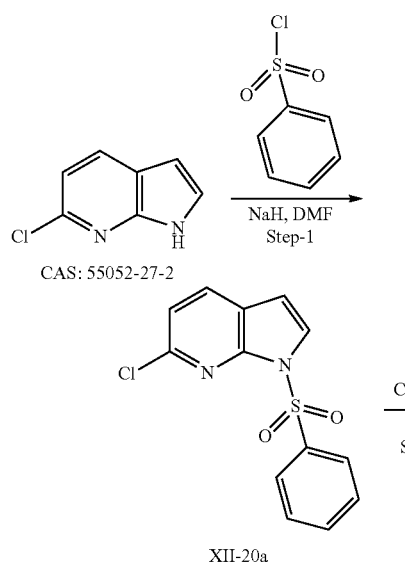

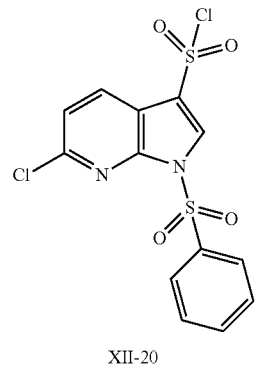

XII-20

Step-1: Synthesis of 1-(benzenesulfonyl)-6-chloro-pyrrolo[2,3-b]pyridine XII-20a To a solution of 6-chloro-1H-pyrrolo[2,3-b]pyridine (1.37 g, 8.97 mmol) in DMF (100 mL), sodium hydride (60% in paraffin, 1 g, 41 mmol) was added. The solution was stirred for 30 min being allowed to warm up from 0° C. to rt. Subsequently, benzenesulfonic acid chloride (1.5 mL, 11.8 mmol) was added dropwise. The suspension was stirred 3 h at room temperature and hydrolyzed with ice water. The resulting solid was filtered off under reduced pressure, washed thoroughly with water (75 mL) and finally with petroleum ether (15 mL). The resulting material was dried at 60° C. and purified by column chromatography (eluent: pure dichloromethane) yielding 856 mg of 1-(benzenesulfonyl)-6-chloro-pyrrolo[2,3-b]pyridine XII-20a as a brownish solid.

Yield: 32%

Step-2: Synthesis of 1-(benzenesulfonyl)-6-chloro-pyrrolo[2,3-b]pyridine-3-sulfonyl chloride XII-20

The obtained 1-(benzenesulfonyl)-6-chloro-pyrrolo[2,3-b]pyridine XII-20a (150 mg, 0.51 mmol) was dissolved in acetonitrile (5 mL) and treated with chlorosulfonic acid (2 mL, 2.91 mmol) dropwise. The mixture was refluxed for 3 h, cooled to room temperature, hydrolyzed with ice water (50 mL) and neutralized with a saturated solution of sodium hydrogen carbonate. The crude product was extracted with dichloromethane (3 times, 50 mL each). The combined organic extracts were dried over MgSO$_4$, filtered and concentrated. The resulting material was purified by column chromatography (eluent: pure dichloromethane) yielding 163 mg of 1-(benzenesulfonyl)-6-chloro-pyrrolo[2,3-b]pyridine-3-sulfonyl chloride XII-20 as a yellowish solid.

Yield: 81%

$^1$H NMR (600 MHz, CDCl$_3$) δ: 8.48 (s, 1H), 8.32 (d, J=7.8 Hz, 2H), 8.18 (d, J=8.3 Hz, 1H), 7.71 (t, J=7.5 Hz, 1H), 7.60 (t, J=7.9 Hz, 2H), 7.41 (d, J=8.4 Hz, 1H).

C.4. Synthesis of 1-(benzenesulfonyl)-6-(cyclopropylmethoxy)indole-3-sulfonyl chloride XII-21

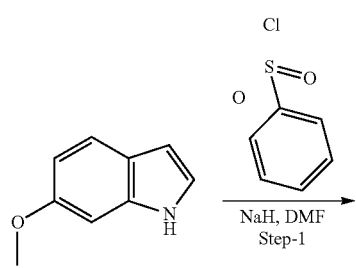

CAS: 3189-13-7

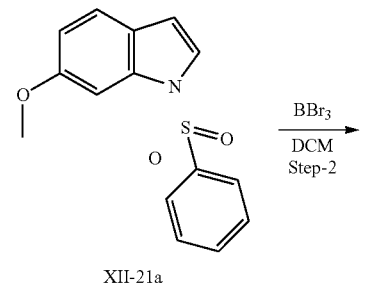

XII-21a

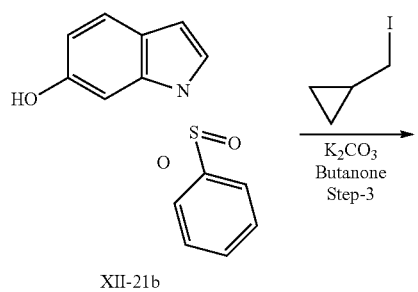

XII-21b

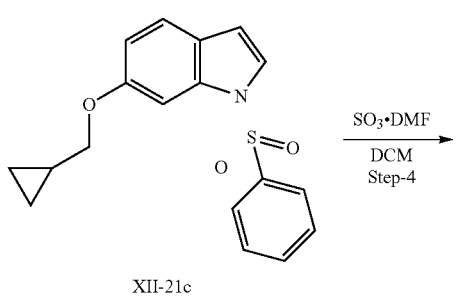

XII-21c

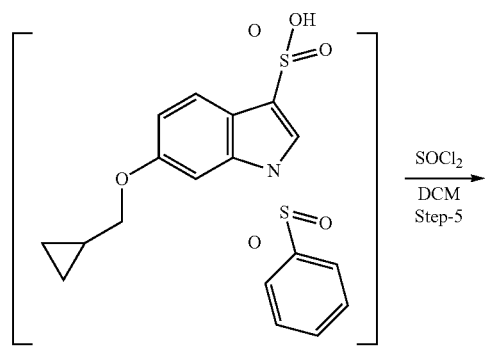

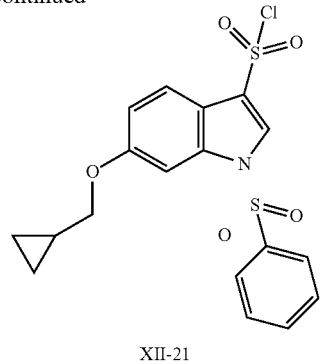

XII-21

Step-1: Synthesis of 1-(benzenesulfonyl)-6-methoxy-indole XII-21a

To a solution of 6-methoxyindole (2.5 g, 17 mmol) in DMF (50 mL), sodium hydride (60% in paraffin, 1.7 g, 71 mmol) was added at 0° C. The suspension was stirred for 30 min then warmed up to room temperature. Subsequently, the solution was treated with benzenesulfonyl chloride (2.8 mL, 3,70 g, 22 mmol) dropwise under stirring. After stirring at room temperature for 2.5 h, ice water was added to the reaction mixture under vigorous stirring. The resulting precipitate was filtered off under reduced pressure, washed thoroughly with water (100 mL) and subsequently with petroleum ether (10 mL). After drying at 60° C., 1-(benzenesulfonyl)-6-methoxy-indole XII-21a was obtained as a colorless solid (3.2 g).

Yield: 65%

$^1$H NMR (600 MHz, CDCl$_3$) δ: 7.87-7.81 (m, 2H), 7.53-7.48 (m, 2H), 7.45-7.39 (m, 3H), 7.36 (d, J=8.5 Hz, 1H), 6.84 (dd, J=8.6/2.3 Hz, 1H), 6.56 (dd, J=3.7/0.9 Hz, 1H), 3.85 (s, 3H).

Step-2: Synthesis of 1-(benzenesulfonyl)indol-6-ol XII-21b

To a solution of 1-(benzenesulfonyl)-6-methoxyindole XII-21a (1 g, 3.5 mmol) in dichloromethane (30 mL), boron tribromide (2.18 g, 0.83 mL, 8.7 mmol) was added at room temperature. After 30 min of stirring at room temperature no further starting material could be detected (TLC control, eluent: pure dichloromethane). The reaction mixture was hydrolyzed by addition of a saturated NaHCO$_3$-solution (70 mL). Water (50 mL) was added and the aqueous phase was extracted with dichloromethane (three times, 75 mL each). The combined organic extracts were dried over MgSO$_4$, filtered and concentrated under reduced pressure. The residue was purified by column chromatography on silica gel 60 (eluent: dichloromethane) yielding 600 mg of 1-(benzenesulfonyl)indol-6-ol XII-21b as a colorless solid.

Yield: 63%

$^1$H NMR (600 MHz, DMSO-d$_6$) δ 9.58 (s, 1H, OH), 7.93-7.85 (m, 2H), 7.74-7.65 (m, 1H), 7.62-7.56 (m, 2H), 7.54 (d, J=3.7 Hz, 1H), 7.39-7.29 (m, 2H), 6.81-6.62 (m, 2H).

Step-3: Synthesis of 1-(benzenesulfonyl)-6-(cyclopropylmethoxy)indole XII-21c A mixture of 1-(benzenesulfonyl)indol-6-ol XII-21b (273 mg, 1.0 mmol), cyclopropylmethyl iodide (224 mg, 1.22 mmol) and potassium carbonate (276 mg, 2.0 mmol) in butanone was heated at 80° C. for 16 h. Subsequently, the solvent was removed under reduced pressure and the residue was treated with water (50 mL) and ethyl acetate (50 mL). The organic phase was separated and the aqueous phase was extracted twice with ethyl acetate (50 mL each). The combined organic extracts were dried over MgSO₄, filtered and evaporated. The residue was purified by column chromatography on silica gel 60 (eluent: pure dichloromethane) resulting in 1-(benzenesulfonyl)-6-(cyclopropylmethoxy)indole XII-21c as a colorless solid (269 mg).

Yield: 82%

Step-4 and 5: Synthesis of 1-(benzenesulfonyl)-6-(cyclopropylmethoxy)indole-3-sulfonyl chloride XII-21

To a solution of 1-(benzenesulfonyl)-6-(cyclopropylmethoxy)indole XII-21c (130 mg, 0.39 mmol) in dichloromethane (2 mL) was added S03-DMF-complex (75 mg, 0.49 mmol). After stirring at room temperature for 1.5 h, thionyl chloride (0.04 mL, 66 mg, 0.55 mmol) was added. After stirring at room temperature for a further 20 h the solvent was evaporated and the oily residue was purified by column chromatography on silica gel 60 (eluent: pure dichloromethane) resulting in 160 mg of 1-(benzenesulfonyl)-6-(cyclopropylmethoxy)indole-3-sulfonyl chloride XII-21 as a colorless solid. The product was not further characterized but directly used for the next steps.

Yield: 95%

C.5. Synthesis of 1-(benzenesulfonyl)-6-methoxy-indole-3-sulfonyl chloride XII-22

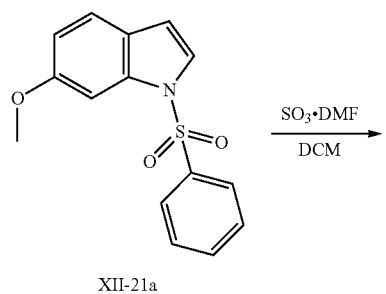

XII-21a

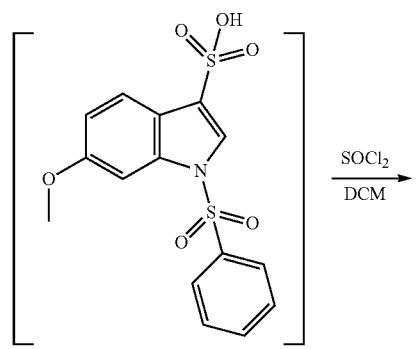

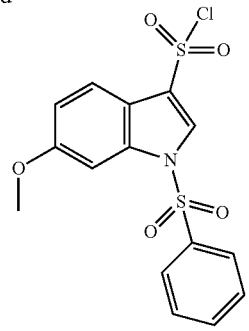

XII-22

A solution of 1-(benzenesulfonyl)-6-methoxyindole XII-21a (500 mg, 1.74 mmol) in dichloromethane (15 mL) was treated with S03-DMF complex (1.2 g, 7.8 mmol) and stirred at room temperature for 2 h (TLC control). The expected intermediate indolesulfonic acid was not isolated. Subsequently, thionyl chloride (1 mL, 14 mmol) was added and the mixture was stirred for 16 h at room temperature. The mixture was hydrolyzed with a saturated solution of NaHCO₃ (50 mL) and extracted with dichloromethane (3 times, 50 mL each). The combined organic extracts were dried over MgSO₄, filtered and concentrated by vacuum evaporation. The residue was purified by column chromatography (silica gel 60, eluent, dichloromethane/petroleum ether=1:1) leading to 1-(benzenesulfonyl)-6-methoxy-indole-3-sulfonyl chloride XII-22 as a colorless solid (504 mg).

Yield: 75%

¹H NMR (600 MHz, CDCl₃) δ: 8.23 (s, 1H), 8.00-7.93 (m, 2H), 7.80 (d, J=8.8 Hz, 1H), 7.70-7.63 (m, 1H), 7.59-7.53 (m, 2H), 7.47 (d, J=2.2 Hz, 1H), 7.06 (dd, J=8.8, 2.2 Hz, 1H), 3.89 (s, 3H).

C.6. Synthesis of 1-(benzenesulfonyl)-6-(tetrahydrofuran-2-ylmethoxy)indole-3-sulfonyl chloride XII-23

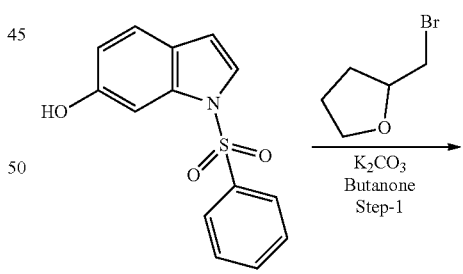

XII-21b

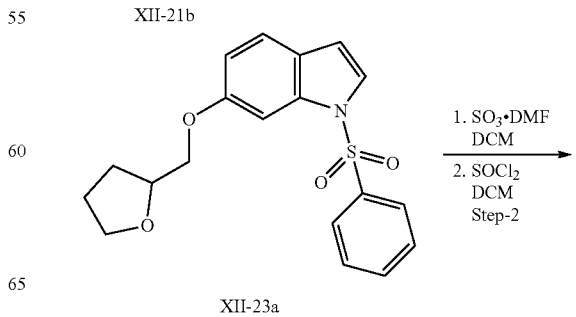

XII-23a

Step-1: Synthesis of 1-(benzenesulfonyl)-6-(tetrahydrofuran-2-ylmethoxy)indole XII-21a

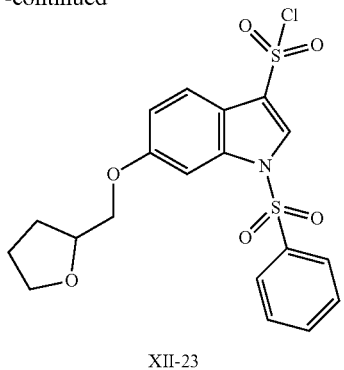

XII-23

A mixture of 1-(benzenesulfonyl)indol-6-ol XII-21b (273 mg, 1.0 mmol), 2-bromomethyltetrahydrofuran (330 mg, 2.0 mmol) and K₂CO₃ (276 mg, 2.0 mmol) in butanone was heated at 85° C. for 3 days. Subsequently, the solvent was removed under reduced pressure and the residue treated with water (50 mL) and ethyl acetate (50 mL). The organic phase was separated and the aqueous phase was extracted twice with ethyl acetate (50 mL each). The combined organic extracts were dried over MgSO₄, filtered and evaporated. The residue was purified by column chromatography on silica gel 60 (eluent: pure dichloromethane) resulting in 1-(benzenesulfonyl)-6-(tetrahydrofuran-2-ylmethoxy)indole XII-23a as a colorless solid (214 mg).

Yield: 60%

Step-2: Synthesis of 1-(benzenesulfonyl)-6-(tetrahydrofuran-2-ylmethoxy)indole-3-sulfonyl chloride XII-23

To a solution of 1-(benzenesulfonyl)-6-(tetrahydrofuran-2-ylmethoxy)indole XII-23a (100 mg, 0.28 mmol) in dichloromethane (2 mL) was added SO₃-DMF-complex (52 mg, 0.34 mmol). After stirring at room temperature for 2 h, thionyl chloride (0.1 mL, 81 mg, 1.4 mmol) was added. After stirring at room temperature for a further 16 h the solvent was evaporated and the oily residue was purified by column chromatography on silica gel 60 (eluent: pure dichloromethane) resulting in 64 mg of 1-(benzenesulfonyl)-6-(tetrahydrofuran-2-ylmethoxy)indole-3-sulfonyl chloride XII-23 as a colorless solid. The product was not further characterized but directly used for the next steps.

Yield: 50%

C.7. Synthesis of 6-chlorobenzofuran-3-sulfonyl chloride XII-24

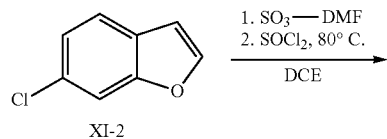

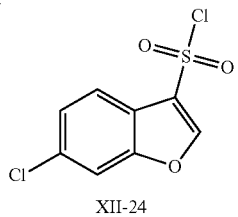

XII-24

To a solution of SO₃-DMF (0.78 g, 4.90 mmol) in 1,2-dichloroethane (10 mL) was added 6-chlorobenzofuran XI-2 (0.50 g, 3.27 mmol) and the reaction mixture was heated at 70° C. for 16 h. The reaction mixture was cooled to 0° C. followed by addition of SOCl₂ (0.52 mL, 7.16 mmol). The reaction mixture was heated at 80° C. for 2 h. Progress of the reaction was monitored by TLC. After completion, the reaction mixture was concentrated under vacuum to afford 6-chlorobenzofuran-3-sulfonyl chloride XII-24 (0.48 g) as a red semi-solid. The product was confirmed by TLC analysis only.

Yield: 60%

C.8. Synthesis of 6-chloro-7-methoxy-1H-indole-3-sulfonyl chloride XII-25

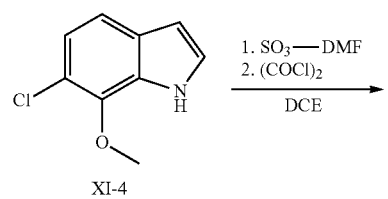

XI-4

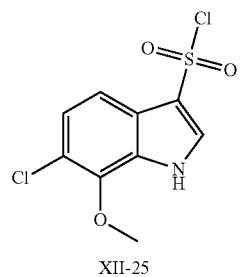

XII-25

To a solution of 6-chloro-7-methoxy-1H-indole XI-4 (0.10 g, 0.55 mmol) in DCE (5 mL) was added SO₃-DMF (0.12 g, 0.82 mmol) and the reaction mixture was stirred at room temperature for 1 h. Progress of the reaction was monitored by TLC. After completion, the reaction mixture was quenched with H₂O (15 mL) and washed with DCM (2×10 mL). The aqueous layer was concentrated under vacuum. The crude obtained was dissolved in DCE (5 mL) followed by addition of oxalyl chloride (0.23 mL, 2.76 mmol) at 0° C. The reaction mixture was stirred at 0° C. for 10 min and at room temperature for 5 h. The reaction mixture was concentrated under vacuum to afford 6-chloro-7-methoxy-1H-indole-3-sulfonyl chloride XII-25 (0.31 g crude) as brown oil.

This compound was used as such for the next reaction without further purification.

¹H NMR (400 MHz, DMSO-d₆) δ 3.88 (s, 3H) 7.02 (d, J=8.80 Hz, 1H) 7.33 (d, J=2.40 Hz, 1H) 7.48 (d, J=8.80 Hz, 1H) 7.95 (s, 1H).

C.9. Synthesis of 6-chloro-7-fluoro-1H-indole-3-sulfonyl chloride XII-26

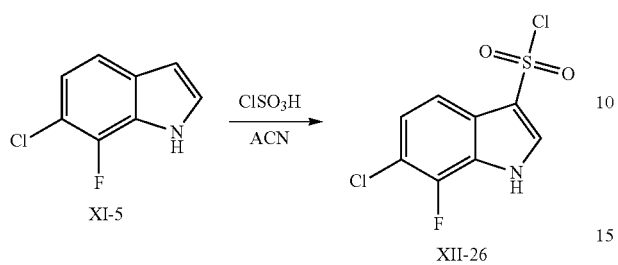

To a solution of 6-chloro-7-fluoro-1H-indole XI-5 (0.2 g, 0.78 mmol) in CH$_3$CN (5 mL) was added ClSO$_3$H (1 mL) at 0° C. and the reaction mixture was stirred at room temperature for 12 h. Progress of the reaction was monitored by TLC and LCMS. After completion, the reaction mixture was diluted with H$_2$O (100 mL) and extracted with EtOAc (2×150 mL).

The organic layer was separated, dried over anhydrous Na$_2$SO$_4$ and concentrated under vacuum to afford 6-chloro-7-fluoro-1H-indole-3-sulfonyl chloride XII-26 (0.2 g) as a brown semi solid.

This compound was used as such for the next reaction without further purification.

Yield: 87%

Basic LCMS Method 2 (ES$^+$): 248.00 (M+H)$^+$ (corresponding sulfonic acid), 89% purity.

$^1$H NMR (400 MHz, DMSO-d$_6$) δ 7.08-7.12 (m, 1H) 7.41-7.44 (m, 1H) 7.53 (d, J=8.31 Hz, 1H) 11.83 (brs, 1H).

C.10. Synthesis of 6-(trifluoromethyl)-1H-pyrrolo[2,3-b]pyridine-3-sulfonyl chloride XII-27

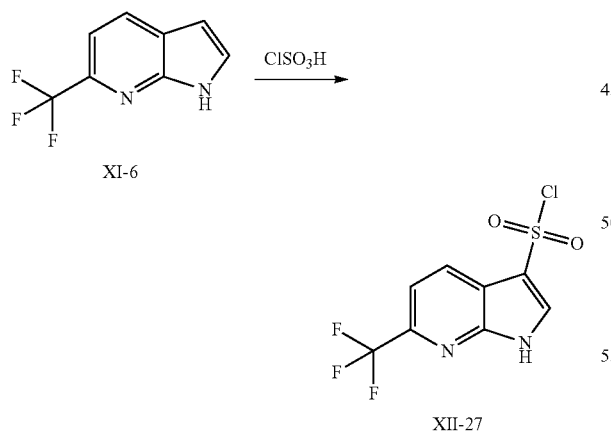

To 6-(trifluoromethyl)-1H-pyrrolo[2,3-b]pyridine XI-6 (0.45 g, 2.16 mmol) was added ClSO$_3$H (4.50 mL) dropwise at 0° C. and the reaction mixture was stirred at same temperature for 10 min. The reaction mixture was then stirred at room temperature for 2 h. Progress of the reaction was monitored by TLC and LCMS. After completion, the reaction mixture was poured in to ice and extracted with EtOAc (60 mL). The organic layer was separated, dried over anhydrous Na$_2$SO$_4$ and concentrated under vacuum to afford 6-(trifluoromethyl)-1H-pyrrolo[2,3-b]pyridine-3-sulfonyl chloride XII-27 (0.41 g) as a brown semi solid.

This compound was used as such for the next reaction without further purification.

Yield: 58%

Basic LCMS Method 2 (ES$^+$): 285 (M+H)$^+$, 83% purity.

$^1$H NMR (400 MHz, DMSO-d$_6$) δ 7.56 (d, J=7.83 Hz, 1H) 7.71 (s, 1H) 8.29 (d, J=8.31 Hz, 1H) 12.12 (brs, 1H).

C.11. Synthesis of 5-bromo-6-chloro-1H-indole-3-sulfonyl chloride XII-28

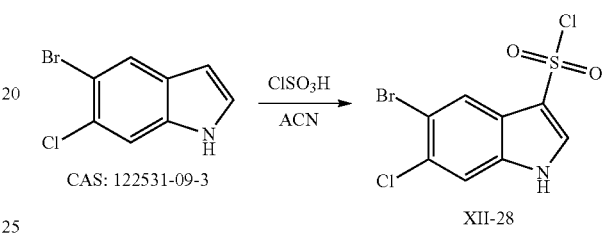

To a solution of 5-bromo-6-chloro-1H-indole (2.00 g, 8.68 mmol) in CH$_3$CN (50 mL) was added ClSO$_3$H (10.1 g, 86.8 mmol) at 0° C. and the reaction mixture was stirred at room temperature for 1 h. Progress of the reaction was monitored by TLC. After completion, the reaction mixture was diluted with ice H$_2$O (100 mL) and extracted with EtOAc (2×50 mL). The organic layer was separated, dried over anhydrous Na$_2$SO$_4$ and concentrated under vacuum to afford 5-bromo-6-chloro-1H-indole-3-sulfonyl chloride XII-28 (2.50 g) as an off-white solid.

This compound was used as such for the next reaction without further purification.

Yield: 88%

$^1$H NMR (400 MHz, DMSO-d$_6$) δ 7.91 (s, 1H) 8.44 (s, 1H) 8.49 (d, J=2.80 Hz, 1H) 12.89 (brs, 1H).

C.12. Synthesis of 7-bromo-6-chloro-1H-indole-3-sulfonyl chloride XII-29

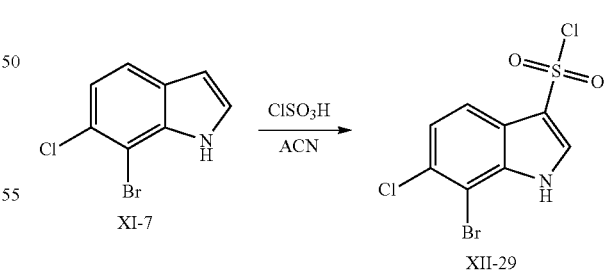

To a solution of 7-bromo-6-chloro-1H-indole XI-7 (1.50 g, 6.26 mmol) in CH$_3$CN (30 mL) was added ClSO$_3$H (2 mL) at 0° C. and the reaction mixture was stirred at same temperature for 15 min. The reaction mixture was then stirred at room temperature for 1 h. Progress of the reaction was monitored by TLC and LCMS. After completion, the reaction mixture was diluted with EtOAc (50 mL) and H2O (100 mL) and aqueous layer was extracted with EtOAc (300 mL). The combined organic layer was dried over anhydrous Na$_2$SO$_4$ and concentrated under vacuum. The crude obtained was purified by washing with pentane (10 mL) to afford 7-bromo-6-chloro-1H-indole-3-sulfonyl chloride XII-29 (1.40 g) as an off-white solid.

Yield: 67%

Basic LCMS Method 2 (ES$^-$): 308.00 (M−H)$^-$ (corresponding sulfonic acid), 98% purity.

$^1$H NMR (400 MHz, DMSO-d$_6$) δ 7.23 (d, J=8.80 Hz, 1H) 7.39 (d, J=2.93 Hz, 1H) 7.73 (d, J=8.31 Hz, 1H) 11.46 (brs, 1H).

C.13. Synthesis of 6-bromo-4-fluoro-1H-indole-3-sulfonyl chloride XII-30

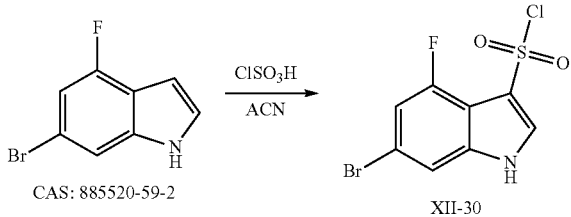

CAS: 885520-59-2

XII-30

To a solution of 6-bromo-4-fluoro-1H-indole (0.25 g, 1.17 mmol) in CH$_3$CN (5 mL) was added ClSO$_3$H (0.40 mL) at 0° C. and the reaction mixture was stirred at same temperature for 1 h. Progress of the reaction was monitored by TLC and LCMS. Reaction was repeated on 0.25 g scale and the crude mixture of 2 reactions was clubbed. After completion, the reaction mixture was quenched with ice H$_2$O (100 mL) and extracted with EtOAc (300 mL). The organic layer was separated, dried over anhydrous Na$_2$SO$_4$ and concentrated under vacuum to afford 6-bromo-4-fluoro-1H-indole-3-sulfonyl chloride XII-30 (0.255 g) as an off-white solid.

This compound was used as such for the next reaction without further purification.

Yield: 22%

Basic LCMS Method 2 (ES$^+$): 294.00 (M+H)$^+$ (corresponding sulfonic acid), 62% purity.

C.14. Synthesis of 6-chloro-5-fluoro-1H-indole-3-sulfonyl chloride XII-31

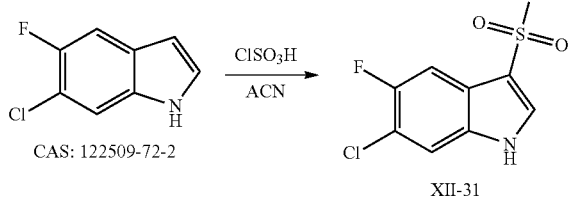

CAS: 122509-72-2

XII-31

To a solution of 6-chloro-5-fluoro-1H-indole (0.50 g, 2.95 mmol) in CH$_3$CN (5 mL) was added ClSO$_3$H (0.5 mL) at 0° C. and the reaction mixture was stirred at room temperature for 2 h. Progress of the reaction was monitored by TLC and LCMS. After completion, the reaction mixture was quenched with ice H$_2$O (20 mL), filtered, washed with H$_2$O (25 mL) and dried under vacuum to afford 6-chloro-5-fluoro-1H-indole-3-sulfonyl chloride XII-31 (0.33 g) as pale brown solid.

This compound was used as such for the next reaction without further purification.

Yield: 42%

$^1$H NMR (400 MHz, DMSO-d$_6$) δ 7.49 (d, J=2.45 Hz, 1H) 7.52-7.57 (m, 2H) 11.33 (brs, 1H).

C.15. Synthesis of 6-chloro-7-(2,2-difluoroethoxy)-1H-indole-3-sulfonyl chloride XII-32

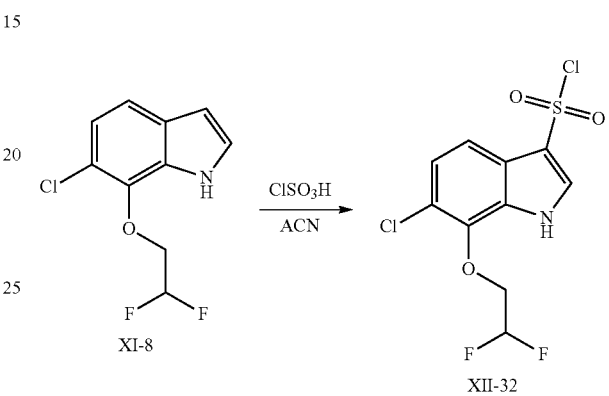

XI-8

XII-32

To a solution of 6-chloro-7-(2,2-difluoroethoxy)-1H-indole XI-8 (0.07 g, 0.30 mmol) in CH$_3$CN (3 mL) was added ClSO$_3$H (0.30 mL) at 0° C. and the reaction mixture was stirred at room temperature for 2 h. Progress of the reaction was monitored by TLC and LCMS. After completion, the reaction mixture was poured in to ice-cold H$_2$O (20 mL) and extracted with EtOAc (15 mL). The organic layer was separated, dried over anhydrous Na$_2$SO$_4$ and concentrated under vacuum to afford 6-chloro-7-(2,2-difluoroethoxy)-1H-indole-3-sulfonyl chloride XII-32 (0.09 g) as pale brown semi solid.

This compound was used as such for the next reaction without further purification.

Yield: 90%

$^1$H NMR (400 MHz, DMSO-d$_6$) δ 4.31-4.46 (m, 2H) 6.30-6.57 (m, 1H) 7.03-7.05 (d, J=8.8 Hz, 1H) 7.38 (s, 1H) 7.78-7.80 (d, J=8.0 Hz, 1H) 11.38 (br s, 1H).

C.16. Synthesis of 5-(benzenesulfonyl)-[1,3]dioxolo[4,5-f]indole-7-sulfonyl chloride XII-33

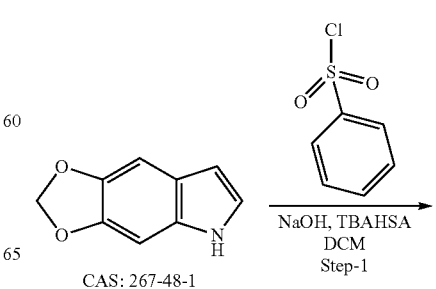

CAS: 267-48-1

NaOH, TBAHSA
DCM
Step-1

C.17. Synthesis of 1-(benzenesulfonyl)-6-methoxy-pyrrolo[2,3-b]pyridine-3-sulfonyl chloride XII-34

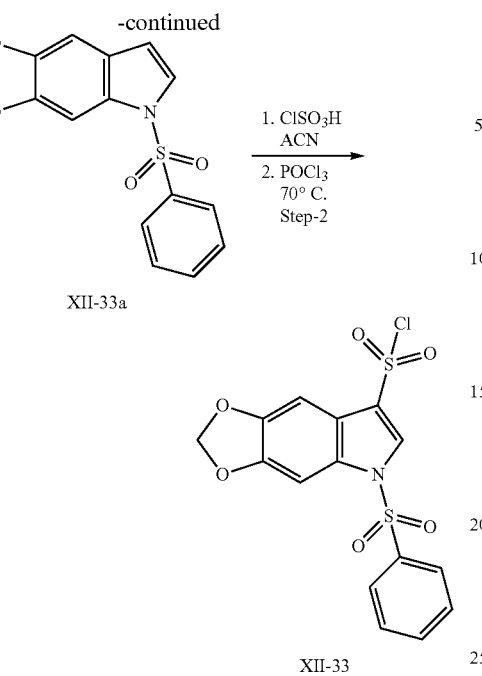

XII-33a

XII-33

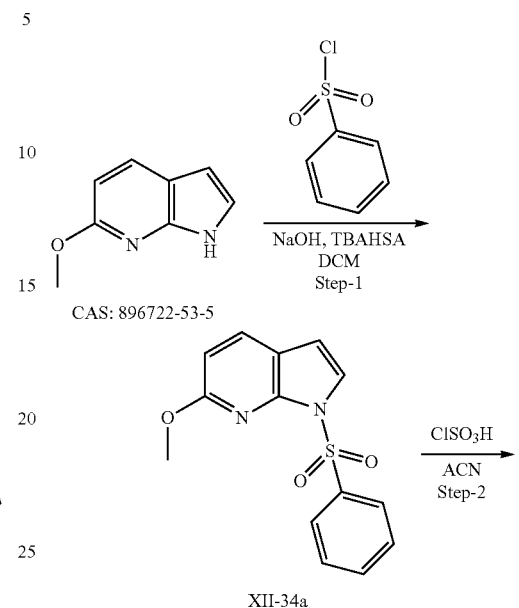

XII-34a

XII-34

Step-1: Synthesis of 5-(benzenesulfonyl)-[1,3]dioxolo[4,5-f]indole XII-33a

A suspension of sodium hydroxide (0.3 g, 7.5 mmol) in dichloromethane (7 mL) was stirred in an ice bath and 5H-[1,3]dioxolo[4,5-f]indole (0.5 g, 3 mmol) was added followed by tetrabutylammonium hydrogen sulfate (0.3 g, 0.08 mmol). Then benzenesulfonyl chloride (0.5 mL, 4 mmol) was added dropwise. The ice bath was then removed and the mixture was stirred at room temperature overnight. When LC/MS showed completion of reaction, the reaction mixture was poured into iced water and extracted with DCM (3 times), combined organic phases were dried over $MgSO_4$ and evaporated to dryness. The product was purified by flash chromatography (eluting with a mixture of DCM and heptane) to provide 0.9 g of 5-(benzenesulfonyl)-[1,3]dioxolo[4,5-f]indole XII-33a as a solid.

Yield: 100%.
Basic LCMS Method 1 ($ES^-$): 300 (M–H)$^-$, 100% purity.
$^1$H NMR (400 MHz, DMSO-$d_6$) δ 7.98-7.58 (m, 6H), 7.44 (s, 1H), 7.07 (s, 1H), 6.70 (s, 1H), 6.04 (s, 2H).

Step-2: Synthesis of 5-(benzenesulfonyl)-[1,3]dioxolo[4,5-f]indole-7-sulfonyl chloride XII-33

A solution of 5-(benzenesulfonyl)-[1,3]dioxolo[4,5-f]indole XII-33a (0.4 g, 1 mmol) in acetonitrile (4 mL) was stirred in an ice bath and chlorosulfonic acid (90 µL, 1.31 mmol) was added. The reaction mixture was stirred overnight at room temperature. Next, phosphorous oxychloride (0.5 mL, 5 mmol) was added and the reaction mixture was heated at 70° C. overnight. It was then poured with stirring into ice-water, extracted twice with chloroform, dried over $MgSO_4$ and evaporated to give 0.25 g of 5-(benzenesulfonyl)-[1,3]dioxolo[4,5-f]indole-7-sulfonyl chloride XII-33 as a solid.

This compound was used as such for the next reaction without further purification.
Yield: 62%.
Basic LCMS Method 1 ($ES^-$): 398 (M–H)$^-$, 100% purity.

Step-1: Synthesis of 1-(benzenesulfonyl)-6-methoxy-pyrrolo[2,3-b]pyridine XII-34a A suspension of sodium hydroxide (0.3 g, 7.5 mmol) in dichloromethane (6 mL) was stirred in an ice bath and 6-methoxy-1H-pyrrolo[2,3-b]pyridine (0.45 g, 3 mmol) was added followed by tetrabutylammonium hydrogen sulfate (0.3 g, 0.08 mmol). Then benzenesulfonyl chloride (0.6 mL, 5 mmol) was added dropwise. The ice bath was then removed and the mixture was stirred at room temperature overnight. When LC/MS showed completion of reaction, the reaction mixture was poured into iced water and extracted with DCM (3 times), combined organic phases were dried over $MgSO_4$ and evaporated to dryness to provide 0.88 g of 1-(benzenesulfonyl)-6-methoxy-pyrrolo[2,3-b]pyridine XII-34a as a solid.

This compound was used as such for the next reaction without further purification.
Yield: 100%.
Basic LCMS Method 1 ($ES^+$): 289 (M+H)$^+$, 94% purity.

Step-2: Synthesis of 1-(benzenesulfonyl)-6-methoxy-pyrrolo[2,3-b]pyridine-3-sulfonyl chloride XII-34

A solution of 1-(benzenesulfonyl)-6-methoxy-pyrrolo[2,3-b]pyridine XII-34a (0.88 g, 3.1 mmol) in acetonitrile (3 mL) was stirred in an ice bath and chlorosulfonic acid (1.5 mL, 22 mmol) was added. The reaction mixture was stirred overnight at 75° C. It was then poured with stirring into ice-water, extracted twice with chloroform, dried over MgSO$_4$ and evaporated to give 0.5 g of 1-(benzenesulfonyl)-6-methoxy-pyrrolo[2,3-b]pyridine-3-sulfonyl chloride XII-34 as a solid.

This compound was used as such for the next reaction without further purification.

Yield: 40%.

Basic LCMS Method 1 (ES$^-$): 394 (M–H)$^-$, 95% purity.

C.18. Synthesis of 1-(benzenesulfonyl)-6-cyano-indole-3-sulfonyl chloride XII-35

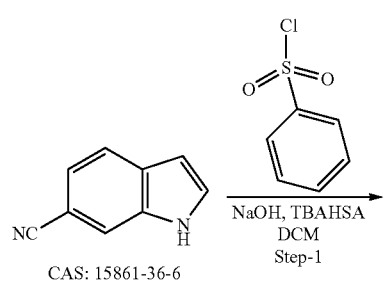

CAS: 15861-36-6

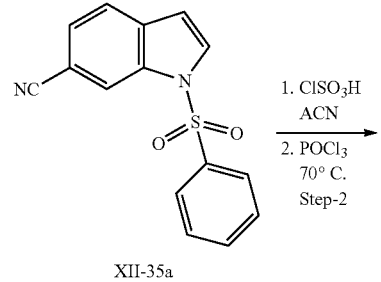

XII-35a

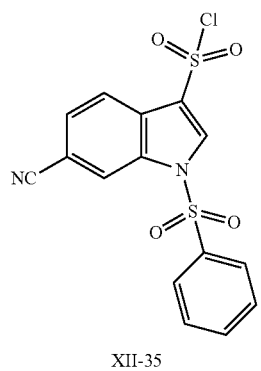

XII-35

Step-1: Synthesis of 1-(benzenesulfonyl)-6-cyano-indole XII-35a

A suspension of sodium hydroxide (0.21 g, 5.25 mmol) in dichloromethane (6 mL) was stirred in an ice bath and 1H-indole-6-carbonitrile (0.3 g, 2 mmol) was added followed by tetrabutylammonium hydrogen sulfate (0.2 g, 0.06 mmol). Then benzenesulfonyl chloride (0.33 mL, 2.6 mmol) was added dropwise. The ice bath was then removed and the mixture was stirred at room temperature overnight. When LC/MS showed completion of reaction, the reaction mixture was poured into iced water and extracted with DCM (3 times), combined organic phases were dried over MgSO$_4$ and evaporated to dryness. The product was purified by flash chromatography (eluting with a mixture of DCM and heptane) to provide 0.58 g of 1-(benzenesulfonyl)-6-cyano-indole XII-35a as a solid.

Yield: 100%.

Basic LCMS Method 1 (ES$^-$): 281 (M–H)$^-$, 99% purity.

$^1$H NMR (400 MHz, DMSO-d$_6$) δ 8.38 (s, 1H), 8.14-8.11 (m, 3H), 7.84-7.61 (m, 5H), 6.94 (s, 1H).

Step-2: Synthesis of 1-(benzenesulfonyl)-6-cyano-indole-3-sulfonyl chloride XII-35

A solution of 1-(benzenesulfonyl)-6-cyano-indole XII-35a (0.3 g, 1 mmol) in acetonitrile (2 mL) was stirred in an ice bath and chlorosulfonic acid (140 µL, 2 mmol) was added. The reaction mixture was stirred overnight at room temperature. Next, phosphorous oxychloride (0.42 mL, 4.5 mmol) was added and the reaction mixture was heated at 70° C. overnight. It was then poured with stirring into ice-water, extracted twice with chloroform, dried over MgSO$_4$ and evaporated to give 0.42 g of 1-(benzenesulfonyl)-6-cyano-indole-3-sulfonyl chloride XII-35 as a solid.

This compound was used as such for the next reaction without further purification.

Yield: 100%.

Basic LCMS Method 1 (ES$^-$): 379 (M–H)$^-$, 100% purity.

C.19. Synthesis of 1-(benzenesulfonyl)-6-bromo-pyrrolo[2,3-b]pyridine-3-sulfonyl chloride XII-36

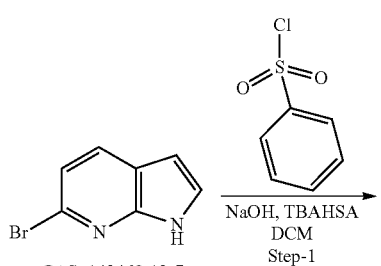

CAS: 143468-13-7

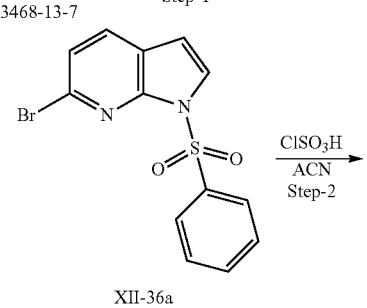

XII-36a

227
-continued

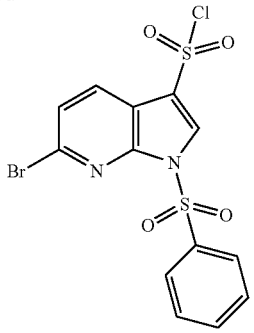

XII-36

Step-1: Synthesis of 1-(benzenesulfonyl)-6-bromo-pyrrolo[2,3-b]pyridine XII-36a A suspension of finely powdered sodium hydroxide (6.3 g, 160 mmol) in dichloromethane (100 mL) was stirred in an ice bath and 6-bromo-pyrrolo[2,3-b]pyridine (10 g, 50.7 mmol) was added in one portion followed by tetrabutylammonium hydrogen sulfate (0.45 g, 1.3 mmol). Then benzenesulfonyl chloride (7.2 mL, 56 mmol) was added dropwise over 10 min and the reaction mixture was stirred at 0° C. for 2 h. When LC/MS showed completion of reaction, the reaction mixture was filtered through a celite pad and the latter was washed with DCM, combined filtrate and washings were evaporated to dryness. The product was triturated in ether, filtered, washed with small amount of ether then hexane and dried, the filtrate was concentrated to give a second crop with a total of 16.8 g of 1-(benzenesulfonyl)-6-bromo-pyrrolo[2,3-b]pyridine XII-36a as pale yellow solid.

Yield: 98%.

Basic LCMS Method 1 (ES$^+$): 337 (M+H)$^+$, 90% purity.

$^1$H NMR (400 MHz, CDCl$_3$) δ 8.28 (t, J=1.4 Hz, 1H), 8.25 (d, J=1.6 Hz, 1H), 7.77-7.59 (m, 3H), 7.59-7.49 (m, 2H), 7.34 (d, J=8.2 Hz, 1H), 6.57 (d, J=4.0 Hz, 1H).

Step-2: Synthesis of 1-(benzenesulfonyl)-6-bromo-pyrrolo[2,3-b]pyridine-3-sulfonyl chloride XII-36

A solution of 1-(benzenesulfonyl)-6-bromo-pyrrolo[2,3-b]pyridine XII-36a (5 g, 14.8 mmol) in acetonitrile (50 mL) was stirred in an ice bath and chlorosulfonic acid (1.5 mL, 22 mmol) was added dropwise over 10 min. The reaction mixture was stirred for 1 h allowing the temperature to rise slowly, then it was stirred at 60° C. overnight. It was then poured with stirring into ice-water, stirred for 20 min, extracted twice with ethyl acetate. The extract was washed with water, a saturated solution of sodium bicarbonate, dried over MgSO$_4$ and evaporated to give 4.23 g of 1-(benzenesulfonyl)-6-bromo-pyrrolo[2,3-b]pyridine-3-sulfonyl chloride XII-36 as an off-white solid.

This compound was used as such for the next reaction without further purification.

Yield: 65%.

$^1$H NMR (400 MHz, CDCl$_3$) δ 8.51 (s, 1H), 8.38 (q, J=1.8 Hz, 1H), 8.35 (t, J=1.7 Hz, 1H), 8.13 (d, J=8.4 Hz, 1H), 7.81-7.72 (m, 1H), 7.70-7.62 (m, 2H), 7.60 (d, J=8.4 Hz, 1H).

C.20. Synthesis of 1-(benzenesulfonyl)-6-(2,2,2-trifluoroethoxy)indole-3-sulfonyl chloride XII-37

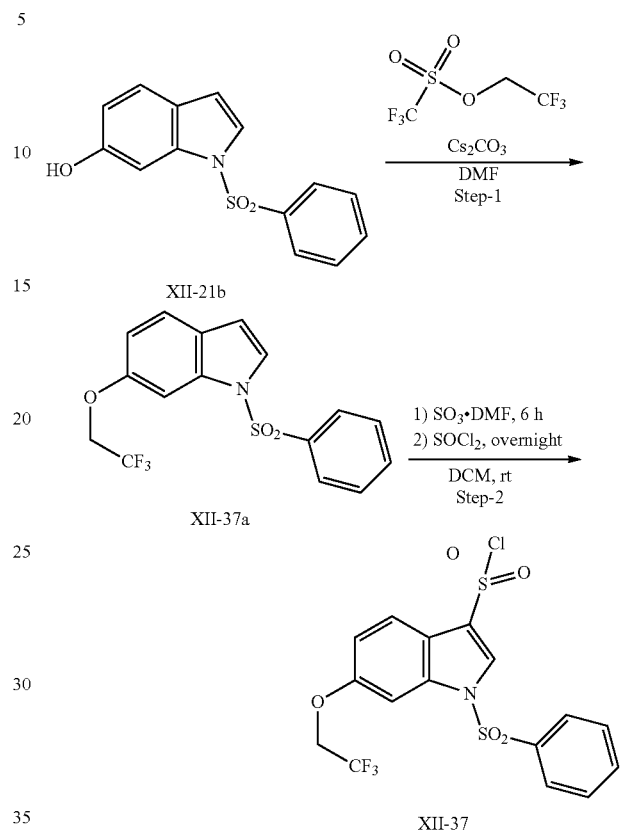

Step-1: Synthesis of 1-(benzenesulfonyl)-6-(2,2,2-trifluoroethoxy)indole XII-37a The indole XII-21 b (500 mg, 1.8 mmol) and cesium carbonate (1.19 g, 3.6 mmol) were placed in 7 mL of DMF. Then 2,2,2-trifluoroethyl trifluoromethanesulfonate (637 mg, 2.7 mmol) was added and the reaction mixture was stirred 1 h at room temperature. Then water was added to precipitate the product which was filtrated to afford 1-(benzenesulfonyl)-6-(2,2,2-trifluoroethoxy)indole XII-37a as a colorless solid (630 mg).

Yield: 97%

$^1$H NMR (600 MHz, CDCl$_3$) δ 7.84 (d, J=7.6 Hz, 2H), 7.63-7.51 (m, 2H), 7.50-7.39 (m, 4H), 6.93-6.88 (m, 1H), 6.59 (d, J=3.8 Hz, 1H), 4.40 (q, J=8.0 Hz, 2H).

Step-2: Synthesis of 1-(benzenesulfonyl)-6-(2,2,2-trifluoroethoxy)indole-3-sulfonyl chloride XII-37

A solution of 1-(benzenesulfonyl)-6-(2,2,2-trifluoroethoxy)indole XII-37a (600 mg, 1.689 mmol) in dichloromethane (10 mL) was treated with S03-DMF complex (517 mg; 3.377 mmol) and stirred at room temperature for 6 h until all starting material was consumed (TLC control). Subsequently, thionyl chloride (1 mL; 13.78 mmol) was added and the mixture was stirred overnight at room temperature. The resulting mixture was quenched with saturated NaHCO$_3$ and extracted twice with dichloromethane. The organic phase were evaporated to dryness and purified by column chromatography (silica gel 60, eluent, dichloromethane/petroleum ether=1:1) leading to 1-(benzenesulfonyl)-6-(2,2,2-trifluoroethoxy)indole-3-sulfonyl chloride XII-37 (306 mg) as a yellowish solid.

Yield: 40%

$^1$H NMR (600 MHz, CDCl$_3$) δ 8.28 (s, 1H), 7.97 (d, J=8.0 Hz, 1H), 7.86 (d, J=8.8 Hz, 1H), 7.74-7.53 (m, 5H), 7.11 (dd, J=8.8, 2.2 Hz, 1H) 4.44 (q, J=7.9 Hz, 2H).

C.21. Synthesis of 6-chlorobenzothiophene-3-sulfonyl chloride XII-38

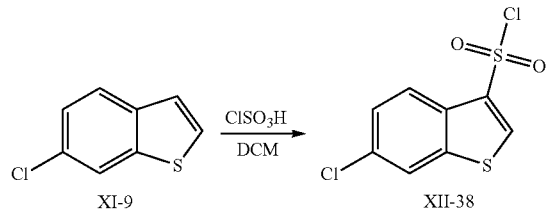

To a solution of 6-chlorobenzothiophene XI-9 (0.30 g, 1.77 mmol) in DCM (15 mL) was added ClSO$_3$H (0.36 mL, 5.33 mmol) at 0° C. and the reaction mixture was stirred at same temperature for 5 h. Progress of the reaction was monitored by TLC. After completion, the reaction mixture was quenched with ice-cold H$_2$O (50 mL) and extracted with EtOAc (2×50 mL). The organic layer was separated, dried over anhydrous Na$_2$SO$_4$ and concentrated under vacuum to afford 6-chlorobenzothiophene-3-sulfonyl chloride XII-38 (0.31 g) as an off-white solid.

Yield: 65%

$^1$H NMR (400 MHz, DMSO-d$_6$) δ 7.42-7.44 (m, 1H) 7.81 (s, 1H) 8.05-8.15 (m, 2H).

C.22. Synthesis of 6-bromo-7-methyl-1H-indole-3-sulfonyl chloride XII-39

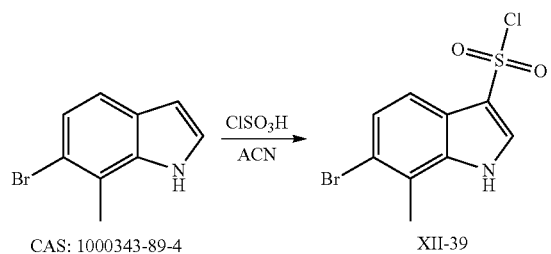

To a solution of 6-bromo-7-methyl-1H-indole (0.12 g, 0.55 mmol) in ACN (1.8 mL) was added ClSO$_3$H (0.15 mL, 2.21 mmol) at 0° C. and the reaction mixture was stirred at room temperature for 2 h. After completion, the reaction mixture was quenched with H$_2$O and extracted with CHCl$_3$ (3×). The organic layers were separated, dried over anhydrous MgSO$_4$ and concentrated under vacuum to afford 6-bromo-7-methyl-1H-indole-3-sulfonyl chloride XII-39 (0.11 g) as a beige solid.

This compound was used as such for the next reaction without further purification.

Yield: 63%

Basic LCMS Method 1 (ES$^-$): 315 (M−H)$^-$, after quenching aliquot with ethylamine prior to the analysis

C.23. Synthesis of 6-nitro-1H-indole-3-sulfonyl chloride XII-40

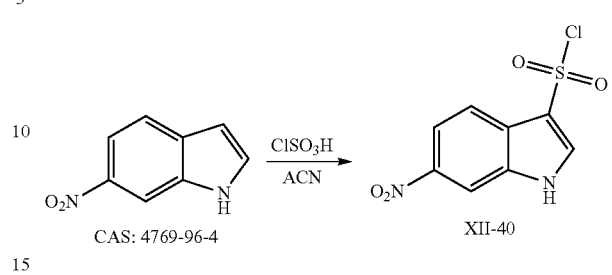

To a solution of 6-nitro-1H-indole (2 g, 12.3 mmol) in CH$_3$CN (30 mL) was added ClSO$_3$H (4 mL) at 0° C. and the reaction mixture was stirred at room temperature for 2 h. Progress of the reaction was monitored by TLC. After completion, the reaction mixture was quenched with ice-cold H$_2$O (150 mL), filtered and washed with H$_2$O (10 mL). The crude obtained was dried under vacuum to afford 6-nitro-1H-indole-3-sulfonyl chloride XII-40 (2.10 g) as a pale yellow solid.

This compound was used as such for the next reaction without further purification.

Yield: 64%

$^1$H NMR (400 MHz, DMSO-d$_6$) δ 7.78 (s, 1H) 7.92 (brs, 2H) 8.31 (s, 1H) 11.82 (brs, 1H).

C.24. Synthesis of 6-chloro-5,7-difluoro-1H-indole-3-sulfonyl chloride XII-41

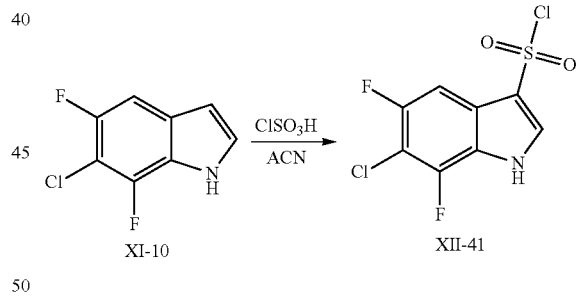

To a solution of 6-chloro-5,7-difluoro-1H-indole XI-10 (700 mg, 3.6 mmol) in CH$_3$CN (15 mL) was added ClSO$_3$H (0.8 mL) at 0° C. and the reaction mixture was stirred at room temperature for 2 h. Progress of the reaction was monitored by TLC and LCMS. After completion, the reaction mixture was diluted with water (50 mL) and extracted with EtOAc (100 mL). The organic layer was separated, dried over anhydrous Na$_2$SO$_4$ and concentrated under vacuum to afford 6-chloro-5,7-difluoro-1H-indole-3-sulfonyl chloride XII-41 (705 mg) as a brown solid.

This compound was used as such for the next reaction without further purification.

Yield: 64%

Basic LCMS Method 2 (ES$^-$): 266 (M−H)$^-$ (corresponding sulfonic acid), 93% purity.

C.25. Synthesis of 6-bromo-7-chloro-1H-indole-3-sulfonyl chloride XII-42

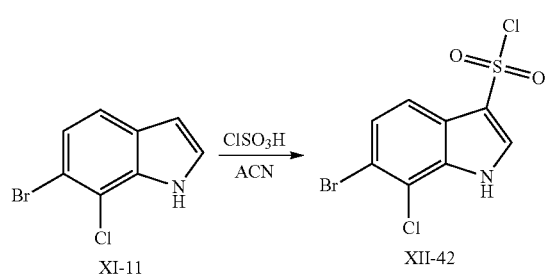

To a solution of 6-bromo-7-chloro-1H-indole XI-11 (145 mg, 0.6 mmol) in CH$_3$CN (3 mL) was added ClSO$_3$H (0.15 mL) at 0° C. and the reaction mixture was stirred at room temperature for 3 h. Progress of the reaction was monitored by TLC and LCMS. After completion, the reaction mixture was poured on crushed ice (20 mL) and the formed solid was filtered and dried to afford 6-bromo-7-chloro-1H-indole-3-sulfonyl chloride XII-42 (90 mg) as a pale brown solid.

This compound was used as such for the next reaction without further purification.

Yield: 44%

Basic LCMS Method 2 (ES$^-$): 308 (M–H)$^-$ (corresponding sulfonic acid), 95% purity.

$^1$H NMR (400 MHz, DMSO-d$_6$) δ 7.32-7.37 (m, 2H) 7.64 (d, J=8.8 Hz, 1H) 11.58 (s, 1H).

C.26. Synthesis of 7-chloro-6-methoxy-1H-indole-3-sulfonyl chloride XII-43

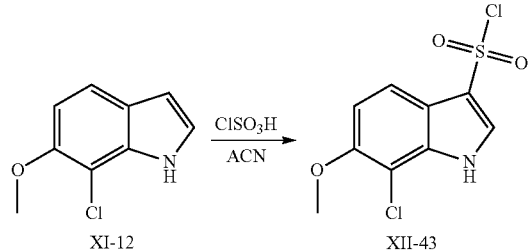

To a solution of 7-chloro-6-methoxy-1H-indole XI-12 (600 mg, 3.22 mmol) in acetonitrile (15 mL). Chlorosulfonic acid (0.6 mL) was added dropwise at −5 to 0° C. The reaction mixture was stirred at room temperature for 3 h. Progress of reaction was monitored by TLC. The reaction mixture was poured on ice water (15 mL) extracted with EtOAc (3×15 mL). Combined organic layers were washed with a brine solution (15 mL), The organic layer was separated, dried over anhydrous Na$_2$SO$_4$ (1.00 g) and concentrated under vacuum. The crude compound was triturated with n-pentane (15 mL) to afford 7-chloro-6-methoxy-1H-indole-3-sulfonyl chloride XII-43 (530 mg) as an off-white solid.

Yield: 58%

$^1$H NMR (400 MHz, DMSO-d$_6$) δ 3.86 (s, 3H) 6.97 (d, J=8.80 Hz, 1H) 7.27 (d, J=2.45 Hz, 1H) 7.63 (d, J=8.31 Hz, 1H) 11.19 (br s, 1H)

C.27. Synthesis of 7-chloro-6-fluoro-1H-indole-3-sulfonyl chloride XII-4

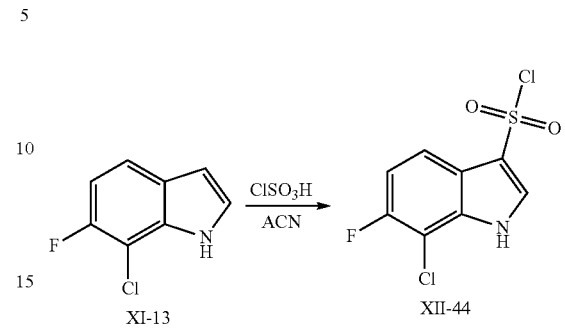

To a solution of 7-chloro-6-fluoro-1H-indole XI-13 (400 mg, 2.08 mmol) in acetonitrile (8 mL) at 0° C. was slowly added ClSO$_3$H (0.345 mL, 5.19 mmol). The reaction mixture was stirred at 0° C. for 1 h and then at room temperature for 2 h. Progress of the reaction was monitored by TLC. After completion, the reaction mixture was poured into ice water (50 mL). The aqueous layer was extracted with ethyl acetate (2×25 mL). The organic layer was separated, dried over anhydrous Na$_2$SO$_4$, filtered and concentrated to afford 7-chloro-6-fluoro-1H-indole-3-sulfonyl chloride XII-44 (430 mg) as a brown semi solid.

The crude product was used for next reaction without further purification.

Yield: 62%

$^1$H NMR (400 MHz, DMSO-d$_6$) δ 7.07 (t, J=9.29 Hz, 1H) 7.38 (d, J=2.45 Hz, 1H) 7.67-7.70 (m, 1H) 11.60 (br s, 1H).

C.28. Synthesis of 1-(benzenesulfonyl)-6-(difluoromethyl)pyrrolo[2,3-b]pyridine-3-sulfonyl chloride XII-45

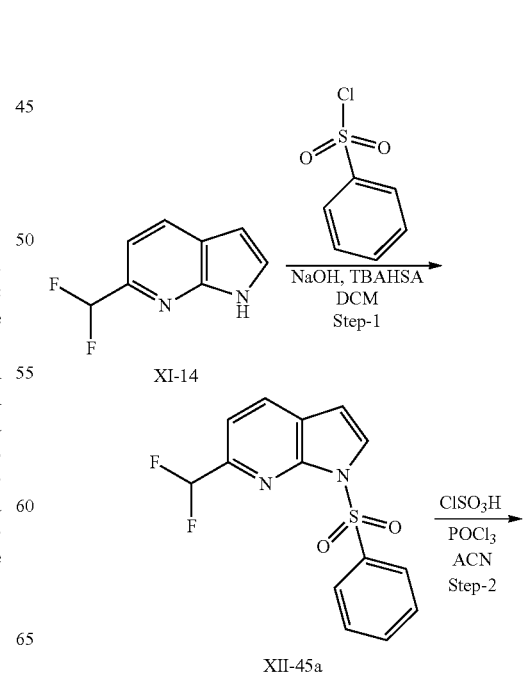

233

-continued

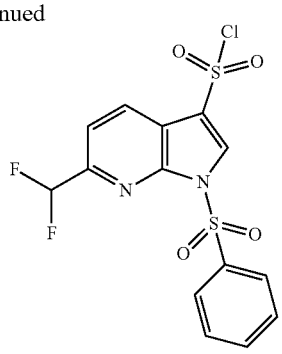

XII-45

Step-1: Synthesis of 1-(benzenesulfonyl)-6-(difluoromethyl)pyrrolo[2,3-b]pyridine XII-45a A suspension of sodium hydroxide (76 mg, 1.88 mmol) in dichloromethane (1 mL) was stirred in an ice bath and 6-(difluoromethyl)-1H-pyrrolo[2,3-b]pyridine XI-14 (125 mg, 0.74 mmol) was added followed by tetrabutylammonium hydrogen sulfate (7.5 g, 0.022 mmol).

Then benzenesulfonyl chloride (105 µL, 0.81 mmol) was added dropwise and the reaction mixture was stirred at room temperature overnight. After completion of reaction, the mixture was filtered through a celite pad and the latter was washed with DCM, combined filtrate and washings were evaporated to dryness. The crude product was purified by chromatography (SiO₂, elution with dichloromethane) to afford 1-(benzenesulfonyl)-6-(difluoromethyl)pyrrolo[2,3-b]pyridine XII-45a (200 mg) as a light brown solid.

Yield: 70%.

Basic LCMS Method 1 (ES⁺): 309 (M+H)⁺, 100% purity.

Step-2: Synthesis of 1-(benzenesulfonyl)-6-(difluoromethyl)pyrrolo[2,3-b]pyridine-3-sulfonyl chloride XII-45

A solution of 1-(benzenesulfonyl)-6-(difluoromethyl)pyrrolo[2,3-b]pyridine XII-45a (76 mg, 0.24 mmol) in acetonitrile (10 mL) was stirred in an ice bath and chlorosulfonic acid (54 µL, 0.78 mmol) was added dropwise and the reaction mixture was stirred for 4 days at 50° C. Then, phosphorous oxychloride (100 µL, 1.06 mmol) was added and the reaction mixture was heated at 70° C. overnight. After cooling, it was then slowly poured into ice-water and extracted with chloroform (3×). The organic layers were dried over magnesium sulfate and evaporated to dryness to give 1-(benzenesulfonyl)-6-chloro-indole-3-sulfonyl chloride XII-19 (100 mg) as a solid.

The crude product was used for next reaction without further purification.

Yield: 95%.

Basic LCMS Method 1 (ES⁻): 387 (M−H)⁻ (corresponding sulfonic acid mass), 88% purity.

234

C.29. Synthesis of 6-chloro-7-(difluoromethoxy)-1H-indole-3-sulfonyl chloride XII-46

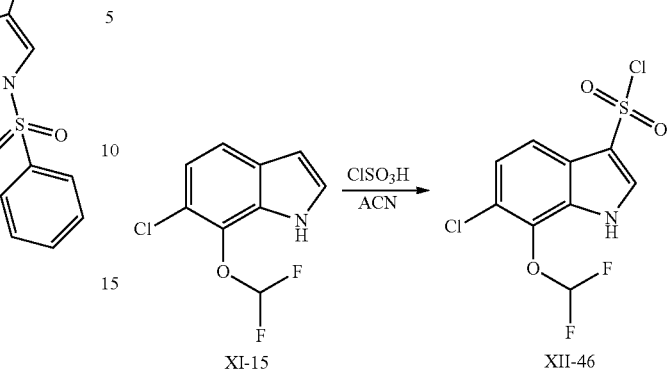

To a solution 6-chloro-7-(difluoromethoxy)-1H-indole XI-15 (0.20 g, 0.86 mmol) in CH₃CN (4 mL) was added ClSO₃H (0.20 mL) slowly at 0° C. and the reaction mixture was stirred at room temperature for 3 h. Progress of the reaction was monitored by TLC and LCMS. After completion, the reaction mixture was poured into crushed ice (20 mL) and extracted with EtOAc (3×10 mL). The organic layer was separated, dried over anhydrous Na₂SO₄ and concentrated under vacuum to afford 6-chloro-7-(difluoromethoxy)-1H-indole-3-sulfonyl chloride XII-46 (0.23 g, crude) as a pale brown solid.

This compound was used as such for the next reaction without further purification.

Basic LCMS Method 2 (ES⁻): 314 (M−H)⁻, 55% purity.
¹H NMR (400 MHz, DMSO-d₆) δ 7.16 (d, J=8.80 Hz, 1H) 7.16 (t, J=73.6 Hz, 1H) 7.39 (d, J=2.40 Hz, 1H) 7.67 (d, J=8.80 Hz, 1H) 11.53 (brs, 1H)

C.30. Synthesis of 6-chloro-7-(trifluoromethyl)-1H-indole-3-sulfonyl chloride XII-47

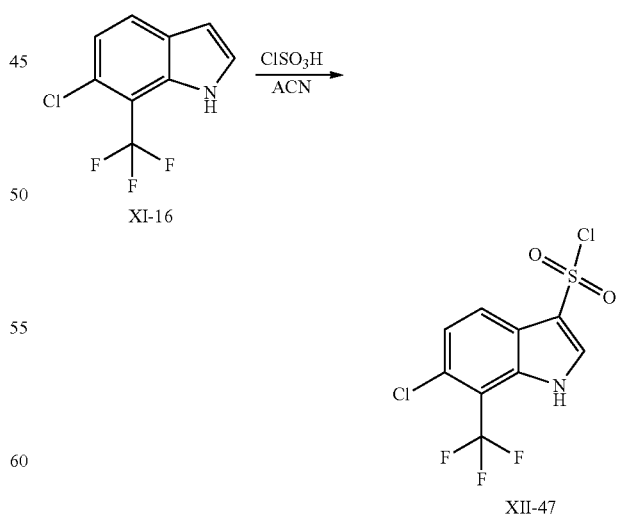

To a stirred solution of 6-chloro-7-(trifluoromethyl)-1H-indole XI-16 (0.52 g, 2.30 mmol) in CH₃CN (10 mL) was added ClSO₃H (1.50 mL) dropwise at 0° C. The reaction mixture was stirred at room temperature for 2 h. Progress of the reaction was monitored by TLC and LCMS. After completion, the reaction mixture was poured into crushed ice (100 mL), stirred for 10 min and extracted with EtOAc (3×40 mL). The organic layer was separated, dried over anhydrous $Na_2SO_4$ and concentrated under vacuum to afford 6-chloro-7-(trifluoromethyl)-1H-indole-3-sulfonyl chloride XII-47 (1.01 g crude) as a brown solid.

This compound was used as such for next reaction without further purification.

Basic LCMS Method 2 (ES⁻): 298 (M−H)⁻ (corresponding sulfonic acid mass), 96% purity.

$^1$H NMR (400 MHz, DMSO-d$_6$) δ 7.31 (d, J=8.80 Hz, 1H) 7.41 (d, J=2.93 Hz, 1H) 8.01 (d, J=8.31 Hz, 1H) 11.27 (brs, 1H).

Example Compounds

D. Synthesis of Compounds of General Formula I

All compounds of the present invention specifically disclosed herein are designated "I-x" wherein any "x" refers to a number identifying the individual compounds. Accordingly, the Example compounds are designated I-1, I-2, I-3 etc. This is irrespective of whether any compound could also be described by any subgeneric Formula herein, e.g. by Formula II, III or IV, and the like.

D.1. Method B. Synthesis of 6-chloro-N-(2,4-difluorophenyl)-1H-indole-3-sulfonamide I-1

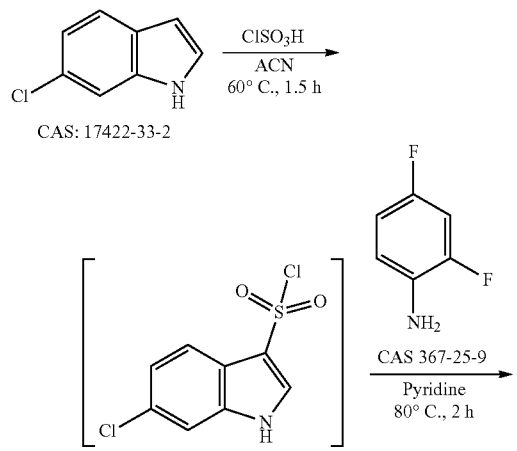

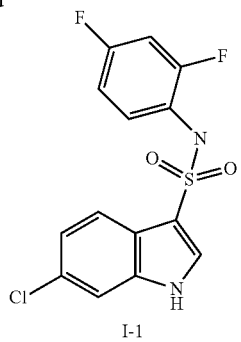

I-1

In a vial, a solution of 6-chloro-indole (630 mg, 4.1 mmol) in acetonitrile (25.2 mL) was stirred in an ice-bath and chlorosulfonic acid (714 µl, 10.7 mmol) was added dropwise and the reaction mixture was stirred for 30 min. The ice-bath was removed and the reaction mixture was heated to 60° C. for 1.5 h. After cooling to room temperature, pyridine (54.6 mL) was added and the solution turned yellow. In a second sealed vial, 2,4-difluoroaniline (25.8 mg, 0.2 mmol) was weighed and an aliquot of the preceding solution was added (1.9 mL, 0.1 mmol). The reaction mixture was stirred at 80° C. for 2 h, then evaporated in an centrifugal evaporator. The residue was purified by reverse phase chromatography in basic mode with MS detection to afford 11.8 mg of 6-chloro-N-(2,4-difluorophenyl)-1H-indole-3-sulfonamide I-1.

Yield: 34%.

Basic LCMS Method 1 (ES⁻): 341 (M−H)⁻, 95% purity.

The following compounds in table 4 were synthesized according to Method B.

TABLE 4

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-2 | 3189-13-7 | 367-34-0 | 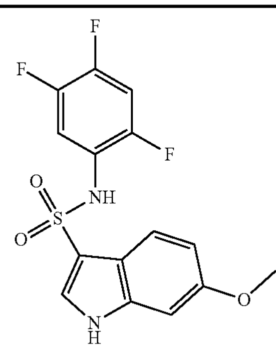 | 6-methoxy-N-(2,4,5-trifluorophenyl)-1H-indole-3-sulfonamide | 3.9 | 355 | 100 |

TABLE 4-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-3 | 17422-33-2 | 533-30-2 | 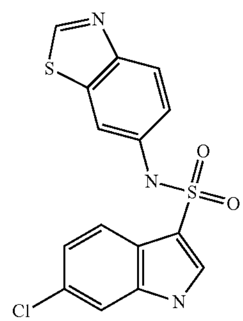 [SMILES: O=S(=O)(Nc1ccc2ncsc2c1)c1c[nH]c2cc(Cl)ccc12] | N-(1,3-benzothiazol-6-yl)-6-chloro-1H-indole-3-sulfonamide | 29 | 362 | 100 |
| I-4 | 17422-33-2 | 2106-05-0 | 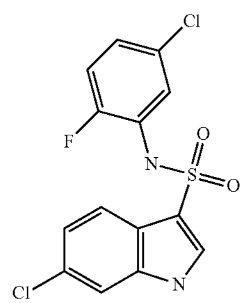 [SMILES: O=S(=O)(Nc1cc(Cl)ccc1F)c1c[nH]c2cc(Cl)ccc12] | 6-chloro-N-(5-chloro-2-fluorophenyl)-1H-indole-3-sulfonamide | 23 | 357 | 93 |
| I-5 | 17422-33-2 | 14268-66-7 | 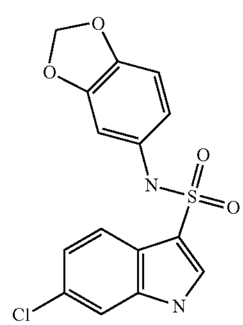 [SMILES: O=S(=O)(Nc1ccc2c(c1)OCO2)c1c[nH]c2cc(Cl)ccc12] | N-(1,3-benzodioxol-5-yl)-6-chloro-1H-indole-3-sulfonamide | 16 | 349 | 94 |
| I-6 | 17422-33-2 | 619-45-4 | 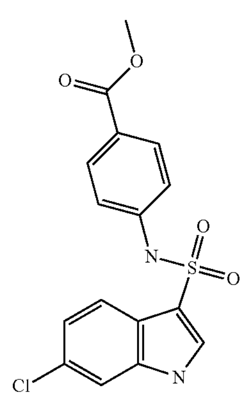 [SMILES: COC(=O)c1ccc(NS(=O)(=O)c2c[nH]c3cc(Cl)ccc23)cc1] | methyl 4-{[(6-chloro-1H-indol-3-yl)sulfonyl]amino}benzoate | 16 | 363 | 100 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-7 | 17422-33-2 | 452-77-7 | 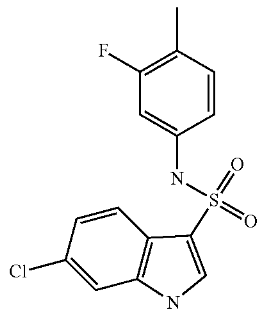 [SMILES: Cc1ccc(NS(=O)(=O)c2c[nH]c3cc(Cl)ccc23)cc1F] | 6-chloro-N-(3-fluoro-4-methylphenyl)-1H-indole-3-sulfonamide | 43 | 337 | 100 |
| I-8 | 17422-33-2 | 57319-65-0 | 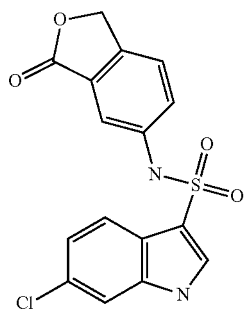 [SMILES: O=C1OCc2ccc(NS(=O)(=O)c3c[nH]c4cc(Cl)ccc34)cc21] | 6-chloro-N-(3-oxo-1,3-dihydro-2-benzofuran-5-yl)-1H-indole-3-sulfonamide | 16 | 361 | 100 |
| I-9 | 17422-33-2 | 367-30-6 | 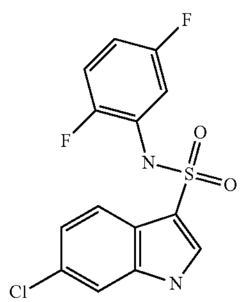 [SMILES: O=S(=O)(Nc1cc(F)ccc1F)c1c[nH]c2cc(Cl)ccc12] | 6-chloro-N-(2,5-difluorophenyl)-1H-indole-3-sulfonamide | 14 | 341 | 100 |
| I-10 | 17422-33-2 | 20503-39-3 | 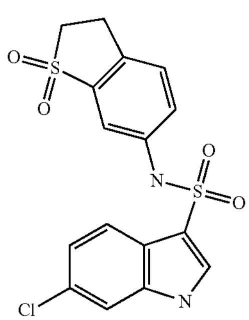 [SMILES: O=S1(=O)CCc2ccc(NS(=O)(=O)c3c[nH]c4cc(Cl)ccc34)cc21] | 6-chloro-N-(1,1-dioxido-2,3-dihydro-1-benzothiophen-6-yl)-1H-indole-3-sulfonamide | 21 | 395 | 98 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-11 | 17422-33-2 | 348-54-9 | 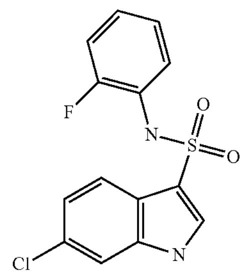 [SMILES: O=S(=O)(Nc1ccccc1F)c1c[nH]c2cc(Cl)ccc12] | 6-chloro-N-(2-fluorophenyl)-1H-indole-3-sulfonamide | 22 | 323 | 100 |
| I-12 | 17422-33-2 | 873-74-5 | 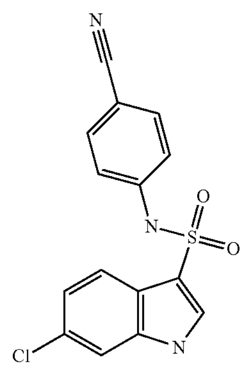 [SMILES: N#Cc1ccc(NS(=O)(=O)c2c[nH]c3cc(Cl)ccc23)cc1] | 6-chloro-N-(4-cyanophenyl)-1H-indole-3-sulfonamide | 15 | 330 | 98 |
| I-13 | 10075-50-0 | 873-74-5 | 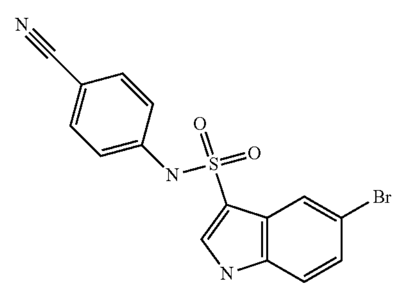 [SMILES: N#Cc1ccc(NS(=O)(=O)c2c[nH]c3ccc(Br)cc23)cc1] | 5-bromo-N-(4-cyanophenyl)-1H-indole-3-sulfonamide | 32 | 374 | 100 |
| I-14 | 467461-40-1 | 873-74-5 | 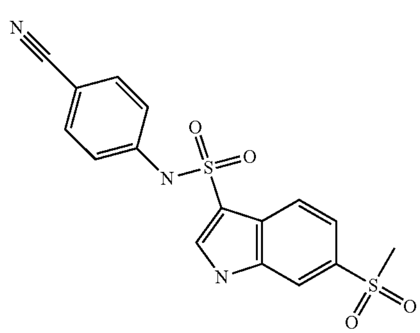 [SMILES: CS(=O)(=O)c1ccc2c(S(=O)(=O)Nc3ccc(C#N)cc3)c[nH]c2c1] | N-(4-cyanophenyl)-6-(methylsulfonyl)-1H-indole-3-sulfonamide | 7.5 | 374 | 100 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-15 | 16066-91-4 | 873-74-5 | 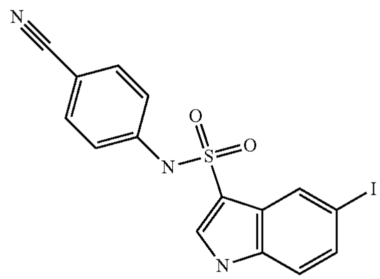 [SMILES: N#Cc1ccc(NS(=O)(=O)c2c[nH]c3ccc(I)cc23)cc1] | N-(4-cyanophenyl)-5-iodo-1H-indole-3-sulfonamide | 29.5 | 422 | 100 |
| I-16 | 53924-05-3 | 873-74-5 | 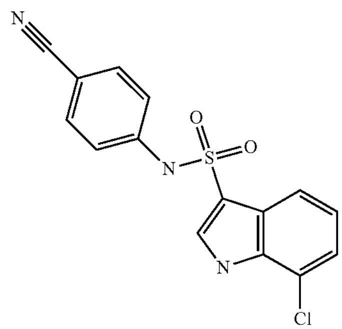 [SMILES: N#Cc1ccc(NS(=O)(=O)c2c[nH]c3c(Cl)cccc23)cc1] | 7-chloro-N-(4-cyanophenyl)-1H-indole-3-sulfonamide | 35.5 | 330 | 100 |
| I-17 | 17422-32-1 | 873-74-5 | 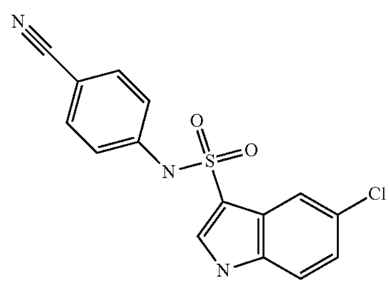 | 5-chloro-N-(4-cyanophenyl)-1H-indole-3-sulfonamide | 23 | 330 | 98 |
| I-18 | 248602-16-6 | 873-74-5 | 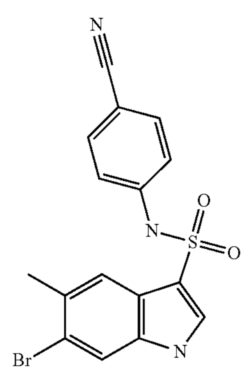 [SMILES: Cc1cc2c(S(=O)(=O)Nc3ccc(C#N)cc3)c[nH]c2cc1Br] | 6-bromo-N-(4-cyanophenyl)-5-methyl-1H-indole-3-sulfonamide | 20 | 388 | 100 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-19 | 267-48-1 | 873-74-5 | 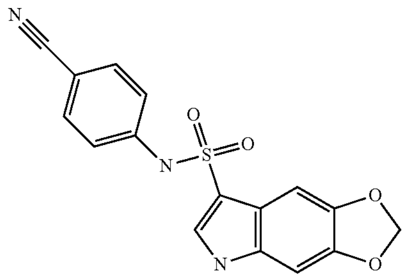 [SMILES: N#Cc1ccc(NS(=O)(=O)c2c[nH]c3cc4c(cc23)OCO4)cc1] | N-(4-cyanophenyl)-5H-[1,3]dioxolo[4,5-f]indole-7-sulfonamide | 20 | 340 | 96 |
| I-20 | 3420-02-8 | 106876-54-4 | 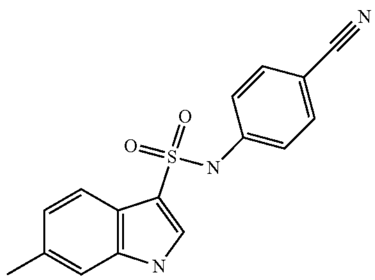 [SMILES: Cc1ccc2c(S(=O)(=O)Nc3ccc(C#N)cc3)c[nH]c2c1] | N-(4-cyanophenyl)-6-methyl-1H-indole-3-sulfonamide | 20 | 310 | 95 |
| I-21 | 17422-33-2 | 372-39-4 | 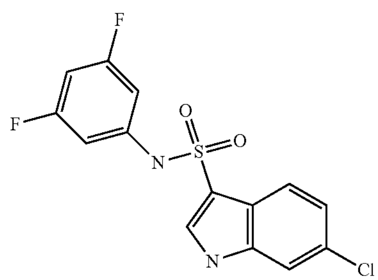 [SMILES: O=S(=O)(Nc1cc(F)cc(F)c1)c1c[nH]c2cc(Cl)ccc12] | 6-chloro-N-(3,5-difluorophenyl)-1H-indole-3-sulfonamide | 30 | 341 | 100 |
| I-22 | 17422-33-2 | 14235-81-5 | 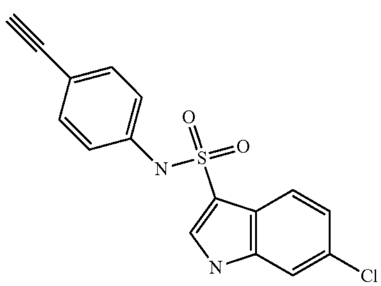 [SMILES: C#Cc1ccc(NS(=O)(=O)c2c[nH]c3cc(Cl)ccc23)cc1] | 6-chloro-N-(4-ethynylphenyl)-1H-indole-3-sulfonamide | 28.5 | 329 | 97 |
| I-23 | 17422-33-2 | 21397-08-0 | 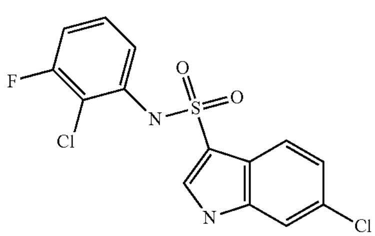 [SMILES: O=S(=O)(Nc1cccc(F)c1Cl)c1c[nH]c2cc(Cl)ccc12] | 6-chloro-N-(2-chloro-3-fluorophenyl)-1H-indole-3-sulfonamide | 14 | 357 | 96 |

TABLE 4-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-24 | 17422-33-2 | 106-47-8 | 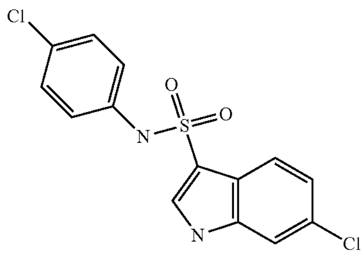 [SMILES: O=S(=O)(Nc1ccc(Cl)cc1)c1c[nH]c2cc(Cl)ccc12] | 6-chloro-N-(4-chlorophenyl)-1H-indole-3-sulfonamide | 8 | 339 | 100 |
| I-25 | 17422-33-2 | 1668-84-4 | 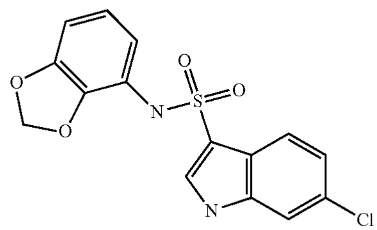 [SMILES: O=S(=O)(Nc1cccc2c1OCO2)c1c[nH]c2cc(Cl)ccc12] | N-(1,3-benzodioxol-4-yl)-6-chloro-1H-indole-3-sulfonamide | 32 | 349 | 100 |
| I-26 | 17422-33-2 | 95-51-2 | 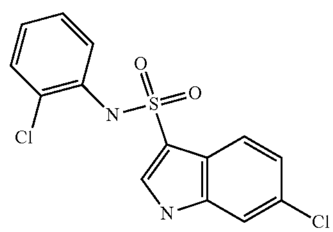 [SMILES: O=S(=O)(Nc1ccccc1Cl)c1c[nH]c2cc(Cl)ccc12] | 6-chloro-N-(2-chlorophenyl)-1H-indole-3-sulfonamide | 23 | 339 | 98 |
| I-27 | 248602-16-6 | 367-30-6 | 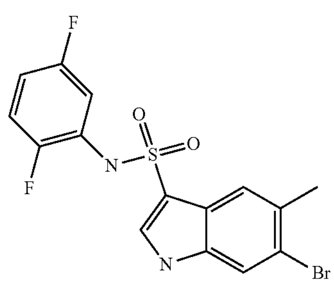 [SMILES: Cc1cc2c(S(=O)(=O)Nc3cc(F)ccc3F)c[nH]c2cc1Br] | 6-bromo-N-(2,5-difluorophenyl)-5-methyl-1H-indole-3-sulfonamide | 43 | 399 | 100 |
| I-28 | 467461-40-1 | 367-30-6 | 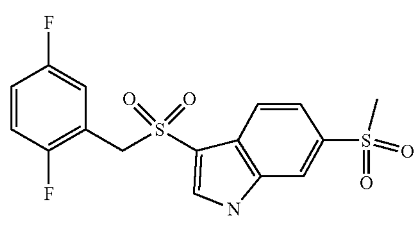 [SMILES: CS(=O)(=O)c1ccc2c(S(=O)(=O)Cc3cc(F)ccc3F)c[nH]c2c1] | N-(2,5-difluorophenyl)-6-(methylsulfonyl)-1H-indole-3-sulfonamide | 18.5 | 385 | 100 |
| I-29 | 3420-02-8 | 1668-84-4 | 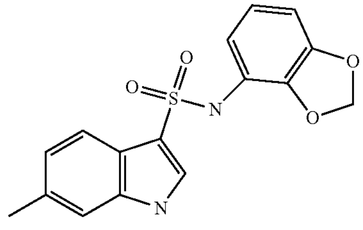 [SMILES: Cc1ccc2c(S(=O)(=O)Nc3cccc4c3OCO4)c[nH]c2c1] | N-(1,3-benzodioxol-4-yl)-6-methyl-1H-indole-3-sulfonamide | 9 | 329 | 80 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-30 | 267-48-1 | 367-30-6 | 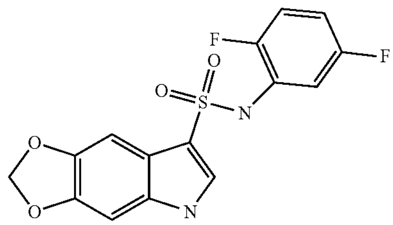 [SMILES: O=S(=O)(Nc1cc(F)ccc1F)c1c[nH]c2cc3c(cc12)OCO3] | N-(2,5-difluorophenyl)-5H-[1,3]dioxolo[4,5-f]indole-7-sulfonamide | 12 | 351 | 100 |
| I-31 | 399-51-9 | 1668-84-4 | 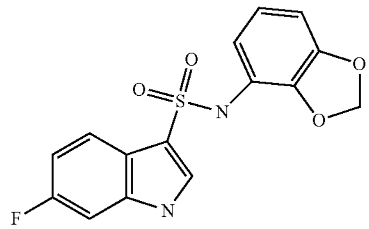 [SMILES: O=S(=O)(Nc1cccc2c1OCO2)c1c[nH]c2cc(F)ccc12] | N-(1,3-benzodioxol-4-yl)-6-fluoro-1H-indole-3-sulfonamide | 44 | 335 | 100 |
| I-32 | 3420-02-8 | 367-30-6 | 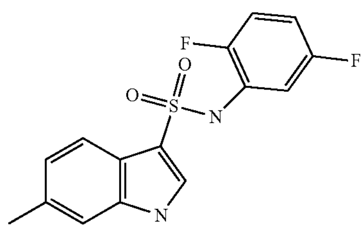 [SMILES: Cc1ccc2c(S(=O)(=O)Nc3cc(F)ccc3F)c[nH]c2c1] | N-(2,5-difluorophenyl)-6-methyl-1H-indole-3-sulfonamide | 7 | 321 | 100 |
| I-33 | 467461-40-1 | 1668-84-4 | 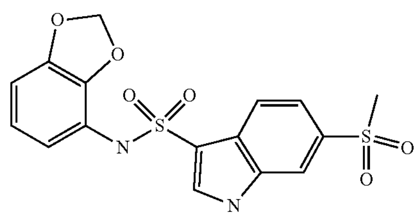 [SMILES: CS(=O)(=O)c1ccc2c(S(=O)(=O)Nc3cccc4c3OCO4)c[nH]c2c1] | N-(1,3-benzodioxol-4-yl)-6-(methylsulfonyl)-1H-indole-3-sulfonamide | 39 | 393 | 100 |
| I-34 | 467461-40-1 | 14235-81-5 | 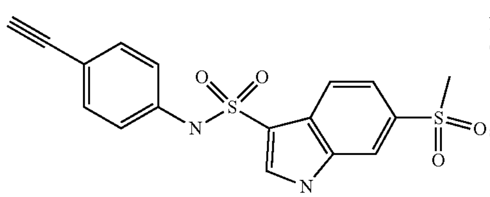 [SMILES: C#Cc1ccc(NS(=O)(=O)c2c[nH]c3cc(S(C)(=O)=O)ccc23)cc1] | N-(4-ethynylphenyl)-6-(methylsulfonyl)-1H-indole-3-sulfonamide | 28.5 | 373 | 90 |
| I-35 | 248602-16-6 | 1668-84-4 | 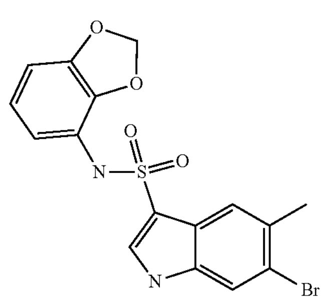 [SMILES: Cc1cc2c(S(=O)(=O)Nc3cccc4c3OCO4)c[nH]c2cc1Br] | N-(1,3-benzodioxol-4-yl)-6-bromo-5-methyl-1H-indole-3-sulfonamide | 65.5 | 407 | 97 |

TABLE 4-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-36 | 467461-40-1 | 1544-85-0 | 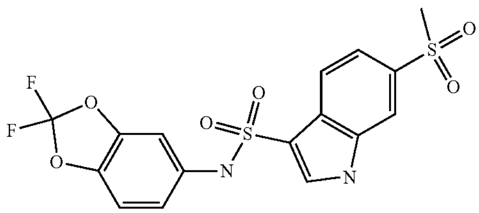 [SMILES: CS(=O)(=O)c1ccc2c(S(=O)(=O)Nc3ccc4c(c3)OC(F)(F)O4)c[nH]c2c1] | N-(2,2-difluoro-1,3-benzodioxol-5-yl)-6-(methylsulfonyl)-1H-indole-3-sulfonamide | 50 | 429 | 100 |
| I-37 | 399-51-9 | 367-30-6 | 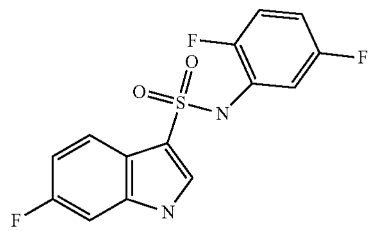 [SMILES: O=S(=O)(Nc1cc(F)ccc1F)c1c[nH]c2cc(F)ccc12] | N-(2,5-difluorophenyl)-6-fluoro-1H-indole-3-sulfonamide | 34 | 325 | 100 |
| I-38 | 17422-33-2 | 1003-99-2 | 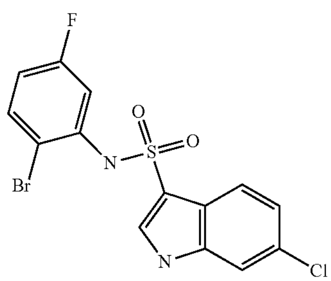 [SMILES: O=S(=O)(Nc1cc(F)ccc1Br)c1c[nH]c2cc(Cl)ccc12] | N-(2-bromo-5-fluorophenyl)-6-chloro-1H-indole-3-sulfonamide | 25.5 | 401 | 94 |
| I-39 | 17422-33-2 | 100-01-6 | 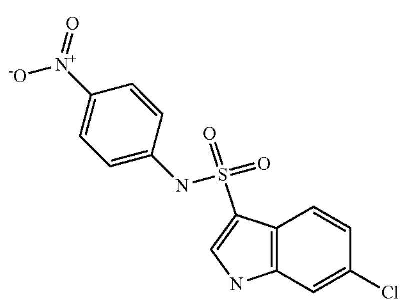 | 6-chloro-N-(4-nitrophenyl)-1H-indole-3-sulfonamide | 15 | 350 | 100 |
| I-40 | 17422-33-2 | 116632-24-7 | 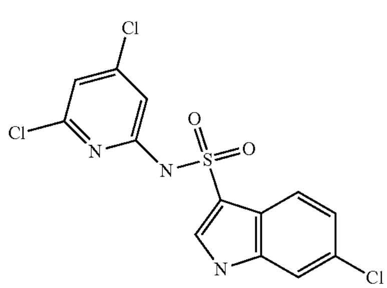 [SMILES: O=S(=O)(Nc1cc(Cl)cc(Cl)n1)c1c[nH]c2cc(Cl)ccc12] | 6-chloro-N-(4,6-dichloropyridin-2-yl)-1H-indole-3-sulfonamide | 1 | 374 | 100 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-41 | 399-51-9 | 367-34-0 | 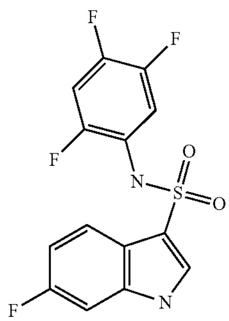 [SMILES: O=S(=O)(Nc1cc(F)c(F)cc1F)c1c[nH]c2cc(F)ccc12] | 6-fluoro-N-(2,4,5-trifluorophenyl)-1H-indole-3-sulfonamide | 38.5 | 343 | 100 |
| I-42 | 13544-43-9 | 29632-74-4 | 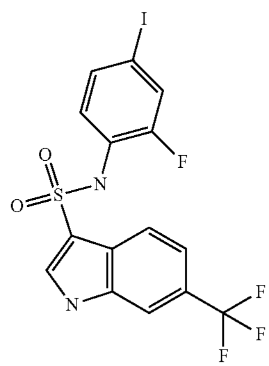 [SMILES: O=S(=O)(Nc1ccc(I)cc1F)c1c[nH]c2cc(C(F)(F)F)ccc12] | N-(2-fluoro-4-iodophenyl)-6-(trifluoromethyl)-1H-indole-3-sulfonamide | 34.5 | 483 | 100 |
| I-43 | 267-48-1 | 57946-56-2 | 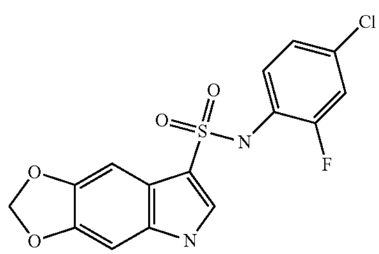 [SMILES: O=S(=O)(Nc1ccc(Cl)cc1F)c1c[nH]c2cc3c(cc12)OCO3] | N-(4-chloro-2-fluorophenyl)-5H-[1,3]dioxolo[4,5-f]indole-7-sulfonamide | 5.8 | 367 | 93 |
| I-44 | 267-48-1 | 29632-74-4 | 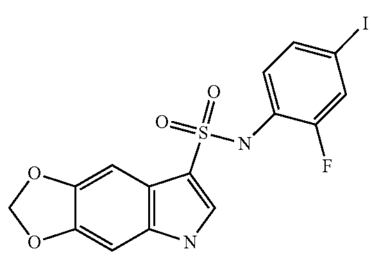 [SMILES: O=S(=O)(Nc1ccc(I)cc1F)c1c[nH]c2cc3c(cc12)OCO3] | N-(2-fluoro-4-iodophenyl)-5H-[1,3]dioxolo[4,5-f]indole-7-sulfonamide | 7 | 459 | 97 |
| I-45 | 233-34-1 | 57946-56-2 | 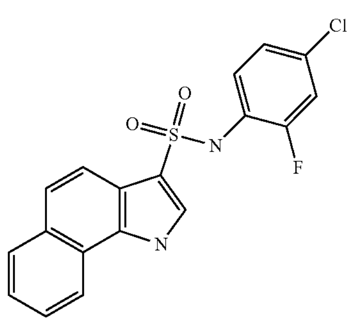 [SMILES: O=S(=O)(Nc1ccc(Cl)cc1F)c1c[nH]c2c1ccc1ccccc12] | N-(4-chloro-2-fluorophenyl)-1H-benzo[g]indole-3-sulfonamide | 3.4 | 373 | 100 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-46 | 267-48-1 | 367-34-0 | 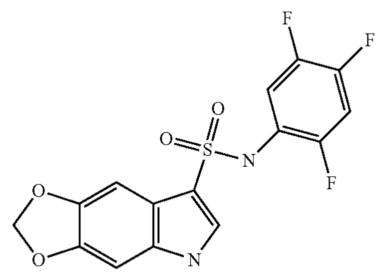 [SMILES: O=S(=O)(Nc1cc(F)c(F)cc1F)c1c[nH]c2cc3c(cc12)OCO3] | N-(2,4,5-trifluorophenyl)-5H-[1,3]dioxolo[4,5-f]indole-7-sulfonamide | 9.5 | 369 | 94 |
| I-47 | 233-34-1 | 29632-74-4 | 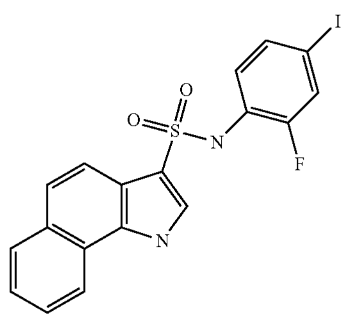 [SMILES: O=S(=O)(Nc1ccc(I)cc1F)c1c[nH]c2c1ccc1ccccc12] | N-(2-fluoro-4-iodophenyl)-1H-benzo[g]indole-3-sulfonamide | 3 | 465 | 100 |
| I-48 | 467461-40-1 | 29632-74-4 | 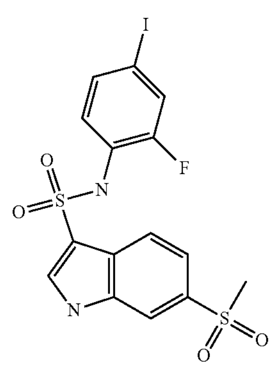 [SMILES: CS(=O)(=O)c1ccc2c(S(=O)(=O)Nc3ccc(I)cc3F)c[nH]c2c1] | N-(2-fluoro-4-iodophenyl)-6-(methylsulfonyl)-1H-indole-3-sulfonamide | 29.4 | 493 | 100 |
| I-49 | 399-51-9 | 29632-74-4 | 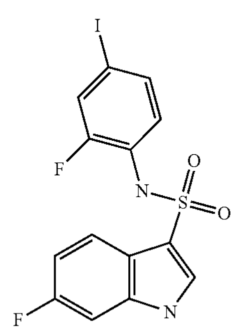 [SMILES: O=S(=O)(Nc1ccc(I)cc1F)c1c[nH]c2cc(F)ccc12] | 6-fluoro-N-(2-fluoro-4-iodophenyl)-1H-indole-3-sulfonamide | 47 | 433 | 98 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-50 | 467461-40-1 | 57946-56-2 | 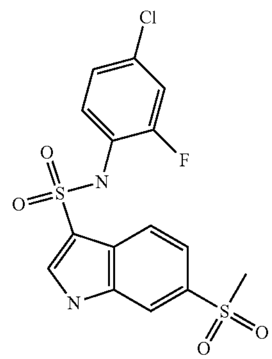 [SMILES: CS(=O)(=O)c1ccc2c(S(=O)(=O)Nc3ccc(Cl)cc3F)c[nH]c2c1] | N-(4-chloro-2-fluorophenyl)-6-(methylsulfonyl)-1H-indole-3-sulfonamide | 13 | 401 | 100 |
| I-51 | 399-51-9 | 57946-56-2 | 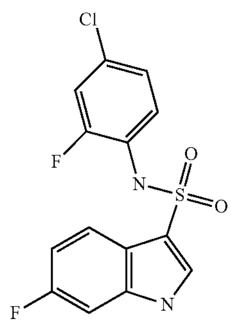 [SMILES: O=S(=O)(Nc1ccc(Cl)cc1F)c1c[nH]c2cc(F)ccc12] | N-(4-chloro-2-fluorophenyl)-6-fluoro-1H-indole-3-sulfonamide | 50 | 341 | 100 |
| I-52 | 233-34-1 | 367-34-0 | 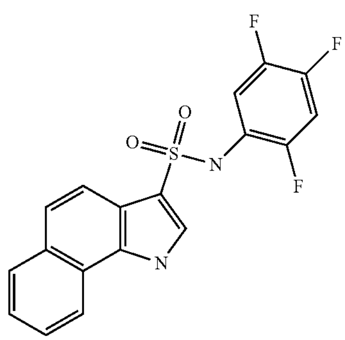 [SMILES: O=S(=O)(Nc1cc(F)c(F)cc1F)c1c[nH]c2c1ccc1ccccc12] | N-(2,4,5-trifluorophenyl)-1H-benzo[g]indole-3-sulfonamide | 3.4 | 375 | 100 |
| I-53 | 13544-43-9 | 57946-56-2 | 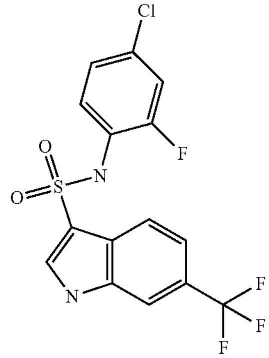 [SMILES: O=S(=O)(Nc1ccc(Cl)cc1F)c1c[nH]c2cc(C(F)(F)F)ccc12] | N-(4-chloro-2-fluorophenyl)-6-(trifluoromethyl)-1H-indole-3-sulfonamide | 41.9 | 391 | 97 |

TABLE 4-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-54 | 13544-43-9 | 367-34-0 | 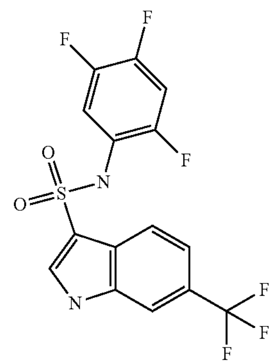 [SMILES: O=S(=O)(Nc1cc(F)c(F)cc1F)c1c[nH]c2cc(C(F)(F)F)ccc12] | 6-(trifluoromethyl)-N-(2,4,5-trifluorophenyl)-1H-indole-3-sulfonamide | 38.2 | 393 | 90 |
| I-55 | 17422-33-2 | 36556-60-2 | 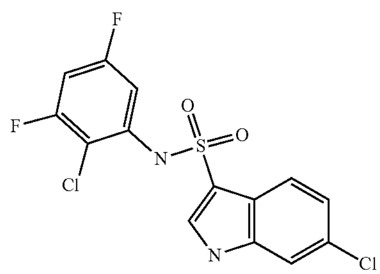 [SMILES: O=S(=O)(Nc1cc(F)cc(F)c1Cl)c1c[nH]c2cc(Cl)ccc12] | 6-chloro-N-(2-chloro-3,5-difluorophenyl)-1H-indole-3-sulfonamide | 2 | 375 | 100 |
| I-56 | 17422-33-2 | 452-80-2 | 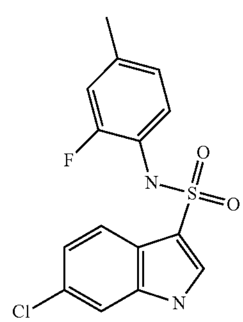 [SMILES: Cc1ccc(NS(=O)(=O)c2c[nH]c3cc(Cl)ccc23)c(F)c1] | 6-chloro-N-(2-fluoro-4-methylphenyl)-1H-indole-3-sulfonamide | 41.6 | 337 | 97 |
| I-57 | 17422-33-2 | 45644-21-1 | 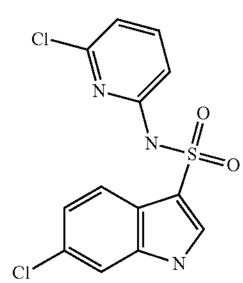 [SMILES: O=S(=O)(Nc1cccc(Cl)n1)c1c[nH]c2cc(Cl)ccc12] | 6-chloro-N-(6-chloropyridin-2-yl)-1H-indole-3-sulfonamide | 7.6 | 340 | 100 |

TABLE 4-continued
| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-58 | 17422-33-2 | 17920-35-3 | 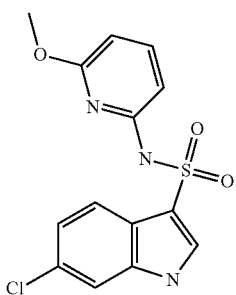 [SMILES: COc1cccc(NS(=O)(=O)c2c[nH]c3cc(Cl)ccc23)n1] | 6-chloro-N-(6-methoxypyridin-2-yl)-1H-indole-3-sulfonamide | 20.7 | 336 | 100 |
| I-59 | 17422-33-2 | 695-34-1 | 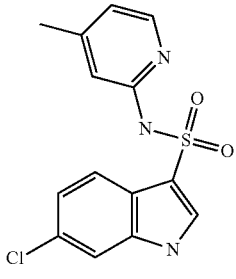 [SMILES: Cc1ccnc(NS(=O)(=O)c2c[nH]c3cc(Cl)ccc23)c1] | 6-chloro-N-(3,5-dichloropyridin-2-yl)-1H-indole-3-sulfonamide | 3.9 | 320 | 100 |
| I-60 | 17422-33-2 | 662117-63-7 | 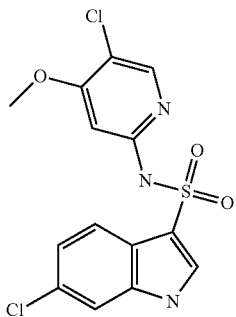 [SMILES: COc1cc(NS(=O)(=O)c2c[nH]c3cc(Cl)ccc23)ncc1Cl] | 6-chloro-N-(5-chloro-4-methoxypyridin-2-yl)-1H-indole-3-sulfonamide | 0.4 | 370 | 100 |
| I-61 | 17422-33-2 | 42182-27-4 | 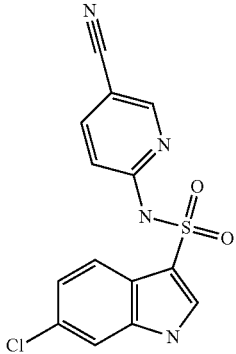 [SMILES: N#Cc1ccc(NS(=O)(=O)c2c[nH]c3cc(Cl)ccc23)nc1] | 6-chloro-N-(5-cyanopyridin-2-yl)-1H-indole-3-sulfonamide | 0.6 | 331 | 98 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-62 | 17422-33-2 | 21717-96-4 | 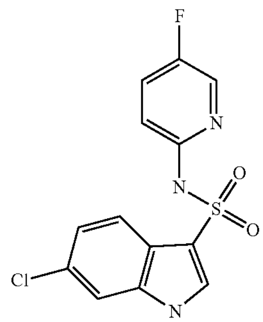 [SMILES: O=S(=O)(Nc1ccc(F)cn1)c1c[nH]c2cc(Cl)ccc12] | 6-chloro-N-(5-fluoropyridin-2-yl)-1H-indole-3-sulfonamide | 20.6 | 324 | 100 |
| I-63 | 17422-33-2 | 1072-98-6 | 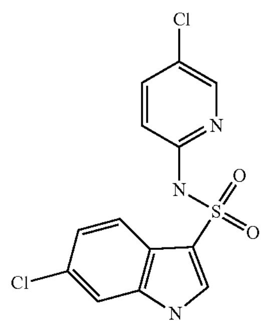 [SMILES: O=S(=O)(Nc1ccc(Cl)cn1)c1c[nH]c2cc(Cl)ccc12] | 6-chloro-N-(5-chloropyridin-2-yl)-1H-indole-3-sulfonamide | 11 | 340 | 100 |
| I-64 | 3189-13-7 | 767-64-6 | 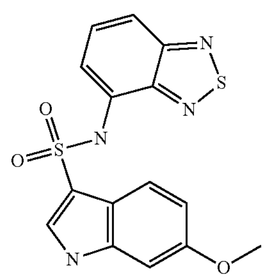 [SMILES: COc1ccc2c(S(=O)(=O)Nc3cccc4nsnc34)c[nH]c2c1] | N-(2,1,3-benzothiadiazol-4-yl)-6-methoxy-1H-indole-3-sulfonamide | 1 | 359 | 100 |
| I-65 | 233-88-5 | 57946-56-2 | 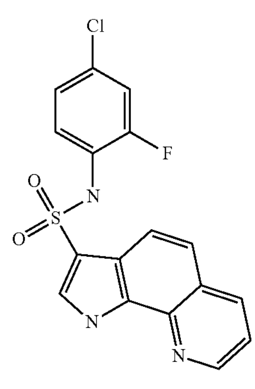 [SMILES: O=S(=O)(Nc1ccc(Cl)cc1F)c1c[nH]c2c1ccc1cccnc12] | N-(4-chloro-2-fluorophenyl)-1H-pyrrolo[3,2-h]quinoline-3-sulfonamide | 10 | 374 | 88 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-66 | 233-88-5 | 106876-54-4 | 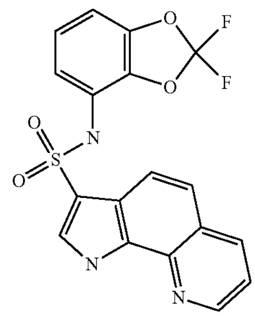 [SMILES: O=S(=O)(Nc1cccc2c1OC(F)(F)O2)c1c[nH]c2c1ccc1cccnc12] | N-(2,2-difluoro-1,3-benzodioxol-4-yl)-1H-pyrrolo[3,2-h]quinoline-3-sulfonamide | 4.2 | 402 | 100 |
| I-67 | 233-88-5 | 367-34-0 | 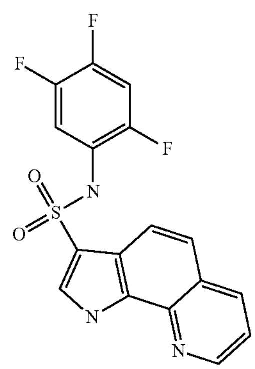 [SMILES: O=S(=O)(Nc1cc(F)c(F)cc1F)c1c[nH]c2c1ccc1cccnc12] | N-(2,4,5-trifluorophenyl)-1H-pyrrolo[3,2-h]quinoline-3-sulfonamide | 8.6 | 376 | 89 |
| I-68 | 15861-36-6 | 120934-03-4 | 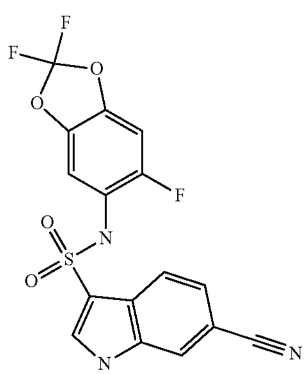 [SMILES: N#Cc1ccc2c(S(=O)(=O)Nc3cc4c(cc3F)OC(F)(F)O4)c[nH]c2c1] | 6-cyano-N-(2,2,6-trifluoro-1,3-benzodioxol-5-yl)-1H-indole-3-sulfonamide | 22.9 | 394 | 100 |
| I-69 | 3189-13-7 | 57946-56-2 | 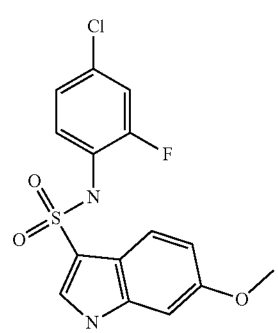 [SMILES: COc1ccc2c(S(=O)(=O)Nc3ccc(Cl)cc3F)c[nH]c2c1] | N-(4-chloro-2-fluorophenyl)-6-methoxy-1H-indole-3-sulfonamide | 2.3 | 353 | 100 |

TABLE 4-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-70 | 233-88-5 | 120934-03-4 | 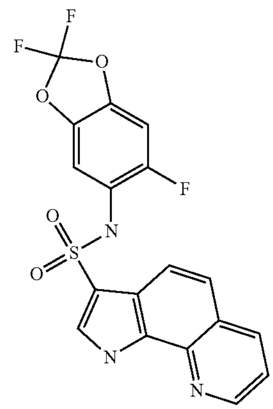 [SMILES: O=S(=O)(Nc1cc2c(cc1F)OC(F)(F)O2)c1c[nH]c2c1ccc1cccnc12] | N-(2,2,6-trifluoro-1,3-benzodioxol-5-yl)-1H-pyrrolo[3,2-h]quinoline-3-sulfonamide | 7.3 | 420 | 100 |
| I-71 | 3189-13-7 | 120934-03-4 | 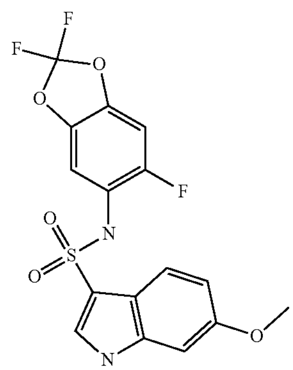 [SMILES: COc1ccc2c(S(=O)(=O)Nc3cc4c(cc3F)OC(F)(F)O4)c[nH]c2c1] | 6-methoxy-N-(2,2,6-trifluoro-1,3-benzodioxol-5-yl)-1H-indole-3-sulfonamide | 3 | 399 | 100 |
| I-72 | 3189-13-7 | 106876-54-4 | 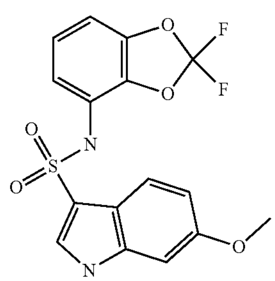 [SMILES: COc1ccc2c(S(=O)(=O)Nc3cccc4c3OC(F)(F)O4)c[nH]c2c1] | N-(2,2-difluoro-1,3-benzodioxol-4-yl)-6-methoxy-1H-indole-3-sulfonamide | 2.3 | 381 | 100 |
| I-73 | 233-88-5 | 767-64-6 | 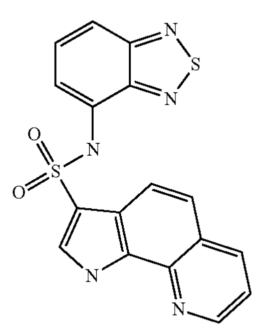 [SMILES: O=S(=O)(Nc1cccc2nsnc12)c1c[nH]c2c1ccc1cccnc12] | N-(2,1,3-benzothiadiazol-4-yl)-1H-pyrrolo[3,2-h]quinoline-3-sulfonamide | 8.1 | 380 | 89 |

TABLE 4-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-74 | 129848-59-5 | 767-64-6 | 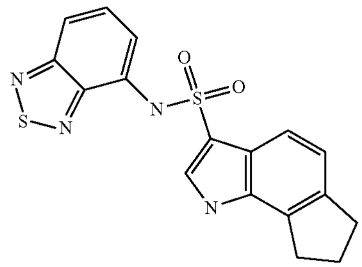 [SMILES: O=S(=O)(Nc1cccc2nsnc12)c1c[nH]c2c3c(ccc12)CCC3] | N-(2,1,3-benzothiadiazol-4-yl)-1,6,7,8-tetrahydrocyclopenta[g]indole-3-sulfonamide | 2.9 | 369 | 82 |
| I-75 | 15861-36-6 | 367-34-0 | 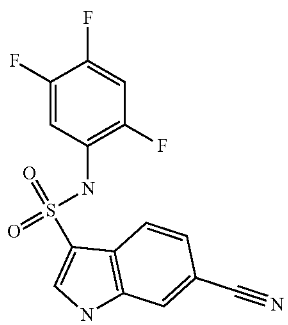 [SMILES: N#Cc1ccc2c(S(=O)(=O)Nc3cc(F)c(F)cc3F)c[nH]c2c1] | 6-cyano-N-(2,4,5-trifluorophenyl)-1H-indole-3-sulfonamide | 22.5 | 350 | 97 |
| I-76 | 15861-36-6 | 57946-56-2 | 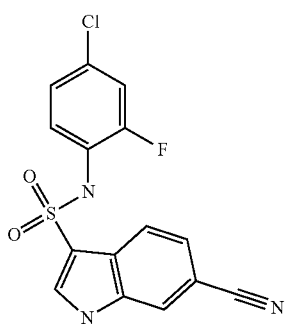 [SMILES: N#Cc1ccc2c(S(=O)(=O)Nc3ccc(Cl)cc3F)c[nH]c2c1] | N-(4-chloro-2-fluorophenyl)-6-cyano-1H-indole-3-sulfonamide | 33.3 | 348 | 90 |

D.2. Method C. Synthesis of 5-chloro-N-(4-cyano-phenyl)-1H-pyrrolo[2,3-b]pyridine-3-sulfonamide I-77

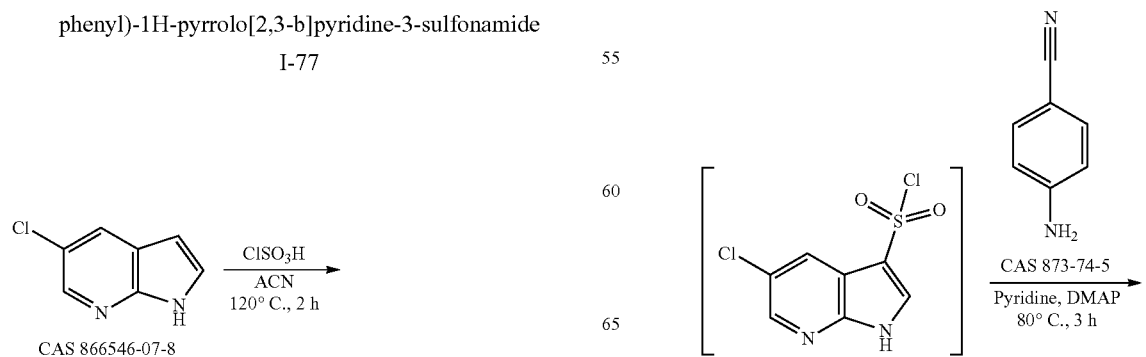

-continued

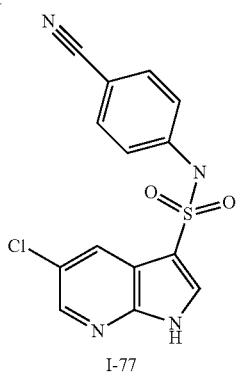

I-77

In a vial, a solution of 5-chloro-1H-pyrrolo[2,3-b]pyridine (24 mg, 0.15 mmol) in acetonitrile (100 μL) was stirred and chlorosulfonic acid (115 μl, 1.69 mmol) was added dropwise and the reaction mixture was heated to 120° C. for 2 h. After cooling to room temperature, pyridine (1 mL) was added. Then, a solution of 4-aminobenzonitrile (35 mg, 0.3 mmol) and 4-dimethylaminopyridine (4 mg, 0.03 mmol) in acetonitrile (100 μL) was added. The reaction mixture was stirred at 80° C. for 3 h, then evaporated in a centrifugal evaporator. The residue was purified by reverse phase chromatography in basic mode with MS detection to afford 5 mg of 5-chloro-N-(4-cyanophenyl)-1H-pyrrolo[2,3-b]pyridine-3-sulfonamide I-77.

Yield: 10%.

Basic LCMS Method 1 (ES⁻): 331 (M−H)⁻, 100% purity.

The following compounds in Table 5 were synthesized according to Method C.

TABLE 5

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-78 | 143468-13-7 | 767-64-6 | 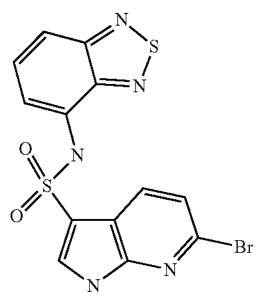 [SMILES: O=S(=O)(Nc1cccc2nsnc12)c1c[nH]c2nc(Br)ccc12] | N-(2,1,3-benzothiadiazol-4-yl)-6-bromo-1H-pyrrolo[2,3-b]pyridine-3-sulfonamide | 6.3 | 408 | 93 |
| I-79 | 898746-50-4 | 873-74-5 | 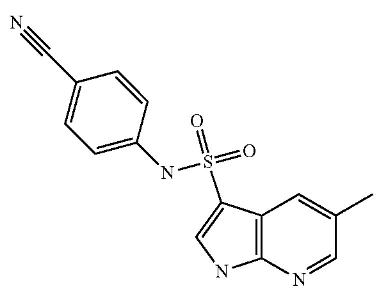 [SMILES: Cc1cnc2[nH]cc(S(=O)(=O)Nc3ccc(C#N)cc3)c2c1] | N-(4-cyanophenyl)-5-iodo-1H-pyrrolo[2,3-b]pyridine-3-sulfonamide | 5.7 | 423 | 100 |
| I-80 | 143468-13-7 | 873-74-5 | 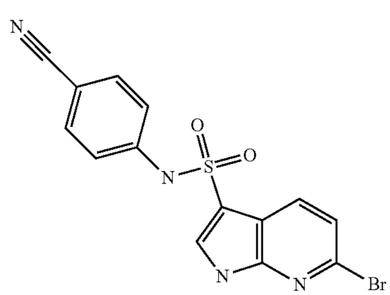 [SMILES: N#Cc1ccc(NS(=O)(=O)c2c[nH]c3nc(Br)ccc23)cc1] | 6-bromo-N-(4-cyanophenyl)-1H-pyrrolo[2,3-b]pyridine-3-sulfonamide | 1.9 | 375 | 96 |

TABLE 5-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-81 | 898746-50-4 | 367-30-6 | 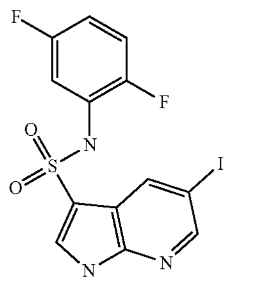 [SMILES: O=S(=O)(Nc1cc(F)ccc1F)c1c[nH]c2ncc(I)cc12] | N-(2,5-difluorophenyl)-5-iodo-1H-pyrrolo[2,3-b]pyridine-3-sulfonamide | 6.9 | 434 | 88 |
| I-82 | 898746-50-4 | 367-25-9 | 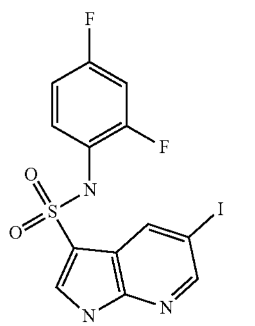 [SMILES: O=S(=O)(Nc1ccc(F)cc1F)c1c[nH]c2ncc(I)cc12] | N-(2,4-difluorophenyl)-5-iodo-1H-pyrrolo[2,3-b]pyridine-3-sulfonamide | 12 | 434 | 100 |
| I-83 | 143468-13-7 | 21397-08-0 | 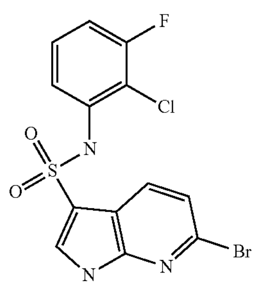 [SMILES: O=S(=O)(Nc1cccc(F)c1Cl)c1c[nH]c2nc(Br)ccc12] | 6-bromo-N-(2-chloro-3-fluorophenyl)-1H-pyrrolo[2,3-b]pyridine-3-sulfonamide | 2 | 402 | 100 |
| I-84 | 55052-27-2 | 14235-81-5 | 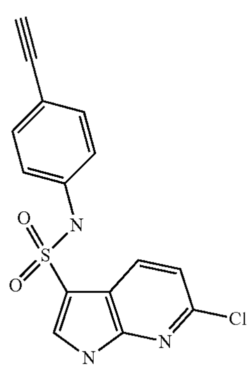 [SMILES: C#Cc1ccc(NS(=O)(=O)c2c[nH]c3nc(Cl)ccc23)cc1] | 6-chloro-N-(4-ethynylphenyl)-1H-pyrrolo[2,3-b]pyridine-3-sulfonamide | 3.4 | 330 | 85 |

TABLE 5-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-85 | 143468-13-7 | 14235-81-5 | 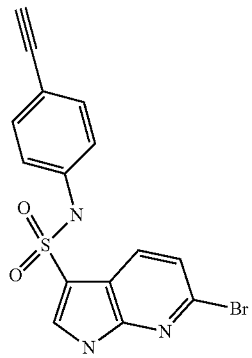 [SMILES: C#Cc1ccc(NS(=O)(=O)c2c[nH]c3nc(Br)ccc23)cc1] | 6-bromo-N-(4-ethynylphenyl)-1H-pyrrolo[2,3-b]pyridine-3-sulfonamide | 6.2 | 374 | 97 |
| I-86 | 55052-27-2 | 367-25-9 | 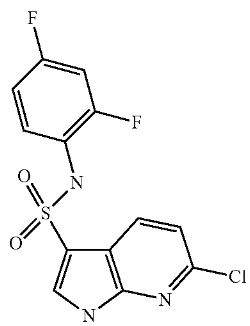 [SMILES: O=S(=O)(Nc1ccc(F)cc1F)c1c[nH]c2nc(Cl)ccc12] | 6-chloro-N-(2,4-difluorophenyl)-1H-pyrrolo[2,3-b]pyridine-3-sulfonamide | 6.2 | 342 | 96 |
| I-87 | 55052-27-2 | 21397-08-0 | 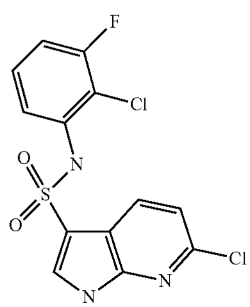 [SMILES: O=S(=O)(Nc1cccc(F)c1Cl)c1c[nH]c2nc(Cl)ccc12] | 6-chloro-N-(2-chloro-3-fluorophenyl)-1H-pyrrolo[2,3-b]pyridine-3-sulfonamide | 2.2 | 358 | 100 |
| I-88 | 143468-13-7 | 367-30-6 | 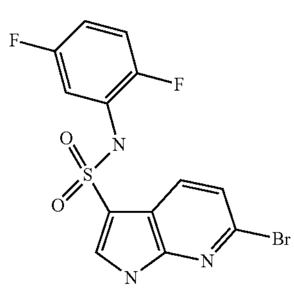 [SMILES: O=S(=O)(Nc1cc(F)ccc1F)c1c[nH]c2nc(Br)ccc12] | 6-bromo-N-(2,5-difluorophenyl)-1H-pyrrolo[2,3-b]pyridine-3-sulfonamide | 5.7 | 386 | 92 |

TABLE 5-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-89 | 143468-13-7 | 372-39-4 | 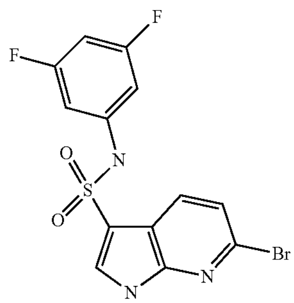 [SMILES: O=S(=O)(Nc1cc(F)cc(F)c1)c1c[nH]c2nc(Br)ccc12] | 6-bromo-N-(3,5-difluorophenyl)-1H-pyrrolo[2,3-b]pyridine-3-sulfonamide | 8.4 | 386 | 100 |
| I-90 | 55052-27-2 | 367-30-6 | 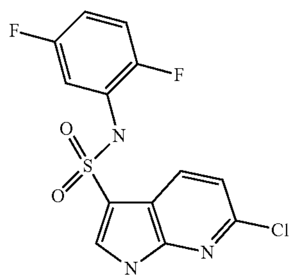 [SMILES: O=S(=O)(Nc1cc(F)ccc1F)c1c[nH]c2nc(Cl)ccc12] | 6-chloro-N-(2,5-difluorophenyl)-1H-pyrrolo[2,3-b]pyridine-3-sulfonamide | 2.1 | 342 | 100 |
| I-91 | 143468-13-7 | 367-25-9 | 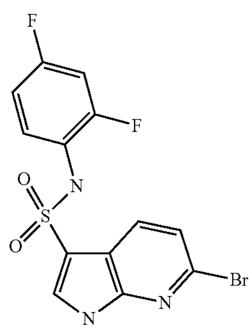 | 6-bromo-N-(2,4-difluorophenyl)-1H-pyrrolo[2,3-b]pyridine-3-sulfonamide | 6.5 | 386 | 100 |
| I-92 | 143468-13-7 | 57319-65-0 | 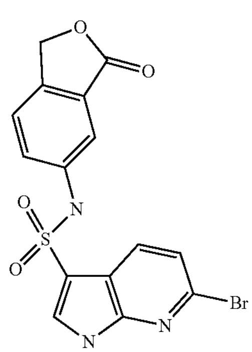 [SMILES: O=C1OCc2ccc(NS(=O)(=O)c3c[nH]c4nc(Br)ccc34)cc21] | 6-bromo-N-(3-oxo-1,3-dihydro-2-benzofuran-5-yl)-1H-pyrrolo[2,3-b]pyridine-3-sulfonamide | 3 | 406 | 100 |

TABLE 5-continued

| No | Indoles XI | Amines X | Structure | Name | Yield (%) | Basic LCMS Method 1 (ES⁻): (M − H)⁻ | Basic LCMS Method 1 (ES⁻): purity (%) |
|---|---|---|---|---|---|---|---|
| I-93 | 55052-27-2 | 767-64-6 | 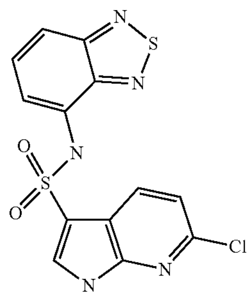 [SMILES: O=S(=O)(Nc1cccc2nsnc12)c1c[nH]c2nc(Cl)ccc12] | N-(2,1,3-benzothiadiazol-4-yl)-6-chloro-1H-pyrrolo[2,3-b]pyridine-3-sulfonamide | 1 | 364 | 100 |
| I-94 | 55052-27-2 | 29632-74-4 | 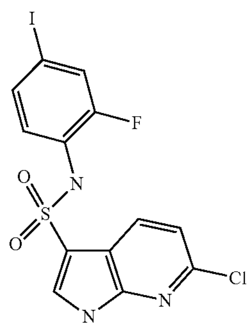 [SMILES: O=S(=O)(Nc1ccc(I)cc1F)c1c[nH]c2nc(Cl)ccc12] | 6-chloro-N-(2-fluoro-4-iodophenyl)-1H-pyrrolo[2,3-b]pyridine-3-sulfonamide | 5.5 | 450 | 100 |
| I-95 | 143468-13-7 | 367-34-0 | 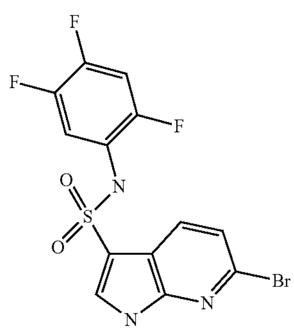 [SMILES: O=S(=O)(Nc1cc(F)c(F)cc1F)c1c[nH]c2nc(Br)ccc12] | 6-bromo-N-(2,4,5-trifluorophenyl)-1H-pyrrolo[2,3-b]pyridine-3-sulfonamide | 2.1 | 404 | 100 |
| I-96 | 55052-27-2 | 1668-84-4 | 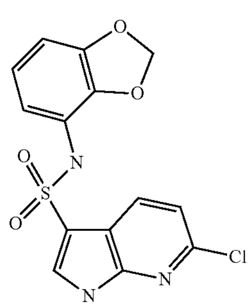 [SMILES: O=S(=O)(Nc1cccc2c1OCO2)c1c[nH]c2nc(Cl)ccc12] | N-(1,3-benzodioxol-4-yl)-6-chloro-1H-pyrrolo[2,3-b]pyridine-3-sulfonamide | 20 | 350 | 100 |

TABLE 5-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-97 | 143468-13-7 | 1668-84-4 | 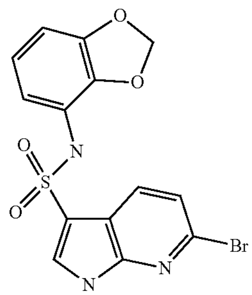 [SMILES: O=S(=O)(Nc1cccc2c1OCO2)c1c[nH]c2nc(Br)ccc12] | N-(1,3-benzodioxol-4-yl)-6-bromo-1H-pyrrolo[2,3-b]pyridine-3-sulfonamide | 2.2 | 394 | 100 |
| I-98 | 898746-50-4 | 767-64-6 | 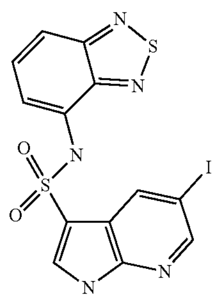 [SMILES: O=S(=O)(Nc1cccc2nsnc12)c1c[nH]c2ncc(I)cc12] | N-(2,1,3-benzothiadiazol-4-yl)-5-iodo-1H-pyrrolo[2,3-b]pyridine-3-sulfonamide | 8.5 | 456 | 100 |
| I-99 | 898746-50-4 | 106876-54-4 | 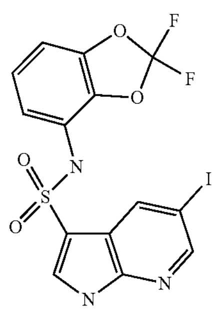 [SMILES: O=S(=O)(Nc1cccc2c1OC(F)(F)O2)c1c[nH]c2ncc(I)cc12] | N-(2,2-difluoro-1,3-benzodioxol-4-yl)-5-iodo-1H-pyrrolo[2,3-b]pyridine-3-sulfonamide | 3.6 | 478 | 100 |
| I-100 | 55052-27-2 | 106876-54-4 | 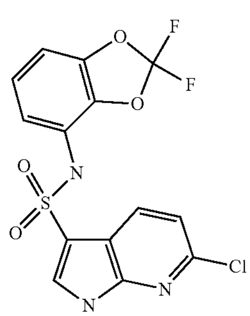 [SMILES: O=S(=O)(Nc1cccc2c1OC(F)(F)O2)c1c[nH]c2nc(Cl)ccc12] | 6-chloro-N-(2,2-difluoro-1,3-benzodioxol-4-yl)-1H-pyrrolo[2,3-b]pyridine-3-sulfonamide | 2.1 | 386 | 98 |

TABLE 5-continued

| No | Indoles XI | Amines X | Structure | Name | Yield (%) | Basic LCMS Method 1 (ES−): (M − H)− | Basic LCMS Method 1 (ES−): purity (%) |
|---|---|---|---|---|---|---|---|
| I-101 | 898746-50-4 | 29632-74-4 | 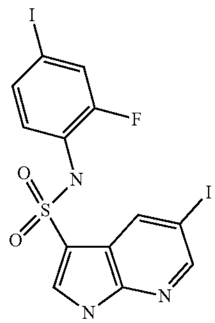 [SMILES: O=S(=O)(Nc1ccc(I)cc1F)c1c[nH]c2ncc(I)cc12] | N-(2-fluoro-4-iodophenyl)-5-iodo-1H-pyrrolo[2,3-b]pyridine-3-sulfonamide | 1.7 | 542 | 100 |
| I-102 | 143468-13-7 | 106876-54-4 | 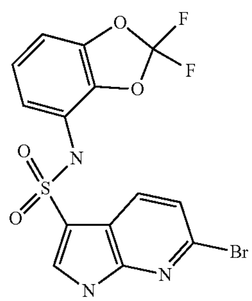 [SMILES: O=S(=O)(Nc1cccc2c1OC(F)(F)O2)c1c[nH]c2nc(Br)ccc12] | 6-bromo-N-(2,2-difluoro-1,3-benzodioxol-4-yl)-1H-pyrrolo[2,3-b]pyridine-3-sulfonamide | 0.6 | 430 | 95 |
| I-103 | 898746-50-4 | 367-34-0 | 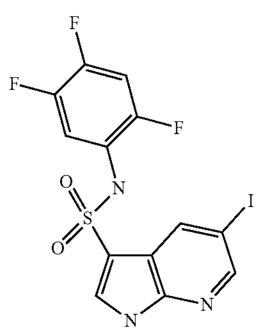 [SMILES: O=S(=O)(Nc1cc(F)c(F)cc1F)c1c[nH]c2ncc(I)cc12] | 5-iodo-N-(2,4,5-trifluorophenyl)-1H-pyrrolo[2,3-b]pyridine-3-sulfonamide | 21 | 452 | 94 |
| I-104 | 143468-13-7 | 29632-74-4 | 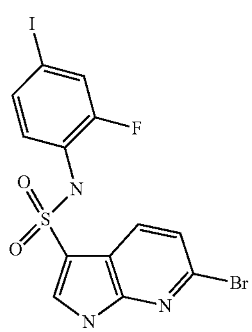 | 6-bromo-N-(2-fluoro-4-iodophenyl)-1H-pyrrolo[2,3-b]pyridine-3-sulfonamide | 4.7 | 494 | 100 |

D.3. Method D. Synthesis of N-(4-cyano-2-fluorophenyl)-1H-indole-3-sulfonamide I-105

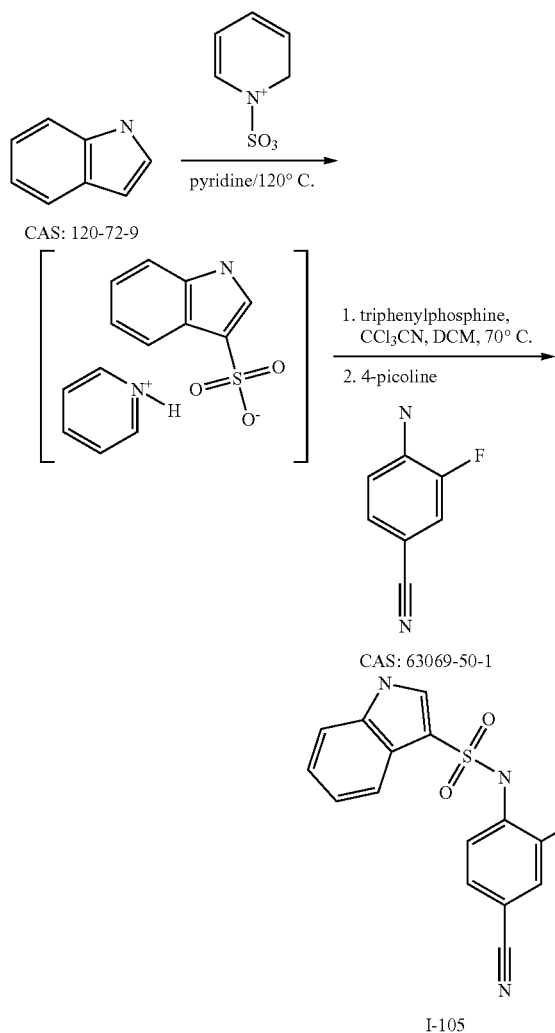

A solution of indole (33.5 mg, 0.29 mmol), sulfur trioxide-pyridine complex (45.43 mg, 0.29 mmol) and pyridine (1 mL) were refluxed for 1 h at 120° C., then the mixture was cooled to room temperature, followed by evaporation of pyridine under vacuum. The resulting suspension was diluted with water (10 mL) and subsequently washed with diethyl ether (3×30 mL). The aqueous phase was then dried under high vacuum (or by lyophilization) to yield a solid residue. To the dry residue, triphenylphosphine (230 mg, 0.86 mmol), trichloroacetonitrile (123 mg, 0.86 mmol), and dichloromethane (1 mL) were added and the resulting mixture was heated at 70° C. for 1 h, followed by the addition of the 4-amino-3-fluorobenzonitrile (46.6 mg, 0.34 mmol) and 4-picoline (239 mg, 2.57 mmol). The resulting mixture was stirred overnight at room temperature. Then the organic phase was diluted with DCM, washed with water, dried over anhydrous magnesium sulfate and evaporated to dryness. The product was purified by column chromatography using petroleum ether (b.p. 60° C.):ethyl acetate, gradient from 4:1 to 3:2 yielding a colorless oil, which on crystallization with acetone and petroleum ether gave 9 mg of N-(4-cyano-2-fluorophenyl)-1H-indole-3-sulfonamide I-105, as a white powder.

Yield: 10%.
Neutral LCMS Method 3 (ES$^+$): 316.05 (M+H)$^+$, 97% purity.
$^1$H NMR (600 MHz, DMSO-d$_6$) δ 12.08 (s, 1H), 10.76 (s, 1H), 8.08 (d, J=3.1 Hz, 1H), 7.83 (d, J=7.9 Hz, 1H), 7.70 (dd, J=10.7, 1.9 Hz, 1H), 7.61-7.48 (m, 2H), 7.49-7.42 (m, 1H), 7.16-7.24 (m, 2H).

The following compounds were synthesized according to Method D:

N-(2,1,3-benzothiadiazol-4-yl)-1H-indole-3-sulfonamide I-106 from 1H-indole CAS 120-72-9 and 2,1,3-benzothiadiazol-4-amine CAS 767-64-6

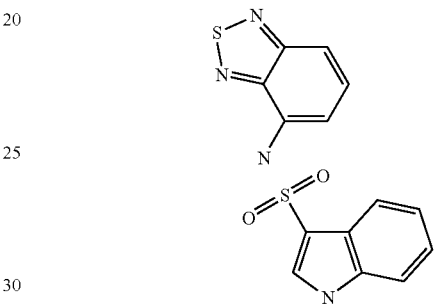

Yield: 15%.
Neutral LCMS Method 3 (ES$^+$): 331.02 (M+H)$^+$, 95% purity.
$^1$H NMR (600 MHz, DMSO-d$_6$) δ 11.99 (d, J=3.3 Hz, 1H), 10.73 (s, 1H), 8.10 (d, J=3.0 Hz, 1H), 7.87 (dd, J=8.1, 1.2 Hz, 1H), 7.65 (dd, J=8.8, 0.9 Hz, 1H), 7.57 (dd, J=8.8, 7.4 Hz, 1H), 7.48 (dd, J=7.5, 0.9 Hz, 1H), 7.39-7.40 (m, 1H), 7.14-7.17 (m, 1H), 7.08-7.11 (m, 1H).

N-(2,1,3-benzothiadiazol-4-yl)-6-fluoro-1H-indole-3-sulfonamide I-107 from 6-fluoro-1H-indole CAS 399-51-9 and 2,1,3-benzothiadiazol-4-amine CAS 767-64-6

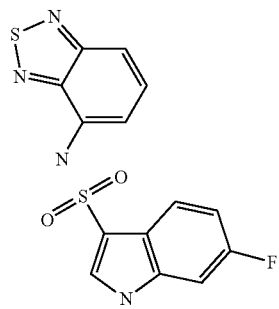

Yield: 13%.
Neutral LCMS Method 3 (ES$^+$): 349.02 (M+H)$^+$, 95% purity.
$^1$H NMR (600 MHz, DMSO-d$_6$) δ 12.02 (s, 1H), 10.80 (s, 1H), 8.09 (d, J=2.9 Hz, 1H), 7.86 (dd, J=8.9, 5.3 Hz, 1H), 7.71-7.62 (m, 1H), 7.58 (dd, J=8.8, 7.5 Hz, 1H), 7.47 (dd, J=7.4, 1.0 Hz, 1H), 7.19 (dd, J=9.7, 2.4 Hz, 1H), 6.98-7.01 (m, 1H).

6-chloro-N-(4-cyano-2-fluorophenyl)-1H-pyrrolo[2,3-b]pyridine-3-sulfonamide I-108 from 6-chloro-1H-pyrrolo[2,3-b]pyridine CAS 55052-27-2 and 4-amino-3-fluoro-benzonitrile CAS 63069-50-1

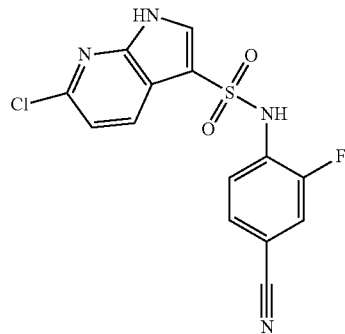 [SMILES: N#Cc1ccc(NS(=O)(=O)c2c[nH]c3nc(Cl)ccc23)c(F)c1]

Yield: 5%.
Neutral LCMS Method 3 (ES+): 351 (M+H)+, 95.0% purity.
$^1$H NMR (600 MHz, DMSO-d$_6$) δ 12.92 (d, J=3.4 Hz, 1H), 10.83 (s, 1H), 8.27 (d, J=2.9 Hz, 1H), 8.22 (d, J=8.3 Hz, 1H), 7.81-7.68 (m, 1H), 7.64-7.50 (m, 2H), 7.37 (d, J=8.3 Hz, 1H).

N-(2,1,3-benzothiadiazol-4-yl)-6-chloro-1H-indole-3-sulfonamide I-109 from 6-chloro-1H-indole CAS 17422-33-2 and 2,1,3-benzothiadiazol-4-amine CAS 767-64-6

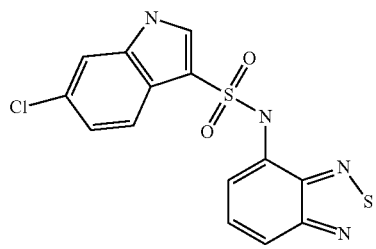 [SMILES: N=C1C=CC=C(NS(=O)(=O)c2c[nH]c3cc(Cl)ccc23)/C1=N/S]

Yield: 31%.
Neutral LCMS Method 3 (ES+): 364.99 (M+H)+, 99.0% purity.
$^1$H NMR (600 MHz, DMSO-d$_6$) δ 12.08 (s, 1H), 10.80 (s, 1H), 8.12 (d, J=2.4 Hz, 1H), 7.86 (d, J=8.6 Hz, 1H), 7.68 (dd, J=8.8, 0.9 Hz, 1H), 7.58 (dd, J=8.8, 7.4 Hz, 1H), 7.50-7.43 (m, 2H), 7.14 (dd, J=8.6, 1.9 Hz, 1H).

N-(2,1,3-benzothiadiazol-4-yl)-6-bromo-1H-indole-3-sulfonamide I-110 from 6-bromo-1H-indole CAS 52415-29-9 and 2,1,3-benzothiadiazol-4-amine CAS 767-64-6

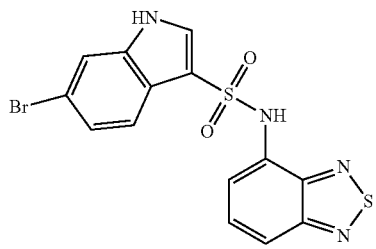 [SMILES: O=S(=O)(Nc1cccc2nsnc12)c1c[nH]c2cc(Br)ccc12]

Yield: 27%.
Neutral LCMS Method 3 (ES+): 408.94 (M+H)+, 94.0% purity.

$^1$H NMR (600 MHz, DMSO-d$_6$) δ 12.07 (s, 1H), 10.80 (s, 1H), 8.10 (d, J=2.6 Hz, 1H), 7.81 (d, J=8.6 Hz, 1H), 7.68 (dd, J=8.8, 0.9 Hz, 1H), 7.65-7.55 (m, 2H), 7.46 (dd, J=7.5, 0.9 Hz, 1H), 7.26 (dd, J=8.6, 1.8 Hz, 1H).

N-(2,1,3-benzothiadiazol-4-yl)-7-bromo-1H-indole-3-sulfonamide I-111 from 7-bromo-1H-indole CAS 51417-51-7 and 2,1,3-benzothiadiazol-4-amine CAS 767-64-6

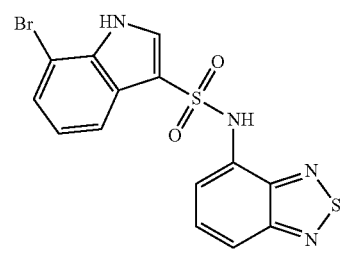 [SMILES: O=S(=O)(Nc1cccc2nsnc12)c1c[nH]c2c(Br)cccc12]

Yield: 25%.
Neutral LCMS Method 3 (ES+): 408.94 (M+H)+, 96.8% purity.
$^1$H NMR (600 MHz, DMSO-d$_6$) δ 12.30 (d, J=3.5 Hz, 1H), 10.86 (s, 1H), 8.10 (d, J=2.8 Hz, 1H), 7.88 (dd, J=8.0, 0.9 Hz, 1H), 7.68 (dd, J=8.8, 0.9 Hz, 1H), 7.58 (dd, J=8.8, 7.4 Hz, 1H), 7.49 (dd, J=7.4, 0.9 Hz, 1H), 7.41 (dd, J=7.7, 0.9 Hz, 1H), 7.06 (t, J=7.9 Hz, 1H).

N-(4-cyano-2-fluorophenyl)-6-methoxy-1H-indole-3-sulfonamide I-112 from 6-methoxy-1H-indole CAS 3189-13-7 and 4-amino-3-fluoro-benzonitrile CAS 63069-50-1

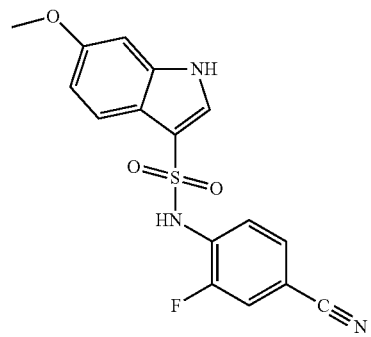 [SMILES: COc1ccc2c(S(=O)(=O)Nc3ccc(C#N)cc3F)c[nH]c2c1]

Yield: 18%.
Neutral LCMS Method 3 (ES+): 345.3 (M+H)+, 97.33% purity.
$^1$H NMR (500 MHz, DMSO-d$_6$) δ 11.96-11.74 (m, 1H), 10.69 (s, 1H), 7.93 (d, J=3.0 Hz, 1H), 7.76-7.63 (m, 2H), 7.60-7.46 (m, 2H), 6.93 (dd, J=2.3, 0.6 Hz, 1H), 6.82 (dd, J=8.8, 2.3 Hz, 1H), 3.76 (s, 3H).

289

N-(4-cyano-2-fluorophenyl)-6-fluoro-1H-indole-3-sulfonamide I-113 from 6-fluoro-1H-indole CAS 399-51-9 and 4-amino-3-fluoro-benzonitrile CAS 63069-50-1

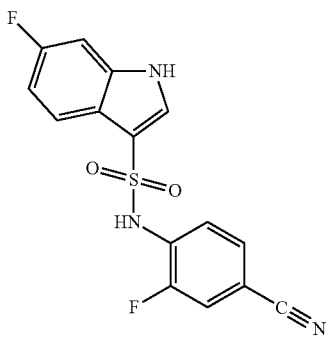 [SMILES: N#Cc1ccc(NS(=O)(=O)c2c[nH]c3cc(F)ccc23)c(F)c1]

Yield: 21%.

Neutral LCMS Method 3 (ES+): 333.3 (M+H)+, 98.49% purity.

¹H NMR (500 MHz, DMSO-d₆) δ 11.96-11.74 (m, 1H), 10.69 (s, 1H), 7.93 (d, J=3.0 Hz, 1H), 7.76-7.63 (m, 2H), 7.60-7.46 (m, 2H), 6.93 (dd, J=2.3, 0.6 Hz, 1H), 6.82 (dd, J=8.8, 2.3 Hz, 1H), 3.76 (s, 3H).

6-bromo-N-(4-cyano-2-fluorophenyl)-1H-indole-3-sulfonamide I-114 from 6-bromo-1H-indole CAS 52415-29-9 and 4-amino-3-fluoro-benzonitrile CAS 63069-50-1

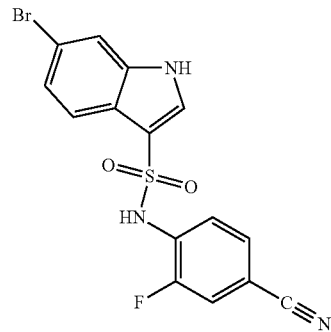

Yield: 25%.

Neutral LCMS Method 3 (ES+): 394.2 (M+H)+, 99.34% purity.

¹H NMR (500 MHz, DMSO-d₆) δ 12.23-12.10 (m, 1H), 10.77 (s, 1H), 8.09 (d, J=3.0 Hz, 1H), 7.79-7.70 (m, 2H), 7.66 (d, J=1.8 Hz, 1H), 7.55 (dd, J=3.5, 1.6 Hz, 2H), 7.34 (dd, J=8.6, 1.8 Hz, 1H).

290

N-(4-cyano-2-fluorophenyl)-7-methoxy-1H-indole-3-sulfonamide I-115 from 7-methoxy-1H-indole CAS 3189-22-8 and 4-amino-3-fluoro-benzonitrile CAS 63069-50-1

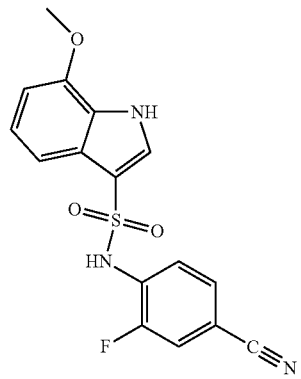 [SMILES: COc1cccc2c(S(=O)(=O)Nc3ccc(C#N)cc3F)c[nH]c12]

Yield: 17%.

Neutral LCMS Method 3 (ES+): 345.3 (M+H)+, 100% purity.

¹H NMR (500 MHz, DMSO-d₆) δ 12.46-12.02 (m, 1H), 10.72 (s, 1H), 7.91 (d, J=3.1 Hz, 1H), 7.70 (dd, J=10.8, 1.8 Hz, 1H), 7.61-7.52 (m, 2H), 7.40 (d, J=8.1 Hz, 1H), 7.10 (t, J=7.9 Hz, 1H), 6.79 (d, J=7.8 Hz, 1H), 3.90 (s, 3H).

6-chloro-N-(4-cyano-2-fluorophenyl)-1H-indole-3-sulfonamide I-116 from 6-chloro-1H-indole CAS 17422-33-2 and 4-amino-3-fluoro-benzonitrile CAS 63069-50-1

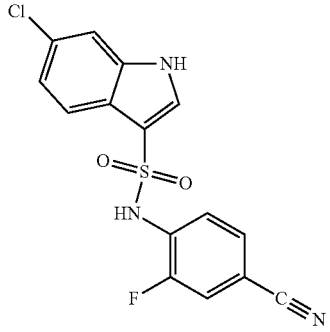 [SMILES: N#Cc1ccc(NS(=O)(=O)c2c[nH]c3cc(Cl)ccc23)c(F)c1]

Yield: 28%.

Neutral LCMS Method 3 (ES+): 349.7 (M+H)+, 100% purity.

¹H NMR (500 MHz, DMSO-d₆) δ 12.17 (d, J=3.3 Hz, 1H), 10.77 (s, 1H), 8.10 (d, J=2.9 Hz, 1H), 7.82 (d, J=8.6 Hz, 1H), 7.75-7.71 (m, 1H), 7.57-7.53 (m, 2H), 7.52 (s, 1H), 7.23 (dd, J=8.6, 1.9 Hz, 1H).

7-chloro-N-(4-cyano-2,5-difluorophenyl)-1H-indole-3-sulfonamide I-117 from 7-chloro-1H-indole CAS 53924-05-3 and 4-amino-2,5-difluoro-benzonitrile CAS 112279-61-5

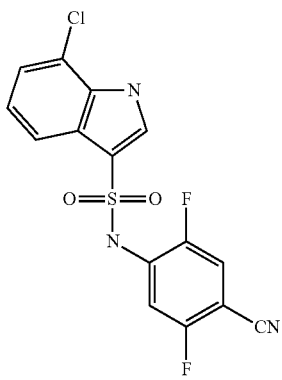 [SMILES: N#Cc1cc(F)c(NS(=O)(=O)c2c[nH]c3c(Cl)cccc23)cc1F]

Yield: 42%.
Neutral LCMS Method 3 (ES+): 337.99 (M+H)+, 98% purity.
$^1$H NMR (600 MHz, DMSO-$d_6$) δ 12.65 (s, 1H), 11.25 (s, 1H), 8.35 (d, J=3.1 Hz, 1H), 7.89-7.80 (m, 2H), 7.49 (dd, J=10.9, 6.3 Hz, 1H), 7.36 (dd, J=7.7, 0.9 Hz, 1H), 7.23 (t, J=7.9 Hz, 1H).

D.4. Method E. Synthesis of N-(4-chloro-2,5-difluorophenyl)-1H-pyrrolo[3,2-h]quinoline-3-sulfonamide I-118

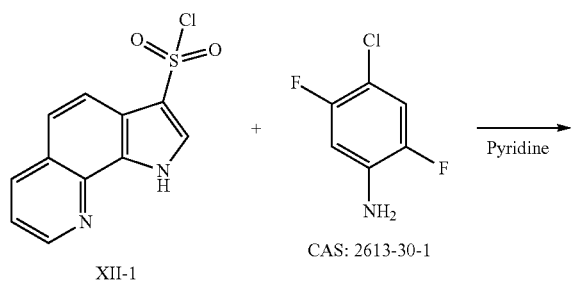

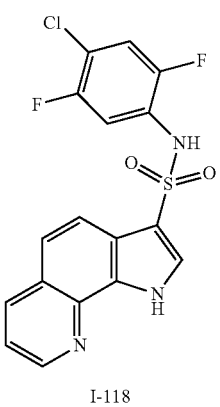

I-118

To a solution of 1H-pyrrolo[3,2-H]quinoline-3-sulfonyl chloride (140 mg, 0.52 mmol) in pyridine (1.5 mL) was added 4-chloro-2,5-difluoroaniline (90 mg, 0.55 mmol). The reaction mixture was stirred at room temperature for 4 h and then evaporated to dryness. The residue was triturated in a mixture of water/acetonitrile (8/2) and sonicated. The solid suspension was filtered, rinsed with water, dried under vacuum at 35° C., to afford 105 mg of N-(4-chloro-2,5-difluorophenyl)-1H-pyrrolo[3,2-h]quinoline-3-sulfonamide I-118, as a beige solid.

Yield: 50%.

Basic LCMS Method 1 (ES+): 394 (M+H)+, 99% purity.

$^1$H NMR (400 MHz, DMSO-$d_6$) δ 13.26 (s, 1H), 10.51 (s, 1H), 8.93 (dd, J=4.4, 1.6 Hz, 1H), 8.46 (dd, J=8.3, 1.6 Hz, 1H), 8.04-7.65 (m, 3H), 7.59 (m, 1H), 7.51 (dd, J=9.8, 6.8 Hz, 1H), 7.40 (dd, J=10.4, 7.0 Hz, 1H).

The following compounds in Table 6 may be synthesized according to a method analogous to Method E.

TABLE 6

| No | Sulfonyl chlorides XII | Amines X | Conditions, Time | Purification conditions | Yield (%) |
|---|---|---|---|---|---|
| I-119 | XII-1 | 767-63-5 | rt, 4 h | — | 41 |
| I-120 | XII-2 | 873-74-5 | 70° C., 8 h | 10-35% EtOAc/Hexane | 8 |
| I-121 | XII-3 | 452-80-2 | 80° C., 4 h | Basic prep LCMS Method 1 | 37 |
| I-122 | XII-4 | 80936-82-9 | 80° C., 16 h | 2% MeOH in DCM | 57 |
| I-123 | XII-4 | 106876-54-4 | 80° C., 5 h | 40% EtOAc/Hexane | 49 |
| I-124 | XII-4 | 7251-09-4 | 80° C., 4 h | 0-30% EtOAc/Hexane | 19 |
| I-125 | XII-4 | 120934-03-4 | 80° C., 4 h | 20-24% EtOAc/Hexane | 37 |
| I-126 | XII-4 | 177476-76-5 | 80° C., 3 h | 15-20% EtOAc/Hexane | 37 |
| I-127 | XII-4 | X-1 | 80° C., 16 h | 1% MeOH in DCM | 18 |
| I-128 | XII-4 | 21717-95-3 | 80° C., 16 h | 30% EtOAc/Hexane | 58 |
| I-129 | XII-4 | 42409-58-5 | 70° C., 16 h | 10% MeOH in DCM | 22 |
| I-130 | XII-4 | X-2 | 60° C., 1 h | 10-30% EtOAc/Hexane | 59 |
| I-131 | XII-4 | X-3 | 85° C., 16 h | 0-10% EtOAc/Hexane | 12 |
| I-132 | XII-4 | X-4 | 80° C., 16 h | 20-30% EtOAc/Hexane | 16 |
| I-133 | XII-5 | 873-74-5 | 80° C., 16 h | 0.4% MeOH in DCM | 22 |
| I-134 | XII-6 | 873-74-5 | 80° C., 16 h | 50% EtOAc/Hexane | 45 |
| I-135 | XII-6 | 120934-03-4 | 80° C., 16 h | 60% EtOAc/Hexane | 34 |

TABLE 6-continued

| No | Sulfonyl chlorides XII | Amines X | Conditions, Time | Purification conditions | Yield (%) |
|---|---|---|---|---|---|
| I-136 | XII-6 | 367-34-0 | 80° C., 16 h | 20% EtOAc/Hexane | 82 |
| I-137 | XII-6 | 106876-54-4 | 80° C., 16 h | 15-25% EtOAc/Hexane | 21 |
| I-138 | XII-4 | 369-35-7 | 85° C., 4 h | 50% EtOAc/Hexane | 38 (crude) |
| I-139 | XII-24 | 873-74-5 | 85° C., 16 h | 20% EtOAc/Hexane | 5 |
| I-140 | XII-4 | 29632-74-4 | 70° C., 2 h | Basic prep LCMS Method 1 | 23 |
| I-141 | XII-4 | 57946-56-2 | 80° C., 2 h | Basic prep LCMS Method 1 | 29 |
| I-142 | XII-4 | X-6 | 80° C., 5 h | 20-40% EtOAc/Petroleum ether then Neutral RP-HPLC Method 2 | 7 |
| I-143 | XII-4 | 247071-37-0 | 80° C., 5 h | 20-40% EtOAc/Petroleum ether then Neutral RP-HPLC Method 2 | 11 |
| I-144 | XII-7 | X-5 | 80° C., 3 h | 20-40% EtOAc/Petroleum ether | 14 |
| I-145 | XII-8 | 112279-61-5 | 80° C., 18 h | 5-25% EtOAc/Cyclohexane | 26 |
| I-146 | XII-9 | 112279-61-5 | 80° C., 18 h | 5-25% EtOAc/Cyclohexane | 11 |
| I-147 | XII-4 | 874-37-3 | rt, 8 h | 5-25% EtOAc/Cyclohexane | 10 |
| I-148 | XII-10 | 112279-61-5 | 80° C., 2 h | 5-25% EtOAc/Cyclohexane | 32 |
| I-149 | XII-10 | 53312-80-4 | 80° C., 2 h | 5-25% EtOAc/Cyclohexane | 46 |
| I-150 | XII-10 | 63069-50-1 | 80° C., 2 h | 5-25% EtOAc/Cyclohexane | 16 |
| I-151 | XII-3 | 112279-61-5 | 80° C., 2 h | 5-25% EtOAc/Cyclohexane | 28 |
| I-152 | XII-3 | 63069-50-1 | 80° C., 2 h | 5-25% EtOAc/Cyclohexane | 58 |
| I-153 | XII-11 | 112279-61-5 | 80° C., 2 h | 5-25% EtOAc/Cyclohexane | 68 |
| I-154 | XII-11 | 63069-50-1 | 80° C., 2 h | 5-25% EtOAc/Cyclohexane | 73 |
| I-155 | XII-3 | 767-64-6 | 80° C., 2 h | 5-25% EtOAc/Cyclohexane | 42 |
| I-156 | XII-11 | 767-64-6 | 80° C., 2 h | 5-25% EtOAc/Cyclohexane | 75 |
| I-157 | XII-3 | 874-37-3 | 80° C., 2 h | 5-25% EtOAc/Cyclohexane | 65 |
| I-158 | XII-10 | 874-37-3 | 80° C., 2 h | 5-25% EtOAc/Cyclohexane | 44 |
| I-159 | XII-3 | 873-74-5 | 80° C., 2 h | 5-25% EtOAc/Cyclohexane | 22 |
| I-160 | XII-3 | X-5 | 80° C., 2 h | 5-25% EtOAc/Cyclohexane | 33 |
| I-161 | XII-4 | X-10 | 80° C., 2 h | 5-25% EtOAc/Cyclohexane | 28 |
| I-162 | XII-4 | X-5 | 70° C., 16 h | 20% EtOAc/Petroleum ether | 23 |
| I-163 | XII-4 | X-9 | 70° C., 16 h | 33% EtOAc/Petroleum ether | 18 |
| I-164 | XII-12 | 112279-61-5 | 70° C., 16 h | 40% EtOAc/Petroleum ether | 52 |
| I-165 | XII-13 | 112279-61-5 | 70° C., 16 h | 40% EtOAc/Petroleum ether | 55 |
| I-166 | XII-12 | 767-64-6 | 70° C., 16 h | 40% EtOAc/Petroleum ether | 65 |
| I-167 | XII-14 | 112279-61-5 | 70° C., 16 h | 40% EtOAc/Petroleum ether | 44 |
| I-168 | XII-12 | 63069-50-1 | 70° C., 16 h | 40% EtOAc/Petroleum ether | 63 |
| I-169 | XII-13 | 874-37-3 | 80° C., 3 h | 40% EtOAc/Petroleum ether | 62 |
| I-170 | XII-15 | 63069-50-1 | 70° C., 16 h | 40% EtOAc/Petroleum ether then Neutral RP-HPLC Method 2 | 43 |
| I-171 | XII-13 | 873-74-5 | 70° C., 16 h | 40% EtOAc/Petroleum ether then Neutral RP-HPLC Method 2 | 35 |
| I-172 | XII-13 | X-5 | 80° C., 3 h | 40% EtOAc/Petroleum ether | 65 |
| I-173 | XII-16 | 367-24-8 | 70° C., 16 h | 40% EtOAc/Petroleum ether | 61 |

TABLE 6-continued

| No | Sulfonyl chlorides XII | Amines X | Conditions, Time | Purification conditions | Yield (%) |
|---|---|---|---|---|---|
| I-174 | XII-16 | 57946-56-2 | 70° C., 16 h | 40% EtOAc/Petroleum ether | 64 |
| I-175 | XII-3 | 1268392-91-1 | 70° C., 16 h | 40% EtOAc/Petroleum ether | 35 |
| I-176 | XII-7 | 112279-61-5 | 80° C., 5 h | 50% EtOAc/Petroleum ether | 29 |
| I-177 | XII-17 | 63069-50-1 | rt, 5 h | Neutral RP-HPLC Method 2 | 4 |
| I-178 | XII-7 | 873-74-5 | rt, 16 h | Neutral RP-HPLC Method 2 | 48 |
| I-179 | XII-7 | 874-37-3 | rt, 16 h | Neutral RP-HPLC Method 2 | 40 |
| I-180 | XII-4 | 3544-25-0 | 80° C., 16 h | 33% EtOAc/Petroleum ether | 8 |
| I-181 | XII-4 | 20925-27-3 | 80° C., 16 h | 33% EtOAc/Petroleum ether | 5 |
| I-182 | XII-4 | 110301-23-0 | 80° C., 16 h | 33% EtOAc/Petroleum ether | 7 |
| I-183 | XII-6 | 874-37-3 | 80° C., 2 h | 25-100% EtOAc/Cyclohexane | 19 |
| I-184 | XII-18 | 112279-61-5 | 80° C., 2 h | 25-100% EtOAc/Cyclohexane | 6 |
| I-185 | XII-4 | 112279-61-5 | 80° C., 2 h | 25-100% EtOAc/Cyclohexane | 60 |
| I-186 | XII-18 | 767-64-6 | 80° C., 2 h | 25-100% EtOAc/Cyclohexane | 30 |
| I-187 | XII-16 | 112279-61-5 | 80° C., 2 h | 25-100% EtOAc/Cyclohexane | 7 |
| I-188 | XII-6 | 112279-61-5 | 80° C., 2 h | 25-100% EtOAc/Cyclohexane | 6 |
| I-189 | XII-18 | 63069-50-1 | 80° C., 2 h | 25-100% EtOAc/Cyclohexane | 3 |
| I-190 | XII-18 | 873-74-5 | 80° C., 2 h | 25-100% EtOAc/Cyclohexane | 8 |
| I-191 | XII-3 | 246847-98-3 | 70° C., 16 h | 33% EtOAc/Petroleum ether | 21 |
| I-192 | XII-18 | 874-37-3 | 80° C., 2 h | 25-100% EtOAc/Cyclohexane | 16 |
| I-193 | XII-6 | X-5 | 80° C., 2 h | 25-100% EtOAc/Cyclohexane | 16 |
| I-194 | XII-4 | X-11 | rt, 4 h | 30-70% EtOAc/Hexane | 10 |
| I-195 | XII-4 | X-12 | 80° C., 16 h | 40% EtOAc/Hexane | 11 |
| I-196 | XII-25 | 367-34-0 | 80° C., 3 h | 10-30% EtOAc/Hexane | 17 |
| I-197 | XII-4 | X-13 | 65° C., 3 h | 25-30% EtOAc/Hexane | 12 |
| I-198 | XII-24 | 2613-30-1 | 70° C., 16 h | 10-20% EtOAc/Hexane | 1 |
| I-199 | XII-4 | X-14 | 80° C., 4 h | 30% EtOAc/Hexane | 6 |
| I-200 | XII-4 | X-15 | 80° C., 3 h | 50% EtOAc/Hexane | 6 |
| I-242 | XII-26 | 2613-30-1 | 80° C., 16 h | 40% EtOAc/Hexane | 11 |
| I-243 | XII-4 | X-17 | 70° C., 4 h | 20-40% EtOAc/Hexane | 33 |
| I-244 | XII-25 | 2613-30-1 | 80° C., 16 h | 30% EtOAc/Hexane | 20 |
| I-245 | XII-4 | X-16 | DMAP cat., 80° C., 16 h | 40% EtOAc/Hexane | 2 |
| I-246 | XII-4 | X-18 | 70° C., 5 h | 10-20% EtOAc/Hexane | 32 |
| I-247 | XII-27 | 2613-30-1 | 80° C., 8 h | 20% EtOAc/Hexane | 8 |
| I-248 | XII-28 | 2613-30-1 | 80° C., 16 h | 10-40% EtOAc/Hexane | 8 |
| I-249 | XII-29 | 2613-30-1 | DMAP cat., 80° C., 5 h | 40% EtOAc/Hexane | 51 |
| I-251 | XII-30 | 2613-30-1 | DMAP cat., 80° C., 12 h | 40% EtOAc/Hexane | 10 |
| I-252 | XII-4 | X-19 | DMAP cat., 90° C., 16 h | 40% EtOAc/Hexane | 6 |
| I-253 | XII-4 | X-20 | DMAP cat., 90° C., 14 h | 40% EtOAc/Hexane | 10 |
| I-254 | XII-4 | X-21 | DMAP cat., 80° C., 18 h | 40% EtOAc/Hexane | 4 |
| I-255 | XII-4 | X-22 | DMAP cat., 80° C., 14 h | 40% EtOAc/Hexane | 14 |
| I-257 | XII-4 | X-23 | 80° C., 16 h | 40% EtOAc/Hexane | 25 |
| I-258 | XII-31 | 63069-50-1 | 80° C., 16 h | 30-70% EtOAc/Hexane | 9 |
| I-259 | XII-24 | 112279-60-4 | 70° C., 16 h | 0-5% EtOAc/Hexane | 12 |
| I-260 | XII-4 | X-24 | 70° C., 6 h | 30-35% EtOAc/Hexane | 47 |
| I-262 | XII-32 | 2613-30-1 | 80° C., 16 h | 30% EtOAc/Hexane | 46 |
| I-263 | XII-31 | 2613-30-1 | 80° C., 16 h | 10-30% EtOAc/Hexane | 27 |
| I-264 | XII-4 | X-25 | 80° C., 16 h | 30-90% EtOAc/Hexane | 13 |
| I-265 | XII-4 | X-26 | DMAP cat., 80° C., 16 h | 10% MeOH in DCM | 27 |
| I-289 | XII-3 | 1441723-24-5 | rt, 4 h | 20% EtOAc/petroleum ether | 46 |

TABLE 6-continued

| No | Sulfonyl chlorides XII | Amines X | Conditions, Time | Purification conditions | Yield (%) |
|---|---|---|---|---|---|
| I-304 | XII-3 | X-14 | 120° C., 5 h | 30-50% EtOAc/heptane then Basic prep LCMS Method 1 | 7 |
| I-305 | XII-1 | 112279-60-4 | rt, 48 h | — | 5 |
| I-306 | XII-1 | 1008112-39-7 | rt, 48 h | Basic prep LCMS Method 1 | 2 |
| I-309 | XII-25 | X-21 | 80° C., 12 h | Basic prep LCMS Method 1 | 19 |
| I-311 | XII-38 | 873-74-5 | 70° C., 1 h | 10-20% EtOAc/Hexane | 12 |
| I-312 | XII-38 | 2613-30-1 | 70° C., 16 h | 10-20% EtOAc/Hexane | 44 |
| I-313 | XII-38 | X-23 | 70° C., 16 h | 15-20% EtOAc/Hexane | 12 |
| I-314 | XII-38 | X-21 | 80° C., 16 h | 8-12% EtOAc/Hexane | 5 |
| I-315 | XII-38 | X-22 | 80° C., 16 h | 10-15% EtOAc/Hexane | 21 |
| I-319 | XII-26 | X-21 | Cat. DMAP, 80° C., 16 h | Basic prep LC | 3 |
| I-320 | XII-6 | X-22 | Cat. DMAP, 80° C., 24 h | 50% EtOAc/Hexane | 14 |
| I-321 | XII-29 | X-21 | Cat. DMAP, 80° C., 16 h | 40% EtOAc/Hexane | 34 |
| I-322 | XII-29 | X-22 | Cat. DMAP, 100° C., 24 h | Basic prep LC | 12 |
| I-323 | XII-6 | X-20 | Cat. DMAP, 80° C., 16 h | 40% EtOAc/Hexane | 9 |
| I-324 | XII-28 | X-22 | Cat. DMAP, 90° C., 32 h | 65% EtOAc/Hexane | 25 |
| I-325 | XII-6 | X-19 | Cat. DMAP, 100° C., 24 h | Basic prep LC | 3 |
| I-326 | XII-39 | 246847-98-3 | 80° C., 2 h | 50% EtOAc/heptane | 9 |
| I-327 | XII-4 | X-27 | 80° C., 4 h | 40-45% EtOAc/Hexane | 56 |
| I-328 | XII-1 | X-21 | 120° C., 2 h | 40-80% EtOAc/heptane | 10 |
| I-329 | XII-3 | X-21 | 120° C., 4 h | — | 73 |
| I-334 | XII-40 | 63069-50-1 | Cat. DMAP, 85° C., 16 h | 25% EtOAc/Hexane | 22 |
| I-339 | XII-31 | X-21 | Cat. DMAP, 100° C., 24 h | Basic prep LC | 12 |
| I-340 | XII-41 | X-21 | Cat. DMAP, 80° C., 16 h | 40% EtOAc/Hexane | 31 |
| I-341 | XII-29 | 63069-50-1 | 100° C., 24 h | 40-80% EtOAc/Hexane | 72 |
| I-342 | XII-24 | X-23 | 70° C., 16 h | Basic prep LC | 18 |
| I-343 | XII-28 | 63069-50-1 | Cat. DMAP, 80° C., 16 h | 65% EtOAc/Hexane | 12 |
| I-344 | XII-4 | X-28 | Cat. DMAP, 90° C., 12 h | 40% EtOAc/Hexane | 25 |
| I-345 | XII-4 | X-29 | 80° C., 16 h | 40-60% EtOAc/Hexane | 17 |
| I-346 | XII-24 | X-21 | 70° C., 16 h | 15-20% EtOAc/Hexane then Basic prep LC | 4 |
| I-347 | XII-42 | 2613-30-1 | 80° C., 16 h | 25-40% EtOAc/Hexane | 15 |
| I-348 | XII-4 | X-30 | Cat. DMAP, 100° C., 24 h | Basic prep LC | 22 |
| I-349 | XII-4 | X-31 | Cat. DMAP, 100° C., 12 h | 35-48% EtOAc/Hexane | 6 |
| I-350 | XII-4 | X-32 | Cat. DMAP, 100° C., 16 h | 50-60% EtOAc/Hexane | 5 |
| I-351 | XII-40 | X-22 | 70° C., 16 h | 40-50% EtOAc/Hexane | 47 |
| I-354 | XII-26 | X-22 | Cat. DMAP, 80° C., 16 h | 40% EtOAc/Hexane | 46 |
| I-355 | XII-26 | X-30 | Cat. DMAP, 80° C., 18 h | Basic prep LC | 8 |
| I-356 | XII-43 | X-21 | Cat. DMAP, 80° C., 16 h | 30% EtOAc/Hexane | 10 |
| I-357 | XII-44 | X-21 | Cat. DMAP, 90° C., 16 h | 30% EtOAc/Hexane | 11 |
| I-358 | XII-26 | X-29 | Cat. DMAP, 80° C., 16 h | 40% EtOAc/Hexane | 32 |
| I-360 | XII-1 | X-23 | rt, 6 h | — | 72 |
| I-361 | XII-1 | X-33 | rt, 20 h | — | 63 |
| I-362 | XII-1 | X-34 | rt, 6 h | — | 61 |
| I-364 | XII-4 | X-35 | Cat. DMAP, 100° C., 16 h | 35% EtOAc/Hexane | 16 |
| I-365 | XII-4 | X-36 | Cat. DMAP, 80° C., 18 h | 35% EtOAc/Hexane | 10 |
| I-366 | XII-46 | X-29 | Cat. DMAP, 80° C., 12 h | 45-55% EtOAc/Hexane | 15 |
| I-367 | XII-47 | X-30 | 90° C., 16 h | 50-60% EtOAc/Hexane | 7 |

N-(2,1,3-benzoxadiazol-4-yl)-1H-pyrrolo[3,2-h]quinoline-3-sulfonamide I-119

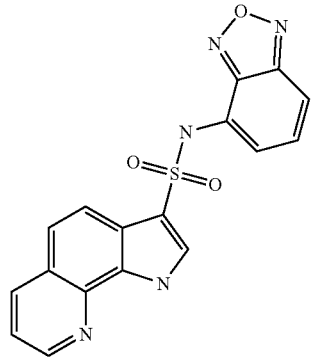 [SMILES: O=S(=O)(Nc1cccc2nonc12)c1c[nH]c2c1ccc1cccnc12]

Basic LCMS Method 1 (ES⁺): 366 (M+H)⁺, 98% purity.
¹H NMR (400 MHz, DMSO-d₆) δ 13.29 (s, 1H), 11.35 (s, 1H), 8.90 (dd, J=4.4, 1.6 Hz, 1H), 8.42 (dd, J=8.3, 1.6 Hz, 1H), 8.14 (s, 1H), 8.08 (d, J=8.7 Hz, 1H), 7.67 (d, J=8.8 Hz, 1H), 7.63-7.42 (m, 3H), 7.32 (d, J=7.2 Hz, 1H).

N-(4-cyanophenyl)-5,6-difluoro-1H-indole-3-sulfonamide I-120

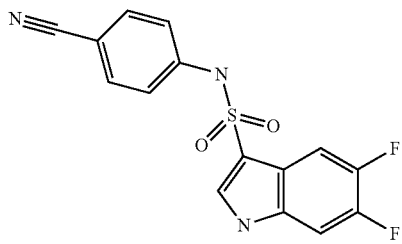 [SMILES: N#Cc1ccc(NS(=O)(=O)c2c[nH]c3cc(F)c(F)cc23)cc1]

Basic LCMS Method 2 (ES⁺): 334 (M+H)⁺, 99% purity.
¹H NMR (400 MHz, DMSO-d₆) δ 7.24 (d, J=8.7 Hz, 2H) 7.52 (dd, J=10.7, 7.0 Hz, 1H) 7.65 (d, J=8.7 Hz, 2H) 7.74 (dd, J=10.9, 7.9 Hz, 1H) 8.21 (d, J=2.8 Hz, 1H) 10.95 (s, 1H) 12.26 (s, 1H).

N-(2-fluoro-4-methylphenyl)-1H-benzo[g]indole-3-sulfonamide I-121

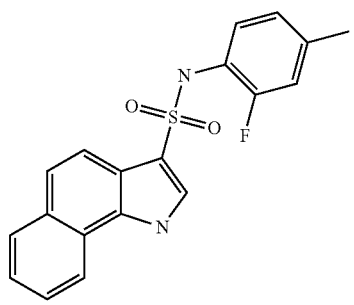 [SMILES: Cc1ccc(NS(=O)(=O)c2c[nH]c3c2ccc2ccccc23)c(F)c1]

Basic LCMS Method 1 (ES⁺): 355 (M+H)⁺, 98% purity.
¹H NMR (400 MHz, DMSO-d₆) δ 12.83 (s, 1H), 9.78 (s, 1H), 8.40 (dd, J=8.2, 1.0 Hz, 1H), 7.98 (dd, J=8.2, 1.2 Hz, 1H), 7.83-7.90 (m, 2H), 7.68-7.56 (m, 2H), 7.51 (ddd, J=8.1, 6.9, 1.2 Hz, 1H), 7.15 (t, J=8.2 Hz, 1H), 6.94-6.79 (m, 2H), 2.18 (s, 3H)

6-chloro-N-(4-(methoxymethyl)phenyl)-1H-indole-3-sulfonamide I-122

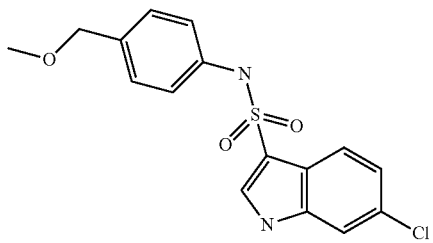 [SMILES: COCc1ccc(NS(=O)(=O)c2c[nH]c3cc(Cl)ccc23)cc1]

Basic LCMS Method 2 (ES⁻): 349 (M−H)⁻, 99% purity.
¹H NMR (400 MHz, DMSO-d₆) δ 3.19 (s, 3H) 4.22 (s, 2H) 7.01-7.06 (m, 2H) 7.08-7.13 (m, 2H) 7.20 (dd, J=8.56, 1.71 Hz, 1H) 7.48 (d, J=1.47 Hz, 1H) 7.80 (d, J=8.56 Hz, 1H) 7.98 (s, 1H) 10.19 (brs, 1H) 12.02 (brs, 1H).

6-chloro-N-(2,2-difluoro-1,3-benzodioxol-4-yl)-1H-indole-3-sulfonamide I-123

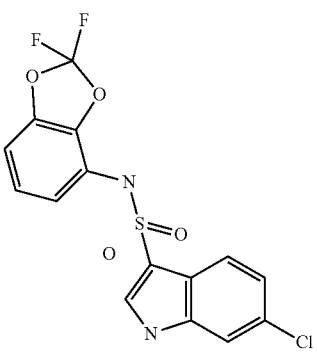

Basic LCMS Method 2 (ES⁻): 385 (M−H)⁻, 99% purity.
¹H NMR (400 MHz, DMSO-d₆) δ 6.95 (d, J=7.82 Hz, 1H) 7.06 (t, J=8.31 Hz, 1H) 7.11-7.15 (m, 1H) 7.18 (dd, J=8.56, 1.71 Hz, 1H) 7.52 (d, J=1.47 Hz, 1H) 7.64 (d, J=8.80 Hz, 1H) 7.94 (d, J=2.93 Hz, 1H) 10.34 (s, 1H) 12.11 (brs, 1H).

6-chloro-N-(4-cyano-3-methoxyphenyl)-1H-indole-3-sulfonamide I-124

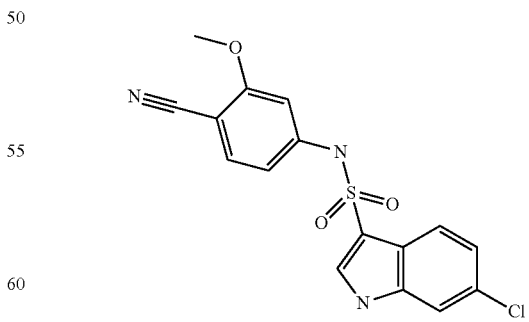

Basic LCMS Method 2 (ES⁻): 360 (M−H)⁻, 99% purity.
¹H NMR (400 MHz, DMSO-d₆) δ 3.79 (s, 3H) 6.76 (d, J=8.31 Hz, 1H) 6.87 (s, 1H) 7.26 (d, J=8.56 Hz, 1H) 7.44-7.56 (m, 2H) 7.83 (d, J=8.80 Hz, 1H) 8.24 (s, 1H) 10.96 (s, 1H) 12.20 (brs, 1H).

301

6-chloro-N-(2,2,6-trifluoro-1,3-benzodioxol-5-yl)-1H-indole-3-sulfonamide I-125

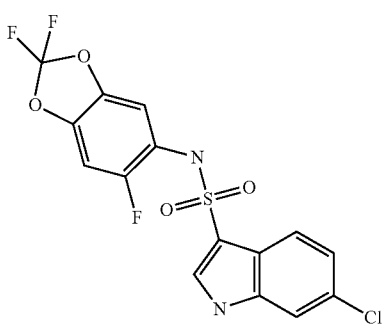 [SMILES: O=S(=O)(Nc1cc2c(cc1F)OC(F)(F)O2)c1c[nH]c2cc(Cl)ccc12]

Basic LCMS Method 2 (ES⁻): 403 (M−H)⁻, 98% purity.
¹H NMR (400 MHz, DMSO-$d_6$) δ 7.18 (dd, J=8.56, 1.71 Hz, 1H) 7.29 (d, J=6.36 Hz, 1H) 7.41 (d, J=8.80 Hz, 1H) 7.50 (s, 1H) 7.68 (d, J=8.80 Hz, 1H) 7.89 (d, J=2.93 Hz, 1H) 10.06 (s, 1H) 12.06 (brs, 1H).

6-chloro-N-(4-cyano-2-methoxyphenyl)-1H-indole-3-sulfonamide I-126

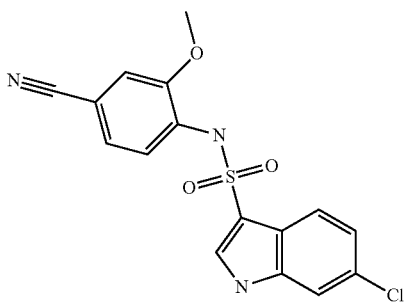 [SMILES: COc1cc(C#N)ccc1NS(=O)(=O)c1c[nH]c2cc(Cl)ccc12]

Basic LCMS Method 2 (ES⁻): 360 (M−H)⁻, 97% purity.
¹H NMR (400 MHz, DMSO-$d_6$) δ 3.62 (s, 3H) 7.22 (dd, J=8.80, 1.47 Hz, 1H) 7.28-7.33 (m, 2H) 7.46 (d, J=8.31 Hz, 1H) 7.51 (s, 1H) 7.86 (d, J=8.31 Hz, 1H) 8.05 (d, J=2.45 Hz, 1H) 9.85 (s, 1H) 12.10 (brs, 1H).

6-chloro-N-(7-fluoro-2,1,3-benzothiadiazol-4-yl)-1H-indole-3-sulfonamide I-127

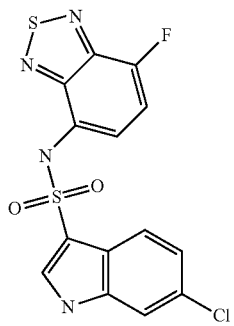 [SMILES: O=S(=O)(Nc1ccc(F)c2nsnc12)c1c[nH]c2cc(Cl)ccc12]

Basic LCMS Method 2 (ES⁻): 381 (M−H)⁻, 97% purity.
¹H NMR (400 MHz, DMSO-$d_6$) δ 7.13 (d, J=8.80 Hz, 1H) 7.38-7.42 (m, 2H) 7.44 (s, 1H) 7.76 (d, J=8.31 Hz, 1H) 8.02 (brs, 1H) 10.72 (s, 1H) 12.05 (brs, 1H).

302

6-chloro-N-(3-fluoropyridin-2-yl)-1H-indole-3-sulfonamide I-128

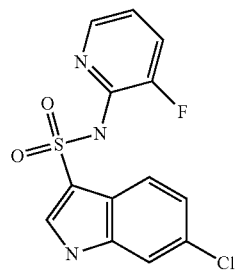 [SMILES: O=S(=O)(Nc1ncccc1F)c1c[nH]c2cc(Cl)ccc12]

Basic LCMS Method 2 (ES⁺): 326 (M+H)⁺, 99% purity.
¹H NMR (400 MHz, DMSO-$d_6$) δ 7.02-7.08 (m, 1H) 7.22 (d, J=8.31 Hz, 1H) 7.52 (s, 1H) 7.61 (t, J=9.29 Hz, 1H) 7.87 (d, J=7.83 Hz, 1H) 7.96-8.02 (m, 1H) 8.10 (s, 1H) 10.86 (s, 1H) 12.09 (s, 1H).

N-(5-bromo-3-methoxypyridin-2-yl)-6-chloro-1H-indole-3-sulfonamide I-129

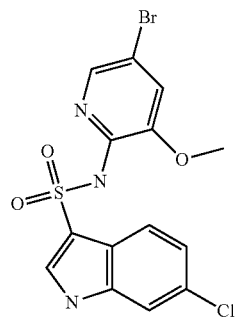 [SMILES: COc1cc(Br)cnc1NS(=O)(=O)c1c[nH]c2cc(Cl)ccc12]

Basic LCMS Method 2 (ES⁺): 416 (M+H)⁺. 99% purity.
¹H NMR (400 MHz, DMSO-$d_6$) δ 3.78 (s, 3H) 7.21 (dd, J=8.56, 1.71 Hz, 1H) 7.50 (s, 2H) 7.79 (d, J=1.96 Hz, 1H) 7.94 (d, J=8.31 Hz, 1H) 8.09 (d, J=2.45 Hz, 1H) 10.25 (s, 1H) 12.06 (brs, 1H).

N-(7-bromo-2,2-difluoro-1,3-benzodioxol-4-yl)-6-chloro-1H-indole-3-sulfonamide I-130

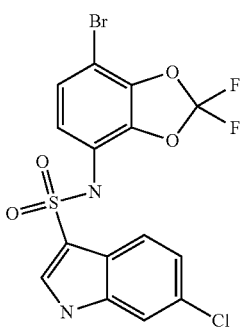 [SMILES: O=S(=O)(Nc1ccc(Br)c2c1OC(F)(F)O2)c1c[nH]c2cc(Cl)ccc12]

Basic LCMS Method 2 (ES⁻): 463 (M−H)⁻, 97% purity.
¹H NMR (400 MHz, DMSO-$d_6$) δ 6.91 (d, J=8.80 Hz, 1H) 7.19 (d, J=8.31 Hz, 1H) 7.30 (d, J=9.29 Hz, 1H) 7.48-7.57 (m, 1H) 7.64-7.72 (m, 1H) 7.94 (d, J=2.45 Hz, 1H) 10.44 (brs, 1H) 12.13 (brs, 1H).

6-chloro-N-(5-fluoro-2,1,3-benzothiadiazol-4-yl)-1H-indole-3-sulfonamide I-131

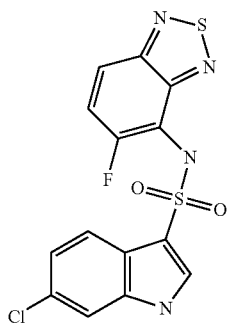 [SMILES: O=S(=O)(Nc1c(F)ccc2nsnc12)c1c[nH]c2cc(Cl)ccc12]

Basic LCMS Method 2 (ES⁺): 383 (M+H)⁺, 99% purity.
$^1$H NMR (400 MHz, DMSO-d$_6$) δ 7.04 (dd, J=8.80, 1.96 Hz, 1H) 7.40 (d, J=8.80 Hz, 1H) 7.48 (d, J=1.47 Hz, 1H) 7.72 (t, J=9.78 Hz, 1H) 7.83 (d, J=1.96 Hz, 1H) 8.05 (dd, J=9.29, 4.40 Hz, 1H) 10.13 (s, 1H) 11.98 (brs, 1H).

6-chloro-N-(6-cyano-2,2-difluoro-1,3-benzodioxol-4-yl)-1H-indole-3-sulfonamide I-132

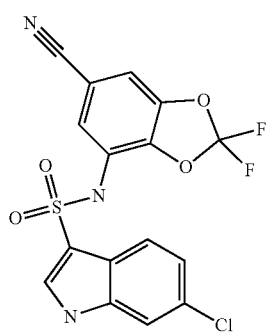 [SMILES: N#Cc1cc(NS(=O)(=O)c2c[nH]c3cc(Cl)ccc23)c2c(c1)OC(F)(F)O2]

Basic LCMS Method 2 (ES⁻): 410.00 (M−H)⁻, 92% purity.
$^1$H NMR (400 MHz, DMSO-d$_6$) δ 7.21 (dd, J=8.56, 1.71 Hz, 1H) 7.45 (s, 1H) 7.52 (d, J=1.47 Hz, 1H) 7.65 (d, J=8.80 Hz, 1H) 7.78 (s, 1H) 8.10 (d, J=2.93 Hz, 1H) 10.82 (brs, 1H) 12.20 (brs, 1H).

N-(4-cyanophenyl)-6-cyclopropyl-1H-indole-3-sulfonamide I-133

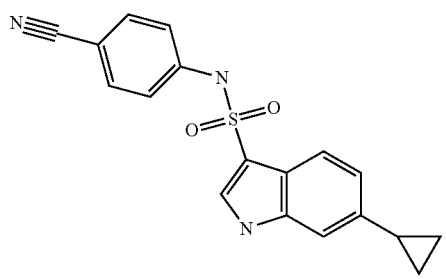 [SMILES: NCc1ccc(NS(=O)(=O)c2c[nH]c3cc(C4CC4)ccc23)cc1]

Basic LCMS Method 2 (ES⁻): 336.00 (M−H)⁻, 99% purity.
$^1$H NMR (400 MHz, DMSO-d$_6$) δ 0.58-0.69 (m, 2H) 0.86-0.98 (m, 2H) 1.91-2.02 (m, 1H) 6.90 (d, J=8.31 Hz, 1H) 7.12 (s, 1H) 7.19 (d, J=8.31 Hz, 2H) 7.59 (d, J=8.80 Hz, 2H) 7.67 (d, J=8.31 Hz, 1H) 8.03 (brs, 1H) 10.92 (brs, 1H) 11.87 (brs, 1H).

6-bromo-N-(4-cyanophenyl)-1H-indole-3-sulfonamide I-134

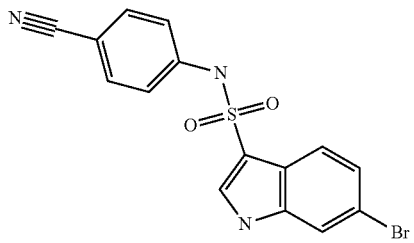 [SMILES: NCc1ccc(NS(=O)(=O)c2c[nH]c3cc(Br)ccc23)cc1]

$^1$H NMR (400 MHz, DMSO-d$_6$) δ 7.23 (d, J=8.31 Hz, 2H) 7.36 (d, J=8.80 Hz, 1H) 7.59-7.67 (m, 3H) 7.74-7.79 (m, 1H) 8.17 (s, 1H) 10.98 (brs, 1H) 12.19 (brs, 1H).

6-bromo-N-(2,2,6-trifluoro-1,3-benzodioxol-5-yl)-1H-indole-3-sulfonamide I-135

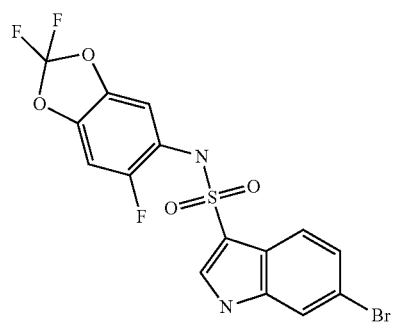 [SMILES: O=S(=O)(Nc1cc2c(cc1F)OC(F)(F)O2)c1c[nH]c2cc(Br)ccc12]

Basic LCMS Method 2 (ES⁺): 448.80 (M+H)⁺, 86% purity.
$^1$H NMR (400 MHz, DMSO-d$_6$) δ 7.34 (d, J=6.40 Hz, 1H) 7.43 (d, J=8.80 Hz, 1H) 7.71 (d, J=8.80 Hz, 1H) 7.95 (d, J=8.80 Hz, 1H) 8.03 (s, 1H) 8.17 (brs, 1H) 10.20 (brs, 1H) 12.51 (brs, 1H).

6-bromo-N-(2,4,5-trifluorophenyl)-1H-indole-3-sulfonamide I-136

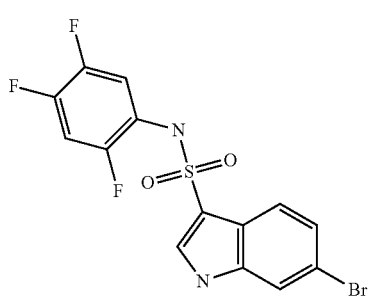 [SMILES: O=S(=O)(Nc1cc(F)c(F)cc1F)c1c[nH]c2cc(Br)ccc12]

Basic LCMS Method 2 (ES⁺): 405.00 (M+H)⁺, 94% purity.
$^1$H NMR (400 MHz, DMSO-d$_6$) δ 7.31-7.36 (m, 2H) 7.44-7.51 (m, 1H) 7.63-7.68 (m, 2H) 7.94 (d, J=2.93 Hz, 1H) 10.21 (s, 1H) 12.11 (brs, 1H).

305

6-bromo-N-(2,2-difluoro-1,3-benzodioxol-4-yl)-1H-indole-3-sulfonamide I-137

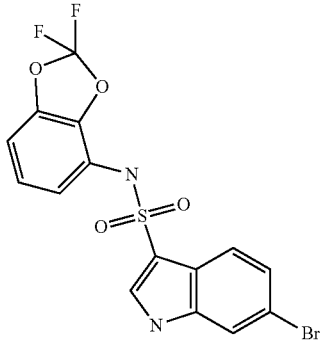 [SMILES: O=S(=O)(Nc1cccc2c1OC(F)(F)O2)c1c[nH]c2cc(Br)ccc12]

Basic LCMS Method 2 (ES⁺): 431.00 (M+H)⁺, 93% purity.
¹H NMR (400 MHz, DMSO-d$_6$) δ 6.94 (dd, J=8.31, 0.98 Hz, 1H) 7.06 (t, J=8.31 Hz, 1H) 7.11-7.15 (m, 1H) 7.28-7.32 (m, 1H) 7.60 (d, J=8.80 Hz, 1H) 7.66 (d, J=1.47 Hz, 1H) 7.93 (d, J=2.93 Hz, 1H) 10.34 (s, 1H) 12.11 (brs, 1H).

6-chloro-N-(2-fluoro-4-nitro-phenyl)-1H-indole-3-sulfonamide I-138

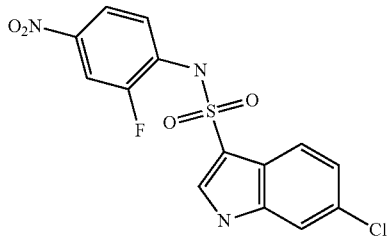 [SMILES: O=[N+]([O-])c1ccc(NS(=O)(=O)c2c[nH]c3cc(Cl)ccc23)c(F)c1]

Basic LCMS Method 2 (ES⁻): 368.00 (M−H)⁻, 39% purity.

6-chloro-N-(4-cyanophenyl)-1-benzofuran-3-sulfonamide I-139

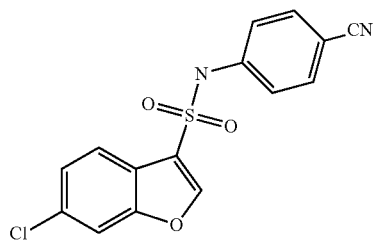

Basic LCMS Method 2 (ES⁻): 331.00 (M−H)⁻, 99% purity.
¹H NMR (400 MHz, DMSO-d$_6$) δ 7.27 (d, J=8.31 Hz, 2H) 7.48-7.57 (m, 1H) 7.70 (d, J=8.31 Hz, 2H) 7.84 (s, 1H) 7.96 (s, 1H) 8.93 (s, 1H) 11.44 (brs, 1H).

306

6-chloro-N-(2-fluoro-4-iodophenyl)-1H-indole-3-sulfonamide I-140

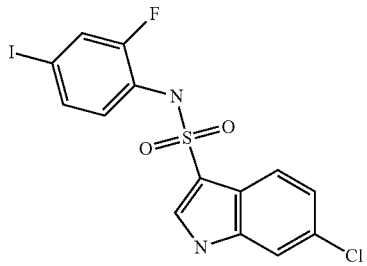 [SMILES: O=S(=O)(Nc1ccc(I)cc1F)c1c[nH]c2cc(Cl)ccc12]

Basic LCMS Method 1 (ES⁺): 451 (M+H)⁺, 99% purity.
¹H NMR (400 MHz, DMSO-d$_6$) δ 12.07 (s, 1H), 10.11 (s, 1H), 7.91 (d, J=2.4 Hz, 1H), 7.76 (d, J=8.6 Hz, 1H), 7.54-7.47 (s, dd, 2H), 7.44 (dd, J=8.4, 1.8 Hz, 1H), 7.21 (dd, J=8.6, 1.9 Hz, 1H), 7.08 (t, J=8.4 Hz, 1H).

6-chloro-N-(4-chloro-2-fluorophenyl)-1H-indole-3-sulfonamide I-141

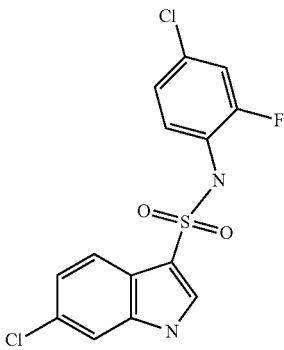 [SMILES: O=S(=O)(Nc1ccc(Cl)cc1F)c1c[nH]c2cc(Cl)ccc12]

Basic LCMS Method 1 (ES⁻): 357 (M−H)⁻, 98% purity.
¹H NMR (400 MHz, DMSO-d$_6$) δ 12.07 (s, 1H), 10.10 (s, 1H), 7.89 (d, J=2.1 Hz, 1H), 7.73 (d, J=8.6 Hz, 1H), 7.52 (d, J=1.8 Hz, 1H), 7.36-7.25 (m, 2H), 7.24-7.12 (m, 2H).

N-(2,1,3-benzoselenadiazol-4-yl)-6-chloro-1H-indole-3-sulfonamide I-142

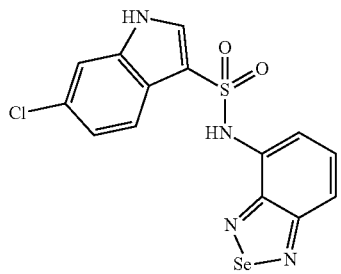 [SMILES: O=S(=O)(Nc1cccc2n[se]nc12)c1c[nH]c2cc(Cl)ccc12]

Neutral LCMS Method 3 (ES⁺): 412.93 (M+H)⁺, 98% purity.
¹H NMR (600 MHz, DMSO-d$_6$) δ 12.07 (s, 1H), 10.29 (s, 1H), 8.12 (s, 1H), 7.85 (d, J=8.6 Hz, 1H), 7.46-7.44 (m, 1H), 7.44-7.42 (m, 1H), 7.41 (d, J=9.0 Hz, 1H), 7.27 (dd, J=6.5, 1.7 Hz, 1H), 7.13 (dd, J=8.6, 1.9 Hz, 1H).

307

6-chloro-N-(4-cyano-2-fluoro-5-methoxyphenyl)-1H-indole-3-sulfonamide I-143

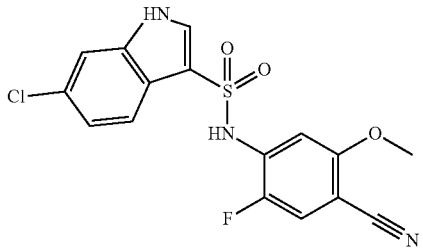 [SMILES: COc1cc(NS(=O)(=O)c2c[nH]c3cc(Cl)ccc23)c(F)cc1C#N]

Neutral LCMS Method 3 (ES+): 379.02 (M+H)+, 96% purity.
¹H NMR (600 MHz, DMSO-d₆) δ 12.13 (s, 1H), 10.83 (s, 1H), 8.15 (d, J=2.3 Hz, 1H), 7.84 (d, J=8.6 Hz, 1H), 7.60-7.46 (m, 2H), 7.23 (dd, J=8.6, 1.9 Hz, 1H), 7.12 (d, J=6.5 Hz, 1H), 3.78 (s, 3H).

6-chloro-N-(6-fluoro-2,1,3-benzothiadiazol-5-yl)-1H-pyrrolo[2,3-b]pyridine-3-sulfonamide I-144

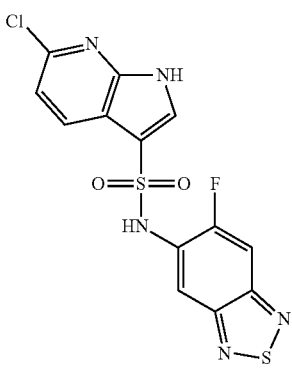 [SMILES: O=S(=O)(Nc1cc2nsnc2cc1F)c1c[nH]c2nc(Cl)ccc12]

Neutral LCMS Method 3 (ES+): 383.97 (M+H)+, 99% purity.
¹H NMR (600 MHz, DMSO-d₆) δ 12.89 (s, 1H), 10.79 (s, 1H), 8.36 (d, J=2.8 Hz, 1H), 8.29 (d, J=8.3 Hz, 1H), 7.94-7.79 (m, 2H), 7.36 (d, J=8.3 Hz, 1H).

N-(4-cyano-2,5-difluorophenyl)-1H-indole-3-sulfonamide I-145

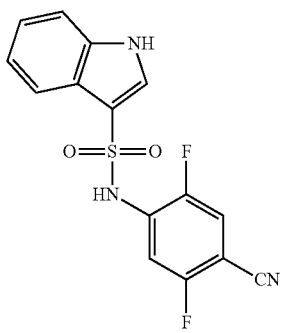 [SMILES: N#Cc1cc(F)c(NS(=O)(=O)c2c[nH]c3ccccc23)cc1F]

Neutral LCMS Method 3 (ES+): 334.03 (M+H)+, 99% purity.
¹H NMR (500 MHz, DMSO-d₆) δ 12.17 (s, 1H), 11.16 (s, 1H), 8.27 (d, J=3.1 Hz, 1H), 7.90-7.86 (m, 1H), 7.83 (dd, J=10.3, 6.0 Hz, 1H), 7.51-7.42 (m, 2H), 7.23-7.24 (m, 2H).

308

N-(4-cyano-2,5-difluorophenyl)-6-(2-methoxyethoxy)-1H-indole-3-sulfonamide I-146

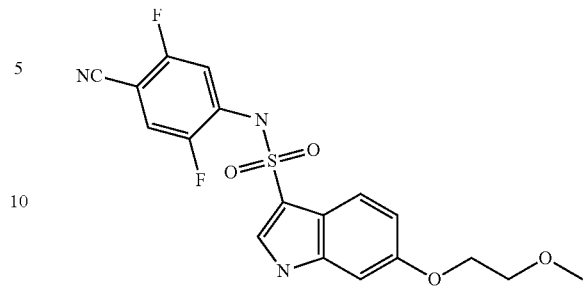

Neutral LCMS Method 3 (ES+): 408.07 (M+H)+, 99% purity.
¹H NMR (600 MHz, DMSO-d₆) δ 11.95 (s, 1H), 11.13 (s, 1H), 8.12 (d, J=3.0 Hz, 1H), 7.84 (dd, J=10.2, 5.9 Hz, 1H), 7.73 (d, J=8.8 Hz, 1H), 7.43 (dd, J=11.0, 6.3 Hz, 1H), 6.96 (d, J=2.2 Hz, 1H), 6.87 (dd, J=8.8, 2.3 Hz, 1H), 4.19-3.99 (m, 2H, CH₂), 3.66 (dd, J=5.6, 3.6 Hz, CH₂), 3.30 (s, 3H, CH₃).

N-(2,1,3-benzothiadiazol-5-yl)-6-chloro-1H-indole-3-sulfonamide I-147

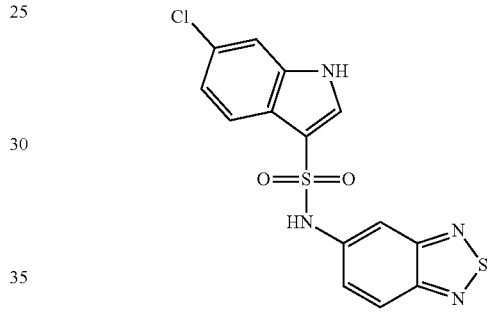

Neutral LCMS Method 3 (ES+): 364.98 (M+H)+, 99% purity.
¹H NMR (500 MHz, DMSO-d₆) δ 12.14 (s, 1H), 10.95-10.90 (m, 1H), 8.25 (s, 1H), 7.92 (dd, J=9.5, 0.7 Hz, 1H), 7.87 (d, J=8.6 Hz, 1H), 7.60 (dd, J=2.1, 0.7 Hz, 1H), 7.52-7.46 (m, 2H), 7.24 (dd, J=8.6, 1.9 Hz, 1H).

N-(4-cyano-2,5-difluorophenyl)-1,6,7,8-tetrahydrocyclopenta[g]indole-3-sulfonamide I-148

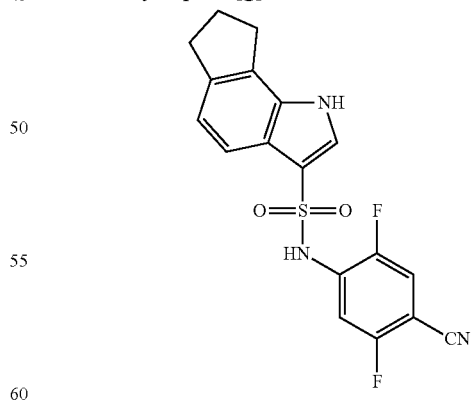

Neutral LCMS Method 3 (ES+): 374.06 (M+H)+, 98% purity.
¹H NMR (600 MHz, DMSO-d₆) δ 12.02 (s, 1H), 11.14 (s, 1H), 8.21 (d, J=3.0 Hz, 1H), 7.82 (dd, J=10.3, 5.9 Hz, 1H), 7.66 (d, J=8.1 Hz, 1H), 7.44 (dd, J=11.1, 6.3 Hz, 1H), 7.11 (d, J=8.1 Hz, 1H), 3.01 (t, J=7.4 Hz, 2H), 2.94 (t, J=7.4 Hz, 2H), 2.10 (p, J=7.4 Hz, 2H).

309

N-(4-cyano-3-fluorophenyl)-1,6,7,8-tetrahydrocyclopenta[g]indole-3-sulfonamide I-149

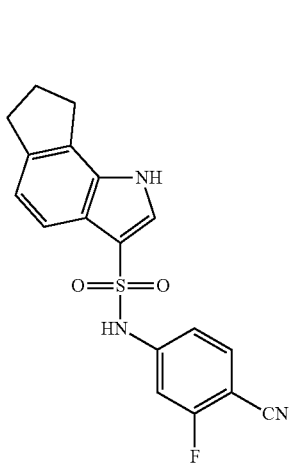 [SMILES: N#Cc1ccc(NS(=O)(=O)c2c[nH]c3c4c(ccc23)CCC4)cc1F]

Neutral LCMS Method 3 (ES$^+$): 356.07 (M+H)$^+$, 95% purity.

$^1$H NMR (500 MHz, DMSO-d$_6$) δ 12.12 (s, 1H), 11.19 (s, 1H), 8.18 (d, J=3.1 Hz, 1H), 7.68 (dd, J=8.6, 7.6 Hz, 1H), 7.61 (dd, J=8.1, 0.9 Hz, 1H), 7.13-7.07 (m, 2H), 7.04 (dd, J=8.6, 2.1 Hz, 1H), 3.01 (t, J=7.4 Hz, 2H), 2.93 (t, J=7.4 Hz, 2H), 2.09 (p, J=7.4 Hz, 2H).

N-(4-cyano-2-fluorophenyl)-1,6,7,8-tetrahydrocyclopenta[g]indole-3-sulfonamide I-150

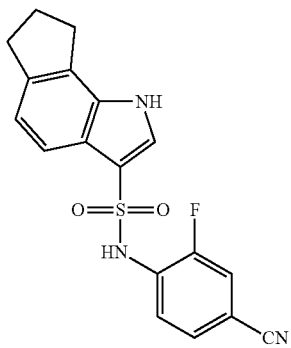 [SMILES: N#Cc1ccc(NS(=O)(=O)c2c[nH]c3c4c(ccc23)CCC4)c(F)c1]

Neutral LCMS Method 3 (ES$^+$): 356.07 (M+H)$^+$, 98% purity.

$^1$H NMR (500 MHz, DMSO-d$_6$) δ 12.05 (s, 1H), 10.72 (s, 1H), 8.01 (d, J=3.1 Hz, 1H), 7.71 (dd, J=10.7, 1.8 Hz, 1H), 7.62 (dd, J=8.1, 0.8 Hz, 1H), 7.58 (dd, J=8.6, 7.8 Hz, 1H), 7.55-7.52 (m, 1H), 7.08 (d, J=8.2 Hz, 1H), 3.01 (t, J=7.4 Hz, 2H), 2.94 (t, J=7.4 Hz, 2H), 2.10 (p, J=7.4 Hz, 2H).

310

N-(4-cyano-2,5-difluorophenyl)-1H-benzo[g]indole-3-sulfonamide I-151

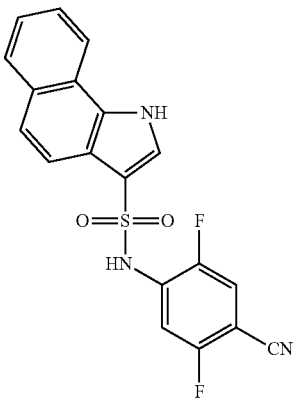 [SMILES: N#Cc1cc(F)c(NS(=O)(=O)c2c[nH]c3c2ccc2ccccc23)cc1F]

Neutral LCMS Method 3 (ES$^+$): 384.05 (M+H)$^+$, 96% purity.

$^1$H NMR (500 MHz, DMSO-d$_6$) δ 13.06 (s, 1H), 11.22 (s, 1H), 8.41 (dd, J=8.3, 1.2 Hz, 1H), 8.36 (d, J=3.1 Hz, 1H), 8.02-7.95 (m, 2H), 7.82 (dd, J=10.3, 5.9 Hz, 1H), 7.69 (d, J=8.7 Hz, 1H), 7.60-7.62 (m, 1H), 7.55-7.47 (m, 2H).

N-(4-cyano-2-fluorophenyl)-1H-benzo[g]indole-3-sulfonamide I-152

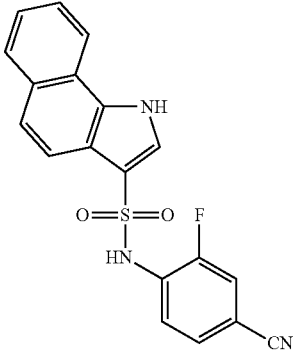 [SMILES: N#Cc1ccc(NS(=O)(=O)c2c[nH]c3c2ccc2ccccc23)c(F)c1]

Neutral LCMS Method 3 (ES$^+$): 366.06 (M+H)$^+$, 99% purity.

$^1$H NMR (500 MHz, DMSO-d$_6$) δ 12.97 (s, 1H), 10.80 (s, 1H), 8.37-8.39 (m, 1H), 8.16 (d, J=3.1 Hz, 1H), 8.00-7.96 (m, 1H), 7.93 (d, J=8.7 Hz, 1H), 7.70 (dd, J=10.7, 1.8 Hz, 1H), 7.67-7.58 (m, 3H), 7.57-7.46 (m, 2H).

311

6-(benzyloxy)-N-(4-cyano-2,5-difluorophenyl)-1H-indole-3-sulfonamide I-153

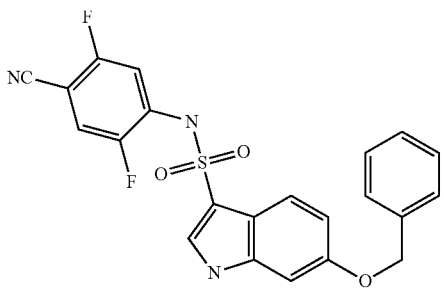 [SMILES: N#Cc1cc(F)c(NS(=O)(=O)c2c[nH]c3cc(OCc4ccccc4)ccc23)cc1F]

Neutral LCMS Method 3 (ES⁺): 440.08 (M+H)⁺, 98% purity.
¹H NMR (600 MHz, DMSO-$d_6$) δ 11.95 (s, 1H), 11.13 (s, 1H), 8.12 (d, J=3.0 Hz, 1H), 7.84 (dd, J=10.2, 5.9 Hz, 1H), 7.75 (d, J=8.8 Hz, 1H), 7.47-7.41 (m, 3H), 7.39 (t, J=7.6 Hz, 2H), 7.34-7.30 (m, 1H), 7.02 (d, J=2.2 Hz, 1H), 6.95 (dd, J=8.8, 2.3 Hz, 1H), 5.12 (s, 2H).

6-(benzyloxy)-N-(4-cyano-2-fluorophenyl)-1H-indole-3-sulfonamide I-154

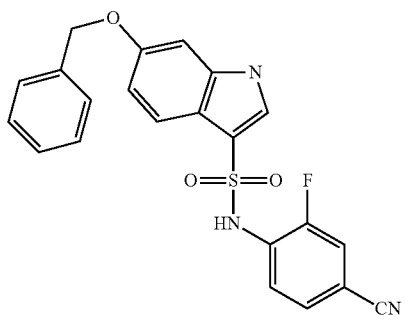 [SMILES: N#Cc1ccc(NS(=O)(=O)c2c[nH]c3cc(OCc4ccccc4)ccc23)c(F)c1]

Neutral LCMS Method 3 (ES⁺): 422.08 (M+H)⁺, 97% purity.
¹H NMR (500 MHz, DMSO-$d_6$) δ 11.86 (s, 1H), 10.70 (s, 1H), 7.94 (d, J=2.9 Hz, 1H), 7.74-7.69 (m, 2H), 7.60-7.52 (m, 2H), 7.47-7.43 (m, 2H), 7.41-7.37 (m, 2H), 7.35-7.29 (m, 1H), 7.02 (d, J=2.2 Hz, 1H), 6.93 (dd, J=8.8, 2.3 Hz, 1H), 5.12 (s, 2H).

N-(2,1,3-benzothiadiazol-4-yl)-1H-benzo[g]indole-3-sulfonamide I-155

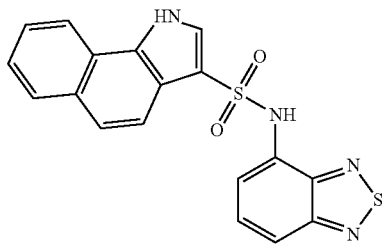 [SMILES: O=S(=O)(Nc1cccc2nsnc12)c1c[nH]c2c1ccc1ccccc12]

Neutral LCMS Method 3 (ES⁺): 381.04 (M+H)⁺, 95.2% purity.
¹H NMR (500 MHz, DMSO-$d_6$) δ 12.88 (s, 1H), 10.80 (s, 1H), 8.36 (dq, J=8.3, 0.9 Hz, 1H), 8.18 (d, J=3.0 Hz, 1H), 7.98 (d, J=8.8 Hz, 1H), 7.93 (dt, J=8.4, 0.8 Hz, 1H), 7.66 (dd, J=8.7, 1.1 Hz, 1H), 7.55 (m, 3H), 7.54 (dd, J=7.4, 1.1 Hz, 1H), 7.46-7.48 (m, 1H).

312

N-(2,1,3-benzothiadiazol-4-yl)-6-(benzyloxy)-1H-indole-3-sulfonamide I-156

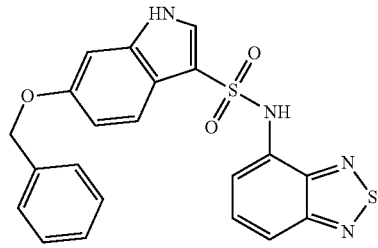 [SMILES: O=S(=O)(Nc1cccc2nsnc12)c1c[nH]c2cc(OCc3ccccc3)ccc12]

Neutral LCMS Method 3 (ES⁺): 437.07 (M+H)⁺, 99% purity.
¹H NMR (600 MHz, DMSO-$d_6$) δ 11.78 (s, 1H), 10.70 (s, 1H), 7.97 (d, J=2.9 Hz, 1H), 7.77 (d, J=8.8 Hz, 1H), 7.66 (dd, J=8.7, 0.9 Hz, 1H), 7.57 (dd, J=8.8, 7.4 Hz, 1H), 7.47 (dd, J=7.5, 1.0 Hz, 1H), 7.44-7.40 (m, 2H), 7.37 (t, J=7.6 Hz, 2H), 7.33-7.28 (m, 1H), 6.96 (d, J=2.2 Hz, 1H), 6.85 (dd, J=8.8, 2.3 Hz, 1H), 5.08 (s, 2H).

N-(2,1,3-benzothiadiazol-5-yl)-1H-benzo[g]indole-3-sulfonamide I-157

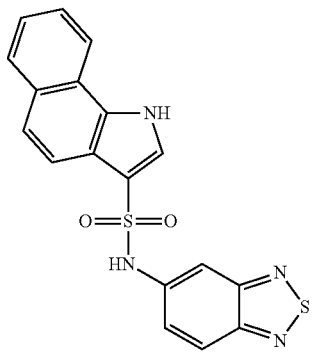 [SMILES: O=S(=O)(Nc1ccc2nsnc2c1)c1c[nH]c2c1ccc1ccccc12]

Neutral LCMS Method 3 (ES⁺): 381.04 (M+H)⁺, 97% purity.
¹H NMR (500 MHz, DMSO-$d_6$) δ 12.95 (s, 1H), 10.96 (s, 1H), 8.36 (dd, J=8.3, 1.2 Hz, 1H), 8.31 (d, J=2.8 Hz, 1H), 7.99 (d, J=8.8 Hz, 1H), 7.97-7.94 (m, 1H), 7.90 (dd, J=9.4, 0.7 Hz, 1H), 7.69-7.64 (m, 2H), 7.56-7.58 (m, 1H), 7.53 (dd, J=9.4, 2.2 Hz, 1H), 7.46-7.48 (m, 1H).

N-(2,1,3-benzothiadiazol-5-yl)-1,6,7,8-tetrahydrocyclopenta[g]indole-3-sulfonamide I-158

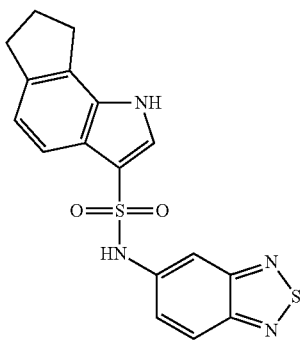 [SMILES: O=S(=O)(Nc1ccc2nsnc2c1)c1c[nH]c2c3c(ccc12)CCC3]

313

Neutral LCMS Method 3 (ES+): 371.05 (M+H)+, 100% purity.

$^1$H NMR (500 MHz, DMSO-d$_6$) δ 12.02 (s, 1H), 10.85 (s, 1H), 8.14 (d, J=3.0 Hz, 1H), 7.89 (dd, J=9.4, 0.7 Hz, 1H), 7.69-7.65 (m, 1H), 7.59 (dd, J=2.2, 0.7 Hz, 1H), 7.50 (dd, J=9.4, 2.2 Hz, 1H), 7.09 (d, J=8.1 Hz, 1H), 2.97 (t, J=7.4 Hz, 2H), 2.90 (t, J=7.4 Hz, 2H), 2.11-2.00 (m, 2H).

N-(4-cyanophenyl)-1H-benzo[g]indole-3-sulfonamide I-159

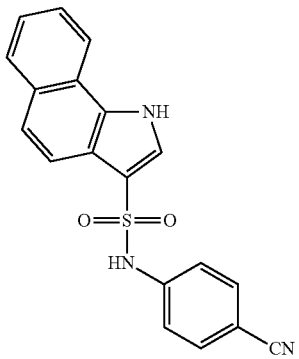 [SMILES: N#Cc1ccc(NS(=O)(=O)c2c[nH]c3c2ccc2ccccc23)cc1]

Neutral LCMS Method 3 (ES+): 348.07 (M+H)+, 98% purity.

$^1$H NMR (500 MHz, DMSO-d$_6$) δ 12.96 (s, 1H), 10.97 (s, 1H), 8.39 (dd, J=8.3, 1.2 Hz, 1H), 8.22 (d, J=2.9 Hz, 1H), 7.95 (dd, J=19.9, 8.5 Hz, 2H), 7.67 (d, J=8.8 Hz, 1H), 7.64-7.57 (m, 3H), 7.50-7.52 (m, 1H), 7.32-7.25 (m, 2H).

N-(6-fluoro-2,1,3-benzothiadiazol-5-yl)-1H-benzo[g]indole-3-sulfonamide I-160

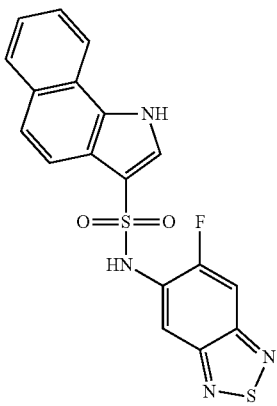 [SMILES: O=S(=O)(Nc1cc2nsnc2cc1F)c1c[nH]c2c1ccc1ccccc12]

Neutral LCMS Method 3 (ES+): 399.03 (M+H)+, 97% purity.

$^1$H NMR (500 MHz, DMSO-d$_6$) δ 12.97 (s, 1H), 10.79 (s, 1H), 8.37-8.39 (m, 1H), 8.27 (d, J=3.1 Hz, 1H), 8.00 (d, J=8.8 Hz, 1H), 7.98-7.94 (m, 1H), 7.90 (d, J=7.8 Hz, 1H), 7.86 (d, J=10.8 Hz, 1H), 7.68-7.64 (m, 1H), 7.57-7.59 (m, 1H), 7.48-7.51 (m, 1H).

314

N-(2,1,3-benzoselenadiazol-5-yl)-6-chloro-1H-indole-3-sulfonamide I-161

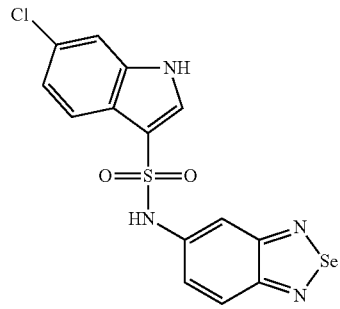 [SMILES: O=S(=O)(Nc1ccc2n[se]nc2c1)c1c[nH]c2cc(Cl)ccc12]

Neutral LCMS Method 3 (ES+): 412.93 (M+H)+, 98% purity.

$^1$H NMR (500 MHz, DMSO-d$_6$) δ 12.14 (s, 1H), 10.81 (s, 1H), 8.22 (s, 1H), 7.88 (d, J=8.6 Hz, 1H), 7.67 (d, J=10.3 Hz, 1H), 7.50 (d, J=2.0 Hz, 1H), 7.39-7.33 (m, 2H), 7.25 (dd, J=8.6, 1.9 Hz, 1H).

6-chloro-N-(6-fluoro-2,1,3-benzothiadiazol-5-yl)-1H-indole-3-sulfonamide I-162

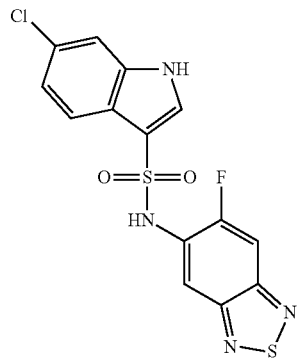 [SMILES: O=S(=O)(Nc1cc2nsnc2cc1F)c1c[nH]c2cc(Cl)ccc12]

Neutral LCMS Method 3 (ES+): 383.09 (M+H)+, 97% purity.

$^1$H NMR (500 MHz, DMSO-d$_6$) δ 12.16 (s, 1H), 10.76 (s, 1H), 8.22 (s, 1H), 7.80-7.92 (m, 3H), 7.51 (s, 1H), 7.18-7.28 (m, 1H).

6-chloro-N-(7-cyano-2,1,3-benzothiadiazol-4-yl)-1H-indole-3-sulfonamide I-163

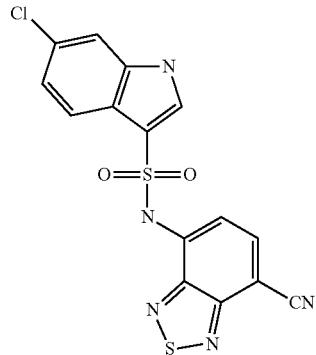 [SMILES: N#Cc1ccc(NS(=O)(=O)c2c[nH]c3cc(Cl)ccc23)c2nsnc12]

315

Neutral LCMS Method 3 (ES⁺): 390.3 (M+H)⁺, 95% purity.

¹H NMR (500 MHz, DMSO-d₆) δ 11.52 (s, 1H), 7.74-7.85 (m, 1H), 7.68 (d, J=8.5 Hz, 1H), 7.24-7.45 (m, 2H), 7.04-7.11 (m, 1H), 6.94 (d, J=8.4 Hz, 1H).

N-(4-cyano-2,5-difluorophenyl)-4,6-difluoro-1H-indole-3-sulfonamide I-164

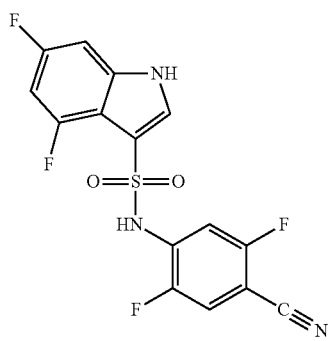 [SMILES: N#Cc1cc(F)c(NS(=O)(=O)c2c[nH]c3cc(F)cc(F)c23)cc1F]

Neutral LCMS Method 3 (ES⁺): 369.2 (M+H)⁺, 95% purity.

¹H NMR (600 MHz, DMSO-d₆) δ 12.47 (s, 1H), 11.04 (s, 1H), 8.25 (d, J=3.0 Hz, 1H), 7.85 (dd, J=10.1, 5.8 Hz, 1H), 7.43 (dd, J=10.9, 6.2 Hz, 1H), 7.16 (dd, J=8.7, 2.1 Hz, 1H), 7.05 (td, J=10.5, 2.2 Hz, 1H).

N-(4-cyano-2,5-difluorophenyl)-6-fluoro-1H-indole-3-sulfonamide I-165

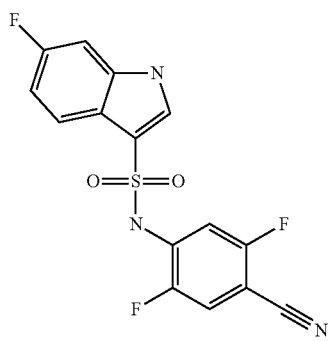 [SMILES: N#Cc1cc(F)c(NS(=O)(=O)c2c[nH]c3cc(F)ccc23)cc1F]

Neutral LCMS Method 3 (ES⁺): 351.3 (M+H)⁺, 98% purity.

¹H NMR (600 MHz, DMSO-d₆) δ 12.28-12.11 (m, 1H), 11.18 (s, 1H), 8.26 (d, J=3.0 Hz, 1H), 7.84 (ddd, J=14.4, 9.5, 5.6 Hz, 2H), 7.43 (dd, J=11.0, 6.4 Hz, 1H), 7.27 (dd, J=9.5, 2.4 Hz, 1H), 7.10 (td, J=9.3, 2.4 Hz, 1H).

316

N-(2,1,3-benzothiadiazol-4-yl)-4,6-difluoro-1H-indole-3-sulfonamide I-166

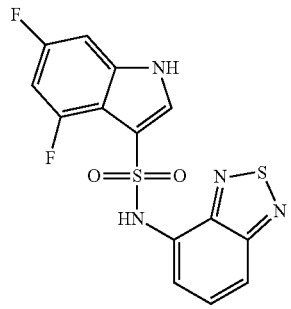

Neutral LCMS Method 3 (ES⁺): 366.3 (M+H)⁺, 99% purity.

¹H NMR (600 MHz, DMSO-d₆) δ 12.26 (s, 1H), 10.16 (s, 1H), 8.07 (s, 1H), 7.70 (dd, J=8.9, 0.9 Hz, 1H), 7.58 (dd, J=8.8, 7.4 Hz, 1H), 7.47 (dd, J=7.4, 0.9 Hz, 1H), 7.08 (dd, J=9.0, 2.1 Hz, 1H), 6.96 (td, J=10.4, 2.2 Hz, 1H).

7-bromo-N-(4-cyano-2,5-difluorophenyl)-1H-indole-3-sulfonamide I-167

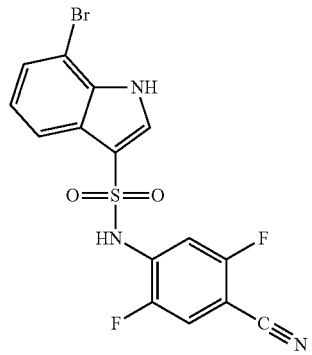 [SMILES: N#Cc1cc(F)c(NS(=O)(=O)c2c[nH]c3c(Br)cccc23)cc1F]

Neutral LCMS Method 3 (ES⁺): 412.2 (M+H)⁺, 99% purity.

¹H NMR (500 MHz, DMSO-d₆) δ 12.75-12.27 (m, 1H), 11.22 (s, 1H), 8.30 (d, J=3.1 Hz, 1H), 8.01-7.72 (m, 2H), 7.55-7.38 (m, 2H), 7.17 (t, J=7.8 Hz, 1H).

N-(4-cyano-2-fluorophenyl)-4,6-difluoro-1H-indole-3-sulfonamide I-168

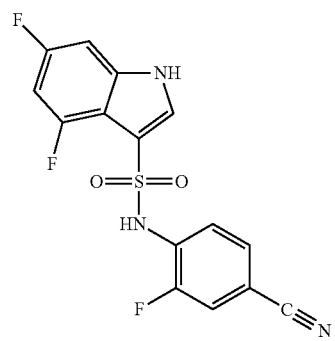 [SMILES: N#Cc1ccc(NS(=O)(=O)c2c[nH]c3cc(F)cc(F)c23)c(F)c1]

Neutral LCMS Method 3 (ES⁺): 351.3 (M+H)⁺, 98% purity.

¹H NMR (500 MHz, DMSO-d$_6$) δ 12.36 (s, 1H), 10.56 (s, 1H), 8.08 (d, J=2.5 Hz, 1H), 7.80-7.68 (m, 1H), 7.59-7.49 (m, 2H), 7.15 (dd, J=9.0, 2.1 Hz, 1H), 7.03 (m, J=10.8, 10.1, 2.1 Hz, 1H).

N-(2,1,3-benzothiadiazol-5-yl)-6-fluoro-1H-indole-3-sulfonamide I-169

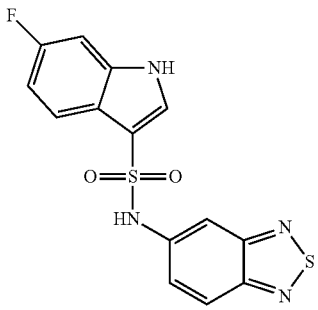 [SMILES: O=S(=O)(Nc1ccc2nsnc2c1)c1c[nH]c2cc(F)ccc12]

Neutral LCMS Method 3 (ES⁺): 348.3 (M+H)⁺, 97% purity.

¹H NMR (500 MHz, DMSO-d$_6$) δ 12.08 (s, 1H), 10.91 (s, 1H), 8.20 (dd, J=7.1, 2.4 Hz, 1H), 7.91 (dd, J=9.4, 0.7 Hz, 1H), 7.86 (dd, J=8.8, 5.3 Hz, 1H), 7.59 (dd, J=2.2, 0.7 Hz, 1H), 7.48 (dd, J=9.4, 2.2 Hz, 1H), 7.22 (m, J=9.6, 2.4, 0.5 Hz, 1H), 7.08 (m, J=9.7, 8.8, 2.4 Hz, 1H).

N-(4-cyano-2-fluorophenyl)-6-(propan-2-yl)-1H-indole-3-sulfonamide I-170

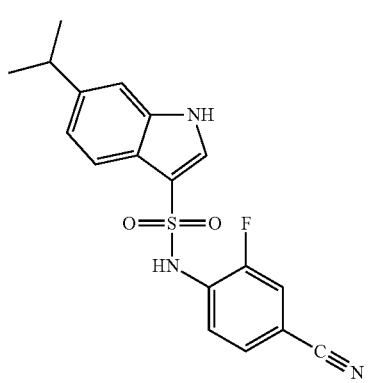 [SMILES: CC(C)c1ccc2c(S(=O)(=O)Nc3ccc(C#N)cc3F)c[nH]c2c1]

Neutral LCMS Method 3 (ES⁺): 357.4 (M+H)⁺, 95% purity.

¹H NMR (500 MHz, DMSO-d$_6$) δ 11.93 (d, J=3.0 Hz, 1H), 10.74 (s, 1H), 8.02 (d, J=3.0 Hz, 1H), 7.84-7.68 (m, 2H), 7.61-7.44 (m, 2H), 7.27 (t, J=0.9 Hz, 1H), 7.10 (dd, J=8.3, 1.5 Hz, 1H), 2.96 (d, J=6.9 Hz, 1H), 1.21 (d, J=6.9 Hz, 7H).

N-(4-cyanophenyl)-6-fluoro-1H-indole-3-sulfonamide I-171

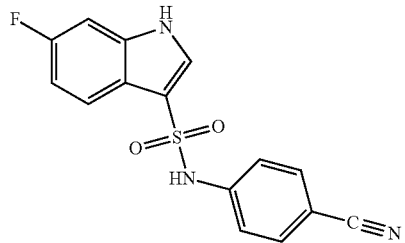 [SMILES: N#Cc1ccc(NS(=O)(=O)c2c[nH]c3cc(F)ccc23)cc1]

Neutral LCMS Method 3 (ES⁺): 315.32 (M+H)⁺, 97% purity.

¹H NMR (600 MHz, DMSO-d$_6$) δ 12.12 (s, 1H), 10.95 (s, 1H), 8.39-8.06 (m, 1H), 7.80 (dd, J=8.8, 5.2 Hz, 1H), 7.68-7.56 (m, 2H), 7.34-7.14 (m, 3H), 7.08 (m, J=9.6, 8.8, 2.4 Hz, 1H).

6-fluoro-N-(6-fluoro-2,1,3-benzothiadiazol-5-yl)-1H-indole-3-sulfonamide I-172

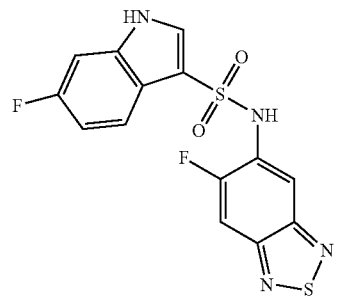 [SMILES: O=S(=O)(Nc1cc2nsnc2cc1F)c1c[nH]c2cc(F)ccc12]

Neutral LCMS Method 3 (ES⁺): 366.3 (M+H)⁺, 99% purity.

¹H NMR (600 MHz, DMSO-d$_6$) δ 12.11 (d, J=3.2 Hz, 1H), 10.76 (s, 1H), 8.19 (d, J=3.0 Hz, 1H), 8.04-7.69 (m, 3H), 7.24 (dd, J=9.5, 2.4 Hz, 1H), 7.08 (m, J=9.7, 8.8, 2.4 Hz, 1H).

N-(4-bromo-2-fluorophenyl)-6-methyl-1H-indole-3-sulfonamide I-173

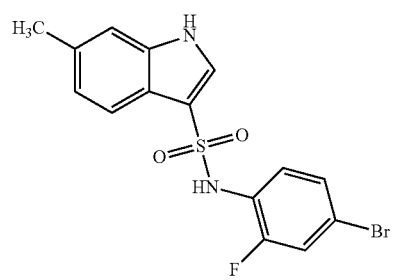

Neutral LCMS Method 3 (ES⁺): 383.2 (M+H)⁺, 95% purity.

¹H NMR (600 MHz, DMSO-d$_6$) δ 11.81 (d, J=3.1 Hz, 1H), 10.01 (s, 1H), 7.77 (d, J=3.0 Hz, 1H), 7.63 (d, J=8.2 Hz,

1H), 7.40 (dd, J=9.9, 2.1 Hz, 1H), 7.32-7.14 (m, 3H), 6.98 (dd, J=8.3, 1.5 Hz, 1H), 2.38 (s, 3H).

N-(4-chloro-2-fluorophenyl)-6-methyl-1H-indole-3-sulfonamide I-174

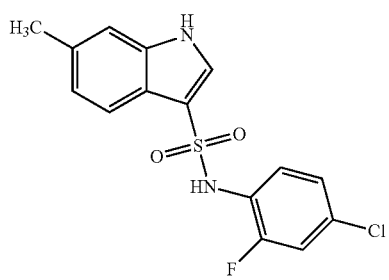 [SMILES: Cc1ccc2c(S(=O)(=O)Nc3ccc(Br)cc3F)c[nH]c2c1]

Neutral LCMS Method 3 (ES+): 338.7 (M+H)+, 95% purity.

¹H NMR (600 MHz, DMSO-d$_6$) δ 11.81 (d, J=3.0 Hz, 1H), 9.99 (s, 1H), 7.77 (d, J=2.9 Hz, 1H), 7.62 (d, J=8.1 Hz, 1H), 7.34-7.22 (m, 3H), 7.14 (m, J=8.7, 2.4, 1.1 Hz, 1H), 6.98 (dd, J=8.1, 1.4 Hz, 1H), 2.38 (s, 3H).

N-(4-chloro-5-fluoro-2-methoxyphenyl)-1H-benzo[g]indole-3-sulfonamide I-175

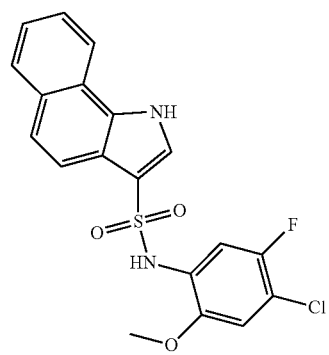 [SMILES: COc1cc(Cl)c(F)cc1NS(=O)(=O)c1c[nH]c2c1ccc1ccccc12]

Neutral LCMS Method 3 (ES+): 404.8 (M+H)+, 95% purity.

¹H NMR (600 MHz, DMSO-d$_6$) δ 12.85 (d, J=3.3 Hz, 1H), 9.63 (s, 1H), 8.38 (d, J=8.2 Hz, 1H), 8.03 (d, J=2.8 Hz, 1H), 7.95 (dd, J=30.6, 8.4 Hz, 2H), 7.70-7.57 (m, 2H), 7.49 (m, J=8.1, 6.8, 1.2 Hz, 1H), 7.31 (d, J=10.6 Hz, 1H), 7.01 (d, J=6.9 Hz, 1H), 3.37 (s, 3H).

6-chloro-N-(4-cyano-2,5-difluorophenyl)-1H-pyrrolo[2,3-b]pyridine-3-sulfonamide I-176

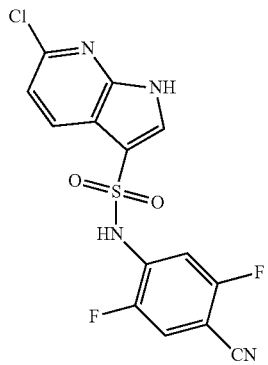 [SMILES: N#Cc1cc(F)c(NS(=O)(=O)c2c[nH]c3nc(Cl)ccc23)cc1F]

Neutral LCMS Method 3 (ES+): 369.2 (M+H)+, 98% purity.

¹H NMR (500 MHz, DMSO-d$_6$) δ 12.97 (br, 1H, NH), 11.20 (br, 1H, NH), 8.46 (d, J=3.0 Hz, 1H), 8.28 (d, J=8.3 Hz, 1H), 7.86 (dd, J=10.3, 6.0 Hz, 1H), 7.47 (dd, J=10.8, 6.4 Hz, 1H), 7.40 (d, J=8.2 Hz, 1H).

6-bromo-N-(4-cyano-2-fluorophenyl)-1H-pyrrolo[2,3-b]pyridine-3-sulfonamide I-177

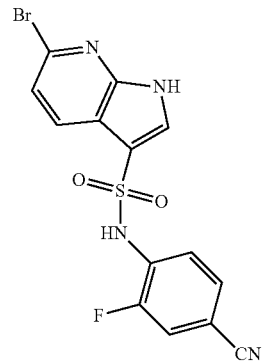 [SMILES: N#Cc1ccc(NS(=O)(=O)c2c[nH]c3nc(Br)ccc23)c(F)c1]

Neutral LCMS Method 3 (ES+): 395.2 (M+H)+, 99% purity.

¹H NMR (500 MHz, DMSO-d$_6$) δ 12.91 (br, 1H, NH), 10.81 (br, 1H, NH), 8.24 (s, 1H), 8.13 (d, J=8.3 Hz, 1H), 7.70-7.76 (m, 1H), 7.52-7.58 (m, 2H), 7.48 (d, J=8.3 Hz, 1H).

321

6-chloro-N-(4-cyanophenyl)-1H-pyrrolo[2,3-b]pyridine-3-sulfonamide I-178

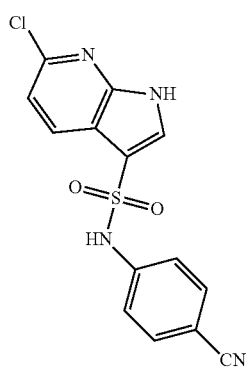 [SMILES: N#Cc1ccc(NS(=O)(=O)c2c[nH]c3nc(Cl)ccc23)cc1]

Neutral LCMS Method 3 (ES+): 333.1 (M+H)+, 97% purity.

$^1$H NMR (500 MHz, DMSO-d$_6$) δ 12.90 (br, 1H, NH), 11.00 (br, 1H, NH), 8.33 (s, 1H), 8.20 (d, J=8.3 Hz, 1H), 7.64 (d, J=8.8 Hz, 2H), 7.37 (d, J=8.4 Hz, 1H), 7.23 (d, J=8.9 Hz, 2H).

N-(2,1,3-benzothiadiazol-5-yl)-6-chloro-1H-pyrrolo[2,3-b]pyridine-3-sulfonamide I-179

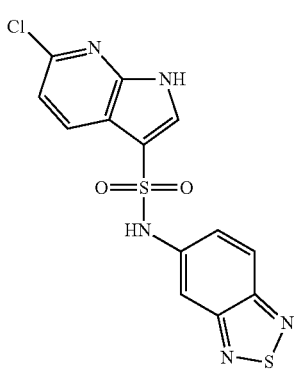 [SMILES: O=S(=O)(Nc1ccc2nsnc2c1)c1c[nH]c2nc(Cl)ccc12]

Neutral LCMS Method 3 (ES+): 366.0 (M+H)+, 96% purity.

$^1$H NMR (500 MHz, DMSO-d$_6$) δ 12.87 (br, 1H, NH), 10.97 (br, 1H, NH), 8.41 (s, 1H), 8.26 (d, J=8.4 Hz, 1H), 7.92 (dd, J=9.4, 0.7 Hz, 1H), 7.61 (dd, J=2.2, 0.6 Hz, 1H), 7.47 (dd, J=9.4, 2.2 Hz, 1H), 7.37 (d, J=8.3 Hz, 1H).

322

6-chloro-N-[4-(cyanomethyl)phenyl]-1H-indole-3-sulfonamide I-180

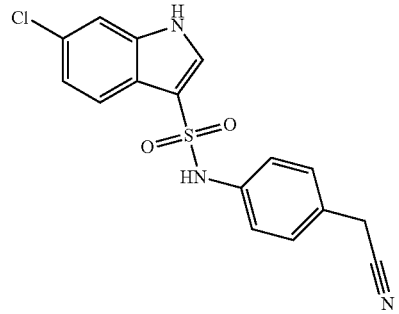 [SMILES: N#CCc1ccc(NS(=O)(=O)c2c[nH]c3cc(Cl)ccc23)cc1]

Neutral LCMS Method 3 (ES+): 346.2 (M+H)+, 98% purity.

$^1$H NMR (500 MHz, DMSO-d$_6$) δ: 12.03 (br, 1H), 10.24 (br, 1H), 7.79 (dd, J=8.6, 0.5 Hz, 1H), 7.48 (dd, J=1.9, 0.5 Hz, 1H), 7.20 (dd, J=10.5, 8.7 Hz, 2H), 7.15-7.11 (m, 7H), 7.10-7.06 (m, 3H), 3.84 (s, 2H) ppm.

6-chloro-N-(3-chloro-4-cyanophenyl)-1H-indole-3-sulfonamide I-181

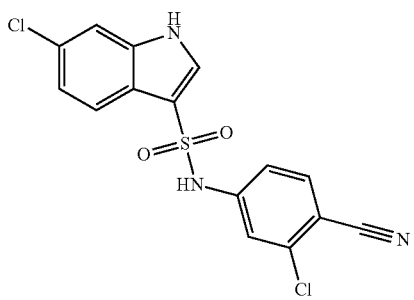 [SMILES: N#Cc1ccc(NS(=O)(=O)c2c[nH]c3cc(Cl)ccc23)cc1Cl]

Neutral LCMS Method 3 (ES+): 383.0 (M+NH$_4$)+, 98% purity.

6-chloro-N-(4-cyano-2,6-difluorophenyl)-1H-indole-3-sulfonamide I-182

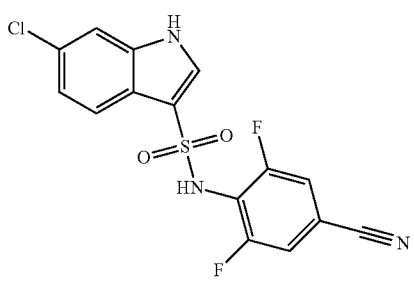 [SMILES: N#Cc1cc(F)c(NS(=O)(=O)c2c[nH]c3cc(Cl)ccc23)c(F)c1]

Neutral LCMS Method 3 (ES+): 385.2 (M+H)+, 92% purity.

$^1$H NMR (500 MHz, DMSO-d$_6$) δ: 12.09 (br, 1H), 10.10 (br, 1H), 7.87 (d, J=3.0 Hz, 1H), 7.78-7.72 (m, 2H), 7.60 (d, J=8.5 Hz, 1H), 7.54 (dd, J=1.9, 0.6 Hz, 1H), 7.19 (dd, J=8.6, 1.9 Hz, 1H).

N-(2,1,3-benzothiadiazol-5-yl)-6-bromo-1H-indole-3-sulfonamide I-183

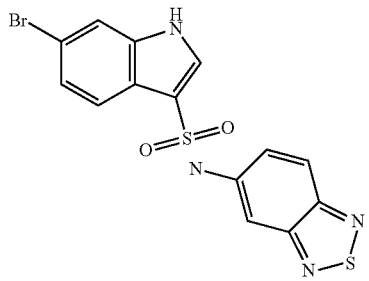

Neutral LCMS Method 3 (ES+): 411.2 (M+H)+, 97% purity.
$^1$H NMR (600 MHz, DMSO-d$_6$) δ: 12.47 (d, J=3.2 Hz, 1H), 10.86 (s, 1H), 8.30 (d, J=3.4 Hz, 1H), 8.04 (d, J=8.4 Hz, 1H), 7.82 (s, 1H), 7.75-7.68 (m, 1H), 7.55-7.58 (m, 2H), 7.52 (d, J=8.6 Hz, 1H).

N-(4-cyano-2,5-difluorophenyl)-6-(trifluoromethyl)-1H-indole-3-sulfonamide I-184

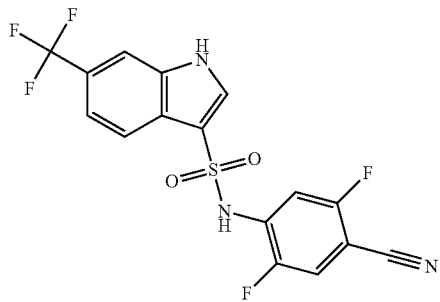 [SMILES: N#Cc1cc(F)c(NS(=O)(=O)c2c[nH]c3cc(C(F)(F)F)ccc23)cc1F]

Neutral LCMS Method 3 (ES+): 402.0 (M+H)+, 99% purity.
$^1$H NMR (600 MHz, DMSO-d$_6$) δ: 12.55 (d, J=3.2 Hz, 1H), 11.26 (s, 1H), 8.48 (d, J=3.2 Hz, 1H), 8.07 (d, J=8.4 Hz, 1H), 7.88-7.84 (m, 1H), 7.83 (s, 1H), 7.55 (d, J=8.1 Hz, 1H), 7.46 (dd, J=10.9, 6.3 Hz, 1H).

6-chloro-N-(4-cyano-2,5-difluorophenyl)-1H-indole-3-sulfonamide I-185

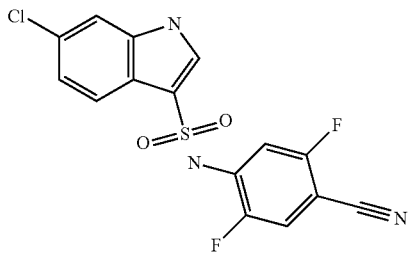

Neutral LCMS Method 3 (ES+): 385.1 (M+NH$_4$)+, 98% purity.
$^1$H NMR (500 MHz, DMSO-d$_6$) δ: 12.26 (d, J=3.0 Hz, 1H), 11.17 (s, 1H), 8.29 (d, J=3.0 Hz, 1H), 7.86 (d, J=8.6 Hz, 1H), 7.84 (dd, J=11.1, 6.0 Hz, 1H), 7.53 (d, J=2.0 Hz, 1H), 7.44 (dd, J=11.0, 6.4 Hz, 1H), 7.26 (dd, J=8.6, 1.9 Hz, 1H).

N-(2,1,3-benzothiadiazol-4-yl)-6-(trifluoromethyl)-1H-indole-3-sulfonamide I-186

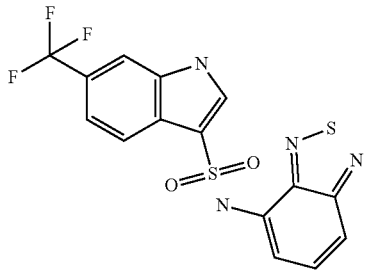

Neutral LCMS Method 3 (ES+): 399.1 (M+H)+, 92% purity.
$^1$H NMR (500 MHz, DMSO-d$_6$) δ: 12.35 (s, 1H), 10.87 (s, 1H), 8.31 (d, J=2.7 Hz, 1H), 8.06 (d, J=8.5 Hz, 1H), 7.76 (dd, J=1.5, 0.8 Hz, 1H), 7.69 (dd, J=8.8, 0.9 Hz, 1H), 7.58 (dd, J=8.8, 7.4 Hz, 1H), 7.49 (dd, J=7.4, 0.9 Hz, 1H), 7.43 (dd, J=8.5, 1.6 Hz, 1H).

N-(4-cyano-2,5-difluorophenyl)-6-methyl-1H-indole-3-sulfonamide I-187

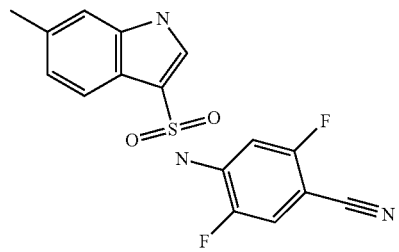

Neutral LCMS Method 3 (ES+): 365.1 (M+NH$_4$)+, 96% purity.

6-bromo-N-(4-cyano-2,5-difluorophenyl)-1H-indole-3-sulfonamide I-188

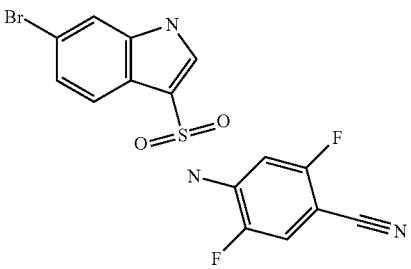

Neutral LCMS Method 3 (ES+): 429.2 (M+NH$_4$)+, 98% purity.
$^1$H NMR (600 MHz, DMSO-d$_6$) δ: 12.26 (s, 1H), 11.19 (s, 1H), 8.28 (d, J=3.0 Hz, 1H), 7.84 (dd, J=10.3, 5.9 Hz, 1H), 7.81 (d, J=8.6 Hz, 1H), 7.67 (s, 1H), 7.43 (dd, J=10.9, 6.3 Hz, 1H), 7.37 (d, J=8.5 Hz, 1H).

N-(4-cyano-2-fluorophenyl)-6-(trifluoromethyl)-1H-indole-3-sulfonamide I-189

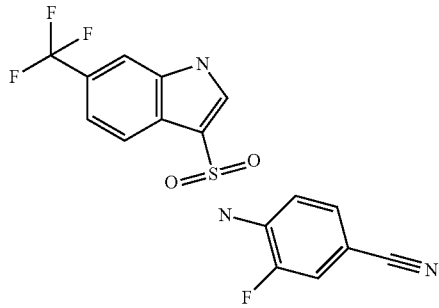

Neutral LCMS Method 3 (ES⁺): 401.3 (M+NH₄)⁺, 95% purity.

¹H NMR (600 MHz, DMSO-d₆) δ: 12.46 (d, J=3.4 Hz, 1H), 10.86 (s, 1H), 8.30 (d, J=3.0 Hz, 1H), 8.03 (d, J=8.5 Hz, 1H), 7.82 (s, 1H), 7.76-7.69 (m, 1H), 7.55-7.58 (m, 2H), 7.52 (dd, J=8.6, 1.6 Hz, 1H).

N-(4-cyanophenyl)-6-(trifluoromethyl)-1H-indole-3-sulfonamide I-190

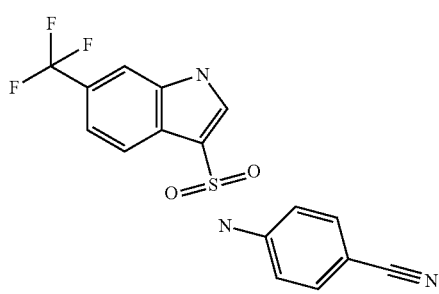

Neutral LCMS Method 3 (ES⁺): 383.3 (M+NH₄)⁺, 98% purity.

¹H NMR (600 MHz, DMSO-d₆) δ: 12.46 (s, 1H), 11.04 (s, 1H), 8.37 (s, 1H), 8.02 (d, J=8.5 Hz, 1H), 7.81 (s, 1H), 7.62 (d, J=8.7 Hz, 2H), 7.53 (d, J=8.7 Hz, 1H), 7.24 (d, J=8.8 Hz, 2H).

N-(5-chloro-3-fluoropyridin-2-yl)-1H-benzo[g]indole-3-sulfonamide I-191

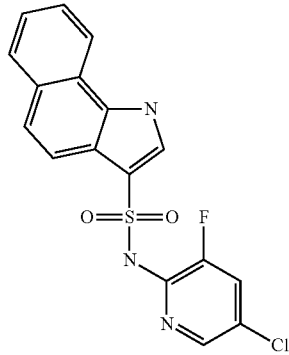 [SMILES: O=S(=O)(Nc1ncc(Cl)cc1F)c1c[nH]c2c1ccc1ccccc12]

Neutral LCMS Method 3 (ES⁺): 375.8 (M+H)⁺, 96% purity.

¹H NMR (600 MHz, DMSO-d₆) δ 12.91 (d, J=3.3 Hz, 1H), 11.06 (s, 1H), 8.40 (dd, J=8.2, 1.2 Hz, 1H), 8.09 (dd, J=31.3, 2.6 Hz, 2H), 8.01-7.86 (m, 3H), 7.72-7.54 (m, 2H), 7.49 (m, J=8.1, 6.9, 1.2 Hz, 1H).

N-(2,1,3-benzothiadiazol-5-yl)-6-(trifluoromethyl)-1H-indole-3-sulfonamide I-192

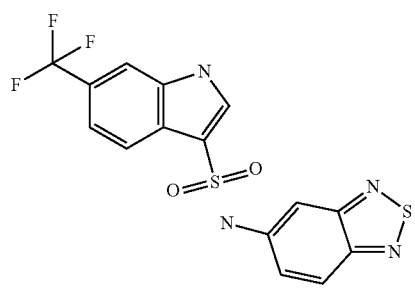

Neutral LCMS Method 3 (ES⁺): 399 (M+H)⁺, 99% purity.

¹H NMR (600 MHz, DMSO-d₆) δ: 12.43 (s, 1H), 11.02 (s, 1H), 8.45 (s, 1H), 8.08 (d, J=8.5 Hz, 1H), 7.91 (d, J=9.4 Hz, 1H), 7.78 (s, 1H), 7.61 (d, J=2.5 Hz, 1H), 7.53 (dd, J=8.5, 1.6 Hz, 1H), 7.48 (dd, J=9.4, 2.2 Hz, 1H).

6-bromo-N-(6-fluoro-2,1,3-benzothiadiazol-5-yl)-1H-indole-3-sulfonamide I-193

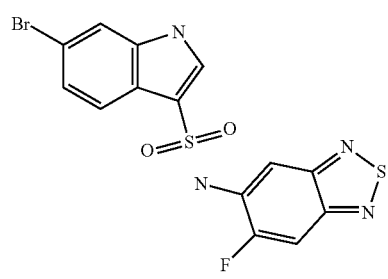

Neutral LCMS Method 3 (ES⁺): 429.1 (M+H)⁺, 99% purity.

327

6-chloro-N-[5-(cyanomethyl)-3-methoxypyridin-2-yl]-1H-indole-3-sulfonamide I-194

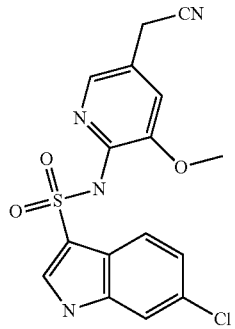 [SMILES: COc1cc(CC#N)cnc1NS(=O)(=O)c1c[nH]c2cc(Cl)ccc12]

Basic LC-MS Method 2 (ES$^+$): 377 (M+H)$^+$, 100% purity.
$^1$H NMR (600 MHz, DMSO-d$_6$) δ 3.76 (s, 3H) 3.90 (s, 2H) 7.20-7.28 (m, 2H) 7.50 (d, J=1.47 Hz, 1H) 7.66 (s, 1H) 7.95 (d, J=8.31 Hz, 1H) 8.10 (s, 1H) 10.11 (brs, 1H) 12.03 (brs, 1H).

6-chloro-N-[4-chloro-5-(difluoromethoxy)-2-fluorophenyl]-1H-indole-3-sulfonamide I-195

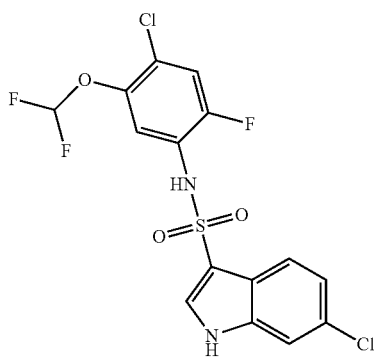 [SMILES: O=S(=O)(Nc1cc(OC(F)F)c(Cl)cc1F)c1c[nH]c2cc(Cl)ccc12]

Basic LC-MS Method 2 (ES$^-$): 423 (M–H)$^-$, 99% purity.
$^1$H NMR (400 MHz, DMSO-d$_6$) δ 7.12 (t, J=72 Hz, 1H) 7.21 (dd, J=8.8, 2.0 Hz, 1H) 7.28-7.33 (m, 1H) 7.50-7.55 (m, 2H) 7.75 (d, J=8.8 Hz, 1H) 7.94 (d, J=2.45 Hz, 1H) 10.41 (brs, 1H) 12.12 (brs, 1H).

6-chloro-7-methoxy-N-(2,4,5-trifluorophenyl)-1H-indole-3-sulfonamide I-196

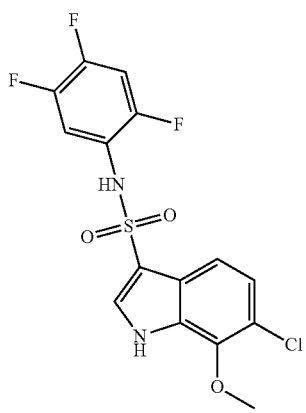 [SMILES: COc1c(Cl)ccc2c(S(=O)(=O)Nc3cc(F)c(F)cc3F)c[nH]c12]

Basic LC-MS Method 2 (ES$^-$): 389 (M–H)$^-$, 97% purity.
$^1$H NMR (400 MHz, DMSO-d$_6$) δ 3.89 (s, 3H) 7.20 (d, J=8.00 Hz, 1H) 7.29-7.36 (m, 1H) 7.42-7.49 (m, 2H) 7.92 (d, J=2.40 Hz, 1H) 10.22 (s, 1H) 12.47 (s, 1H).

328

6-chloro-N-(7-fluoro-2,1,3-benzoxadiazol-4-yl)-1H-indole-3-sulfonamide I-197

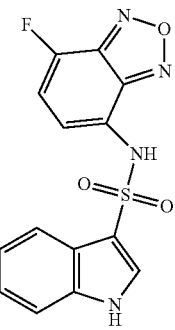

Basic LC-MS Method 2 (ES$^-$): 365 (M–H)$^-$, 98% purity.
$^1$H NMR (400 MHz, DMSO-d$_6$) δ 7.13-7.17 (m, 1H) 7.21 (d, J=8.8 Hz, 1H) 7.30-7.34 (m, 1H) 7.50 (s, 1H) 7.83 (d, J=9.2 Hz, 1H) 8.2 (d, J=2.8 Hz, 1H) 11.15 (brs, 1H) 12.16 (brs, 1H).

6-chloro-N-(4-chloro-2,5-difluorophenyl)-1-benzofuran-3-sulfonamide I-198

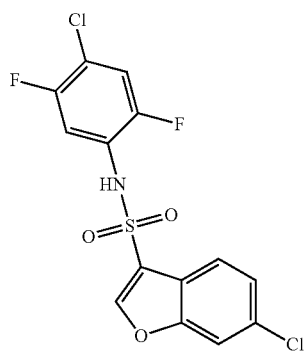 [SMILES: O=S(=O)(Nc1cc(F)c(Cl)cc1F)c1coc2cc(Cl)ccc12]

Basic LC-MS Method 2 (ES$^-$): 376 (M–H)$^-$, 99% purity.
$^1$H NMR (400 MHz, DMSO-d$_6$) δ 7.38-7.44 (m, 1H) 7.51 (d, J=8.40 Hz, 1H) 7.60 (t, J=8.40 Hz, 1H) 7.78 (d, J=8.00 Hz, 1H) 7.97 (s, 1H) 8.74 (s, 1H) 10.99 (s, 1H).

6-chloro-N-(5-chloro-3,6-difluoropyridin-2-yl)-1H-indole-3-sulfonamide I-199

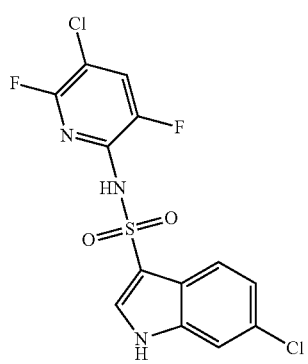 [SMILES: O=S(=O)(Nc1nc(F)c(Cl)cc1F)c1c[nH]c2cc(Cl)ccc12]

Basic LC-MS Method 2 (ES$^+$): 378 (M+H)$^+$, 96% purity.
$^1$H NMR (400 MHz, DMSO-d$_6$) δ 7.26 (dd, J=8.80, 1.47 Hz, 1H) 7.55 (d, J=1.47 Hz, 1H) 7.88 (d, J=8.31 Hz, 1H) 8.15 (d, J=2.93 Hz, 1H) 8.21 (t, J=7.83 Hz, 1H) 11.49 (brs, 1H) 12.22 (brs, 1H).

6-chloro-N-(3,6-difluoropyridin-2-yl)-1H-indole-3-sulfonamide I-200

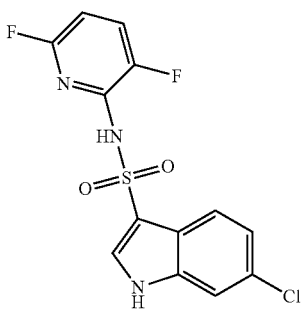 [SMILES: O=S(=O)(Nc1nc(F)ccc1F)c1c[nH]c2cc(Cl)ccc12]

Basic LC-MS Method 2 (ES⁻): 344 (M−H)⁻, 93% purity.
$^1$H NMR (400 MHz, DMSO-$d_6$) δ 6.75 (d, J=8.31 Hz, 1H) 7.24 (dd, J=8.5, 1.71 Hz, 1H) 7.54 (d, J=1.5 Hz, 1H) 7.75-7.83 (m, 1H) 7.88 (d, J=8.3 Hz, 1H) 8.13 (d, J=2.9 Hz, 1H) 11.25 (brs, 1H) 12.18 (brs, 1H).

6-chloro-N-(4-chloro-2,5-difluorophenyl)-7-fluoro-1H-indole-3-sulfonamide I-242

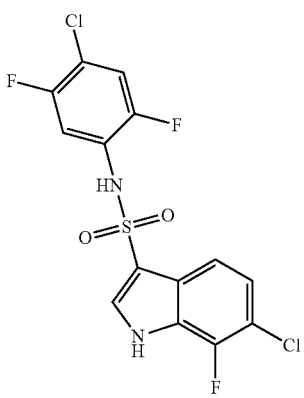 [SMILES: O=S(=O)(Nc1cc(F)c(Cl)cc1F)c1c[nH]c2c(F)c(Cl)ccc12]

Basic LC-MS Method 2 (ES⁻): 393 (M−H)⁻, 97% purity.
$^1$H NMR (400 MHz, DMSO-$d_6$) δ 7.26-7.39 (m, 2H) 7.51-7.62 (m, 2H) 8.13 (s, J=2.45 Hz, 1H) 10.55 (s, 1H) 12.90 (brs, 1H).

6-chloro-N-(6-fluoro-3-oxo-1,3-dihydro-2-benzofuran-5-yl)-1H-indole-3-sulfonamide I-243

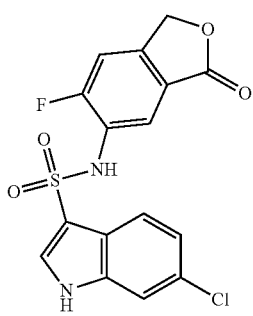 [SMILES: O=C1OCc2cc(F)c(NS(=O)(=O)c3c[nH]c4cc(Cl)ccc34)cc21]

Basic LC-MS Method 2 (ES⁺): 381 (M+H)⁺, 99% purity.
$^1$H NMR (400 MHz, DMSO-$d_6$) δ 5.28 (s, 2H) 7.23 (dd, J=8.56, 1.71 Hz, 1H) 7.46 (d, J=9.29 Hz, 1H) 7.52 (d, J=1.96 Hz, 1H) 7.67 (d, J=6.85 Hz, 1H) 7.77 (d, J=8.80 Hz, 1H) 7.97 (d, J=2.93 Hz, 1H) 10.44 (s, 1H) 12.11 (brs, 1H).

6-chloro-N-(4-chloro-2,5-difluorophenyl)-7-methoxy-1H-indole-3-sulfonamide I-244

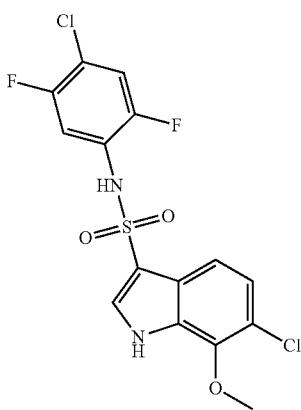 [SMILES: COc1c(Cl)ccc2c(S(=O)(=O)Nc3cc(F)c(Cl)cc3F)c[nH]c12]

Basic LC-MS Method 2 (ES⁻): 405 (M−H)⁻, 98% purity.
$^1$H NMR (400 MHz, DMSO-$d_6$) δ 3.90 (s, 3H) 7.24 (d, J=8.31 Hz, 1H) 7.34-7.40 (m, 1H) 7.52-7.59 (m, 2H) 8.06 (d, J=2.93 Hz, 1H) 10.52 (s, 1H) 12.54 (brs, 1H).

N-(5-bromo-3,6-difluoropyridin-2-yl)-6-chloro-1H-indole-3-sulfonamide I-245

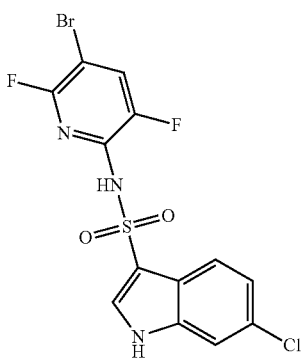 [SMILES: O=S(=O)(Nc1nc(F)c(Br)cc1F)c1c[nH]c2cc(Cl)ccc12]

Basic LC-MS Method 2 (ES⁺): 422 (M+H)⁺, 97% purity.
$^1$H NMR (400 MHz, DMSO-$d_6$) δ 7.24 (d, J=7.82 Hz, 1H) 7.54 (s, 1H) 7.87 (d, J=8.31 Hz, 1H) 8.13 (s, 1H) 8.21-8.28 (m, 1H) 11.48 (brs, 1H) 12.18 (brs, 1H).

331

6-chloro-N-[4-(2,2-difluoroethoxy)-2,5-difluorophenyl]-1H-indole-3-sulfonamide I-246

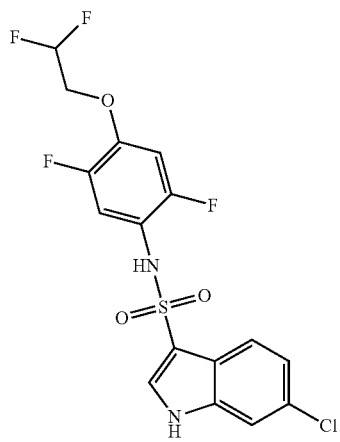 [SMILES: O=S(=O)(Nc1cc(F)c(OCC(F)F)cc1F)c1c[nH]c2cc(Cl)ccc12]

Basic LC-MS Method 2 (ES⁻): 421 (M−H)⁻, 95% purity.

$^1$H NMR (400 MHz, DMSO-$d_6$) δ 4.26-4.36 (m, 2H) 6.35 (t, J=54 Hz, 1H) 7.02-7.18 (m, 2H) 7.20 (dd, J=8.56, 1.71 Hz, 1H) 7.51 (d, J=1.47 Hz, 1H) 7.69 (d, J=8.31 Hz, 1H) 7.86 (d, J=2.45 Hz, 1H) 9.94 (s, 1H) 12.04 (brs, 1H).

N-(4-chloro-2,5-difluorophenyl)-6-(trifluoromethyl)-1H-pyrrolo[2,3-b]pyridine-3-sulfonamide I-247

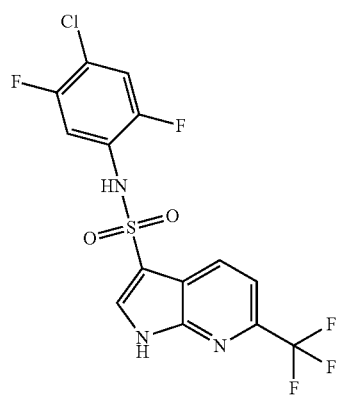 [SMILES: O=S(=O)(Nc1cc(F)c(Cl)cc1F)c1c[nH]c2nc(C(F)(F)F)ccc12]

Basic LC-MS Method 2 (ES⁻): 410 (M−H)⁻, 99% purity.

$^1$H NMR (400 MHz, DMSO-$d_6$) δ 7.34-7.39 (m, 1H) 7.48-7.54 (m, 1H) 7.79 (d, J=8.31 Hz, 1H) 8.41 (d, J=8.31 Hz, 1H) 8.46 (s, 1H) 10.60 (s, 1H) 13.18 (brs, 1H).

332

5-bromo-6-chloro-N-(4-chloro-2,5-difluorophenyl)-1H-indole-3-sulfonamide I-248

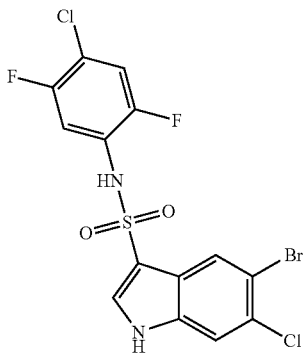

Basic LC-MS Method 2 (ES⁻): 455 (M−H)⁻, 95% purity.

$^1$H NMR (400 MHz, DMSO-$d_6$) δ 7.32-7.36 (m, 1H) 7.50-7.56 (m, 1H) 7.73 (s, 1H) 8.07-8.13 (m, 2H) 10.50 (s, 1H) 12.29 (brs, 1H).

7-bromo-6-chloro-N-(4-chloro-2,5-difluorophenyl)-1H-indole-3-sulfonamide I-249

Basic LC-MS Method 2 (ES⁻): 455 (M−H)⁻, 98% purity.

$^1$H NMR (400 MHz, DMSO-$d_6$) δ 7.38 (dd, J=10.03, 7.09 Hz, 1H) 7.43 (d, J=8.31 Hz, 1H) 7.53-7.59 (m, 1H) 7.79 (d, J=8.31 Hz, 1H) 8.07 (d, J=2.93 Hz, 1H) 10.57 (s, 1H) 12.53 (brs, 1H).

333

6-bromo-N-(4-chloro-2,5-difluorophenyl)-4-fluoro-1H-indole-3-sulfonamide I-251

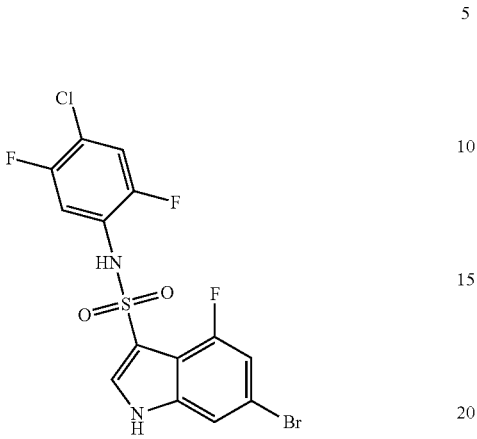

Basic LC-MS Method 2 (ES+): 439 (M+H)+, 98% purity.
¹H NMR (400 MHz, DMSO-d$_6$) δ 7.26 (d, J=10.29 Hz, 1H) 7.32-7.39 (m, 1H) 7.52 (d, J=1.25 Hz, 1H) 7.56 (m, 1H) 8.06 (s, 1H) 10.27 (s, 1H) 12.39 (brs, 1H).

6-chloro-N-{3,6-difluoro-5-[(1E)-3-methoxyprop-1-en-1-yl]pyridin-2-yl}-1H-indole-3-sulfonamide I-252

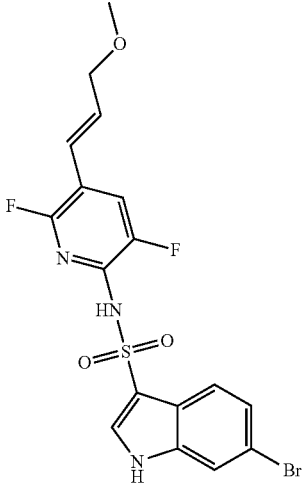 [SMILES: COC/C=C/c1cc(F)c(NS(=O)(=O)c2c[nH]c3cc(Br)ccc23)nc1F]

Basic LC-MS Method 2 (ES+): 414 (M+H)+, 99% purity.
¹H NMR (400 MHz, DMSO-d$_6$) δ 3.26 (s, 3H) 4.01 (brs, 2H) 6.43 (brs, 2H) 7.20-7.29 (m, 1H) 7.54 (s, 1H) 7.88 (d, J=8.80 Hz, 1H) 8.08 (t, J=8.80 Hz, 1H) 8.13 (brs, 1H) 11.28 (brs, 1H) 12.18 (brs, 1H).

334

6-chloro-N-[3,6-difluoro-5-(3-methoxypropyl)pyridin-2-yl]-1H-indole-3-sulfonamide I-253

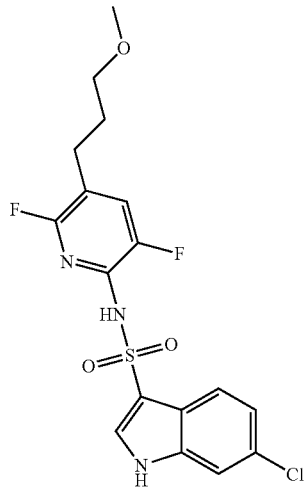

Basic LC-MS Method 2 (ES+): 416 (M+H)+, 98% purity.
¹H NMR (400 MHz, DMSO-d$_6$) δ 1.65-1.75 (m, 2H) 3.18 (s, 3H) 3.26 (t, J=6.11 Hz, 2H) 7.20-7.27 (m, 1H) 7.54 (d, J=1.96 Hz, 1H) 7.73 (dd, J=9.29, 7.83 Hz, 1H) 7.84 (d, J=8.80 Hz, 1H) 8.09 (d, J=2.93 Hz, 1H) 11.00 (s, 1H) 12.15 (brs, 1H) (2H's merged in solvent peak).

6-chloro-N-(5-chloro-3-fluoro-6-methoxypyridin-2-yl)-1H-indole-3-sulfonamide I-254

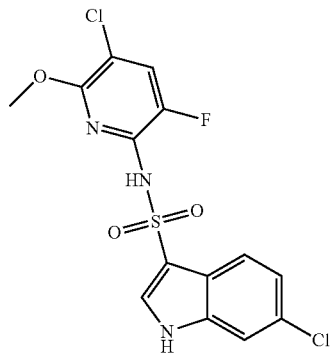 [SMILES: COc1nc(NS(=O)(=O)c2c[nH]c3cc(Cl)ccc23)c(F)cc1Cl]

Basic LC-MS Method 2 (ES+): 390 (M+H)+, 95% purity.
¹H NMR (400 MHz, DMSO-d$_6$) δ 3.63 (s, 3H) 7.23 (dd, J=8.56, 1.71 Hz, 1H) 7.54 (d, J=1.96 Hz, 1H) 7.84 (d, J=8.80 Hz, 1H) 7.94 (d, J=8.80 Hz, 1H) 8.16 (d, J=2.93 Hz, 1H) 11.11 (s, 1H) 12.11 (brs, 1H).

335

6-chloro-N-[5-(cyanomethyl)-3-fluoro-6-methoxy-pyridin-2-yl]-1H-indole-3-sulfonamide I-255

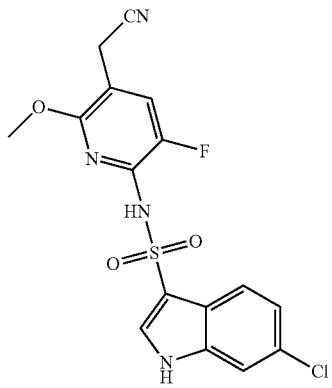 [SMILES: COc1nc(NS(=O)(=O)c2c[nH]c3cc(Cl)ccc23)c(F)cc1CC#N]

Basic LC-MS Method 2 (ES⁺): 395 (M+H)⁺, 98% purity.
¹H NMR (400 MHz, DMSO-d$_6$) δ 3.62 (s, 3H) 3.70 (s, 2H) 7.22 (dd, J=8.80, 1.96 Hz, 1H) 7.54 (d, J=1.96 Hz, 1H) 7.62 (d, J=9.78 Hz, 1H) 7.85 (d, J=8.31 Hz, 1H) 8.15 (d, J=2.93 Hz, 1H) 11.02 (s, 1H) 12.08 (brs, 1H).

6-chloro-N-[4-(cyanomethoxy)-2,5-difluorophenyl]-1H-indole-3-sulfonamide I-257

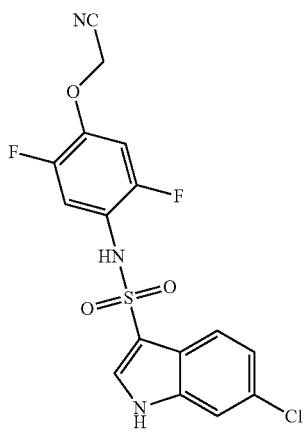 [SMILES: N#CCOc1cc(F)c(NS(=O)(=O)c2c[nH]c3cc(Cl)ccc23)cc1F]

Basic LC-MS Method 2 (ES⁻): 396 (M–H)⁻, 98% purity.
¹H NMR (400 MHz, DMSO-d$_6$) δ 5.18 (s, 2H) 7.14-7.27 (m, 3H) 7.52 (d, J=1.96 Hz, 1H) 7.67 (d, J=8.80 Hz, 1H) 7.91 (d, J=2.45 Hz, 1H) 10.05 (s, 1H) 12.07 (brs, 1H).

6-chloro-N-(4-cyano-2-fluorophenyl)-5-fluoro-1H-indole-3-sulfonamide I-258

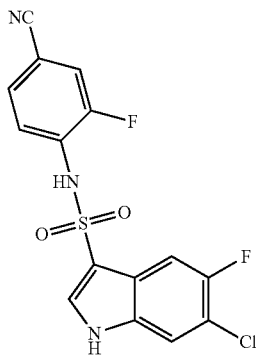 [SMILES: N#Cc1ccc(NS(=O)(=O)c2c[nH]c3cc(Cl)c(F)cc23)c(F)c1]

Basic LC-MS Method 2 (ES⁻): 366 (M–H)⁻, 97% purity.
¹H NMR (400 MHz, DMSO-d$_6$) δ 7.57 (d, J=3.91 Hz, 2H) 7.69 (d, J=6.36 Hz, 1H) 7.74-7.81 (m, 2H) 8.20 (d, J=2.93 Hz, 1H) 10.81 (s, 1H) 12.31 (brs, 1H).

336

N-(4-bromo-2,5-difluorophenyl)-6-chloro-1-benzofuran-3-sulfonamide I-259

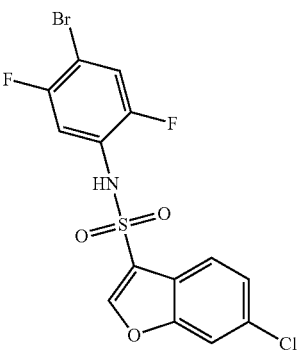 [SMILES: O=S(=O)(Nc1cc(F)c(Br)cc1F)c1coc2cc(Cl)ccc12]

Basic LC-MS Method 2 (ES⁺): 422 (M+H)⁺, 99% purity.
¹H NMR (400 MHz, DMSO-d$_6$) δ 7.36-7.40 (m, 1H) 7.51 (dd, J=8.56, 1.71 Hz, 1H) 7.62-7.66 (m, 1H) 7.78 (d, J=8.31 Hz, 1H) 7.96 (d, J=1.47 Hz, 1H) 8.76 (s, 1H) 11.00 (brs, 1H).

6-chloro-N-[4-(cyclopropylmethoxy)-2,5-difluoro-phenyl]-1H-indole-3-sulfonamide I-260

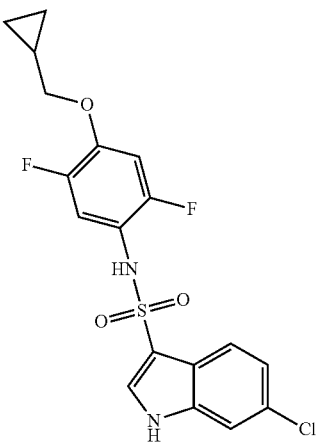 [SMILES: O=S(=O)(Nc1cc(F)c(OCC2CC2)cc1F)c1c[nH]c2cc(Cl)ccc12]

Basic LC-MS Method 2 (ES⁻): 411 (M–H)⁻, 98% purity.

¹H NMR (400 MHz, DMSO-d$_6$) δ 0.24-0.31 (m, 2H) 0.50-0.57 (m, 2H) 1.12-1.21 (m, 1H) 3.79 (d, J=6.85 Hz, 2H) 6.92-7.05 (m, 2H) 7.20 (dd, J=8.56, 1.71 Hz, 1H) 7.52 (d, J=1.47 Hz, 1H) 7.69 (d, J=8.31 Hz, 1H) 7.84 (d, J=1.96 Hz, 1H) 9.83 (s, 1H) 12.03 (brs, 1H).

337

6-chloro-N-(4-chloro-2,5-difluorophenyl)-7-(2,2-difluoroethoxy)-1H-indole-3-sulfonamide I-262

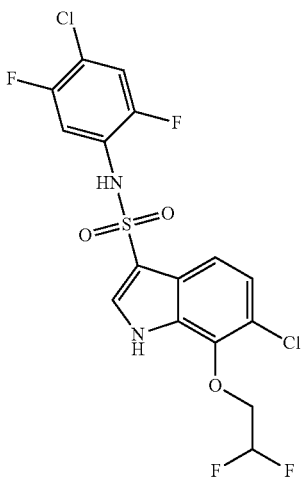 [SMILES: O=S(=O)(Nc1cc(F)c(Cl)cc1F)c1c[nH]c2c(OCC(F)F)c(Cl)ccc12]

Basic LC-MS Method 2 (ES⁻): 455 (M−H)⁻. 99% purity.

$^1$H NMR (400 MHz, DMSO-d$_6$) δ 4.36-4.41 (m, 2H) 6.27-6.59 (m, 1H) 7.26 (d, J=8.68 Hz, 1H) 7.33-7.37 (m, 1H) 7.52-7.56 (m, 1H) 7.58 (d, J=8.68 Hz, 1H) 8.12 (d, J=2.81 Hz, 1H) 10.54 (s, 1H) 12.46 (brs, 1H).

6-chloro-N-(4-chloro-2,5-difluorophenyl)-5-fluoro-1H-indole-3-sulfonamide I-263

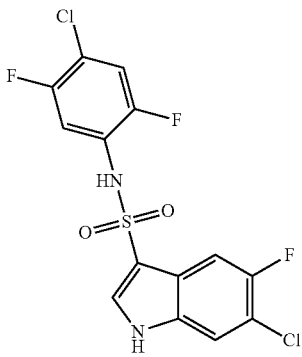 [SMILES: O=S(=O)(Nc1cc(F)c(Cl)cc1F)c1c[nH]c2cc(Cl)c(F)cc12]

Basic LC-MS Method 2 (ES⁻): 393 (M−H)⁻, 95% purity.

$^1$H NMR (400 MHz, DMSO-d$_6$) δ 7.37 (dd, J=10.51, 7.09 Hz, 1H) 7.56 (dd, J=10.27, 6.85 Hz, 1H) 7.68 (d, J=6.36 Hz, 1H) 7.73 (d, J=10.27 Hz, 1H) 8.13 (d, J=2.93 Hz, 1H) 10.50 (s, 1H) 12.26 (brs, 1H).

338

6-chloro-N-(3,5-dimethoxypyridin-2-yl)-1H-indole-3-sulfonamide I-264

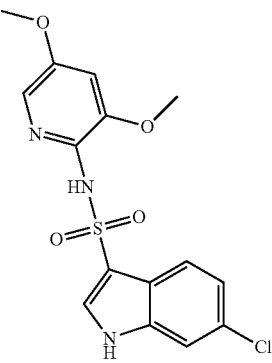 [SMILES: COc1cnc(NS(=O)(=O)c2c[nH]c3cc(Cl)ccc23)c(OC)c1]

Basic LC-MS Method 2 (ES⁺): 368 (M+H)⁺, 95% purity.

$^1$H NMR (400 MHz, DMSO-d$_6$) δ 3.66 (s, 3H) 3.75 (s, 3H) 6.94 (d, J=2.45 Hz, 1H) 7.14-7.24 (m, 1H) 7.46-7.51 (m, 2H) 7.85-7.89 (m, 1H) 7.95 (s, 1H) 9.64 (brs, 1H) 11.95 (brs, 1H).

6-chloro-N-(6-fluoro-3-oxo-2,3-dihydro-1H-isoindol-5-yl)-1H-indole-3-sulfonamide I-265

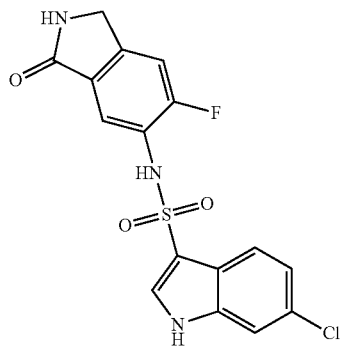 [SMILES: O=C1NCc2cc(F)c(NS(=O)(=O)c3c[nH]c4cc(Cl)ccc34)cc21]

Basic LC-MS Method 2 (ES⁺): 380 (M+H)⁺, 98% purity.

$^1$H NMR (400 MHz, DMSO-d$_6$) δ 4.25 (s, 2H) 7.21 (dd, J=8.80, 1.96 Hz, 1H) 7.33 (d, J=9.78 Hz, 1H) 7.49-7.53 (m, 2H) 7.77 (d, J=8.80 Hz, 1H) 7.89 (d, J=2.93 Hz, 1H) 8.59 (s, 1H) 10.21 (s, 1H) 12.07 (d, J=1.96 Hz, 1H).

N-(4-cyano-5-fluoro-2-methoxyphenyl)-1H-benzo[g]indole-3-sulfonamide I-289

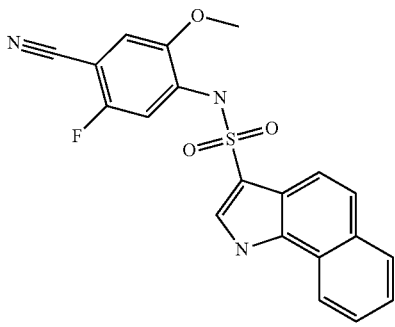 [SMILES: COc1cc(C#N)c(F)cc1NS(=O)(=O)c1c[nH]c2c1ccc1ccccc12]

Neutral LCMS Method 3 (ES⁺): 396.4 (M+H)⁺, 95.0% purity.
$^1$H NMR (600 MHz, DMSO-$d_6$) δ: 12.99 (s, 1H), 10.27 (s, 1H), 8.39 (dd, J=8.3, 1.2 Hz, 1H), 8.30 (d, J=3.0 Hz, 1H), 8.12-7.94 (m, 2H), 7.66 (d, J=8.7 Hz, 1H), 7.62-7.60 (m, 1H), 7.51-7.49 (m, 1H), 7.40 (d, J=11.2 Hz, 1H), 7.34 (d, J=5.9 Hz, 1H), 3.65 (s, 3H).

N-(5-chloro-3,6-difluoropyridin-2-yl)-1H-benzo[g]indole-3-sulfonamide I-304

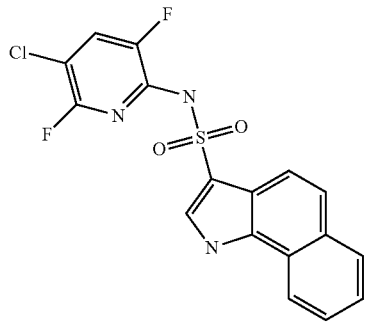 [SMILES: O=S(=O)(Nc1nc(F)c(Cl)cc1F)c1c[nH]c2c1ccc1ccccc12]

Basic LCMS Method 1 (ES⁺): 394 (M+H)⁺, 100% purity.
$^1$H NMR (400 MHz, DMSO-$d_6$) δ 13.01 (s, 1H), 11.48 (s, 1H), 8.42 (dd, J=8.2, 1.0 Hz, 1H), 8.18 (d, J=3.2 Hz, 2H), 8.00 (dd, J=8.5, 6.5 Hz, 2H), 7.68 (d, J=8.8 Hz, 1H), 7.57 (dddd, J=54.0, 8.2, 6.9, 1.2 Hz, 2H).

N-(4-bromo-2,5-difluorophenyl)-1H-pyrrolo[3,2-h]quinoline-3-sulfonamide I-305

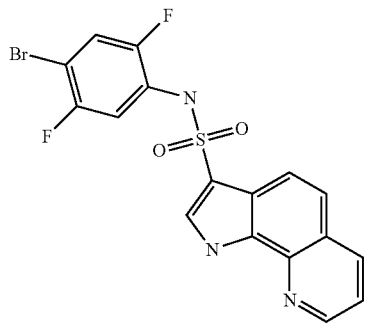 [SMILES: O=S(=O)(Nc1cc(F)c(Br)cc1F)c1c[nH]c2c1ccc1cccnc12]

Basic LCMS Method 1 (ES⁺): 438 (M+H)⁺, 95% purity.
$^1$H NMR (400 MHz, DMSO-$d_6$) δ 13.23 (s, 1H), 10.51 (s, 1H), 8.92 (dd, J=4.4, 1.7 Hz, 1H), 8.44 (dd, J=8.2, 1.7 Hz, 1H), 8.04-7.91 (m, 2H), 7.69 (d, J=8.7 Hz, 1H), 7.57 (dt, J=10.4, 5.2 Hz, 2H), 7.36 (dd, J=10.0, 6.8 Hz, 1H).

N-(4-ethynyl-2-fluorophenyl)-1H-pyrrolo[3,2-h]quinoline-3-sulfonamide I-306

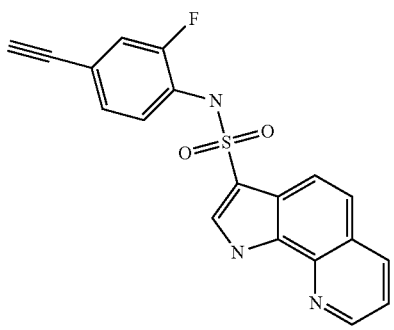 [SMILES: C#Cc1ccc(NS(=O)(=O)c2c[nH]c3c2ccc2cccnc23)c(F)c1]

Basic LCMS Method 1 (ES⁺): 366 (M+H)⁺, 97% purity.

6-chloro-N-(5-chloro-3-fluoro-6-methoxypyridin-2-yl)-7-methoxy-1H-indole-3-sulfonamide I-309

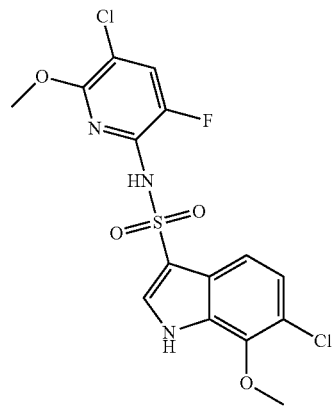 [SMILES: COc1nc(NS(=O)(=O)c2c[nH]c3c(OC)c(Cl)ccc23)c(F)cc1Cl]

Basic LC-MS Method 2 (ES⁺): 420 (M+H)⁺, 99% purity.
$^1$H NMR (400 MHz, DMSO-$d_6$) δ 3.60 (s, 3H) 3.90 (s, 3H) 7.19 (d, J=8.80 Hz, 1H) 7.58 (d, J=8.80 Hz, 1H) 7.81 (brs, 1H) 8.02 (s, 1H) 11.12 (brs, 1H) 12.37 (brs, 1H).

6-chloro-N-(4-cyanophenyl)-1-benzothiophene-3-sulfonamide I-311

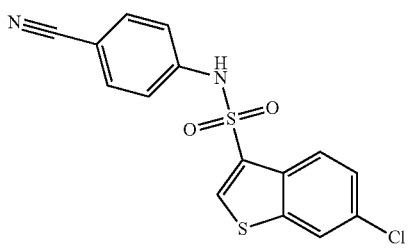 [SMILES: N#Cc1ccc(NS(=O)(=O)c2csc3cc(Cl)ccc23)cc1]

Basic LC-MS Method 2 (ES⁻): 347 (M−H)⁻, 99% purity.
$^1$H NMR (400 MHz, DMSO-$d_6$) δ 7.21 (d, J=8.31 Hz, 2H) 7.62 (dd, J=8.80, 1.96 Hz, 1H) 7.66 (d, J=8.80 Hz, 2H) 8.16 (d, J=8.80 Hz, 1H) 8.29 (d, J=1.96 Hz, 1H) 8.78 (s, 1H) 11.40 (s, 1H).

341

6-chloro-N-(4-chloro-2,5-difluorophenyl)-1-benzo-
thiophene-3-sulfonamide I-312

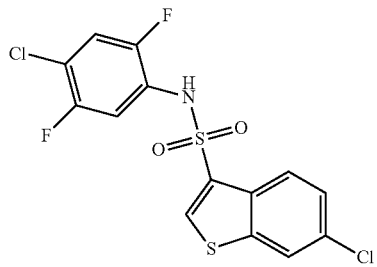 [SMILES: O=S(=O)(Nc1cc(F)c(Cl)cc1F)c1csc2cc(Cl)ccc12]

Basic LC-MS Method 2 (ES⁻): 392 (M−H)⁻, 99% purity.
$^1$H NMR (400 MHz, DMSO-$d_6$) δ 7.34-7.39 (m, 1H) 7.56-7.63 (m, 2H) 8.15 (d, J=8.80 Hz, 1H) 8.31 (d, J=1.96 Hz, 1H) 8.58 (s, 1H) 10.91 (br s, 1H).

6-chloro-N-[4-(cyanomethoxy)-2,5-difluorophenyl]-
1-benzothiophene-3-sulfonamide I-313

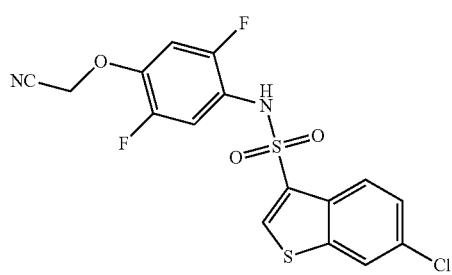 [SMILES: N#CCOc1cc(F)c(NS(=O)(=O)c2csc3cc(Cl)ccc23)cc1F]

Basic LC-MS Method 2 (ES⁻): 413 (M−H)⁻, 98% purity.
$^1$H NMR (400 MHz, DMSO-$d_6$) δ 5.20 (s, 2H) 7.17-7.30 (m, 2H) 7.59 (dd, J=8.80, 1.96 Hz, 1H) 8.06 (d, J=8.80 Hz, 1H) 8.31 (d, J=1.96 Hz, 1H) 8.46 (s, 1H) 10.54 (s, 1H).

6-chloro-N-(5-chloro-3-fluoro-6-methoxypyridin-2-
yl)-1-benzothiophene-3-sulfonamide I-314

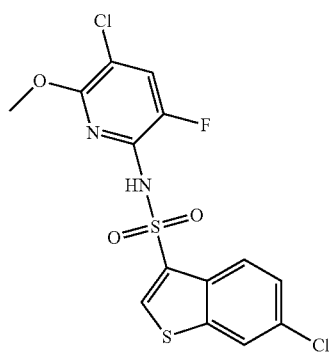

Basic LC-MS Method 2 (ES⁻): 405 (M−H)⁻, 99% purity.
$^1$H NMR (400 MHz, DMSO-$d_6$) δ 3.57 (s, 3H) 7.61 (d, J=4.40 Hz, 1H) 8.00 (d, J=5.38 Hz, 1H) 8.20-8.22 (m, 1H) 8.31 (s, 1H) 8.77 (s, 1H) 11.64 (br s, 1H).

342

6-chloro-N-[5-(cyanomethyl)-3-fluoro-6-methoxy-
pyridin-2-yl]-1-benzothiophene-3-sulfonamide I-315

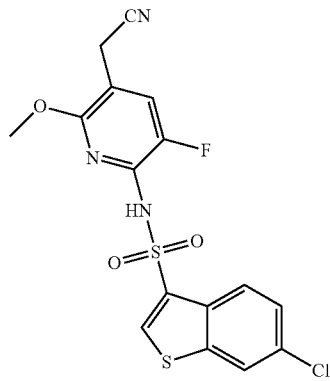 [SMILES: COc1nc(NS(=O)(=O)c2csc3cc(Cl)ccc23)c(F)cc1CC#N]

Basic LC-MS Method 2 (ES⁺): 412 (M+H)⁺, 99% purity.
$^1$H NMR (400 MHz, DMSO-$d_6$) δ 3.56 (s, 3H) 3.71 (s, 2H) 7.60 (dd, J=8.80, 1.96 Hz, 1H) 7.68 (d, J=9.29 Hz, 1H) 8.23 (d, J=8.31 Hz, 1H) 8.31 (d, J=1.96 Hz, 1H) 8.77 (s, 1H) 11.57 (brs, 1H).

6-chloro-N-(5-chloro-3-fluoro-6-methoxypyridin-2-
yl)-7-fluoro-1H-indole-3-sulfonamide I-319

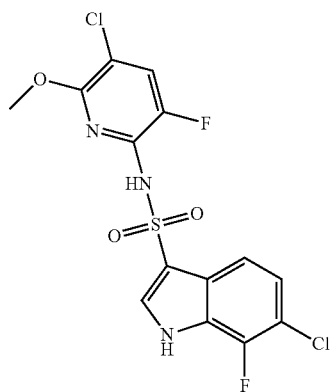 [SMILES: COc1nc(NS(=O)(=O)c2c[nH]c3c(F)c(Cl)ccc23)c(F)cc1Cl]

Basic LC-MS Method 2 (ES⁺): 408 (M+H)⁺, 99% purity.
$^1$H NMR (400 MHz, DMSO-$d_6$) δ 3.62 (s, 3H) 7.30-7.34 (m, 1H) 7.67 (d, J=8.80 Hz, 1H) 7.94 (d, J=8.80 Hz, 1H) 8.22 (d, J=1.47 Hz, 1H) 11.19 (s, 1H) 12.85 (br s, 1H)

343
6-bromo-N-[5-(cyanomethyl)-3-fluoro-6-methoxy-pyridin-2-yl]-1H-indole-3-sulfonamide I-320

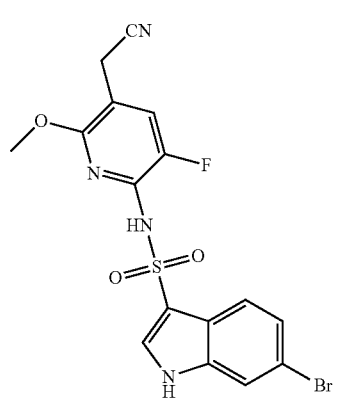 [SMILES: COc1nc(NS(=O)(=O)c2c[nH]c3cc(Br)ccc23)c(F)cc1CC#N]

Basic LC-MS Method 2 (ES⁻): 438 (M−H)⁻, 97% purity.

¹H NMR (400 MHz, DMSO-d$_6$) δ 3.62 (s, 3H) 3.70 (s, 2H) 7.34 (d, J=8.31 Hz, 1H) 7.62 (d, J=9.78 Hz, 1H) 7.68 (s, 1H) 7.80 (d, J=8.31 Hz, 1H) 8.14 (d, J=2.45 Hz, 1H) 11.03 (s, 1H) 12.09 (br s, 1H)

7-bromo-6-chloro-N-(5-chloro-3-fluoro-6-methoxy-pyridin-2-yl)-1H-indole-3-sulfonamide I-321

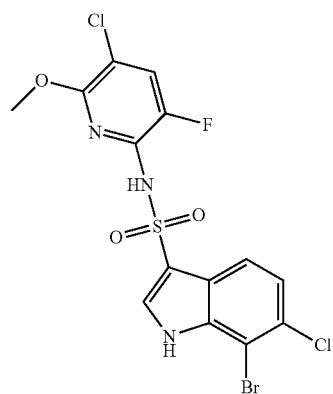

Basic LC-MS Method 2 (ES⁺): 468 (M+H)⁺, 98% purity.

¹H NMR (400 MHz, DMSO-d$_6$) δ 3.63 (s, 3H) 7.42 (d, J=8.31 Hz, 1H) 7.85 (d, J=8.31 Hz, 1H) 7.95 (d, J=8.80 Hz, 1H) 8.14 (d, J=2.93 Hz, 1H) 11.20 (s, 1H) 12.48 (br s, 1H)

344
7-bromo-6-chloro-N-[5-(cyanomethyl)-3-fluoro-6-methoxypyridin-2-yl]-1H-indole-3-sulfonamide I-322

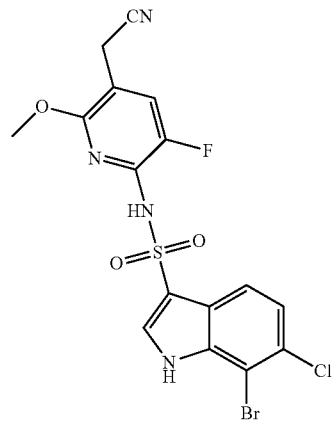 [SMILES: COc1nc(NS(=O)(=O)c2c[nH]c3c(Br)c(Cl)ccc23)c(F)cc1CC#N]

Basic LC-MS Method 2 (ES⁺): 473 (M+H)⁺, 98% purity.

¹H NMR (400 MHz, DMSO-d$_6$) δ 3.63 (s, 3H) 3.70 (s, 2H) 7.42 (d, J=8.31 Hz, 1H) 7.62 (d, J=9.78 Hz, 1H) 7.86 (d, J=8.80 Hz, 1H) 8.13 (br s, 1H) 11.12 (s, 1H) 12.44 (br s, 1H)

6-bromo-N-[3,6-difluoro-5-(3-methoxypropyl)pyridin-2-yl]-1H-indole-3-sulfonamide I-323

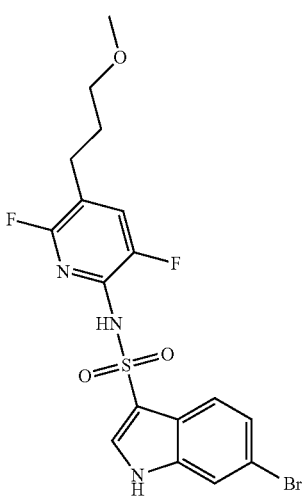

Basic LC-MS Method 2 (ES⁻): 458 (M−H)⁻, 96% purity.

¹H NMR (400 MHz, Methanol-d$_4$) δ 1.72-1.83 (m, 2H) 2.56 (t, J=7.65 Hz, 2H) 3.15-3.28 (m, 5H) 7.31 (dd, J=8.53, 1.76 Hz, 1H) 7.45 (dd, J=9.54, 7.78 Hz, 1H) 7.64 (d, J=1.76 Hz, 1H) 7.85 (d, J=8.78 Hz, 1H) 8.03 (s, 1H).

345

5-bromo-6-chloro-N-[5-(cyanomethyl)-3-fluoro-6-methoxypyridin-2-yl]-1H-indole-3-sulfonamide I-324

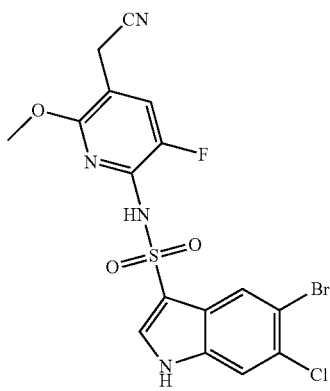 [SMILES: COc1nc(NS(=O)(=O)c2c[nH]c3cc(Cl)c(Br)cc23)c(F)cc1CC#N]

Basic LC-MS Method 2 (ES+): 473 (M+H)+, 98% purity.
¹H NMR (400 MHz, DMSO-d₆) δ 3.65 (s, 3H) 3.71 (s, 2H) 7.64 (d, J=9.78 Hz, 1H) 7.75 (s, 1H) 8.21 (d, J=1.96 Hz, 1H) 8.25 (s, 1H) 11.03 (br s, 1H) 12.22 (br s, 1H).

6-bromo-N-{3,6-difluoro-5-[(1E)-3-methoxyprop-1-en-1-yl]pyridin-2-yl}-1H-indole-3-sulfonamide I-325

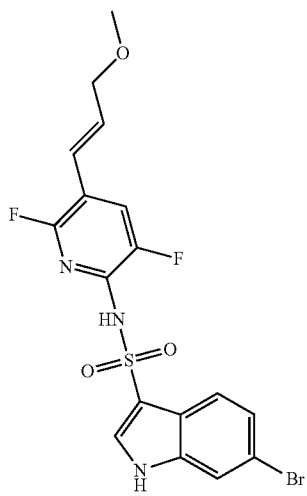 [SMILES: COC/C=C/c1cc(F)c(NS(=O)(=O)c2c[nH]c3cc(Br)ccc23)nc1F]

Basic LC-MS Method 2 (ES+): 458 (M+H)+, 99% purity.
¹H NMR (400 MHz, DMSO-d₆) δ 3.25 (s, 3H) 4.01 (d, J=2.93 Hz, 2H) 6.41 (s, 2H) 7.34 (d, J=8.80 Hz, 1H) 7.67 (s, 1H) 7.83 (d, J=8.80 Hz, 1H) 8.03-8.13 (m, 2H) 11.29 (br s, 1H) 12.14 (brs, 1H)

346

6-bromo-N-(5-chloro-3-fluoropyridin-2-yl)-7-methyl-1H-indole-3-sulfonamide I-326

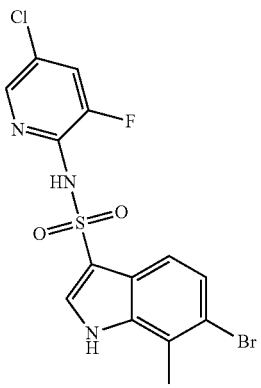 [SMILES: Cc1c(Br)ccc2c(S(=O)(=O)Nc3ncc(Cl)cc3F)c[nH]c12]

Basic LC-MS Method 1 (ES+): 418 (M+H)+, 90% purity.

6-chloro-N-(6-fluoro-1-methyl-3-oxo-1,3-dihydro-2-benzofuran-5-yl)-1H-indole-3-sulfonamide I-327

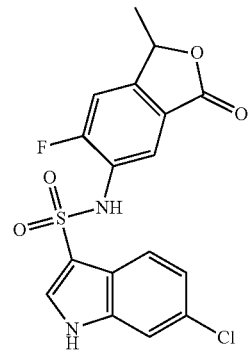 [SMILES: CC1OC(=O)c2cc(NS(=O)(=O)c3c[nH]c4cc(Cl)ccc34)c(F)cc21]

Basic LC-MS Method 2 (ES+): 395 (M+H)+, 97% purity.
¹H NMR (400 MHz, DMSO-d₆) δ 1.48 (d, J=6.85 Hz, 3H) 5.54-5.61 (m, 1H) 7.22 (dd, J=8.80, 1.96 Hz, 1H) 7.51-7.55 (m, 2H) 7.65 (d, J=6.85 Hz, 1H) 7.73 (d, J=8.80 Hz, 1H) 7.99 (d, J=2.93 Hz, 1H) 10.43 (s, 1H) 12.12 (brs, 1H).

N-(5-chloro-3-fluoro-6-methoxypyridin-2-yl)-1H-pyrrolo[3,2-h]quinoline-3-sulfonamide I-328

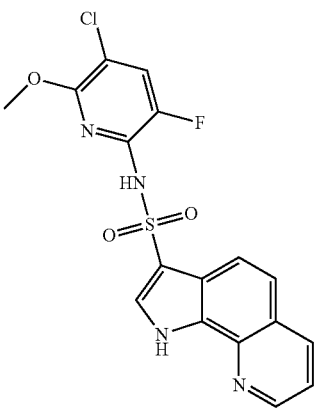 [SMILES: COc1nc(NS(=O)(=O)c2c[nH]c3c2ccc2cccnc23)c(F)cc1Cl]

Basic LC-MS Method 1 (ES−): 405 (M−H)−, 97% purity.
¹H NMR (400 MHz, DMSO-d₆) δ 13.21 (s, 1H), 11.17 (s, 1H), 8.93 (dd, J=4.4, 1.6 Hz, 1H), 8.45 (dd, J=8.3, 1.6 Hz, 1H), 8.14-8.02 (m, 2H), 7.93 (d, J=8.5 Hz, 1H), 7.71 (d, J=8.7 Hz, 1H), 7.58 (dd, J=8.2, 4.4 Hz, 1H), 3.64 (s, 3H).

347

N-(5-chloro-3-fluoro-6-methoxypyridin-2-yl)-1H-benzo[g]indole-3-sulfonamide I-329

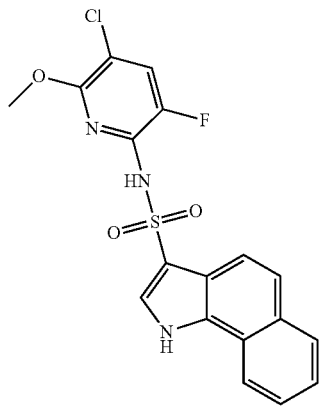 [SMILES: COc1nc(NS(=O)(=O)c2c[nH]c3c2ccc2ccccc23)c(F)cc1Cl]

Basic LC-MS Method 1 (ES+): 406 (M+H)+, 96% purity.
¹H NMR (400 MHz, DMSO-d$_6$) δ 12.95 (s, 1H), 11.13 (s, 1H), 8.43 (d, J=8.3 Hz, 1H), 8.21 (s, 1H), 8.07-7.79 (m, 3H), 7.74-7.36 (m, 3H), 3.67 (s, 3H).

6-nitro-N-(4-cyano-2-fluorophenyl)-1H-indole-3-sulfonamide I-334

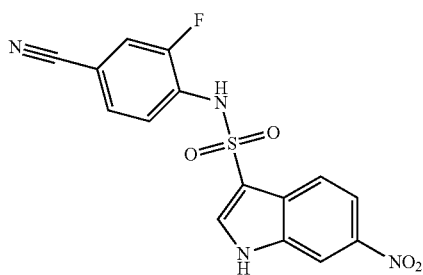 [SMILES: N#Cc1ccc(NS(=O)(=O)c2c[nH]c3cc([N+](=O)[O-])ccc23)c(F)c1]

Basic LC-MS Method 2 (ES−): 359 (M−H)−, 98% purity.
¹H NMR (400 MHz, DMSO-d$_6$) δ 7.58 (brs, 2H) 7.76 (d, J=10.27 Hz, 1H) 7.95-8.03 (m, 1H) 8.06-8.15 (m, 1H) 8.38-8.44 (m, 2H) 10.94 (brs, 1H) 12.73 (brs, 1H).

6-chloro-N-(5-chloro-3-fluoro-6-methoxypyridin-2-yl)-5-fluoro-1H-indole-3-sulfonamide I-339

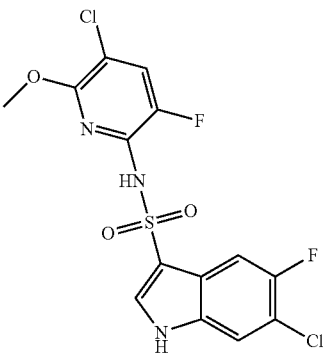 [SMILES: COc1nc(NS(=O)(=O)c2c[nH]c3cc(Cl)c(F)cc23)c(F)cc1Cl]

Basic LC-MS Method 2 (ES−): 406 (M−H)−, 98% purity.
¹H NMR (400 MHz, DMSO-d$_6$) δ 3.64 (s, 3H) 7.69 (d, J=6.36 Hz, 1H) 7.78 (d, J=9.78 Hz, 1H) 7.94 (d, J=8.80 Hz, 1H) 8.21 (d, J=2.93 Hz, 1H) 11.07 (s, 1H) 12.19 (br s, 1H)

348

6-chloro-N-(5-chloro-3-fluoro-6-methoxypyridin-2-yl)-5,7-difluoro-1H-indole-3-sulfonamide I-340

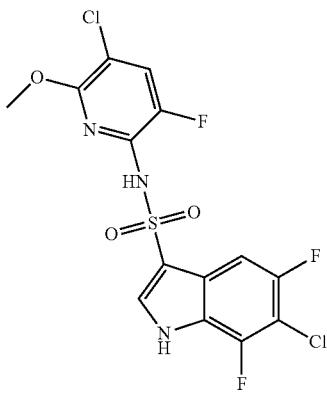 [SMILES: COc1nc(NS(=O)(=O)c2c[nH]c3c(F)c(Cl)c(F)cc23)c(F)cc1Cl]

Basic LC-MS Method 2 (ES+): 426 (M+H)+, 99% purity.
¹H NMR (400 MHz, DMSO-d$_6$) δ 3.65 (s, 3H) 7.70 (d, J=9.78 Hz, 1H) 7.97 (d, J=9.29 Hz, 1H) 8.33 (d, J=1.96 Hz, 1H) 11.17 (s, 1H) 13.00 (br s, 1H)

7-bromo-6-chloro-N-(4-cyano-2-fluorophenyl)-1H-indole-3-sulfonamide I-341

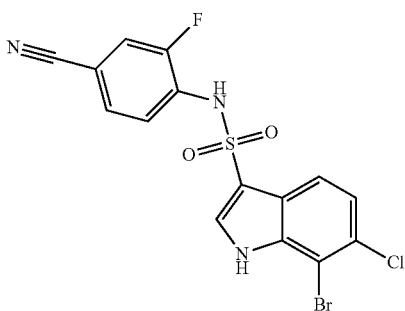 [SMILES: N#Cc1ccc(NS(=O)(=O)c2c[nH]c3c(Br)c(Cl)ccc23)c(F)c1]

Basic LC-MS Method 2 (ES−): 426 (M−H)−, 97% purity.
¹H NMR (400 MHz, DMSO-d$_6$) δ 7.44 (d, J=8.37 Hz, 1H) 7.56-7.60 (m, 2H) 7.74-7.79 (m, 1H) 7.84 (d, J=8.37 Hz, 1H) 8.14 (d, J=2.95 Hz, 1H) 10.89 (br s, 1H) 12.58 (d, J=1.97 Hz, 1H).

6-chloro-N-[4-(cyanomethoxy)-2,5-difluorophenyl]-1-benzofuran-3-sulfonamide I-342

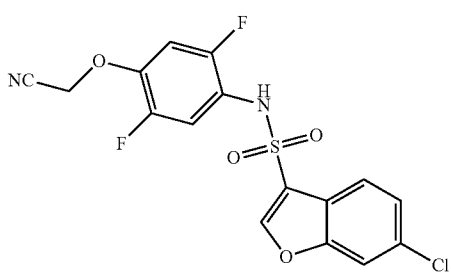

Basic LC-MS Method 2 (ES−): 397 (M−H)−. 99% purity.
¹H NMR (400 MHz, DMSO-d$_6$) δ 5.21 (s, 2H) 7.26-7.33 (m, 2H) 7.49 (dd, J=8.31, 1.47 Hz, 1H) 7.67 (d, J=8.31 Hz, 1H) 7.97 (d, J=1.47 Hz, 1H) 8.66 (s, 1H) 10.63 (s, 1H).

5-bromo-6-chloro-N-(4-cyano-2-fluorophenyl)-1H-indole-3-sulfonamide I-343

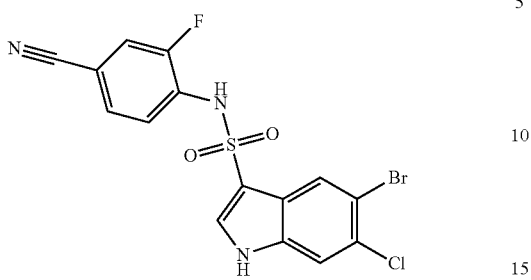

Basic LC-MS Method 2 (ES⁻): 426 (M−H)⁻, 97% purity.
$^1$H NMR (400 MHz, DMSO-d$_6$) δ 7.55-7.60 (m, 2H) 7.71-7.83 (m, 2H) 8.17-8.21 (m, 2H) 10.82 (s, 1H) 12.35 (br s, 1H).

6-chloro-N-[3-methoxy-5-(trifluoromethyl)pyridin-2-yl]-1H-indole-3-sulfonamide I-344

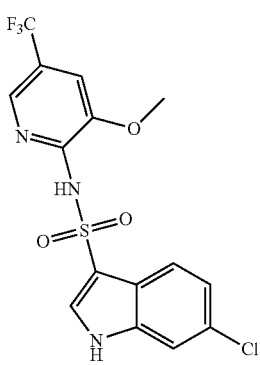 [SMILES: COc1cc(C(F)(F)F)cnc1NS(=O)(=O)c1c[nH]c2cc(Cl)ccc12]

Basic LC-MS Method 2 (ES⁺): 406 (M+H)⁺, 96% purity.
$^1$H NMR (400 MHz, DMSO-d$_6$) δ 3.87 (s, 3H) 7.23 (d, J=8.31 Hz, 1H) 7.51 (s, 2H) 7.98 (d, J=8.31 Hz, 1H) 8.06 (s, 1H) 8.18 (s, 1H) 10.67 (brs, 1H) 12.13 (brs, 1H).

6-chloro-N-(3,5-difluoro-6-methoxypyridin-2-yl)-1H-indole-3-sulfonamide I-345

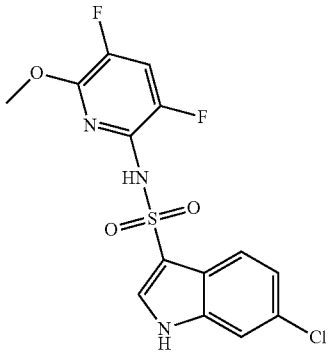

Basic LC-MS Method 2 (ES⁺): 374 (M+H)⁺, 99% purity.
$^1$H NMR (400 MHz, DMSO-d$_6$) δ 3.55 (s, 3H) 7.19 (dd, J=8.80, 1.96 Hz, 1H) 7.51 (d, J=1.96 Hz, 1H) 7.76 (d, J=8.31 Hz, 1H) 7.86 (t, J=9.29 Hz, 1H) 8.06 (d, J=2.93 Hz, 1H) 10.73 (s, 1H) 12.05 (br s, 1H).

6-chloro-N-(5-chloro-3-fluoro-6-methoxypyridin-2-yl)-1-benzofuran-3-sulfonamide I-346

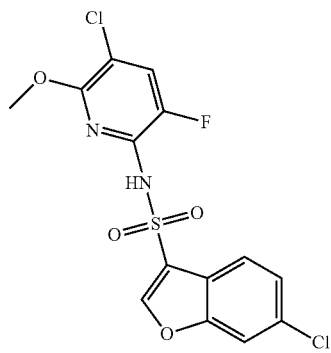 [SMILES: COc1nc(NS(=O)(=O)c2coc3cc(Cl)ccc23)c(F)cc1Cl]

Basic LC-MS Method 2 (ES⁻): 389 (M−H)⁻, 99% purity.
$^1$H NMR (400 MHz, DMSO-d$_6$) δ 3.59 (s, 3H) 7.52 (dd, J=8.56, 1.71 Hz, 1H) 7.89 (d, J=8.31 Hz, 1H) 7.99 (d, J=1.47 Hz, 1H) 8.03 (d, J=8.80 Hz, 1H) 8.91 (s, 1H) 11.66 (br s, 1H).

6-bromo-7-chloro-N-(4-chloro-2,5-difluorophenyl)-1H-indole-3-sulfonamide I-347

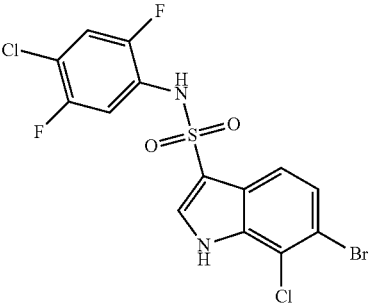 [SMILES: O=S(=O)(Nc1cc(F)c(Cl)cc1F)c1c[nH]c2c(Cl)c(Br)ccc12]

Basic LC-MS Method 2 (ES⁺): 455 (M+H)⁺, 98% purity.
$^1$H NMR (400 MHz, DMSO-d$_6$) δ 7.36-7.40 (m, 1H) 7.53-7.58 (m, 2H) 7.69 (d, J=8.8 Hz, 1H) 8.09 (d, J=3.2 Hz, 1H) 10.57 (s, 1H), 12.69 (brs, 1H).

351

6-chloro-N-(3,6-difluoro-5-methylpyridin-2-yl)-1H-indole-3-sulfonamide I-348

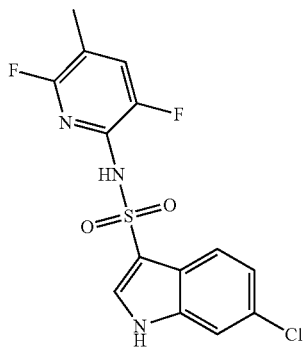 [SMILES: Cc1cc(F)c(NS(=O)(=O)c2c[nH]c3cc(Cl)ccc23)nc1F]

Basic LC-MS Method 2 (ES+): 358 (M+H)+, 99% purity.

$^1$H NMR (400 MHz, DMSO-d$_6$) δ 2.08 (s, 3H) 7.22 (dd, J=8.56, 1.71 Hz, 1H) 7.53 (d, J=1.96 Hz, 1H) 7.72 (t, J=8.80 Hz, 1H) 7.84 (d, J=8.31 Hz, 1H) 8.08 (d, J=2.93 Hz, 1H) 10.98 (s, 1H) 12.13 (brs, 1H).

N-(5-bromo-6-fluoro-3-methoxypyridin-2-yl)-6-chloro-1H-indole-3-sulfonamide I-349

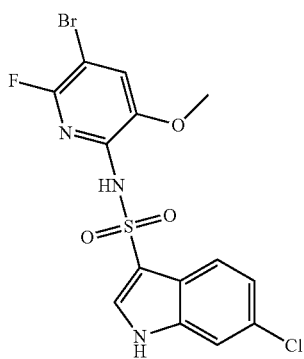 [SMILES: COc1cc(Br)c(F)nc1NS(=O)(=O)c1c[nH]c2cc(Cl)ccc12]

Basic LC-MS Method 2 (ES+): 434 (M+H)+, 97% purity.

$^1$H NMR (400 MHz, DMSO-d$_6$) δ 3.78 (s, 3H) 7.22 (d, J=8.8 Hz, 1H) 7.53 (s, 1H) 7.73 (d, J=7.2 Hz, 1H) 7.94 (d, J=8.8 Hz, 1H) 8.11 (d, J=3.2 Hz, 1H) 10.65 (s, 1H), 12.13 (brs, 1H).

352

6-chloro-N-[5-(cyanomethyl)-6-fluoro-3-methoxypyridin-2-yl]-1H-indole-3-sulfonamide I-350

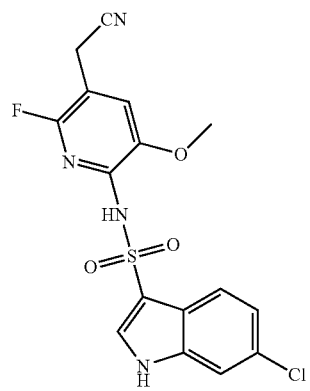 [SMILES: COc1cc(CC#N)c(F)nc1NS(=O)(=O)c1c[nH]c2cc(Cl)ccc12]

Basic LC-MS Method 2 (ES+): 395 (M+H)+, 97% purity.

$^1$H NMR (400 MHz, DMSO-d$_6$) δ 3.76 (s, 3H) 3.87 (s, 2H) 7.21 (dd, J=8.80 Hz, 0.80 Hz, 1H) 7.47 (d, J=8.40 Hz, 1H) 7.52 (d, J=0.80 Hz, 1H) 7.95 (d, J=8.80 Hz, 1H) 8.10 (d, J=2.80 Hz, 1H) 10.55 (s, 1H), 12.12 (brs, 1H).

N-[5-(cyanomethyl)-3-fluoro-6-methoxypyridin-2-yl]-6-nitro-1H-indole-3-sulfonamide I-351

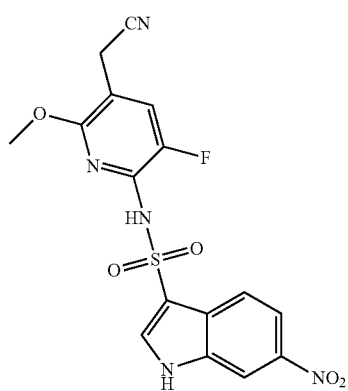 [SMILES: COc1nc(NS(=O)(=O)c2c[nH]c3cc([N+](=O)[O-])ccc23)c(F)cc1CC#N]

Basic LC-MS Method 2 (ES+): 406 (M+H)+, 88% purity.

$^1$H NMR (400 MHz, DMSO-d$_6$) δ 3.60 (s, 3H) 3.70 (s, 2H) 7.64 (d, J=9.78 Hz, 1H) 8.02-8.06 (m, 1H) 8.07-8.11 (m, 1H) 8.42 (d, J=1.96 Hz, 1H) 8.50 (s, 1H) 11.20 (s, 1H) 12.62 (brs, 1H).

353

6-chloro-N-[5-(cyanomethyl)-3-fluoro-6-methoxy-pyridin-2-yl]-7-fluoro-1H-indole-3-sulfonamide I-354

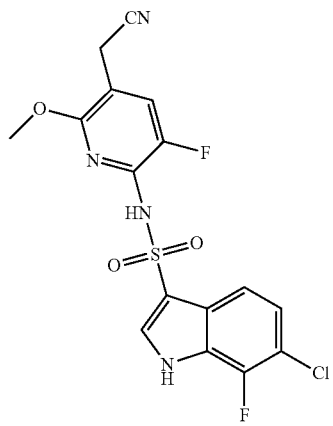 [SMILES: COc1nc(NS(=O)(=O)c2c[nH]c3c(F)c(Cl)ccc23)c(F)cc1CC#N]

Basic LC-MS Method 2 (ES⁺): 413 (M+H)⁺, 99% purity.
¹H NMR (400 MHz, DMSO-d$_6$) δ 3.56 (s, 3H) 3.61 (s, 2H) 7.23-7.27 (m, 1H) 7.55 (d, J=9.84 Hz, 1H) 7.59 (d, J=8.86 Hz, 1H) 8.12 (s, 1H) 11.13 (br s, 1H) 12.85 (br s, 1H)

6-chloro-N-(3,6-difluoro-5-methylpyridin-2-yl)-7-fluoro-1H-indole-3-sulfonamide I-355

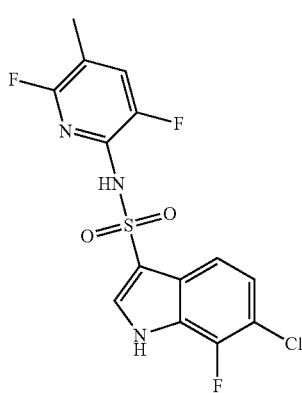 [SMILES: Cc1cc(F)c(NS(=O)(=O)c2c[nH]c3c(F)c(Cl)ccc23)nc1F]

Basic LC-MS Method 2 (ES⁺): 376 (M+H)⁺, 99% purity.
¹H NMR (400 MHz, DMSO-d$_6$) δ 2.09 (s, 3H) 7.32 (dd, J=8.56, 6.60 Hz, 1H) 7.67 (d, J=8.80 Hz, 1H) 7.71-7.77 (m, 1H) 8.13 (s, 1H) 11.07 (br s, 1H) 12.87 (br s, 1H)

354

7-chloro-N-(5-chloro-3-fluoro-6-methoxypyridin-2-yl)-6-methoxy-1H-indole-3-sulfonamide I-356

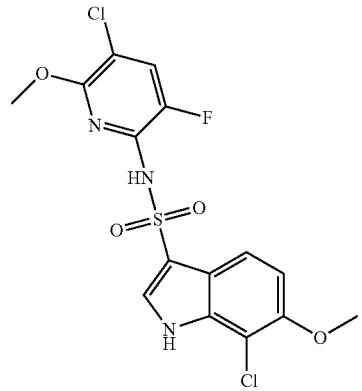

Basic LC-MS Method 2 (ES⁻): 418 (M−H)⁻, 96% purity.
¹H NMR (400 MHz, DMSO-d$_6$) δ 3.62 (s, 3H) 3.85 (s, 3H) 7.09 (d, J=8.80 Hz, 1H) 7.73 (d, J=8.80 Hz, 1H) 7.88 (d, J=9.29 Hz, 1H) 7.95 (s, 1H) 11.12 (br s, 1H) 12.14 (br s, 1H)

7-chloro-N-(5-chloro-3-fluoro-6-methoxypyridin-2-yl)-6-fluoro-1H-indole-3-sulfonamide I-357

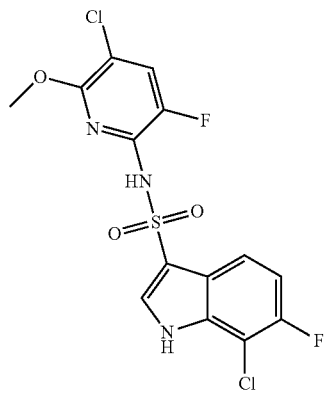 [SMILES: COc1nc(NS(=O)(=O)c2c[nH]c3c(Cl)c(F)ccc23)c(F)cc1Cl]

Basic LC-MS Method 2 (ES⁻): 406 (M−H)⁻, 95% purity.
¹H NMR (400 MHz, DMSO-d$_6$) δ 3.61 (s, 3H) 7.25 (t, J=9.54 Hz, 1H) 7.79 (dd, J=8.80, 4.40 Hz, 1H) 7.91 (d, J=8.80 Hz, 1H) 8.13 (d, J=2.45 Hz, 1H) 11.13 (br s, 1H) 12.61 (br s, 1H)

355
6-chloro-N-(3,5-difluoro-6-methoxypyridin-2-yl)-7-fluoro-1H-indole-3-sulfonamide I-358

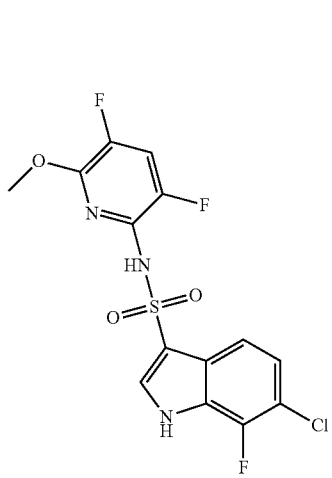 [SMILES: COc1nc(NS(=O)(=O)c2c[nH]c3c(F)c(Cl)ccc23)c(F)cc1F]

Basic LC-MS Method 2 (ES⁻): 390 (M−H)⁻, 99% purity.

$^1$H NMR (400 MHz, DMSO-d$_6$) δ 3.58 (s, 3H) 7.30 (t, J=7.34 Hz, 1H) 7.61 (d, J=8.31 Hz, 1H) 7.90 (t, J=9.29 Hz, 1H) 8.16 (s, 1H) 10.84 (s, 1H) 12.82 (br s, 1H)

N-[4-(cyanomethoxy)-2,5-difluorophenyl]-1H-pyrrolo[3,2-h]quinoline-3-sulfonamide I-360

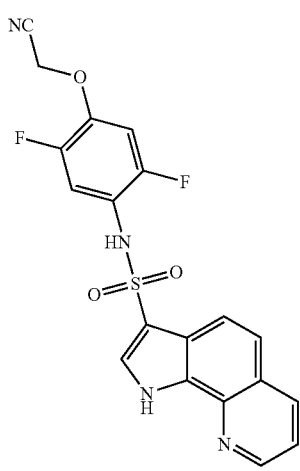

Neutral LCMS Method 3 (ES⁺): 415 (M+H)⁺, 98% purity.

$^1$H NMR (400 MHz, DMSO-d$_6$) δ 13.19 (s, 1H), 10.09 (s, 1H), 8.91 (d, J=3.0 Hz, 1H), 8.42 (dd, J=8.5, 1.7 Hz, 1H), 7.89-7.82 (m, 2H), 7.66 (d, J=8.7 Hz, 1H), 7.57 (dd, J=8.2, 4.3 Hz, 1H), 7.22 (td, J=11.6, 7.3 Hz, 2H), 5.16 (s, 2H).

356
N-[4-(cyanomethyl)-2,5-difluorophenyl]-1H-pyrrolo[3,2-h]quinoline-3-sulfonamide I-361

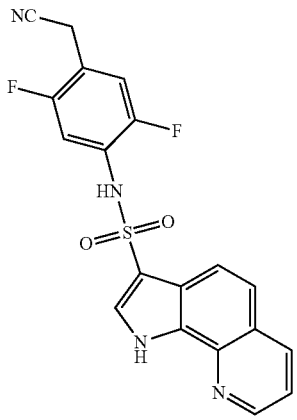 [SMILES: N#CCc1cc(F)c(NS(=O)(=O)c2c[nH]c3c2ccc2cccnc23)cc1F]

Neutral LCMS Method 3 (ES⁺): 399 (M+H)⁺, 96% purity.

$^1$H NMR (400 MHz, DMSO-d$_6$) δ 13.24 (s, 1H), 10.49 (s, 1H), 8.91 (dd, J=4.3, 1.7 Hz, 1H), 8.43 (dd, J=8.2, 1.7 Hz, 1H), 8.02-7.95 (m, 2H), 7.69 (d, J=8.7 Hz, 1H), 7.57 (dd, J=8.2, 4.3 Hz, 1H), 7.30 (dd, J=10.8, 6.5 Hz, 1H), 7.20 (dd, J=10.4, 6.7 Hz, 1H), 3.91 (s, 2H).

N-[4-(2-cyanoethyl)-2,5-difluorophenyl]-1H-pyrrolo[3,2-h]quinoline-3-sulfonamide I-362

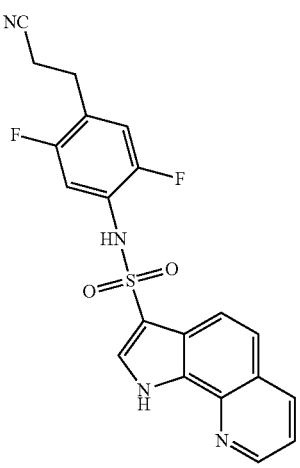 [SMILES: N#CCCc1cc(F)c(NS(=O)(=O)c2c[nH]c3c2ccc2cccnc23)cc1F]

Neutral LCMS Method 3 (ES⁺): 413 (M+H)⁺, 99% purity.

$^1$H NMR (400 MHz, DMSO-d$_6$) δ 13.22 (s, 1H), 10.33 (s, 1H), 8.91 (dd, J=4.3, 1.6 Hz, 1H), 8.43 (dd, J=8.2, 1.7 Hz, 1H), 7.95 (s, 1H), 7.92 (d, J=8.7 Hz, 1H), 7.67 (d, J=8.7 Hz, 1H), 7.57 (dd, J=8.2, 4.3 Hz, 1H), 7.17 (ddd, J=17.9, 10.7, 6.6 Hz, 2H), 2.79 (t, J=7.2 Hz, 2H), 2.76-2.71 (m, 2H).

357

6-chloro-N-[3,6-difluoro-5-(2-fluoroethoxy)pyridin-2-yl]-1H-indole-3-sulfonamide I-364

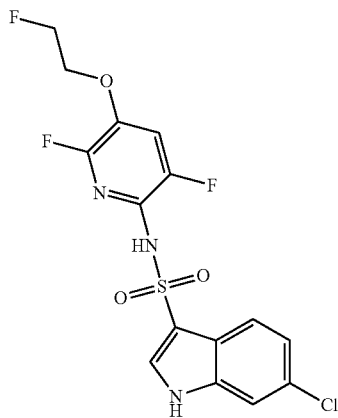 [SMILES: O=S(=O)(Nc1nc(F)c(OCCF)cc1F)c1c[nH]c2cc(Cl)ccc12]

Basic LC-MS Method 2 (ES+): 406 (M+H)+, 97% purity.

$^1$H NMR (400 MHz, DMSO-d$_6$) δ 4.24-4.29 (m, 1H) 4.31-4.36 (m, 1H) 4.60-4.65 (m, 1H) 4.72-4.77 (m, 1H) 7.18 (dd, J=8.61, 1.72 Hz, 1H) 7.51 (d, J=1.48 Hz, 1H) 7.70 (d, J=8.86 Hz, 1H) 7.78 (dd, J=9.84, 8.37 Hz, 1H) 7.95 (d, J=2.95 Hz, 1H) 10.49 (s, 1H) 12.06 (brs, 1H).

6-chloro-N-[3,6-difluoro-5-(2-methoxyethoxy)pyridin-2-yl]-1H-indole-3-sulfonamide I-365

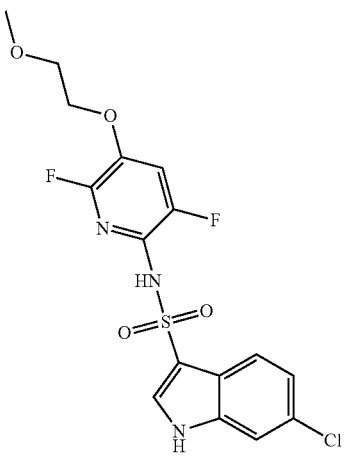 [SMILES: COCCOc1cc(F)c(NS(=O)(=O)c2c[nH]c3cc(Cl)ccc23)nc1F]

Basic LC-MS Method 2 (ES+): 418 (M+H)+, 99% purity.

$^1$H NMR (400 MHz, DMSO-d$_6$) δ 3.24 (s, 3H) 3.58-3.60 (m, 2H) 4.12-4.17 (m, 2H) 7.17 (dd, J=8.31, 1.96 Hz, 1H) 7.50 (d, J=1.96 Hz, 1H) 7.68 (d, J=8.80 Hz, 1H) 7.71-7.77 (m, 1H) 7.93 (d, J=2.45 Hz, 1H) 10.41 (brs, 1H) 12.05 (brs, 1H).

358

6-chloro-7-(difluoromethoxy)-N-(3,5-difluoro-6-methoxypyridin-2-yl)-1H-indole-3-sulfonamide I-366

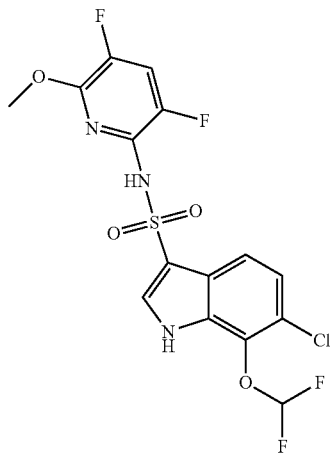 [SMILES: COc1nc(NS(=O)(=O)c2c[nH]c3c(OC(F)F)c(Cl)ccc23)c(F)cc1F]

Basic LC-MS Method 2 (ES+): 440 (M+H)+, 99% purity.

$^1$H NMR (400 MHz, DMSO-d$_6$) δ 3.55 (s, 3H) 7.21 (t, J=73.2 Hz, 1H) 7.35 (d, J=9.20 Hz, 1H) 7.73 (d, J=8.40 Hz, 1H) 7.90 (t, J=8.80 Hz, 1H) 8.09 (s, 1H) 10.81 (s, 1H), 12.52 (brs, 1H).

6-chloro-N-(3,6-difluoro-5-methylpyridin-2-yl)-7-(trifluoromethyl)-1H-indole-3-sulfonamide I-367

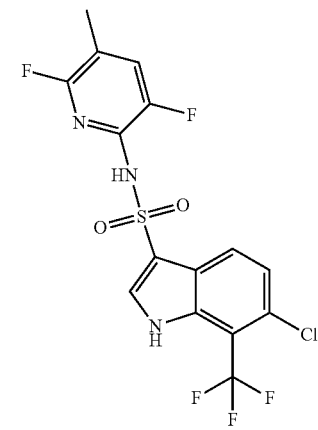 [SMILES: Cc1cc(F)c(NS(=O)(=O)c2c[nH]c3c(C(F)(F)F)c(Cl)ccc23)nc1F]

Basic LC-MS Method 2 (ES+): 426 (M+H)+, 98% purity.

$^1$H NMR (400 MHz, DMSO-d$_6$) δ 2.09 (s, 3H) 7.53 (d, J=8.40 Hz, 1H) 7.69-8.02 (m, 1H) 8.07 (s, 1H) 8.16 (d, J=8.40 Hz, 1H) 11.15 (brs, 1H) 12.25 (brs, 1H).

D.5. Method F. Synthesis of N-(2,1,3-benzoxadiazol-5-yl)-6-chloro-1H-indole-3-sulfonamide I-201

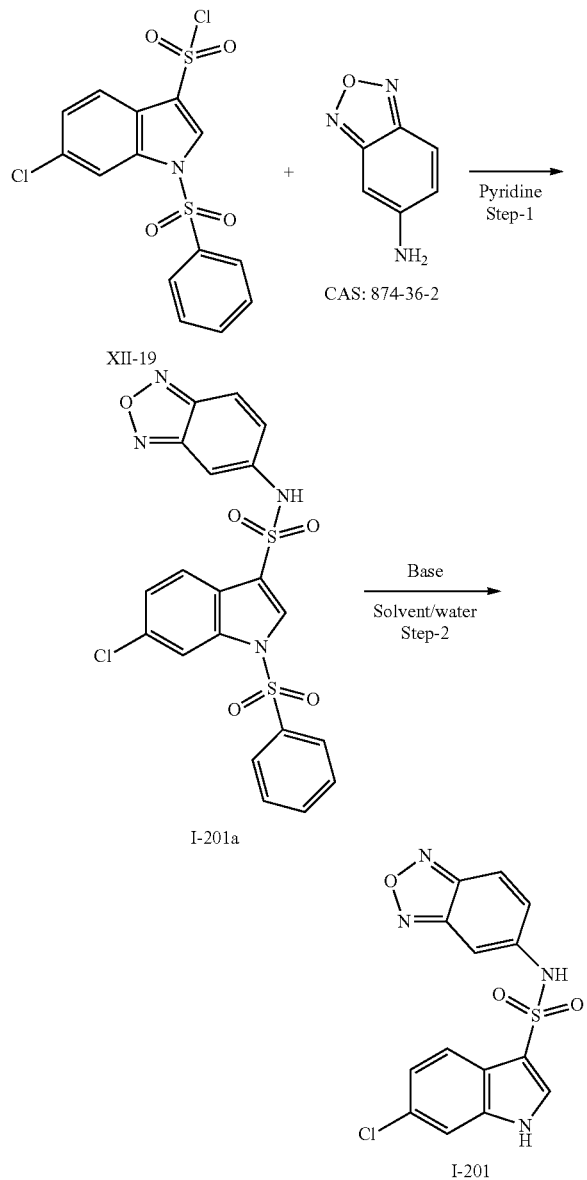

Step-1: Synthesis of 1-(benzenesulfonyl)-N-(2,1,3-benzoxadiazol-5-yl)-6-chloro-indole-3-sulfonamide I-201a In a sealed vial, 1-(benzenesulfonyl)-6-chloro-indole-3-sulfonyl chloride XII-19 (192 mg, 0.49 mmol) was dissolved in pyridine (4 mL) under argon. 2,1,3-benzoxadiazol-5-amine (135 mg, 1 mmol) was added and stirred at room temperature overnight. The reaction mixture was evaporated to dryness then the residue was taken into DCM. The organic phase was washed with HCl 1N and brine, dried over $MgSO_4$ and evaporated. The dark oil residue solidified on standing and was then triturated in ACN/water (8/2), sonicated and filtered, washed with water and dried under vacuum to provide 170 mg of 1-(benzenesulfonyl)-N-(2,1,3-benzoxadiazol-5-yl)-6-chloro-indole-3-sulfonamide I-201a as a yellow solid.

Yield: 71%.

Basic LCMS Method 1 (ES$^-$): 487 (M–H)$^-$, 100% purity.

$^1$H NMR (400 MHz, DMSO-d$_6$) δ 11.52 (s, 1H), 8.99 (s, 1H), 8.16-8.10 (m, 2H), 7.98 (d, J=1.8 Hz, 1H), 7.91 (dd, J=9.1, 3.2 Hz, 2H), 7.63 (t, J=7.5 Hz, 1H), 7.56-7.51 (m, 2H), 7.43-7.36 (m, 2H), 7.25 (dd, J=9.6, 1.9 Hz, 1H).

Step-2: Synthesis of N-(2,1,3-benzoxadiazol-5-yl)-6-chloro-1H-indole-3-sulfonamide I-201

In a sealed tube, 1-(benzenesulfonyl)-N-(2,1,3-benzoxadiazol-5-yl)-6-chloro-indole-3-sulfonamide I-201a (170 mg, 0.34 mmol) was suspended in methanol (4 mL). Water (1 mL) was added, then potassium carbonate (200 mg, 1.45 mmol) and was stirred at room temperature overnight. The reaction mixture was evaporated to dryness. The residue was dissolved in EtOAc and washed with HCl 1N and water, dried over $MgSO_4$ and evaporated. The residue was purified over silica eluting with heptane/EtOAc (1/1). After evaporation, it provided 170 mg of N-(2,1,3-benzoxadiazol-5-yl)-6-chloro-1H-indole-3-sulfonamide I-201 as a bright yellow solid.

Yield: 88%.

Basic LCMS Method 1 (ES$^-$): 347 (M–H)$^-$, 97% purity.

$^1$H NMR (400 MHz, DMSO-d$_6$) δ 12.27 (s, 1H), 11.22 (s, 1H), 8.41 (d, J=2.8 Hz, 1H), 7.94 (d, J=9.5 Hz, 1H), 7.87 (d, J=8.6 Hz, 1H), 7.54 (d, J=1.8 Hz, 1H), 7.38 (d, J=1.7 Hz, 1H), 7.34 (dd, J=9.5, 1.9 Hz, 1H), 7.29 (dd, J=8.6, 1.9 Hz, 1H).

The following compounds in Table 7 may be synthesized according methods analogous to Method F.

TABLE 7

| No | Sulfonyl chlorides XII | Amines X | Conditions, Time (Step-1) | Yield (%) | Conditions, Time (Step-2) | Purification conditions | Yield (%) |
|---|---|---|---|---|---|---|---|
| I-202 | XII-19 | 246847-98-3 | 80° C., 2 h | crude | $K_2CO_3$, MeOH, rt, overnight | Basic prep LCMS Method 1 | 29 |
| I-203 | XII-19 | 367-34-0 | rt, 1 h 30 | 94 | $K_2CO_3$, MeOH, rt, 1 h | DCM/Heptane | 28 |
| I-204 | XII-19 | 2613-30-1 | rt, 2 h | 84 | $K_2CO_3$, MeOH, rt, overnight | DCM/MeOH | 32 |
| I-205 | XII-19 | 4519-40-8 | 80° C., 3 h | crude | $Cs_2CO_3$, MeOH, rt, 2 h | 10% EtOAc/petroleum ether | 68 |

TABLE 7-continued

| No | Sulfonyl chlorides XII | Amines X | Conditions, Time (Step-1) | Yield (%) | Conditions, Time (Step-2) | Purification conditions | Yield (%) |
|---|---|---|---|---|---|---|---|
| I-206 | XII-19 | X-7 | 80° C., 3 h | crude | Cs$_2$CO$_3$, MeOH, rt, 2 h | 20% EtOAc/petroleum ether | 59 |
| I-207 | XII-19 | X-8 | 80° C., 3 h | crude | Cs$_2$CO$_3$, MeOH, rt, 2 h | 20% EtOAc/petroleum ether | 23 |
| I-208 | XII-19 | 1268392-91-1 | 80° C., 3 h | crude | Cs$_2$CO$_3$, MeOH, rt, 2 h | 40% EtOAc/petroleum ether | 32 |
| I-209 | XII-19 | 72115-06-1 | 80° C., 2 h | crude | Cs$_2$CO$_3$, MeOH, rt, 2 h | Recrystallisation in Et$_2$O | 55 |
| I-210 | XII-19 | 1008112-39-7 | 80° C., 2 h | crude | Cs$_2$CO$_3$, MeOH, rt, 2 h | 5% MeOH/DCM | 13 |
| I-211 | XII-19 | 74784-70-6 | 80° C., 2 h | crude | Cs$_2$CO$_3$, MeOH, rt, 2 h | 25% EtOAc/DCM | 30 |
| I-212 | XII-19 | 367-24-8 | 100° C., 2 h | crude | Cs$_2$CO$_3$, MeOH, rt, 2 h | 5% MeOH/DCM | 35 |
| I-213 | XII-19 | 112279-60-4 | 100° C., 2 h | crude | Cs$_2$CO$_3$, MeOH, rt, 2 h | 1% MeOH/DCM | 58 |
| I-214 | XII-19 | 116759-33-2 | 100° C., 2 h | crude | Cs$_2$CO$_3$, MeOH, rt, 2 h | 1% MeOH/DCM | 34 |
| I-215 | XII-19 | 1240257-25-3 | 100° C., 2 h | crude | Cs$_2$CO$_3$, MeOH, rt, 2 h | 5% MeOH/DCM | 61 |
| I-216 | XII-19 | 767-63-5 | 100° C., 2 h | crude | Cs$_2$CO$_3$, MeOH, rt, 2 h | 5% MeOH/DCM | 17 |
| I-217 | XII-19 | 2993-24-0 | 100° C., 2 h | crude | Cs$_2$CO$_3$, MeOH, rt, 2 h | 5% MeOH/DCM | 68 |
| I-218 | XII-19 | 106-40-1 | 100° C., 2 h | crude | Cs$_2$CO$_3$, MeOH, rt, 2 h | 5% MeOH/DCM | 51 |
| I-219 | XII-19 | 73792-22-0 | 100° C., 2 h | crude | Cs$_2$CO$_3$, MeOH, rt, 2 h | 6% MeOH/DCM | 40 |
| I-220 | XII-21 | 63069-50-1 | 100° C., 2 h | crude | Cs$_2$CO$_3$, MeOH, rt, 2 h | 5% MeOH/DCM | 34 |
| I-221 | XII-22 | 2613-30-1 | 80° C., 1 h | crude | Cs$_2$CO$_3$, MeOH, rt, 2 h | 5% MeOH/DCM | 58 |
| I-222 | XII-23 | 63069-50-1 | 100° C., 1 h | crude | Cs$_2$CO$_3$, MeOH, rt, 2 h | 5% MeOH/DCM | 27 |
| I-223 | XII-20 | 367-34-0 | rt, 1 h | 85 | K$_2$CO$_3$, MeOH, rt, 1 h | Basic prep LCMS Method 1 | 23 |
| I-224 | XII-20 | 57946-56-2 | rt, 16 h | crude | K$_2$CO$_3$, MeOH, rt, 16 h | Basic prep LCMS Method 1 | 25 |
| I-225 | XII-20 | 120934-03-4 | rt, 16 h | crude | K$_2$CO$_3$, MeOH, rt, 16 h | Basic prep LCMS Method 1 | 14 |
| I-226 | XII-20 | X-1 | rt, 16 h | crude | K$_2$CO$_3$, MeOH, rt, 16 h | Basic prep LCMS Method 1 | 19 |
| I-227 | XII-20 | 2613-30-1 | rt, 2 h | 58 | K$_2$CO$_3$, MeOH, rt, 16 h | Basic prep LCMS Method 1 | 49 |
| I-228 | XII-20 | 112279-60-4 | rt, 2 h | 44 | K$_2$CO$_3$, MeOH, rt, 3 h | Basic prep LCMS Method 1 | 39 |
| I-266 | XII-20 | 1341923-15-6 | rt, 16 h | 77 | K$_2$CO$_3$, Dioxane, 105° C., 24 h | 0-5% MeOH/DCM | 77 |
| I-267 | XII-19 | 1341923-15-6 | 50° C., 48 h | crude | K$_2$CO$_3$, Dioxane, 100° C., 48 h | Basic prep LCMS Method 1 | 51 |
| I-268 | XII-20 | 3710-42-7 | rt, 16 h | 89 | K$_2$CO$_3$, Dioxane, 105° C., 24 h | 0-5% MeOH/DCM | 60 |
| I-269 | XII-19 | 114973-22-7 | 50° C., 48 h | crude | K$_2$CO$_3$, Dioxane, 100° C., 48 h | Basic prep LCMS Method 1 | 10 |
| I-270 | XII-19 | 3710-42-7 | 50° C., 48 h | crude | K$_2$CO$_3$, Dioxane, 100° C., 48 h | Basic prep LCMS Method 1 | 59 |
| I-271 | XII-33 | 2613-30-1 | rt, 16 h | 36 | K$_2$CO$_3$, Dioxane, 105° C., 6 days | Recrystallisation in ACN | 27 |

TABLE 7-continued

| No | Sulfonyl chlorides XII | Amines X | Conditions, Time (Step-1) | Yield (%) | Conditions, Time (Step-2) | Purification conditions | Yield (%) |
|---|---|---|---|---|---|---|---|
| I-272 | XII-34 | 112279-60-4 | rt, 1 h | 40 | $K_2CO_3$, MeOH, 90° C., 5 days | 0-10% MeOH/DCM | 25 |
| I-273 | XII-20 | 123572-58-7 | rt, 16 h | 67 | $K_2CO_3$, Dioxane, 105° C., 48 h | Recrystallisation in ACN | 34 |
| I-274 | XII-22 | 1008112-39-7 | rt, 2 h | 30 | $K_2CO_3$, Dioxane, 105° C., 24 h | 0-5% MeOH/DCM | 30 |
| I-275 | XII-19 | 358672-65-8 | 50° C., 16 h | crude | $K_2CO_3$, Dioxane, 100° C., 3 days | Basic prep LCMS Method 1 | 13 |
| I-276 | XII-19 | 123572-58-7 | rt, 16 h | 71 | $K_2CO_3$, Dioxane, 105° C., 48 h | 50-0% Heptane/DCM | 38 |
| I-277 | XII-35 | 2613-30-1 | rt, 16 h | 38 | $K_2CO_3$, Dioxane, 105° C., 3 days | Recrystallisation in ACN | 20 |
| I-278 | XII-36 | 57946-56-2 | rt, 16 h | 44 | $K_2CO_3$, MeOH, 50° C., 16 h | 0-40% EtOAc/Hexane | 47 |
| I-279 | XII-19 | 1211590-31-6 | 50° C., 16 h | crude | $K_2CO_3$, Dioxane, 100° C., 3 days | Basic prep LCMS Method 1 | 20 |
| I-280 | XII-19 | 20511-12-0 | 50° C., 16 h | crude | $K_2CO_3$, Dioxane, 100° C., 3 days | Basic prep LCMS Method 1 | 31 |
| I-281 | XII-34 | 2613-30-1 | rt, 2 h | 86 | $K_2CO_3$, Dioxane, 105° C., 28 h | Recrystallisation in ACN | 30 |
| I-282 | XII-35 | 1341923-15-6 | rt, 16 h | 95 | $K_2CO_3$, Dioxane, 105° C., 24 h | Recrystallisation in ACN | 25 |
| I-283 | XII-34 | 1008112-39-7 | rt, 2 h | 40 | $K_2CO_3$, MeOH, 70° C., 4 days | 0-10% MeOH/DCM | 48 |
| I-284 | XII-20 | X-17 | rt, 16 h | 85 | $K_2CO_3$, Dioxane, 105° C., 24 h | DCM | 3 |
| I-285 | XII-22 | 112279-60-4 | 80° C., 2 h | crude | $K_2CO_3$, rt, 2 h | 5% EtOAc/DCM | 28 |
| I-286 | XII-19 | 1441723-24-5 | 80° C., 4 h | crude | $Cs_2CO_3$, rt, 2 h | 20% EtOAc/ Petroleum ether | 65 |
| I-287 | XII-22 | 69409-98-9 | 80° C., 2 h | crude | $K_2CO_3$, rt, 1.5 h | 5% EtOAc/DCM Crystallization in EtOAc/Petroleum ether | 15 |
| I-288 | XII-22 | 1441723-24-5 | 80° C., 2 h | crude | $Cs_2CO_3$, rt, 3 h | 5% EtOAc/DCM | 12 |
| I-290 | XII-6 | 246847-98-3 | 80° C., 2 h | crude | $Cs_2CO_3$, rt, 2 h | 7.5% EtOAc/DCM | 45 |
| I-291 | XII-22 | 112279-61-5 | 80° C., 1 night | crude | $K_2CO_3$, rt, 2 h | DCM | 17 |
| I-292 | XII-20 | 1441723-24-5 | 80° C., 2 h | crude | $Cs_2CO_3$, rt, 2 h | 50% EtOAc/ Petroleum ether | 24 |
| I-293 | XII-22 | 367-24-8 | 80° C., 2 h | crude | $Cs_2CO_3$, rt, 3 h | 5% EtOAc/DCM | 22 |
| I-294 | XII-37 | 63069-50-1 | 80° C., 2 h | crude | $K_2CO_3$, rt, 2 h | 5% EtOAc/DCM | 39 |
| I-295 | XII-7 | 1240257-25-3 | 80° C., 2 h | crude | $Cs_2CO_3$, rt, 3 h | 5% EtOAc/DCM | 20 |
| I-296 | XII-7 | 69409-98-9 | 80° C., 2 h | crude | $Cs_2CO_3$, rt, 1.5 h | 5% EtOAc/DCM | 29 |
| I-297 | XII-19 | 852062-17-0 | 80° C., 2 h | crude | $Cs_2CO_3$, rt, 4 h | 5% MeOH/DCM | 4 |

TABLE 7-continued

| No | Sulfonyl chlorides XII | Amines X | Conditions, Time (Step-1) | Yield (%) | Conditions, Time (Step-2) | Purification conditions | Yield (%) |
|---|---|---|---|---|---|---|---|
| I-298 | XII-19 | 394223-61-1 | 80° C., 2 h | crude | Cs$_2$CO$_3$, rt, 3 h | 5% EtOAc/DCM | 60 |
| I-299 | XII-19 | 69409-98-9 | 80° C., 2 h | crude | Cs$_2$CO$_3$, rt, 4 h | 5% MeOH/DCM | 38 |
| I-300 | XII-37 | 2613-30-1 | 80° C., 2 h | crude | K$_2$CO$_3$, rt, 3 h | 5% EtOAc/DCM | 60 |
| I-301 | XII-19 | 81282-60-2 | 80° C., 3 h | crude | Cs$_2$CO$_3$, rt, 2 h | 20% EtOAc/DCM | 39 |
| I-302 | XII-19 | 732306-31-9 | 80° C., 16 h | crude | Cs$_2$CO$_3$, rt, 2 h | 30% EtOAc/ Petroleum ether | 35 |
| I-303 | XII-20 | 114973-22-7 | 0° C., 5 h | 17 | K$_2$CO$_3$, Dioxane/water, 4 h | 30-50% EtOAc/ heptane | 48 |
| I-307 | XII-20 | X-14 | 70° C., 20 h | — | Deprotection during step-1 | Basic prep LCMS Method 1 | 6 |
| I-308 | XII-19 | 155906-13-1 | 80° C., 15 h | crude | K$_2$CO$_3$, 70° C., Dioxane/water 24 h | 5% to 20% DCM/ Petroleum ether | 14 |
| I-336 | XII-20 | X-21 | 120° C., 2 h | — | Deprotection during step-1 | 5% EtOH/DCM | 23 |
| I-363 | XII-45 | 1341923-15-6 | rt, 16 h | 30 | TBAF, THF, 35° C., 6 days | 5% MeOH/DCM | 50 |

6-chloro-N-(5-chloro-3-fluoropyridin-2-yl)-1H-indole-3-sulfonamide I-202

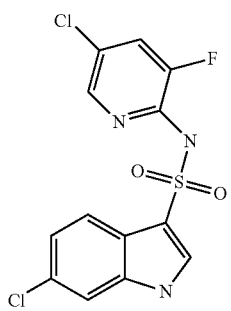 [SMILES: O=S(=O)(Nc1ncc(Cl)cc1F)c1c[nH]c2cc(Cl)ccc12]

Basic LCMS Method 1 (ES$^+$): 360 (M+H)$^+$, 97% purity.
$^1$H NMR (400 MHz, DMSO-d$_6$) δ 12.25 (s, 1H), 11.07 (s, 1H), 8.08 (d, J=3.5 Hz, 2H), 7.95 (d, J=10.1 Hz, 1H), 7.87 (d, J=8.6 Hz, 1H), 7.55 (s, 1H), 7.23 (m, 1H)

6-chloro-N-(2,4,5-trifluorophenyl)-1H-indole-3-sulfonamide I-203

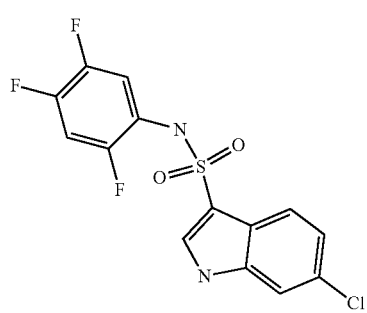 [SMILES: O=S(=O)(Nc1cc(F)c(F)cc1F)c1c[nH]c2cc(Cl)ccc12]

Basic LCMS Method 1 (ES$^+$): 361.2 (M+H)$^+$, 100% purity.

$^1$H NMR (400 MHz, DMSO-d$_6$) δ 11.29 (s, 1H), 7.78 (d, J=8.5 Hz, 1H), 7.57 (d, J=1.9 Hz, 1H), 7.37 (d, J=1.9 Hz, 1H), 7.14-7.00 (m, 2H), 6.94 (td, J=11.1, 8.1 Hz, 1H).

6-chloro-N-(4-chloro-2,5-difluorophenyl)-1H-indole-3-sulfonamide I-204

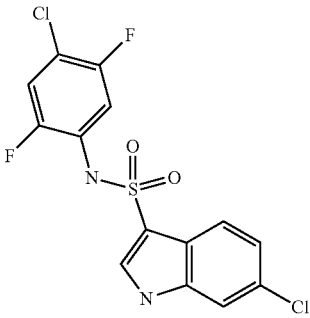 [SMILES: O=S(=O)(Nc1cc(F)c(Cl)cc1F)c1c[nH]c2cc(Cl)ccc12]

Basic LCMS Method 1 (ES$^-$): 375.2 (M−H)$^-$, 100% purity.

$^1$H NMR (400 MHz, DMSO-d$_6$) δ 12.13 (s, 1H), 10.46 (s, 1H), 8.04 (d, J=2.8 Hz, 1H), 7.78 (d, J=8.6 Hz, 1H), 7.59-7.47 (m, 2H), 7.34 (dd, J=10.4, 7.0 Hz, 1H), 7.23 (dd, J=8.6, 1.9 Hz, 1H).

367

6-chloro-N-(2,3-difluorophenyl)-1H-indole-3-sulfonamide I-205

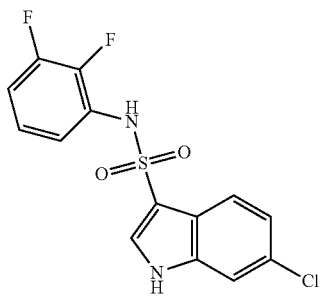 [SMILES: O=S(=O)(Nc1cccc(F)c1F)c1c[nH]c2cc(Cl)ccc12]

Neutral LCMS Method 3 (ES+): 343.2 (M+H)+, 97% purity.

$^1$H NMR (500 MHz, DMSO-d$_6$) δ 12.08 (s, 1H), 10.24 (s, 1H), 7.94 (s, 1H), 7.72 (d, J=8.6 Hz, 1H), 7.53 (s, 1H), 7.21 (d, J=8.6 Hz, 1H), 7.01-7.17 (m, 3H).

6-chloro-N-[4-(cyanomethyl)-2-fluorophenyl]-1H-indole-3-sulfonamide I-206

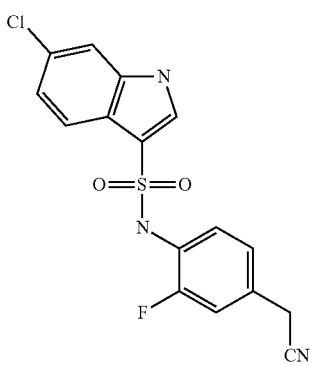 [SMILES: N#CCc1ccc(NS(=O)(=O)c2c[nH]c3cc(Cl)ccc23)c(F)c1]

Neutral LCMS Method 3 (ES+): 364.1 (M+H)+, 98% purity.

$^1$H NMR (600 MHz, DMSO-d$_6$) δ 12.04 (s, 1H), 10.04 (s, 1H), 7.90 (s, 1H), 7.73 (d, J=8.6 Hz, 1H), 7.52 (s, 1H), 7.32 (s, 1H), 7.19 (d, J=8.6 Hz, 1H), 7.07 (d, J=7.0 Hz, 2H), 3.95 (s, 2H).

368

6-chloro-N-[4-(1-cyanoethyl)-2-fluorophenyl]-1H-indole-3-sulfonamide I-207

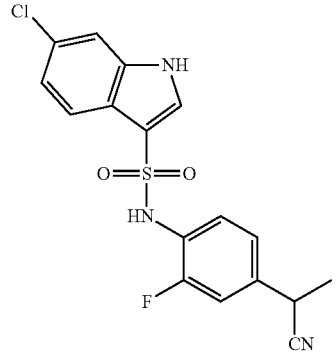 [SMILES: CC(C#N)c1ccc(NS(=O)(=O)c2c[nH]c3cc(Cl)ccc23)c(F)c1]

Neutral LCMS Method 3 (ES+): 378.2 (M+H)+, 94% purity.

$^1$H NMR (500 MHz, DMSO-d$_6$) δ 10.12 (s, 1H), 8.01 (s, 1H), 7.70-7.71 (m, 2H), 7.34-7.36 (m, 1H), 7.09-7.25 (m, 3H), 4.23 (q, J=7.2 Hz, 1H), 1.48 (d, J=7.2 Hz, 3H).

6-chloro-N-(4-chloro-5-fluoro-2-methoxyphenyl)-1H-indole-3-sulfonamide I-208

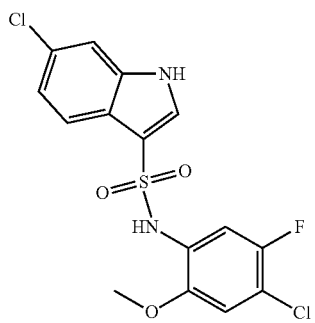 [SMILES: COc1cc(Cl)c(F)cc1NS(=O)(=O)c1c[nH]c2cc(Cl)ccc12]

Neutral LCMS Method 3 (ES+): 389.2 (M+H)+, 95% purity.

$^1$H NMR (600 MHz, DMSO-d$_6$) δ 12.03 (s, 1H), 9.63 (s, 1H), 7.95 (s, 1H), 7.80 (d, J=8.6 Hz, 1H), 7.50 (d, J=1.9 Hz, 1H), 7.34-7.16 (m, 2H), 7.03 (d, J=6.9 Hz, 1H), 3.39 (s, 3H).

6-chloro-N-(4-cyano-3-methylphenyl)-1H-indole-3-sulfonamide I-209

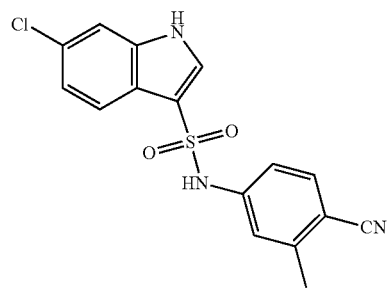 [SMILES: Cc1cc(NS(=O)(=O)c2c[nH]c3cc(Cl)ccc23)ccc1C#N]

Neutral LCMS Method 3 (ES+): 346 (M+H)+, 95% purity.
$^1$H NMR (500 MHz, DMSO-d$_6$) δ: 12.16 (s, 1H), 10.87 (s, 1H), 8.20 (s, 1H), 7.82 (d, J=8.5 Hz, 1H), 7.68-7.41 (m, 2H), 7.24 (dd, J=8.6, 2.0 Hz, 1H), 7.10 (d, J=2.1 Hz, 1H), 7.06 (dd, J=8.5, 2.2 Hz, 1H), 2.33 (s, 3H).

6-chloro-N-(4-ethynyl-2-fluorophenyl)-1H-indole-3-sulfonamide I-210

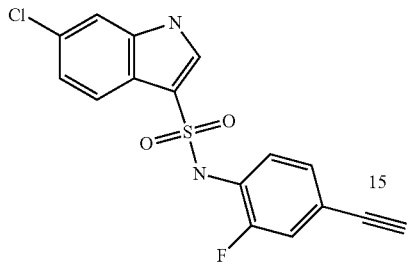 [SMILES: C#Cc1ccc(NS(=O)(=O)c2c[nH]c3cc(Cl)ccc23)c(F)c1]

Neutral LCMS Method 3 (ES⁺): 349 (M+H)⁺, 96% purity.
¹H NMR (600 MHz, DMSO-d₆) δ: 12.08 (s, 1H), 10.25 (s, 1H), 7.95 (s, 1H), 7.77 (d, J=8.5 Hz, 1H), 7.51 (s, 1H), 7.35-7.32 (m, 1H), 7.23-7.18 (m, 3H), 4.17 (s, 1H).

6-chloro-N-[5-(trifluoromethyl)pyridin-2-yl]-1H-indole-3-sulfonamide I-211

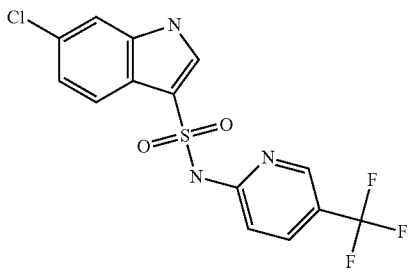 [SMILES: O=S(=O)(Nc1ccc(C(F)(F)F)cn1)c1c[nH]c2cc(Cl)ccc12]

Neutral LCMS Method 3 (ES⁺): 376.4 (M+H)⁺, 84% purity.
¹H NMR (600 MHz, DMSO-d₆) δ: 12.17 (s, 1H), 11.62 (s, 1H), 8.49 (d, J=2.6 Hz, 1H), 8.20 (d, J=2.8 Hz, 1H), 7.98 (dd, J=8.8, 2.5 Hz, 1H), 7.88 (d, J=8.6 Hz, 1H), 7.51 (d, J=1.9 Hz, 1H), 7.24 (dd, J=8.7, 2.0 Hz, 1H), 7.22 (d, J=8.9 Hz, 1H).

N-(4-bromo-2-fluorophenyl)-6-chloro-1H-indole-3-sulfonamide I-212

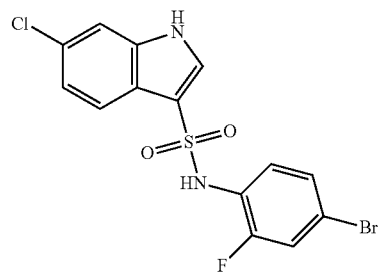 [SMILES: O=S(=O)(Nc1ccc(Br)cc1F)c1c[nH]c2cc(Cl)ccc12]

Neutral LCMS Method 3 (ES⁺): 405 (M+H)⁺, 95% purity.
¹H NMR (500 MHz, DMSO-d₆) δ: 12.05 (s, 1H), 10.08 (s, 1H), 7.89 (d, J=1.5 Hz, 1H), 7.73 (d, J=8.6 Hz, 1H), 7.51 (d, J=1.9 Hz, 1H), 7.41 (dd, J=10.0, 2.2 Hz, 1H), 7.31-7.26 (m, 1H), 7.23 (t, J=8.5 Hz, 1H), 7.19 (dd, J=8.6, 1.9 Hz, 1H).

N-(4-bromo-2,5-difluorophenyl)-6-chloro-1H-indole-3-sulfonamide I-213

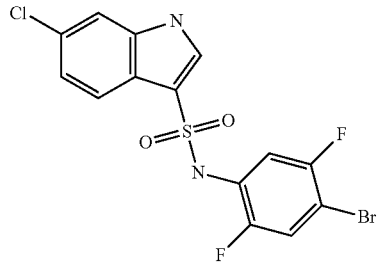 [SMILES: O=S(=O)(Nc1cc(F)c(Br)cc1F)c1c[nH]c2cc(Cl)ccc12]

Neutral LCMS Method 3 (ES⁺): 402.9 (M+H)⁺, 97% purity.
¹H NMR (500 MHz, DMSO-d₆) δ: 12.12 (s, 1H), 10.45 (s, 1H), 8.04 (d, J=2.9 Hz, 1H), 7.78 (d, J=8.6 Hz, 1H), 7.59 (dd, J=9.6, 6.4 Hz, 1H), 7.52 (d, J=1.9 Hz, 1H), 7.30 (dd, J=9.9, 6.8 Hz, 1H), 7.22 (dd, J=8.6, 1.9 Hz, 1H).

6-chloro-N-(4-chloro-2-fluoro-5-methylphenyl)-1H-indole-3-sulfonamide I-214

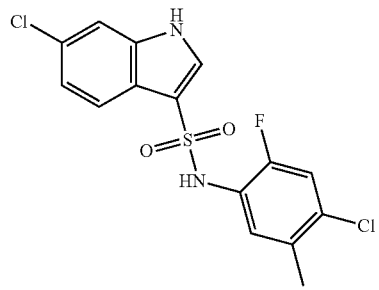 [SMILES: Cc1cc(NS(=O)(=O)c2c[nH]c3cc(Cl)ccc23)c(F)cc1Cl]

Neutral LCMS Method 3 (ES⁺): 472.9 (M+H)⁺, 98% purity.
¹H NMR (500 MHz, DMSO-d₆) δ: 12.03 (s, 1H), 10.00 (s, 1H), 7.91 (s, 1H), 7.73 (d, J=8.6 Hz, 1H), 7.51 (d, J=1.9 Hz, 1H), 7.26 (t, J=9.4 Hz, 2H), 7.19 (dd, J=8.6, 1.9 Hz, 1H), 3.29 (s, 3H).

6-chloro-N-[2-fluoro-4-(pentafluoro-lambda~6~-sulfanyl)phenyl]-1H-indole-3-sulfonamide I-215

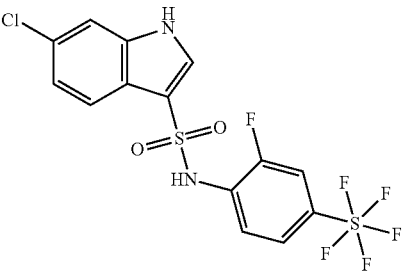 [SMILES: O=S(=O)(Nc1ccc(S(F)(F)(F)(F)F)cc1F)c1c[nH]c2cc(Cl)ccc12]

Neutral LCMS Method 3 (ES⁻): 448.9 (M−H)⁻, 96% purity.

¹H NMR (500 MHz, DMSO-d₆) δ: 12.16 (s, 1H), 10.72 (s, 1H), 8.08 (d, J=3.0 Hz, 1H), 7.81 (d, J=8.6 Hz, 1H), 7.80 (dd, J=2.5, 15 Hz, 1H), 7.64 (dd, J=9.1, 2.5 Hz, 1H), 7.62-7.57 (m, 1H), 7.52 (d, J=1.7 Hz, 1H), 7.22 (dd, J=8.6, 1.9 Hz, 1H).

N-(2,1,3-benzoxadiazol-4-yl)-6-chloro-1H-indole-3-sulfonamide I-216

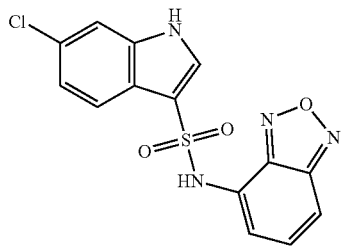 [SMILES: O=S(=O)(Nc1cccc2nonc12)c1c[nH]c2cc(Cl)ccc12]

Neutral LCMS Method 3 (ES⁺): 348.9 (M+H)⁺, 95% purity.
¹H NMR (600 MHz, DMSO-d₆) δ: 12.17 (d, J=3.2 Hz, 1H), 11.28 (s, 1H), 8.17 (d, J=3.0 Hz, 1H), 7.88 (d, J=8.6 Hz, 1H), 7.59 (d, J=9.0 Hz, 1H), 7.49 (d, J=1.9 Hz, 1H), 7.45 (dd, J=9.0, 7.2 Hz, 1H), 7.24 (d, J=7.2 Hz, 1H), 7.20 (dd, J=8.6, 1.9 Hz, 1H).

6-chloro-N-[4-(pentafluoro-lambda6-sulfanyl)phenyl]-1H-indole-3-sulfonamide I-217

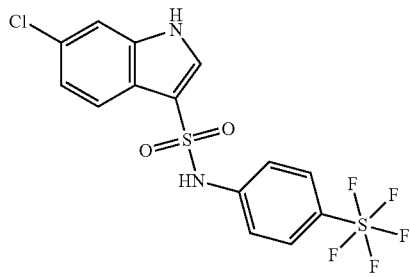 [SMILES: O=S(=O)(Nc1ccc(S(F)(F)(F)(F)F)cc1)c1c[nH]c2cc(Cl)ccc12]

Neutral LCMS Method 3 (ES⁻): 431 (M−H)⁻, 98% purity.
¹H NMR (500 MHz, DMSO-d₆) δ: 12.15 (s, 1H), 10.90 (s, 1H), 8.14 (s, 1H), 7.82 (d, J=8.6 Hz, 1H), 7.77-7.62 (m, 2H), 7.51 (d, J=1.9 Hz, 1H), 7.29-7.16 (m, 3H).

N-(4-bromophenyl)-6-chloro-1H-indole-3-sulfonamide I-218

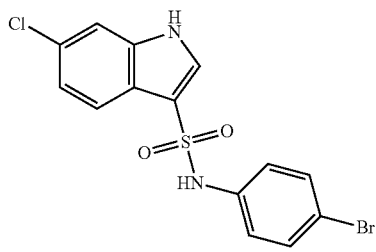 [SMILES: O=S(=O)(Nc1ccc(Br)cc1)c1c[nH]c2cc(Cl)ccc12]

Neutral LCMS Method 3 (ES⁻): 484.9 (M−H)⁻, 95% purity.
¹H NMR (600 MHz, DMSO-d₆) δ: 12.06 (s, 1H), 10.35 (s, 1H), 8.00 (s, 1H), 7.79 (d, J=8.6 Hz, 1H), 7.49 (d, J=1.9 Hz, 1H), 7.37-7.30 (m, 2H), 7.21 (dd, J=8.6, 2.0 Hz, 1H), 7.06-6.98 (m, 2H).

N-(4-acetyl-2-fluorophenyl)-6-chloro-1H-indole-3-sulfonamide I-219

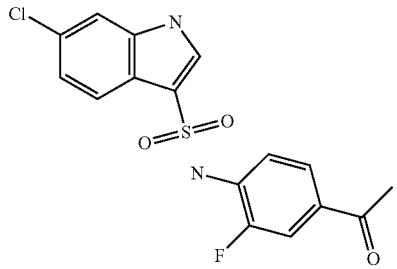

Neutral LCMS Method 3 (ES⁻): 365 (M−H)⁻, 99% purity.
¹H NMR (500 MHz, DMSO-d₆): δ 12.12 (s, 1H), 10.58 (s, 1H), 8.06 (d, J=2.2 Hz, 1H), 7.84 (d, J=8.6 Hz, 1H), 7.66 (dd, J=8.5, 2.0 Hz, 1H), 7.60 (dd, J=11.4, 1.9 Hz, 1H), 7.55-7.48 (m, 2H), 7.22 (dd, J=8.6, 1.9 Hz, 1H), 2.46 (s, 3H).

N-(4-cyano-2-fluorophenyl)-6-(cyclopropylmethoxy)-1H-indole-3-sulfonamide I-220

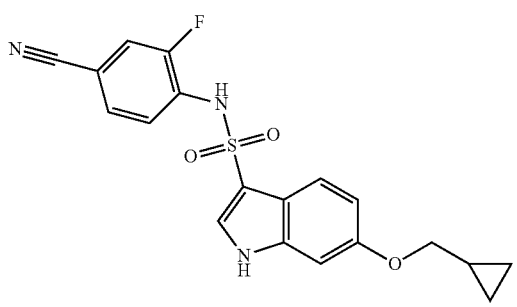 [SMILES: N#Cc1ccc(NS(=O)(=O)c2c[nH]c3cc(OCC4CC4)ccc23)c(F)c1]

Neutral LCMS Method 3 (ES⁺): 403 (M+NH₄)⁺, 96% purity.
¹H NMR (500 MHz, DMSO-d₆) δ: 11.81 (d, J=3.0 Hz, 1H), 10.68 (s, 1H), 7.91 (d, J=2.9 Hz, 1H), 7.71 (dd, J=10.7, 1.7 Hz, 1H), 7.67 (d, J=8.8 Hz, 1H), 7.61-7.46 (m, 2H), 6.90 (d, J=2.2 Hz, 1H), 6.83 (dd, J=8.8, 2.2 Hz, 1H), 3.80 (d, J=6.9 Hz, 2H), 1.32-1.14 (m, 1H), 0.68-0.51 (m, 2H), 0.37-0.15 (m, 2H).

373
N-(4-chloro-2,5-difluorophenyl)-6-methoxy-1H-indole-3-sulfonamide I-221

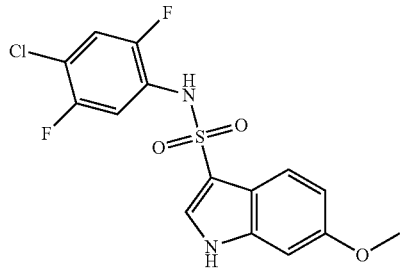 [SMILES: COc1ccc2c(S(=O)(=O)Nc3cc(F)c(Cl)cc3F)c[nH]c2c1]

Neutral LCMS Method 3 (ES⁺): 373 (M+H)⁺. 97% purity.
$^1$H NMR (500 MHz, DMSO-$d_6$) δ: 11.79 (s, 1H), 10.35 (s, 1H), 7.86 (d, J=2.9 Hz, 1H), 7.64 (d, J=8.8 Hz, 1H), 7.50 (dd, J=9.9, 6.9 Hz, 1H), 7.32 (dd, J=10.5, 6.9 Hz, 1H), 6.93 (d, J=2.2 Hz, 1H), 6.82 (dd, J=8.8, 2.3 Hz, 1H), 3.76 (s, 3H).

N-(4-cyano-2-fluorophenyl)-6-(tetrahydrofuran-2-ylmethoxy)-1H-indole-3-sulfonamide I-222

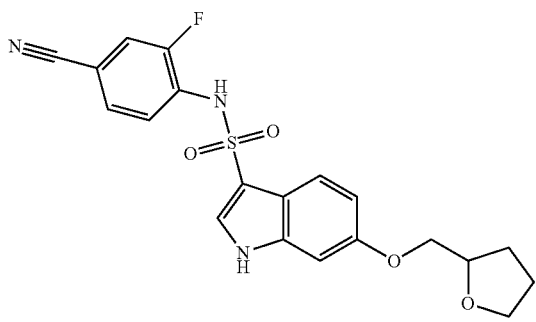 [SMILES: N#Cc1ccc(NS(=O)(=O)c2c[nH]c3cc(OCC4CCCO4)ccc23)c(F)c1]

Neutral LCMS Method 3 (ES⁺): 316 (M+H)⁺, 97% purity.
$^1$H NMR (500 MHz, DMSO-$d_6$) δ: 11.83 (s, 1H), 10.68 (s, 1H), 7.92 (d, J=3.0 Hz, 1H), 7.71 (dd, J=10.7, 1.7 Hz, 1H), 7.68 (d, J=8.8 Hz, 1H), 7.60-7.46 (m, 2H), 6.94 (d, J=2.3 Hz, 1H), 6.83 (dd, J=8.8, 2.3 Hz, 1H), 4.14 (qd, J=6.7, 4.2 Hz, 1H), 3.92 (qd, J=10.1, 5.1 Hz, 2H), 3.78 (dt, J=8.2, 6.7 Hz, 1H), 3.66 (td, J=7.7, 6.2 Hz, 1H), 1.99 (dddd, J=12.2, 8.5, 7.2, 5.3 Hz, 1H), 1.92-1.74 (m, 2H), 1.67 (ddt, J=12.0, 8.6, 6.9 Hz, 1H).

6-chloro-N-(2,4,5-trifluorophenyl)-1H-pyrrolo[2,3-b]pyridine-3-sulfonamide I-223

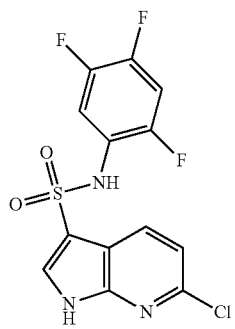 [SMILES: O=S(=O)(Nc1cc(F)c(F)cc1F)c1c[nH]c2nc(Cl)ccc12]

Basic LCMS Method 1 (ES⁺): 362.2 (M+H)⁺, 99% purity.
$^1$H NMR (400 MHz, DMSO-$d_6$) δ 12.83 (s, 1H), 10.27 (s, 1H), 8.19-7.98 (m, 2H), 7.47 (m, J=10.0 Hz, 1H), 7.37 (m, J=9.2 Hz, 2H).

374
6-chloro-N-(4-chloro-2-fluorophenyl)-1H-pyrrolo[2,3-b]pyridine-3-sulfonamide I-224

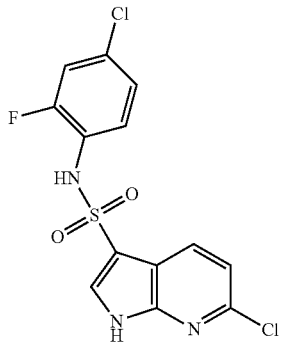 [SMILES: O=S(=O)(Nc1ccc(Cl)cc1F)c1c[nH]c2nc(Cl)ccc12]

Basic LCMS Method 1 (ES⁺): 360.2 (M+H)⁺, 99% purity.
$^1$H NMR (400 MHz, DMSO-$d_6$) δ 12.80 (s, 1H), 10.17 (s, 1H), 8.12 (d, J=8.3 Hz, 1H), 8.04 (s, 1H), 7.34 (m, J=8.8 Hz, 2H), 7.28 (t, J=8.6 Hz, 1H), 7.18 (d, J=8.6 Hz, 1H).

6-chloro-N-(2,2,6-trifluoro-1,3-benzodioxol-5-yl)-1H-pyrrolo[2,3-b]pyridine-3-sulfonamide I-225

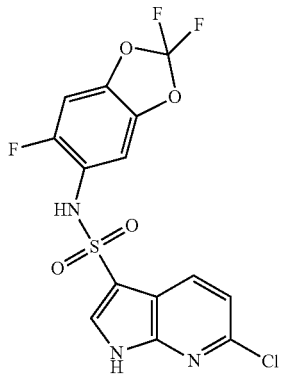 [SMILES: O=S(=O)(Nc1cc2c(cc1F)OC(F)(F)O2)c1c[nH]c2nc(Cl)ccc12]

Basic LCMS Method 1 (ES⁺): 406.2 (M+H)⁺, 99% purity.
$^1$H NMR (400 MHz, DMSO-$d_6$) δ 12.78 (s, 1H), 10.15 (s, 1H), 8.10 (d, J=8.4 Hz, 1H), 8.04 (s, 1H), 7.43 (d, J=9.1 Hz, 1H), 7.34 (m, J=7.3, 4.5 Hz, 2H).

6-chloro-N-(7-fluoro-2,1,3-benzothiadiazol-4-yl)-1H-pyrrolo[2,3-b]pyridine-3-sulfonamide I-226

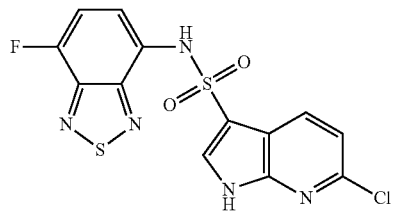 [SMILES: O=S(=O)(Nc1ccc(F)c2nsnc12)c1c[nH]c2nc(Cl)ccc12]

Basic LCMS Method 1 (ES⁺): 384.2 (M+H)⁺, 97% purity.
$^1$H NMR (400 MHz, DMSO-$d_6$) δ 12.78 (s, 1H), 10.79 (s, 1H), 8.22-8.12 (m, 2H), 7.51-7.39 (m, 2H), 7.29 (d, J=8.3 Hz, 1H).

375

6-chloro-N-(4-chloro-2,5-difluorophenyl)-1H-pyrrolo[2,3-b]pyridine-3-sulfonamide I-227

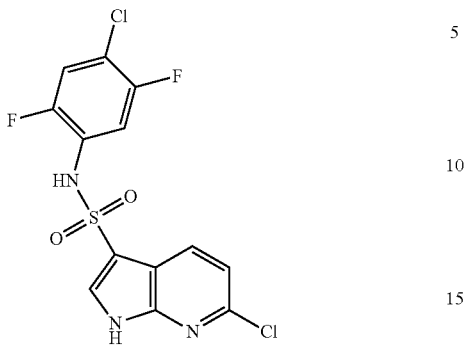

Basic LCMS Method 1 (ES⁻): 376.2 (M−H)⁻, 99% purity.
$^1$H NMR (400 MHz, DMSO-$d_6$) δ 12.87 (s, 1H), 10.52 (s, 1H), 8.26-8.12 (m, 2H), 7.55 (dd, J=9.9, 6.8 Hz, 1H), 7.37 (dd, J=9.5, 7.0 Hz, 2H).

N-(4-bromo-2,5-difluorophenyl)-6-chloro-1H-pyrrolo[2,3-b]pyridine-3-sulfonamide I-228

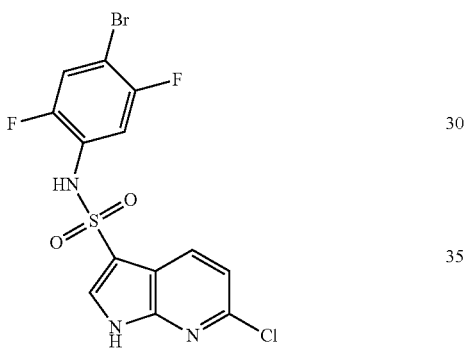

Basic LCMS Method 1 (ES⁻): 420 (M−H)⁻, 97% purity.
$^1$H NMR (400 MHz, DMSO-$d_6$) δ 12.87 (s, 1H), 10.52 (s, 1H), 8.25-8.15 (m, 2H), 7.63 (dd, J=9.7, 6.4 Hz, 1H), 7.38 (d, J=8.3 Hz, 1H), 7.34 (dd, J=9.7, 6.8 Hz, 1H).

6-chloro-N-[4-(difluoromethoxy)-2,5-difluorophenyl]-1H-pyrrolo[2,3-b]pyridine-3-sulfonamide I-266

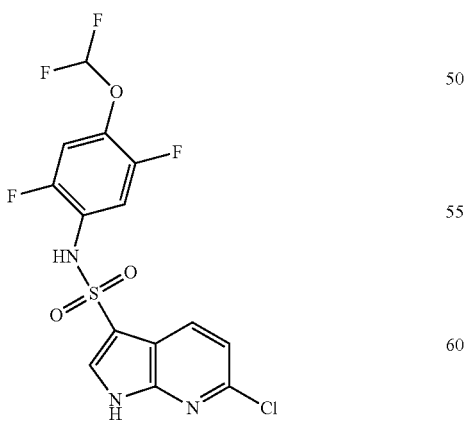

Basic LCMS Method 1 (ES⁺): 410 (M+H)⁺, 99% purity.
$^1$H NMR (400 MHz, DMSO-$d_6$) δ 12.85 (s, 1H), 10.38 (s, 1H), 8.15 (d, 1H), 8.13 (d, J=8.4 Hz, 1H), 7.38-7.34 (d, 1H), 7.34-7.27 (m, 2H), 7.08 (t, J=72.9 Hz, 1H).

376

6-chloro-N-[4-(difluoromethoxy)-2,5-difluorophenyl]-1H-indole-3-sulfonamide I-267

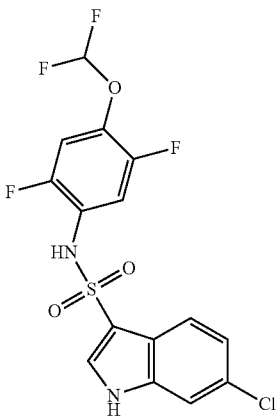 [SMILES: O=S(=O)(Nc1cc(F)c(OC(F)F)cc1F)c1c[nH]c2cc(Cl)ccc12]

Basic LCMS Method 1 (ES⁻): 407 (M−H)⁻, 97% purity.

6-chloro-N-(2,5-difluoro-4-methylphenyl)-1H-pyrrolo[2,3-b]pyridine-3-sulfonamide I-268

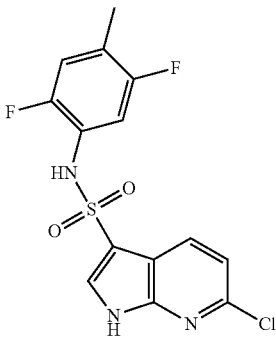 [SMILES: Cc1cc(F)c(NS(=O)(=O)c2c[nH]c3nc(Cl)ccc23)cc1F]

Basic LCMS Method 1 (ES⁺): 358 (M+H)⁺, 98% purity.
$^1$H NMR (400 MHz, DMSO-$d_6$) δ 12.80 (s, 1H), 10.19 (s, 1H), 8.18-8.07 (m, 2H), 7.36 (d, J=8.3 Hz, 1H), 7.06 (ddd, J=11.0, 6.7, 2.2 Hz, 2H), 2.12 (s, J=1.9 Hz, 3H).

6-chloro-N-[2,5-difluoro-4-(trifluoromethyl)phenyl]-1H-indole-3-sulfonamide I-269

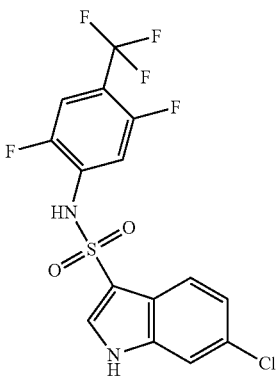 [SMILES: O=S(=O)(Nc1cc(F)c(C(F)(F)F)cc1F)c1c[nH]c2cc(Cl)ccc12]

Basic LCMS Method 1 (ES⁻): 409 (M−H)⁻, 100% purity.

6-chloro-N-(2,5-difluoro-4-methylphenyl)-1H-indole-3-sulfonamide I-270

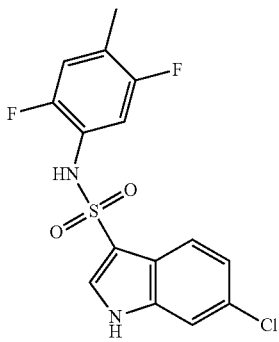 [SMILES: Cc1cc(F)c(NS(=O)(=O)c2c[nH]c3cc(Cl)ccc23)cc1F]

Basic LCMS Method 1 (ES+): 357 (M+H)+, 99% purity

N-(4-chloro-2,5-difluorophenyl)-5H-[1,3]dioxolo[4,5-f]indole-7-sulfonamide I-271

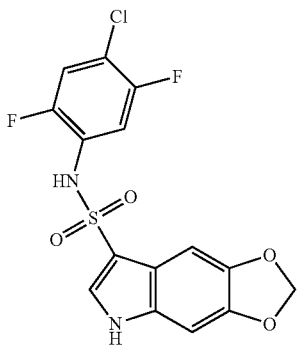 [SMILES: O=S(=O)(Nc1cc(F)c(Cl)cc1F)c1c[nH]c2cc3c(cc12)OCO3]

Basic LCMS Method 1 (ES−): 385 (M−H)−, 99% purity.
¹H NMR (400 MHz, DMSO-d₆) δ 11.81 (s, 1H), 10.37 (s, 1H), 7.81 (d, J=3.1 Hz, 1H), 7.54 (dd, J=10.0, 6.9 Hz, 1H), 7.33 (dd, J=10.6, 7.0 Hz, 1H), 7.25 (s, 1H), 6.97 (s, 1H), 6.00 (s, 2H).

N-(4-bromo-2,5-difluorophenyl)-6-methoxy-1H-pyrrolo[2,3-b]pyridine-3-sulfonamide I-272

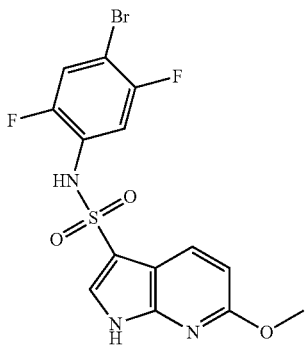

Basic LCMS Method 1 (ES+): 418 (M+H)+, 99% purity.
¹H NMR (400 MHz, DMSO-d₆) δ 12.45 (s, 1H), 10.43 (s, 1H), 8.04 (d, J=8.6 Hz, 1H), 7.88 (d, J=3.0 Hz, 1H), 7.62 (dd, J=9.7, 6.4 Hz, 1H), 7.32 (dd, J=9.9, 6.9 Hz, 1H), 6.73 (d, J=8.6 Hz, 1H), 3.87 (s, 3H).

6-chloro-N-[2-fluoro-4-(trifluoromethoxy)phenyl]-1H-pyrrolo[2,3-b]pyridine-3-sulfonamide I-273

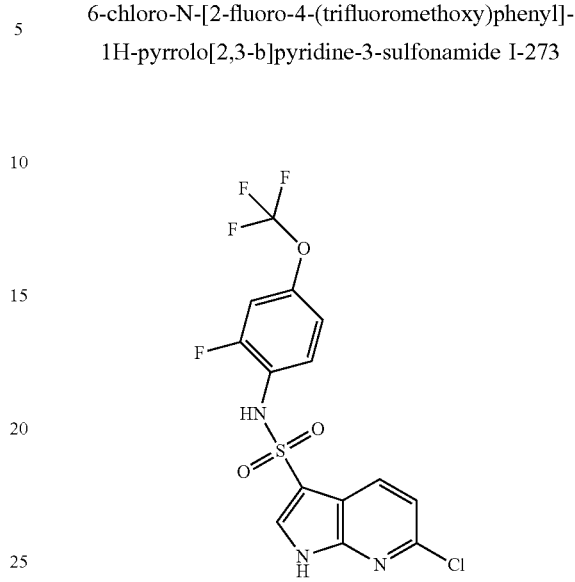

Basic LCMS Method 1 (ES+): 410 (M+H)+, 99% purity.
¹H NMR (400 MHz, DMSO-d₆) δ 12.83 (s, 1H), 10.23 (s, 1H), 8.08 (d, J=1.6 Hz, 1H), 8.06 (d, J=8.4 Hz, 1H), 7.39 (t, J=8.9 Hz, 1H), 7.32 (dd, J=8.1, 2.6 Hz, 2H), 7.21-7.13 (m, 1H).

N-(4-ethynyl-2-fluorophenyl)-6-methoxy-1H-indole-3-sulfonamide I-274

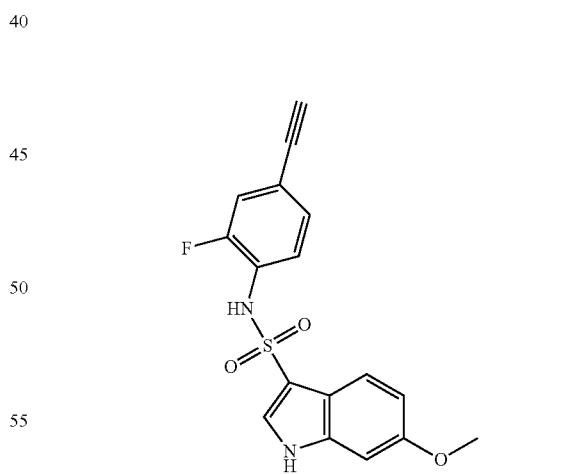

Basic LCMS Method 1 (ES−): 343 (M−H)−, 96% purity.
¹H NMR (400 MHz, DMSO-d₆) δ 11.76 (s, J=3.0 Hz, 1H), 10.17 (s, 1H), 7.78 (d, J=2.8 Hz, 1H), 7.64 (d, J=8.8 Hz, 1H), 7.34 (t, J=8.3 Hz, 1H), 7.26-7.13 (m, 2H), 6.93 (d, J=2.2 Hz, 1H), 6.81 (dd, J=8.8, 2.2 Hz, 1H), 4.18 (s, 1H), 3.77 (s, 3H).

379

N-(5-bromo-6-chloropyridin-2-yl)-6-chloro-1H-indole-3-sulfonamide I-275

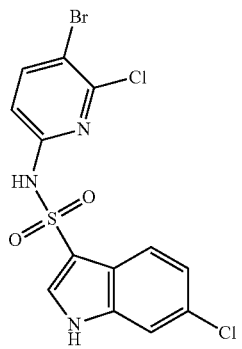 [SMILES: O=S(=O)(Nc1ccc(Br)c(Cl)n1)c1c[nH]c2cc(Cl)ccc12]

Basic LCMS Method 1 (ES⁻): 418 (M−H)⁻, 96% purity 6-chloro-N-[2-fluoro-4-(trifluoromethoxy)phenyl]-1H-indole-3-sulfonamide I-276

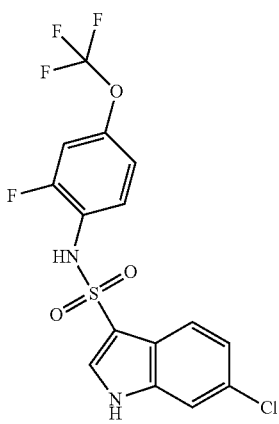 [SMILES: O=S(=O)(Nc1ccc(OC(F)(F)F)cc1F)c1c[nH]c2cc(Cl)ccc12]

Basic LCMS Method 1 (ES⁻): 407 (M−H)⁻, 96% purity. $^1$H NMR (400 MHz, DMSO-d$_6$) δ 12.08 (s, 1H), 10.15 (s, 1H), 7.92 (d, J=2.7 Hz, 1H), 7.67 (d, J=8.6 Hz, 1H), 7.52 (d, J=1.9 Hz, 1H), 7.39 (t, J=8.9 Hz, 1H), 7.29 (dd, J=10.6, 2.7 Hz, 1H), 7.16 (ddd, J=11.4, 8.9, 2.2 Hz, 2H).

N-(4-chloro-2,5-difluorophenyl)-6-cyano-1H-indole-3-sulfonamide I-277

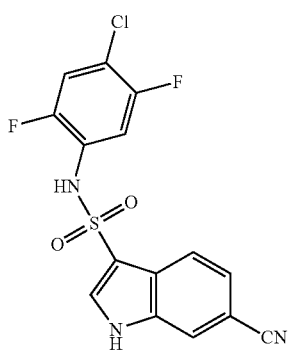 [SMILES: N#Cc1ccc2c(S(=O)(=O)Nc3cc(F)c(Cl)cc3F)c[nH]c2c1]

Basic LCMS Method 1 (ES⁻): 366 (M−H)⁻, 100% purity. $^1$H NMR (400 MHz, DMSO-d$_6$) δ 12.56 (s, 1H), 10.54 (s, 1H), 8.26 (d, J=2.4 Hz, 1H), 8.00 (d, J=1.3 Hz, 1H), 7.94 (d, J=8.4 Hz, 1H), 7.63-7.47 (m, 2H), 7.36 (dd, J=10.3, 6.9 Hz, 1H).

380

6-bromo-N-(4-chloro-2-fluorophenyl)-1H-pyrrolo[2,3-b]pyridine-3-sulfonamide I-278

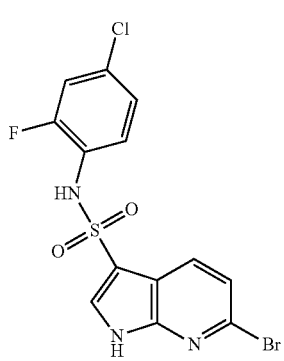 [SMILES: O=S(=O)(Nc1ccc(Cl)cc1F)c1c[nH]c2nc(Br)ccc12]

Basic LCMS Method 1 (ES⁻): 402 (M−H)⁻, 97% purity. $^1$H NMR (400 MHz, DMSO-d$_6$) δ 12.85 (s, 1H), 10.20 (s, 1H), 8.04 (d, J=8.3 Hz, 2H), 7.48 (d, J=8.3 Hz, 1H), 7.35 (dd, J=10.3, 2.3 Hz, 1H), 7.29 (t, J=8.5 Hz, 1H), 7.19 (ddd, J=8.6, 2.3, 1.0 Hz, 1H).

6-chloro-N-(3-fluoro-5-methylpyridin-2-yl)-1H-indole-3-sulfonamide I-279

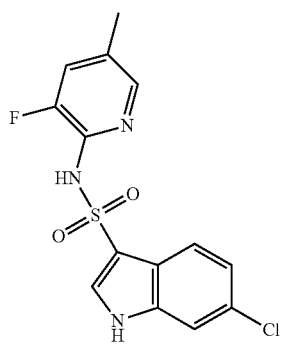 [SMILES: Cc1cnc(NS(=O)(=O)c2c[nH]c3cc(Cl)ccc23)c(F)c1]

Basic LCMS Method 1 (ES⁻): 338 (M−H)⁻, 99% purity.

6-chloro-N-(5-iodopyridin-2-yl)-1H-indole-3-sulfonamide I-280

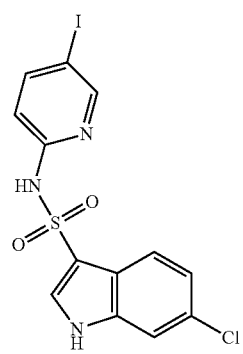 [SMILES: O=S(=O)(Nc1ccc(I)cn1)c1c[nH]c2cc(Cl)ccc12]

Basic LCMS Method 1 (ES⁻): 432 (M−H)⁻, 91% purity.

381

N-(4-chloro-2,5-difluorophenyl)-6-methoxy-1H-pyrrolo[2,3-b]pyridine-3-sulfonamide I-281

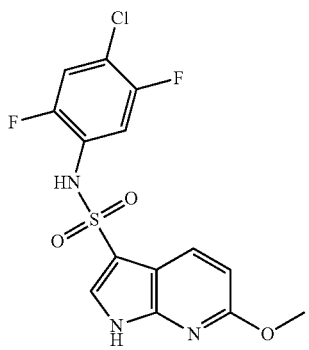

Basic LCMS Method 1 (ES⁺): 374 (M+H)⁺, 100% purity.

$^1$H NMR (400 MHz, DMSO-d$_6$) δ 12.45 (s, J=2.9 Hz, 1H), 10.42 (s, 1H), 8.04 (d, J=8.6 Hz, 1H), 7.88 (d, J=2.9 Hz, 1H), 7.54 (dd, J=9.9, 6.8 Hz, 1H), 7.36 (dd, J=10.4, 6.9 Hz, 1H), 6.73 (d, J=8.6 Hz, 1H), 3.88 (s, 3H).

6-cyano-N-[4-(difluoromethoxy)-2,5-difluorophenyl]-1H-indole-3-sulfonamide I-282

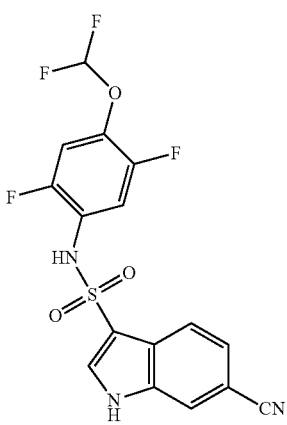 [SMILES: N#Cc1ccc2c(S(=O)(=O)Nc3cc(F)c(OC(F)F)cc3F)c[nH]c2c1]

Basic LCMS Method 1 (ES⁻): 398 (M−H)⁻, 100% purity.

$^1$H NMR (400 MHz, DMSO-d$_6$) δ 12.54 (s, 1H), 10.40 (s, 1H), 8.22 (d, J=2.8 Hz, 1H), 8.00 (dd, J=1.4, 0.7 Hz, 1H), 7.88 (d, J=8.3 Hz, 1H), 7.55 (dd, J=8.4, 1.4 Hz, 1H), 7.38-7.25 (m, 2H), 7.16 (s, 1H).

382

N-(4-ethynyl-2-fluorophenyl)-6-methoxy-1H-pyrrolo[2,3-b]pyridine-3-sulfonamide I-283

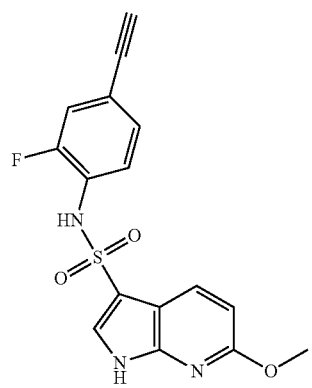 [SMILES: C#Cc1ccc(NS(=O)(=O)c2c[nH]c3nc(OC)ccc23)c(F)c1]

Basic LCMS Method 1 (ES⁺): 346 (M+H)⁺, 97% purity.

$^1$H NMR (400 MHz, DMSO-d$_6$) δ 12.4 (s, 1H), 10.21 (s, 1H), 8.00 (d, J=8.7 Hz, 1H), 7.76 (s, 1H), 7.35 (d, J=8.0 Hz, 1H), 7.20 (m, 2H), 6.70 (d, J=8.6 Hz, 1H) 4.20 (s, 1H), 3.87 (s, 3H).

6-chloro-N-(6-fluoro-3-oxo-1,3-dihydro-2-benzofuran-5-yl)-1H-pyrrolo[2,3-b]pyridine-3-sulfonamide I-284

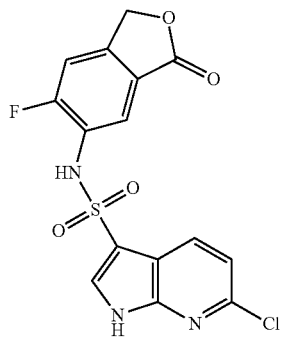 [SMILES: O=C1OCc2cc(F)c(NS(=O)(=O)c3c[nH]c4nc(Cl)ccc34)cc21]

Basic LCMS Method 1 (ES⁻): 380 (M−H)⁻, 98% purity.

$^1$H NMR (400 MHz, DMSO-d$_6$) δ 12.83 (s, 1H), 10.48 (s, 1H), 8.15 (d, J=8.3 Hz, 1H), 8.11 (d, J=2.4 Hz, 1H), 7.68 (d, J=6.9 Hz, 1H), 7.47 (d, J=9.5 Hz, 1H), 7.37 (d, J=8.3 Hz, 1H), 5.30 (s, 2H).

N-(4-bromo-2,5-difluorophenyl)-6-methoxy-1H-indole-3-sulfonamide I-285

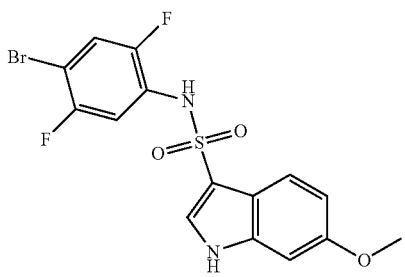 [SMILES: COc1ccc2c(S(=O)(=O)Nc3cc(F)c(Br)cc3F)c[nH]c2c1]

Neutral LCMS Method 3 (ES⁺): 417 (M+H)⁺, 98% purity
1H NMR (500 MHz, DMSO-d6) δ: 11.79 (d, J=3.0 Hz, 1H), 10.37 (s, 1H), 7.87 (d, J=2.9 Hz, 1H), 7.65 (d, J=8.8 Hz, 1H), 7.58 (dd, J=9.7, 6.4 Hz, 1H), 7.29 (dd, J=10.0, 6.8 Hz, 1H), 6.93 (d, J=2.2 Hz, 1H), 6.82 (dd, J=8.8, 2.3 Hz, 1H), 3.76 (s, 3H).

6-chloro-N-(4-cyano-5-fluoro-2-methoxyphenyl)-1H-indole-3-sulfonamide I-286

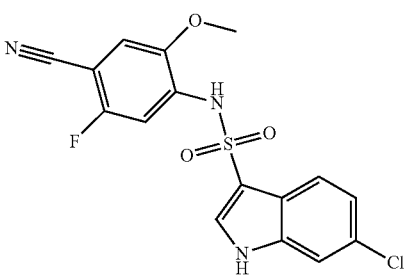 [SMILES: COc1cc(C#N)c(F)cc1NS(=O)(=O)c1c[nH]c2cc(Cl)ccc12]

Neutral LCMS Method 3 (ES⁺): 380.7 (M+H)⁺, 97% purity.
$^1$H NMR (600 MHz, DMSO-d$_6$) δ: 12.19 (s, 1H), 10.27 (s, 1H), 8.23 (s, 1H), 7.90 (d, J=8.6 Hz, 1H), 7.52 (s, 1H), 7.38-7.33 (m, 2H), 7.23 (dd, J=8.6, 1.9 Hz, 1H), 3.65 (s, 3H).

N-(2-fluoro-4-(trifluoromethyl)phenyl)-6-methoxy-1H-indole-3-sulfonamide I-287

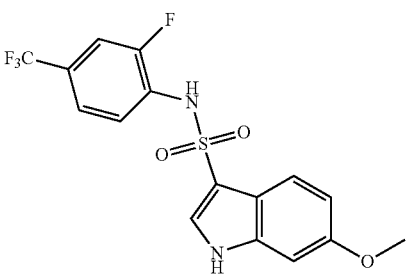 [SMILES: COc1ccc2c(S(=O)(=O)Nc3ccc(C(F)(F)F)cc3F)c[nH]c2c1]

Neutral LCMS Method 3 (ES⁺): 389 (M+H)⁺, 99% purity.
1H NMR (500 MHz, DMSO-d$_6$) δ: 11.79 (s, 1H), 10.48 (s, 1H), 7.86 (d, J=2.9 Hz, 1H), 7.67 (d, J=8.8 Hz, 1H), 7.62-7.50 (m, 2H), 7.47-7.37 (m, 1H), 6.92 (d, J=2.2 Hz, 1H), 6.81 (dd, J=8.8, 2.3 Hz, 1H), 3.75 (s, 3H).

N-(4-cyano-5-fluoro-2-methoxyphenyl)-6-methoxy-1H-indole-3-sulfonamide I-288

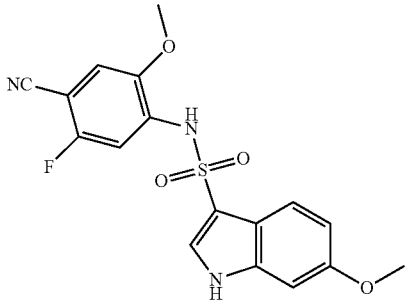 [SMILES: COc1ccc2c(S(=O)(=O)Nc3cc(F)c(C#N)cc3OC)c[nH]c2c1]

Neutral LCMS Method 3 (ES⁺): 376 (M+H)⁺, 98% purity.
$^1$H NMR (500 MHz, DMSO-d$_6$) δ: 11.86 (d, J=3.0 Hz, 1H), 10.11 (s, 1H), 8.05 (d, J=2.9 Hz, 1H), 7.75 (d, J=8.8 Hz, 1H), 7.35 (d, J=6.0 Hz, 1H), 7.32 (d, J=11.2 Hz, 1H), 6.93 (d, J=2.3 Hz, 1H), 6.83 (dd, J=8.8, 2.3 Hz, 1H), 3.75 (s, 3H), 3.68 (s, 3H).

6-Bromo-N-(5-chloro-3-fluoropyridin-2-yl)-1H-indole-3-sulfonamide I-290

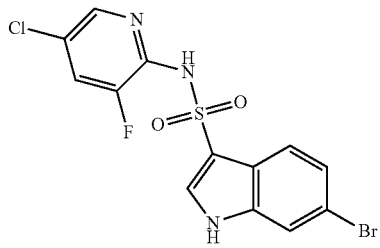 [SMILES: O=S(=O)(Nc1ncc(Cl)cc1F)c1c[nH]c2cc(Br)ccc12]

Neutral LCMS Method 3 (ES⁺): 404 (M+H)⁺, 98% purity.

N-(4-cyano-2,5-difluorophenyl)-6-methoxy-1H-indole-3-sulfonamide I-291

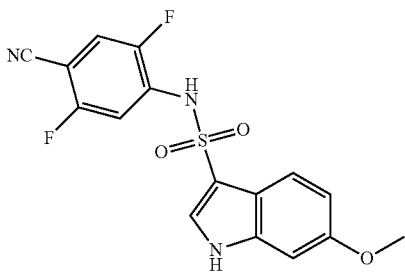 [SMILES: COc1ccc2c(S(=O)(=O)Nc3cc(F)c(C#N)cc3F)c[nH]c2c1]

Neutral LCMS Method 3 (ES⁺): 381 (M+NH$_4$)⁺, 98% purity.
$^1$H NMR (500 MHz, DMSO-d$_6$) δ: 11.93 (br s, 1H), 11.11 (s, 1H), 8.12 (d, J=3.0 Hz, 1H), 7.83 (dd, J=10.3, 6.0 Hz, 1H), 7.73 (d, J=8.7 Hz, 1H), 7.43 (dd, J=11.1, 6.4 Hz, 1H), 6.95 (d, J=2.3 Hz, 1H), 6.86 (dd, J=8.8, 2.3 Hz, 1H), 3.77 (s, 3H).

6-chloro-N-(4-cyano-5-fluoro-2-methoxyphenyl)-1H-pyrrolo[2,3-b]pyridine-3-sulfonamide I-292

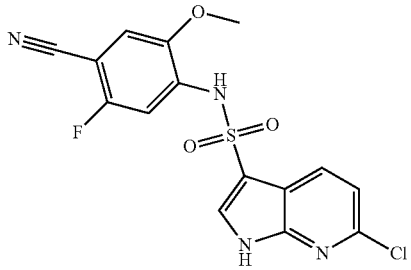 [SMILES: COc1cc(C#N)c(F)cc1NS(=O)(=O)c1c[nH]c2nc(Cl)ccc12]

Neutral LCMS Method 3 (ES$^+$): 381 (M+H)$^+$, 95.0% purity.
$^1$H NMR (600 MHz, DMSO-d$_6$) δ: 12.90 (s, 1H), 10.36 (s, 1H), 8.40 (d, J=2.3 Hz, 1H), 8.34 (d, J=8.4 Hz, 1H), 7.45-7.34 (m, 3H), 3.63 (s, 3H).

N-(4-bromo-2-fluorophenyl)-6-methoxy-1H-indole-3-sulfonamide I-293

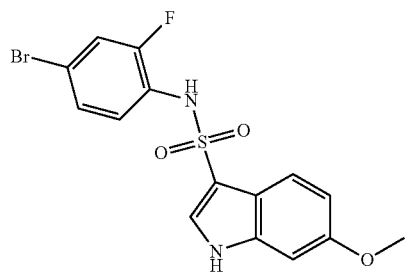 [SMILES: COc1ccc2c(S(=O)(=O)Nc3ccc(Br)cc3F)c[nH]c2c1]

Neutral LCMS Method 3 (ES$^+$): 399 (M+H)$^+$, 98% purity.
$^1$H NMR (500 MHz, DMSO-d$_6$) δ: 11.72 (s, 1H), 9.97 (s, 1H), 7.71 (d, J=2.1 Hz, 1H), 7.61 (d, J=8.8 Hz, 1H), 7.40 (dd, J=10.0, 2.1 Hz, 1H), 7.32-7.16 (m, 2H), 6.92 (d, J=2.3 Hz, 1H), 6.79 (dd, J=8.8, 2.3 Hz, 1H), 3.76 (s, 3H).

N-(4-cyano-2-fluorophenyl)-6-(2,2,2-trifluoroethoxy)-1H-indole-3-sulfonamide I-294

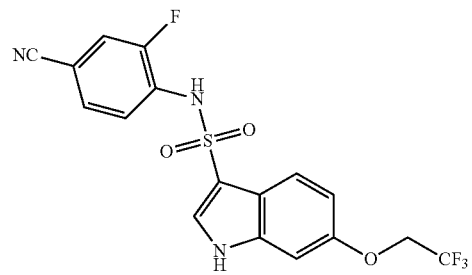 [SMILES: N#Cc1ccc(NS(=O)(=O)c2c[nH]c3cc(OCC(F)(F)F)ccc23)c(F)c1]

Neutral LCMS Method 3 (ES$^+$): 414 (M+H)$^+$, 99% purity.
$^1$H NMR (500 MHz, DMSO-d$_6$) δ: 11.99 (d, J=2.9 Hz, 1H), 10.71 (s, 1H), 7.98 (d, J=2.9 Hz, 1H), 7.75 (d, J=8.8 Hz, 1H), 7.71 (dd, J=10.7, 1.7 Hz, 1H), 7.61-7.49 (m, 2H), 7.07 (d, J=2.3 Hz, 1H), 6.95 (dd, J=8.8, 2.3 Hz, 1H), 4.75 (q, J=8.9 Hz, 2H).

6-chloro-N-[2-fluoro-4-(pentafluoro-lambda~6~-sulfanyl)phenyl]-1H-pyrrolo[2,3-b]pyridine-3-sulfonamide I-295

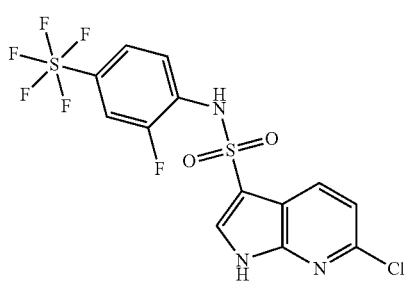 [SMILES: O=S(=O)(Nc1ccc(S(F)(F)(F)(F)F)cc1F)c1c[nH]c2nc(Cl)ccc12]

Neutral LCMS Method 3 (ES$^+$): 452 (M+H)$^+$, 99% purity.
$^1$H NMR (600 MHz, DMSO-d$_6$) δ: 12.90 (s, 1H), 10.80 (s, 1H), 8.23 (s, 1H), 8.22 (d, J=8.4 Hz, 1H), 7.82 (dd, J=10.9, 2.6 Hz, 1H), 7.64 (dd, J=9.2, 2.5 Hz, 1H), 7.61-7.56 (m, 1H), 7.36 (d, J=8.3 Hz, 1H).

6-chloro-N-[2-fluoro-4-(trifluoromethyl)phenyl]-1H-pyrrolo[2,3-b]pyridine-3-sulfonamide I-296

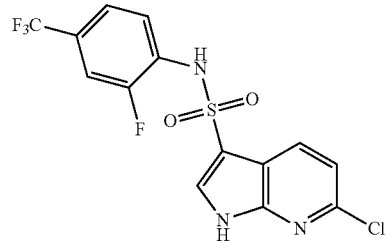 [SMILES: O=S(=O)(Nc1ccc(C(F)(F)F)cc1F)c1c[nH]c2nc(Cl)ccc12]

Neutral LCMS Method 3 (ES$^+$): 394 (M+H)$^+$, 95% purity.
$^1$H NMR (500 MHz, DMSO-d$_6$) δ: 12.87 (s, 1H), 10.64 (s, 1H), 8.20 (d, J=8.4 Hz, 1H), 8.18 (s, 1H), 7.64-7.52 (m, 2H), 7.50-7.42 (m, 1H), 7.35 (d, J=8.3 Hz, 1H).

6-chloro-N-[3-fluoro-5-(trifluoromethyl)pyridin-2-yl]-1H-indole-3-sulfonamide I-297

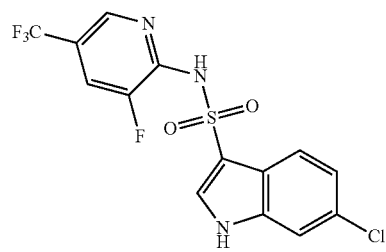 [SMILES: O=S(=O)(Nc1ncc(C(F)(F)F)cc1F)c1c[nH]c2cc(Cl)ccc12]

Neutral LCMS Method 3 (ES$^+$): 394 (M+H)$^+$, 89% purity

387

6-chloro-N-(2,5-difluoro-4-methoxyphenyl)-1H-indole-3-sulfonamide I-298

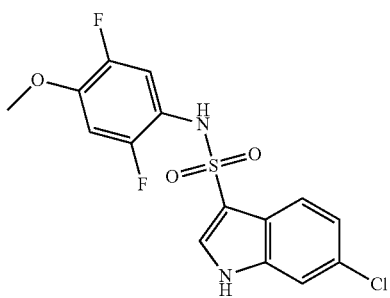 [SMILES: COc1cc(F)c(NS(=O)(=O)c2c[nH]c3cc(Cl)ccc23)cc1F]

Neutral LCMS Method 3 (ES+): 373 (M+H)+, 99% purity.
$^1$H NMR (500 MHz, DMSO-$d_6$) δ: 12.00 (s, 1H), 9.80 (s, 1H), 7.83 (s, 1H), 7.69 (d, J=8.5 Hz, 1H), 7.51 (d, J=1.9 Hz, 1H), 7.19 (dd, J=8.6, 1.9 Hz, 1H), 7.00 (ddd, J=11.6, 10.3, 7.7 Hz, 2H), 3.74 (s, 3H).

6-chloro-N-[2-fluoro-4-(trifluoromethyl)phenyl]-1H-indole-3-sulfonamide I-299

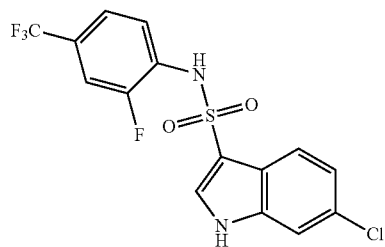 [SMILES: O=S(=O)(Nc1ccc(C(F)(F)F)cc1F)c1c[nH]c2cc(Cl)ccc12]

Neutral LCMS Method 3 (ES+): 393 (M+H)+, 98% purity.
$^1$H NMR (500 MHz, DMSO-$d_6$) δ 12.13 (d, J=2.9 Hz, 1H), 10.57 (s, 1H), 8.04 (d, J=2.9 Hz, 1H), 7.80 (d, J=8.6 Hz, 1H), 7.64-7.54 (m, 2H), 7.52 (d, J=1.9 Hz, 1H), 7.46 (dd, J=8.5, 2.1 Hz, 1H), 7.21 (dd, J=8.6, 1.9 Hz, 1H).

N-(4-chloro-2,5-difluorophenyl)-6-(2,2,2-trifluoro-ethoxy)-1H-indole-3-sulfonamide I-300

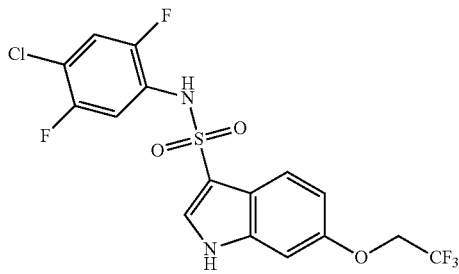 [SMILES: O=S(=O)(Nc1cc(F)c(Cl)cc1F)c1c[nH]c2cc(OCC(F)(F)F)ccc12]

Neutral LCMS Method 3 (ES+): 441 (M+H)+, 97% purity.
$^1$H NMR (600 MHz, DMSO-$d_6$) δ: 11.95 (d, J=3.1 Hz, 1H), 10.40 (s, 1H), 7.92 (d, J=2.8 Hz, 1H), 7.70 (d, J=8.8 Hz, 1H), 7.50 (d, J=9.9, 6.8 Hz, 1H), 7.32 (dd, J=10.5, 6.9 Hz, 1H), 7.07 (d, J=2.3 Hz, 1H), 6.94 (dd, J=8.8, 2.3 Hz, 1H), 4.76 (q, J=8.9 Hz, 2H).

388

6-chloro-N-(2-oxo-2,3-dihydro-1,3-benzoxazol-7-yl)-1H-indole-3-sulfonamide I-301

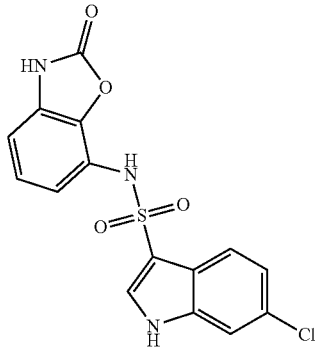 [SMILES: O=c1[nH]c2cccc(NS(=O)(=O)c3c[nH]c4cc(Cl)ccc34)c2o1]

Neutral LCMS Method 3 (ES+): 364 (M+H)+, 94.0% purity.
$^1$H NMR (500 MHz, DMSO-$d_6$) δ: 12.04 (s, 1H), 11.55 (s, 1H), 10.18 (s, 1H), 7.93 (s, 1H), 7.68 (d, J=8.6 Hz, 1H), 7.52-7.48 (m, 1H), 7.16 (dd, J=8.6, 1.9 Hz, 1H), 6.98 (dd, J=8.3, 7.8 Hz, 1H), 6.87 (dd, J=8.4, 1.1 Hz, 1H), 6.79 (dd, J=7.7, 1.1 Hz, 1H).

6-chloro-N-(3,5-difluoropyridin-2-yl)-1H-indole-3-sulfonamide I-302

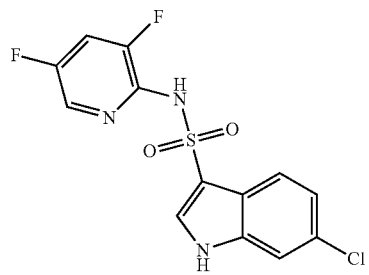 [SMILES: O=S(=O)(Nc1ncc(F)cc1F)c1c[nH]c2cc(Cl)ccc12]

Neutral LCMS Method 3 (ES+): 344 (M+H)+, 97.8% purity
$^1$H NMR (600 MHz, DMSO-$d_6$) δ: 12.08 (s, 1H), 10.78 (s, 1H), 8.10 (s, 1H), 8.04 (s, 1H), 7.89-7.80 (m, 1H), 7.79 (d, J=8.6 Hz, 1H), 7.52 (s, 1H), 7.21 (dd, J=8.6, 1.9 Hz, 1H).

6-chloro-N-[2,5-difluoro-4-(trifluoromethyl)phenyl]-1H-pyrrolo[2,3-b]pyridine-3-sulfonamide I-303

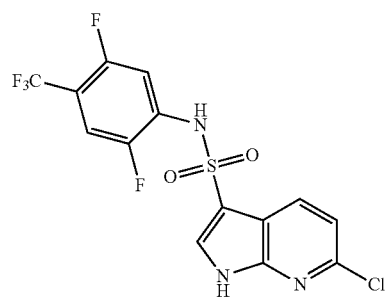 [SMILES: O=S(=O)(Nc1cc(F)c(C(F)(F)F)cc1F)c1c[nH]c2nc(Cl)ccc12]

Basic LCMS Method 1 (ES−): 410 (M−H)−, 97% purity.
$^1$H NMR (400 MHz, DMSO-$d_6$) δ 12.94 (s, 1H), 11.04 (s, 1H), 8.40 (d, J=2.9 Hz, 1H), 8.28 (d, J=8.3 Hz, 1H), 7.71-7.60 (m, 1H), 7.48 (dd, J=12.1, 6.3 Hz, 1H), 7.40 (d, J=8.3 Hz, 1H).

389

6-chloro-N-(5-chloro-3,6-difluoropyridin-2-yl)-1H-pyrrolo[2,3-b]pyridine-3-sulfonamide I-307

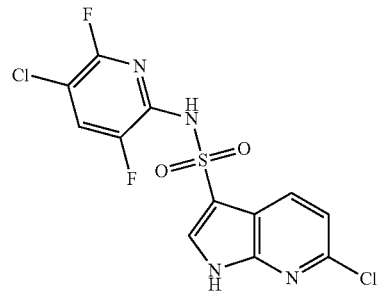 [SMILES: O=S(=O)(Nc1nc(F)c(Cl)cc1F)c1c[nH]c2nc(Cl)ccc12]

Basic LCMS Method 1 (ES⁺): 379 (M+H)⁺, 100% purity.

6-chloro-N-(2,5-difluoro-4-iodophenyl)-1H-indole-3-sulfonamide I-308

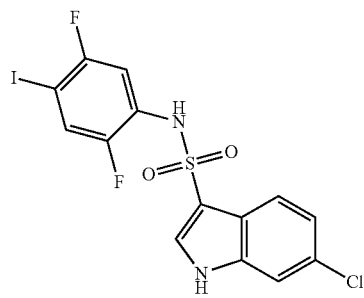 [SMILES: O=S(=O)(Nc1cc(F)c(I)cc1F)c1c[nH]c2cc(Cl)ccc12]

Neutral LCMS Method 3 (ES⁺): 469 (M+H)⁺, 95% purity.
$^1$H NMR (600 MHz, DMSO-d$_6$) δ: 12.13 (d, J=3.0 Hz, 1H), 10.45 (s, 1H), 8.04 (d, J=2.9 Hz, 1H), 7.79 (d, J=8.6 Hz, 1H), 7.63 (dd, J=9.4, 5.7 Hz, 1H), 7.52 (d, J=1.8 Hz, 1H), 7.23 (dd, J=8.6, 1.9 Hz, 1H), 7.20 (dd, J=9.1, 6.5 Hz, 1H).

6-chloro-N-(5-chloro-3-fluoro-6-methoxypyridin-2-yl)-1H-pyrrolo[2,3-b]pyridine-3-sulfonamide I-336

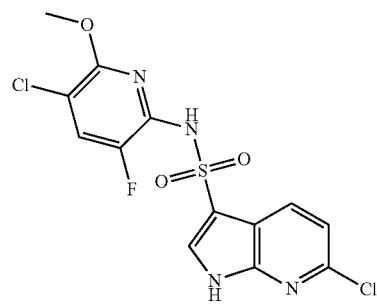 [SMILES: COc1nc(NS(=O)(=O)c2c[nH]c3nc(Cl)ccc23)c(F)cc1Cl]

Basic LCMS Method 1 (ES⁻): 389 (M−H)⁻, 98% purity.
$^1$H NMR (400 MHz, DMSO-d$_6$) δ 12.87 (s, 1H), 11.17 (s, 1H), 8.29 (dd, J=18.4, 5.6 Hz, 2H), 7.98 (d, J=9.0 Hz, 1H), 7.39 (d, J=8.4 Hz, 1H), 3.63 (s, 3H).

390

N-[4-(difluoromethoxy)-2,5-difluorophenyl]-6-(difluoromethyl)-1H-pyrrolo[2,3-b]pyridine-3-sulfonamide I-363

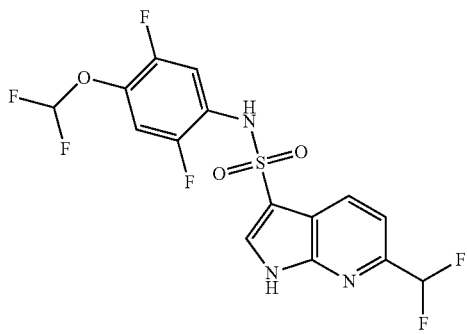 [SMILES: O=S(=O)(Nc1cc(F)c(OC(F)F)cc1F)c1c[nH]c2nc(C(F)F)ccc12]

Basic LCMS Method 1 (ES⁻): 424 (M−H)⁻, 95% purity.
$^1$H NMR (400 MHz, DMSO-d$_6$) δ 12.97 (s, 1H), 10.44 (s, 1H), 8.43-8.18 (m, 2H), 7.59 (d, J=8.2 Hz, 1H), 7.43-6.85 (m, 4H)

D.6. Method G: Synthesis of N-(4-cyano-2-fluorophenyl)-6-(pyridin-3-yl)-1H-indole-3-sulfonamide I-229

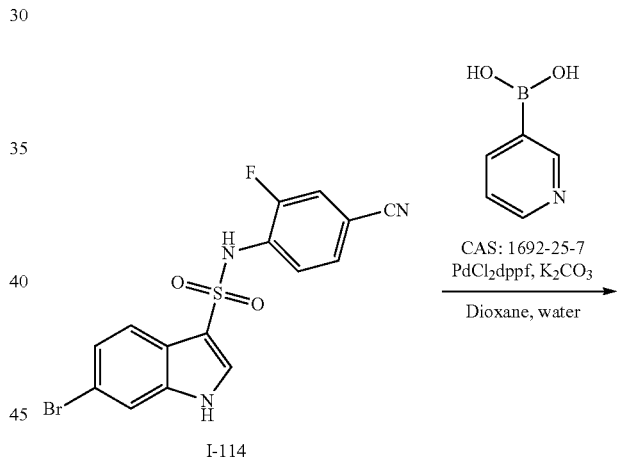

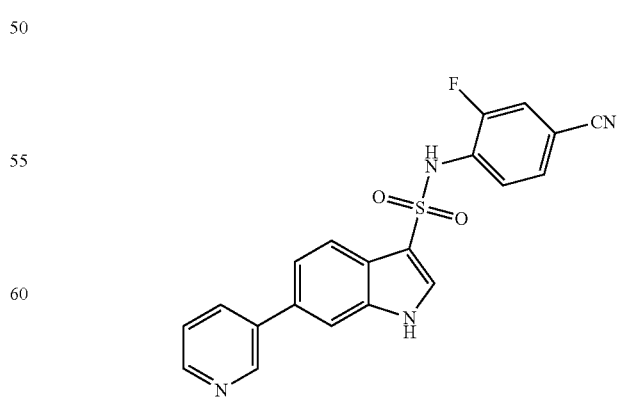

A mixture of 6-bromo-N-(4-cyano-2-fluorophenyl)-1H-indole-3-sulfonamide I-114 (70 mg, 0.18 mmol), 3-pyridylboronic acid (0.22 mmol) and potassium carbonate (76 mg, 0.55 mmol) was dissolved in dioxane:water (2.5:1, 5.8 mL) and flushed with argon via a septum. Subsequently, [1,1'-bis(diphenylphosphino)ferrocene]dichloropalladium (7 mg) was added and the reaction mixture was stirred in an argon atmosphere at 95° C. for 16 h. The mixture was diluted with an aqueous ammonium chloride solution and extracted three times with ethyl acetate. The combined organic layers were washed with brine, dried over MgSO$_4$ and concentrated by rotary evaporation. The crude mixture was purified by column chromatography eluting with 1% methanol in dichloromethane. It afforded 70 mg of N-(4-cyano-2-fluorophenyl)-6-(pyridin-3-yl)-1H-indole-3-sulfonamide I-229 as beige solid.

Yield: 39%.

Neutral LCMS Method 3 (ES$^+$): 393.1 (M+H)$^+$, 99% purity.

$^1$H NMR (600 MHz, DMSO-d$_6$) δ 12.24 (s, 1H), 10.83 (s, 1H), 8.86-8.93 (m, 1H), 8.55 (d, J=4.5 Hz, 1H), 8.15 (d, J=3.0 Hz, 1H), 8.07 (dt, J=7.9, 1.9 Hz, 1H), 7.95 (d, J=8.4 Hz, 1H), 7.74-7.76 (m, 1H), 7.73 (dd, J=10.7, 1.6 Hz, 1H), 7.59 (t, J=8.2 Hz, 1H), 7.53-7.57 (m, 2H), 7.48 (dd, J=7.9, 4.8 Hz, 1H).

The following compounds were synthesized according to Method G:

N-(4-cyano-2-fluorophenyl)-6-(thiophen-3-yl)-1H-indole-3-sulfonamide I-230 from 3-thienylboronic acid CAS 6165-69-1, Purified with 20% Ethyl Acetate in Cyclohexane

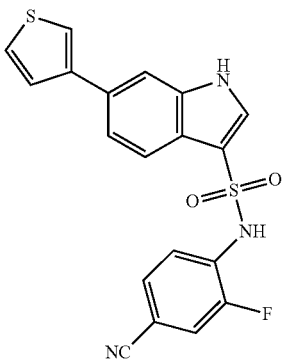 [SMILES: N#Cc1ccc(NS(=O)(=O)c2c[nH]c3cc(-c4ccsc4)ccc23)c(F)c1]

Yield: 69%.

Neutral LCMS Method 3 (ES$^+$): 396.0 (M+H)$^+$, 95% purity.

$^1$H NMR (500 MHz, DMSO-d$_6$) δ 12.07-12.15 (m, 1H), 10.77 (s, 1H), 8.08 (d, J=3.0 Hz, 1H), 7.81-7.87 (m, 2H), 7.69-7.74 (m, 2H), 7.61-7.64 (m, 1H), 7.53-7.61 (m, 4H).

N-(4-cyano-2-fluorophenyl)-6-(pyridin-4-yl)-1H-indole-3-sulfonamide I-231 from 4-pyridylboronic acid CAS 1692-15-5

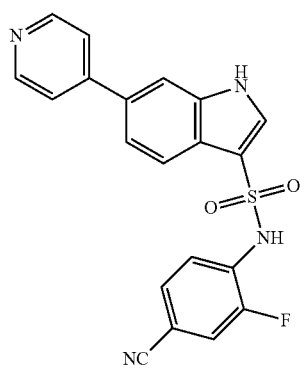 [SMILES: N#Cc1ccc(NS(=O)(=O)c2c[nH]c3cc(-c4ccncc4)ccc23)c(F)c1]

Yield: 25%.

Neutral LCMS Method 3 (ES$^+$): 393.1 (M+H)$^+$, 99% purity.

$^1$H NMR (500 MHz, DMSO-d$_6$) δ 12.28 (d, J=2.4 Hz, 1H), 10.82 (s, 1H), 8.62 (d, J=5.5 Hz, 2H), 8.17 (d, J=3.1 Hz, 1H), 7.96 (d, J=8.4 Hz, 1H), 7.83-7.85 (m, 1H), 7.70-7.74 (m, 3H), 7.53-7.65 (m, 3H).

N-(4-cyano-2-fluorophenyl)-6-(4-methoxyphenyl)-1H-indole-3-sulfonamide I-232 from (4-methoxyphenyl)boronic acid CAS 5720-07-0, Purified with 25% Ethyl Acetate in Cyclohexane

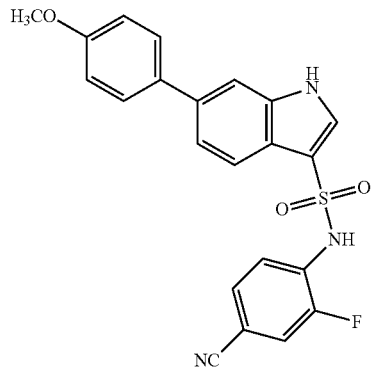 [SMILES: COc1ccc(-c2ccc3c(S(=O)(=O)Nc4ccc(C#N)cc4F)c[nH]c3c2)cc1]

Yield: 24%.

Neutral LCMS Method 3 (ES$^+$): 420.1 (M+H)$^+$, 97% purity.

$^1$H NMR (600 MHz, DMSO-d$_6$) δ 12.06-12.13 (m, 2H), 10.79 (s, 2H), 8.08 (d, J=2.9 Hz, 1H), 7.87 (d, J=8.4 Hz, 1H), 7.72 (d, J=10.1 Hz, 1H), 7.52-7.64 (m, 5H), 7.45 (dd, J=8.4, 1.4 Hz, 1H), 7.02 (d, J=8.8 Hz, 2H), 3.79 (s, 3H).

N-(4-cyano-2-fluorophenyl)-6-phenyl-1H-indole-3-sulfonamide I-233 from phenylboronic acid CAS 98-80-6, Purified with 33% Ethyl Acetate in Cyclohexane

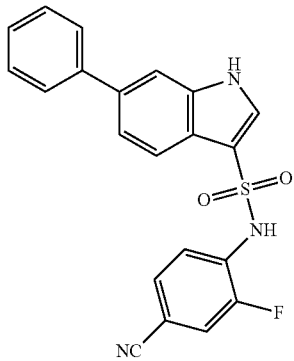 [SMILES: N#Cc1ccc(NS(=O)(=O)c2c[nH]c3cc(-c4ccccc4)ccc23)c(F)c1]

Yield: 57%.

Neutral LCMS Method 3 (ES$^+$): 390.1 (M+H)$^+$, 95% purity.

$^1$H NMR (500 MHz, DMSO-d$_6$) δ 12.13-12.19 (m, 1H), 10.79 (s, 1H), 8.12 (d, J=3.0 Hz, 1H), 7.91 (d, J=8.4 Hz, 1H), 7.72 (dd, J=10.7, 1.8 Hz, 1H), 7.64-7.69 (m, 3H), 7.53-7.62 (m, 2H), 7.50 (dd, J=8.4, 1.6 Hz, 1H), 7.43-7.48 (m, 2H), 7.32-7.37 (m, 1H).

N-(4-cyano-2-fluorophenyl)-6-(3,5-dimethyl-1,2-oxazol-4-yl)-1H-indole-3-sulfonamide I-234 from (3,5-dimethylisoxazol-4-yl)boronic acid CAS 16114-47-9, Purified with 66% Ethyl Acetate in Petroleum Ether

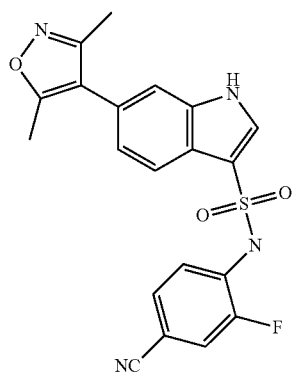 [SMILES: Cc1noc(C)c1-c1ccc2c(S(=O)(=O)Nc3ccc(C#N)cc3F)c[nH]c2c1]

Yield: 34%.

Neutral LCMS Method 3 (ES$^+$): 411.2 (M+H)$^+$, 98% purity.

$^1$H NMR (500 MHz, DMSO-d$_6$) δ 12.15 (s, 1H), 10.82 (s, 1H), 8.14 (d, J=3.0 Hz, 1H), 7.91 (d, J=8.3 Hz, 1H), 7.73 (d, J=10.8 Hz, 1H), 7.61 (t, J=8.2 Hz, 1H), 7.56 (d, J=8.5 Hz, 1H), 7.43 (s, 1H), 7.19 (dd, J=8.3, 1.3 Hz, 1H), 2.21 (s, 3H), 2.39 (s, 3H)

N-(4-cyano-2-fluorophenyl)-6-(thiophen-2-yl)-1H-indole-3-sulfonamide I-235 from 2-thienylboronic acid CAS 6165-68-0, Purified with 50% Ethyl Acetate in Petroleum Ether

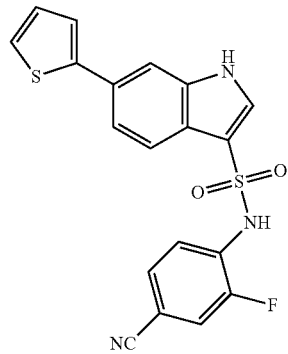 [SMILES: N#Cc1ccc(NS(=O)(=O)c2c[nH]c3cc(-c4cccs4)ccc23)c(F)c1]

Yield: 94%.

Neutral LCMS Method 3 (ES$^+$): 398.1 (M+H)$^+$, 96% purity.

$^1$H NMR (500 MHz, DMSO-d$_6$) δ 12.12 (d, J=2.4 Hz, 1H), 10.82 (s, 1H), 8.11 (d, J=3.0 Hz, 1H), 7.85 (d, J=8.4 Hz, 1H), 7.73 (dd, J=10.8, 1.5 Hz, 1H), 7.67 (d, J=1.0 Hz, 1H), 7.46-7.61 (m, 5H), 7.12 (dd, J=5.1, 3.7 Hz, 1H).

N-(4-chloro-2,5-difluorophenyl)-6-(thiophen-3-yl)-1H-indole-3-sulfonamide I-236 from 3-thienylboronic acid CAS 6165-69-1, Purified with 33% Ethyl Acetate in Petroleum Ether

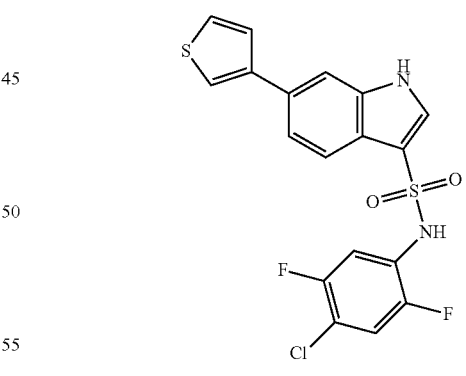

Yield: 76%.

Neutral LCMS Method 3 (ES$^+$): 425.1 (M+H)$^+$, 100% purity.

$^1$H NMR (600 MHz, DMSO-d$_6$) δ 12.06 (s, 1H), 10.44 (s, 1H), 8.01 (d, J=3.0 Hz, 1H), 7.83 (dd, J=2.9, 1.3 Hz, 1H), 7.79 (d, J=8.4 Hz, 1H), 7.70-7.73 (m, 1H), 7.63 (dd, J=5.0, 2.9 Hz, 1H), 7.53-7.58 (m, 2H), 7.51 (dd, J=9.9, 6.9 Hz, 1H), 7.35 (dd, J=10.5, 7.0 Hz, 1H).

D.7. Synthesis of N-(4-cyanophenyl)-6-(methylsulfinyl)-1H-indole-3-sulfonamide I-237

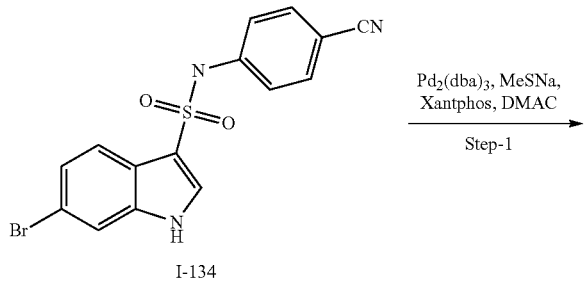

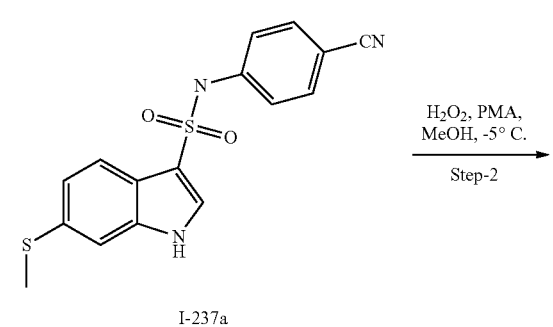

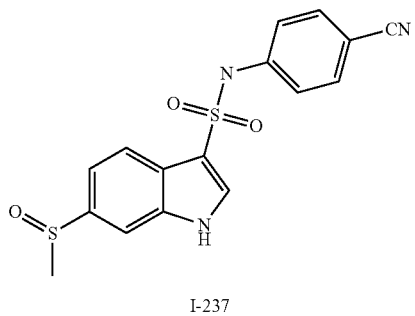

Step-1: Synthesis of N-(4-cyanophenyl)-6-(methylthio)-1H-indole-3-sulfonamide I-237a To a solution of 6-bromo-N-(4-cyanophenyl)-1H-indole-3-sulfonamide I-134 (0.05 g, 0.13 mmol) in N,N-dimethylacetamide (2 mL) was added Xantphos (0.016 g, 0.03 mmol) and sodium methanethiolate (0.012 g, 0.16 mmol) and the reaction mixture was purged with argon for 5 min. Pd$_2$(dba)$_3$ (0.02 g, 0.03 mmol) was added and the reaction mixture was again purged with argon for 5 min. The reaction mixture was heated in microwave at 180° C. for 30 min. Progress of the reaction was monitored by TLC and LCMS. After completion, the reaction mixture was quenched with saturated NH$_4$Cl (50 mL) and saturated NaHCO$_3$ (50 mL) and extracted with EtOAc (20 mL). The organic layer was separated, washed with brine (10 mL), dried over anhydrous Na$_2$SO$_4$ and concentrated in vacuum. The crude obtained was purified by column chromatography (silica, 100-200 mesh, 2% MeOH in DCM) to afford 0.04 g of N-(4-cyanophenyl)-6-(methylthio)-1H-indole-3-sulfonamide I-237a as an off-white solid.

Yield: 88%.

Basic LCMS Method 2 (ES$^-$): 341.95 (M–H)$^-$, 97% purity.

$^1$H NMR (400 MHz, DMSO-d$_6$) δ 7.14 (d, J=8.80 Hz, 1H) 7.22 (d, J=8.80 Hz, 2H) 7.30 (s, 1H) 7.62 (d, J=8.31 Hz, 2H) 7.74 (d, J=8.80 Hz, 1H) 8.08 (s, 1H) 10.93 (brs, 1H) 11.99 (brs, 1H) (3H's merged in solvent peak).

Step-2: Synthesis of N-(4-cyanophenyl)-6-(methylsulfinyl)-1H-indole-3-sulfonamide I-237

To a solution of N-(4-cyanophenyl)-6-(methylthio)-1H-indole-3-sulfonamide I-237a (0.12 g, 0.34 mmol) in MeOH (14 mL) was added phosphomolybdic acid (0.13 g, 0.07 mmol) followed by dropwise addition of H$_2$O$_2$ (0.004 mL, 0.34 mmol) at −5° C. The reaction mixture was stirred at −5° C. for 1 h. Progress of the reaction was monitored by TLC and LCMS. After completion, the reaction mixture was quenched with saturated Na$_2$S$_2$O$_3$ (50 mL) solution and saturated NaHCO$_3$ (10 mL) solution and extracted with EtOAc (3×50 mL). The organic layer was separated, washed with brine (50 mL), dried over anhydrous Na$_2$SO$_4$ and concentrated under vacuum. The crude obtained was purified by column chromatography (silica, 100-200 mesh, 3% MeOH in DCM) to afford 0.12 g of N-(4-cyanophenyl)-6-(methylsulfinyl)-1H-indole-3-sulfonamide I-237 as light brown solid.

Yield: 95%.

Basic LCMS Method 2 (ES$^-$): 360 (M–H)$^-$, 99% purity.

$^1$H NMR (400 MHz, DMSO-d$_6$) δ 2.71 (s, 3H) 7.23 (d, J=8.80 Hz, 2H) 7.45 (d, J=8.80 Hz, 1H) 7.62 (d, J=8.80 Hz, 2H) 7.79 (s, 1H) 7.97 (s, 1H) 8.31 (brs, 1H) 11.03 (s, 1H) 12.41 (brs, 1H).

D.8. Synthesis of 6-(methylsulfonyl)-N-(2,2,6-trifluoro-1,3-benzodioxol-5-yl)-1H-indole-3-sulfonamide I-238

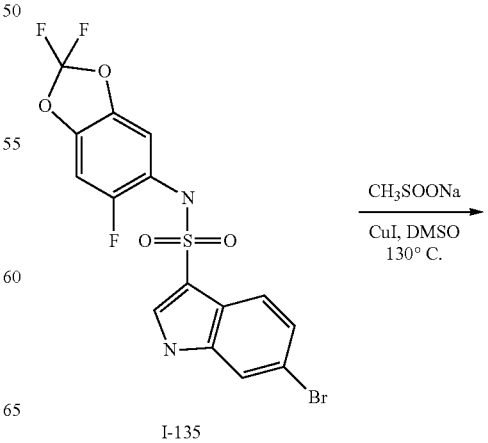

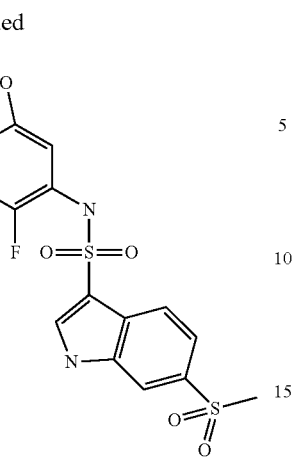

I-238

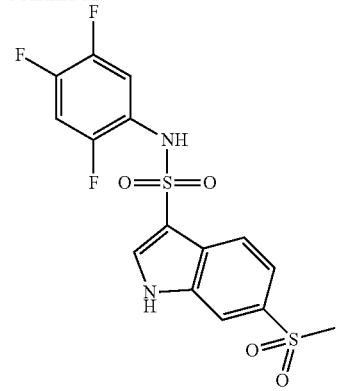

I-239

To a solution of 6-bromo-N-(2,2,6-trifluoro-1,3-benzodioxol-5-yl)-1H-indole-3-sulfonamide I-135 (0.18 g, 0.40 mmol) in DMSO (4 mL) was added sodium methane sulfinate (0.18 g, 1.80 mmol) and CuI (0.34 g, 1.78 mmol). The reaction mixture was heated at 130° C. for 16 h. Progress of the reaction was monitored by TLC and LCMS. After completion, the reaction mixture was quenched with H₂O (20 mL) and extracted with EtOAc (30 mL). The organic layer was separated, washed with brine (100 mL), dried over anhydrous Na₂SO₄ and concentrated in vacuum. The crude obtained was purified by column chromatography (silica, 100-200 mesh, 5% MeOH in DCM) to afford 0.022 g of 6-(methylsulfonyl)-N-(2,2,6-trifluoro-1,3-benzodioxol-5-yl)-1H-indole-3-sulfonamide I-238 as an off-white solid.

Yield: 12%.

Basic LCMS Method 2 (ES⁻): 447 (M–H)⁻, 96% purity.

¹H NMR (400 MHz, DMSO-d₆) δ 3.22 (s, 3H) 7.34 (d, J=6.36 Hz, 1H) 7.44 (d, J=8.80 Hz, 1H) 7.71 (dd, J=8.31, 1.47 Hz, 1H) 7.95 (d, J=8.31 Hz, 1H) 8.03 (s, 1H) 8.17 (d, J=2.93 Hz, 1H) 10.20 (s, 1H) 12.51 (brs, 1H).

D.9. Synthesis of 6-methylsulfonyl-N-(2,4,5-trifluorophenyl)-1H-indole-3-sulfonamide I-239

To a solution of 6-bromo-N-(2,4,5-trifluorophenyl)-1H-indole-3-sulfonamide I-136 (0.40 g, 0.98 mmol) in DMSO (15 mL) was added sodium methane sulfinate (0.45 g, 4.41 mmol) and CuI (0.84 g, 4.41 mmol). The reaction mixture was heated at 130° C. for 16 h. Progress of the reaction was monitored by TLC and LCMS. After completion, the reaction mixture was quenched with saturated NH₄Cl (30 mL) and saturated NaHCO₃ (60 mL) solution. The product was extracted with EtOAc (60 mL). The organic layer was separated, dried over anhydrous Na₂SO₄ and concentrated under vacuum. The crude obtained was purified by flashcolumn chromatography to afford 6-methylsulfonyl-N-(2,4,5-trifluorophenyl)-1H-indole-3-sulfonamide I-239 (0.02 g, 5%) as a white solid.

Yield: 5%.

Basic LCMS Method 2 (ES⁻): 403.00 (M–H)⁻, 99% purity.

¹H NMR (400 MHz, DMSO-d₆) δ 3.22 (s, 3H) 7.31-7.41 (m, 1H) 7.41-7.53 (m, 1H) 7.72 (d, J=8.31 Hz, 1H) 7.96 (d, J=8.31 Hz, 1H) 8.04 (s, 1H) 8.22 (d, J=2.45 Hz, 1H) 10.34 (s, 1H) 12.54 (brs, 1H).

D.10. Synthesis of N-(2,2-difluoro-1,3-benzodioxol-4-yl)-6-methylsulfonyl-1H-indole-3-sulfonamide I-240

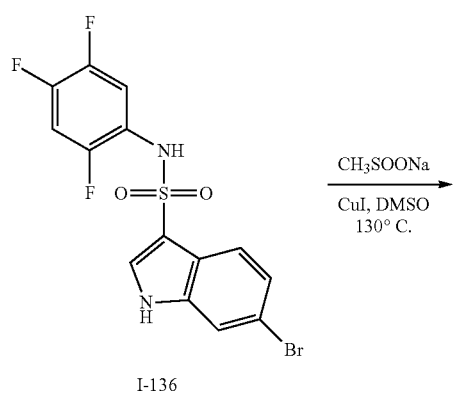

I-136

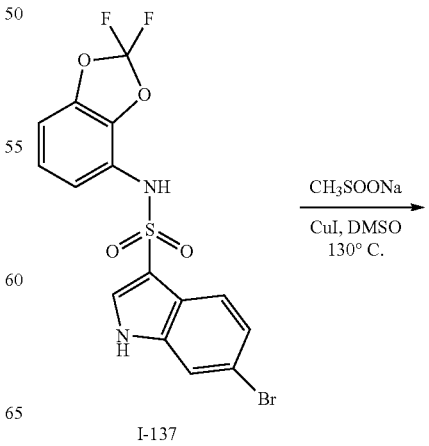

I-137

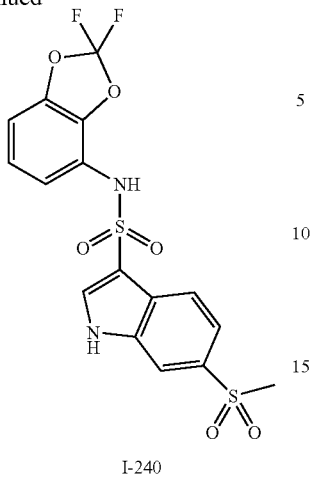

I-240

To a solution of 6-bromo-N-(2,2-difluoro-1,3-benzodioxol-4-yl)-1H-indole-3-sulfonamide I-137 (0.13 g, 0.30 mmol) in DMSO (4 mL) was added sodium methane sulfinate (0.15 g, 1.50 mmol) and CuI (0.28 g, 1.50 mmol). The reaction mixture was heated at 130° C. for 16 h. Progress of the reaction was monitored by TLC and LCMS. After completion, the reaction mixture was quenched with saturated NH₄Cl (50 mL) and saturated NaHCO₃ (50 mL) solution. The product was extracted with EtOAc (4×50 mL). The organic layer was separated, washed with brine (2×50 mL), dried over anhydrous Na₂SO₄ and concentrated under vacuum. The crude obtained was purified by column chromatography (silica, 100-200 mesh, 55 to 65% EtOAc in hexanes) to afford 0.032 g of N-(2,2-difluoro-1,3-benzodioxol-4-yl)-6-methylsulfonyl-1H-indole-3-sulfonamide I-240 as an off-white solid.

Yield: 25%.

Basic LCMS Method 2 (ES⁻): 429.00 (M−H)⁻, 99% purity.

¹H NMR (400 MHz, DMSO-d₆) δ 3.19 (s, 3H) 6.95 (d, J=8.31 Hz, 1H) 7.07 (t, J=8.07 Hz, 1H) 7.11-7.17 (m, 1H) 7.69 (d, J=8.80 Hz, 1H) 7.88 (d, J=8.31 Hz, 1H) 8.03 (s, 1H) 8.22 (d, J=2.45 Hz, 1H) 10.46 (s, 1H) 12.54 (brs, 1H).

D.11. Synthesis of N-(4-azido-2-fluorophenyl)-6-chloro-1H-indole-3-sulfonamide I-241

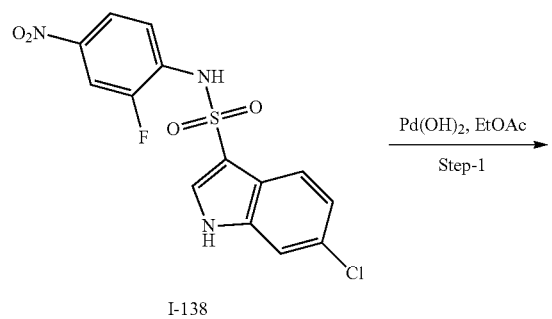

I-138

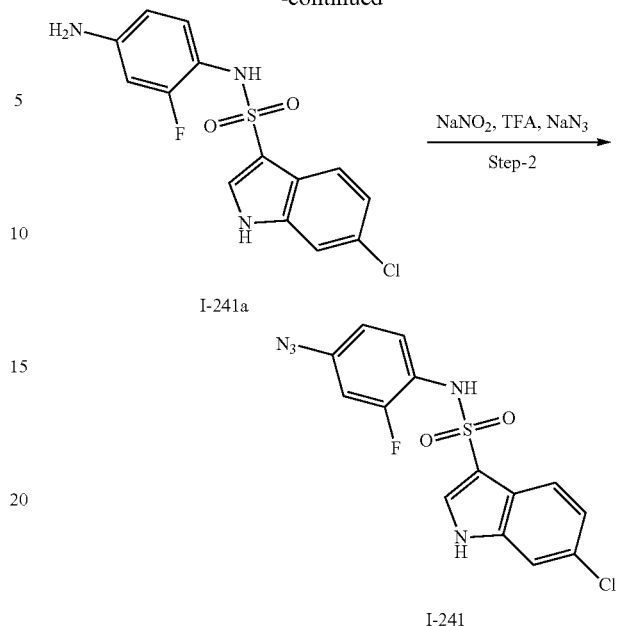

Step-1: Synthesis of N-(4-amino-2-fluorophenyl)-6-chloro-1H-indole-3-sulfonamide I-241a To a solution of 6-chloro-N-(2-fluoro-4-nitro-phenyl)-1H-indole-3-sulfonamide I-138 (0.32 g, 0.87 mmol) in EtOAc (15 mL) was added Pd(OH)₂ (0.10 g) at 0° C. and the reaction mixture was stirred at room temperature for 3 h under hydrogen pressure. Progress of the reaction was monitored by TLC and LCMS. After completion, the reaction mixture was filtered through a celite pad, washed with EtOAc (3×20 mL) and the filtrate was concentrated in vacuum. The crude obtained was washed with pentane (10 mL) and dried in vacuum to afford N-(4-amino-2-fluorophenyl)-6-chloro-1H-indole-3-sulfonamide I-241a (0.33 g crude) as a grey solid.

This compound was used as such for the next reaction without further purification.

Basic LCMS Method 2 (ES⁻): 338.00 (M−H)⁻, 80% purity.

¹H NMR (400 MHz, DMSO-d₆) δ 5.33 (s, 2H) 6.12-6.18 (m, 2H) 6.60 (t, J=8.80 Hz, 1H) 7.16 (d, J=8.40 Hz, 1H) 7.51 (s, 1H) 7.64-7.69 (m, 2H) 9.14 (s, 1H) 11.92 (s, 1H).

Step-2: Synthesis of N-(4-azido-2-fluorophenyl)-6-chloro-1H-indole-3-sulfonamide I-241

To a solution of N-(4-amino-2-fluorophenyl)-6-chloro-1H-indole-3-sulfonamide I-241a (0.15 g, 0.44 mmol) in TFA (3 mL) was added NaNO₂ (0.12 g, 1.77 mmol) portion wise at 0° C. and the reaction mixture was stirred at same temperature for 30 min. NaN₃ (0.09 g, 1.46 mmol) was added portion wise at 0° C. and the reaction mixture was stirred at 0° C. for 30 min. Progress of the reaction was monitored by TLC and LCMS. After completion, the reaction mixture was poured in to ice-cold H₂O (10 mL) and extracted with EtOAc (2×10 mL). The organic layer was separated, washed with brine (10 mL), dried over anhydrous Na₂SO₄ and concentrated in vacuum. The crude obtained was purified by column chromatography (silica, 100-200 mesh, 30% EtOAc in hexanes) to afford 0.03 g of N-(4-azido-2-fluorophenyl)-6-chloro-1H-indole-3-sulfonamide I-241 as a yellow solid.

Yield: 19%.

Basic LCMS Method 2 (ES⁻): 364.00 (M–H)⁻, 96% purity.

¹H NMR (400 MHz, DMSO-d₆) δ 6.83-6.99 (m, 2H) 7.16-7.31 (m, 2H) 7.52 (s, 1H) 7.68-7.77 (m, 1H) 7.84 (brs, 1H) 9.94 (s, 1H) 12.04 (brs, 1H).

D.12. Synthesis of 6-chloro-N-(4-chloro-2,5-difluorophenyl)-7-(3,5-dimethyl-1,2-oxazol-4-yl)-1H-indole-3-sulfonamide I-250

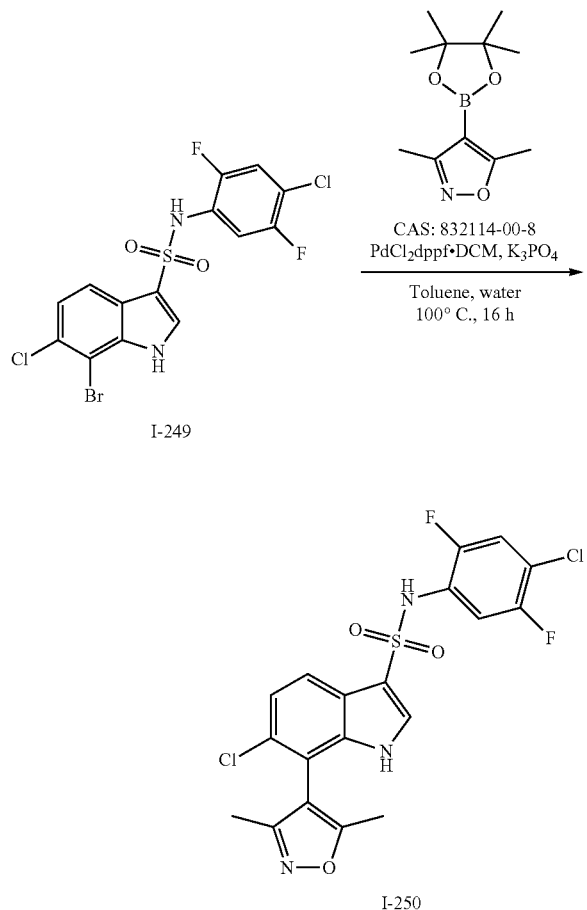

To a solution of 7-bromo-6-chloro-N-(4-chloro-2,5-difluorophenyl)-1H-indole-3-sulfonamide I-249 (0.16 g, 0.35 mmol) and 3,5-dimethylisoxazole-4-boronic acid pinacol ester (0.39 g, 1.73 mmol) in toluene (8 mL) and H₂O (1 mL) was added K₃PO₄ (0.22 g, 1.04 mmol). The reaction mixture was purged with argon for 20 min followed by addition of PdCl₂(dppf).DCM (0.03 g, 0.03 mmol). The reaction mixture was heated at 100° C. for 16 h.

Progress of the reaction was monitored by TLC and LCMS. After completion, the reaction mixture was diluted with H₂O (100 mL) and extracted with EtOAc (200 mL). The organic layer was separated, dried over anhydrous Na₂SO₄ and concentrated under vacuum. The crude obtained was purified by Combi-flash column chromatography (40% EtOAc in hexanes) to afford 6-chloro-N-(4-chloro-2,5-difluorophenyl)-7-(3,5-dimethyl-1,2-oxazol-4-yl)-1H-indole-3-sulfonamide I-250 (0.04 g) as a white solid.

Yield: 24%.

Basic LCMS Method 2 (ES⁻): 470.00 (M–H)⁻, 98% purity.

¹H NMR (400 MHz, DMSO-d₆) δ 1.98 (s, 3H) 2.15 (s, 3H) 7.31-7.38 (m, 1H) 7.41 (d, J=8.80 Hz, 1H) 7.56 (dd, J=9.78, 6.85 Hz, 1H) 7.85 (d, J=8.80 Hz, 1H) 8.01 (d, J=3.42 Hz, 1H) 10.54 (s, 1H) 12.15 (brs, 1H).

D.13. Synthesis of 6-chloro-N-(4-chloro-2,5-difluorophenyl)-7-cyano-1H-indole-3-sulfonamide I-256

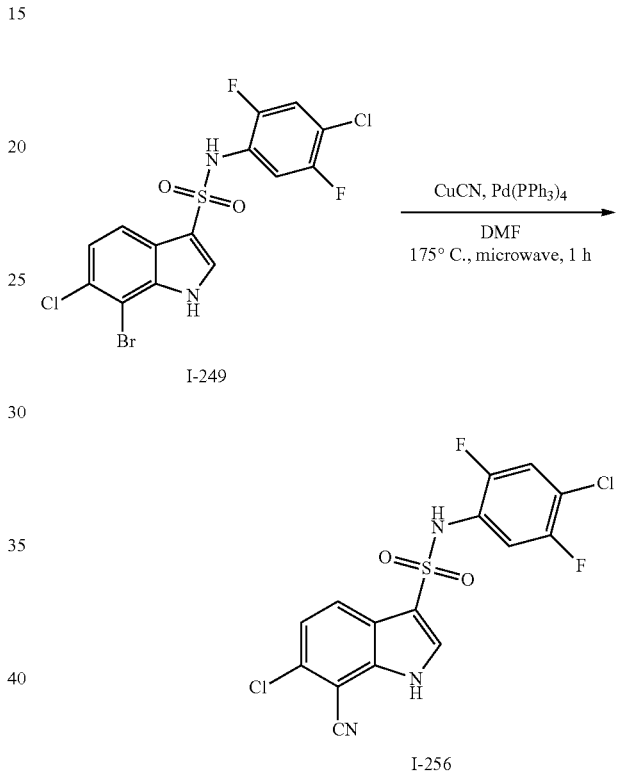

To a solution of 7-bromo-6-chloro-N-(4-chloro-2,5-difluorophenyl)-1H-indole-3-sulfonamide I-249 (0.13 g, 0.28 mmol) in DMF (9 mL) was added CuCN (0.05 g, 0.56 mmol) and the reaction mixture was purged with argon for 20 min. Pd(PPh₃)₄ (0.03 g, 0.03 mmol) was added and the reaction mixture was heated in microwave at 175° C. for 1 h. Progress of the reaction was monitored by TLC and LCMS. After completion, the reaction mixture was diluted with H₂O (100 mL) and EtOAc (100 mL), filtered through celite and extracted with EtOAc (100 mL). The organic layer was separated, dried over anhydrous Na₂SO₄ and concentrated under vacuum. The crude obtained was purified by prep HPLC to afford 6-chloro-N-(4-chloro-2,5-difluorophenyl)-7-cyano-1H-indole-3-sulfonamide I-256 (0.023 g, 20%) as a white solid.

Yield: 20%.

Basic LCMS Method 2 (ES⁻): 400 (M–H)⁻, 99% purity.

¹H NMR (400 MHz, DMSO-d₆) δ 7.35 (dd, J=10.27, 6.97 Hz, 1H) 7.50-7.56 (m, 2H) 8.07 (d, J=8.68 Hz, 1H) 8.16 (s, 1H) 10.58 (brs, 1H) 13.2 (brs, 1H).

D.14. Synthesis of 6-chloro-N-(4-chloro-2,5-difluorophenyl)-7-(methylsulfonyl)-1H-indole-3-sulfonamide I-261

D.15. Method H: Synthesis of 6-chloro-N-(5-chloro-3,6-difluoropyridin-2-yl)-7-methoxy-1H-indole-3-sulfonamide I-310

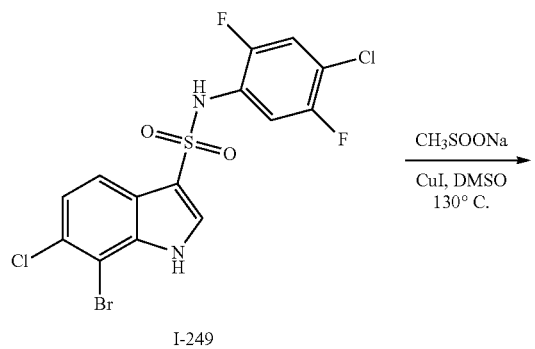

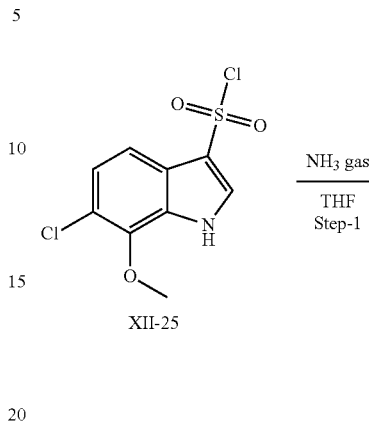

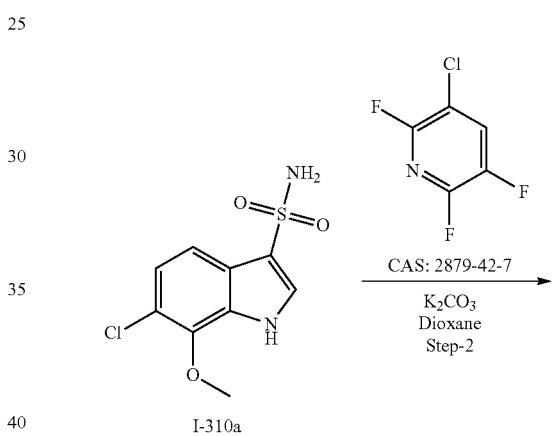

To a solution of 7-bromo-6-chloro-N-(4-chloro-2,5-difluorophenyl)-1H-indole-3-sulfonamide I-249 (0.15 g, 0.32 mmol) in DMSO (10 mL) was added CuI (0.25 g, 1.29 mmol) and sodium methanesulfonate (0.13 g, 1.29 mmol). The reaction mixture was heated at 130° C. for 6 h. Progress of the reaction was monitored by TLC and LCMS. After completion, the reaction mixture was diluted with saturated NH₄Cl (35 mL), saturated NaHCO₃ (15 mL) and extracted with EtOAc (2×50 mL). The organic layer was separated, dried over anhydrous Na₂SO₄ and concentrated under vacuum. The crude obtained was purified by column chromatography (silica, 100-200 mesh, 40% EtOAc in hexanes) to afford 6-chloro-N-(4-chloro-2,5-difluorophenyl)-7-(methylsulfonyl)-1H-indole-3-sulfonamide I-261 (0.015 g) as an off-white solid.

Yield: 10%.

Basic LCMS Method 2 (ES⁻): 453 (M−H)⁻, 98% purity.

¹H NMR (400 MHz, DMSO-d₆) δ 3.52 (s, 3H) 7.36-7.40 (m, 1H) 7.55 (d, J=8.80 Hz, 2H) 7.88 (d, J=3.42 Hz, 1H) 8.10 (d, J=8.80 Hz, 1H) 10.65 (brs, 1H) 11.76 (brs, 1H).

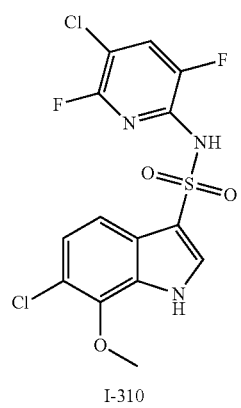

Step-1: Synthesis of 6-chloro-7-methoxy-1H-indole-3-sulfonamide I-310a

To a solution of 6-chloro-7-methoxy-1H-indole-3-sulfonyl chloride XII-25 (170 mg, 0.265 mmol) in THF (10 mL), NH₃ gas was purged at 0° C. for 10 min. The reaction mixture was stirred at room temperature for 30 min. Progress of the reaction was monitored by TLC. After completion, the reaction mixture was concentrated under vacuum. The crude material was washed with DCM:Hexane (1:4, 10 mL) to afford 6-chloro-7-methoxy-1H-indole-3-sulfonamide I-310a (150 mg) as brown solid.

This compound was used as such for the next reaction without further purification.

Yield: 78%.

Basic LCMS Method 2 (ES⁺): 259 (MH)⁺, 36% purity.

Step-2: Synthesis of 6-chloro-N-(5-chloro-3,6-difluoropyridin-2-yl)-7-methoxy-1H-indole-3-sulfonamide I-310

To a stirred solution of 6-chloro-7-methoxy-1H-indole-3-sulfonamide I-310a (100 mg, 0.384 mmol) and 3-chloro-2,5,6-trifluoro-pyridine (64.3 mg, 0.384 mmol) in 1,4-Dioxane (10 mL), K₂CO₃ (53 mg, 0.384 mmol) was added at RT. The reaction mixture was heated at 100° C. for 8 h. Progress of the reaction was monitored by TLC. After completion, the reaction mixture was filtered through a celite bed. The filtrate was concentrated under vacuo. The crude obtained was purified by column chromatography (silica, 100-200 mesh, 10-50% EtOAc in hexanes) to afford 60 mg; which was re-purified by Prep-TLC using 40% EtOAc in hexane to afford 6-chloro-N-(5-chloro-3,6-difluoro-2-pyridyl)-7-methoxy-1H-indole-3-sulfonamide I-310 (14 mg) as an off white solid.

Yield: 9%.

Basic LCMS Method 2 (ES⁻): 406 (M−H)⁻, 97% purity.

$^1$H NMR (400 MHz, DMSO-d₆) δ 3.91 (s, 3H) 7.25 (d, J=8.80 Hz, 1H) 7.63 (d, J=8.31 Hz, 1H) 8.10 (br s, 1H) 8.17-8.24 (m, 1H) 11.52 (br s, 1H) 12.58 (brs, 1H).

The following compounds in Table 8 may be synthesized according methods analogous to Method H.

N-(5-chloro-3,6-difluoropyridin-2-yl)-1H-pyrrolo[3,2-h]quinoline-3-sulfonamide I-316

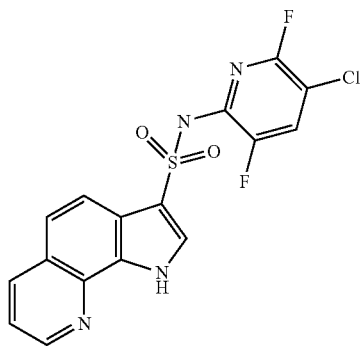 [SMILES: O=S(=O)(Nc1nc(F)c(Cl)cc1F)c1c[nH]c2c1ccc1cccnc12]

Basic LCMS Method 1 (ES⁺): 395 (M+H)⁺, 98% purity.

$^1$H NMR (400 MHz, DMSO-d₆) δ 13.29 (s, 1H), 11.52 (s, 1H), 8.92 (dd, J=4.3, 1.7 Hz, 1H), 8.45 (dd, J=8.2, 1.7 Hz, 1H), 8.23-8.03 (m, 3H), 7.72 (d, J=8.8 Hz, 1H), 7.58 (dd, J=8.2, 4.3 Hz, 1H).

N-(5-chloro-3,6-difluoropyridin-2-yl)-1,6,7,8-tetrahydrocyclopenta[g]indole-3-sulfonamide I-317

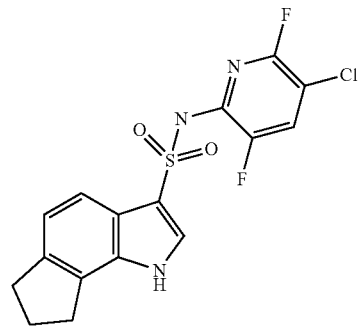 [SMILES: O=S(=O)(Nc1nc(F)c(Cl)cc1F)c1c[nH]c2c3c(ccc12)CCC3]

Basic LCMS Method 1 (ES⁺): 384 (M+H)⁺, 93% purity.

TABLE 8

| No | Sulfonyl chlorides XII | Conditions, Time (Step-1) | Yield (%) | Fluoro pyridine (Step-2) | Conditions, Time (Step-2) | Purification conditions | Yield (%) |
|---|---|---|---|---|---|---|---|
| I-316 | XII-1 | DCM, 16 h | 51 | 2879-42-7 | CsCO₃, DMF, 140° C., mw, 1 h | 30-60% AcOEt/Heptane | 12 |
| I-317 | XII-10 | NH4OH aq, ACN, 1 h | 70 | 2879-42-7 | CsCO₃, DMF, 70° C., 2 h | Basic prep LCMS Method 1 | 20 |

D.16. Synthesis of N-(4-chloro-2,5-difluorophenyl)-2-fluoro-6-methoxy-1H-indole-3-sulfonamide I-318

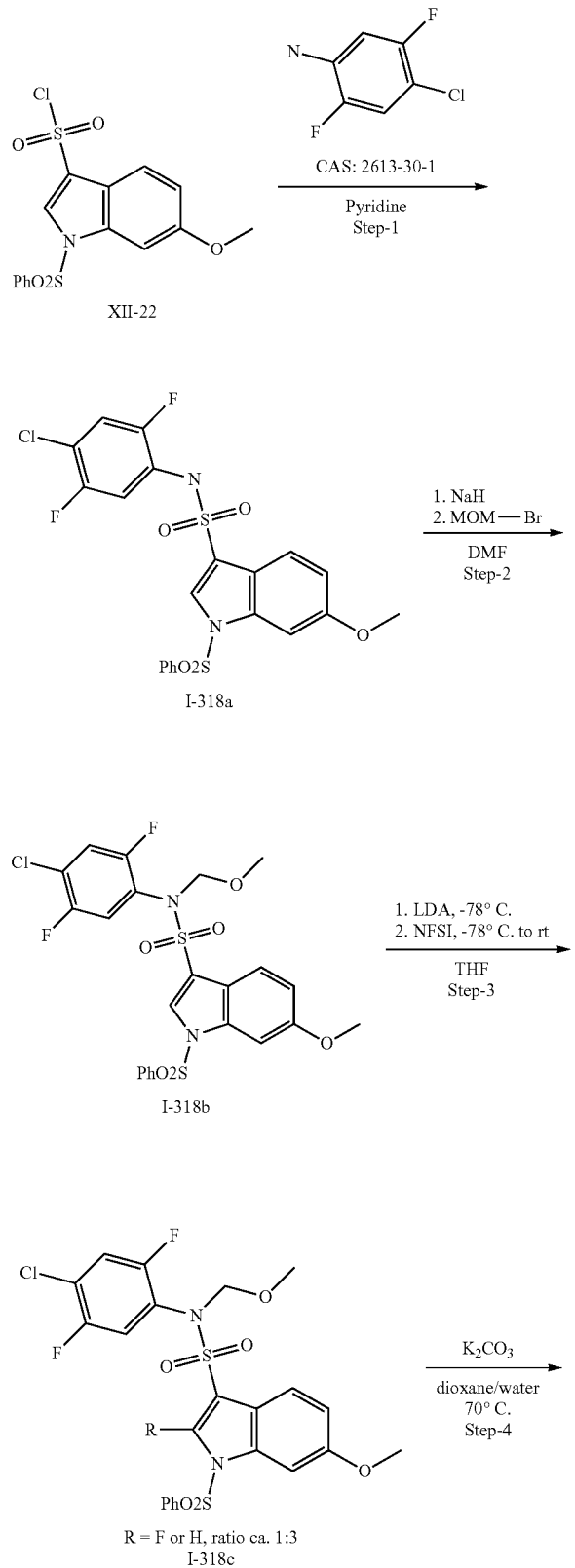

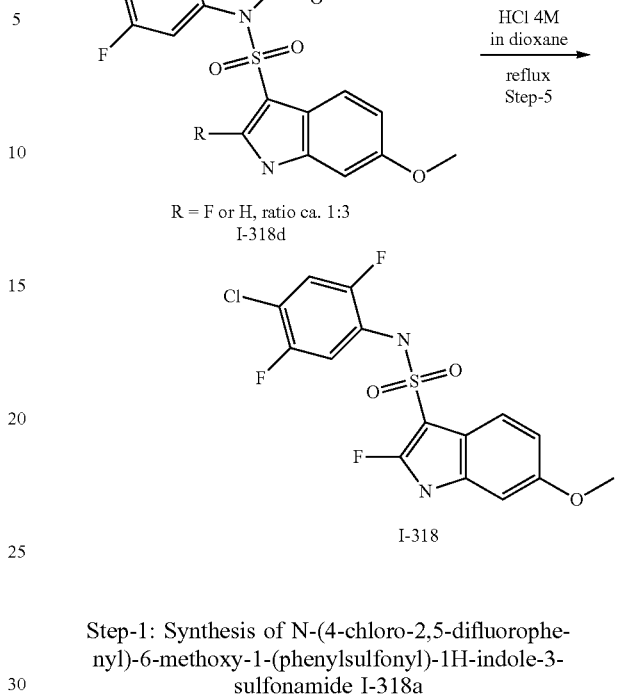

Step-1: Synthesis of N-(4-chloro-2,5-difluorophenyl)-6-methoxy-1-(phenylsulfonyl)-1H-indole-3-sulfonamide I-318a Indole XII-22 (1.348 g, 3.49 mmol) and 4-chloro-2,5-difluoroaniline (569 mg, 3.48 mmol) were heated 1 h in pyridine (5 mL) at 80° C. The oily residue was diluted with ethyl acetate, washed twice with brine, dried over magnesium sulfate and evaporated to dryness. The crude residue was then dissolved in methanol (150 mL) and refluxed to dissolve most of the product. The solution was then evaporated to ca. 50 mL. After cooling to rt the precipitate was filtered. It was then taken up in dichloromethane (12 mL), sonicated, and filtered again to afford the desired product I-318a (763 mg) as an off-white solid. Purification of the mother waters by flash chromatography (SiO$_2$, dichloromethane) yielded additional 273 mg of desired product I-318a Yield: 58%

Neutral LCMS Method 3 (ES$^+$): 512.9 (M+H)$^+$, 97% purity.

$^1$H NMR (600 MHz, CDCl$_3$) δ: 8.03 (s, 1H), 7.84 (d, J=7.5 Hz, 2H), 7.63 (t, J=7.5 Hz, 1H), 7.58 (d, J=8.8 Hz, 1H), 7.49 (t, J=7.8 Hz, 2H), 7.46 (d, J=2.2 Hz, 1H), 7.43 (dd, J=9.6, 6.8 Hz, 1H), 7.06 (br s, 1H, NH), 6.97-6.92 (m, 2H), 3.87 (s, 3H).

Step-2: Synthesis of N-(4-chloro-2,5-difluorophenyl)-6-methoxy-N-(methoxymethyl)-1-(phenylsulfonyl)-1H-indole-3-sulfonamide I-318b I-318a (200 mg, 0.39 mmol) and sodium hydride (60% dispersion in mineral oil, 19 mg, 0.47 mmol) were placed in dry dimethylformamide (2.5 mL) under argon atmosphere. The solution was stirred at rt for 15 min, then bromomethyl methyl ether (36 μL, 0.47 mmol) in dry DMF (1.5 mL) was added and the solution was stirred at rt for 2.5 h. The reaction mixture was quenched with water, extracted three times with ethyl acetate, washed with brine, dried over magnesium sulfate and evaporated to dryness. The crude residue was purified by flash chromatography (SiO$_2$, CombiFlash, 10% to 20% AcOEt in Petroleum Ether) to afford the desired product I-318b (187 mg) as a colorless oil.

Yield: 86%

$^1$H NMR (600 MHz, CDCl$_3$) δ: 7.92-7.86 (m, 3H), 7.65 (t, J=7.7 Hz, 1H), 7.52 (t, J=7.9 Hz, 2H), 7.49 (s, 1H), 7.42 (d, J=9.1 Hz, 1H), 7.12 (dd, J=8.7, 6.3 Hz, 1H), 7.02 (dd, J=9.0, 6.4 Hz, 1H), 6.93 (dd, J=8.7, 2.4 Hz, 1H), 5.01 (d, J=2.2 Hz, 2H), 3.89 (d, J=2.1 Hz, 3H), 3.42 (d, J=2.1 Hz, 3H).

Neutral LCMS Method 3 (ES$^+$): 574.1 (M+NH$_4$)$^+$, 98% purity.

Step-3: Synthesis of N-(4-chloro-2,5-difluorophenyl)-2-fluoro-6-methoxy-N-(methoxymethyl)-1-(phenylsulfonyl)-1H-indole-3-sulfonamide I-318c I-318b (160 mg, 0.287 mmol) was placed in a flask in dry tetrahydrofuran (1.5 mL) under argon atmosphere, and the solution was cooled to −78° C. Then lithium diisopropylamide was freshly prepared by adding dropwise n-Buli (1.6 M in hexanes, 341 µL 0.545 mmol) at −78° C. to a solution of diisopropylamine (81 µL, 0.574 mmol) in dry tetrahydrofuran (2 mL) This solution was then added dropwise to the reaction mixture, that was subsequently stirred at −78° C. for 50 min. N-Fluorobenzenesulfonimide (136 mg, 0.430 mmol) in dry tetrahydrofuran (2 mL) was then added and the reaction mixture was allowed to slowly reach room temperature overnight. The solution was then quenched with water, extracted three times with dichloromethane, washed with brine, dried over magnesium sulfate and evaporated to dryness. The crude residue was purified by flash chromatography (SiO$_2$, CombiFlash, 10% to 20% AcOEt in Petroleum Ether) to afford the desired product I-318c, in a mixture with the starting material I-318b (ratio ca. 1:3, 66 mg), as a light yellow oil.

This compound was used as such for the next reaction without additional purification.

Neutral LCMS Method 3 (ES$^+$): 592.0 (M+NH$_4$)$^+$.

Step-4: Synthesis of N-(4-chloro-2,5-difluorophenyl)-2-fluoro-6-methoxy-N-(methoxymethyl)-1H-indole-3-sulfonamide I-318d I-318c (in a mixture with I-318b ratio ca. 1:3, 60 mg, ca. 0.13 mmol) and potassium carbonate (73 mg, 0.525 mmol) were placed in dioxane (2 mL) and water (1 mL) and stirred for 4 h at 70° C. Then the reaction mixture was treated with 0.1 M hydrochloric acid aqueous solution (4 mL), extracted twice with ethyl acetate, washed with brine, evaporated to dryness and dried over magnesium sulfate to afford the desired compound I-318d, in a mixture with the corresponding non-fluorinated compound (ratio ca. 1:3, 39 mg), as a light green solid.

This compound was used as such for the next reaction without further purification.

Neutral LCMS Method 3 (ES$^+$): 452.1 (M+NH$_4$)$^+$.

Step-5: Synthesis of N-(4-chloro-2,5-difluorophenyl)-2-fluoro-6-methoxy-1H-indole-3-sulfonamide I-318

I-318d (in a mixture with the corresponding non-fluorinated compound, ratio ca. 1:3, 39 mg, ca. 0.09 mmol) was placed in a solution of hydrogen chlorid 4 M in dioxane (2 mL) and was refluxed overnight. The reaction mixture was then quenched with saturated hydrogen sodium carbonate aqueous solution, extracted three times with dichloromethane, washed with brine, dried over magnesium sulfate and evaporated to dryness. The crude residue was purified by preparative HPLC (Basic prep LCMS Method 1) to afford the pure desired product I-318 (4 mg)

Yield: 7% (2 steps)

Basic LCMS Method 1 (ES$^-$): 389 (M−H)$^-$, 100% purity.

D.17. Synthesis of ethyl 3-(6-{[(6-chloro-1H-indol-3-yl)sulfonyl]amino}-2,5-difluoropyridin-3-yl)propanoate I-331

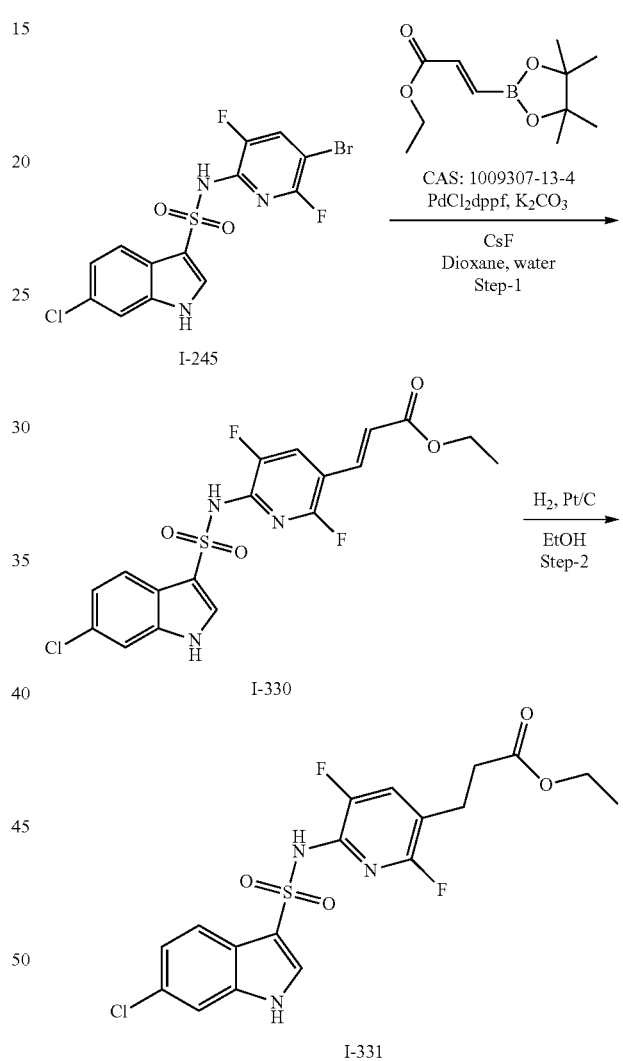

Step-1: Synthesis of ethyl (2E)-3-(6-{[(6-chloro-1H-indol-3-yl)sulfonyl]amino}-2,5-difluoropyridin-3-yl)prop-2-enoate I-330

A mixture of N-(5-bromo-3,6-difluoropyridin-2-yl)-6-chloro-1H-indole-3-sulfonamide I-245 (100 mg, 0.24 mmol), 2-ethoxycarbonylvinylboronic acid pinacol ester (64 mg, 0.28 mmol), [1,1'-bis(diphenylphosphino)ferrocene]dichloropalladium (19 mg, 0.024 mmol), cesium fluoride (72 mg, 0.47 mmol) and potassium carbonate (99 mg, 0.71 mmol) was dissolved in dioxane:water (3:1, 2 mL) and flushed with argon via a septum. Subsequently, the reaction mixture was stirred at 120° C. for 20 min in a microwave. The mixture was diluted with water and extracted twice with ethyl acetate. The combined organic layers were dried over MgSO$_4$ and concentrated by rotary evaporation. The crude mixture was purified by preparative HPLC (Basic prep LCMS Method 1). It afforded 68 mg of ethyl (2E)-3-(6-{[(6-chloro-1H-indol-3-yl)sulfonyl]amino}-2,5-difluoropyridin-3-yl)prop-2-enoate I-330 as a beige solid.

Yield: 65%.

Basic LCMS Method 1 (ES$^-$): 440 (M–H)$^-$, 98% purity.

Step-2: Synthesis of ethyl 3-(6-{[(6-chloro-1H-indol-3-yl)sulfonyl]amino}-2,5-difluoropyridin-3-yl)propanoate I-331

To a solution of ethyl (2E)-3-(6-{[(6-chloro-1H-indol-3-yl)sulfonyl]amino}-2,5-difluoropyridin-3-yl)prop-2-enoate I-330 (0.65 g, 3.26 mmol) in EtOH (1.5 mL) was added Pt/C (6 mg) and the reaction mixture was stirred at room temperature for 16 h under hydrogen pressure (3.5 bar). After completion, the reaction mixture was filtered through a celite pad and the filtrate was concentrated under vacuum. The crude mixture was purified by two successive preparative HPLC (basic and acidic) to afford 4 mg of 3-(6-{[(6-chloro-1H-indol-3-yl)sulfonyl]amino}-2,5-difluoropyridin-3-yl)propanoate I-331 as a white solid.

Yield: 6%.

Basic LCMS Method 1 (ES$^-$): 442 (M–H)$^-$, 97% purity.
$^1$H NMR (400 MHz, DMSO-d$_6$) δ 12.14 (s, 1H), 11.06 (s, 1H), 8.09 (d, J=2.7 Hz, 1H), 7.84 (d, J=8.6 Hz, 1H), 7.75 (t, J=8.6 Hz, 1H), 7.54 (d, J=1.9 Hz, 1H), 7.22 (dd, J=8.6, 1.9 Hz, 1H), 3.99 (q, J=7.1 Hz, 2H), 2.75-2.52 (m, 4H), 1.08 (t, J=7.1 Hz, 3H).

D.18. Synthesis of 6-chloro-N-[5-(2-ethoxyethyl)-3,6-difluoropyridin-2-yl]-1H-indole-3-sulfonamide I-333

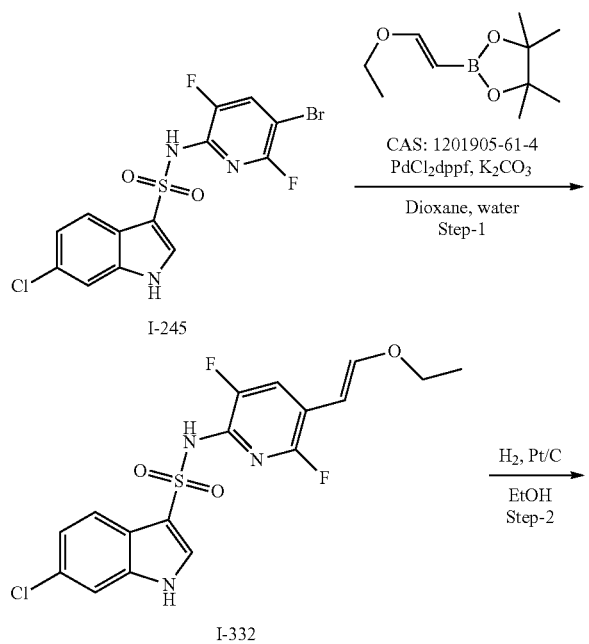

Step-1: Synthesis of 6-chloro-N-{5-[(E)-2-ethoxyethenyl]-3,6-difluoropyridin-2-yl}-1H-indole-3-sulfonamide I-332

A mixture of N-(5-bromo-3,6-difluoropyridin-2-yl)-6-chloro-1H-indole-3-sulfonamide I-245 (100 mg, 0.24 mmol), (E)-1-ethoxyethene-2-boronic acid pinacol ester (58 mg, 0.28 mmol), [1,1'-bis(diphenylphosphino)ferrocene]dichloropalladium (19 mg, 0.024 mmol) and potassium carbonate (99 mg, 0.71 mmol) was dissolved in dioxane:water (3:1, 2 mL) and flushed with argon via a septum. Subsequently, the reaction mixture was stirred at 120° C. for 20 min in a microwave. The mixture was diluted with water and extracted twice with ethyl acetate. The combined organic layers were dried over MgSO$_4$ and concentrated by rotary evaporation. The crude mixture was purified by preparative HPLC (Basic prep LCMS Method 1). It afforded 25 mg of 6-chloro-N-{5-[(E)-2-ethoxyethenyl]-3,6-difluoropyridin-2-yl}-1H-indole-3-sulfonamide I-332 as a beige solid.

Yield: 26%.

Basic LCMS Method 1 (ES$^-$): 412 (M–H)$^-$, 94% purity.

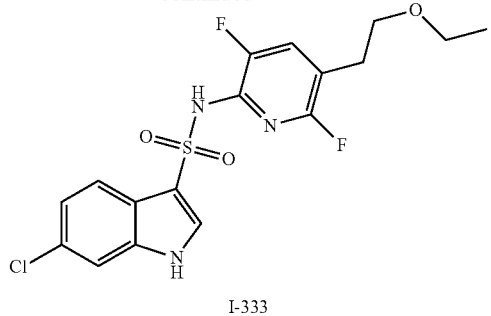

I-333

Step-2: Synthesis of 6-chloro-N-[5-(2-ethoxyethyl)-3,6-difluoropyridin-2-yl]-1H-indole-3-sulfonamide I-333

To a solution of 6-chloro-N-{5-[(E)-2-ethoxyethenyl]-3,6-difluoropyridin-2-yl}-1H-indole-3-sulfonamide I-332 (0.20 g, 0.05 mmol) in EtOH (0.5 mL) was added Pt/C (15 mg) and the reaction mixture was stirred at 50° C. for 16 h under hydrogen pressure (4 bar). After completion, the reaction mixture was filtered through a celite pad and the filtrate was concentrated under vacuum. The crude mixture was purified by preparative HPLC (Basic prep LCMS Method 1) to afford 10 mg of 6-chloro-N-[5-(2-ethoxyethyl)-3,6-difluoropyridin-2-yl]-1H-indole-3-sulfonamide I-333 as a white solid.

Yield: 50%.

Basic LCMS Method 1 (ES$^-$): 414 (M–H)$^-$, 98% purity.
$^1$H NMR (400 MHz, DMSO-d$_6$) δ 12.12 (s, 1H), 11.05 (s, 1H), 8.09 (d, J=2.9 Hz, 1H), 7.86 (d, J=8.6 Hz, 1H), 7.73 (t, J=8.7 Hz, 1H), 7.54 (d, J=1.9 Hz, 1H), 7.23 (dd, J=8.6, 1.9 Hz, 1H), 3.50 (t, J=6.5 Hz, 2H), 3.40 (d, J=6.9 Hz, 2H), 2.67 (t, J=6.5 Hz, 2H), 1.04 (t, J=7.0 Hz, 3H).

D.19. Synthesis of 6-azido-N-(4-cyano-2-fluorophenyl)-1H-indole-3-sulfonamide I-335

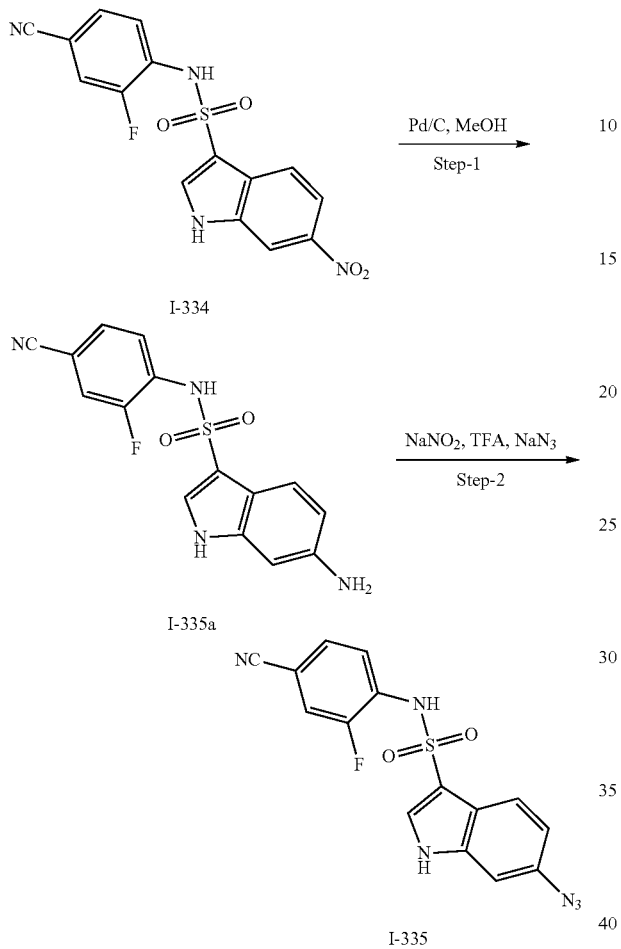

Step-1: Synthesis of 6-amino-N-(4-cyano-2-fluorophenyl)-1H-indole-3-sulfonamide I-335a To a solution of 6-nitro-N-(4-cyano-2-fluorophenyl)-1H-indole-3-sulfonamide I-334 (0.50 g, 1.37 mmol) in MeOH (20 mL) was added Pd/C (0.10 g, 1.02 mmol). The reaction mixture was stirred at room temperature for 3 h under hydrogen pressure. Progress of the reaction was monitored by TLC and LCMS. After completion, the reaction mixture was filtered through celite and the filtrate was concentrated under vacuum to afford 6-amino-N-(4-cyano-2-fluorophenyl)-1H-indole-3-sulfonamide I-335a (0.40 g) as a pale yellow solid.

This compound was used as such for the next reaction without further purification.

Yield: 90%.

Basic LCMS Method 2 (ES⁺): 331 (M+H)⁺, 83% purity.

Step-2: Synthesis of 6-azido-N-(4-cyano-2-fluorophenyl)-1H-indole-3-sulfonamide I-335

To a solution of 6-amino-N-(4-cyano-2-fluorophenyl)-1H-indole-3-sulfonamide I-335a (0.20 g, 0.50 mmol) in TFA (5 mL) was added NaNO$_2$ (0.14 g, 2.02 mmol) at 0° C. and the reaction mixture was stirred at same temperature for 30 min. NaN$_3$ (0.11 g, 1.77 mmol) was added at 0° C. and the reaction mixture was stirred at same temperature for 30 min. Progress of the reaction was monitored by TLC and LCMS. After completion, the reaction mixture was diluted with H$_2$O (150 mL) and extracted with EtOAc (200 mL). The organic layer was separated, washed with brine (100 mL), dried over anhydrous Na$_2$SO$_4$ and concentrated under vacuum. The crude obtained was purified by combi-flash column chromatography (25% EtOAc in hexanes) to afford 6-azido-N-(4-cyano-2-fluorophenyl)-1H-indole-3-sulfonamide I-335 (0.06 g, 31%) as a yellow solid.

Yield: 31%.

Basic LCMS Method 2 (ES⁻): 355 (M−H)⁻, 93% purity.

$^1$H NMR (400 MHz, DMSO-d$_6$) δ 6.99 (dd, J=8.00 Hz, 2.00 Hz, 1H) 7.17 (d, J=2.00 Hz, 1H) 7.54-7.59 (m, 2H) 7.74 (d, J=10.0 Hz, 1H) 7.84 (d, J=8.80 Hz, 1H) 8.07 (d, J=2.80 Hz, 1H) 10.80 (brs, 1H) 12.06 (brs, 1H).

D.20. Synthesis of 6-chloro-N-(5-ethyl-3,6-difluoropyridin-2-yl)-1H-indole-3-sulfonamide I-338

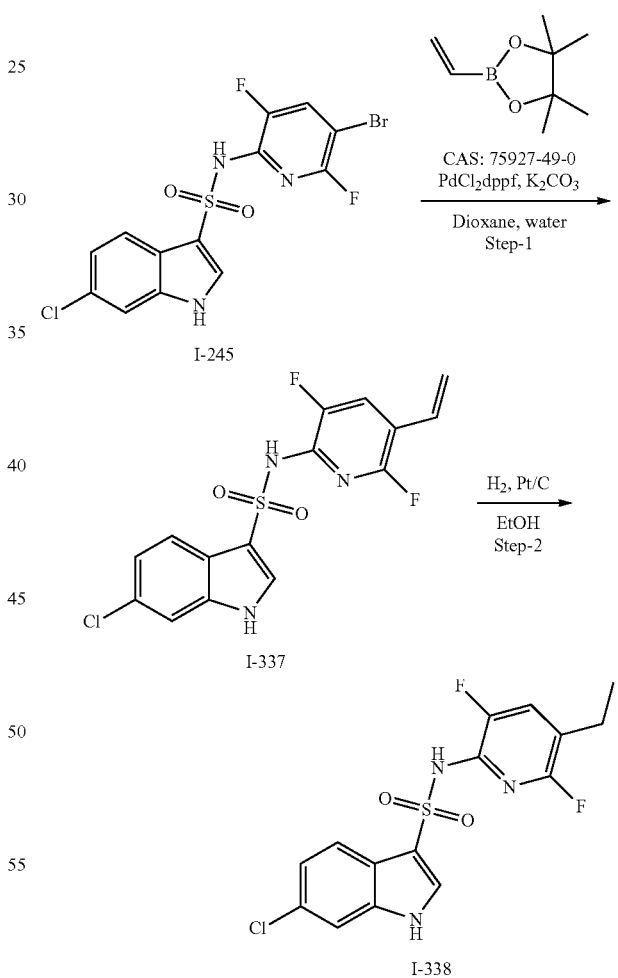

Step-1: Synthesis of 6-chloro-N-{5-[(E)-2-ethoxyethenyl]-3,6-difluoropyridin-2-yl}-1H-indole-3-sulfonamide I-332

A mixture of N-(5-bromo-3,6-difluoropyridin-2-yl)-6-chloro-1H-indole-3-sulfonamide I-245 (150 mg, 0.35 mmol), vinylboronic acid pinacol ester (69 mg, 0.42 mmol), [1,1'-bis(diphenylphosphino)ferrocene]dichloropalladium (29 mg, 0.035 mmol) and potassium carbonate (149 mg, 1.06 mmol) was dissolved in dioxane:water (3:1, 3 mL) and flushed with argon via a septum. Subsequently, the reaction mixture was stirred at 120° C. for 40 min in a microwave. The mixture was diluted with water and extracted twice with ethyl acetate. The combined organic layers were dried over MgSO$_4$ and concentrated under vacuum. The crude mixture was purified by preparative HPLC (Basic prep LCMS Method 1). It afforded 21 mg of 6-chloro-N-(5-ethenyl-3,6-difluoropyridin-2-yl)-1H-indole-3-sulfonamide I-337 as a beige solid.

Yield: 11%.

Basic LCMS Method 1 (ES$^-$): 368 (M–H)$^-$, 90% purity.

Step-2: Synthesis of 6-chloro-N-(5-ethyl-3,6-difluoropyridin-2-yl)-1H-indole-3-sulfonamide I-338

To a solution of 6-chloro-N-(5-ethenyl-3,6-difluoropyridin-2-yl)-1H-indole-3-sulfonamide I-337 (85 mg, 0.17 mmol) in EtOH (1.7 mL) was added Pt/C (17 mg) and the reaction mixture was stirred at room temperature for 16 h under hydrogen pressure (3.5 bar). After completion, the reaction mixture was filtered through a celite pad and the filtrate was concentrated under vacuum. The crude mixture was purified by preparative HPLC (Basic prep LCMS Method 1) to afford 9 mg of 6-chloro-N-(5-ethyl-3,6-difluoropyridin-2-yl)-1H-indole-3-sulfonamide I-338 as a white solid.

Yield: 14%.

Basic LCMS Method 1 (ES$^-$): 370 (M–H)$^-$, 99% purity.

$^1$H NMR (400 MHz, DMSO-d$_6$) δ 12.11 (s, 1H), 10.99 (s, 1H), 8.08 (s, 1H), 7.85 (s, 1H), 7.73 (s, 1H), 7.55 (d, J=5.5 Hz, 1H), 7.23 (d, J=7.7 Hz, 1H), 2.47 (t, 2H), 1.09 (d, J=7.3 Hz, 3H).

D.21. Synthesis of 6-azido-N-[5-(cyanomethyl)-3-fluoro-6-methoxypyridin-2-yl]-1H-indole-3-sulfonamide I-353

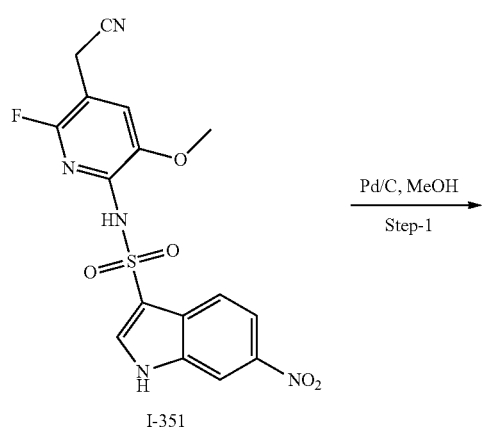

I-351

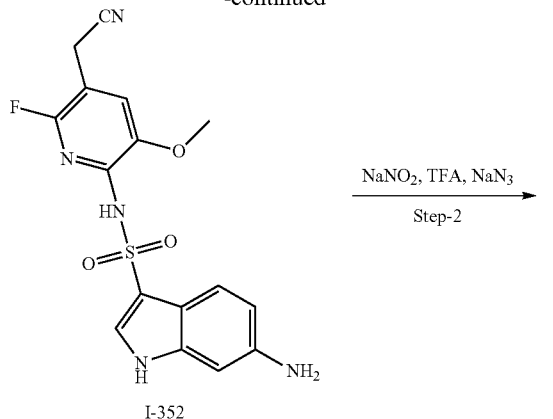

I-352

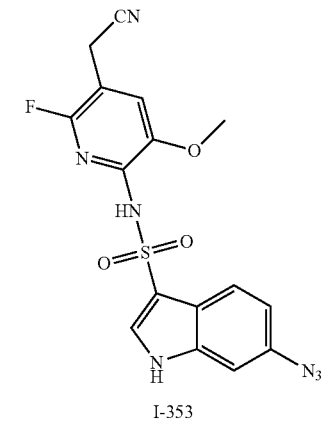

I-353

Step-1: Synthesis of 6-amino-N-[5-(cyanomethyl)-3-fluoro-6-methoxypyridin-2-yl]-1H-indole-3-sulfonamide I-352

To a solution of N-[5-(cyanomethyl)-3-fluoro-6-methoxypyridin-2-yl]-6-nitro-1H-indole-3-sulfonamide I-351 (0.32 g, 0.69 mmol) in MeOH (20 mL) was added 10% Pd/C (0.30 g, 2.82 mmol) and the reaction mixture was stirred at room temperature for 1 h under hydrogen pressure. Progress of reaction was monitored by TLC and LCMS. After completion, the reaction mixture was filtered through a pad of Celite®, washed with MeOH (3×15 mL) and filtrate was concentrated under vacuum to afford 6-amino-N-[5-(cyanomethyl)-3-fluoro-6-methoxypyridin-2-yl]-1H-indole-3-sulfonamide I-352 (0.241 g) as a pale brown solid.

This compound was used as such for the next reaction without further purification.

Yield: 74%.

Basic LCMS Method 2 (ES$^+$): 376 (M+H)$^+$, 79% purity.

Step-2: Synthesis of 6-azido-N-(4-cyano-2-fluorophenyl)-1H-indole-3-sulfonamide I-353

To a solution of 6-amino-N-[5-(cyanomethyl)-3-fluoro-6-methoxypyridin-2-yl]-1H-indole-3-sulfonamide I-352 (0.03 g, 0.06 mmol) in TFA (2 mL) was added NaNO$_2$ (0.02 g, 0.25 mmol) at 0° C. and the reaction mixture was stirred at same temperature for 30 min. NaN$_3$ (0.01 g, 0.22 mmol) was added at 0° C. and the reaction mixture was stirred at same temperature for 30 min. Progress of reaction was monitored by TLC and LCMS. After completion, the reaction mixture was diluted with H$_2$O (40 mL) and extracted with EtOAc (2×30 mL). The organic layer was separated, washed with brine (20 mL), dried over anhydrous Na₂SO₄ and concentrated under vacuum. The reaction was repeated on 0.20 g and the crude obtained from 2 reactions was blended in EtOAc (20 mL) and concentrated under vacuum. The crude obtained was purified by combi-flash column chromatography (25% EtOAc in hexanes) to afford 6-azido-N-[5-(cyanomethyl)-3-fluoro-6-methoxypyridin-2-yl]-1H-indole-3-sulfonamide I-353 (0.032 g) as a pale brown solid Yield: 13%.

Basic LCMS Method 2 (ES⁻): 400 (M−H)⁻, 96% purity.

¹H NMR (400 MHz, DMSO-d₆) δ 3.63 (s, 3H) 3.70 (s, 2H) 6.97 (d, J=8.03 Hz, 1H) 7.20 (s, 1H) 7.62 (d, J=9.54 Hz, 1H) 7.87 (d, J=8.28 Hz, 1H) 8.12 (s, 1H) 11.03 (brs, 1H) 11.97 (brs, 1H).

D.22. Synthesis of ethyl 2-(6-{[(6-chloro-1H-indol-3-yl)sulfonyl]amino}-2,5-difluoropyridin-3-yl)cyclopropanecarboxylate I-359

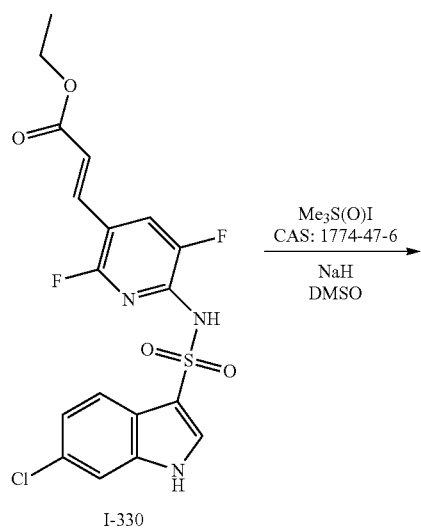

I-330

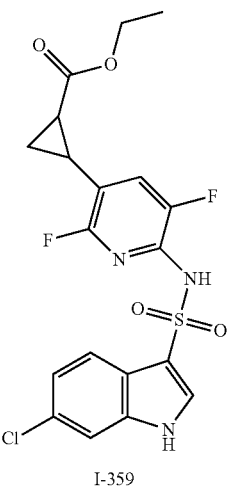

I-359

Trimethylsulfoxonium iodide (66.75 mg, 0.30 mmol) and sodium hydride (11.59 mg, 0.29 mmol) were mixed in dimethyl sulfoxide (1.0 ml). The reaction mixture was stirred until a limpid colorless solution was obtained. Ethyl (2E)-3-(6-{[(6-chloro-1H-indol-3-yl)sulfonyl]amino}-2,5-difluoropyridin-3-yl)prop-2-enoate I-330 (100 mg, 0.23 mmol) was then added and the reaction mixture was stirred at room temperature for 20 minutes then heated at 50° C. overnight. A new colorless solution of mixed trimethylsulfoxonium iodide (66.75 mg, 0.30 mmol) and sodium hydride (11.59 mg, 0.29 mmol) in dimethyl sulfoxide (1.0 mL) was added to the reaction mixture and heating was maintained at 50° C. for 3 hours. The reaction mixture was diluted by water and extracted three times with ethyl acetate. The organic layer was dried on magnesium sulfate, concentrated under vacuum and the crude compound was purified by chromatography (Preparative TLC—elution with dichloromethane/MeOH—95/5) to afford 12 mg of ethyl 2-(6-{[(6-chloro-1H-indol-3-yl)sulfonyl]amino}-2,5-difluoropyridin-3-yl)cyclopropanecarboxylate I-359, as a yellow solid.

Yield: 10%.

Basic LCMS Method 1 (ES⁺): 456 (M+H)⁺, 88% purity.

Additional examples in Table 9 were prepared following previously described methods:

TABLE 9

| IUPAC Name | Structure | |
|---|---|---|
| 6-chloro-N-(3,6-difluoro-5-methylpyridin-2-yl)-1H-pyrrolo[2,3-b]pyridine-3-sulfonamide | 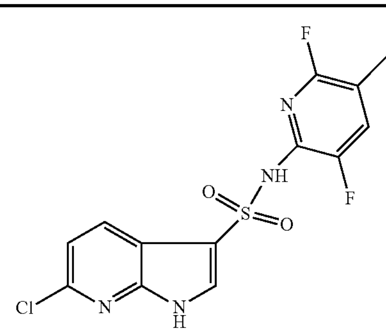 | I-368 |

TABLE 9-continued
| IUPAC Name | Structure | |
|---|---|---|
| N-(5-bromo-3-fluoropyridin-2-yl)-6-chloro-1H-indole-3-sulfonamide | 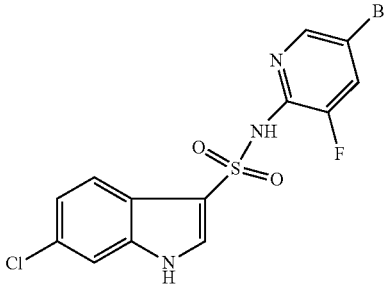 | I-369 |
| 6-chloro-N-(3,5-difluoro-6-methoxypyridin-2-yl)-7-(trifluoromethyl)-1H-indole-3-sulfonamide | 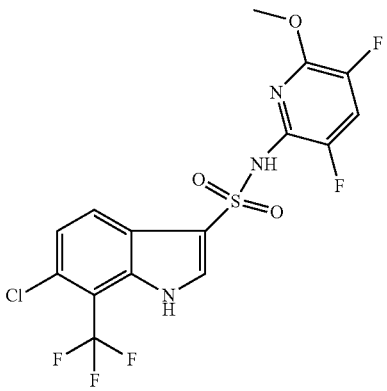 [SMILES: COc1nc(NS(=O)(=O)c2c[nH]c3c(C(F)(F)F)c(Cl)ccc23)c(F)cc1F] | I-370 |
| N-(4-bromo-2,5-difluorophenyl)-6-(methylsulfinyl)-1H-indole-3-sulfonamide | 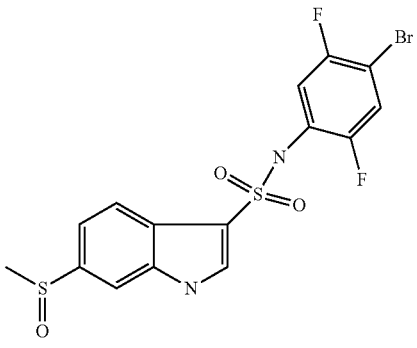 [SMILES: CS(=O)c1ccc2c(S(=O)(=O)Nc3cc(F)c(Br)cc3F)c[nH]c2c1] | I-371 |
| N-(2,5-difluoro-4-methylphenyl)-6-(methylsulfinyl)-1H-indole-3-sulfonamide | 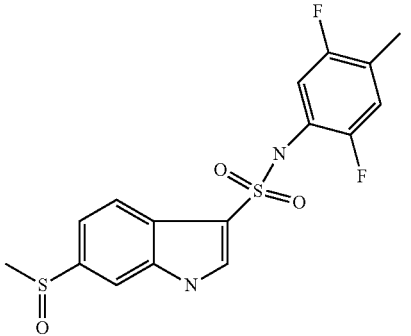 | I-372 |

TABLE 9-continued

| IUPAC Name | Structure |
|---|---|
| N-[4-(difluoromethoxy)-2,5-difluorophenyl]-6-(methylsulfinyl)-1H-indole-3-sulfonamide | I-373 |
| N-(5-chloro-3-fluoropyridin-2-yl)-1H-pyrrolo[3,2-h]quinoline-3-sulfonamide | I-374 |

Examples were tested and activities in $Ca^{2+}$ and cAMP assays are reported in the Table 10 further below.

B. Biology/Pharmacology:

b-I. Cell Cultures

GPR17 Recombinant Cell Line

Flp-In T-REx CHO cells stably expressing human GPR17 receptor (CHO hGPR17) from Evi Kostenis' lab (Bonn University, Germany) were cultured at 37° C. in a humidified atmosphere of 5% $CO_2$. Cells were grown in DMEM with Nutrient Mixture F-12 supplemented with hygromycin B (500 µg/mL) and blasticidin (30 µg/mL). Expression from the Flp-In locus was induced by treatment with doxycycline (1 µg/mL) for 16-20 h prior assays.

Primary Oligodendrocytes

Primary oligodendrocyte progenitor cells (OPCs) were isolated from the forebrains of Wistar rat pups at postnatal day 0 to 2. Cerebra were mechanically dissociated with a syringe and two different hollow needles (first 1.2×40 and then 0.60×30). Clump-free cell suspension was filtered through a 70-µm cell strainer and plated into poly-D-lysine-coated 75-cm² culture flasks in DMEM supplemented with 10% (v/v) heat-inactivated fetal calf serum, penicillin (100 units/mL), and streptomycin (0.1 mg/mL) with medium exchanged every second day. After 8 to 11 days at 37° C. in a humidified atmosphere of 5% $CO_2$, mixed cultures were shaken at 240 rpm for 14-24 h to detach OPCs from astrocytes and microglia. To further enrich for OPCs, the suspension was plated onto uncoated Petri dishes for 45 min. Then, OPCs were seeded into poly-L-ornithine-coated plates and maintained at 37° C. in a humidified atmosphere of 5% $CO_2$ in proliferating Neurobasal medium supplemented with 2% (v/v) B27, 2 mM GlutaMAX, 100 units/mL penicillin, 0.1 mg/mL streptomycin, 10 ng/mL PDGF-AA, and 10 ng/mL basic FGF changing the medium every second day.

B-II: Functional In Vitro GPR17 Assays

B-II-1: Calcium Mobilization Functional Assay

GPR17 is a G-protein coupled receptor. GPR17 activation triggers Gq-type G-protein signaling resulting in endoplasmic reticulum calcium ($Ca^{2+}$) stores release in cytosol which can be measured using Calcium 5 dye, a fluorescent indicator dye of cytosolic $Ca^{2+}$ levels. All Examples were tested in GPR17 $Ca^{2+}$ assay to determine (screen) their GPR17 modulating activity.

Description of $Ca^{2+}$ assay

CHO hGPR17 were defrosted and seeded at a density of 20,000 cells per well into black 384-well plates with clear bottom. Cells were incubated overnight at 37° C. in a humidified atmosphere of 5% $CO_2$. Sixteen to twenty hours after seeding, CHO hGPR17 were loaded for 60 min with Calcium 5 dye, a cytosolic $Ca^{2+}$ indicator fluorescent dye, according to manufacturer's instructions. Fluorescent signal relative to cytosolic $Ca^{2+}$ concentration was recorded over time at room temperature in FLIPR Tetra reader. Cells were first incubated for 30 minutes at room temperature in HBSS Hepes buffer pH 7.4 containing increasing concentrations of test compounds (typically $10^{-11}$M to $10^{-6}$M). Then, 50 nM MDL29,951, a GPR17 agonist, was added to the cells. Inhibitory effects of varying concentrations test compounds were measured and resulting $pIC_{50}$s were determined. All incubations were performed in duplicate and results were compared to a concentration response curve of GPR17 agonist and antagonist reference compounds. Analysis and curve fitting were performed in ActivityBase XE using XLfit 4-parameter logistic equation $y=A+((B-A)/(1+((C/x)^D)))$ where A, B, C and D stand for minimum y, maximum y, $IC_{50}$ and slope, respectively.

Results of $Ca^{2+}$ Assay

When tested in $Ca^{2+}$ mobilization assay, compounds of the Examples preferably exhibit values of $pIC_{50}$ greater than or equal to 6.5; more preferably greater than or equal to 7.5, and even more preferably greater than or equal to 8.5. The activities of the Example compounds tested are depicted in the table in Section B2B below. The activity ranges A, B and C refer to $pIC_{50}$ values in the $Ca^{2+}$ assay as follows: "A": $pIC_{50}$<7.5, "B": $pIC_{50}$ 7.5<x≤8.5, "C": $pIC_{50}$>8.5

B-IIB. cAMP Accumulation Functional Assay

GPR17 activation can also recruit Gi-type G-protein signaling, resulting in a decrease of intracellular cyclic adenosine monophosphate (cAMP). Intracellular cAMP changes can be measured using the HTRF cAMP dynamic assay kit from CisBio (Codolet, France). Using homogenous time-resolved fluorescence technology (HTRF), the assay is based on competition between native cAMP produced by cells and cAMP labelled with the dye d2. The tracer binding was determined by an anti-cAMP antibody labeled with cryptate. Representative compounds which were active in the $Ca^{2+}$ assay were also tested in this GPR17 cAMP assay. This was done as a confirmation test with some representative Examples but not with all compounds of the present invention.

Description of cAMP Assay

CHO hGPR17 were detached with PBS containing EDTA and dispatched in black 384-well plates with 5,000 cells per well. Cells were first incubated for 30 minutes at room temperature in HBSS Hepes (pH 7.4) containing vehicle or varying concentrations of test GPR17 antagonist/inverse agonist compounds. Then, a dose response curve of MDL29,951 GPR17 agonist (typically from $10^{-5}$M to $10^{-10}$M) was added on vehicle and on each test GPR17 antagonist/inverse agonist compound concentration in a final volume of 20 μL HBSS Hepes buffer (pH 7.4) containing 1% DMSO, 5 μM forskolin and 0.1 mM IBMX. After 60 minutes incubation at room temperature, the reaction is terminated and the cells lysed by adding the d2 detection reagent and the cryptate reagent in 10 μL lysis buffer each according to manufacturer's instructions. After 60 minutes incubation, changes in cAMP concentrations are measured according to manufacturer's instructions using an Envision plate reader with laser excitation. All incubations were performed in duplicate. Data was analyzed using GraphPad Prism software using the 4-parameter logistic equation to measure MDL29,951 $pEC_{50}$s in absence and presence of GPR17 antagonist/inverse agonist test compounds. Dose ratio (DR) were plotted against antagonist concentrations and Schild analysis provided estimated affinity $pA_2$ of GPR17 antagonist/inverse agonist test compounds.

Results of cAMP Assay

When tested in cAMP assay, compounds of the Examples typically exhibit values of $pA_2$ greater than or equal to 6.5; preferably greater than or equal to 7.5; more preferably greater than or equal to 8.5. The activities of the Example compounds tested are depicted in the table below. The activity ranges A, B and C refer to $pA_2$ values in the cAMP assay as follows: "A": $pA_2$<7.5, "B": $pA_2$ 7.5<x≤8.5, "C": $pA_2$>8.5.

The following table 10 shows the $pIC_{50}$ and $pA_2$ values of the Example compounds tested in the $Ca_{2+}$ and the cAMP assay. Blanks in the $pA_2$ column indicate that the respective compounds was not yet tested, or that the result was not yet available.

TABLE 10

| Ex No | $Ca^{2+}$ assay $pIC_{50}$ | cAMP assay $pA_2$ | Ex No | $Ca^{2+}$ assay $pIC_{50}$ | cAMP assay $pA_2$ | Ex No | $Ca^{2+}$ assay $pIC_{50}$ | cAMP assay $pA_2$ |
|---|---|---|---|---|---|---|---|---|
| I-99 | A | | I-160 | C | B | I-1 | A | A |
| I-92 | A | A | I-154 | C | B | I-80 | C | B |
| I-91 | A | A | I-153 | C | B | I-78 | C | B |
| I-90 | A | A | I-152 | C | C | I-25 | C | B |
| I-89 | A | | I-151 | C | C | I-228 | C | C |
| I-87 | A | | I-150 | B | C | I-227 | C | C |
| I-86 | A | | I-148 | C | | I-213 | C | C |
| I-84 | A | | I-143 | C | C | I-202 | C | B |
| I-82 | A | | I-142 | C | C | I-194 | C | C |
| I-81 | A | | I-140 | C | C | I-193 | C | C |
| I-8 | A | A | I-134 | C | C | I-192 | C | |
| I-77 | A | | I-133 | C | B | I-190 | C | |
| I-76 | A | A | I-12 | C | B | I-189 | C | C |
| I-75 | A | | I-118 | C | C | I-188 | C | C |
| I-74 | A | | I-116 | C | C | I-185 | C | C |
| I-72 | A | | I-114 | C | C | I-184 | C | C |
| I-71 | A | | I-110 | C | C | I-183 | C | C |
| I-70 | A | | I-109 | C | B | I-182 | C | B |
| I-7 | A | | I-104 | C | C | I-179 | C | B |
| I-69 | A | A | I-157 | B | | I-177 | C | C |
| I-68 | A | | I-155 | B | C | I-170 | C | C |
| I-64 | A | | I-149 | B | | I-165 | C | |
| I-63 | A | B | I-147 | B | B | I-67 | B | B |
| I-62 | A | | I-145 | B | | I-66 | B | B |
| I-61 | A | | I-144 | B | | I-65 | B | B |
| I-60 | A | A | I-141 | B | C | I-55 | B | B |
| I-6 | A | | I-14 | B | B | I-50 | B | B |
| I-59 | A | A | I-139 | B | A | I-48 | B | B |
| I-58 | A | | I-132 | B | B | I-4 | A | B |
| I-57 | A | | I-129 | B | B | I-39 | B | A |
| I-56 | A | B | I-127 | B | B | I-241 | B | B |
| I-54 | A | | I-126 | B | B | I-242 | B | C |
| I-53 | A | | I-125 | B | B | I-238 | B | B |
| I-52 | A | B | I-124 | B | B | I-235 | B | C |
| I-51 | A | | I-123 | B | B | I-233 | B | A |

TABLE 10-continued

| Ex No | Ca²⁺ assay pIC₅₀ | cAMP assay pA₂ | Ex No | Ca²⁺ assay pIC₅₀ | cAMP assay pA₂ | Ex No | Ca²⁺ assay pIC₅₀ | cAMP assay pA₂ |
|---|---|---|---|---|---|---|---|---|
| I-5 | A | | I-119 | B | B | I-230 | B | B |
| I-49 | A | B | I-113 | B | A | I-229 | B | B |
| I-47 | A | | I-112 | B | B | I-224 | B | B |
| I-46 | A | | I-108 | B | B | I-223 | B | A |
| I-45 | A | | I-107 | B | B | I-221 | B | B |
| I-44 | A | B | I-102 | B | | I-220 | B | B |
| I-43 | A | | I-212 | B | C | I-219 | B | B |
| I-42 | A | | I-210 | B | C | I-216 | B | B |
| I-41 | A | | I-206 | B | C | I-215 | B | B |
| I-40 | A | | I-204 | B | C | I-196 | A | |
| I-38 | A | | I-203 | B | C | I-19 | A | |
| I-37 | A | | I-20 | B | | I-180 | A | |
| I-36 | A | | I-199 | B | C | I-175 | A | B |
| I-35 | A | | I-195 | B | C | I-171 | A | |
| I-34 | A | | I-191 | B | C | I-17 | A | |
| I-33 | A | | I-187 | B | | I-169 | A | |
| I-32 | A | | I-186 | B | B | I-166 | A | |
| I-31 | A | | I-181 | B | B | I-164 | A | |
| I-30 | A | | I-18 | B | | I-163 | A | |
| I-3 | A | | I-178 | B | B | I-16 | A | |
| I-29 | A | | I-176 | B | | I-158 | A | |
| I-28 | A | | I-174 | B | B | I-156 | A | |
| I-27 | A | | I-173 | B | B | I-15 | A | |
| I-26 | A | | I-172 | B | | I-146 | A | |
| I-240 | A | A | I-168 | B | | I-131 | A | |
| I-24 | A | A | I-167 | B | | I-130 | A | |
| I-239 | A | A | I-161 | B | | I-13 | A | |
| I-237 | A | A | I-159 | B | B | I-128 | A | |
| I-236 | A | A | I-117 | A | | I-122 | A | |
| I-234 | A | | I-115 | A | | I-121 | A | |
| I-232 | A | | I-111 | A | | I-120 | A | |
| I-231 | A | | I-11 | A | | I-197 | A | |
| I-23 | A | | I-106 | A | | I-85 | B | B |
| I-226 | A | | I-105 | A | | I-83 | B | B |
| I-225 | A | B | I-103 | A | | I-79 | B | A |
| I-222 | A | | I-101 | A | | I-73 | B | C |
| I-22 | A | | I-100 | A | B | I-201 | A | C |
| I-218 | A | | I-10 | A | | I-200 | B | B |
| I-217 | A | | I-98 | B | B | I-2 | A | |
| I-214 | A | | I-97 | B | B | I-198 | B | B |
| I-211 | A | | I-96 | B | A | I-207 | A | |
| I-21 | A | | I-95 | B | B | I-205 | A | |
| I-209 | A | | I-94 | B | B | I-9 | B | B |
| I-208 | A | B | I-93 | B | B | I-88 | B | B |
| I-162 | C | C | I-243 | B | B | I-244 | B | C |
| I-245 | C | C | I-246 | C | C | I-247 | B | C |
| I-248 | B | B | I-250 | B | B | I-251 | B | B |
| I-252 | C | C | I-253 | C | C | I-254 | C | C |
| I-255 | C | C | I-256 | C | C | I-257 | C | C |
| I-258 | C | B | I-259 | B | C | I-260 | B | B |
| I-261 | B | B | I-262 | B | C | I-263 | B | B |
| I-264 | A | A | I-265 | B | A | I-266 | C | C |
| I-267 | C | C | I-268 | C | C | I-269 | C | C |
| I-270 | C | C | I-271 | C | C | I-272 | B | C |
| I-273 | B | B | I-274 | B | B | I-275 | B | B |
| I-276 | B | B | I-277 | B | C | I-278 | B | C |
| I-279 | B | B | I-280 | B | B | I-281 | B | B |
| I-282 | B | B | I-283 | B | B | I-284 | B | A |
| I-285 | C | C | I-286 | C | C | I-287 | C | B |
| I-288 | C | B | I-289 | C | C | I-290 | C | C |
| I-291 | C | C | I-292 | B | B | I-293 | B | B |
| I-294 | B | B | I-295 | B | B | I-296 | B | B |
| I-297 | B | B | I-298 | B | C | I-299 | B | C |
| I-300 | B | B | I-301 | B | B | I-302 | B | B |
| I-303 | C | C | I-304 | C | C | I-305 | C | C |
| I-306 | B | C | I-307 | B | B | I-308 | C | C |
| I-309 | C | C | I-310 | C | C | I-311 | B | B |
| I-312 | B | B | I-313 | B | B | I-314 | B | B |
| I-315 | C | C | I-316 | B | B | I-317 | B | B |
| I-318 | B | B | I-319 | C | C | I-320 | C | |
| I-321 | C | C | I-322 | C | | I-323 | C | C |
| I-324 | C | C | I-325 | C | C | I-326 | B | C |
| I-327 | C | C | I-328 | C | C | I-329 | C | C |
| I-330 | B | C | I-331 | C | C | I-332 | B | C |
| I-333 | C | C | I-335 | B | B | I-336 | C | B |
| I-337 | B | C | I-338 | C | C | I-339 | C | B |

TABLE 10-continued

| Ex No | Ca$^{2+}$ assay pIC$_{50}$ | cAMP assay pA$_2$ | Ex No | Ca$^{2+}$ assay pIC$_{50}$ | cAMP assay pA$_2$ | Ex No | Ca$^{2+}$ assay pIC$_{50}$ | cAMP assay pA$_2$ |
|---|---|---|---|---|---|---|---|---|
| I-340 | B | B | I-341 | C | C | I-342 | B | B |
| I-343 | B | C | I-344 | B | B | I-345 | B | B |
| I-346 | B | B | I-347 | B | C | I-348 | C | B |
| I-349 | C | C | I-350 | C | C | I-351 | B | B |
| I-352 | B | B | I-353 | C | C | I-354 | C | C |
| I-355 | C | B | I-356 | B | B | I-357 | B | B |
| I-358 | B | B | I-359 | B | B | I-360 | C | C |
| I-361 | C | C | I-362 | B | C | I-363 | B | B |
| I-364 | C | C | I-365 | B | B | I-366 | B | B |

B-11C: Oligodendrocyte Maturation/Myelination Assays

The effects of negative modulators of GPR17 on primary oligodendrocytes maturation/myelination can be assessed in vitro by immunoassays using antibodies directed against Myelin Basic Protein (MBP), as marker for mature oligodendrocytes.

Description of MBP Western Blot/Oligodendrocyte/Myelination Assay

After 3-4 days in proliferation medium, rat primary OPCs were seeded at 25,000 cells per cm$^2$ in 12-well tissue culture plates and switched to growth factor-free Neurobasal medium to induce spontaneous in vitro differentiation and GPR17 protein expression. For terminal differentiation and quantification analyses of protein expression, after 24-48 h the growth factor-free medium was supplemented with 0.20 ng/mL triiodothyronine (T3) and 10 ng/mL ciliary neurotrophic factor together with 1 µM GPR17 antagonist/inverse agonists test compounds or vehicle for additional 3 days. Following compound treatment, cells were washed twice with ice-cold PBS and lysed in ice-cold lysis buffer (25 mM Tris, pH 7.4, 150 mM NaCl, 1 mM EDTA, 1% Triton X-100, 1% IGEPAL) supplemented with protease inhibitor mixture. Lysates were rotated 20 min at 4° C. and centrifuged at 15,000×g at 4° C. for 10 min. Protein concentration was determined using the Pierce BCA Protein Assay according to manufacturer's instructions. 7.5-15 µg of protein were separated by 10% SDS-polyacrylamide gel electrophoresis and transferred to nitrocellulose membrane by electroblotting. After washing, membranes were blocked with Roti-Block for 1 h at room temperature and incubated overnight at 4° C. in Roti-Block with MBP antibody (1:5000, LifeSpan BioSciences). Membranes were washed 3 times with PBS containing 0.1% Tween and then incubated for 1 h at room temperature with a horseradish peroxidase-conjugated goat anti-mouse IgG antibody in Roti-Block. The immunoreactive proteins were visualized by chemiluminescence using Amersham Biosciences ECL Prime Western blotting detection reagent and quantified by densitometry using Gelscan software. To normalize for equal loading and protein transfer, membranes were reprobed with an antibody against β-actin (1:2500, BioLegend; secondary antibody goat anti-rabbit IgG antibody HRP (ABIN)). Changes in MBP expression level in the presence of test compounds were compared to MBP expression in control conditions.

Description of MBP Fiber Plates/Oligodendrocyte Maturation/Myelination Assay

OPCs were seeded at 16,000-22,000 cells per cm$^2$ in Mimetix Aligned 96-well fiber plates (Electrospining company). After 2 days in proliferation medium and 2 days in growth factor-free Neurobasal medium to induce spontaneous in vitro differentiation and GPR17 protein expression, vehicle or 1 µM antagonist/inverse agonist test compounds were added in terminal differentiation medium supplemented with 0.20 ng/mL triiodothyronine and 10 ng/mL ciliary neurotrophic factor for 6 days, changing the medium after 3 days. Then cells were fixed in 4% paraformaldehyde, followed by PBS washes, permeabilization in 0.1% TritonX-100 in PBS and blocking with 10% goat serum and 1% bovine serum albumin in phosphate-buffered saline. MBP antibody was diluted in blocking buffer (1:2000) and incubated for 1 h at 37° C. Cells were washed in PBS again and incubated 1 h with Cy2-conjugated secondary antibodies against mouse IgG (Millipore, 1:500). After PBS washes, cells were stained with 0.2 µg/mL DAPI, washed again and mounted with Mowiol. Fluorescent images were taken by using a Zeiss AxioObserver.Z1 microscope with ApoTome Imaging System and a Plan-Apochromat 20×/0.8 objective, with an eGFP filter (excitation 470/40 nm; emission 525/50 nm) and DAPI filter (excitation 365 nm; emission 445/50 nm). At least 15 random areas for control (terminal differentiation medium with 0.1% DMSO) and for test compounds were imaged using the same settings processed with Zeiss ZEN2.3 software. Changes in number myelinated fibers was reported by group of fiber lengths (0 to 40 µm, 41 to 60 µm, 61 to 80, 81 to 100, 101 to 120 and >120 µm)) in the absence or presence of GPR17 negative modulator.

Results of Oligodendrocytes Maturation/Myelination Assays

As depicted FIG. 1, when tested on primary rat OPCs in maturation/myelination western blot assay, representative compounds of the Examples increased MBP expression, marker for mature oligodendrocytes.

Figures 2, 4:
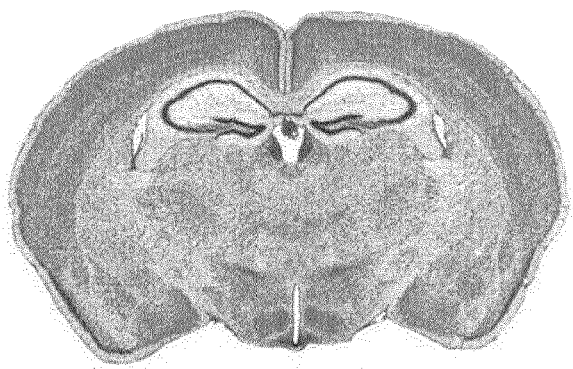
FIG. 2 shows the effect of a compound of the present invention (I-116) on the length of myelin sheats expressed by OPCs. After administration to OPCs, compound I-116 induced the formation of longer myelin sheats compared to OPS after addition of a vehicle alone.

The effect of Example I-116 on MBP expression was confirmed in the MBP fiber plates oligodendrocyte maturation/myelination assay. Compound I-116 induced longer myelin sheaths as depicted on following graph. This data is shown in FIG. 2.

B-III: Determination of Plasma and Brain Exposure

Few Example compounds were tested to determine plasma and brain exposure.

Determination of Brain/Plasma Ratio (Brain Kp)

Male Sprague Dawley rats (n=2 per time point) were used to determine the brain penetration of the compounds at 15, 45 and 120 min after 3 mg/kg of intraperitoneal administration.

At each time point, following anesthesia (inhalation of isoflurane) and blood collection (1 mL cardiac puncture into tubes containing K2EDTA) rats were exsanguinated and the brain perfused via the left ventricle (50 mL of heparinized NaCl 0.9% (0.15 UI/mL) flow 50 mL/min).

Brain was collected and weighed. Plasma was obtained from blood samples by centrifugation (3000 g for 15 min at 4° C.). Brain and plasma samples were frozen until time of analysis.

At the time of analysis, brain samples were homogenized in plasma (1:4 v:v) and together with plasma samples, following protein precipitation, were analyzed by HPLC/MS-MS analysis.

Results

An Example compound (Example I-1) is shown on FIG. 3. Compound I-1 displayed brain concentrations paralleling plasma exposure approximately 45 minutes after administration B-IV: In Vivo Testing of an Example Compound in the Acute Cuprizone Mice Model Compound I-228 was tested in the well-established toxic demyelination cuprizone mice model [see references 1-3 at the end of this Section]. In this model, feeding of cuprizone to young adult mice induces oligodendrocytes cell death which is closely followed by microglia and astrocytes activation. Cuprizone feeding for 5 weeks leads to severe and homogenous demyelination of the corpus callosum which can be reversed when the toxic treatment is interrupted (remyelination phase).

Animals and Cuprizone intoxication. C57Bl/6J mice (Janvier, France) were bred and maintained in a pathogen-free environment with a maximum of five animals per cage. Animals have undergone routine cage maintenance and microbiological monitoring according to the Federation of European Laboratory Animal Science Associations recommendations. Food (cuprizone or standard chow) and water were available ad libitum. Demyelination was induced by feeding 8-week-old (+/−19-21 g) male mice with a diet containing 0.25% cuprizone [bis(cyclohexanone)oxaldihydrazone; Sigma-Aldrich, Inc., USA] mixed into a ground standard rodent chow for 5 weeks.

Tissue preparation and evaluation: For histological and immunohistochemical studies, mice were anaesthetized with ketamine (100 mg-kg-1; i.p.) and xylazine (10 mg-kg-1; i.p.), transcardially perfused with ice-cold PBS followed by transcardial perfusion with 3.7% paraformaldehyde solution (pH 7.4). Post-fixation was performed for 12 h at 4° C. in the same fixative. Brains were then embedded in paraffin, and coronary sectioned into 5 µm sections at the level 265 (i.e. Region 1) and 285 (i.e. Region 2) according to the mouse brain atlas by Sidman et al. (http://www.hms.harvard.edu/research/brain/atlas.html). The myelin marker protein PLP has been visualized by means of immunohistochemistry. To this end, paraffin-embedded sections were de-waxed, rehydrated and washed in PBS. Unspecific bindings were omitted by incubating the slides for 1 h with blocking solution at room temperature. The slides were incubated overnight with the primary antibody diluted in blocking solution (Immunologic, Netherlands). On day two the slides were washed in PBS, quenched in $H_2O_2$ and again washed in PBS. For the visualization of epitope-primary antibody complexes, we have used EnVision® polymer secondary antibodies (Dako, Germany). This system is based on a horseradish peroxidase-labelled polymer which is conjugated with secondary antibodies. The labeled polymer does not contain avidin or biotin. Consequently, nonspecific staining resulting from endogenous avidin-biotin activity is eliminated or significantly reduced. Additional negative controls have been performed by either omitting the primary antibody or incubating slides with respective concentrations of IgG-subtypes. No specific staining has been observed in these control slides.

The intensity of the reaction product of anti-PLP immunohistochemistry was measured semi-quantitatively using a Nikon Eclipse E-200 (50×) microscope coupled to a CCD camera and Image J-software. To this end, the region of interest was outlined (i.e. midline of the corpus callosum, see highlighted in FIG. 4-1), and the picture converted to an 8-bit greyscale image. Afterwards, a binary picture was created by applying an auto threshold algorithm, and the relative area of the signal was measured. For Region 1, the Yen algorithm was applied, whereas for Region 2, the Shanbhag/Moments algorithm was applied, respectively (see also FIG. 4-2).

Since the slides of all the groups were separately stained, a correction factor was applied to allow direct comparison of the results. This correction factor was determined based on visual inspection of the slides under the microscope. The used correction factors were of 0.33, 0.75 and 7 respectively, depending on the regions analyzed. Two consecutive sections per region were analyzed. Values for each section were used for statistics.

In order to evaluate demyelination in LFB-stained sections, magnitude of myelination was scored in the corpus callosum between 100 and 0. A score of 100 is equivalent to the myelin status of a mouse not treated with cuprizone, whereas zero is equivalent to a totally demyelinated corpus callosum. Myelination values were obtained by inspection of two consecutive slides, one value per doublet was assessed.

Experimental design. Mice were fed with cuprizone for 5 weeks and were allowed to recover from the intoxication for 11 days until tissue samples collection (i.e. remyelination period). Vehicle or drug treatment started after three full weeks of cuprizone feeding and were pursued until the end of the experiment (i.e. up to week 6.5). The drug was daily administered orally (PO at a volume of administration of 10 mL/kg. The experimental conditions were 1) vehicle 2) 6 mg/kg 3) 20 mg/kg and, 60 mg/kg with a number of 10 animals per condition.

References: 1. Kipp et al, 2009 Acta Neuropathol 118: 723;
2. Kipp et al, 2011, Brain Behav Immun 25: 1554-1568;
3. Slowik et al, 2015, Br J Pharmacol 172: 80-92.

Statistical Analysis.

The IHC analysis were done blind and to do so, the treatment group assignment was only disclosed after the quality check and the statistical analysis. Data were analysed using parametric statistical analysis and Statistica software (StatSoft Inc., OK, USA). The dependent variable was the quantification of PLP measured in the corpus callosum. As the analyses aimed at comparing four doses (0, 6, 20 and 60 mg/kg), one-way ANOVA was applied. The between-mean differences was tested using Tukey's Honestly Significant Difference (HSD) test. As necessary, logarithmic transformations to normalise raw data prior to the statistical analysis, was performed to more precisely meet the assumption of homogeneity of variances (Levene's test) and Gaussian distribution. For the sake of clarity, however, means of the raw values are presented in the figures. Statistical significance was set at $p<0.05$. Data are expressed as mean±SEM.

Results.

The one-way ANOVA showed significant effect of the dose [$F(3,70)=3.28$, $p<0.001$] and Tukey post hoc test showed that the two groups treated with the dose of 6 and 20 mg/kg had significant higher PLP levels in the comparison to the vehicle-treated group ($p<0.01$), see FIG. 5.

CONCLUSION

Compound I-228 accelerates the reappearance of the myelin-associated proteins after oral administration at 6 mg/kg and 20 mg/kg in the cuprizone model. PLP being a marker of myelin, these results show that GPR17 inhibition by the compounds of the present invention either prevent demyelination or, more likely, promote remyelination after cuprizone-induced demyelination. This is in line with the recently published data obtained in the LPC induced demyelination with GPR17 ko mice (Ou et al., 2016).

The invention claimed is:
1. A compound having Formula I-2,

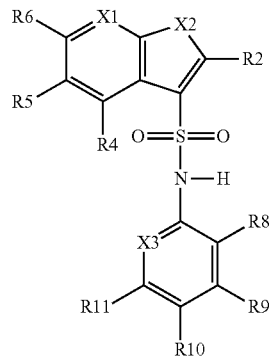

Formula I-2 wherein
X1 is N or C(R7),
X2 is NH, S or O,
X3 is N or C(R12),
R2 is selected from hydrogen, fluoro, chloro, bromo, iodo and methoxy,
R4 is selected from hydrogen, methoxy and halogen,
R5 is selected from hydrogen, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfinyl, and $C_{1-3}$alkylsulfonyl, wherein each alkyl or alkoxy may optionally be substituted one or more times with a substituent selected from halogen, $C_{1-3}$ alkoxy, cyano, azido, hydroxyl, $C_{1-3}$alkylamino and di($C_{1-3}$alkyl)amino, or R5 forms a ring together with R6,
R6 is selected from hydrogen, fluoro, chloro, bromo, iodo, cyano, azido, unsubstituted or substituted $C_{1-3}$ alkyl, unsubstituted or substituted $C_{1-3}$ alkoxy, unsubstituted or substituted $C_{2-3}$ alkenyl, unsubstituted or substituted $C_{2-3}$ alkynyl, unsubstituted or substituted $C_{1-3}$ alkylcarbonyl, unsubstituted or substituted $C_{1-3}$ alkoxycarbonyl, unsubstituted or substituted $C_{1-3}$ alkylsulfinyl, unsubstituted or substituted $C_{1-3}$ alkylsulfonyl, unsubstituted or substituted benzylsulfonyl, unsubstituted or substituted benzylsulfinyl, unsubstituted or substituted $C_{3-7}$ cycloalkyl, unsubstituted or substituted $C_{3-7}$ cycloalkyl($C_{1-3}$)alkyl, unsubstituted or substituted $C_{3-7}$ heterocycloalkyl, unsubstituted or substituted $C_{3-7}$ heterocycloalkyl($C_{1-3}$)alkyl, unsubstituted or substituted $C_{3-6}$ cycloalkoxy, unsubstituted or substituted $C_{3-6}$ heterocycloalkoxy, unsubstituted or substituted $C_{1-5}$alkoxy($C_{1-5}$)alkyl, unsubstituted or substituted $C_{1-3}$alkoxy($C_{1-3}$)alkoxy, unsubstituted or substituted ($C_{3-6}$)cycloalkyl($C_{1-3}$)alkoxy, unsubstituted or substituted ($C_{3-6}$)heterocycloalkyl($C_{1-3}$)alkoxy, unsubstituted or substituted phenyl, unsubstituted or substituted phenyloxy, unsubstituted or substituted thienyl, unsubstituted or substituted pyridyl, unsubstituted or substituted oxazole, unsubstituted or substituted thiazole, unsubstituted or substituted isoxazole, unsubstituted or substituted phenyl($C_{1-3}$)alkoxy,
wherein each optional substitution in R6 is selected from one or more of the group consisting of fluoro, chloro, bromo, unsubstituted or fluorinated methyl, unsubstituted or fluorinated methoxy, hydroxy and cyano, or
(i) R6 forms together with R7 and the carbon atoms to which R6 and R7 are attached, an unsubstituted or substituted phenyl, unsubstituted or substituted pyridyl, unsubstituted or substituted cyclopentyl or unsubstituted or substituted cyclohexyl,
wherein each substitution, if present, is selected from halogen, hydroxy, cyano, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$) alkyl, $C_{3-7}$ heterocycloalkyl($C_{1-3}$)alkyl, $C_{1-6}$ alkoxy, and $C_{1-6}$ alkoxy($C_{1-3}$)alkyl, wherein each alkyl or alkoxy can be unsubstituted or substituted with one or more substituents selected from halogen and $C_{1-3}$ alkoxy,
or
(ii) R6 forms together with R5 and the carbon atoms to which R6 and R5 are attached, a 1,3-dioxolane which may be unsubstituted or substituted with one or two substituents selected from fluoro and methyl,
R7 is selected from hydrogen, halogen, cyano, $C_{1-3}$ alkyl, $C_{1-3}$ alkoxy, $C_{1-3}$ alkylcarbonyl, $C_{1-3}$ alkoxycarbonyl, $C_{1-3}$ alkylsulfonyl, $C_{1-3}$ alkylsulfinyl, $C_{5-6}$ heteroaryl, and $C_{5-6}$ heteroaryl($C_{1-3}$) alkoxy, wherein each alkyl or alkoxy moiety can be unsubstituted or substituted with one or more substituents selected from the group consisting of halogen, halo($C_{1-6}$)alkoxy, and $C_{1-3}$ alkoxy, and wherein each heteroaryl can be unsubstituted or substituted with one or more substituents selected from the group consisting of halogen, methyl, hydroxy, and methoxy, or R7 forms a ring together with R6,
R8 is selected from hydrogen, $C_{1-3}$ alkyl, $C_{1-3}$ alkoxy, cyano, and halogen, wherein each alkyl or alkoxy can be unsubstituted or substituted with one or more substituents selected from halogen, cyano and methoxy, or R8 forms a ring system together with R9, as described herein,
R9 is selected from hydrogen, $C_{1-3}$ alkyl, $C_{2-3}$ alkoxy, fluoro, chloro, bromo and iodo, wherein each alkyl or alkoxy can be unsubstituted or substituted with one or more substituents selected from halogen and methoxy,
or R9 forms together with R8 or R10 and the ring to which they are attached a bicyclic ring system selected from 2,1,3-benzothiadiazole, 2,1,3-benzoselenadiazole, 2,1,3-benzoxadiazole, 1,3-benzothiazole, 1,3-benzoxazole which may be unsubstituted or may be partially hydrogenated and substituted with oxo, 2-oxo-2,3-dihydro-1,3-benzoxazol, 1,3-benzodioxole which may be unsubstituted or substituted with one or two substituents selected from fluoro and methyl, 2,2-difluoro-1,3-benzodioxol, 2,3-dihydrobenzothiophene which may be unsubstituted or substituted with one or two oxo groups, 1,1-dioxido-2,3-dihydro-1-benzothiophen, 1,3-dihydro-2-benzofuran which may be unsubstituted or substituted with one or two groups selected from oxo, fluoro and methyl, 3-oxo-1,3-dihydro-2-benzofuran, 1-methyl-3-oxo-1,3-dihydro-2-benzofuran, dihydroisoindol which may be unsubstituted or substituted with one or more substituents selected from oxo, fluoro and methyl, and 3-oxo-2,3-dihydro-1H-isoindol,
R10 is selected from hydrogen, fluoro, chloro, bromo, iodo, $C_{1-5}$ alkyl, $C_{1-5}$ alkoxy, $C_{2-4}$ alkenyl, $C_{2-4}$ alkynyl, $C_{3-4}$ cycloalkyl, $C_{3-4}$heterocycloalkyl, cyano, cyanomethyl, cyanomethoxy, $C_{1-3}$ alkylcarbonyl, $C_{1-3}$ alkoxycarbonyl, azido, pentafluorosulfanyl, and nitro, wherein each alkyl, alkenyl, alkynyl or alkoxy can be unsubstituted or substituted with one or more substituents selected from halogen, unsubstituted or fluorinated $C_{1-3}$ alkoxy, unsubstituted or fluorinated $C_{1-3}$ alkoxycarbonyl, unsubstituted or fluorinated $C_{1-3}$ alkylcarbonyl, cyano, hydroxy, cyclopropyl and pyridyl, wherein the pyridyl may be optionally substituted with halogen, unsubstituted or fluorinated methyl and/or unsubstituted or fluorinated methoxy, and wherein any cycloalkyl or heterocycloalkyl can be unsubstituted or substituted with a group selected from halogen, cyano, hydroxy($C_{1-2}$)alkyl, $C_{1-2}$alkoxy and $C_{1-2}$alkoxycarbonyl, or R10 forms a ring system together with R9, R11 is selected from hydrogen, $C_{1-3}$ alkyl, $C_{1-3}$ alkoxy, fluoro, chloro, bromo, iodo, cyano, $C_{1-3}$ alkylcarbonyl, and $C_{1-3}$ alkoxycarbonyl, wherein each alkyl and alkoxy can be unsubstituted or substituted with one or more substituents selected from fluoro, chloro, bromo, iodo and $C_{1-3}$ alkoxy, R12, if present, is selected from hydrogen, $C_{1-3}$ alkyl, $C_{1-3}$ alkoxy, fluoro, chloro, bromo, and iodo, wherein each alkyl and alkoxy can be unsubstituted or substituted with one or more substituents selected from fluoro, chloro, bromo, iodo and $C_{1-3}$ alkoxy, wherein at least one of R5, R6 and R7 is different from hydrogen, wherein at least one of R8, R9, R10, and R11 is different from hydrogen, and pharmaceutically acceptable salts, solvates, isotopes and co-crystals thereof.

2. A compound according to claim 1, wherein
X1 is N or C(R7),
X2 is NH, S or O,
X3 is N or C(R12),
R2 and R4 are both hydrogen,
R5 is selected from hydrogen, fluoro, chloro and bromo,
R6 is selected from fluoro, chloro, bromo, iodo, cyano, azido, methyl, ethyl, propyl, isopropyl, trifluoromethyl, ethenyl, ethynyl, propargyl, methylsulfinyl, methylsulfonyl, cyclopropyl, cyclopropyloxy, cyclopropylmethyl, methoxy, ethoxy, propoxy, methoxyethoxy, ethoxymethoxy, cyclopropylmethoxy, oxetanyl, oxetanylmethoxy, tetrahydrofuranyl, tetrahydrofuranylmethoxy, phenyl, benzyloxy, phenyloxy, benzylsulfinyl, thienyl, pyridyl, oxazole, thiazole, and isoxazole, wherein each phenyl, thienyl, pyridyl, oxazol, thiazole and isoxazol can be optionally substituted one or more times with a substitution selected from halogen, methoxy, and methyl, and wherein each alkyl, alkenyl, alkynyl, and alkoxy group can be substituted one or more times with fluoro, methoxy, fluoromethoxy, and hydroxy,
or R6 forms together with R7 and the carbon atoms to which R6 and R7 are attached, a ring selected from phenyl, pyridyl, cyclohexyl, and cyclopentyl, each of which can be unsubstituted or further substituted with one or more residues selected from halogen, hydroxy, unsubstituted or fluorinated methyl, and unsubstituted or fluorinated methoxy,
R7 is selected from hydrogen, fluoro, chloro, bromo, iodo, cyano, methylsulfinyl, methylsulfonyl, methoxy, fluoromethoxy, fluoroethoxy, methyl, fluoromethyl, and fluoroethyl, or R7 forms a ring together with R6,
R8 is selected from hydrogen, fluoro, chloro, bromo, iodo, methoxy, fluoromethoxy, cyano, methyl, and fluoromethyl, or R8 forms a ring system together with R9,
R9 is selected from hydrogen, fluoro and chloro,
or R9 forms together with R8 or R10 and the ring to which they are attached a bicyclic ring system selected from 2,1,3-benzothiadiazole, 2,1,3-benzoxadiazole, 2-oxo-2,3-dihydro-1,3-benzoxazole and 1,3-benzodioxole, which is optionally substituted with two fluoros,
or R9 forms together with R10 and the ring to which they are attached a bicyclic ring system selected from 3-oxo-2,3-dihydro-1H-isoindol, 2,3-dihydro-1-benzothiophene, which is substituted with one or two oxo, and optionally methylated 3-oxo-1,3-dihydro-2-benzofuran,
R10 is selected from hydrogen, fluoro, chloro, bromo, iodo, methyl, ethyl, n-propyl, isopropyl, ethenyl, n-propenyl, isopropenyl, ethynyl, propargyl, fluoro($C_{1-3}$)alkyl, methoxy, ethoxy, propoxy, fluoro($C_{1-3}$)alkoxy, $C_{1-3}$alkoxy($C_{1-3}$)alkyl, $C_{1-3}$alkoxy($C_{1-3}$)alkoxy, $C_{1-3}$alkoxy($C_{2-3}$)alkenyl, $C_{1-3}$alkoxy($C_{2-3}$)alkynyl, $C_{1-3}$alkoxycarbonyl($C_{1-3}$)alkyl, $C_{1-3}$alkylcarbonyl($C_{1-3}$)alkyl, $C_{1-3}$ alkylcarbonyl($C_{1-3}$)alkyloxy, cyano, acetyl, azido, nitro, pentafluorosulfanyl, cyclopropyl, cyclopropyloxy, cyclopropylmethoxy, and ($C_{1-3}$)alkoxycarbonyl, wherein each alkyl, alkenyl, alkynyl and alkoxy group in R10 can be unsubstituted or substituted with one or more residues selected from fluoro, cyano and/or hydroxy, and wherein the cyclopropyl is optionally substituted with one or more residues selected from cyano, optionally fluorinated $C_{1-2}$ alkoxy and optionally fluorinated $C_{1-2}$alkoxycarbonyl, or R10 forms a ring system together with R9,
R11 is selected from hydrogen, fluoro, chloro, bromo, cyano, methyl, fluoromethyl, methoxy and fluoromethoxy,
R12, if present, is selected from hydrogen, fluoro, chloro and bromo,
wherein at least two of R8, R10 and R11 are different from hydrogen,
and pharmaceutically acceptable salts, solvates, isotopes and co-crystals thereof.

3. A compound according to claim 1, wherein
X1 is N or C(R7),
X2 is NH, S or O,
X3 is N or C(R12),
R2 and R4 are both selected from hydrogen and fluoro,
R5 is selected from hydrogen and halogen,
R6 is selected from hydrogen, fluoro, chloro, bromo, iodo, cyano, azido, unsubstituted or fluorinated $C_{1-3}$ alkyl, unsubstituted or fluorinated $C_{1-3}$ alkoxy, methylsulfinyl, methylsulfonyl, cyclopropyl, cyclopropylmethyl, cyclopropylmethoxy, benzyloxy, benzylsulfinyl, thienyl and pyridyl,
R7 is selected from hydrogen, fluoro, chloro, bromo, cyano, methyl, methoxy, fluoromethyl, fluoromethoxy, methylsulfinyl and methylsulfonyl,
R8 is selected from hydrogen, fluoro, chloro, cyano, methoxy and fluoromethoxy,
R9 is hydrogen or fluoro,
R10 is selected from fluoro, chloro, bromo, iodo, azido, cyano, oxetanyl, cyano($C_{1-2}$)alkyl, cyano($C_{1-2}$)alkoxy, cyclopropyl($C_{1-2}$)alkyl, cyclobutyl($C_{1-2}$)alkyl, cyclopropyl($C_{1-2}$)alkoxy, optionally fluorinated $C_{1-2}$alkoxycyclopropyl, optionally fluorinated $C_{1-2}$alkoxycarbonylcyclopropyl, unsubstituted or fluorinated $C_{1-3}$ alkyl, unsubstituted or fluorinated $C_{1-3}$ alkoxy, unsubstituted or fluorinated $C_{2-3}$ alkenyl, unsubstituted or fluorinated $C_{2-3}$ alkynyl, unsubstituted or fluorinated $C_{1-3}$ alkoxy ($C_{1-3}$)alkyl, unsubstituted or fluorinated $C_{1-3}$ alkoxy ($C_{1-3}$)alkoxy, unsubstituted or fluorinated $C_{1-3}$ alkoxy ($C_{2-3}$)alkenyl, and pentafluorosulfanyl,
R11 is selected from hydrogen, fluoro, chloro, methoxy, fluoromethoxy and fluoromethyl, R12, if present, is hydrogen or fluoro,
wherein at least one of R8 and R11 is different from hydrogen,
and pharmaceutically acceptable salts, solvates, isotopes and co-crystals thereof.

4. A compound according to claim 1, wherein
X1 is N or C(R7),
X2 is NH,
X3 is N or CR12,
R2 and R4 are both hydrogen,
R5 is selected from hydrogen, fluoro, chloro and bromo,
R6 is selected from fluoro, bromo, chloro, azido, cyano, methyl, fluoromethyl, ethyl, fluoroethyl, isopropyl, cyclopropyl, cyclopropylmethyl, cyclopropylmethoxy, methoxy, ethoxy, fluoromethoxy, fluoroethoxy, methylsulfinyl, methylsulfonyl, benzyloxy and thienyl,
R7 is selected from hydrogen, methoxy, fluoro, chloro, bromo, cyano, fluoromethoxy, fluoroethoxy, and mono-, di- and trifluoromethyl,
R8 is selected from hydrogen, fluoro, chloro, and methoxy,
R9 is hydrogen or fluoro,
R10 is selected from fluoro, chloro, bromo, cyano, cyanomethyl, cyanoethyl, cyanomethoxy, azido, methyl, ethyl, propyl, ethenyl, propenyl, ethynyl, propargyl, mono-, di-, and trifluoromethyl, cyclopropylmethoxy, cyclopropylethoxy, methoxycyclopropyl, ethoxycyclopropyl, methoxycarbonylcyclopropyl, ethoxycarbonylcyclopropyl, mono-, di- and trifluoromethoxy, mono-, di-, and trifluoroethoxy, ethoxymethyl, methoxyethyl, ethoxyethyl, methoxypropyl, fluoroethoxymethyl, fluoromethoxyethyl, fluoroethoxyethyl, fluoromethoxypropyl, ethoxymethoxy, methoxyethoxy, methoxypropoxy, fluoroethoxymethoxy, fluoromethoxyethoxy, fluoromethoxypropoxy, methoxyethenyl, methoxypropenyl, fluoromethoxyethenyl, ethynyl, propargyl, and pentafluorosulfanyl,
R11 is selected from hydrogen, fluoro, chloro, fluoromethyl, methoxy, and fluoromethoxy,
R12, if present, is hydrogen or fluoro,
wherein at least one of R8 and R11 is different from hydrogen,
and pharmaceutically acceptable salts, solvates, isotopes and co-crystals thereof.

5. A compound according to claim 1 having the structure of Formula II

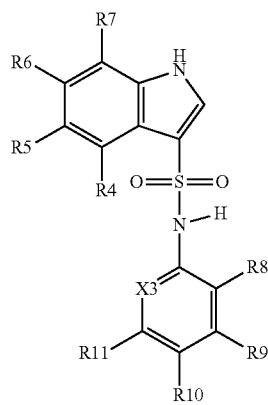

Formula II or having the structure of Formula III

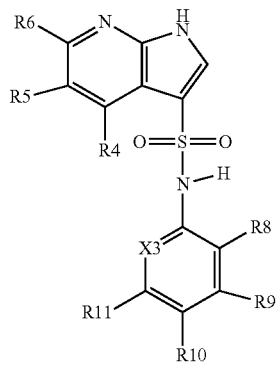

Formula III wherein
X3 is N or C(R12),
R4 is hydrogen,
R5 is selected from hydrogen, fluoro, chloro and bromo,
R6 is selected from fluoro, chloro, bromo, iodo, cyano, azido, methyl, ethyl, n-propyl, isopropyl, trifluoromethyl, methylsulfinyl, methylsulfonyl, cyclopropyl, cyclopropylmethyl, methoxy, ethoxy, methoxymethoxy, methoxyethoxy, ethoxymethoxy, cyclopropylmethoxy, phenyl, benzyloxy, phenyloxy, benzylsulfinyl, benzylsulfonyl, thienyl, pyridyl, oxazole, thiazole, and isoxazole, wherein each alkyl and alkoxy group in R6 can be substituted with one or more residues selected from fluoro, cyano, and hydroxy and wherein each phenyl, thienyl, pyridyl, oxazol, thiazole and isoxazol can be optionally substituted one or more times,
or, in the compounds of formula II, R6 together with R7 and the carbon atoms to which R6 and R7 are attached may form a ring selected from phenyl, pyridyl, cycloxhexyl and cyclopentyl, each of which can be unsubstituted or substituted one or more times with a group selected from methyl, fluorinated methyl, methoxy, fluorinated methoxy, hydroxy, chloro and fluoro,
R7, in the compounds of Formula II, is selected from hydrogen, fluoro, chloro, bromo, iodo, cyano, methoxy, ethoxy, methylsulfinyl, methylsulfonyl, methyl, ethyl, fluoromethyl, fluoroethyl, and fluoro($C_{1-2}$)alkoxy, or R7 forms a ring together with R6,
R8 is selected from hydrogen, fluoro, chloro, bromo, iodo, methoxy, fluoromethyl and fluoromethoxy, or R8 forms a ring system together with R9,
R9 is selected from hydrogen, methyl, fluoro and chloro,
or R9 forms together with R8 or R10 and the ring to which they are attached a bicyclic ring system selected from 2,1,3-benzothiadiazole, 2,1,3-benzoxadiazole, 2-oxo-2,3-dihydro-1,3-benzoxazole and 1,3-benzodioxole, which is optionally substituted with two fluoros,
or R9 forms together with R10 and the ring to which they are attached a bicyclic ring system selected from 3-oxo-2,3-dihydro-1H-isoindol, 1,1-dioxo-2,3-dihydro-1-benzothiophene and 3-oxo-1,3-dihydro-2-benzofuran which can be optionally methylated in 1 position,
R10 is selected from hydrogen, fluoro, chloro, bromo, iodo, unsubstituted or fluorinated $C_{1-3}$ alkenyl including ethenyl and propenyl, unsubstituted or fluorinated $C_{1-3}$alkynyl including ethynyl and propargyl, unsubstituted or fluorinated and/or hydroxylated $C_{1-3}$alkyl including methyl, ethyl, isopropyl and trifluoromethyl, unsubstituted or fluorinated and/or hydroxylated $C_{1-3}$alkoxy including methoxy and fluoro($C_{1-2}$)alkoxy, cyano, cyanomethyl, cyanomethoxy, cyclopropyl, cyclopropylmethoxy, cyclopropylethoxy, acetyl, azido, nitro, pentafluorosulfanyl, unsubstituted or fluorinated and/or hydroxylated $C_{1-3}$alkoxy($C_{1-3}$)alkyl, unsubstituted or fluorinated and/or hydroxylated $C_{1-3}$alkoxy ($C_{1-3}$)alkoxy, unsubstituted or fluorinated and/or hydroxylated $C_{1-3}$alkoxy($C_{2-3}$)alkenyl, unsubstituted or fluorinated and/or hydroxylated $C_{1-3}$ alkoxy($C_{2-3}$)alkynyl, unsubstituted or fluorinated and/or hydroxylated $C_{1-3}$alkoxycarbonyl ($C_{1-3}$)alkyl, and unsubstituted or fluorinated and/or hydroxylated $C_{1-3}$alkoxycarbonyl($C_{1-3}$)alkenyl, wherein each cyclopropyl group in R10 may be unsubstituted or further substituted with one or more substituents selected from fluoro, chloro, cyano, optionally fluorinated $C_{1-2}$alkoxy and optionally fluorinated $C_{1-2}$alkoxycarbonyl, or R10 forms a ring system together with R9, R11 is selected from hydrogen, fluoro, chloro, bromo, unsubstituted or fluorinated methyl, and unsubstituted or fluorinated methoxy, R12, if present, is selected from hydrogen, fluoro, chloro, or bromo, wherein at least one of R8, R10 and R11, is different from hydrogen and unsubstituted alkyl, and pharmaceutically acceptable salts, solvates, isotopes and co-crystals thereof.

6. A compound according to claim 5, wherein
R4 and R5 are both hydrogen,
R6 is selected from fluoro, chloro, bromo, methoxy, fluoromethoxy and fluoromethyl,
R7, in the compounds of Formula II, is selected from hydrogen, methoxy, fluoro, chloro, bromo, fluoromethyl, fluoromethoxy, fluoroethoxy, methylsulfinyl and methylsulfonyl,
X3 is N or CR12,
R8 is fluoro or methoxy,
R9 is hydrogen,
R10 is selected from fluoro, chloro, bromo, cyano, cyanomethyl, cyanoethyl, cyanomethoxy, unsubstituted or fluorinated $C_{1-3}$ alkyl, unsubstituted or fluorinated $C_{1-3}$ alkoxy, unsubstituted or fluorinated $C_{1-2}$alkoxy($C_{1-3}$)alkyl, unsubstituted or fluorinated $C_{1-2}$alkoxy($C_{2-3}$)alkenyl, unsubstituted or fluorinated $C_{1-2}$alkoxy($C_{1-3}$)alkoxy, pentafluorosulfanyl and cycloalkyl, which is substituted with a substituent selected from $C_{1-2}$alkoxy, fluoro($C_{1-2}$)alkoxy, $C_{1-2}$alkoxycarbonyl and fluoro($C_{1-2}$)alkoxycarbonyl,
R11 is selected from hydrogen, methoxy, fluoromethoxy, fluoromethyl, and fluoro,
R12, if present, is hydrogen or fluoro,
and pharmaceutically acceptable salts, solvates, isotopes and co-crystals thereof.

7. A compound according to claim 5, wherein
R4 is hydrogen,
R5 is selected from hydrogen, fluoro, chloro and bromo,
R6 is selected from fluoro, chloro, bromo, iodo, cyano, methyl, ethyl, isopropyl, fluoromethyl, fluoroethyl, methoxy, fluoromethoxy, fluoroethoxy, cyano, methylsulfinyl, methylsulfonyl, cyclopropyl, phenyl, benzyloxy, 2-thienyl and 3-thienyl,
R7 is selected from hydrogen, fluoro, chloro, bromo, cyano, fluoro($C_{1-2}$)alkyl, and fluoro($C_{1-2}$)alkoxy,
X3 is C(R12),
R8 and R11 are independently selected from hydrogen, fluoro, chloro, cyano, fluoromethyl, methoxy and fluoromethoxy, R9 is hydrogen,
R10 is selected from fluoro, chloro, bromo, iodo, azido, unsubstituted or fluorinated $C_{1-3}$alkyl, unsubstituted or fluorinated $C_{1-3}$alkyloxy, unsubstituted or fluorinated $C_{1-3}$alkoxy($C_{1-3}$)alkyl, unsubstituted or fluorinated $C_{1-3}$alkoxy($C_{1-3}$)alkoxy, unsubstituted or fluorinated $C_{1-3}$alkoxy($C_{2-3}$)alkenyl, pentafluorosulfanyl, ethynyl, propynyl, cyano, cyanomethoxy, and cyanomethyl, and R12 is hydrogen and fluoro, wherein at least one of R8 and R11 is fluoro;

and pharmaceutically acceptable salts, solvates, isotopes and co-crystals thereof.

8. A compound according to claim 5 and having Formula III, wherein

R4 and R5 are both hydrogen,

R6 is selected from hydrogen, fluoro, chloro, bromo, fluoromethyl, methoxy, fluoromethoxy, and cyclopropyl, X3 is C(R12) or N, R8 is selected from hydrogen, methoxy, and halogen, R9 is hydrogen, R10 is selected from fluoro, bromo, chloro, iodo, methyl, fluoro($C_{1-3}$)alkyl, unsubstituted or fluorinated methoxy ($C_{1-3}$)alkyl, unsubstituted or fluorinated $C_{1-3}$alkyloxy, unsubstituted or fluorinated methoxy($C_{1-3}$)alkyloxy, unsubstituted or fluorinated $C_{2-3}$alkenyl, unsubstituted or fluorinated methoxy($C_{2-3}$)alkenyl, ethynyl, propargyl, unsubstituted or fluorinated methoxy($C_{2-3}$)alkynyl, azido, pentafluorosulfanyl, cyanomethyl, cyanoethyl, and cyano, R11 is hydrogen, fluoro, chloro, or methoxy, R12, if present, is hydrogen or fluoro, and pharmaceutically acceptable salts, solvates, isotopes and co-crystals thereof.

9. A compound according to claim 5 and having formula III, wherein

R4 and R5 are both hydrogen,

R6 is selected from chloro, bromo, methoxy, mono-, di-, and trifluoromethyl,

X3 is C(R12) or N,

R8 is selected from hydrogen, fluoro, chloro, methoxy and fluoromethoxy,

R9 is hydrogen,

R10 is selected from fluoro, chloro, bromo, cyano, cyanomethyl, cyanoethyl, cyanomethoxy, mono-, di-, and trifluoromethyl, mono-, di-, and trifluoromethoxy, mono-, di-, and trifluoroethoxy, unsubstituted or fluorinated $C_{1-2}$alkoxy($C_{1-3}$)alkoxy, unsubstituted or fluorinated $C_{1-2}$alkoxy($C_{1-3}$)alkyl, unsubstituted or fluorinated $C_{2-3}$alkenyl, unsubstituted or fluorinated $C_{1-2}$alkoxy($C_{2-3}$)alkenyl, and $C_{2-3}$alkynyl, R11 is selected from hydrogen, methoxy, fluoro and chloro and R12, if present, is hydrogen or fluoro;

and pharmaceutically acceptable salts, solvates, isotopes and co-crystals thereof.

10. A compound according to claim 1, wherein X3 is N, thus having the structure of Formula VI:

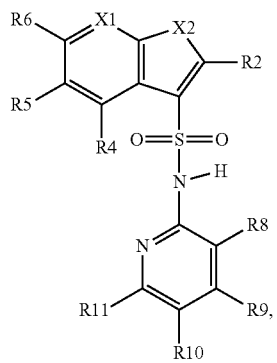

Formula VI wherein X1, X2, R2, R4, R5, R6, R8, R9, R10 and R11 have the meaning as described in claim 1; and pharmaceutically acceptable salts, solvates, isotopes and co-crystals thereof.

11. A compound according to claim 10, wherein
X1 is C—R7 or N,
X2 is NH,
R2 and R4 are both hydrogen,
R5 is selected from hydrogen, fluoro, chloro and bromo,
R6 is selected from fluoro, chloro, bromo, cyano, azido, $C_{1-3}$alkyl, $C_{1-3}$alkyloxy, cyclopropyl, cyclopropyloxy, oxetanyl, tetrahydrofuranyl, methylsulfonyl, methylsulfinyl, thienyl, pyridyl, and benzyloxy, wherein each alkyl or alkoxy group in R6 can be unsubstituted or substituted with one or more groups selected from fluoro, chloro, bromo, unsubstituted or fluorinated $C_{1-2}$alkyloxy and cyclopropyl and wherein each cyclopropyl, thienyl, pyridyl and phenyl group in R6 can be substituted with one or more groups selected from halogen, methoxy, fluoromethoxy, methyl, fluoromethyl and cyano,
or R6 forms together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution in R7, if present, is selected from hydroxy, halogen, methyl and methoxy, wherein each methyl or methoxy can be unsubstituted or fluorinated,
R7, if present, is selected from hydrogen, halogen, cyano, $C_{1-3}$alkyl, $C_{1-3}$alkoxy, methylsulfinyl and methylsulfonyl, wherein each alkyl or alkoxy group in R7 can be unsubstituted or substituted with one or more groups selected from fluoro, chloro, cyano, and unsubstituted or fluorinated $C_{1-2}$alkyloxy, or R7 forms a ring together with R6 as described herein,
R8 is selected from fluoro, chloro, unsubstituted or fluorinated methyl, and unsubstituted or fluorinated methoxy,
R9 is selected from hydrogen, fluoro, methyl, fluoromethyl, methoxy, and fluoromethoxy,
R10 is selected from halogen, $C_{1-3}$alkyl, $C_{1-3}$alkyloxy, $C_{2-3}$alkenyl, $C_{2-3}$alkynyl, $C_{1-3}$ alkylcarbonyl, $C_{3-4}$cycloalkyl, $C_{3-4}$cycloalkyloxy, $C_{3-4}$heterocycloalkyl, $C_{3-4}$heterocycloalkyloxy and cyano, wherein each alkyl, alkenyl, alkynyl or alkoxy can be unsubstituted or substituted with one or more substituents selected from fluoro, chloro, bromo, fluorinated or unsubstituted $C_{1-3}$alkyloxy, fluorinated or unsubstituted $C_{1-3}$alkylcarbonyl, $C_{1-3}$alkoxycarbonyl, $C_{3-5}$cycloalkyl, $C_{3-5}$cycloalkyloxy, $C_{3-5}$heterocycloalkyl, $C_{3-5}$heterocycloalkyloxy, hydroxy and cyano, wherein any $C_{3-5}$cycloalkyl and hetero($C_{3-5}$)cycloalkyl may be unsubstituted or substituted with one or more residues selected from halogen, hydroxy, hydroxymethyl, cyano, fluorinated or unsubstituted methyl, fluorinated or unsubstituted methoxy and fluorinated or unsubstituted $C_{1-3}$alkyloxy($C_{1-3}$)alkyloxy,
R11 is selected from hydrogen, fluoro, chloro, bromo, unsubstituted or fluorinated $C_{1-3}$ alkyl, and unsubstituted or fluorinated $C_{1-3}$ alkyloxy,
and pharmaceutically acceptable salts, solvates, isotopes and co-crystals thereof.

12. A compound according to claim 10 and having one of the following formulae VIa, VIb, VIc or VId:

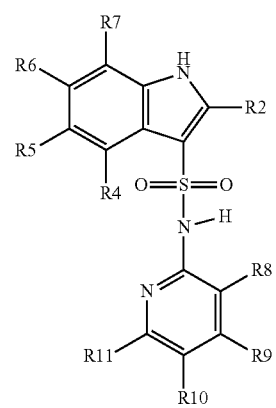

Formula VIa

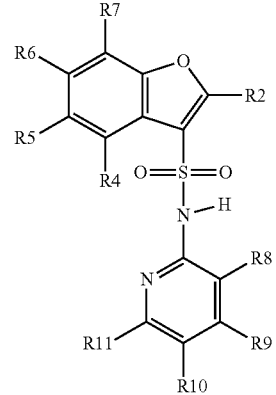

Formula VIb

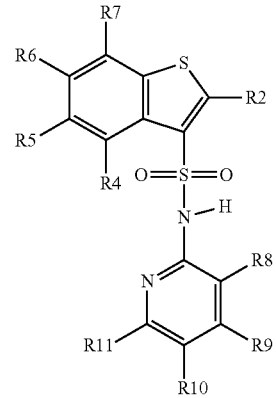

Formula VIc

-continued

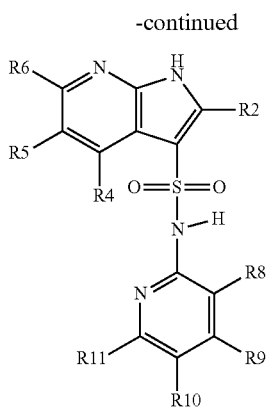

Formula VId wherein
R2 and R4 are both hydrogen,
R5 is selected from hydrogen, fluoro, chloro and bromo,
R6 is selected from fluoro, chloro, bromo, azido, cyano, benzyloxy, methylsulfonyl, methylsulfinyl, $C_{1-3}$alkyl, $C_{1-3}$alkyloxy, cyclopropyl, cyclopropyloxy and cyclopropylmethoxy, wherein each alkyl, alkoxy and cyclopropyl group in R6 can be unsubstituted or substituted with one or more groups selected from fluoro, chloro, bromo and unsubstituted or fluorinated $C_{1-2}$alkyloxy,
wherein in the compounds of formula VIa, VIb or VIc, R6 may also form together with R7 and the carbon atoms to which R6 and R7 are attached, an unsubstituted or substituted phenyl, an unsubstituted or substituted pyridyl, an unsubstituted or substituted cyclopentyl or an unsubstituted or substituted cyclohexyl, wherein each substitution in R7, if present, is selected from hydroxy, halogen, cyano, methyl and methoxy, wherein each methyl or methoxy can be unsubstituted or fluorinated and/or hydroxylated,
R7, if present, is selected from hydrogen, halogen, cyano, $C_{1-3}$alkyl, $C_{1-3}$alkyloxy, $C_{3-6}$ cycloalkyl, $C_{3-6}$ cycloalkyloxy, methylsulfinyl and methylsulfonyl, wherein alkyl, alkoxy or cycloalkyl group in R7 can be unsubstituted or substituted with one or more groups selected from fluoro, chloro, cyano and unsubstituted or fluorinated $C_{1-2}$alkyloxy, or R7 forms a ring together with R6 as described herein,
R8 is selected from hydrogen, fluoro, chloro, unsubstituted or fluorinated methoxy and unsubstituted or fluorinated methyl,
R9 is selected from hydrogen, fluoro, methyl and methoxy,
R10 is selected from hydrogen, halogen, cyano, $C_{1-3}$alkyl, $C_{2-3}$alkenyl, $C_{2-3}$alkynyl, $C_{1-3}$alkyloxy, $C_{3-4}$cycloalkyl, $C_{3-4}$cycloalkyloxy, $C_{3-4}$heterocycloalkyl, and $C_{3-4}$heterocycloalkyloxy, wherein each alkyl, alkenyl, alkynyl and alkyloxy group in R10 can be unsubstituted or substituted with one or more groups selected from fluoro, chloro, bromo, fluorinated or unsubstituted $C_{1-3}$alkyloxy, fluorinated or unsubstituted $C_{1-3}$alkylcarbonyl, fluorinated or unsubstituted $C_{1-3}$alkoxycarbonyl, $C_{3-4}$cycloalkyl, $C_{3-4}$cycloalkyloxy, $C_{3-4}$heterocycloalkyl, $C_{3-4}$heterocycloalkyloxy, hydroxy, and cyano, and wherein each cycloalkyl and heterocycloalkyl group in R10 can be substituted with a residue selected from fluoro, chloro, bromo, hydroxy, hydroxymethyl, fluorinated or unsubstituted $C_{1-3}$alkyl, fluorinated or unsubstituted $C_{1-3}$alkyloxy, fluorinated or unsubstituted $C_{1-2}$alkyloxy$C_{1-2}$alkyloxy and fluorinated or unsubstituted $C_{1-3}$alkoxycarbonyl,
R11 is selected from hydrogen, fluoro, chloro, bromo, unsubstituted or fluorinated methyl, and unsubstituted or fluorinated methoxy,
and pharmaceutically acceptable salts, solvates, isotopes and co-crystals thereof.

13. A compound according to claim 12, and having one of Formula VIa, VIb, VIc and VId, wherein
R2, R4, R5 and R9 are all hydrogen,
R6 is selected from halogen, cyano, $C_{1-3}$alkoxy, $C_{1-3}$alkyl, $C_{3-6}$cycloalkyl preferably $C_{3-4}$cycloalkyl, $C_{3-6}$cycloalkyloxy preferably $C_{3-4}$cycloalkyloxy, $C_{3-6}$heterocycloalkyl, and $C_{3-6}$heterocycloalkyloxy, each of which can be optionally substituted with a residue selected from fluoro and unsubstituted or fluorinated $C_{1-3}$alkoxy,
R7, if present, is selected from hydrogen, halogen, cyano, $C_{1-3}$alkoxy, $C_{1-3}$alkyl, $C_{3-6}$cycloalkyl, $C_{3-6}$cycloalkyloxy, $C_{3-6}$heterocycloalkyl, and $C_{3-6}$heterocycloalkyloxy, each of which can be optionally substituted with a residue selected from fluoro and unsubstituted or fluorinated $C_{1-3}$alkoxy,
R8 is selected from fluoro, methoxy and fluoromethoxy,
R10 is selected from halogen, $C_{1-4}$alkoxy, $C_{1-4}$alkyl, $C_{2-3}$alkenyl, $C_{2-3}$alkynyl, $C_{3-6}$cycloalkyl, $C_{3-6}$Cycloalkyloxy, $C_{3-6}$heterocycloalkyl, and $C_{3-6}$heterocycloalkyloxy, each of which can be optionally substituted with a residue selected from fluoro, cyano and unsubstituted or fluorinated $C_{1-3}$alkoxy, and
R11 is selected from hydrogen, fluoro, methoxy and fluoromethoxy,
and pharmaceutically acceptable salts, solvates, isotopes and co-crystals thereof.

14. A compound according to claim 12, and having one of Formula VIa, VIb, VIc and VId,
wherein
R2, R4 and R5 are all hydrogen,
R6 is selected from fluoro, chloro, bromo, methylsulfinyl, methyl, fluoromethyl, methoxy and fluoromethoxy,
R7, if present, is selected from hydrogen, fluoro, chloro, bromo, unsubstituted or fluorinated $C_1$-2alkyl, unsubstituted or fluorinated $C_{1-2}$alkoxy, methylsulfinyl, and methylsulfonyl,
R8 is selected from hydrogen, fluoro, chloro, methoxy and fluoromethoxy,
R9 is selected from hydrogen, methoxy and fluoro,
R10 is selected from is selected from halogen, cyano, cyanomethyl, cyanoethyl, unsubstituted or fluorinated $C_{1-3}$alkyl, unsubstituted or fluorinated $C_{1-3}$alkoxy, unsubstituted or fluorinated $C_{1-2}$alkoxy($C_{1-3}$)alkyl, unsubstituted or fluorinated $C_{1-2}$alkoxy($C_{1-3}$)alkoxy, unsubstituted or fluorinated $C_{1-2}$alkoxy($C_{2-3}$)alkenyl, unsubstituted or fluorinated $C_{1-2}$alkoxycarbonylcyclopropyl and unsubstituted or fluorinated $C_{1-3}$alkoxycyclopropyl,
R11 is selected from hydrogen, fluoro, chloro, fluoromethyl, methoxy, and fluoromethoxy, wherein at least one of R8 and R10 is different from hydrogen,
and pharmaceutically acceptable salts, solvates, isotopes and co-crystals thereof.

15. A compound according to claim 1, wherein R6 and R7 together with the carbon atoms to which R6 and R7 are attached, form a cycle such that the compound has a structure of one the following Formulae IIa-IIc:

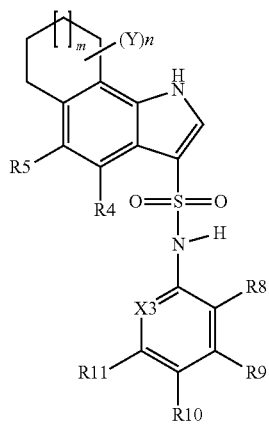

Formula IIa

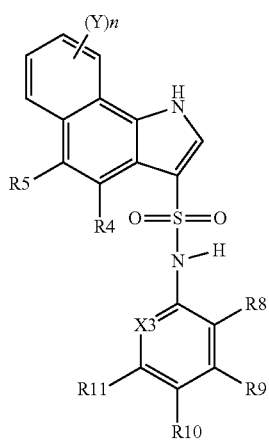

Formula IIb

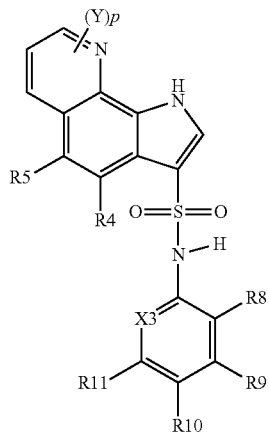

Formula IIc wherein n is any number from 0 to 4, m is 0 or 1, p is any number from 0 to 3, any Y is a substitution independently selected from fluoro, chloro, cyano, hydroxy, methyl, fluoromethyl, methoxy and fluoromethoxy, R4, R5, X3, R8, R9, R10, R11 and R12 (if X3 is C—R12) are as described in the compounds of Formula I, and II herein, and pharmaceutically acceptable salts, solvates, isotopes and co-crystals thereof.

16. A compound according to claim 15, wherein m is 0 or 1, n is 0, 1 or 2, p is 0, 1 or 2, any Y is selected from hydrogen, halogen, hydroxy, unsubstituted or fluorinated methyl and unsubstituted or fluorinated methoxy, R4 and R5 are both hydrogen, R8 is fluoro or methoxy, X3 is N or C(R12), R9 is hydrogen, R10 is selected from halogen, ethynyl, propynyl, cyano, cyanomethyl, cyanoethyl, cyanomethoxy, unsubstituted or fluorinated $(C_{1-3})$alkyl, unsubstituted or fluorinated $(C_{2-3})$alkenyl, unsubstituted or fluorinated $(C_{2-3})$alkynyl, unsubstituted or fluorinated $C_{1-3}$ alkyloxy, unsubstituted or fluorinated methoxy$(C_{1-3})$alkyl, unsubstituted or fluorinated methoxy$(C_{1-3})$alkyloxy, unsubstituted or fluorinated methoxy$(C_{2-3})$alkenyl, unsubstituted or fluorinated methoxy$(C_{2-3})$alkynyl and pentafluorosulfanyl, R11 is selected from hydrogen, fluoro, and methoxy, and R12, if present, is hydrogen or fluoro, and pharmaceutically acceptable salts, solvates, isotopes and co-crystals thereof.

17. A compound according to claim 1, wherein R9 forms a ring with R8 or R10 and the carbon atoms to which they are attached such that the compound has one of the following Formulae IId-IIg

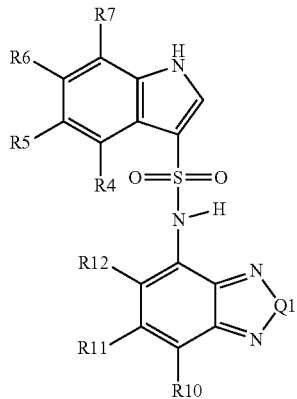

Formula II(d)

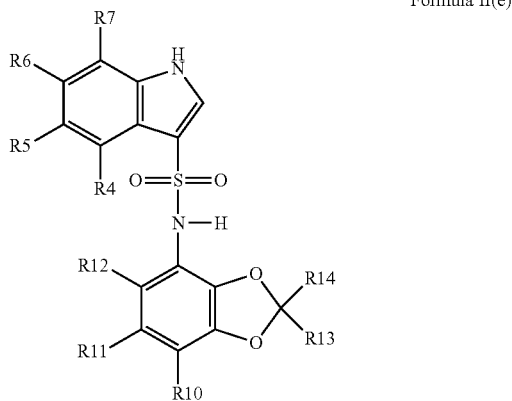

Formula II(e)

-continued

Formula II(f)

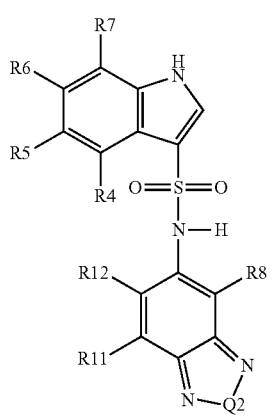

Formula II(g)

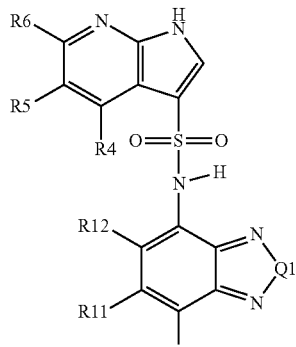

wherein in the compounds
(a) of Formula II(d), Q1 is S or O,
(b) of Formula II(e), R13 and R14 are selected from the group of hydrogen, methyl and fluoro,
(c) of Formula II(f), Q2 is S or O, and
(d) of Formula II(g), R16 is selected from hydrogen, fluoro, hydroxy, methyl, fluoromethyl, methoxy and fluoromethoxy,
and pharmaceutically acceptable salts, solvates, isotopes and co-crystals thereof.

18. A compound according to claim 17, wherein
(a) in Formula II(d), Q1 is S or O,
(b) in Formula II(e), R13 and R14 are both selected from hydrogen and fluoro,
(c) in Formula II(f), Q2 is S or O
(d) in Formula II(g), R16 is selected from hydrogen and methyl, and
R4 is hydrogen,
R5 is selected from hydrogen, fluoro, chloro and bromo,
R6 is selected from fluoro, chloro, bromo, methyl, methoxy, methylsulfonyl, methylsulfinyl, fluoromethyl, fluoromethoxy, cyano, and benzyloxy,
R7 is selected from hydrogen, fluoro, chloro, bromo, methoxy, cyano, methyl, and fluoromethyl,
R8, if present, is selected from hydrogen and halogen,
R10, if present, is selected from hydrogen, fluoro, chloro, bromo, fluoromethyl, fluoromethoxy and cyano,
R11 is selected from hydrogen and fluoro,
R12 is selected from hydrogen, halogen, methoxy and fluoromethyl, and pharmaceutically acceptable salts, solvates, isotopes and co-crystals thereof.

19. (A compound according to claim 1, having a structure of one of the following Formulae III(a) to III(c)

Formula III(a)

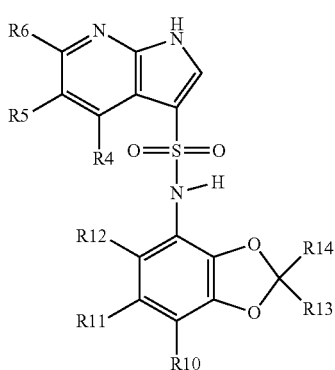

Formula III(b)

Formula III(c)

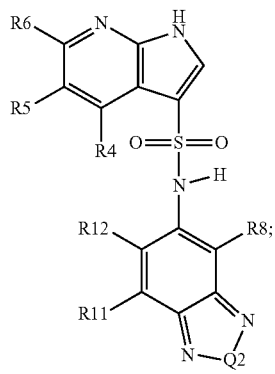

wherein in a compound
(a) of Formula III(a), Q1 is S or O,
(b) of Formula III(b), R13 and R14 are selected from the group of hydrogen, methyl and fluoro, and
(c) in Formula III(c), Q2 is S or O;
and pharmaceutically acceptable salts, solvates, isotopes and co-crystals thereof.

20. A compound according to claim 19, wherein
R4 and R5 are both hydrogen,
R6 is selected from fluoro, chloro, bromo, trifluoromethyl, and phenyl,
R8, if present, is hydrogen or fluoro,
R10, if present, is selected from hydrogen and halogen,
R11 is selected from hydrogen, halogen, trifluoromethyl and cyano,
R12 is selected from hydrogen, halogen and trifluoromethyl, and pharmaceutically acceptable salts, solvates, isotopes and co-crystals thereof.

21. A compound according to claim 1, wherein
(a) at least one of R5, R6 and R7, if R7 is present, and
(b) at least one of R8, R10 and R11 is different from hydrogen;
and pharmaceutically acceptable salts, solvates, isotopes and co-crystals thereof.

22. A compound according to claim 1, wherein the compound is selected from the group consisting of:
N-(4-bromo-2,5-difluorophenyl)-6-chloro-1H-indole-3-sulfonamide,
6-bromo-N-(4-cyano-2,5-difluorophenyl)-1H-indole-3-sulfonamide,
6-chloro-N-[5-(cyanomethyl)-3-fluoro-6-methoxypyridin-2-yl]-1H-indole-3-sulfonamide,
N-(4-chloro-2,5-difluorophenyl)-1H-pyrrolo[3,2-h]quinoline-3-sulfonamide,
N-(4-bromo-2,5-difluorophenyl)-1H-pyrrolo[3,2-h]quinoline-3-sulfonamide,
6-chloro-N-(4-chloro-2,5-difluorophenyl)-1H-indole-3-sulfonamide,
6-chloro-N-[4-(difluoromethoxy)-2,5-difluorophenyl]-1H-indole-3-sulfonamide,
N-[4-(cyanomethyl)-2,5-difluorophenyl]-1H-pyrrolo[3,2-h]quinoline-3-sulfonamide,
6-bromo-N-[3,6-difluoro-5-(3-methoxypropyl)pyridin-2-yl]-1H-indole-3-sulfonamide,
N-(5-bromo-3,6-difluoropyridin-2-yl)-6-chloro-1H-indole-3-sulfonamide,
N-(4-bromo-2,5-difluorophenyl)-6-chloro-1H-pyrrolo[2,3-b]pyridine-3-sulfonamide,
6-chloro-N-(5-chloro-3-fluoro-6-methoxypyridin-2-yl)-7-fluoro-1H-indole-3-sulfonamide,
6-chloro-N-[3,6-difluoro-5-(3-methoxypropyl)pyridin-2-yl]-1H-indole-3-sulfonamide,
5-bromo-6-chloro-N-[5-(cyanomethyl)-3-fluoro-6-methoxypyridin-2-yl]-1H-indole-3-sulfonamide,
6-chloro-N-(5-chloro-3,6-difluoropyridin-2-yl)-1H-indole-3-sulfonamide,
6-chloro-N-(4-chloro-2,5-difluorophenyl)-7-fluoro-1H-indole-3-sulfonamide,
N-(4-cyano-2,5-difluorophenyl)-1H-benzo[g]indole-3-sulfonamide,
7-bromo-6-chloro-N-(5-chloro-3-fluoro-6-methoxypyridin-2-yl)-1H-indole-3-sulfonamide,
6-chloro-N-[4-(cyanomethoxy)-2,5-difluorophenyl]-1H-indole-3-sulfonamide,
N-(5-chloro-3-fluoro-6-methoxypyridin-2-yl)-1H-pyrrolo[3,2-h]quinoline-3-sulfonamide,
6-chloro-N-(4-cyano-5-fluoro-2-methoxyphenyl)-1H-indole-3-sulfonamide,
6-chloro-N-(5-chloro-3-fluoro-6-methoxypyridin-2-yl)-1H-indole-3-sulfonamide,
6-chloro-N-(5-ethyl-3,6-difluoropyridin-2-yl)-1H-indole-3-sulfonamide,
6-chloro-N-{5-[(E)-2-ethoxyethenyl]-3,6-difluoropyridin-2-yl}-1H-indole-3-sulfonamide,
6-chloro-N-(4-chloro-2,5-difluorophenyl)-7-methoxy-1H-indole-3-sulfonamide,
6-chloro-N-(4-chloro-2-fluorophenyl)-1H-indole-3-sulfonamide,
ethyl 3-(6-{[(6-chloro-1H-indol-3-yl)sulfonyl]amino}-2,5-difluoropyridin-3-yl)propanoate,
6-chloro-N-[2,5-difluoro-4-(trifluoromethyl)phenyl]-1H-indole-3-sulfonamide,
6-bromo-N-{3,6-difluoro-5-[(1E)-3-methoxyprop-1-en-1-yl]pyridin-2-yl}-1H-indole-3-sulfonamide,
6-chloro-N-[5-(cyanomethyl)-3-fluoro-6-methoxypyridin-2-yl]-1-benzothiophene-3-sulfonamide,
N-(2,1,3-benzothiadiazol-4-yl)-6-bromo-1H-indole-3-sulfonamide,
6-chloro-N-[4-(2,2-difluoroethoxy)-2,5-difluorophenyl]-1H-indole-3-sulfonamide,
ethyl (2E)-3-(6-{[(6-chloro-1H-indol-3-yl)sulfonyl]amino}-2,5-difluoropyridin-3-yl)prop-2-enoate,
N-(5-chloro-3-fluoropyridin-2-yl)-1H-benzo[g]indole-3-sulfonamide,
N-(4-chloro-2,5-difluorophenyl)-8-(difluoromethyl)-1H-pyrrolo[3,2-h]quinoline-3-sulfonamide,
6-chloro-N-(4-chloro-2,5-difluorophenyl)-1H-pyrrolo[2,3-b]pyridine-3-sulfonamide,
6-chloro-N-(5-chloro-3-fluoro-6-methoxypyridin-2-yl)-7-methoxy-1H-indole-3-sulfonamide,
6-chloro-N-[5-(cyanomethyl)-3-fluoro-6-methoxypyridin-2-yl]-7-fluoro-1H-indole-3-sulfonamide,
6-chloro-N-(2,5-difluoro-4-iodophenyl)-1H-indole-3-sulfonamide,
N-(4-cyano-5-fluoro-2-methoxyphenyl)-1H-benzo[g]indole-3-sulfonamide,
N-[4-(cyanomethoxy)-2,5-difluorophenyl]-1H-pyrrolo[3,2-h]quinoline-3-sulfonamide,
N-(4-cyano-2,5-difluorophenyl)-6-(trifluoromethyl)-1H-indole-3-sulfonamide,
6-chloro-N-(6-fluoro-2,1,3-benzothiadiazol-5-yl)-1H-indole-3-sulfonamide,
6-chloro-N-[4-(difluoromethoxy)-2,5-difluorophenyl]-1H-pyrrolo[2,3-b]pyridine-3-sulfonamide,
N-(2,1,3-benzoselenadiazol-4-yl)-6-chloro-1H-indole-3-sulfonamide,
6-chloro-N-[2,5-difluoro-4-(trifluoromethyl)phenyl]-1H-pyrrolo[2,3-b]pyridine-3-sulfonamide,
6-chloro-N-{3,6-difluoro-5-[(1E)-3-methoxyprop-1-en-1-yl]pyridin-2-yl}-1H-indole-3-sulfonamide,
6-chloro-N-(4-cyano-2-fluorophenyl)-1H-indole-3-sulfonamide,
6-chloro-N-(2,5-difluoro-4-methylphenyl)-1H-indole-3-sulfonamide,
6-chloro-N-[5-(2-ethoxyethyl)-3,6-difluoropyridin-2-yl]-1H-indole-3-sulfonamide,
6-chloro-N-(5-chloro-3,6-difluoropyridin-2-yl)-7-methoxy-1H-indole-3-sulfonamide,
N-(4-cyano-2-fluorophenyl)-6-(thiophen-2-yl)-1H-indole-3-sulfonamide,
6-chloro-N-(4-ethynyl-2-fluorophenyl)-1H-indole-3-sulfonamide,
6-chloro-N-[3-fluoro-5-(trifluoromethyl)pyridin-2-yl]-1H-indole-3-sulfonamide,
6-chloro-N-[2-fluoro-4-(trifluoromethyl)phenyl]-1H-indole-3-sulfonamide,
7-bromo-6-chloro-N-(4-cyano-2-fluorophenyl)-1H-indole-3-sulfonamide,
6-bromo-N-(4-cyano-2-fluorophenyl)-1H-pyrrolo[2,3-b]pyridine-3-sulfonamide,
6-chloro-N-(4-cyano-2,5-difluorophenyl)-1H-indole-3-sulfonamide,
6-bromo-N-(2-fluoro-4-iodophenyl)-1H-pyrrolo[2,3-b]pyridine-3-sulfonamide,
N-(5-bromo-6-fluoro-3-methoxypyridin-2-yl)-6-chloro-1H-indole-3-sulfonamide,
6-chloro-N-(2-fluoro-4-iodophenyl)-1H-indole-3-sulfonamide, 6-chloro-N-[5-(cyanomethyl)-6-fluoro-3-methoxypyridin-2-yl]-1H-indole-3-sulfonamide,
6-bromo-7-chloro-N-(4-chloro-2,5-difluorophenyl)-1H-indole-3-sulfonamide,
6-bromo-N-(6-fluoro-2,1,3-benzothiadiazol-5-yl)-1H-indole-3-sulfonamide,
N-(4-bromo-2,5-difluorophenyl)-6-methoxy-1H-indole-3-sulfonamide,
6-bromo-N-(4-cyano-2-fluorophenyl)-1H-indole-3-sulfonamide,
6-chloro-N-(4-cyano-2-fluoro-5-methoxyphenyl)-1H-indole-3-sulfonamide,
N-(5-chloro-3,6-difluoropyridin-2-yl)-1H-benzo[g]indole-3-sulfonamide,
6-azido-N-[5-(cyanomethyl)-3-fluoro-6-methoxypyridin-2-yl]-1H-indole-3-sulfonamide,
6-chloro-N-[3,6-difluoro-5-(2-fluoroethoxy)pyridin-2-yl]-1H-indole-3-sulfonamide,
6-chloro-N-(6-fluoro-1-methyl-3-oxo-1,3-dihydro-2-benzofuran-5-yl)-1H-indole-3-sulfonamide,
N-(4-chloro-2,5-difluorophenyl)-5H-[1,3]dioxolo[4,5-f]indole-7-sulfonamide,
6-bromo-N-(5-chloro-3-fluoropyridin-2-yl)-1H-indole-3-sulfonamide,
N-[4-(cyanomethoxy)-2,5-difluorophenyl]-6-(difluoromethyl)-1H-indole-3-sulfonamide,
N-(2,1,3-benzothiadiazol-4-yl)-1H-benzo[g]indole-3-sulfonamide,
6-bromo-N-(4-chloro-2-fluorophenyl)-1H-pyrrolo[2,3-b]pyridine-3-sulfonamide,
6-chloro-N-(4-chloro-2,5-difluorophenyl)-7-(2,2-difluoroethoxy)-1H-indole-3-sulfonamide,
6-bromo-N-(4-cyanophenyl)-1H-indole-3-sulfonamide,
N-(2,1,3-benzothiadiazol-5-yl)-6-bromo-1H-indole-3-sulfonamide,
N-(4-cyano-2-fluorophenyl)-6-(propan-2-yl)-1H-indole-3-sulfonamide,
N-(4-cyano-2-fluorophenyl)-6-(trifluoromethyl)-1H-indole-3-sulfonamide,
N-(4-cyano-2,5-difluorophenyl)-6-methoxy-1H-indole-3-sulfonamide,
N-(4-bromo-2,5-difluorophenyl)-6-methoxy-1H-pyrrolo[2,3-b]pyridine-3-sulfonamide,
6-chloro-N-(5-ethenyl-3,6-difluoropyridin-2-yl)-1H-indole-3-sulfonamide,
N-(4-bromo-2,5-difluorophenyl)-6-(methylsulfinyl)-1H-indole-3-sulfonamide,
N-(4-bromo-2,5-difluorophenyl)-6-chloro-1-benzofuran-3-sulfonamide,
N-[4-(difluoromethoxy)-2,5-difluorophenyl]-6-(methylsulfinyl)-1H-indole-3-sulfonamide,
6-chloro-N-(2,4,5-trifluorophenyl)-1H-indole-3-sulfonamide,
N-(4-chloro-2,5-difluorophenyl)-8-hydroxy-1H-pyrrolo[3,2-h]quinoline-3-sulfonamide,
6-chloro-N-(2,5-difluoro-4-methylphenyl)-1H-pyrrolo[2,3-b]pyridine-3-sulfonamide,
6-chloro-N-(4-chloro-2,5-difluorophenyl)-7-cyano-1H-indole-3-sulfonamide,
6-chloro-N-[5-(cyanomethyl)-3-methoxypyridin-2-yl]-1H-indole-3-sulfonamide,
N-[4-(2-cyanoethyl)-2,5-difluorophenyl]-1H-pyrrolo[3,2-h]quinoline-3-sulfonamide,
6-chloro-N-[4-(cyanomethyl)-2-fluorophenyl]-1H-indole-3-sulfonamide,
N-(4-cyano-2-fluorophenyl)-1,6,7,8-tetrahydrocyclopenta[g]indole-3-sulfonamide,
N-(2,1,3-benzothiadiazol-4-yl)-1H-pyrrolo[3,2-h]quinoline-3-sulfonamide,
N-(4-chloro-2,5-difluorophenyl)-6-(trifluoromethyl)-1H-pyrrolo[2,3-b]pyridine-3-sulfonamide,
N-(4-ethynyl-2-fluorophenyl)-1H-pyrrolo[3,2-h]quinoline-3-sulfonamide,
N-(4-bromo-2-fluorophenyl)-6-chloro-1H-indole-3-sulfonamide,
6-bromo-N-(5-chloro-3-fluoropyridin-2-yl)-7-methyl-1H-indole-3-sulfonamide,
6-chloro-N-[4-chloro-5-(difluoromethoxy)-2-fluorophenyl]-1H-indole-3-sulfonamide,
N-(2,1,3-benzoxadiazol-5-yl)-6-chloro-1H-indole-3-sulfonamide,
5-bromo-6-chloro-N-(4-cyano-2-fluorophenyl)-1H-indole-3-sulfonamide,
6-(benzyloxy)-N-(4-cyano-2,5-difluorophenyl)-1H-indole-3-sulfonamide,
N-(6-fluoro-2,1,3-benzothiadiazol-5-yl)-1H-benzo[g]indole-3-sulfonamide,
N-(2,1,3-benzothiadiazol-4-yl)-6-chloro-1H-indole-3-sulfonamide,
6-chloro-N-(3,6-difluoro-5-methylpyridin-2-yl)-1H-indole-3-sulfonamide,
6-chloro-N-(4-cyanophenyl)-1H-indole-3-sulfonamide,
6-chloro-N-(5-chloro-3-fluoropyridin-2-yl)-1H-indole-3-sulfonamide,
N-(4-chloro-2,5-difluorophenyl)-6-methoxy-1H-indole-3-sulfonamide,
N-(4-chloro-2,5-difluorophenyl)-6-(difluoromethyl)-1H-pyrrolo[2,3-b]pyridine-3-sulfonamide,
6-chloro-N-(3-chloro-4-cyanophenyl)-1H-indole-3-sulfonamide,
7-chloro-N-(5-chloro-3-fluoro-6-methoxypyridin-2-yl)-6-fluoro-1H-indole-3-sulfonamide,
6-chloro-N-[2-fluoro-4-(pentafluoro-lambda~6~-sulfanyl)phenyl]-1H-pyrrolo[2,3-b]pyridine-3-sulfonamide,
N-(4-cyanophenyl)-1H-benzo[g]indole-3-sulfonamide,
N-(4-chloro-2-fluorophenyl)-1H-pyrrolo[3,2-h]quinoline-3-sulfonamide,
6-chloro-N-(5-chloro-3-fluoro-6-methoxypyridin-2-yl)-5,7-difluoro-1H-indole-3-sulfonamide,
6-chloro-N-[2-fluoro-4-(trifluoromethyl)phenyl]-1H-pyrrolo[2,3-b]pyridine-3-sulfonamide,
6-chloro-N-[4-(cyanomethoxy)-2,5-difluorophenyl]-1-benzofuran-3-sulfonamide,
N-(4-chloro-2,5-difluorophenyl)-6-cyano-1H-indole-3-sulfonamide,
6-chloro-N-(2,2-difluoro-1,3-benzodioxol-4-yl)-1H-indole-3-sulfonamide,
6-chloro-N-(4-chloro-2,5-difluorophenyl)-7-(methylsulfinyl)-1H-indole-3-sulfonamide,
6-chloro-N-[3,6-difluoro-5-(propan-2-yl)pyridin-2-yl]-1H-indole-3-sulfonamide,
6-chloro-N-(4-chloro-2,5-difluorophenyl)-1-benzofuran-3-sulfonamide,
7-chloro-N-(4-chloro-2,5-difluorophenyl)-6-(methylsulfanyl)-1H-indole-3-sulfonamide,
N-(2,1,3-benzothiadiazol-4-yl)-6-chloro-1H-pyrrolo[2,3-b]pyridine-3-sulfonamide,
6-chloro-N-{5-[(difluoromethoxy)methyl]-3-fluoropyridin-2-yl}-1H-indole-3-sulfonamide,
N-(1,3-benzodioxol-4-yl)-6-chloro-1H-indole-3-sulfonamide,
6-(benzyloxy)-N-(4-cyano-2-fluorophenyl)-1H-indole-3-sulfonamide, 6-chloro-N-(3,6-difluoro-5-methylpyridin-2-yl)-7-fluoro-1H-indole-3-sulfonamide,
N-(4-cyanophenyl)-6-cyclopropyl-1H-indole-3-sulfonamide,
6-chloro-N-(5-chloro-3-fluoro-6-methoxypyridin-2-yl)-5-fluoro-1H-indole-3-sulfonamide,
7-chloro-N-(5-chloro-3-fluoro-6-methoxypyridin-2-yl)-6-methoxy-1H-indole-3-sulfonamide,
6-chloro-N-(4-cyano-5-fluoro-2-methoxyphenyl)-1H-pyrrolo[2,3-b]pyridine-3-sulfonamide,
6-chloro-N-(6-fluoro-3-oxo-1,3-dihydro-2-benzofuran-5-yl)-1H-indole-3-sulfonamide,
ethyl 2-(6-{[(6-chloro-1H-indol-3-yl)sulfonyl]amino}-2,5-difluoropyridin-3-yl)cyclopropanecarboxylate,
N-(2,1,3-benzoxadiazol-4-yl)-6-chloro-1H-indole-3-sulfonamide,
6-chloro-N-(4-cyanophenyl)-1H-pyrrolo[2,3-b]pyridine-3-sulfonamide,
6-chloro-N-(4-chloro-2-fluorophenyl)-1H-pyrrolo[2,3-b]pyridine-3-sulfonamide,
N-(2,1,3-benzoxadiazol-4-yl)-1H-pyrrolo[3,2-h]quinoline-3-sulfonamide,
6-chloro-N-(4-chloro-5-fluoro-2-methoxyphenyl)-1H-indole-3-sulfonamide,
6-chloro-N-(4-chloro-2,5-difluorophenyl)-1-benzothiophene-3-sulfonamide,
6-chloro-N-[4-(cyanomethoxy)-2,5-difluorophenyl]-1-benzothiophene-3-sulfonamide,
N-(2,1,3-benzothiadiazol-4-yl)-6-bromo-1H-pyrrolo[2,3-b]pyridine-3-sulfonamide,
6-bromo-N-(4-cyanophenyl)-1H-pyrrolo[2,3-b]pyridine-3-sulfonamide,
6-chloro-N-(4-cyano-2,6-difluorophenyl)-1H-indole-3-sulfonamide,
6-chloro-N-(5-chloro-3-fluoro-6-methoxypyridin-2-yl)-1H-pyrrolo[2,3-b]pyridine-3-sulfonamide,
N-(5-bromo-3-fluoropyridin-2-yl)-6-chloro-1H-indole-3-sulfonamide,
6-chloro-N-(4-cyano-2-fluorophenyl)-5-fluoro-1H-indole-3-sulfonamide,
N-(2,2-difluoro-1,3-benzodioxol-4-yl)-1H-pyrrolo[3,2-h]quinoline-3-sulfonamide,
N-(5-chloro-3,6-difluoropyridin-2-yl)-1H-pyrrolo[3,2-h]quinoline-3-sulfonamide,
N-(4-bromo-2-fluorophenyl)-6-methyl-1H-indole-3-sulfonamide,
6-bromo-N-(4-chloro-2,5-difluorophenyl)-4-fluoro-1H-indole-3-sulfonamide,
N-(2,1,3-benzothiadiazol-5-yl)-6-chloro-1H-indole-3-sulfonamide,
N-(4-cyano-2-fluorophenyl)-6-methoxy-1H-indole-3-sulfonamide,
N-(4-chloro-2,5-difluorophenyl)-6-methoxy-1H-pyrrolo[2,3-b]pyridine-3-sulfonamide,
6-cyano-N-[4-(difluoromethoxy)-2,5-difluorophenyl]-1H-indole-3-sulfonamide,
N-(4-chloro-2,5-difluorophenyl)-6-(methylsulfinyl)-1H-indole-3-sulfonamide,
6-chloro-N-(6-fluoro-2,1,3-benzoxadiazol-5-yl)-1H-indole-3-sulfonamide,
6-chloro-N-(3,5-difluoro-6-methoxypyridin-2-yl)-1H-indole-3-sulfonamide,
N-(4-cyano-5-fluoro-2-methoxyphenyl)-6-methoxy-1H-indole-3-sulfonamide,
N-[4-(difluoromethoxy)-2,5-difluorophenyl]-6-(difluoromethyl)-1H-pyrrolo[2,3-b]pyridine-3-sulfonamide,
N-(4-cyano-2-fluorophenyl)-6-(thiophen-3-yl)-1H-indole-3-sulfonamide,
N-(4-azido-2-fluorophenyl)-6-chloro-1H-indole-3-sulfonamide,
6-chloro-N-[2-fluoro-4-(trifluoromethoxy)phenyl]-1H-pyrrolo[2,3-b]pyridine-3-sulfonamide,
6-chloro-N-(2-fluoro-4-iodophenyl)-1H-pyrrolo[2,3-b]pyridine-3-sulfonamide,
N-(5-bromo-6-chloropyridin-2-yl)-6-chloro-1H-indole-3-sulfonamide,
N-(5-bromo-3-methoxypyridin-2-yl)-6-chloro-1H-indole-3-sulfonamide,
6-chloro-N-[3-methoxy-5-(trifluoromethyl)pyridin-2-yl]-1H-indole-3-sulfonamide,
6-chloro-N-(2,5-difluorophenyl)-1H-indole-3-sulfonamide,
6-chloro-N-(5-chloro-3-fluoro-6-methoxypyridin-2-yl)-1-benzothiophene-3-sulfonamide,
6-chloro-N-(4-chloro-2,5-difluorophenyl)-7-(methylsulfonyl)-1H-indole-3-sulfonamide,
6-chloro-N-(4-chloro-2,5-difluorophenyl)-5-fluoro-1H-indole-3-sulfonamide,
N-(2-fluoro-4-iodophenyl)-5H-[1,3]dioxolo[4,5-f]indole-7-sulfonamide,
N-[4-(cyanomethoxy)-2,5-difluorophenyl]-6-fluoro-1H-indole-3-sulfonamide,
N-[2-fluoro-4-(trifluoromethyl)phenyl]-6-methoxy-1H-indole-3-sulfonamide
6-chloro-N-[2-fluoro-4-(pentafluoro-lambda~6~-sulfanyl)phenyl]-1H-indole-3-sulfonamide,
6-bromo-N-(2,4,5-trifluorophenyl)-1H-pyrrolo[2,3-b]pyridine-3-sulfonamide,
N-(2-fluoro-4-iodophenyl)-6-(methylsulfonyl)-1H-indole-3-sulfonamide,
6-chloro-N-(7-fluoro-2,1,3-benzothiadiazol-4-yl)-1H-indole-3-sulfonamide,
6-chloro-N-(3,6-difluoro-5-methylpyridin-2-yl)-7-(trifluoromethyl)-1H-indole-3-sulfonamide,
6-chloro-N-(3,5-difluoro-6-methoxypyridin-2-yl)-7-fluoro-1H-indole-3-sulfonamide,
6-chloro-N-[2-fluoro-4-(trifluoromethoxy)phenyl]-1H-indole-3-sulfonamide,
6-chloro-N-(5-chloro-3-fluoro-6-methoxypyridin-2-yl)-1-benzofuran-3-sulfonamide,
6-chloro-N-(5-chloro-3-fluoro-6-methylpyridin-2-yl)-1H-indole-3-sulfonamide,
N-(5-chloro-3-fluoro-6-methoxypyridin-2-yl)-6,7,8,9-tetrahydro-1H-benzo[g]indole-3-sulfonamide,
6-bromo-N-(4-ethynylphenyl)-1H-pyrrolo[2,3-b]pyridine-3-sulfonamide,
6-chloro-N-(2,2,6-trifluoro-1,3-benzodioxol-5-yl)-1H-indole-3-sulfonamide,
6-chloro-N-(4-chloro-2,5-difluorophenyl)-7-(3,5-dimethyl-1,2-oxazol-4-yl)-1H-indole-3-sulfonamide,
6-chloro-N-[5-chloro-3-fluoro-6-(fluoromethyl)pyridin-2-yl]-1H-indole-3-sulfonamide,
6-chloro-N-(3-fluoro-5-methylpyridin-2-yl)-1H-indole-3-sulfonamide,
6-chloro-N-(2,5-difluoro-4-methoxyphenyl)-1H-indole-3-sulfonamide,
N-(4-chloro-2-fluorophenyl)-6-methyl-1H-indole-3-sulfonamide,
N-(5-chloro-3,6-difluoropyridin-2-yl)-1,6,7,8-tetrahydrocyclopenta[g]indole-3-sulfonamide,
6-chloro-N-(5-chloro-3,6-difluoropyridin-2-yl)-7-(3,5-dimethyl-1,2-oxazol-4-yl)-1H-indole-3-sulfonamide, 6-bromo-N-(2-chloro-3-fluorophenyl)-1H-pyrrolo[2,3-b]pyridine-3-sulfonamide,
6-chloro-N-(5-chloro-3,6-difluoropyridin-2-yl)-1H-pyrrolo[2,3-b]pyridine-3-sulfonamide,
6-(methylsulfonyl)-N-(2,2,6-trifluoro-1,3-benzodioxol-5-yl)-1H-indole-3-sulfonamide,
6-chloro-N-[3,6-difluoro-5-(prop-1-en-2-yl)pyridin-2-yl]-1H-indole-3-sulfonamide,
N-(5-chloro-3-fluoropyridin-2-yl)-1H-pyrrolo[3,2-h]quinoline-3-sulfonamide,
N-(2,1,3-benzothiadiazol-4-yl)-6-fluoro-1H-indole-3-sulfonamide,
6-chloro-N-(5-chloro-2-fluorophenyl)-1H-indole-3-sulfonamide,
N-(4-chloro-5-fluoro-2-methoxyphenyl)-1H-benzo[g]indole-3-sulfonamide,
6-chloro-7-(difluoromethoxy)-N-(3,5-difluoro-6-methoxypyridin-2-yl)-1H-indole-3-sulfonamide,
N-(4-chloro-2-fluorophenyl)-6-(methylsulfonyl)-1H-indole-3-sulfonamide,
6-bromo-N-(2,5-difluorophenyl)-1H-pyrrolo[2,3-b]pyridine-3-sulfonamide,
N-(1,3-benzodioxol-4-yl)-6-bromo-1H-pyrrolo[2,3-b]pyridine-3-sulfonamide,
N-(2,1,3-benzothiadiazol-4-yl)-6-(trifluoromethyl)-1H-indole-3-sulfonamide,
N-(4-bromo-2-fluorophenyl)-6-methoxy-1H-indole-3-sulfonamide,
N-(4-cyano-2-fluorophenyl)-6-(2,2,2-trifluoroethoxy)-1H-indole-3-sulfonamide,
N-(2,4,5-trifluorophenyl)-1H-pyrrolo[3,2-h]quinoline-3-sulfonamide,
N-(4-cyano-2-fluorophenyl)-6-(cyclopropylmethoxy)-1H-indole-3-sulfonamide,
N-(4-ethynyl-2-fluorophenyl)-6-methoxy-1H-pyrrolo[2,3-b]pyridine-3-sulfonamide,
6-chloro-N-(4-cyano-2-methoxyphenyl)-1H-indole-3-sulfonamide,
N-(2,1,3-benzothiadiazol-5-yl)-6-chloro-1H-pyrrolo[2,3-b]pyridine-3-sulfonamide,
N-(4-ethynyl-2-fluorophenyl)-6-methoxy-1H-indole-3-sulfonamide,
6-chloro-N-[3,6-difluoro-5-(2-methoxyethoxy)pyridin-2-yl]-1H-indole-3-sulfonamide,
6-chloro-N-[4-(cyclopropylmethoxy)-2,5-difluorophenyl]-1H-indole-3-sulfonamide,
6-chloro-N-[5-(difluoromethoxy)-3,6-difluoropyridin-2-yl]-1H-indole-3-sulfonamide,
N-(2,1,3-benzothiadiazol-5-yl)-6-(trifluoromethyl)-1H-indole-3-sulfonamide,
6-bromo-N-[5-(cyanomethyl)-3-fluoro-6-methoxypyridin-2-yl]-1H-indole-3-sulfonamide,
N-(4-cyano-2,5-difluorophenyl)-1,6,7,8-tetrahydrocyclopenta[g]indole-3-sulfonamide,
7-bromo-6-chloro-N-[5-(cyanomethyl)-3-fluoro-6-methoxypyridin-2-yl]-1H-indole-3-sulfonamide,
N-(4-cyano-2,5-difluorophenyl)-6-fluoro-1H-indole-3-sulfonamide,
N-(4-cyanophenyl)-6-(trifluoromethyl)-1H-indole-3-sulfonamide,
N-(4-cyano-2,5-difluorophenyl)-6-methyl-1H-indole-3-sulfonamide,
6-bromo-N-(2,2-difluoro-1,3-benzodioxol-4-yl)-1H-pyrrolo[2,3-b]pyridine-3-sulfonamide,
N-(2,1,3-benzoselenadiazol-5-yl)-6-chloro-1H-indole-3-sulfonamide,
N-(4-cyanophenyl)-6-methyl-1H-indole-3-sulfonamide,
6-chloro-N-(6-fluoro-2,1,3-benzothiadiazol-5-yl)-1H-pyrrolo[2,3-b]pyridine-3-sulfonamide,
7-bromo-N-(4-cyano-2,5-difluorophenyl)-1H-indole-3-sulfonamide,
6-chloro-N-(3,6-difluoro-5-methylpyridin-2-yl)-1H-pyrrolo[2,3-b]pyridine-3-sulfonamide,
N-(2,5-difluoro-4-methylphenyl)-6-(methylsulfinyl)-1H-indole-3-sulfonamide,
6-fluoro-N-(6-fluoro-2,1,3-benzothiadiazol-5-yl)-1H-indole-3-sulfonamide;

and pharmaceutically acceptable salts, solvates, isotopes and co-crystals thereof.

23. A compound according to claim 1 comprising at least one isotope selected from (a) $^{11}$C, $^{13}$N, $^{15}$O, $^{18}$F, $^{76}$Br and $^{124}$I and/or (b) $^{99m}$Tc, $^{111}$IN, $^{82}$Rb, $^{137}$Cs, $^{123}$I, $^{125}$I, $^{131}$I, $^{67}$Ga, $^{192}$IR and $^{201}$Tl in an amount suitable for (a) PET and/or (b) SPECT imaging, respectively.

24. A pharmaceutical composition comprising a compound according to claim 1 or a pharmaceutically acceptable salt, solvate, isotope or co-crystal thereof; and a pharmaceutical acceptable carrier.

25. A compound according to claim 1, wherein

X1 is N or C(R7),

X2 is NH, S or O,

R4 and R5 are both hydrogen,

R6 is selected from fluoro, chloro, bromo, cyano, azido, methyl, ethyl, isopropyl, fluoromethyl, cyclopropyl, methoxy, fluoromethoxy, methylsulfinyl, methylsulfonyl, thien-2-yl, thien-3-yl, and benzyloxy, R7 is selected from hydrogen, methoxy, fluoro, chloro, bromo, cyano, mono-, di-, and trifluoromethyl, methylsulfinyl, methylsulfonyl, and fluoro($C_{1-2}$)alkoxy, X3 is N or C(R12), R8 is selected from fluoro and methoxy, R9 is hydrogen, R10 is selected from fluoro, chloro, bromo, azido, cyano, cyanomethyl, cyanoethyl, cyanomethoxy, cyclopropyl ($C_{1-2}$)alkyl, cyclopropyl($C_{1-2}$)alkoxy, $C_{1-2}$alkoxycyclopropyl, $C_{1-2}$alkoxycarbonylcyclopropyl, unsubstituted or fluorinated $C_{1-3}$ alkyl, unsubstituted or fluorinated $C_{1-3}$ alkoxy, unsubstituted or fluorinated $C_{2-3}$ alkenyl, unsubstituted or fluorinated $C_{2-3}$ alkynyl, unsubstituted or fluorinated $C_{1-3}$ alkoxy($C_{1-3}$)alkyl, unsubstituted or fluorinated $C_{1-3}$ alkoxy($C_{1-3}$)alkoxy, unsubstituted or fluorinated $C_{1-3}$ alkoxy($C_{2-3}$)alkenyl, and pentafluorosulfanyl, R11 is selected from hydrogen, fluoro and methoxy, R12, if present, is hydrogen, and pharmaceutically acceptable salts, solvates, isotopes and co-crystals thereof.

26. A compound according to claim 1, wherein the compound corresponds in structure to Formula III:

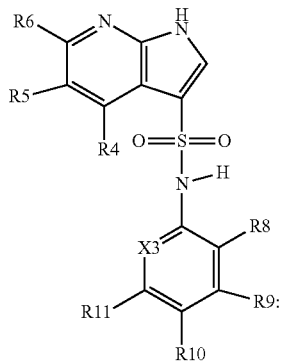

Formula III wherein
R4 and R5 are both hydrogen,
R6 is chloro or bromo,
X3 is C(R12), R12 is hydrogen or fluoro,
R8 is selected from hydrogen, methoxy, and halogen,
R9 is hydrogen,
R10 is selected from fluoro, bromo, chloro, iodo, trifluoromethyl, difluoroethoxy, trifluoromethoxy, trifluoroethoxy, ethynyl, azido, acetyl, pentafluorosulfanyl, cyanomethyl, and cyano,
R11 is hydrogen, fluoro, chloro, or methoxy,
and pharmaceutically acceptable salts, solvates, isotopes and co-crystals thereof.

27. A compound according to claim 1, wherein the compound corresponds in structure to Formula III:

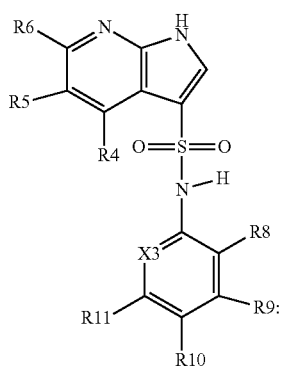

Formula III wherein
R4 and R5 are both hydrogen,
R6 is selected from methyl, fluoromethyl, methoxy, fluoromethoxy, chloro or bromo,
X3 is C(R12),
R8 is hydrogen, methoxy, or fluoro,
R9 is hydrogen,
R10 is selected from fluoro, bromo, chloro, iodo, mono-, di- and trifluoromethyl, mono-, di- and trifluoromethoxy, mono-, di-, and trifluoroethoxy, pentafluorosulfanyl, ethynyl and cyano, and
R11 and R12 are independently selected from hydrogen and fluoro;
and pharmaceutically acceptable salts, solvates, isotopes and co-crystals thereof.

28. A compound according to claim 1, wherein R7, if present, is hydrogen; and pharmaceutically acceptable salts, solvates, isotopes and co-crystals thereof.

29. A compound according to claim 1, wherein R6 is chloro; and pharmaceutically acceptable salts, solvates, isotopes and co-crystals thereof.

30. A compound according to claim 28, wherein the compound corresponds in structure to Formula II:

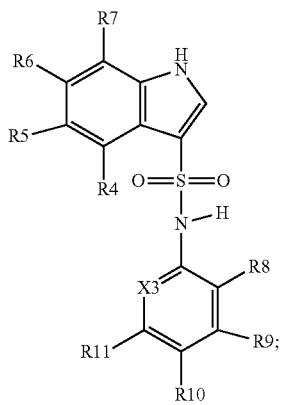

Formula II and pharmaceutically acceptable salts, solvates, isotopes and co-crystals thereof.

31. A compound according to claim 29, wherein the compound corresponds in structure to Formula II or Formula III:

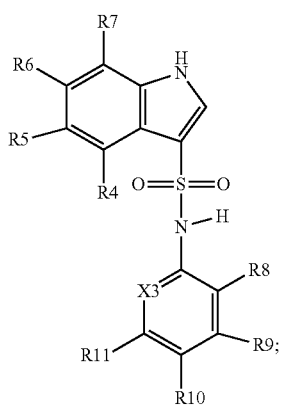

Formula II

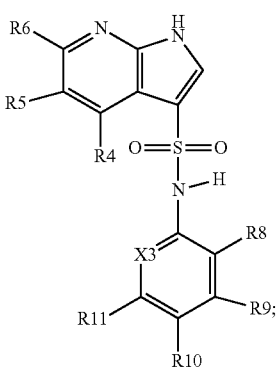

Formula III

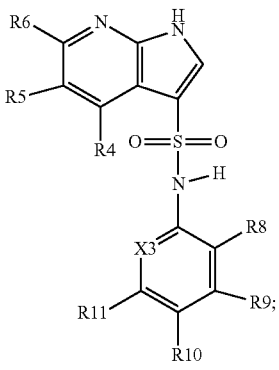

and pharmaceutically acceptable salts, solvates, isotopes and co-crystals thereof.

32. A compound according to claim 22, wherein the compound is 6-chloro-N-[4-(difluoromethoxy)-2,5-difluorophenyl]-1H-pyrrolo[2,3-b]pyridine-3-sulfonamide or a pharmaceutically acceptable salt or solvate thereof.

33. A compound according to claim 22, wherein the compound is 6-chloro-N-(4-chloro-2,5-difluorophenyl)-1H-pyrrolo[2,3-b]pyridine-3-sulfonamide or a pharmaceutically acceptable salt or solvate thereof.

34. A compound according to claim 22, wherein the compound is N-(4-bromo-2,5-difluorophenyl)-6-chloro-1H-pyrrolo[2,3-b]pyridine-3-sulfonamide or a pharmaceutically acceptable salt or solvate thereof.

35. A compound according to claim 22, wherein the compound is 6-chloro-N-[2,5-difluoro-4-(trifluoromethyl)phenyl]-1H-pyrrolo[2,3-b]pyridine-3-sulfonamide or a pharmaceutically acceptable salt or solvate thereof.

36. A compound according to claim 22, wherein the compound is 6-bromo-N-(4-chloro-2-fluorophenyl)-1H-pyrrolo[2,3-b]pyridine-3-sulfonamide or a pharmaceutically acceptable salt or solvate thereof.

37. A compound according to claim 22, wherein the compound is 6-chloro-N-(2,5-difluoro-4-methylphenyl)-1H-pyrrolo[2,3-b]pyridine-3-sulfonamide or a pharmaceutically acceptable salt or solvate thereof.

38. A compound according to claim 22, wherein the compound is N-(4-chloro-2,5-difluorophenyl)-6-(trifluoromethyl)-1H-pyrrolo[2,3-b]pyridine-3-sulfonamide or a pharmaceutically acceptable salt or solvate thereof.

39. A compound according to claim 22, wherein the compound is N-[4-(difluoromethoxy)-2,5-difluorophenyl]-6-(difluoromethyl)-1H-pyrrolo[2,3-b]pyridine-3-sulfonamide or a pharmaceutically acceptable salt or solvate thereof.

40. A compound according to claim 22, wherein the compound is 6-chloro-N-(5-chloro-3-fluoro-6-methoxypyridin-2-yl)-1H-indole-3-sulfonamide or a pharmaceutically acceptable salt or solvate thereof.

41. A compound according to claim 22, wherein the compound is N-(5-bromo-3,6-difluoropyridin-2-yl)-6-chloro-1H-indole-3-sulfonamide or a pharmaceutically acceptable salt or solvate thereof.

42. A compound according to claim 22, wherein the compound is 6-chloro-N-[3,6-difluoro-5-(3-methoxypropyl)pyridin-2-yl]-1H-indole-3-sulfonamide or a pharmaceutically acceptable salt or solvate thereof.

43. A compound according to claim 22, wherein the compound is 6-chloro-N-(5-chloro-3,6-difluoropyridin-2-yl)-1H-indole-3-sulfonamide or a pharmaceutically acceptable salt or solvate thereof.

44. A compound according to claim 22, wherein the compound is 6-chloro-N-[3,6-difluoro-5-(2-fluoroethoxy)pyridin-2-yl]-1H-indole-3-sulfonamide or a pharmaceutically acceptable salt or solvate thereof.

45. A compound according to claim 22, wherein the compound is 6-chloro-N-[5-(cyanomethyl)-3-fluoro-6-methoxypyridin-2-yl]-1H-indole-3-sulfonamide or a pharmaceutically acceptable salt or solvate thereof.

46. A compound according to claim 22, wherein the compound is 6-chloro-N-(5-chloro-3-fluoro-6-methoxypyridin-2-yl)-7-fluoro-1H-indole-3-sulfonamide or a pharmaceutically acceptable salt or solvate thereof.

47. A compound according to claim 22, wherein the compound is 6-chloro-N-{13,6-difluoro-5-[(1E)-3-methoxyprop-1-en-1-yl]pyridin-2-yl}-1H-indole-3-sulfonamide or a pharmaceutically acceptable salt or solvate thereof.

* * * * *

UNITED STATES PATENT AND TRADEMARK OFFICE
CERTIFICATE OF CORRECTION

PATENT NO. : 11,345,662 B2
APPLICATION NO. : 16/474245
DATED : May 31, 2022
INVENTOR(S) : Christa E. Mueller et al.

It is certified that error appears in the above-identified patent and that said Letters Patent is hereby corrected as shown below:

In the Specification

Column 2, Line 48, replace "amyotropic" with --amyotrophic--
Column 3, Line 18, replace "immunosupressive" with --immunosuppressive--
Column 20, Line 10, replace "cycloalkyl($C_{1-3}$))" with --cycloalkyl($C_{1-3}$)--
Column 26, Line 2, replace "fluoroor" with --fluoro or--
Column 73, Line 18, replace "heteroaryl(C1-2)alkyl," with --heteroaryl($C_{1-2}$)alkyl,--
Column 73, Line 59, replace "nsubstituted" with --unsubstituted--
Column 73, Line 60, replace "unsubstitued" with --unsubstituted--
Column 77, Line 43, replace "fluro($C_{1-3}$)alkoxy" with --fluoro($C_{1-3}$)alkoxy--
Column 82, Line 36, replace "Via-c," with --VIa-c,--
Column 87, Line 48, replace "$C_{1-3}$alkoxycycylopropyl," with --$C_{1-3}$alkoxycyclopropyl,--
Column 87, Line 50, replace "$C_{1-2}$alkoxy($C_{1-2}$)alkoxycycylopropyl," with --$C_{1-2}$alkoxy($C_{1-2}$)alkoxycyclopropyl,--
Column 88, Line 2, replace "Via-c," with --VIa-c,--
Column 89, Line 22, replace "cycylopropyl," with --cyclopropyl,--
Column 89, Line 32, replace "VI e," with --VIe,--
Column 90, Line 23, replace "VI g," with --VIg,--
Column 90, Line 67, replace "fluro," with --fluoro,--
Column 109, Line 40, replace "endogeneous" with --endogenous--
Column 110, Line 9, replace "Demylination" with --Demyelination--
Column 112, Line 29, replace "demelination" with --demyelination--
Column 112, Line 41, replace "Neuromyeltis" with --Neuromyelitis--
Column 125, Line 15, replace "C8-10" with --$C_{8-10}$--
Column 126, Line 14, replace "$C_5$-6)" with --$C_{5-6}$)--
Column 128, Line 38, replace "C2-C4" with --$C_2$-$C_4$--
Column 131, Line 56, replace "R 4" with --R4--
Column 132, Line 4, replace "X 2" with --X2--
Column 137, Line 59, replace "istope" with --isotope--
Column 153, Line 10, replace "$Na_2S2O_3$" with --$Na_2S_2O_3$--

Signed and Sealed this
Eighth Day of November, 2022

Katherine Kelly Vidal
*Director of the United States Patent and Trademark Office*

CERTIFICATE OF CORRECTION (continued)
U.S. Pat. No. 11,345,662 B2

Column 167, Line 57, replace "1H" with --$^1$H--
Column 167, Line 57, replace "DMSO-d6)" with --DMSO-$d_6$)--
Column 168, Line 14, replace "1H" with --$^1$H--
Column 168, Line 14, replace "DMSO-d6)" with --DMSO-$d_6$)--
Column 175, Line 35, replace "Na2CO3" with --$Na_2CO_3$--
Column 182, Line 41, replace "Na2S2O3" with --$Na_2S_2O_3$--
Column 191, Line 32, replace "NH4Cl" with --$NH_4Cl$--
Column 215, Line 22, replace "S03-DMF-complex" with --$SO_3$-DMF-complex--
Column 216, Line 19, replace "S03-DMF" with --$SO_3$-DMF--
Column 220, Line 66, replace "H2O" with --$H_2O$--
Column 228, Line 60, replace "S03-DMF" with --$SO_3$-DMF--
Column 383, Line 19, replace "1H" with --$^1$H--
Column 383, Line 19, replace "DMSO-d6)" with --DMSO-$d_6$)--
Column 383, Line 66, replace "1H" with --$^1$H--
Column 396, Line 29, replace "Na2S2O3" with --$Na_2S_2O_3$--
Column 405, Table 8 third entry of third column, replace "NH4OH" with --$NH_4OH$--
Column 424, Line 29, replace "Ca2+" with --$Ca^{2+}$--
Column 427, Line 58, replace "3-aetin" with --β-actin--

In the Claims

Column 442, Claim 14, Line 44, replace "$C_1$-2alkyl," with --$C_{1-2}$alkyl,--
Column 445, Claim 18, Line 51, after "O", insert --,--
Column 446, Claim 19, Line 3, replace "(A" with --A--
Column 452, Claim 22, Line 29, after "indole-3-sulfonamide", insert --,--
Column 458, Claim 47, Line 30, replace "6-chloro-N-{13,6-difluoro-5-[(1E)-3-" with --6-chloro-N-{3,6-difluoro-5-[(1E)-3- --